(12) United States Patent
Rees-Smith et al.

(10) Patent No.: US 9,073,992 B2
(45) Date of Patent: Jul. 7, 2015

(54) HUMAN ANTI TSHR ANTIBODIES

(75) Inventors: Bernard Rees-Smith, Cardiff (GB); Jane Sanders, Cardiff (GB); Jadwiga Furmaniak, Cardiff (GB)

(73) Assignee: RSR Ltd., Cardiff, South Glamorgan (GB)

( * ) Notice: Subject to any disclaimer, the term of this patent is extended or adjusted under 35 U.S.C. 154(b) by 578 days.

(21) Appl. No.: 13/142,217

(22) PCT Filed: Dec. 23, 2009

(86) PCT No.: PCT/GB2009/002946
§ 371 (c)(1),
(2), (4) Date: Aug. 26, 2011

(87) PCT Pub. No.: WO2010/073012
PCT Pub. Date: Jul. 1, 2010

(65) Prior Publication Data
US 2011/0300138 A1  Dec. 8, 2011

(30) Foreign Application Priority Data
Dec. 24, 2008 (GB) .................................. 0823562.4
May 22, 2009 (GB) .................................. 0908945.9

(51) Int. Cl.
*C07K 16/28* (2006.01)
(52) U.S. Cl.
CPC ............. *C07K 16/28* (2013.01); *C07K 2299/00* (2013.01); *C07K 2316/95* (2013.01); *C07K 2316/96* (2013.01); *C07K 2317/21* (2013.01); *C07K 2317/55* (2013.01); *C07K 2317/56* (2013.01); *C07K 2317/92* (2013.01); *C07K 2317/75* (2013.01); *C07K 2317/76* (2013.01)

(58) Field of Classification Search
CPC ........ C07H 21/04; C07H 21/00; C07K 16/00; C12N 15/00; C12N 15/63; C12N 2800/00; A61K 39/00; A61K 2039/505
USPC ...................... 530/350, 387.1, 387.3, 388.22; 435/320.1, 325; 536/23.5
See application file for complete search history.

(56) References Cited

FOREIGN PATENT DOCUMENTS

| WO | WO03001863 | A2 | 1/2003 |
|---|---|---|---|
| WO | WO2004050708 | A2 | 6/2004 |
| WO | WO2006016121 | A1 | 2/2006 |
| WO | WO2008025991 | A1 | 3/2008 |
| WO | WO2008091981 | A2 | 7/2008 |
| WO | WO2008099185 | A8 | 7/2009 |

OTHER PUBLICATIONS

Hoermann et al. (Thyroid. 1993 Winter; 3 (4): 273-8).*
Kraiem et al. (Clin Endocrinol (Oxf). Feb. 1992; 36 (2): 211-4).*
Neumann et al. (Expert Rev. Endocrinol. Metab. Nov. 1, 2009; 4 (6): 669; pp. 1-20).*
Jiang et al. (J. Biol. Chem. Feb. 11, 2005; 280 (6): 4656-4662).*
Rudikoff et al (Proc. Natl. Acad. Sci. USA. 1982; 79: 1979-1983).*
Mariuzza et al. (Annu. Rev. Biophys. Biophys. Chem. 1987; 16: 139-159).*
Winkler et al. (J. Immunol. Oct. 15, 2000; 165 (8): 4505-4514).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Sanders et al. (Thyroid. Jul. 2005; 15 (7): 672-82).*
Ajjan et al. (Nature Clinical Practice Endocrinology & Metabolism. 2008; 4: 461-468).*
Ando et al. (J. Clin. Invest. 2002; 110 (11): 1667-1674).*
Bolton et al; Measurement of Thyroid-stimulating Hormone Receptor Autoantibodies by ELISA; Clinical Chemistry; 1999; pp. 2285-2287.
Brünger; Free R value: A novel statistical quantity for assessing the accuracy of crystal structures; Nature; 1992; pp. 472-475.
Carter; Potent antibody therapeutics by design; Nat. Rev. Immunol.; 2006; pp. 343-357.
Chen et al; Suppression of thyrotropin receptor constitutive activity by a monoclonal antibody with inverse agonist activity; Endocrinology; 2007; pp. 2375-2382.
International Written Opinion; Cilensek, Zoran ; Jul. 1, 2010; PCT/GB2009/002946; 17 pages.
Collaborative Computational Project No. 4; The CCP4 Suite: Programs for Protein Crystallography; Acta Cryst.; 1994; pp. 760-763.
Duntas and Cooper; Review on the occasion of a decade of recombinant human TSH: prospects and novel uses; Thyroid; 2008; pp. 509-516.
Evans et al; Potent thyrotrophin receptor-blocking antibodies: a cause of transient congenital hypothyroidism and delayed thyroid development; European Journal of Endocrinology; 2004; pp. 265-268.

(Continued)

*Primary Examiner* — Stephen Rawlings
(74) *Attorney, Agent, or Firm* — Fish & Richardson P.C.

(57) ABSTRACT

According to one aspect there is provided an isolated human antibody molecule which binds to the TSHR and which reduces ligand-induced stimulation of the TSHR but has no effect on TSHR constitutive activity, wherein the isolated human antibody molecule has the characteristic of patient serum TSHR autoantibodies of inhibiting TSH and M22 binding to the TSHR.

12 Claims, 164 Drawing Sheets

(56) References Cited

OTHER PUBLICATIONS

Furmaniak et al; Immunity to the thyroid-stimulating hormone receptor; Springer Seminars in Immunopathology; 1993; pp. 309-321.
Grossmann et al; Novel insights into the molecular mechanisms of human thyrotropin action: structural, physiological, and therapeutic implications for the glycoprotein hormone family; Endocrine Reviews; 1997; pp. 476-501.
Holliger et al; "Diabodies": small bivalent and bispecific antibody fragments; Proc Natl Acad Sci USA ; 1993; pp. 6444-6448.
Jeffreys et al; Characterization of the thyrotropin binding pocket; Thyroid; 2002; pp. 1051-1061.
Kohn et al; Characterization of monoclonal thyroid-stimulating and thyrotropin binding-inhibiting autoantibodies from a Hashimoto's patient whose children had intrauterine and neonatal thyroid disease; J. Clin. Endocrinol. Megab.; 1997; pp. 3998-4009.
Matthews et al; Antibodies to Acetylcholine Receptor in Parous Women with Myasthenia: Evidence for Immunization by Fetal Antigen; Laboratory Investigation; 2002; pp. 1-11.
Morgenthaler et al; Stimulating and blocking thyroid-stimulating hormone (TSH) receptor autoantibodies from patients with Graves' disease and autoimmune hypothyroidism have very similar concentration, TSH receptor affinity, and binding sites; J. Clin. Endocrinol. Metab.; 2007; pp. 1058-1065.
International Preliminary Report on Patentabilty; Mülhausen, Dorothée ; Jun. 29, 2011; PCT/GB2009/002946; 12 pages.
Nagayama et al; Molecular cloning, sequence and functional expression of the cDNA; GenBank Accession No. P16473; 2012; pp. 1-24.
Nuñez et al; Analysis of the thyrotropin receptor-thyrotropin interaction by comparative modeling; Thyroid; 2004; pp. 991-1011.
Oda et al; Binding Characteristics of antibodies to the TSH receptor; Journal of Molecular Endocrinology; 1998; pp. 233-244.
Rees-Smith; A new assay for thyrotropin receptor autoantibodies; Thyroid; 2004; pp. 830-835.
Rees-Smith et al; Autoantibodies to the thyrotropin receptor; Endocrine Reviews; 1988; pp. 106-121.
Rees-Smith et al; TSH receptor—autoantibody interactions; Horm Metab Res; 2009; pp. 448-455.
Rees-Smith et al; TSH receptor antibodies; Thyroid; 2007; pp. 923-938.
Sanders et al; A human monoclonal autoantibody to the thyrotropin receptor with thyroid-stimulating blocking activity; Thyroid; 2008; pp. 735-743.
Sanders et al; Characteristics of a human monoclonal autoantibody to the thyrotropin receptor: sequence structure and function; Thyroid; 2004; pp. 560-570.
Sanders et al; Characteristics of a monoclonal antibody to the thyrotropin receptor that acts as a powerful thyroid-stimulating autoantibody antagonist; Thyroid; 2005; pp. 672-682.
Sanders et al; Crystal structure of the TSH receptor in complex with a thyroid-stimulating autoantibody; Thyroid; 2007; pp. 395-410.
Sanders et al; The interaction of TSH receptor autoantibodies with 125I-labelled TSH receptor; Journal of Clinical Endocrinology and Metabolism; 1999; pp. 3797-3802.
Scatchard; The Attractions of Proteins for. Small Molecules and Ions; Annals of the New York Academy of Sciences; 1949; pp. 660-672.
Schott et al; Thyrotropin receptor autoantibodies in Graves' disease; Trends in Endocrinology and Metablism; 2005; pp. 243-248.
Southgate et al; A receptor assay for the measurement of TSH receptor antibodies in unextracted serum; Clin Endocrinol; 1984; pp. 539-548.
Szkudlinski et al; Thyroid-Stimulating Hormone and Thyroid-Stimulating Hormone Receptor Structure-Function Relationships; Physiololgical Reviews; 2002; pp. 473-502.
Valente et al; Monoclonal antibodies to the thyroptropin receptor: stimulating and blocking antibodies derived from the lymphocytes of patients with Graves disease; Proc. Natl. Acad. Sci. USA; 1982; pp. 6680-6684.
Zophel et al; M22 based (manual) ELISA for TSH-receptor antibody (TRAb) measurement is more sensitive than 2nd generation TRAb assays; Clincia Chimica Acta; 2009.

* cited by examiner

Figure 1a  Time course of binding of $^{125}$I-labelled K1-70 IgG and Fab to TSHR (full length) coated tubes
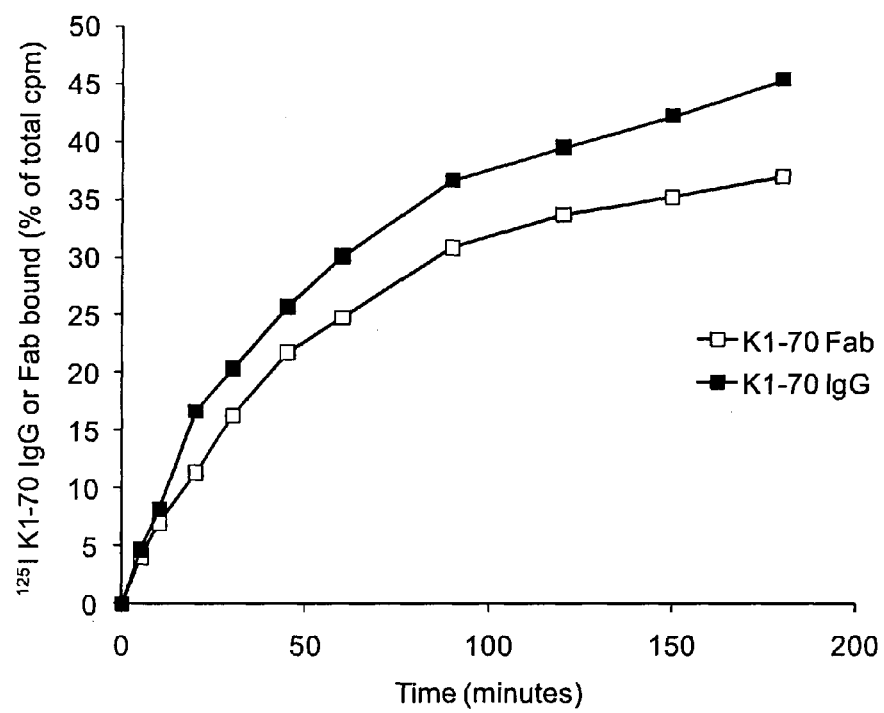
Non specific binding ie binding of labelled K1-70 IgG/Fab to tubes not coated with the TSHR was at below 2% of total cpm added and was not subtracted from the data shown in the Figure.

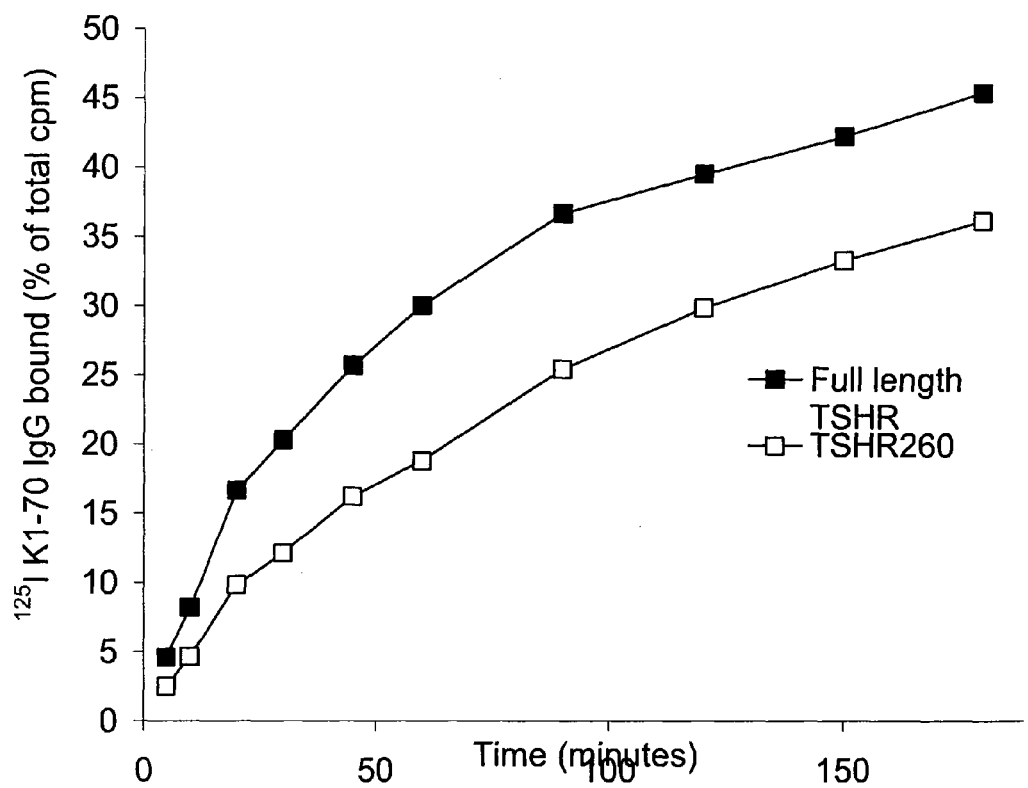
Figure 1b  Time course of binding of $^{125}$I-labelled K1-70 IgG to full length TSHR and TSHR260 coated tubes
Non specific binding ie binding of labelled K1-70 IgG to tubes not coated with the TSHR was at below 2% of total cpm added and was not subtracted from the data shown in the Figure.

Figure 1c  Time course of binding of $^{125}$I-labelled K1-70 Fab to full length TSHR and TSHR260 coated tubes
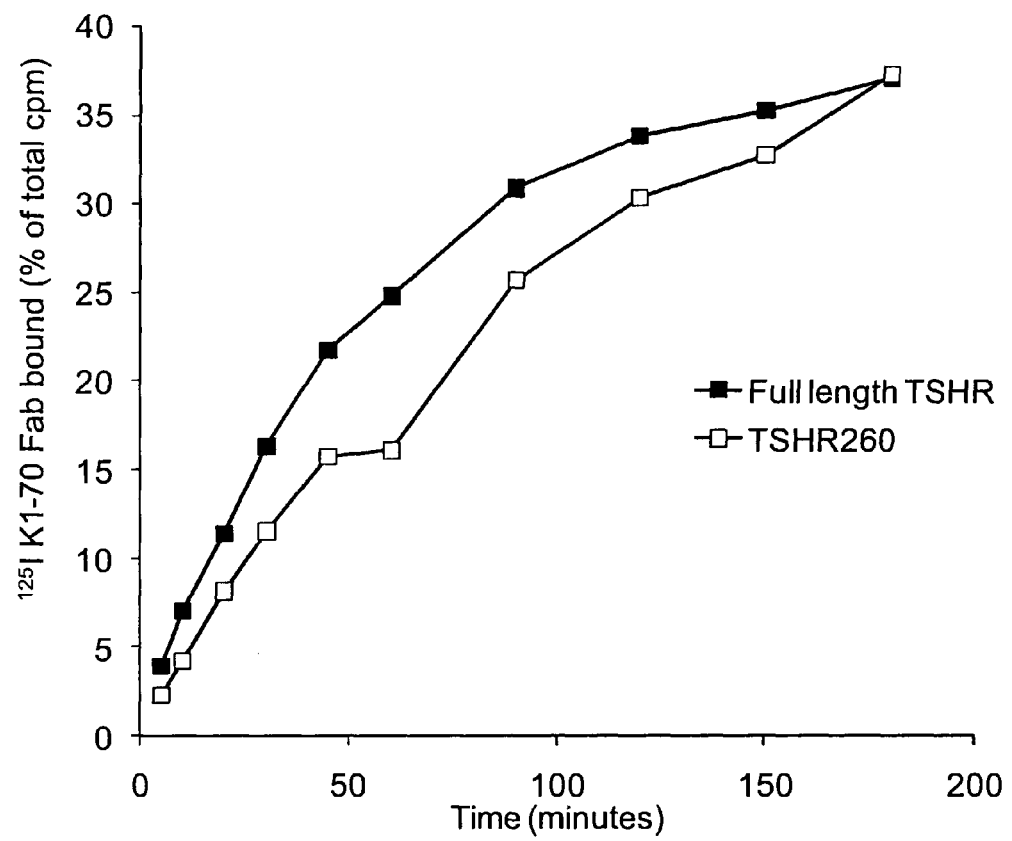
Non specific binding ie binding of labelled K1-70 IgG to tubes not coated with the TSHR was at below 2% of total cpm added and was not subtracted from the data shown in the Figure.

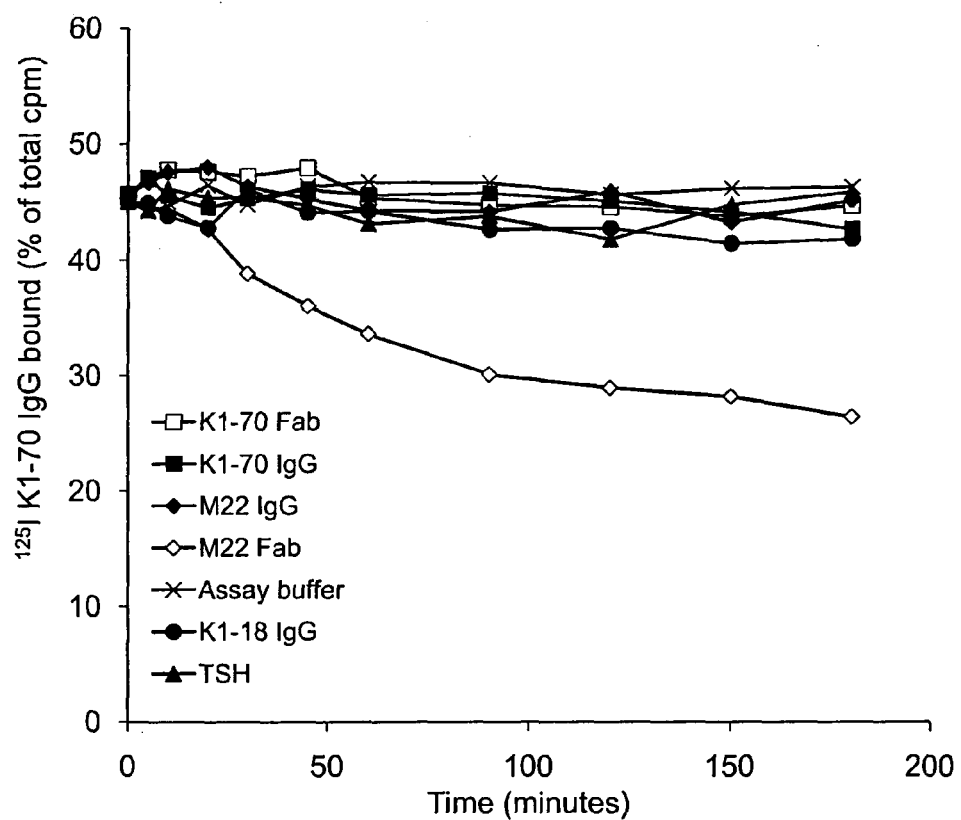
Figure 1d Dissociation of $^{125}$I-K1-70 IgG from TSHR (full length) coated tubes in the presence of various unlabelled ligands Figure 1e  Dissociation of $^{125}$I-K1-70 IgG from TSHR (full length) coated tubes in the presence of K1-18 Fab
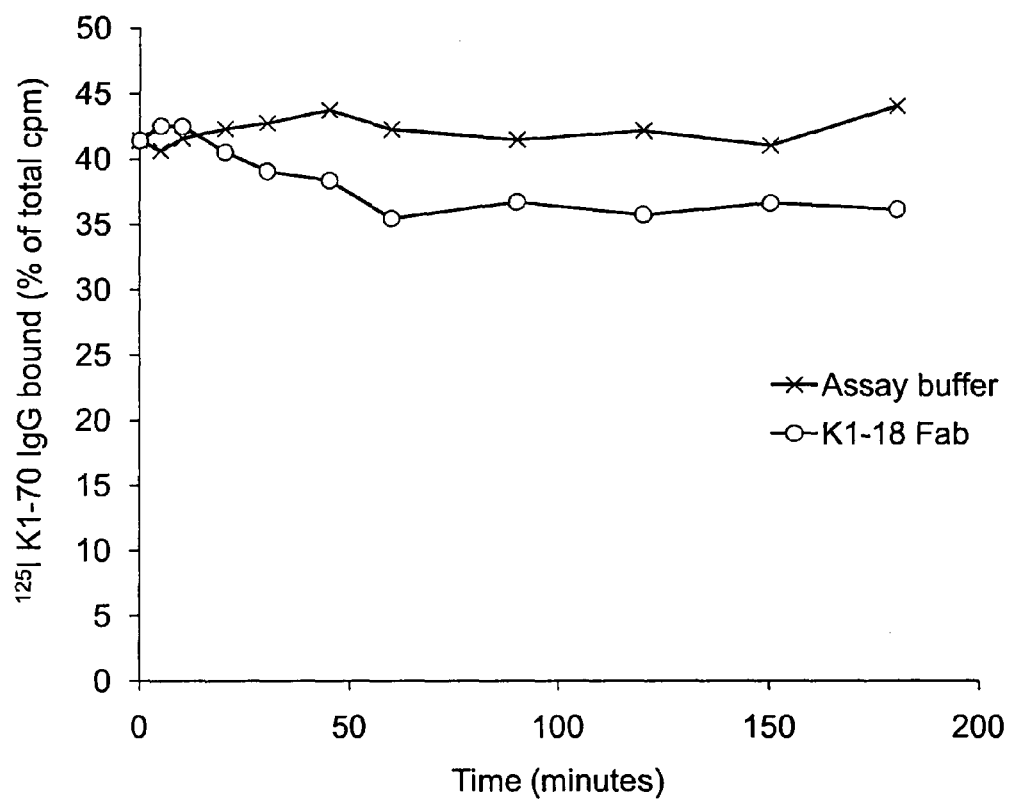

Figure 1f   Dissociation of $^{125}$I-K1-70 Fab from TSHR (full length) coated tubes in the presence of various unlabelled ligands
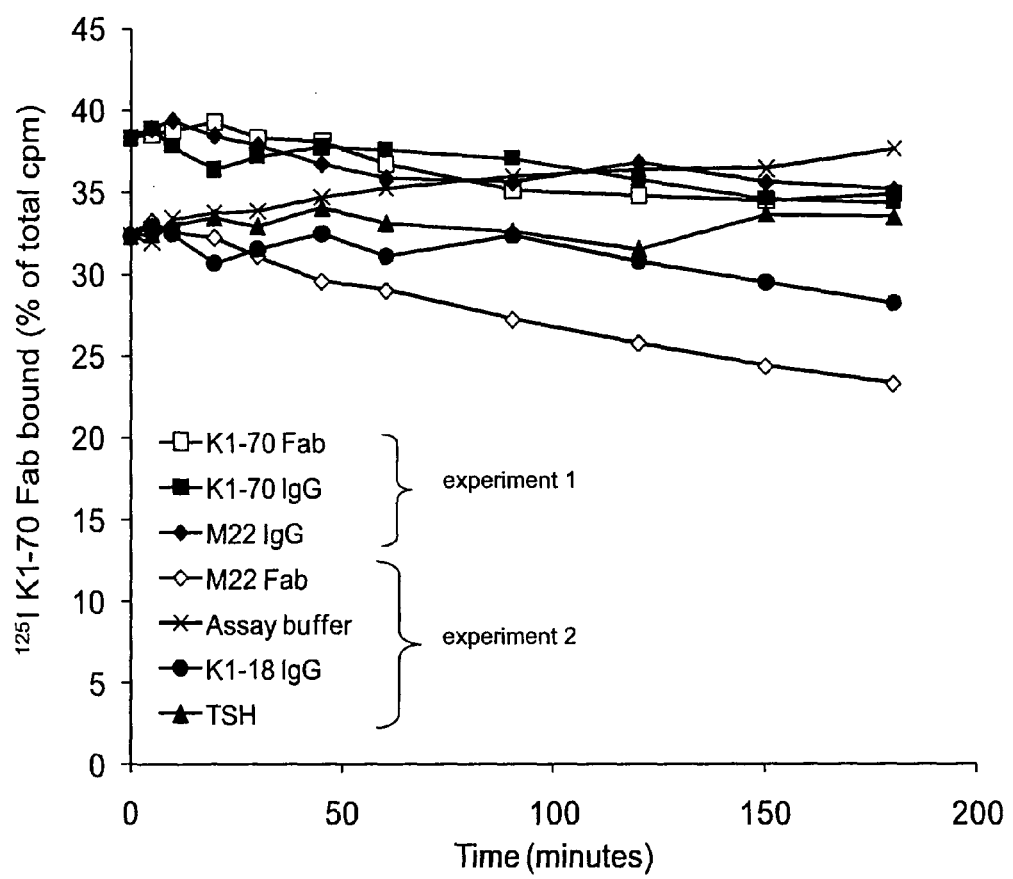
Experiments 1 and 2 were carried out on separate days, with different lots of TSHR coated tubes.

Figure 1g Dissociation of $^{125}$I-K1-70 IgG from TSHR260 coated tubes in the presence of various unlabelled ligands
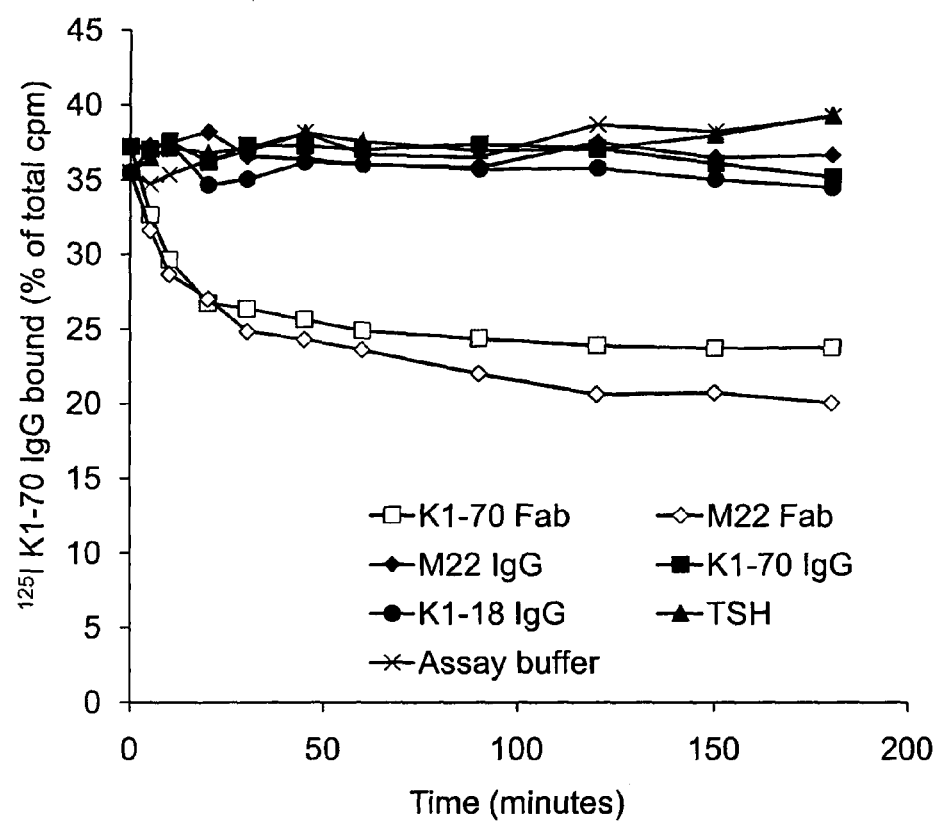

Figure 1h    Dissociation of $^{125}$I-K1-70 IgG from TSHR260 coated tubes in the presence of K1-18 Fab
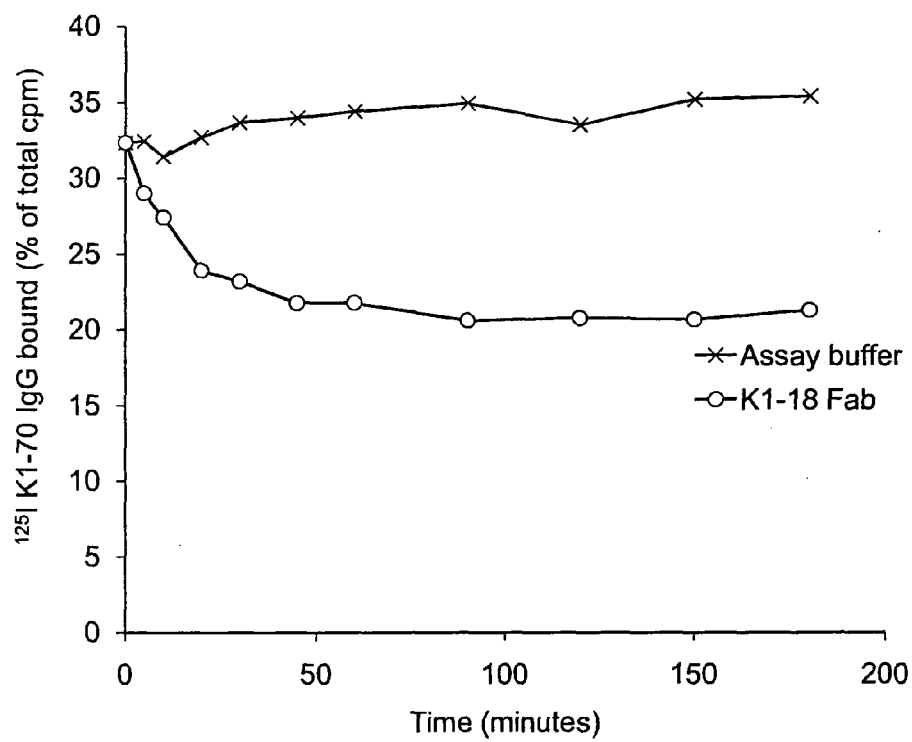

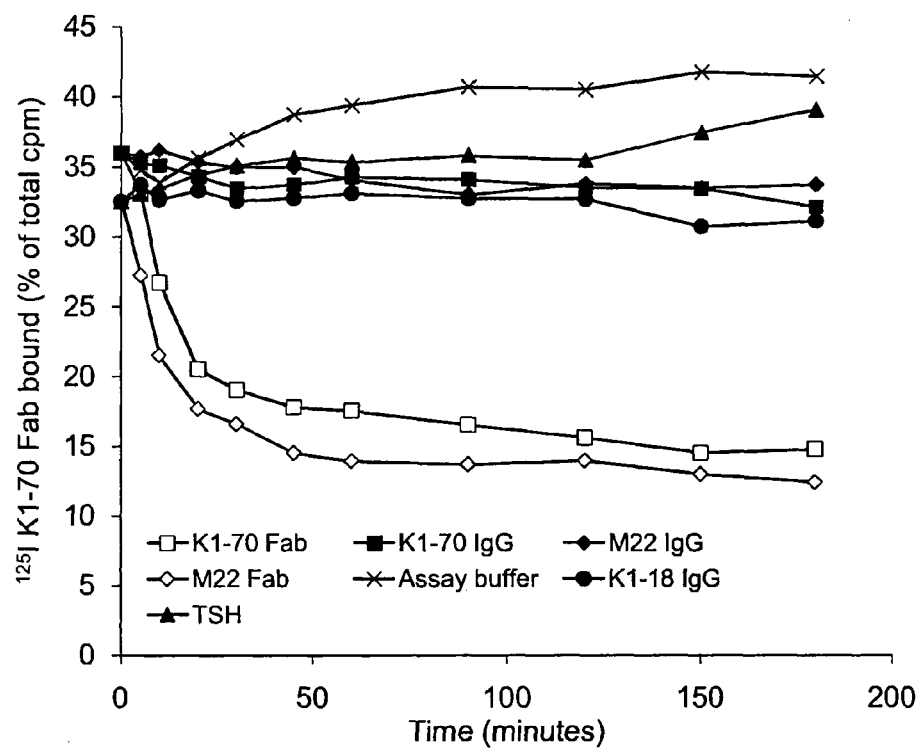
Figure 1i  Dissociation of $^{125}$I-K1-70 Fab from TSHR260 coated tubes in the presence of various unlabelled ligands Figure 1j  Time course of binding of $^{125}$I-labelled K1-18 IgG to full length TSHR and TSHR260 coated tubes
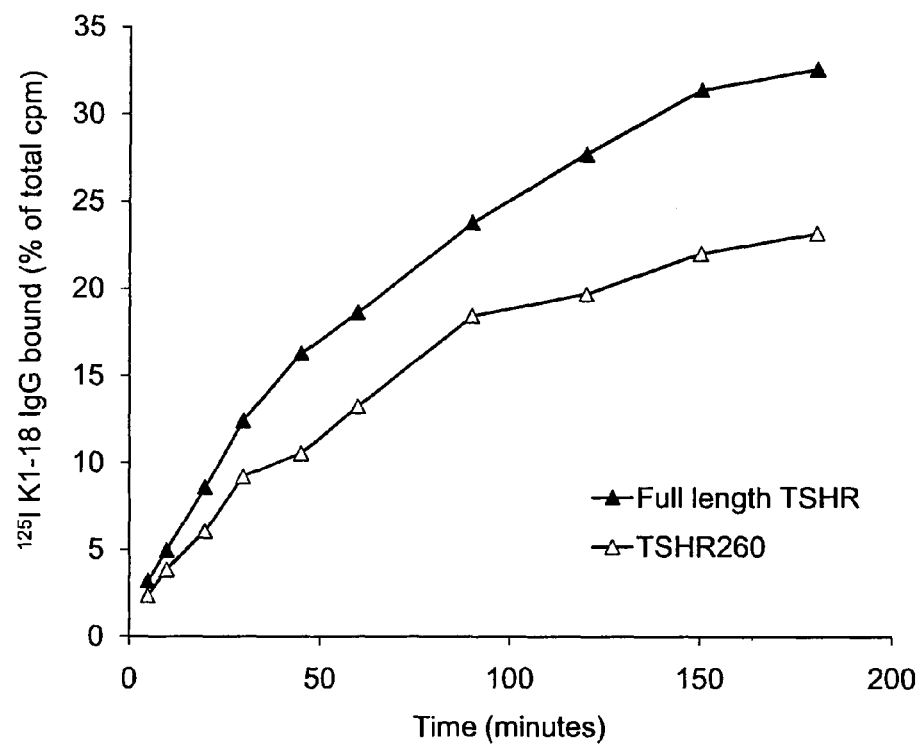

Figure 1k    Dissociation of $^{125}$I-K1-18 IgG from TSHR (full length) coated tubes in the presence of various unlabelled ligands
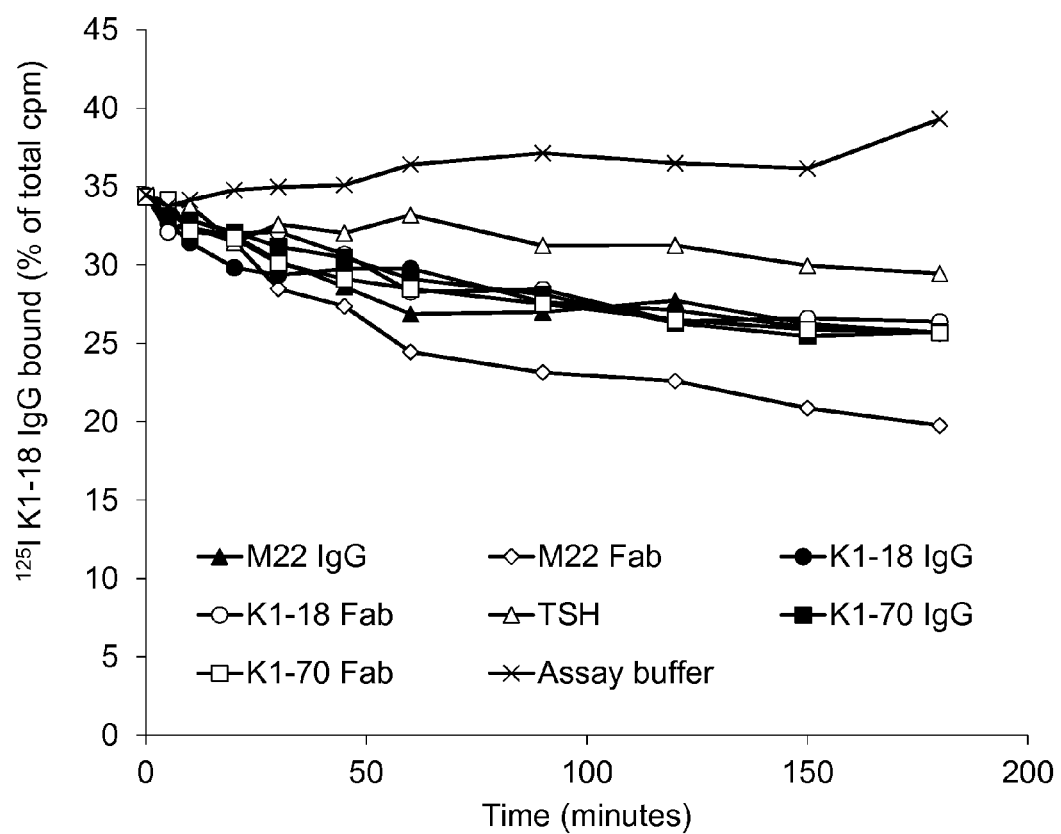

Figure 1I  Dissociation of $^{125}$I-K1-18 IgG from tubes coated with TSHR260 in the presence of various unlabelled ligands
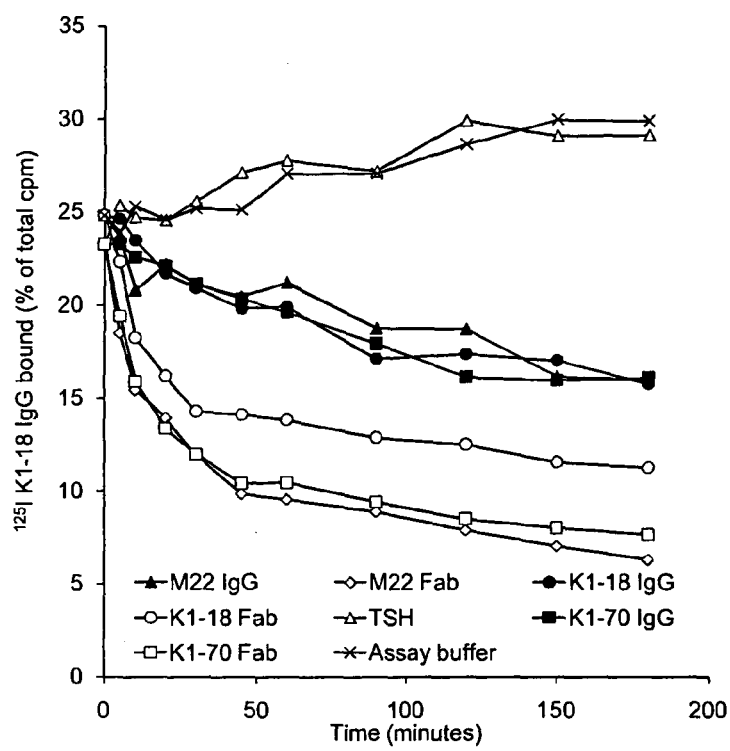

Figure 2a  Comparison of measurements of patient serum TRAbs in a TRAb coated tube assay (based on inhibition of TSH binding) and in a TSHR260-AP ELISA
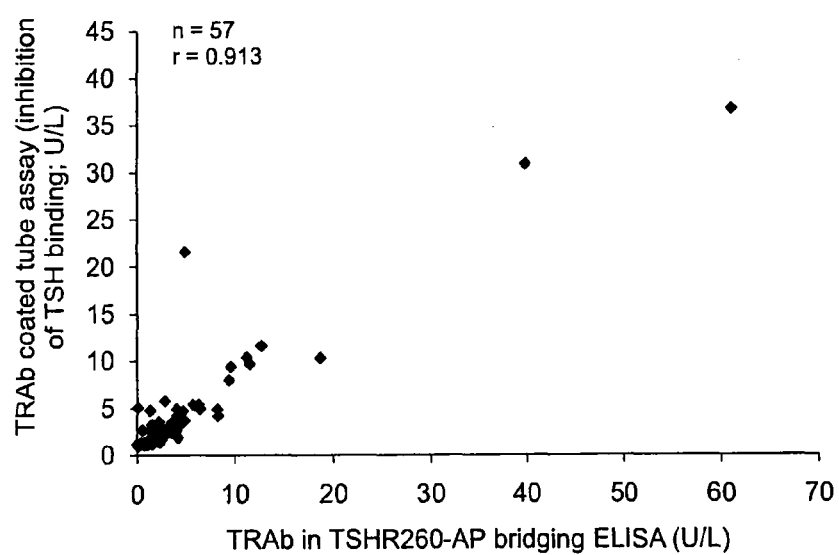

Figure 2b   Comparison of measurements by ELISAs based on inhibition of M22 Fab binding to full length TSHR and by inhibition of M22 Fab binding to TSHR260
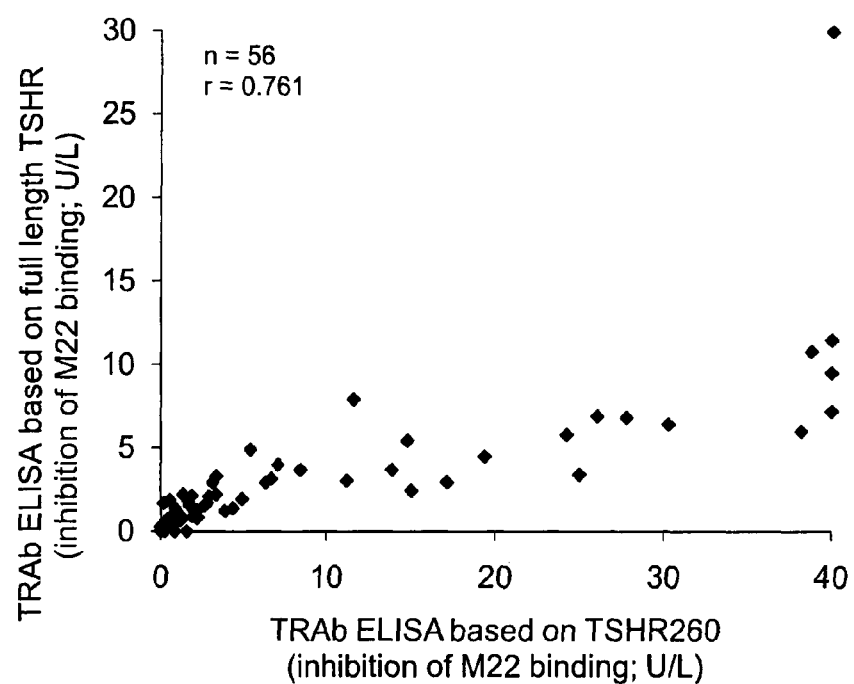

Figure 2c  Comparison of measurements of patient serum TRAbs in a TRAb coated tube assay (based on inhibition of TSH binding to full length TSHR) and by inhibition of M22 Fab binding to TSHR260 coated plates in an ELISA
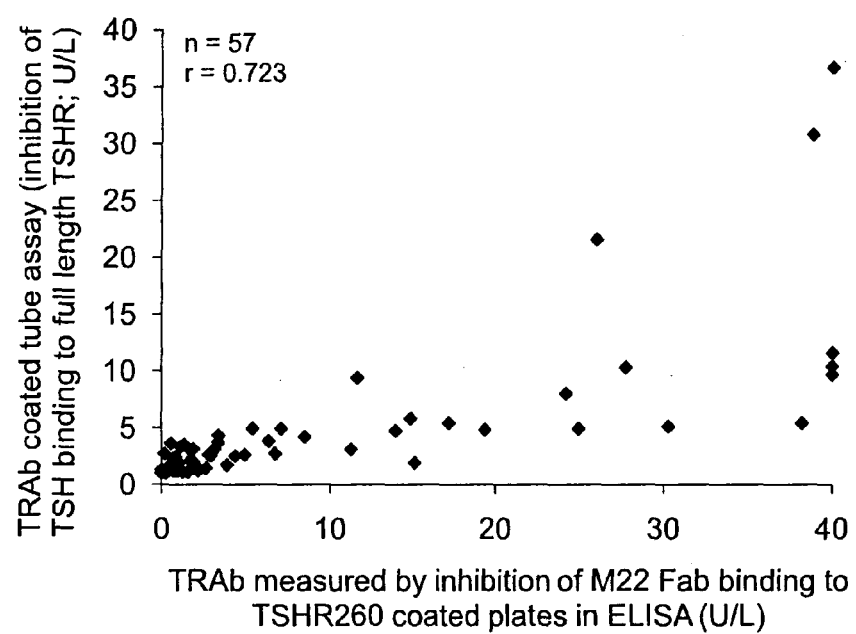

Figure 2d  Comparison of measurements of patient serum TRAbs in a TRAb ELISA (based on inhibition of M22 Fab binding to full length TSHR) and in a TSHR260-AP ELISA
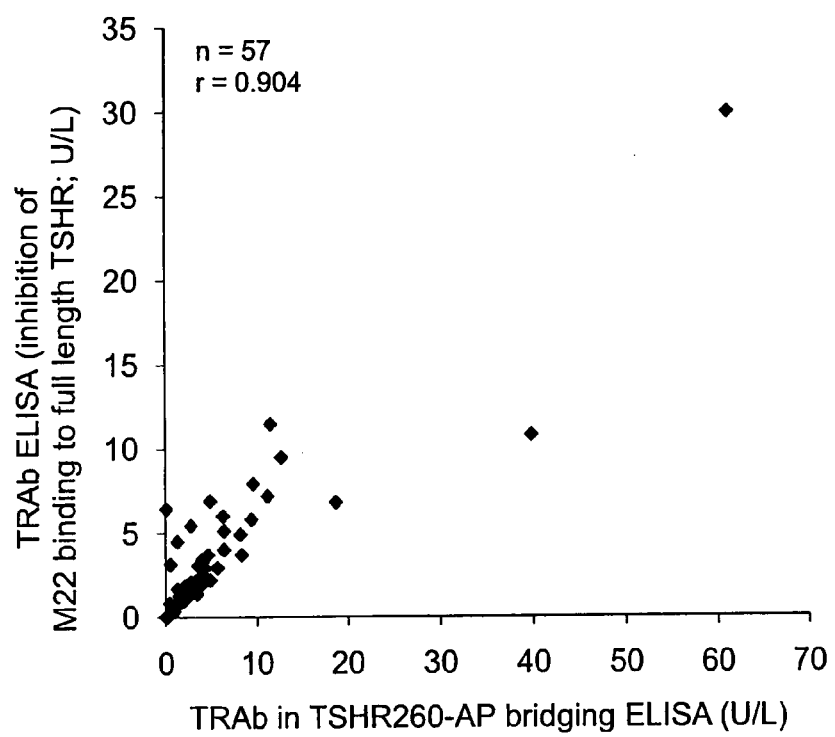

Figure 3a   K1-18 heavy chain DNA

GAAGTGCAGCTGGTGGAGTCTGGAGCAGAGGTGAAAAAGCCCGGGGAGTC

TCTGAAGATCTCCTGCAAGGGTTCTGGATACAGCTTTACCAACTACTGGA

TCGGCTGGGTGCGCCAGATGCCCGGGAAAGGCCTGGAGTGGATGGGGATC

ATCTATCCTTATGACTCTGATACCAGATATAGCCCGTCCTTCGAAGGCCA

GGTCACCATCTCAGCCGACAAGTCCATCAGGACCGCCTACCTGCACTGGA

GCAGCCTGAAGGCCTCGGACACCGCCATGTATTACTGTGTGAGACCCCGC

GATGGGAGCTATCCTTATGATGCTTTTGATATCTGGGGCCAAGGGACAAT

GGTCACCGTCTCTTCAGCCTCCACCAAGGGCCCATCGGTCTTCCCCCTGG

CACCCTCCTCCAAGAGCACCTCTGGGGGCACAGCGGCCCTGGGCTGCCTG

GTCAAGGACTACTTCCCCGAACCGGTGACGGTGTCGTGGAACTCAGGCGC

CCTGACCAGCGGCGTGCACACCTTCCCGGCTGTCCTACAGTCCTCAGGAC

TCTACTCCCTCAGCAGCGTGGTGACCGTGCCCTCCAGCAGCTTGGGCACC

CAGACCTACATCTGCAACGTGAATCACAAGCCCAGCAACACCAAGGTGGA

CAAGAGAGTTGAGCCCAAATCTTGTGACAAAACTAGT

Figure 3a – CONT.

| | |
|---|---:|
| GAAGTGCAGCTGGTGGAGTCTGGAGCAGAGGTGAAAAAGCCCGGGGAGTC<br>pcr primer | 50 |
| TCTGAAGATCTCCTGCAAGGGTTCTGGATACAGCTTTACC AACTACTGGA<br>　　　　　　　　　　　　　　　　　　　　　　　CDR I | 100 |
| TCGGC TGGGTGCGCCAGATGCCCGGGAAAGGCCTGGAGTGGATGGGG ATC<br>　　　　　　　　　　　　　　　　　　　　　　　　CDR II | 150 |
| ATCTATCCTTATGACTCTGATACCAGATATAGCCCGTCCTTCGAAGGC CA | 200 |
| GGTCACCATCTCAGCCGACAAGTCCATCAGGACCGCCTACCTGCACTGGA | 250 |
| GCAGCCTGAAGGCCTCGGACACCGCCATGTATTACTGTGTGAGA CCCCGC<br>　　　　　　　　　　　　　　　　　　　　　　　　CDR III | 300 |
| GATGGGAGCTATCCTTATGATGCTTTTGATATC TGGGGCCAAGGGACAAT | 350 |
| GGTCACCGTCTCTTCAGCCTCCACCAAGGGCCCATCGGTCTTCCCCCTGG<br>　　　　　　　　　constant region | 400 |
| CACCCTCCTCCAAGAGCACCTCTGGGGGCACAGCGGCCCTGGGCTGCCTG | 450 |
| GTCAAGGACTACTTCCCCGAACCGGTGACGGTGTCGTGGAACTCAGGCGC | 500 |
| CCTGACCAGCGGCGTGCACACCTTCCCGGCTGTCCTACAGTCCTCAGGAC | 550 |
| TCTACTCCCTCAGCAGCGTGGTGACCGTGCCCTCCAGCAGCTTGGGCACC | 600 |
| CAGACCTACATCTGCAACGTGAATCACAAGCCCAGCAACACCAAGGTGGA | 650 |
| CAAGAGAGTTGAGCCCAAATCTTGTGACAAAACTAGT<br>　　　　　　　　PCR primer | 687 |

Figure 3b K1-18 heavy chain protein

EVQLVESGAEVKKPGESLKISCKGSGYSFTNYWIGWVRQMPGKGLEWMGI

IYPYDSDTRYSPSFEGQVTISADKSIRTAYLHWSSLKASDTAMYYCVRPR

DGSYPYDAFDIWGQGTMVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKRVEPKSCDKTS

EVQLVESGAEVKKPGESLKISCKGSGYSFT NYWIG WVRQMPGKGLEWMG I          50
PCR primer                      CDR I

IYPYDSDTRYSPSFEG QVTISADKSIRTAYLHWSSLKASDTAMYYCVR PR             100
CDR II

DGSYPYDAFDI WGQGTMVTVSSASTKGPSVFPLAPSSKSTSGGTAALGCL              150
CDR III                  constant region

VKDYFPEPVTVSWNSGALTSGVHTFPAVLQSSGLYSLSSVVTVPSSSLGT               200

QTYICNVNHKPSNTKVDKRVEPKSCDKTS                                    229
                  PCR primer

Figure 3c     K1-18 heavy chain DNA

ATGGGGTCAACCGCCATCCTCGCCCTCCTCCTGGGTGTTCTCCAAGGAGTCTGTGGCGAGGTGCAGCTGGTGCAGTC

TGGAGCAGAGGTGAAAAAGCCCGGGGAGTCTCTGAAGATCTCCTGCAAGGGTTCTGGATACAGCTTTACCAACTACT

GGATCGGCTGGGTGCGCCAGATGCCCGGGAAAGGCCTGGAGTGGATGGGGATCATCTATCCTTATGACTCTGATACC

AGATATAGCCCGTCCTTCGAAGGCCAGGTCACCATCTCAGCCGACAAGTCCATCAGGACCGCCTACCTGCACTGGAG

CAGCCTGAAGGCCTCGGACACCGCCATGTATTACTGTGTGAGACCCCGCGATGGGAGCTATCCTTATGATGCTTTTG

ATATCTGGGGCCAAGGGACAATGGTCACCGTCTCTTCAGCCTCCACCAAGGGCCCATCGGTCTTCCCCCTGGCACCC

TCCTCCAAGAGCACCTCTGGGGGCACAGCGGCCCTGGGCTGCCTGGTCAAGGACTACTTCCCCGAACCGGTGACGGT

GTCGTGGAACTCAGGCGCCCTGACCAGCGGCGTGCACACCTTCCCGGCTGTCCTACAGTCCTCAGGACTCTACTCCC

TCAGCAGCGTGGTGACCGTGCCCTCCAGCAGCTTGGGCACCCAGACCTACATCTGCAACGTGAATCACAAGCCCAGC

AACACCAAGGTGGACAAGACAGTTGAGCGCAAATCT

Figure 3d  K1-18 heavy chain protein

MGSTAILALLLGVLQGVCGEVQLVQSGAEVKKPGESLKISCKGSGYSFTNYWIGWVRQMPGKGLEWMGIIYPYDSDT

RYSPSFEGQVTISADKSIRTAYLHWSSLKASDTAMYYCVRPRDGSYPYDAFDIWGQGTMVTVSSASTKGPSVFPLAP

SSKSTSGGTAALGCLVKDYFPEPVTVSWNSGALTSGVHTFPAVLQSSGLYSLSSVVTVPSSSLGTQTYICNVNHKPS

NTKVDKTVERKS

```
mgstailalllgvlqgvcgEVQLVQSGAEVKKPGESLKISCKGSGYSFTN
PCR primer   leader                                    CDR I
             sequence
```

```
YWIGWVRQMPGKGLEWMG IIYPYDSDTRYSPSFEG QVTISADKSIRTAYL
                        CDR II
```

HWSSLKASDTAMYYCVR PRDGSYPYDAFDI WGQGTMVTVSSASTKGPSVF
                  CDR III                  constant region

PLAPSSKSTSGGTAALGCLVKDYFPEPVTVSWNSGALTSGVHTFPAVLQS

SGLYSLSSVVTVPSSSLGTQTYICNVNHKPSNTKVDKTVERKS
                                         PCR primer

Figure 4a  K1-18 light chain DNA

GAAATTGTGTTGACGCAGTCTCCAGGCACCCTGTCTTTGTCTCCAGGGGA

AAGAGCCACCCTCTCCTGCAGGGCCAGTCAGAGTGTTAGCAACAACTACT

TAGCCTGGTACCAGCAGAAGCCTGGCCAGGCTCCCAGGCTCCTCATCTAT

GGTGCATCCAGCAGGGCCACTGGCATCCCAGACAGGTTCAGTGGCAGTGG

GTCTGGGACAGACTTCACTCTCACCATCAGCAGACTGGAGCCTGAAGATT

TTGCAGTGTATTACTGTCAGCATTGTGGTAGCTCACTGAGGGCGTTCGGC

CAAGGGACCAAGGTGGAAATCAAACGAACTGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAACTCTACGCCTGCGAAGTCACCCATCAG

GGCCTGAGCTCGCCCGTC

Figure 4a – CONT.

| | |
|---|---|
| <u>GAAATTGTGTTGACGCAGT</u>CTCCAGGCACCCTGTCTTTGTCTCCAGGGGA | 50 |
| PCR primer | |
| AAGAGCCACCCTCTCCTGCAGGGCCAGTCAGAGTGTTAGCAACAACTACT | 100 |
|                       CDR I | |
| TAGCCTGGTACCAGCAGAAGCCTGGCCAGGCTCCCAGGCTCCTCATCTAT | 150 |
| GGTGCATCCAGCAGGGCCACTGGCATCCCAGACAGGTTCAGTGGCAGTGG | 200 |
| CDR II | |
| GTCTGGGACAGACTTCACTCTCACCATCAGCAGACTGGAGCCTGAAGATT | 250 |
| TTGCAGTGTATTACTGTCAGCATTGTGGTAGCTCACTGAGGGCGTTCGGC | 300 |
|                 CDR III | |
| CAAGGGACCAAGGTGGAAATCAAACGAACTGTGGCTGCACCATCTGTCTT | 350 |
|                     constant region | |
| CATCTTCCCGCCATCTGATGAGCAGTTGAAATCTGGAACTGCCTCTGTTG | 400 |
| TGTGCCTGCTGAATAACTTCTATCCCAGAGAGGCCAAAGTACAGTGGAAG | 450 |
| GTGGATAACGCCCTCCAATCGGGTAACTCCCAGGAGAGTGTCACAGAGCA | 500 |
| GGACAGCAAGGACAGCACCTACAGCCTCAGCAGCACCCTGACGCTGAGCA | 550 |
| AAGCAGACTACGAGAAACACAAACTCTACGCCTGCGAAGTCACCCATCAG | 600 |
| <u>GGCCTGAGCTCGCCCGTC</u> | 618 |
| PCR primer | |

Figure 4b   K1-18 light chain protein

EIVLTQSPGTLSLSPGERATLSCRASQSVSNNYLAWYQQKPGQAPRLLIY

GASSRATGIPDRFSGSGSGTDFTLTISRLEPEDFAVYYCQHCGSSLRAFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKLYACEVTHQ

GLSSPV

EIVLTQSPGTLSLSPGERATLSC|RASQSVSNNYLA|WYQQKPGQAPRLLIY          50
PCR primer                 CDR I

|GASSRAT|GIPDRFSGSGSGTDFTLTISRLEPEDFAVYYC|QHCGSSLRA|FG          100
CDR II                                          CDR
                                                III

QGTKVEIKRTVAAPSVFIFPPSDEQLKSGTASVVCLLNNFYPREAKVQWK             150
            constant region

VDNALQSGNSQESVTEQDSKDSTYSLSSTLTLSKADYEKHKLYACEVTHQ             200

GLSSPV                                                         206
PCR primer

Figure 4c   K1-18 light chain DNA

```
ATGGAAACCCCAGCGCAGCTTCTCTTCCTCCTGCTACTCTGGCTCCCAGATACCACCGGAGAAATTGTGTTGACGCA
GTCTCCAGGCACCCTGTCTTTGTCTCCAGGGGAAAGAGCCACCCTCTCCTGCAGGGCCAGTCAGAGTGTTAGCAACA
ACTACTTAGCCTGGTACCAGCAGAAGCCTGGCCAGGCTCCCAGGCTCCTCATCTATGGTGCATCCAGCAGGGCCACT
GGCATCCCAGACAGGTTCAGTGGCAGTGGGTCTGGGACAGACTTCACTCTCACCATCAGCAGACTGGAGCCTGAAGA
TTTTGCAGTGTATTACTGTCAGCATTGTGGTAGCTCACTGAGGGCGTTCGGCCAAGGGACCAAGGTGGAAATCAAAC
GAACTGTGGCTGCACCATCTGTCTTCATCTTCCCGCCATCTGATGAGCAGTTGAAATCTGGAACTGCCTCTGTTGTG
TGCCTGCTGAATAACTTCTATCCCAGAGAGGCCAAAGTACAGTGGAAGGTGGATAACGCCCTCCAATCGGGTAACTC
CCAGGAGAGTGTCACAGAGCAGGACAGCAAGGACAGCACCTACAGCCTCAGCAGCACCCTGACGCTGAGCAAAGCAG
ACTACGAGAAACACAAACTCTACGCCTGCGAAGTCACCCATCAGGGCCTGAGCTCGCCCGTCACA
```

Figure 4c – CONT.

```
atggaaacccagcgcagcttctcttcctcctgctactctggctcccaga
PCR primer              leader sequence taccacggaGAAATTGTGTTGACGCAGTCTCCAGGCACCCTGTCTTTGT CTCCAGGGGAAAGAGCCACCCTCTCCTGCAGGGCCAGTCAGAGTGTTAGC
                                CDR I

AACAACTACTTAGCCTGGTACCAGCAGAAGCCTGGCCAGGCTCCCAGGCT

CCTCATCTATGGTGCATCCAGCAGGGCCACTGGCATCCCAGACAGGTTCA
              CDR II

GTGGCAGTGGGTCTGGGACAGACTTCACTCTCACCATCAGCAGACTGGAG

CCTGAAGATTTTGCAGTGTATTACTGTCAGCATTGTGGTAGCTCACTGAG
                              CDR III

GGCGTTCGGCCAAGGGACCAAGGTGGAAATCAAACGAACTGTGGCTGCAC
                                    constant region

CATCTGTCTTCATCTTCCCGCCATCTGATGAGCAGTTGAAATCTGGAACT

GCCTCTGTTGTGTGCCTGCTGAATAACTTCTATCCCAGAGAGGCCAAAGT

ACAGTGGAAGGTGGATAACGCCCTCCAATCGGGTAACTCCCAGGAGAGTG

TCACAGAGCAGGACAGCAAGGACAGCACCTACAGCCTCAGCAGCACCCTG

ACGCTGAGCAAAGCAGACTACGAGAAACACAAACTCTACGCCTGCGAAGT

CACCCATCAGGGCCTGAGCTCGCCCGTCACA
              PCR primer
```

Figure 4d   K1-18 light chain protein

METPAQLLFLLLLWLPDTTGEIVLTQSPGTLSLSPGERATLSCRASQSVSNNYLAWYQQKPGQAPRLLIYGASSRAT
GIPDRFSGSGSGTDFTLTISRLEPEDFAVYYCQHCGSSLRAFGQGTKVEIKRTVAAPSVFIFPPSDEQLKSGTASVV
CLLNNFYPREAKVQWKVDNALQSGNSQESVTEQDSKDSTYSLSSTLTLSKADYEKHKLYACEVTHQGLSSPVT metpaqllflllwlpdttgEIVLTQSPGTLSLSPGERATLSC|RASQSVS|
PCR primer    leader                        CDR I
              sequence

|NNYLA|WYQQKPGQAPRLLIY|GASSRAT|GIPDRFSGSGSGTDFTLTISRLE
                      CDR II

PEDFAVYYC|QHCGSSLRA|FGQGTKVEIKRTVAAPSVFIFPPSDEQLKSGT
         CDR III              constant region

ASVVCLLNNFYPREAKVQWKVDNALQSGNSQESVTEQDSKDSTYSLSSTL

TLSKADYEKHKLYACEVTHQGLSSPVT
            PCR primer

Figure 5a    K1-70 heavy chain DNA

CAGGTTCAGCTGGTGCAGTCTGGAGCAGAGGTGAAAAAGCCCGGGCAGTC

TCTGAAGATCTCCTGTAAGGCTTCTGGATACAGCTTAACCGACAACTGGA

TCGGCTGGGTGCGCCAGAAGCCCGGGAAAGGCCTGGAGTGGATGGGGATC

ATCTATCCTGGTGACTCTGACACCAGATACAGTCCGTCCTTCCAAGGCCA

GGTCACCATCTCAGCCGACAAGTCCATCAACACCGCCTACCTGCAGTGGA

GCAGCCTGAAGGCCTCGGACACCGCCATATATTACTGTGTGGGACTCGAT

TGGAACTACAACCCCCTGCGATACTGGGGCCCGGGAACCCTGGTCACCGT

CTCCTCAGCCTCCACCAAGGGCCCATCGGTCTTCCCCCTGGCACCCTCCT

CCAAGAGCACCTCTGGGGGCACAGCGGCCCTGGGCTGCCTGGTCAAGGAC

TACTTCCCCGAACCGGTGACGGTGTCGTGGAACTCAGGCGCCCTGACCAG

CGGCGTGCACACCTTCCCGGCTGTCCTACAGTCCTCAGGACTCTACTCCC

TCAGCAGCGTGGTGACCGTGCCCTCCAGCAGCTTGGGCACCCAGACCTAC

ATCTGCAACGTGAATCACAAGCCCAGCAACACCAAGGTGGACAAGAAAGT

TGAGCCCAAATCTTGTGACAAAACTAGTG

Figure 5a – CONT.

```
CAGGTTCAGCTGGTGCAGTCTGGAGCAGAGGTGAAAAAGCCCGGGCAGTC          50
PCR primer

TCTGAAGATCTCCTGTAAGGCTTCTGGATACAGCTTAACC GACAACTGGA         100
                                         CDR I

TCGGC TGGGTGCGCCAGAAGCCCGGGAAAGGCCTGGAGTGGATGGGG ATC        150
                                                 CDR
II
ATCTATCCTGGTGACTCTGACACCAGATACAGTCCGTCCTTCCAAGGC CA         200

GGTCACCATCTCAGCCGACAAGTCCATCAACACCGCCTACCTGCAGTGGA         250

GCAGCCTGAAGGCCTCGGACACCGCCATATATTACTGTGTGGGA CTCGAT        300
                                             CDR III

TGGAACTACAACCCCCTGCGATAC TGGGGCCCGGGAACCCTGGTCACCGT        350

CTCCTCAGCCTCCACCAAGGGCCCATCGGTCTTCCCCCTGGCACCCTCCT        400
              constant region
CCAAGAGCACCTCTGGGGGCACAGCGGCCCTGGGCTGCCTGGTCAAGGAC        450

TACTTCCCCGAACCGGTGACGGTGTCGTGGAACTCAGGCGCCCTGACCAG        500

CGGCGTGCACACCTTCCCGGCTGTCCTACAGTCCTCAGGACTCTACTCCC        550

TCAGCAGCGTGGTGACCGTGCCCTCCAGCAGCTTGGGCACCCAGACCTAC        600

ATCTGCAACGTGAATCACAAGCCCAGCAACACCAAGGTGGACAAGAAAGT        650

TGAGCCCAAATCTTGTGACAAAACTAGTG                             679
     PCR primer
```

Figure 5b   K1-70 heavy chain protein

QVQLVQSGAEVKKPGQSLKISCKASGYSLTDNWIGWVRQKPGKGLEWMGI

IYPGDSDTRYSPSFQGQVTISADKSINTAYLQWSSLKASDTAIYYCVGLD

WNYNPLRYWGPGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTS

| | |
|---|---|
| QVQLVQSGAEVKKPGQSLKISCKASGYSLT DNWIG WVRQKPGKGLEWMG I | 50 |
| PCR primer                    CDR I           CDR II | |
| IYPGDSDTRYSPSFQG QVTISADKSINTAYLQWSSLKASDTAIYYCVG LD | 100 |
| CDR III | |
| WNYNPLRY WGPGTLVTVSSASTKGPSVFPLAPSSKSTSGGTAALGCLVKD | 150 |
|                    constant region | |
| YFPEPVTVSWNSGALTSGVHTFPAVLQSSGLYSLSSVVTVPSSSLGTQTY | 200 |
| ICNVNHKPSNTKVDKKVEPKSCDKTS | 226 |
|                    PCR primer | |

Figure 5c      K1-70 heavy chain DNA

ATGGGGTCAACCGCCATCCTCGCCCTCCTCCTGGCTGTTCTCCAGGGAGTCTGTGCCGAGGTGCAGCTGGTGCAGTC
TGGAGCAGAGGTGAAAAAGCCCGGGCAGTCTCTGAAGATCTCCTGTAAGGCTTCTGGATACAGCTTAACCGACAACT
GGATCGGCTGGGTGCGCCAGAAGCCCGGGAAAGGCCTGGAGTGGATGGGGATCATCTATCCTGGTGACTCTGACACC
AGATACAGTCCGTCCTTCCAAGGCCAGGTCACCATCTCAGCCGACAAGTCCATCAACACCGCCTACCTGCAGTGGAG
CAGCCTGAAGGCCTCGGACACCGCCATATATTACTGTGTGGGACTCGATTGGAACTACAACCCCCTGCGATACTGGG
GCCCGGGAACCCTGGTCACCGTCTCCTCAGCCTCCACCAAGGGCCCATCGGTCTTCCCCCTGGCACCCTCCTCCAAG
AGCACCTCTGGGGGCACAGCGGCCCTGGGCTGCCTGGTCAAGGACTACTTCCCCGAACCGGTGACGGTGTCGTGGAA
CTCAGGCGCCCTGACCAGCGGCGTGCACACCTTCCCGGCTGTCCTACAGTCCTCAGGACTCTACTCCCTCAGCAGCG
TGGTGACCGTGCCCTCCAGCAGCTTGGGCACCCAGACCTACATCTGCAACGTGAATCACAAGCCCAGCAACACCAAG
GTGGACAAGACAGTTGAGCGCAAATCT

Figure 5c – CONT.

<u>atggggtcaaccgccatcctcgccctcctcctggctgttctccaggagt</u>
PCR primer              leader sequence ctgtgccGAGGTGCAGCTGGTGCAGTCTGGAGCAGAGGTGAAAAAGCCCG GGCAGTCTCTGAAGATCTCCTGTAAGGCTTCTGGATACAGCTTAACC|GAC|
                                                                      CDR I

|AACTGGATCGGC|TGGGTGCGCCAGAAGCCCGGGAAAGGCCTGGAGTGGAT

GGGG|ATCATCTATCCTGGTGACTCTGACACCAGATACAGTCCGTCCTTCC|
      CDR II

|AAGGC|CAGGTCACCATCTCAGCCGACAAGTCCATCAACACCGCCTACCTG

CAGTGGAGCAGCCTGAAGGCCTCGGACACCGCCATATATTACTGTGTGGG

A|CTCGATTGGAACTACAACCCCCTGCGATAC|TGGGGCCCGGGAACCCTGG
  CDR III

TCACCGTCTCCTCAGCCTCCACCAAGGGCCCATCGGTCTTCCCCCTGGCA
                            constant region

CCCTCCTCCAAGAGCACCTCTGGGGGCACAGCGGCCCTGGGCTGCCTGGT

CAAGGACTACTTCCCCGAACCGGTGACGGTGTCGTGGAACTCAGGCGCCC

TGACCAGCGGCGTGCACACCTTCCCGGCTGTCCTACAGTCCTCAGGACTC

TACTCCCTCAGCAGCGTGGTGACCGTGCCCTCCAGCAGCTTGGGCACCCA

GACCTACATCTGCAACGTGAATCACAAGCCCAGCAACACCAAGGTGGAC<u>A</u>

<u>AGACAGTTGAGCGCAAATCT</u>
PCR primer

Figure 5d   K1-70 heavy chain protein

MGSTAILALLLAVLQGVCAEVQLVQSGAEVKKPGQSLKISCKASGYSLTDNWIGWVRQKPGKGLEWMGIIYPGDSDT

RYSPSFQGQVTISADKSINTAYLQWSSLKASDTAIYYCVGLDWNYNPLRYWGPGTLVTVSSASTKGPSVFPLAPSSK

STSGGTAALGCLVKDYFPEPVTVSWNSGALTSGVHTFPAVLQSSGLYSLSSVVTVPSSSLGTQTYICNVNHKPSNTK

VDKTVERKS

<u>mgstailalllavlqgvca</u>EVQLVQSGAEVKKPGQSLKISCKASGYSLT|D|
PCR primer    leader                                            CDR I
              sequence

|NWIG|VRQKPGKGLEWMG|IIYPGDSDTRYSPSFQG|QVTISADKSINTAYL
                  CDR II

QWSSLKASDTAIYYCVG|LDWNYNPLRY|WGPGTLVTVSSASTKGPSVFPLA
                 CDR III                  constant region

PSSKSTSGGTAALGCLVKDYFPEPVTVSWNSGALTSGVHTFPAVLQSSGL

YSLSSVVTVPSSSLGTQTYICNVNHKPSNTKVDK<u>TVERKS</u>
                                    PCR primer

Figure 6a     K1-70 light chain DNA

CTGCCTGTGCTGACTCAGCCACCCTCAGTGTCCGTGTCCCCAGGACAGAC

AGCCAGCATCACCTGCTCTGGAGATAAATTGGGGGATAAATATGCTTGCT

GGTATCAGCAGAAGCCAGGCCAGTCCCCTGTGCTGGTCATCTATCAAGAT

AGCAAGCGGCCCTCAGGGATCCCTGAGCGATTCTCTGGCTCCAACTCTGG

GAACACAGCCACTCTGACCATCAGCGGGACCCAGGCTATGGATGAGGCTG

ACTATTACTGTCAGGCGTGGGACAGCAGCACTGCCGTGGTATTCGGCGGA

GGGACCAAGCTGACCGTCCTAGGTCAGCCCAAGGCTGCCCCCTCGGTCAC

TCTGTTCCCGCCCTCCTCTGAGGAGCTTCAAGCCAACAAGGCCACACTGG

TGTGTCTCATAAGTGACTTCTACCCGGGAGCCGTGACAGTGGCCTGGAAG

GCAGATAGCAGCCCCGTCAAGGCGGGAGTGGAGACCACCACACCCTCCAA

ACAAAGCAACAACAAGTACGCGGCCAGCAGCTATCTGAGCCTGACGCCTG

AGCAGTGGAAGTCCCACAGAAGCTACAGCTGCCAGGTCACGCATGAAGGG

AGCACCGTGGAGAAGACAGTGGCCCCTACAGAATGTTCA

Figure 6a – CONT.

| | |
|---|---|
| <u>CTGCCTGTGCTGACTCAG</u>CCACCCTCAGTGTCCGTGTCCCCAGGACAGAC<br>PCR primer | 50 |
| AGCCAGCATCACCTGC|TCTGGAGATAAATTGGGGGATAAATATGCTTGC|T<br>                   CDR I | 100 |
| GGTATCAGCAGAAGCCAGGCCAGTCCCCTGTGCTGGTCATCTAT|CAAGAT<br>                                           CDR II | 150 |
| |AGCAAGCGGCCCTCA|GGGATCCCTGAGCGATTCTCTGGCTCCAACTCTGG | 200 |
| GAACACAGCCACTCTGACCATCAGCGGGACCCAGGCTATGGATGAGGCTG | 250 |
| ACTATTACTGT|CAGGCGTGGGACAGCAGCACTGCCGTGGTA|TTCGGCGGA<br>          CDR III | 300 |
| GGGACCAAGCTGACCGTCCTAGGTCAGCCCAAGGCTGCCCCCTCGGTCAC<br>                                constant region | 350 |
| TCTGTTCCCGCCCTCCTCTGAGGAGCTTCAAGCCAACAAGGCCACACTGG | 400 |
| TGTGTCTCATAAGTGACTTCTACCCGGGAGCCGTGACAGTGGCCTGGAAG | 450 |
| GCAGATAGCAGCCCCGTCAAGGCGGGAGTGGAGACCACCACACCCTCCAA | 500 |
| ACAAAGCAACAACAAGTACGCGGCCAGCAGCTATCTGAGCCTGACGCCTG | 550 |
| AGCAGTGGAAGTCCCACAGAAGCTACAGCTGCCAGGTCACGCATGAAGGG | 600 |
| AGCACCGTGGAGAAGACAGTGGCC<u>CCTACAGAATGTTCA</u><br>                                    PCR primer | 639 |

Figure 6b   K1-70 light chain protein

LPVLTQPPSVSVSPGQTASITCSGDKLGDKYACWYQQKPGQSPVLVIYQD

SKRPSGIPERFSGSNSGNTATLTISGTQAMDEADYYCQAWDSSTAVVFGG

GTKLTVLGQPKAAPSVTLFPPSSEELQANKATLVCLISDFYPGAVTVAWK

ADSSPVKAGVETTTPSKQSNNKYAASSYLSLTPEQWKSHRSYSCQVTHEG

STVEKTVAPTECS

| | |
|---|---|
| LPVLTQPPSVSVSPGQTASITC SGDKLGDKYAC WYQQKPGQSPVLVIY QD | 50 |
| PCR primer                CDR I | |
|     CDR II | |
| SKRPS GIPERFSGSNSGNTATLTISGTQAMDEADYYC QAWDSSTAVV FGG | 100 |
|                                         CDR III | |
| GTKLTVLGQPKAAPSVTLFPPSSEELQANKATLVCLISDFYPGAVTVAWK | 150 |
|         constant region | |
| ADSSPVKAGVETTTPSKQSNNKYAASSYLSLTPEQWKSHRSYSCQVTHEG | 200 |
| STVEKTVAPTECS | 213 |
|         PCR primer | |

Figure 6c  K1-70 light chain DNA (preferred)

ATGGCCTGGTCTCCTCTCCTCCTCACCCTTCTCATTCACTGCACAGGGTCCTGGGCCCAGTCTGTGTTGACGCAGCC
GCCCTCAGTGTCTGCGGCCCCAGGACAGAAGGTCACCATTTCCTGCTCCGGAAGCAGCTCCGACATTGGGAGTAATT
ATGTATCCTGGTACCAGCAGTTCCCGGGAACAGCCCCCAAACTCCTCATTTATGACAATAATAAGCGACCCTCAGCG
ATTCCTGACCGATTCTCTGGCTCCAAGTCTGGCACGTCAGCCACCCTGGGCATCACCGGACTCCAGACTGGGGACGA
GGCCGATTATTACTGCGGAACATGGGATAGCAGACTGGGTATTGCTGTGTTCGGAGGAGGCACCCAGCTGACCGTCC
TCGGTCAGCCCAAGGCTGCCCCATCGGTCACTCTGTTCCCACCCTCCTCTGAGGAGCTTCAAGCCAACAAGGCCACA
CTGGTGTGTCTCGTAAGTGACTTCTACCCGGGAGCCGTGACAGTGGCCTGGAAGGCAGATGGCAGCCCCGTCAAGGT
GGGAGTGGAGACCACCAAACCCTCCAAACAAAGCAACAACAAGTATGCGGCCAGCAGCTACCTGAGCCTGACGCCCG
AGCAGTGGAAGTCCCACAGAAGCTACAGCTGCCGGGTCACGCATGAAGGGAGCACCGTGGAGAAGACAGTGGCCCCT
ACAGAATGTTCA

Figure 6c – CONT.

atggctggtctctctctcctcaccttctcattcactgcacagggtc
PCR primer          leader sequence ctgggccAGTCTGTGTTGACGCAGCCGCCCTCAGTGTCTGCGGCCCCAG

GACAGAAGGTCACCATTTCCTGCTCCGGAAGCAGCTCCGACATTGGGAGT
                        CDR I

AATTATGTATCCTGGTACCAGCAGTTCCCGGGAACAGCCCCCAAACTCCT

CATTTATGACAATAATAAGCGACCCTCAGCGATTCCTGACCGATTCTCTG
        CDR II

GCTCCAAGTCTGGCACGTCAGCCACCCTGGGCATCACCGGACTCCAGACT

GGGGACGAGGCCGATTATTACTGCGGAACATGGGATAGCAGACTGGGTAT
                        CDR III

TGCTGTGTTCGGAGGAGGCACCCAGCTGACCGTCCTCGGTCAGCCCAAGG
                                            constant region

CTGCCCCATCGGTCACTCTGTTCCCACCCTCCTCTGAGGAGCTTCAAGCC

AACAAGGCCACACTGGTGTGTCTCGTAAGTGACTTCTACCCGGGAGCCGT

GACAGTGGCCTGGAAGGCAGATGGCAGCCCCGTCAAGGTGGGAGTGGAGA

CCACCAAACCCTCCAAACAAAGCAACAACAAGTATGCGGCCAGCAGCTAC

CTGAGCCTGACGCCCGAGCAGTGGAAGTCCCACAGAAGCTACAGCTGCCG

GGTCACGCATGAAGGGAGCACCGTGGAGAAGACAGTGGCCCCTACAGAAT
                                          PCR primer

GTTCA

Figure 6d    K1-70 light chain protein (preferred)

MAWSPLLLTLLIHCTGSWAQSVLTQPPSVSAAPGQKVTISCSGSSSDIGSNYVSWYQQFPGTAPKLLIYDNNKRPSA

IPDRFSGSKSGTSATLGITGLQTGDEADYYCGTWDSRLGIAVFGGGTQLTVLGQPKAAPSVTLFPPSSEELQANKAT

LVCLVSDFYPGAVTVAWKADGSPVKVGVETTKPSKQSNNKYAASSYLSLTPEQWKSHRSYSCRVTHEGSTVEKTVAP

TECS

```
mawsplllrllihctgswaQSVLTQPPSVSAAPGQKVTISC SGSSSDIGS
PCR primer    leader                              CDR I
              sequence
```

```
NYVS WYQQFPGTAPKLLIY DNNKRPS AIPDRFSGSKSGTSATLGITGLQT
                        CDR II
```

```
GDEADYYC GTWDSRLGIAV FGGGTQLTVLGQPKAAPSVTLFPPSSEELQA
         CDR III                constant region
```

NKATLVCLVSDFYPGAVTVAWKADGSPVKVGVETTKPSKQSNNKYAASSY

LSLTPEQWKSHRSYSCRVTHEGSTVEKTVAPTECS
                                PCR primer

Figure 6e    K1-70 light chain N-terminal sequence (amino acids 2-21; the first N-terminal amino acid was removed by treatment with pyroglutamate aminopeptidase to enable the Edman reaction)

```
SVLTQPPSVSAAPGQKVTIS
```

Figure 7a    The consensus amino acid sequence of the human TSHR (accession no.P16473, http://www.ncbi.nlm.nih.gov/entrez/viewer.fcgi?db=protein&val=62298994). The leader sequence (amino acids 1-21) is shown in lowercase.

| | | | | | |
|---|---|---|---|---|---|
| mrpadllqlv | llldlprdlg | gMGCSSPPCE | CHQEEDFRVT | CKDIQRIPSL | PPSTQTLKLI |
| ETHLRTIPSH | AFSNLPNISR | IYVSIDVTLQ | QLESHSFYNL | SKVTHIEIRN | TRNLTYIDPD |
| ALKELPLLKF | LGIFNTGLKM | FPDLTKVYST | DIFFILEITD | NPYMTSIPVN | AFQGLCNETL |
| TLKLYNNGFT | SVQGYAFNGT | KLDAVYLNKN | KYLTVIDKDA | FGGVYSGPSL | LDVSQTSVTA |
| LPSKGLEHLK | ELIARNTWTL | KKLPLSLSFL | HLTRADLSYP | SHCCAFKNQK | KIRGILESLM |
| CNESSMQSLR | QRKSVNALNS | PLHQEYEENL | GDSIVGYKEK | SKFQDTHNNA | HYYVFFEEQE |
| DEIIGFGQEL | KNPQEETLQA | FDSHYDYTIC | GDSEDMVCTP | KSDEFNPCED | IMGYKFLRIV |
| VWFVSLLALL | GNVFVLLILL | TSHYKLNVPR | FLMCNLAFAD | FCMGMYLLLI | ASVDLYTHSE |
| YYNHAIDWQT | GPGCNTAGFF | TVFASELSVY | TLTVITLERW | YAITFAMRLD | RKIRLRHACA |
| IMVGGWVCCF | LLALLPLVGI | SSYAKVSICL | PMDTETPLAL | AYIVFVLTLN | IVAFVIVCCC |
| YVKIYITVRN | PQYNPGDKDT | KIAKRMAVLI | FTDFICMAPI | SFYALSAILN | KPLITVSNSK |
| ILLVLFYPLN | SCANPFLYAI | FTKAFQRDVF | ILLSKFGICK | RQAQAYRGQR | VPPKNSTDIQ |
| VQKVTHDMRQ | GLHNMEDVYE | LIENSHLTPK | KQGQISEEYM | QTVL | |

Figure 7b The consensus amino acid sequence of the human TSHR (amino acids 1-260 including the leader sequence (amino acids 1-21) shown in lowercase). A 6 histidine sequence added at the C-terminus (following asparagines at position 260) is shown in bold

```
mrpadllqlv  llldlprdlg  gMGCSSPPCE  CHQEEDFRVT  CKDIQRIPSL  PPSTQTLKLI

ETHLRTIPSH  AFSNLPNISR  IYVSIDVTLQ  QLESHSFYNL  SKVTHIEIRN  TRNLTYIDPD

ALKELPLLKF  LGIFNTGLKM  FPDLTKVYST  DIFFILEITD  NPYMTSIPVN  AFQGLCNETL

TLKLYNNGFT  SVQGYAFNGT  KLDAVYLNKN  KYLTVIDKDA  FGGVYSGPSL  LDVSQTSVTA

LPSKGLEHLK  ELIARNTWTL  NHHHHHH
```

Figure 7c  The amino acid sequence of the humanTSHR LRD C-CAP with C-terminal 6 histidine tag. The leader sequence (amino acids 1-21) are shown in lowercase

```
mrpadllqlv  llldlprdlg  gMGCSSPPCE  CHQEEDFRVT  CKDIQRIPSL  PPSTQTLKLI
ETHLRTIPSH  AFSNLPNISR  IYVSIDVTLQ  QLESHSFYNL  SKVTHIEIRN  TRNLTYIDPD
ALKELPLLKF  LGIFNTGLKM  FPDLTKVYST  DIFFILEITD  NPYMTSIPVN  AFQGLCNETL
TLKLYNNGFT  SVQGYAFNGT  KLDAVYLNKN  KYLTVIDKDA  FGGVYSGPSL  LDVSQTSVTA
LPSKGLEHLK  ELIARNTWTL  KKLPLSLSFL  HLTRADLSYP  SHCCAFKNQK  KIRGILESLM
CNESSYDYTI  CGDSEDMVCT  PKSDEFNPCE  HHHHHH
```

Figure 8　　Coordinates of K1-70 Fab

```
HEADER     ----                                      XX-XXX-9-    xxxx
COMPND     ---
REMARK   3
REMARK   3 REFINEMENT.
REMARK   3   PROGRAM     : REFMAC 5.5.0072
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :   2.22
REMARK   3   RESOLUTION RANGE LOW  (ANGSTROMS) :  44.86
REMARK   3   DATA CUTOFF            (SIGMA(F)) : NONE
REMARK   3   COMPLETENESS FOR RANGE        (%) :  97.66
REMARK   3   NUMBER OF REFLECTIONS             :  51482
REMARK   3
REMARK   3  FIT TO DATA USED IN REFINEMENT.
REMARK   3   CROSS-VALIDATION METHOD          : THROUGHOUT
REMARK   3   FREE R VALUE TEST SET SELECTION  : RANDOM
REMARK   3   R VALUE     (WORKING + TEST SET) : 0.21907
REMARK   3   R VALUE            (WORKING SET) : 0.21667
REMARK   3   FREE R VALUE                     : 0.26396
REMARK   3   FREE R VALUE TEST SET SIZE   (%) : 5.1
REMARK   3   FREE R VALUE TEST SET COUNT      : 2775
REMARK   3
REMARK   3  FIT IN THE HIGHEST RESOLUTION BIN.
REMARK   3   TOTAL NUMBER OF BINS USED           :     20
REMARK   3   BIN RESOLUTION RANGE HIGH           :  2.220
REMARK   3   BIN RESOLUTION RANGE LOW            :  2.278
REMARK   3   REFLECTION IN BIN     (WORKING SET) :   3724
REMARK   3   BIN COMPLETENESS (WORKING+TEST) (%) :  96.83
REMARK   3   BIN R VALUE           (WORKING SET) :  0.307
REMARK   3   BIN FREE R VALUE SET COUNT          :    217
REMARK   3   BIN FREE R VALUE                    :  0.378
REMARK   3
REMARK   3  NUMBER OF NON-HYDROGEN ATOMS USED IN REFINEMENT.
REMARK   3   ALL ATOMS               :       6699
REMARK   3
REMARK   3  B VALUES.
REMARK   3   FROM WILSON PLOT           (A**2) : NULL
REMARK   3   MEAN B VALUE      (OVERALL, A**2) : 32.714
REMARK   3   OVERALL ANISOTROPIC B VALUE.
REMARK   3    B11 (A**2) :    -1.25
REMARK   3    B22 (A**2) :     2.71
REMARK   3    B33 (A**2) :    -1.25
REMARK   3    B12 (A**2) :     0.00
REMARK   3    B13 (A**2) :     0.75
REMARK   3    B23 (A**2) :     0.00
REMARK   3
REMARK   3  ESTIMATED OVERALL COORDINATE ERROR.
REMARK   3   ESU BASED ON R VALUE                            (A):   0.257
REMARK   3   ESU BASED ON FREE R VALUE                       (A):   0.217
REMARK   3   ESU BASED ON MAXIMUM LIKELIHOOD                 (A):   0.158
REMARK   3   ESU FOR B VALUES BASED ON MAXIMUM LIKELIHOOD (A**2):   6.315
REMARK   3
REMARK   3 CORRELATION COEFFICIENTS.
REMARK   3   CORRELATION COEFFICIENT FO-FC      :  0.949
REMARK   3   CORRELATION COEFFICIENT FO-FC FREE :  0.927
REMARK   3
```

Figure 8 – CONT.

```
REMARK   3   RMS DEVIATIONS FROM IDEAL VALUES          COUNT    RMS     WEIGHT
REMARK   3    BOND LENGTHS REFINED ATOMS        (A):    6514 ; 0.014 ; 0.022
REMARK   3    BOND LENGTHS OTHERS               (A):    4237 ; 0.001 ; 0.020
REMARK   3    BOND ANGLES REFINED ATOMS   (DEGREES):    8927 ; 1.488 ; 1.955
REMARK   3    BOND ANGLES OTHERS          (DEGREES):   10432 ; 0.888 ; 3.003
REMARK   3    TORSION ANGLES, PERIOD 1    (DEGREES):     857 ; 6.849 ; 5.000
REMARK   3    TORSION ANGLES, PERIOD 2    (DEGREES):     216 ;36.386 ;24.861
REMARK   3    TORSION ANGLES, PERIOD 3    (DEGREES):     951 ;16.906 ;15.000
REMARK   3    TORSION ANGLES, PERIOD 4    (DEGREES):      11 ;18.673 ;15.000
REMARK   3    CHIRAL-CENTER RESTRAINTS       (A**3):    1017 ; 0.087 ; 0.200
REMARK   3    GENERAL PLANES REFINED ATOMS      (A):    7293 ; 0.007 ; 0.021
REMARK   3    GENERAL PLANES OTHERS             (A):    1216 ; 0.001 ; 0.020
REMARK   3
REMARK   3   ISOTROPIC THERMAL FACTOR RESTRAINTS.     COUNT    RMS     WEIGHT
REMARK   3    MAIN-CHAIN BOND REFINED ATOMS  (A**2):    4278 ; 0.743 ; 1.500
REMARK   3    MAIN-CHAIN BOND OTHER ATOMS    (A**2):    1731 ; 0.144 ; 1.500
REMARK   3    MAIN-CHAIN ANGLE REFINED ATOMS (A**2):    6916 ; 1.379 ; 2.000
REMARK   3    SIDE-CHAIN BOND REFINED ATOMS  (A**2):    2236 ; 1.903 ; 3.000
REMARK   3    SIDE-CHAIN ANGLE REFINED ATOMS (A**2):    2010 ; 3.036 ; 4.500
REMARK   3
REMARK   3  NCS RESTRAINTS STATISTICS
REMARK   3   NUMBER OF NCS GROUPS : NULL
REMARK   3
REMARK   3  TWIN DETAILS
REMARK   3   NUMBER OF TWIN DOMAINS  : NULL
REMARK   3
REMARK   3
REMARK   3  TLS DETAILS
REMARK   3   NUMBER OF TLS GROUPS  : NULL
REMARK   3
REMARK   3
REMARK   3  BULK SOLVENT MODELLING.
REMARK   3   METHOD USED :  MASK
REMARK   3   PARAMETERS FOR MASK CALCULATION
REMARK   3   VDW PROBE RADIUS    :   1.40
REMARK   3   ION PROBE RADIUS    :   0.80
REMARK   3   SHRINKAGE RADIUS    :   0.80
REMARK   3
REMARK   3  OTHER REFINEMENT REMARKS:
REMARK   3  HYDROGENS HAVE BEEN ADDED IN THE RIDING POSITIONS
REMARK   3  U VALUES      : REFINED INDIVIDUALLY
REMARK   3
REMARK   [No title given]
SSBOND   1 CYS A    22     CYS A    92
SSBOND   2 CYS A   142     CYS A   208
SSBOND   3 CYS C    22     CYS C    92
SSBOND   4 CYS C   142     CYS C   208
SSBOND   5 CYS B    23     CYS B    88
SSBOND   6 CYS B   134     CYS B   194
SSBOND   7 CYS D    23     CYS D    88
SSBOND   8 CYS D   134     CYS D   194
CISPEP   1 PHE A   148     PRO A   149                    0.00
CISPEP   2 GLU A   150     PRO A   151                    0.00
CISPEP   3 TYR B   140     PRO B   141                    0.00
CISPEP   4 PHE C   148     PRO C   149                    0.00
CISPEP   5 GLU C   150     PRO C   151                    0.00
CISPEP   6 TYR D   140     PRO D   141                    0.00
CRYST1   70.180   62.140  131.030  90.00  98.29  90.00 P 1 21 1
```

Figure 8 – CONT.

```
SCALE1        0.014249  0.000000  0.002076      0.00000
SCALE2        0.000000  0.016093  0.000000      0.00000
SCALE3        0.000000  0.000000  0.007712      0.00000
ATOM      1   N    GLN A   1      38.061   -3.592   66.895  1.00 41.03      A  N
ATOM      2   CA   GLN A   1      36.758   -3.846   67.593  1.00 39.95      A  C
ATOM      4   CB   GLN A   1      36.944   -4.668   68.859  1.00 40.33      A  C
ATOM     11   C    GLN A   1      36.080   -2.516   67.908  1.00 39.20      A  C
ATOM     12   O    GLN A   1      34.930   -2.338   67.534  1.00 39.71      A  O
ATOM     16   N    VAL A   2      36.777   -1.598   68.586  1.00 38.20      A  N
ATOM     17   CA   VAL A   2      36.258   -0.226   68.806  1.00 37.19      A  C
ATOM     19   CB   VAL A   2      36.917    0.479   70.008  1.00 37.15      A  C
ATOM     21   CG1  VAL A   2      36.330    1.908   70.212  1.00 34.81      A  C
ATOM     25   CG2  VAL A   2      36.773   -0.372   71.272  1.00 36.30      A  C
ATOM     29   C    VAL A   2      36.483    0.662   67.575  1.00 37.15      A  C
ATOM     30   O    VAL A   2      37.612    0.841   67.128  1.00 37.22      A  O
ATOM     32   N    GLN A   3      35.404    1.211   67.031  1.00 36.48      A  N
ATOM     33   CA   GLN A   3      35.485    2.095   65.887  1.00 36.23      A  C
ATOM     35   CB   GLN A   3      35.074    1.355   64.601  1.00 36.36      A  C
ATOM     38   CG   GLN A   3      35.996    1.588   63.378  1.00 41.25      A  C
ATOM     41   CD   GLN A   3      35.251    1.585   62.005  1.00 45.22      A  C
ATOM     42   OE1  GLN A   3      35.582    2.372   61.100  1.00 45.42      A  O
ATOM     43   NE2  GLN A   3      34.243    0.714   61.863  1.00 46.72      A  N
ATOM     46   C    GLN A   3      34.537    3.266   66.148  1.00 34.98      A  C
ATOM     47   O    GLN A   3      33.350    3.051   66.434  1.00 34.03      A  O
ATOM     49   N    LEU A   4      35.060    4.485   66.068  1.00 33.47      A  N
ATOM     50   CA   LEU A   4      34.230    5.674   66.077  1.00 32.90      A  C
ATOM     52   CB   LEU A   4      34.876    6.789   66.887  1.00 32.86      A  C
ATOM     55   CG   LEU A   4      34.993    6.528   68.385  1.00 33.36      A  C
ATOM     57   CD1  LEU A   4      35.732    7.660   69.092  1.00 32.38      A  C
ATOM     61   CD2  LEU A   4      33.607    6.282   69.018  1.00 32.62      A  C
ATOM     65   C    LEU A   4      34.035    6.115   64.631  1.00 32.85      A  C
ATOM     66   O    LEU A   4      35.002    6.357   63.918  1.00 34.56      A  O
ATOM     68   N    VAL A   5      32.785    6.198   64.211  1.00 32.01      A  N
ATOM     69   CA   VAL A   5      32.393    6.423   62.855  1.00 31.72      A  C
ATOM     71   CB   VAL A   5      31.324    5.386   62.500  1.00 32.43      A  C
ATOM     73   CG1  VAL A   5      30.791    5.589   61.074  1.00 32.92      A  C
ATOM     77   CG2  VAL A   5      31.879    3.968   62.721  1.00 33.09      A  C
ATOM     81   C    VAL A   5      31.775    7.807   62.728  1.00 30.89      A  C
ATOM     82   O    VAL A   5      30.715    8.061   63.283  1.00 31.93      A  O
ATOM     84   N    GLN A   6      32.437    8.713   62.027  1.00 29.82      A  N
ATOM     85   CA   GLN A   6      31.972   10.097   61.912  1.00 28.45      A  C
ATOM     87   CB   GLN A   6      33.130   11.087   62.064  1.00 27.80      A  C
ATOM     90   CG   GLN A   6      33.716   11.042   63.462  1.00 26.92      A  C
ATOM     93   CD   GLN A   6      34.628   12.206   63.821  1.00 25.67      A  C
ATOM     94   OE1  GLN A   6      35.734   11.990   64.257  1.00 27.99      A  O
ATOM     95   NE2  GLN A   6      34.129   13.421   63.738  1.00 24.61      A  N
ATOM     98   C    GLN A   6      31.248   10.323   60.618  1.00 28.45      A  C
ATOM     99   O    GLN A   6      31.564    9.709   59.611  1.00 29.25      A  O
ATOM    101   N    SER A   7      30.288   11.237   60.637  1.00 28.18      A  N
ATOM    102   CA   SER A   7      29.512   11.565   59.456  1.00 27.75      A  C
ATOM    104   CB   SER A   7      28.270   12.395   59.846  1.00 28.05      A  C
ATOM    107   OG   SER A   7      28.647   13.553   60.597  1.00 29.10      A  O
ATOM    109   C    SER A   7      30.383   12.312   58.465  1.00 26.46      A  C
ATOM    110   O    SER A   7      31.472   12.766   58.795  1.00 26.06      A  O
ATOM    112   N    GLY A   8      29.911   12.420   57.235  1.00 26.33      A  N
ATOM    113   CA   GLY A   8      30.765   12.828   56.151  1.00 25.91      A  C
ATOM    116   C    GLY A   8      31.005   14.328   56.130  1.00 26.32      A  C
ATOM    117   O    GLY A   8      30.308   15.105   56.806  1.00 26.37      A  O
```

Figure 8 – CONT.

```
ATOM    119  N    ALA A    9      31.958  14.731  55.303  1.00 26.31      A    N
ATOM    120  CA   ALA A    9      32.346  16.144  55.150  1.00 26.77      A    C
ATOM    122  CB   ALA A    9      33.390  16.307  54.042  1.00 25.41      A    C
ATOM    126  C    ALA A    9      31.139  16.989  54.852  1.00 26.28      A    C
ATOM    127  O    ALA A    9      30.180  16.527  54.275  1.00 28.00      A    O
ATOM    129  N    GLU A   10      31.196  18.249  55.238  1.00 26.25      A    N
ATOM    130  CA   GLU A   10      30.062  19.110  55.111  1.00 25.55      A    C
ATOM    132  CB   GLU A   10      29.462  19.384  56.511  1.00 26.10      A    C
ATOM    135  CG   GLU A   10      28.805  18.148  57.192  1.00 27.86      A    C
ATOM    138  CD   GLU A   10      27.379  17.933  56.784  1.00 29.00      A    C
ATOM    139  OE1  GLU A   10      26.859  18.679  55.926  1.00 29.68      A    O
ATOM    140  OE2  GLU A   10      26.770  17.025  57.356  1.00 30.45      A    O
ATOM    141  C    GLU A   10      30.502  20.423  54.537  1.00 24.06      A    C
ATOM    142  O    GLU A   10      31.543  20.947  54.918  1.00 23.45      A    O
ATOM    144  N    VAL A   11      29.671  21.004  53.696  1.00 23.28      A    N
ATOM    145  CA   VAL A   11      30.011  22.300  53.111  1.00 23.88      A    C
ATOM    147  CB   VAL A   11      30.266  22.203  51.620  1.00 24.18      A    C
ATOM    149  CG1  VAL A   11      30.668  23.620  51.067  1.00 21.94      A    C
ATOM    153  CG2  VAL A   11      31.342  21.101  51.361  1.00 21.31      A    C
ATOM    157  C    VAL A   11      28.834  23.190  53.303  1.00 24.69      A    C
ATOM    158  O    VAL A   11      27.768  22.863  52.854  1.00 25.13      A    O
ATOM    160  N    LYS A   12      29.029  24.310  53.986  1.00 25.04      A    N
ATOM    161  CA   LYS A   12      27.914  25.103  54.459  1.00 26.04      A    C
ATOM    163  CB   LYS A   12      27.657  24.807  55.959  1.00 26.27      A    C
ATOM    166  CG   LYS A   12      27.128  23.391  56.246  1.00 28.22      A    C
ATOM    169  CD   LYS A   12      25.686  23.341  55.916  1.00 31.62      A    C
ATOM    172  CE   LYS A   12      25.064  22.070  56.293  1.00 33.33      A    C
ATOM    175  NZ   LYS A   12      23.648  22.167  56.008  1.00 33.77      A    N
ATOM    179  C    LYS A   12      28.197  26.577  54.277  1.00 26.04      A    C
ATOM    180  O    LYS A   12      29.335  26.991  54.144  1.00 25.17      A    O
ATOM    182  N    LYS A   13      27.131  27.357  54.265  1.00 27.42      A    N
ATOM    183  CA   LYS A   13      27.239  28.813  54.251  1.00 28.77      A    C
ATOM    185  CB   LYS A   13      26.158  29.390  53.367  1.00 30.06      A    C
ATOM    188  CG   LYS A   13      26.400  29.072  51.905  1.00 32.35      A    C
ATOM    191  CD   LYS A   13      25.417  29.806  51.032  1.00 36.42      A    C
ATOM    194  CE   LYS A   13      25.374  29.252  49.594  1.00 39.04      A    C
ATOM    197  NZ   LYS A   13      24.008  28.736  49.231  1.00 41.62      A    N
ATOM    201  C    LYS A   13      27.094  29.348  55.663  1.00 28.55      A    C
ATOM    202  O    LYS A   13      26.458  28.702  56.505  1.00 27.17      A    O
ATOM    204  N    PRO A   14      27.674  30.532  55.925  1.00 28.34      A    N
ATOM    205  CA   PRO A   14      27.589  31.129  57.258  1.00 27.11      A    C
ATOM    207  CB   PRO A   14      28.312  32.468  57.099  1.00 27.85      A    C
ATOM    210  CG   PRO A   14      29.224  32.251  55.877  1.00 28.50      A    C
ATOM    213  CD   PRO A   14      28.338  31.443  54.965  1.00 28.38      A    C
ATOM    216  C    PRO A   14      26.134  31.344  57.598  1.00 26.49      A    C
ATOM    217  O    PRO A   14      25.347  31.635  56.718  1.00 23.98      A    O
ATOM    218  N    GLY A   15      25.775  31.118  58.862  1.00 26.74      A    N
ATOM    219  CA   GLY A   15      24.390  31.237  59.286  1.00 27.03      A    C
ATOM    222  C    GLY A   15      23.597  29.961  59.262  1.00 28.01      A    C
ATOM    223  O    GLY A   15      22.561  29.844  59.945  1.00 28.00      A    O
ATOM    225  N    GLN A   16      24.071  28.974  58.513  1.00 27.70      A    N
ATOM    226  CA   GLN A   16      23.319  27.750  58.431  1.00 28.22      A    C
ATOM    228  CB   GLN A   16      23.713  26.915  57.207  1.00 28.21      A    C
ATOM    231  CG   GLN A   16      23.205  27.536  55.895  1.00 28.83      A    C
ATOM    234  CD   GLN A   16      23.486  26.658  54.713  1.00 30.43      A    C
ATOM    235  OE1  GLN A   16      24.624  26.277  54.482  1.00 30.66      A    O
ATOM    236  NE2  GLN A   16      22.438  26.278  53.992  1.00 32.45      A    N
ATOM    239  C    GLN A   16      23.545  26.991  59.694  1.00 28.82      A    C
```

Figure 8 – CONT.

```
ATOM    240  O    GLN A  16      24.550  27.173  60.369  1.00 29.45      A  O
ATOM    242  N    SER A  17      22.580  26.152  60.013  1.00 29.04      A  N
ATOM    243  CA   SER A  17      22.699  25.186  61.087  1.00 29.86      A  C
ATOM    245  CB   SER A  17      21.297  24.786  61.568  1.00 29.97      A  C
ATOM    248  OG   SER A  17      20.911  25.749  62.516  1.00 34.60      A  O
ATOM    250  C    SER A  17      23.406  23.914  60.641  1.00 28.94      A  C
ATOM    251  O    SER A  17      23.327  23.516  59.462  1.00 28.78      A  O
ATOM    253  N    LEU A  18      24.038  23.248  61.597  1.00 28.07      A  N
ATOM    254  CA   LEU A  18      24.675  21.975  61.334  1.00 27.68      A  C
ATOM    256  CB   LEU A  18      26.114  22.167  60.811  1.00 27.02      A  C
ATOM    259  CG   LEU A  18      26.868  20.868  60.410  1.00 25.74      A  C
ATOM    261  CD1  LEU A  18      26.153  20.012  59.309  1.00 25.00      A  C
ATOM    265  CD2  LEU A  18      28.241  21.191  59.919  1.00 25.43      A  C
ATOM    269  C    LEU A  18      24.745  21.104  62.567  1.00 27.62      A  C
ATOM    270  O    LEU A  18      25.151  21.557  63.602  1.00 26.27      A  O
ATOM    272  N    LYS A  19      24.460  19.820  62.381  1.00 28.08      A  N
ATOM    273  CA   LYS A  19      24.627  18.821  63.396  1.00 28.78      A  C
ATOM    275  CB   LYS A  19      23.239  18.294  63.775  1.00 29.10      A  C
ATOM    278  CG   LYS A  19      23.204  17.335  64.935  1.00 31.63      A  C
ATOM    281  CD   LYS A  19      21.732  17.030  65.332  1.00 33.60      A  C
ATOM    284  CE   LYS A  19      21.623  16.747  66.827  1.00 34.80      A  C
ATOM    287  NZ   LYS A  19      20.219  16.487  67.341  1.00 32.71      A  N
ATOM    291  C    LYS A  19      25.470  17.700  62.807  1.00 28.19      A  C
ATOM    292  O    LYS A  19      25.046  17.062  61.850  1.00 28.77      A  O
ATOM    294  N    ILE A  20      26.643  17.450  63.356  1.00 27.75      A  N
ATOM    295  CA   ILE A  20      27.430  16.303  62.914  1.00 28.12      A  C
ATOM    297  CB   ILE A  20      28.859  16.705  62.450  1.00 27.37      A  C
ATOM    299  CG1  ILE A  20      29.725  17.116  63.618  1.00 28.36      A  C
ATOM    302  CD1  ILE A  20      31.137  17.549  63.210  1.00 28.24      A  C
ATOM    306  CG2  ILE A  20      28.757  17.817  61.410  1.00 27.20      A  C
ATOM    310  C    ILE A  20      27.470  15.211  63.984  1.00 28.35      A  C
ATOM    311  O    ILE A  20      27.205  15.458  65.178  1.00 28.28      A  O
ATOM    313  N    SER A  21      27.798  14.003  63.564  1.00 29.14      A  N
ATOM    314  CA   SER A  21      27.590  12.854  64.429  1.00 30.25      A  C
ATOM    316  CB   SER A  21      26.418  12.018  63.911  1.00 30.68      A  C
ATOM    319  OG   SER A  21      26.754  11.341  62.711  1.00 31.84      A  O
ATOM    321  C    SER A  21      28.777  11.976  64.564  1.00 30.78      A  C
ATOM    322  O    SER A  21      29.643  11.887  63.667  1.00 31.08      A  O
ATOM    324  N    CYS A  22      28.786  11.276  65.682  1.00 30.73      A  N
ATOM    325  CA   CYS A  22      29.808  10.317  65.975  1.00 31.75      A  C
ATOM    327  CB   CYS A  22      30.803  10.920  66.912  1.00 31.48      A  C
ATOM    330  SG   CYS A  22      31.894   9.691  67.511  1.00 33.53      A  S
ATOM    332  C    CYS A  22      29.202   9.061  66.624  1.00 33.03      A  C
ATOM    333  O    CYS A  22      28.734   9.112  67.762  1.00 32.76      A  O
ATOM    335  N    LYS A  23      29.237   7.947  65.900  1.00 33.70      A  N
ATOM    336  CA   LYS A  23      28.571   6.716  66.288  1.00 34.58      A  C
ATOM    338  CB   LYS A  23      27.655   6.289  65.126  1.00 35.41      A  C
ATOM    341  CG   LYS A  23      26.748   5.082  65.354  1.00 38.61      A  C
ATOM    344  CD   LYS A  23      26.202   4.638  64.029  1.00 44.88      A  C
ATOM    347  CE   LYS A  23      25.278   3.428  64.110  1.00 48.06      A  C
ATOM    350  NZ   LYS A  23      25.501   2.443  62.966  1.00 50.08      A  N
ATOM    354  C    LYS A  23      29.637   5.641  66.602  1.00 34.46      A  C
ATOM    355  O    LYS A  23      30.544   5.361  65.786  1.00 34.70      A  O
ATOM    357  N    ALA A  24      29.584   5.082  67.797  1.00 33.77      A  N
ATOM    358  CA   ALA A  24      30.580   4.095  68.170  1.00 34.00      A  C
ATOM    360  CB   ALA A  24      30.931   4.176  69.639  1.00 32.50      A  C
ATOM    364  C    ALA A  24      30.089   2.696  67.772  1.00 33.62      A  C
ATOM    365  O    ALA A  24      28.890   2.435  67.758  1.00 33.12      A  O
```

Figure 8 – CONT.

```
ATOM    367  N    SER A   25      31.045    1.850   67.382  1.00 33.88      A   N
ATOM    368  CA   SER A   25      30.834    0.430   67.099  1.00 33.69      A   C
ATOM    370  CB   SER A   25      31.206    0.118   65.641  1.00 34.01      A   C
ATOM    373  OG   SER A   25      30.056    0.230   64.825  1.00 37.14      A   O
ATOM    375  C    SER A   25      31.714   -0.357   68.040  1.00 32.87      A   C
ATOM    376  O    SER A   25      32.825    0.055   68.335  1.00 33.66      A   O
ATOM    378  N    GLY A   26      31.241   -1.504   68.503  1.00 32.68      A   N
ATOM    379  CA   GLY A   26      32.019   -2.309   69.441  1.00 32.53      A   C
ATOM    382  C    GLY A   26      32.344   -1.587   70.746  1.00 31.91      A   C
ATOM    383  O    GLY A   26      33.295   -1.925   71.423  1.00 31.77      A   O
ATOM    385  N    TYR A   27      31.536   -0.602   71.095  1.00 32.81      A   N
ATOM    386  CA   TYR A   27      31.833    0.368   72.184  1.00 33.89      A   C
ATOM    388  CB   TYR A   27      32.808    1.428   71.653  1.00 33.69      A   C
ATOM    391  CG   TYR A   27      33.524    2.344   72.655  1.00 33.81      A   C
ATOM    392  CD1  TYR A   27      33.362    3.732   72.611  1.00 34.40      A   C
ATOM    394  CE1  TYR A   27      34.040    4.566   73.501  1.00 33.86      A   C
ATOM    396  CZ   TYR A   27      34.897    4.035   74.401  1.00 35.93      A   C
ATOM    397  OH   TYR A   27      35.597    4.839   75.292  1.00 40.96      A   O
ATOM    399  CE2  TYR A   27      35.079    2.660   74.455  1.00 36.03      A   C
ATOM    401  CD2  TYR A   27      34.393    1.840   73.581  1.00 34.01      A   C
ATOM    403  C    TYR A   27      30.501    1.033   72.534  1.00 34.21      A   C
ATOM    404  O    TYR A   27      29.891    1.633   71.665  1.00 34.34      A   O
ATOM    406  N    SER A   28      30.020    0.885   73.767  1.00 35.63      A   N
ATOM    407  CA   SER A   28      28.781    1.555   74.190  1.00 36.57      A   C
ATOM    409  CB   SER A   28      27.918    0.699   75.138  1.00 37.09      A   C
ATOM    412  OG   SER A   28      26.642    1.322   75.357  1.00 36.34      A   O
ATOM    414  C    SER A   28      29.049    2.897   74.859  1.00 36.63      A   C
ATOM    415  O    SER A   28      29.811    3.015   75.800  1.00 36.48      A   O
ATOM    417  N    LEU A   29      28.330    3.896   74.395  1.00 37.55      A   N
ATOM    418  CA   LEU A   29      28.407    5.220   74.996  1.00 37.99      A   C
ATOM    420  CB   LEU A   29      27.957    6.278   73.983  1.00 37.33      A   C
ATOM    423  CG   LEU A   29      28.830    6.539   72.756  1.00 38.98      A   C
ATOM    425  CD1  LEU A   29      28.543    7.956   72.208  1.00 38.20      A   C
ATOM    429  CD2  LEU A   29      30.297    6.386   73.064  1.00 38.44      A   C
ATOM    433  C    LEU A   29      27.573    5.318   76.272  1.00 38.35      A   C
ATOM    434  O    LEU A   29      27.523    6.384   76.898  1.00 37.68      A   O
ATOM    436  N    THR A   30      26.928    4.227   76.689  1.00 39.71      A   N
ATOM    437  CA   THR A   30      26.251    4.251   77.994  1.00 40.66      A   C
ATOM    439  CB   THR A   30      25.051    3.234   78.127  1.00 40.53      A   C
ATOM    441  OG1  THR A   30      25.523    1.921   78.373  1.00 44.75      A   O
ATOM    443  CG2  THR A   30      24.189    3.218   76.894  1.00 37.82      A   C
ATOM    447  C    THR A   30      27.275    4.158   79.134  1.00 40.96      A   C
ATOM    448  O    THR A   30      27.033    4.669   80.209  1.00 41.65      A   O
ATOM    450  N    ASP A   31      28.431    3.554   78.877  1.00 41.88      A   N
ATOM    451  CA   ASP A   31      29.476    3.386   79.897  1.00 42.66      A   C
ATOM    453  CB   ASP A   31      29.764    1.892   80.128  1.00 43.71      A   C
ATOM    456  CG   ASP A   31      28.497    1.066   80.379  1.00 47.27      A   C
ATOM    457  OD1  ASP A   31      27.522    1.603   80.964  1.00 49.89      A   O
ATOM    458  OD2  ASP A   31      28.495   -0.137   79.998  1.00 51.66      A   O
ATOM    459  C    ASP A   31      30.803    4.065   79.519  1.00 42.08      A   C
ATOM    460  O    ASP A   31      31.847    3.746   80.105  1.00 42.10      A   O
ATOM    462  N    ASN A   32      30.782    4.954   78.518  1.00 40.76      A   N
ATOM    463  CA   ASN A   32      31.979    5.704   78.146  1.00 39.74      A   C
ATOM    465  CB   ASN A   32      32.679    5.052   76.946  1.00 39.76      A   C
ATOM    468  CG   ASN A   32      33.186    3.644   77.260  1.00 39.91      A   C
ATOM    469  OD1  ASN A   32      34.193    3.484   77.937  1.00 40.69      A   O
ATOM    470  ND2  ASN A   32      32.472    2.626   76.780  1.00 38.56      A   N
ATOM    473  C    ASN A   32      31.612    7.134   77.830  1.00 38.72      A   C
```

Figure 8 – CONT.

| | | | | | | | | | | | |
|---|---|---|---|---|---|---|---|---|---|---|---|
| ATOM | 474 | O | ASN | A | 32 | 30.444 | 7.427 | 77.628 | 1.00 38.68 | A | O |
| ATOM | 476 | N | TRP | A | 33 | 32.624 | 8.002 | 77.788 | 1.00 37.54 | A | N |
| ATOM | 477 | CA | TRP | A | 33 | 32.464 | 9.419 | 77.513 | 1.00 36.78 | A | C |
| ATOM | 479 | CB | TRP | A | 33 | 33.245 | 10.222 | 78.521 | 1.00 36.96 | A | C |
| ATOM | 482 | CG | TRP | A | 33 | 32.726 | 10.175 | 79.920 | 1.00 39.80 | A | C |
| ATOM | 483 | CD1 | TRP | A | 33 | 32.510 | 9.061 | 80.687 | 1.00 41.28 | A | C |
| ATOM | 485 | NE1 | TRP | A | 33 | 32.064 | 9.434 | 81.937 | 1.00 42.35 | A | N |
| ATOM | 487 | CE2 | TRP | A | 33 | 32.011 | 10.798 | 82.010 | 1.00 40.99 | A | C |
| ATOM | 488 | CD2 | TRP | A | 33 | 32.414 | 11.303 | 80.749 | 1.00 39.55 | A | C |
| ATOM | 489 | CE3 | TRP | A | 33 | 32.435 | 12.684 | 80.550 | 1.00 39.02 | A | C |
| ATOM | 491 | CZ3 | TRP | A | 33 | 32.039 | 13.520 | 81.597 | 1.00 39.76 | A | C |
| ATOM | 493 | CH2 | TRP | A | 33 | 31.629 | 12.983 | 82.837 | 1.00 40.90 | A | C |
| ATOM | 495 | CZ2 | TRP | A | 33 | 31.607 | 11.626 | 83.057 | 1.00 40.06 | A | C |
| ATOM | 497 | C | TRP | A | 33 | 33.010 | 9.795 | 76.133 | 1.00 35.78 | A | C |
| ATOM | 498 | O | TRP | A | 33 | 33.983 | 9.192 | 75.642 | 1.00 35.20 | A | O |
| ATOM | 500 | N | ILE | A | 34 | 32.415 | 10.823 | 75.534 | 1.00 33.55 | A | N |
| ATOM | 501 | CA | ILE | A | 34 | 32.837 | 11.284 | 74.221 | 1.00 32.00 | A | C |
| ATOM | 503 | CB | ILE | A | 34 | 31.721 | 11.140 | 73.191 | 1.00 31.80 | A | C |
| ATOM | 505 | CG1 | ILE | A | 34 | 31.506 | 9.670 | 72.845 | 1.00 31.67 | A | C |
| ATOM | 508 | CD1 | ILE | A | 34 | 32.758 | 9.004 | 72.292 | 1.00 30.73 | A | C |
| ATOM | 512 | CG2 | ILE | A | 34 | 32.053 | 11.975 | 71.906 | 1.00 29.12 | A | C |
| ATOM | 516 | C | ILE | A | 34 | 33.220 | 12.754 | 74.289 | 1.00 31.86 | A | C |
| ATOM | 517 | O | ILE | A | 34 | 32.426 | 13.577 | 74.739 | 1.00 30.29 | A | O |
| ATOM | 519 | N | GLY | A | 35 | 34.436 | 13.059 | 73.846 | 1.00 31.21 | A | N |
| ATOM | 520 | CA | GLY | A | 35 | 34.873 | 14.439 | 73.658 | 1.00 31.94 | A | C |
| ATOM | 523 | C | GLY | A | 35 | 34.943 | 14.887 | 72.192 | 1.00 31.44 | A | C |
| ATOM | 524 | O | GLY | A | 35 | 34.911 | 14.064 | 71.256 | 1.00 30.69 | A | O |
| ATOM | 526 | N | TRP | A | 36 | 35.090 | 16.192 | 72.009 | 1.00 31.05 | A | N |
| ATOM | 527 | CA | TRP | A | 36 | 35.222 | 16.767 | 70.675 | 1.00 31.30 | A | C |
| ATOM | 529 | CB | TRP | A | 36 | 33.982 | 17.552 | 70.305 | 1.00 30.75 | A | C |
| ATOM | 532 | CG | TRP | A | 36 | 32.807 | 16.706 | 70.007 | 1.00 31.05 | A | C |
| ATOM | 533 | CD1 | TRP | A | 36 | 31.810 | 16.394 | 70.862 | 1.00 29.48 | A | C |
| ATOM | 535 | NE1 | TRP | A | 36 | 30.892 | 15.590 | 70.234 | 1.00 31.27 | A | N |
| ATOM | 537 | CE2 | TRP | A | 36 | 31.270 | 15.394 | 68.937 | 1.00 29.21 | A | C |
| ATOM | 538 | CD2 | TRP | A | 36 | 32.479 | 16.070 | 68.752 | 1.00 30.88 | A | C |
| ATOM | 539 | CE3 | TRP | A | 36 | 33.087 | 16.027 | 67.494 | 1.00 26.80 | A | C |
| ATOM | 541 | CZ3 | TRP | A | 36 | 32.476 | 15.337 | 66.495 | 1.00 27.08 | A | C |
| ATOM | 543 | CH2 | TRP | A | 36 | 31.275 | 14.655 | 66.699 | 1.00 26.62 | A | C |
| ATOM | 545 | CZ2 | TRP | A | 36 | 30.648 | 14.682 | 67.915 | 1.00 29.81 | A | C |
| ATOM | 547 | C | TRP | A | 36 | 36.436 | 17.672 | 70.581 | 1.00 30.61 | A | C |
| ATOM | 548 | O | TRP | A | 36 | 36.633 | 18.500 | 71.439 | 1.00 31.74 | A | O |
| ATOM | 550 | N | VAL | A | 37 | 37.233 | 17.481 | 69.535 | 1.00 29.53 | A | N |
| ATOM | 551 | CA | VAL | A | 37 | 38.476 | 18.216 | 69.311 | 1.00 29.28 | A | C |
| ATOM | 553 | CB | VAL | A | 37 | 39.674 | 17.267 | 69.298 | 1.00 29.40 | A | C |
| ATOM | 555 | CG1 | VAL | A | 37 | 41.007 | 18.019 | 69.037 | 1.00 30.04 | A | C |
| ATOM | 559 | CG2 | VAL | A | 37 | 39.786 | 16.553 | 70.607 | 1.00 29.50 | A | C |
| ATOM | 563 | C | VAL | A | 37 | 38.374 | 18.931 | 67.955 | 1.00 28.98 | A | C |
| ATOM | 564 | O | VAL | A | 37 | 37.968 | 18.331 | 66.944 | 1.00 28.41 | A | O |
| ATOM | 566 | N | ARG | A | 38 | 38.675 | 20.223 | 67.967 | 1.00 29.32 | A | N |
| ATOM | 567 | CA | ARG | A | 38 | 38.788 | 21.009 | 66.747 | 1.00 29.81 | A | C |
| ATOM | 569 | CB | ARG | A | 38 | 38.198 | 22.387 | 66.940 | 1.00 29.72 | A | C |
| ATOM | 572 | CG | ARG | A | 38 | 38.161 | 23.221 | 65.658 | 1.00 30.20 | A | C |
| ATOM | 575 | CD | ARG | A | 38 | 37.463 | 24.537 | 65.859 | 1.00 30.02 | A | C |
| ATOM | 578 | NE | ARG | A | 38 | 38.304 | 25.547 | 66.498 | 1.00 33.82 | A | N |
| ATOM | 580 | CZ | ARG | A | 38 | 37.895 | 26.793 | 66.733 | 1.00 36.47 | A | C |
| ATOM | 581 | NH1 | ARG | A | 38 | 36.681 | 27.164 | 66.379 | 1.00 37.44 | A | N |
| ATOM | 584 | NH2 | ARG | A | 38 | 38.704 | 27.678 | 67.291 | 1.00 38.80 | A | N |
| ATOM | 587 | C | ARG | A | 38 | 40.252 | 21.127 | 66.302 | 1.00 30.14 | A | C |

Figure 8 – CONT.

```
ATOM    588  O   ARG A  38      41.162  21.273  67.129  1.00 30.80      A   O
ATOM    590  N   GLN A  39      40.475  21.024  64.995  1.00 29.78      A   N
ATOM    591  CA  GLN A  39      41.777  21.297  64.406  1.00 29.38      A   C
ATOM    593  CB  GLN A  39      42.523  20.016  64.062  1.00 29.55      A   C
ATOM    596  CG  GLN A  39      43.906  20.276  63.422  1.00 29.62      A   C
ATOM    599  CD  GLN A  39      44.778  19.050  63.417  1.00 30.20      A   C
ATOM    600  OE1 GLN A  39      44.343  17.986  63.004  1.00 31.83      A   O
ATOM    601  NE2 GLN A  39      46.020  19.194  63.861  1.00 31.03      A   N
ATOM    604  C   GLN A  39      41.527  22.114  63.164  1.00 30.19      A   C
ATOM    605  O   GLN A  39      41.010  21.592  62.184  1.00 28.48      A   O
ATOM    607  N   LYS A  40      41.795  23.419  63.257  1.00 31.74      A   N
ATOM    608  CA  LYS A  40      41.702  24.329  62.108  1.00 33.03      A   C
ATOM    610  CB  LYS A  40      41.774  25.795  62.557  1.00 33.43      A   C
ATOM    613  CG  LYS A  40      40.554  26.289  63.320  1.00 36.51      A   C
ATOM    616  CD  LYS A  40      40.273  27.822  63.150  1.00 40.28      A   C
ATOM    619  CE  LYS A  40      40.322  28.579  64.483  1.00 43.84      A   C
ATOM    622  NZ  LYS A  40      39.271  29.689  64.609  1.00 45.71      A   N
ATOM    626  C   LYS A  40      42.830  24.015  61.103  1.00 33.81      A   C
ATOM    627  O   LYS A  40      43.832  23.362  61.448  1.00 33.52      A   O
ATOM    629  N   PRO A  41      42.664  24.440  59.852  1.00 34.32      A   N
ATOM    630  CA  PRO A  41      43.664  24.018  58.878  1.00 35.22      A   C
ATOM    632  CB  PRO A  41      43.119  24.533  57.525  1.00 35.80      A   C
ATOM    635  CG  PRO A  41      41.729  25.058  57.780  1.00 34.99      A   C
ATOM    638  CD  PRO A  41      41.605  25.288  59.268  1.00 35.10      A   C
ATOM    641  C   PRO A  41      45.050  24.596  59.169  1.00 35.61      A   C
ATOM    642  O   PRO A  41      45.195  25.817  59.340  1.00 35.22      A   O
ATOM    643  N   GLY A  42      46.030  23.692  59.254  1.00 36.25      A   N
ATOM    644  CA  GLY A  42      47.424  24.017  59.550  1.00 37.18      A   C
ATOM    647  C   GLY A  42      47.681  24.372  61.000  1.00 37.91      A   C
ATOM    648  O   GLY A  42      48.728  24.931  61.320  1.00 38.86      A   O
ATOM    650  N   LYS A  43      46.721  24.093  61.887  1.00 38.20      A   N
ATOM    651  CA  LYS A  43      46.843  24.507  63.282  1.00 37.59      A   C
ATOM    653  CB  LYS A  43      45.746  25.505  63.683  1.00 38.43      A   C
ATOM    656  CG  LYS A  43      45.542  26.717  62.748  1.00 41.36      A   C
ATOM    659  CD  LYS A  43      46.808  27.587  62.538  1.00 45.27      A   C
ATOM    662  CE  LYS A  43      46.935  28.739  63.552  1.00 47.69      A   C
ATOM    665  NZ  LYS A  43      48.136  29.621  63.266  1.00 50.39      A   N
ATOM    669  C   LYS A  43      46.778  23.261  64.151  1.00 36.49      A   C
ATOM    670  O   LYS A  43      46.718  22.138  63.647  1.00 34.96      A   O
ATOM    672  N   GLY A  44      46.808  23.475  65.465  1.00 35.85      A   N
ATOM    673  CA  GLY A  44      46.851  22.382  66.422  1.00 35.65      A   C
ATOM    676  C   GLY A  44      45.484  21.909  66.864  1.00 35.17      A   C
ATOM    677  O   GLY A  44      44.454  22.242  66.264  1.00 34.99      A   O
ATOM    679  N   LEU A  45      45.486  21.120  67.926  1.00 35.75      A   N
ATOM    680  CA  LEU A  45      44.262  20.521  68.480  1.00 35.33      A   C
ATOM    682  CB  LEU A  45      44.577  19.150  69.073  1.00 35.55      A   C
ATOM    685  CG  LEU A  45      45.366  18.223  68.157  1.00 35.03      A   C
ATOM    687  CD1 LEU A  45      45.697  16.905  68.844  1.00 32.57      A   C
ATOM    691  CD2 LEU A  45      44.566  18.001  66.857  1.00 34.27      A   C
ATOM    695  C   LEU A  45      43.717  21.447  69.549  1.00 35.66      A   C
ATOM    696  O   LEU A  45      44.495  22.036  70.312  1.00 35.74      A   O
ATOM    698  N   GLU A  46      42.388  21.592  69.585  1.00 35.51      A   N
ATOM    699  CA  GLU A  46      41.701  22.338  70.625  1.00 35.35      A   C
ATOM    701  CB  GLU A  46      41.088  23.603  70.062  1.00 35.03      A   C
ATOM    704  CG  GLU A  46      42.032  24.534  69.368  1.00 35.81      A   C
ATOM    707  CD  GLU A  46      41.259  25.511  68.523  1.00 37.54      A   C
ATOM    708  OE1 GLU A  46      41.034  25.201  67.328  1.00 36.49      A   O
ATOM    709  OE2 GLU A  46      40.801  26.534  69.074  1.00 35.91      A   O
```

Figure 8 – CONT.

```
ATOM    710  C   GLU A  46      40.581  21.491  71.242  1.00 35.90      A    C
ATOM    711  O   GLU A  46      39.798  20.879  70.507  1.00 36.50      A    O
ATOM    713  N   TRP A  47      40.530  21.445  72.579  1.00 35.61      A    N
ATOM    714  CA  TRP A  47      39.486  20.728  73.308  1.00 35.62      A    C
ATOM    716  CB  TRP A  47      39.874  20.551  74.781  1.00 35.83      A    C
ATOM    719  CG  TRP A  47      38.923  19.682  75.558  1.00 38.06      A    C
ATOM    720  CD1 TRP A  47      38.090  20.068  76.589  1.00 38.95      A    C
ATOM    722  NE1 TRP A  47      37.379  18.984  77.048  1.00 38.23      A    N
ATOM    724  CE2 TRP A  47      37.736  17.880  76.323  1.00 38.31      A    C
ATOM    725  CD2 TRP A  47      38.695  18.281  75.371  1.00 37.86      A    C
ATOM    726  CE3 TRP A  47      39.223  17.326  74.504  1.00 39.33      A    C
ATOM    728  CZ3 TRP A  47      38.777  16.019  74.594  1.00 39.47      A    C
ATOM    730  CH2 TRP A  47      37.818  15.644  75.552  1.00 40.29      A    C
ATOM    732  CZ2 TRP A  47      37.292  16.559  76.426  1.00 39.63      A    C
ATOM    734  C   TRP A  47      38.235  21.537  73.263  1.00 34.55      A    C
ATOM    735  O   TRP A  47      38.268  22.719  73.603  1.00 34.14      A    O
ATOM    737  N   MET A  48      37.125  20.931  72.842  1.00 33.49      A    N
ATOM    738  CA  MET A  48      35.862  21.673  72.822  1.00 32.83      A    C
ATOM    740  CB  MET A  48      35.118  21.405  71.527  1.00 32.10      A    C
ATOM    743  CG  MET A  48      35.941  21.688  70.274  1.00 31.48      A    C
ATOM    746  SD  MET A  48      34.973  21.325  68.798  1.00 25.00      A    S
ATOM    747  CE  MET A  48      33.732  22.617  68.878  1.00 24.93      A    C
ATOM    751  C   MET A  48      34.949  21.333  74.015  1.00 33.05      A    C
ATOM    752  O   MET A  48      34.203  22.179  74.516  1.00 32.70      A    O
ATOM    754  N   GLY A  49      34.975  20.082  74.439  1.00 32.45      A    N
ATOM    755  CA  GLY A  49      34.122  19.657  75.534  1.00 32.59      A    C
ATOM    758  C   GLY A  49      33.835  18.168  75.454  1.00 32.99      A    C
ATOM    759  O   GLY A  49      34.340  17.440  74.563  1.00 31.48      A    O
ATOM    761  N   ILE A  50      32.988  17.727  76.378  1.00 33.00      A    N
ATOM    762  CA  ILE A  50      32.812  16.315  76.627  1.00 32.98      A    C
ATOM    764  CB  ILE A  50      33.790  15.874  77.721  1.00 33.24      A    C
ATOM    766  CG1 ILE A  50      34.053  14.367  77.652  1.00 33.21      A    C
ATOM    769  CD1 ILE A  50      35.191  13.968  78.530  1.00 34.22      A    C
ATOM    773  CG2 ILE A  50      33.274  16.289  79.106  1.00 32.52      A    C
ATOM    777  C   ILE A  50      31.389  16.073  77.066  1.00 33.14      A    C
ATOM    778  O   ILE A  50      30.738  16.982  77.577  1.00 33.05      A    O
ATOM    780  N   ILE A  51      30.910  14.854  76.853  1.00 33.23      A    N
ATOM    781  CA  ILE A  51      29.594  14.446  77.285  1.00 33.73      A    C
ATOM    783  CB  ILE A  51      28.544  14.585  76.144  1.00 33.08      A    C
ATOM    785  CG1 ILE A  51      27.154  14.184  76.648  1.00 32.16      A    C
ATOM    788  CD1 ILE A  51      25.978  14.743  75.875  1.00 28.16      A    C
ATOM    792  CG2 ILE A  51      28.939  13.739  74.933  1.00 33.52      A    C
ATOM    796  C   ILE A  51      29.651  12.993  77.771  1.00 35.33      A    C
ATOM    797  O   ILE A  51      30.361  12.182  77.191  1.00 34.69      A    O
ATOM    799  N   TYR A  52      28.928  12.696  78.853  1.00 37.35      A    N
ATOM    800  CA  TYR A  52      28.657  11.328  79.275  1.00 38.70      A    C
ATOM    802  CB  TYR A  52      28.803  11.139  80.794  1.00 39.14      A    C
ATOM    805  CG  TYR A  52      28.552   9.699  81.273  1.00 41.31      A    C
ATOM    806  CD1 TYR A  52      28.899   8.601  80.474  1.00 41.96      A    C
ATOM    808  CE1 TYR A  52      28.672   7.298  80.890  1.00 44.89      A    C
ATOM    810  CZ  TYR A  52      28.105   7.045  82.143  1.00 45.29      A    C
ATOM    811  OH  TYR A  52      27.900   5.737  82.517  1.00 44.43      A    O
ATOM    813  CE2 TYR A  52      27.758   8.107  82.972  1.00 45.28      A    C
ATOM    815  CD2 TYR A  52      27.981   9.436  82.533  1.00 44.42      A    C
ATOM    817  C   TYR A  52      27.239  10.998  78.851  1.00 39.57      A    C
ATOM    818  O   TYR A  52      26.291  11.414  79.516  1.00 40.07      A    O
ATOM    820  N   PRO A  52A     27.079  10.268  77.724  1.00 41.19      A    N
ATOM    821  CA  PRO A  52A     25.753   9.980  77.151  1.00 41.70      A    C
```

Figure 8 – CONT.

```
ATOM    823  CB   PRO A  52A     26.084    9.143   75.909  1.00 41.57      A  C
ATOM    826  CG   PRO A  52A     27.480    9.406   75.620  1.00 41.16      A  C
ATOM    829  CD   PRO A  52A     28.150    9.651   76.912  1.00 41.38      A  C
ATOM    832  C    PRO A  52A     24.824    9.195   78.086  1.00 42.86      A  C
ATOM    833  O    PRO A  52A     23.603    9.291   77.969  1.00 43.51      A  O
ATOM    834  N    GLY A   53     25.407    8.413   78.989  1.00 44.26      A  N
ATOM    835  CA   GLY A   53     24.648    7.645   79.970  1.00 45.66      A  C
ATOM    838  C    GLY A   53     23.625    8.471   80.729  1.00 46.42      A  C
ATOM    839  O    GLY A   53     22.466    8.047   80.876  1.00 46.33      A  O
ATOM    841  N    ASP A   54     24.058    9.651   81.180  1.00 47.22      A  N
ATOM    842  CA   ASP A   54     23.195   10.579   81.899  1.00 48.16      A  C
ATOM    844  CB   ASP A   54     23.577   10.558   83.389  1.00 48.65      A  C
ATOM    847  CG   ASP A   54     24.876   11.296   83.673  1.00 50.90      A  C
ATOM    848  OD1  ASP A   54     25.282   11.397   84.855  1.00 52.26      A  O
ATOM    849  OD2  ASP A   54     25.487   11.794   82.701  1.00 55.93      A  O
ATOM    850  C    ASP A   54     23.210   12.036   81.331  1.00 47.98      A  C
ATOM    851  O    ASP A   54     22.661   12.955   81.955  1.00 47.95      A  O
ATOM    853  N    SER A   55     23.834   12.237   80.162  1.00 47.67      A  N
ATOM    854  CA   SER A   55     23.839   13.550   79.458  1.00 46.90      A  C
ATOM    856  CB   SER A   55     22.423   14.030   79.155  1.00 46.83      A  C
ATOM    859  OG   SER A   55     21.640   12.966   78.659  1.00 48.59      A  O
ATOM    861  C    SER A   55     24.571   14.668   80.178  1.00 45.76      A  C
ATOM    862  O    SER A   55     24.314   15.845   79.922  1.00 46.32      A  O
ATOM    864  N    ASP A   56     25.480   14.312   81.063  1.00 44.12      A  N
ATOM    865  CA   ASP A   56     26.333   15.288   81.704  1.00 43.56      A  C
ATOM    867  CB   ASP A   56     27.068   14.579   82.850  1.00 43.39      A  C
ATOM    870  CG   ASP A   56     27.897   15.506   83.702  1.00 44.43      A  C
ATOM    871  OD1  ASP A   56     27.864   16.737   83.517  1.00 44.77      A  O
ATOM    872  OD2  ASP A   56     28.611   14.970   84.579  1.00 48.72      A  O
ATOM    873  C    ASP A   56     27.319   15.874   80.656  1.00 43.06      A  C
ATOM    874  O    ASP A   56     28.128   15.150   80.074  1.00 41.91      A  O
ATOM    876  N    THR A   57     27.237   17.182   80.432  1.00 42.55      A  N
ATOM    877  CA   THR A   57     28.011   17.861   79.400  1.00 42.74      A  C
ATOM    879  CB   THR A   57     27.057   18.540   78.386  1.00 42.72      A  C
ATOM    881  OG1  THR A   57     26.157   17.560   77.841  1.00 43.16      A  O
ATOM    883  CG2  THR A   57     27.827   19.153   77.249  1.00 42.99      A  C
ATOM    887  C    THR A   57     28.950   18.892   80.037  1.00 42.82      A  C
ATOM    888  O    THR A   57     28.561   19.584   80.970  1.00 43.34      A  O
ATOM    890  N    ARG A   58     30.193   18.978   79.578  1.00 42.64      A  N
ATOM    891  CA   ARG A   58     31.118   20.010   80.078  1.00 43.02      A  C
ATOM    893  CB   ARG A   58     32.043   19.457   81.186  1.00 42.65      A  C
ATOM    902  C    ARG A   58     31.947   20.617   78.937  1.00 43.10      A  C
ATOM    903  O    ARG A   58     32.693   19.914   78.269  1.00 44.44      A  O
ATOM    905  N    TYR A   59     31.827   21.930   78.755  1.00 43.46      A  N
ATOM    906  CA   TYR A   59     32.446   22.657   77.650  1.00 42.85      A  C
ATOM    908  CB   TYR A   59     31.495   23.708   77.101  1.00 42.17      A  C
ATOM    911  CG   TYR A   59     30.236   23.158   76.512  1.00 40.72      A  C
ATOM    912  CD1  TYR A   59     29.075   23.027   77.278  1.00 39.43      A  C
ATOM    914  CE1  TYR A   59     27.900   22.530   76.720  1.00 37.31      A  C
ATOM    916  CZ   TYR A   59     27.888   22.149   75.393  1.00 35.86      A  C
ATOM    917  OH   TYR A   59     26.738   21.651   74.821  1.00 33.81      A  O
ATOM    919  CE2  TYR A   59     29.013   22.281   74.624  1.00 37.37      A  C
ATOM    921  CD2  TYR A   59     30.179   22.785   75.171  1.00 38.00      A  C
ATOM    923  C    TYR A   59     33.678   23.395   78.090  1.00 43.80      A  C
ATOM    924  O    TYR A   59     33.738   23.936   79.206  1.00 44.75      A  O
ATOM    926  N    SER A   60     34.644   23.459   77.190  1.00 43.96      A  N
ATOM    927  CA   SER A   60     35.753   24.365   77.334  1.00 44.35      A  C
ATOM    929  CB   SER A   60     36.759   24.114   76.215  1.00 44.47      A  C
```

Figure 8 – CONT.

```
ATOM    932  OG   SER A  60      37.920  24.914  76.380  1.00 47.76      A    O
ATOM    934  C    SER A  60      35.208  25.795  77.305  1.00 44.29      A    C
ATOM    935  O    SER A  60      34.313  26.108  76.523  1.00 44.38      A    O
ATOM    937  N    PRO A  61      35.705  26.667  78.195  1.00 44.88      A    N
ATOM    938  CA   PRO A  61      35.208  28.065  78.238  1.00 45.02      A    C
ATOM    940  CB   PRO A  61      36.176  28.779  79.199  1.00 44.99      A    C
ATOM    943  CG   PRO A  61      36.865  27.697  79.961  1.00 45.76      A    C
ATOM    946  CD   PRO A  61      36.739  26.397  79.210  1.00 44.78      A    C
ATOM    949  C    PRO A  61      35.217  28.770  76.879  1.00 44.75      A    C
ATOM    950  O    PRO A  61      34.276  29.477  76.550  1.00 44.94      A    O
ATOM    951  N    SER A  62      36.267  28.566  76.095  1.00 44.64      A    N
ATOM    952  CA   SER A  62      36.325  29.140  74.740  1.00 44.75      A    C
ATOM    954  CB   SER A  62      37.718  28.952  74.149  1.00 45.07      A    C
ATOM    957  OG   SER A  62      38.495  28.069  74.952  1.00 47.60      A    O
ATOM    959  C    SER A  62      35.254  28.633  73.750  1.00 43.80      A    C
ATOM    960  O    SER A  62      35.063  29.259  72.711  1.00 44.42      A    O
ATOM    962  N    PHE A  63      34.580  27.515  74.062  1.00 42.13      A    N
ATOM    963  CA   PHE A  63      33.474  26.976  73.240  1.00 40.78      A    C
ATOM    965  CB   PHE A  63      33.808  25.554  72.774  1.00 40.41      A    C
ATOM    968  CG   PHE A  63      34.963  25.505  71.830  1.00 39.48      A    C
ATOM    969  CD1  PHE A  63      34.763  25.673  70.463  1.00 37.74      A    C
ATOM    971  CE1  PHE A  63      35.810  25.670  69.595  1.00 36.52      A    C
ATOM    973  CZ   PHE A  63      37.115  25.498  70.073  1.00 37.30      A    C
ATOM    975  CE2  PHE A  63      37.339  25.343  71.435  1.00 37.41      A    C
ATOM    977  CD2  PHE A  63      36.260  25.358  72.308  1.00 38.86      A    C
ATOM    979  C    PHE A  63      32.113  26.992  73.935  1.00 40.59      A    C
ATOM    980  O    PHE A  63      31.078  26.746  73.312  1.00 39.47      A    O
ATOM    982  N    GLN A  64      32.111  27.284  75.230  1.00 40.77      A    N
ATOM    983  CA   GLN A  64      30.870  27.442  75.956  1.00 40.99      A    C
ATOM    985  CB   GLN A  64      31.164  27.941  77.381  1.00 41.38      A    C
ATOM    988  CG   GLN A  64      29.911  28.176  78.238  1.00 43.82      A    C
ATOM    991  CD   GLN A  64      29.182  26.886  78.583  1.00 45.77      A    C
ATOM    992  OE1  GLN A  64      28.001  26.705  78.243  1.00 48.79      A    O
ATOM    993  NE2  GLN A  64      29.874  25.987  79.269  1.00 45.19      A    N
ATOM    996  C    GLN A  64      29.982  28.445  75.241  1.00 40.20      A    C
ATOM    997  O    GLN A  64      30.407  29.555  74.980  1.00 40.26      A    O
ATOM    999  N    GLY A  65      28.750  28.052  74.941  1.00 39.76      A    N
ATOM   1000  CA   GLY A  65      27.814  28.903  74.237  1.00 39.82      A    C
ATOM   1003  C    GLY A  65      27.935  29.008  72.718  1.00 39.99      A    C
ATOM   1004  O    GLY A  65      27.037  29.549  72.078  1.00 40.05      A    O
ATOM   1006  N    GLN A  66      29.015  28.494  72.139  1.00 39.72      A    N
ATOM   1007  CA   GLN A  66      29.221  28.546  70.682  1.00 40.48      A    C
ATOM   1009  CB   GLN A  66      30.715  28.672  70.358  1.00 40.75      A    C
ATOM   1012  CG   GLN A  66      31.415  29.833  71.069  1.00 43.12      A    C
ATOM   1015  CD   GLN A  66      30.705  31.162  70.846  1.00 45.98      A    C
ATOM   1016  OE1  GLN A  66      30.628  31.659  69.721  1.00 46.21      A    O
ATOM   1017  NE2  GLN A  66      30.154  31.728  71.924  1.00 49.51      A    N
ATOM   1020  C    GLN A  66      28.657  27.296  69.989  1.00 39.72      A    C
ATOM   1021  O    GLN A  66      28.154  27.365  68.881  1.00 40.22      A    O
ATOM   1023  N    VAL A  67      28.680  26.177  70.693  1.00 38.73      A    N
ATOM   1024  CA   VAL A  67      28.303  24.914  70.130  1.00 37.89      A    C
ATOM   1026  CB   VAL A  67      29.581  24.233  69.645  1.00 37.43      A    C
ATOM   1028  CG1  VAL A  67      30.311  23.557  70.800  1.00 37.62      A    C
ATOM   1032  CG2  VAL A  67      29.276  23.325  68.545  1.00 38.96      A    C
ATOM   1036  C    VAL A  67      27.533  24.082  71.157  1.00 37.27      A    C
ATOM   1037  O    VAL A  67      27.625  24.339  72.342  1.00 37.74      A    O
ATOM   1039  N    THR A  68      26.744  23.114  70.694  1.00 36.10      A    N
ATOM   1040  CA   THR A  68      26.031  22.219  71.583  1.00 35.19      A    C
```

Figure 8 – CONT.

| | | | | | | | | | | | |
|---|---|---|---|---|---|---|---|---|---|---|---|
| ATOM | 1042 | CB | THR | A | 68 | 24.519 | 22.348 | 71.394 | 1.00 35.75 | A | C |
| ATOM | 1044 | OG1 | THR | A | 68 | 24.131 | 23.712 | 71.632 | 1.00 35.81 | A | O |
| ATOM | 1046 | CG2 | THR | A | 68 | 23.766 | 21.431 | 72.340 | 1.00 35.62 | A | C |
| ATOM | 1050 | C | THR | A | 68 | 26.478 | 20.774 | 71.384 | 1.00 34.20 | A | C |
| ATOM | 1051 | O | THR | A | 68 | 26.332 | 20.197 | 70.307 | 1.00 34.38 | A | O |
| ATOM | 1053 | N | ILE | A | 69 | 27.053 | 20.205 | 72.436 | 1.00 32.55 | A | N |
| ATOM | 1054 | CA | ILE | A | 69 | 27.362 | 18.795 | 72.493 | 1.00 31.48 | A | C |
| ATOM | 1056 | CB | ILE | A | 69 | 28.624 | 18.564 | 73.318 | 1.00 31.20 | A | C |
| ATOM | 1058 | CG1 | ILE | A | 69 | 29.795 | 19.239 | 72.602 | 1.00 30.37 | A | C |
| ATOM | 1061 | CD1 | ILE | A | 69 | 31.020 | 19.384 | 73.459 | 1.00 28.68 | A | C |
| ATOM | 1065 | CG2 | ILE | A | 69 | 28.865 | 17.069 | 73.564 | 1.00 28.27 | A | C |
| ATOM | 1069 | C | ILE | A | 69 | 26.162 | 18.020 | 73.071 | 1.00 31.77 | A | C |
| ATOM | 1070 | O | ILE | A | 69 | 25.626 | 18.379 | 74.128 | 1.00 31.83 | A | O |
| ATOM | 1072 | N | SER | A | 70 | 25.729 | 16.981 | 72.361 | 1.00 30.60 | A | N |
| ATOM | 1073 | CA | SER | A | 70 | 24.611 | 16.158 | 72.808 | 1.00 30.60 | A | C |
| ATOM | 1075 | CB | SER | A | 70 | 23.280 | 16.622 | 72.196 | 1.00 30.96 | A | C |
| ATOM | 1078 | OG | SER | A | 70 | 23.144 | 16.257 | 70.827 | 1.00 31.95 | A | O |
| ATOM | 1080 | C | SER | A | 70 | 24.844 | 14.701 | 72.451 | 1.00 30.63 | A | C |
| ATOM | 1081 | O | SER | A | 70 | 25.859 | 14.342 | 71.856 | 1.00 28.70 | A | O |
| ATOM | 1083 | N | ALA | A | 71 | 23.890 | 13.863 | 72.818 | 1.00 31.11 | A | N |
| ATOM | 1084 | CA | ALA | A | 71 | 24.050 | 12.434 | 72.632 | 1.00 31.93 | A | C |
| ATOM | 1086 | CB | ALA | A | 71 | 25.048 | 11.865 | 73.640 | 1.00 31.57 | A | C |
| ATOM | 1090 | C | ALA | A | 71 | 22.714 | 11.748 | 72.736 | 1.00 32.53 | A | C |
| ATOM | 1091 | O | ALA | A | 71 | 21.806 | 12.228 | 73.425 | 1.00 33.20 | A | O |
| ATOM | 1093 | N | ASP | A | 72 | 22.605 | 10.639 | 72.018 | 1.00 33.06 | A | N |
| ATOM | 1094 | CA | ASP | A | 72 | 21.427 | 9.781 | 72.002 | 1.00 33.73 | A | C |
| ATOM | 1096 | CB | ASP | A | 72 | 20.636 | 9.949 | 70.690 | 1.00 34.23 | A | C |
| ATOM | 1099 | CG | ASP | A | 72 | 19.399 | 9.049 | 70.627 | 1.00 35.55 | A | C |
| ATOM | 1100 | OD1 | ASP | A | 72 | 18.540 | 9.249 | 69.743 | 1.00 38.48 | A | O |
| ATOM | 1101 | OD2 | ASP | A | 72 | 19.311 | 8.109 | 71.438 | 1.00 38.47 | A | O |
| ATOM | 1102 | C | ASP | A | 72 | 21.956 | 8.360 | 72.210 | 1.00 33.45 | A | C |
| ATOM | 1103 | O | ASP | A | 72 | 22.450 | 7.702 | 71.290 | 1.00 32.90 | A | O |
| ATOM | 1105 | N | LYS | A | 73 | 21.910 | 7.922 | 73.461 | 1.00 33.46 | A | N |
| ATOM | 1106 | CA | LYS | A | 73 | 22.490 | 6.641 | 73.846 | 1.00 33.23 | A | C |
| ATOM | 1108 | CB | LYS | A | 73 | 22.572 | 6.493 | 75.357 | 1.00 33.80 | A | C |
| ATOM | 1111 | CG | LYS | A | 73 | 21.257 | 6.363 | 76.067 | 1.00 35.47 | A | C |
| ATOM | 1114 | CD | LYS | A | 73 | 21.493 | 6.499 | 77.585 | 1.00 39.67 | A | C |
| ATOM | 1117 | CE | LYS | A | 73 | 20.223 | 6.117 | 78.377 | 1.00 42.22 | A | C |
| ATOM | 1120 | NZ | LYS | A | 73 | 20.476 | 6.151 | 79.845 | 1.00 45.12 | A | N |
| ATOM | 1124 | C | LYS | A | 73 | 21.773 | 5.460 | 73.259 | 1.00 32.52 | A | C |
| ATOM | 1125 | O | LYS | A | 73 | 22.373 | 4.424 | 73.053 | 1.00 31.83 | A | O |
| ATOM | 1127 | N | SER | A | 74 | 20.503 | 5.630 | 72.952 | 1.00 32.90 | A | N |
| ATOM | 1128 | CA | SER | A | 74 | 19.722 | 4.559 | 72.368 | 1.00 33.19 | A | C |
| ATOM | 1130 | CB | SER | A | 74 | 18.240 | 4.941 | 72.357 | 1.00 33.02 | A | C |
| ATOM | 1133 | OG | SER | A | 74 | 17.910 | 5.706 | 71.204 | 1.00 33.57 | A | O |
| ATOM | 1135 | C | SER | A | 74 | 20.203 | 4.145 | 70.947 | 1.00 33.34 | A | C |
| ATOM | 1136 | O | SER | A | 74 | 19.959 | 3.012 | 70.514 | 1.00 33.75 | A | O |
| ATOM | 1138 | N | ILE | A | 75 | 20.857 | 5.060 | 70.225 | 1.00 33.58 | A | N |
| ATOM | 1139 | CA | ILE | A | 75 | 21.534 | 4.724 | 68.959 | 1.00 32.91 | A | C |
| ATOM | 1141 | CB | ILE | A | 75 | 20.907 | 5.471 | 67.755 | 1.00 33.22 | A | C |
| ATOM | 1143 | CG1 | ILE | A | 75 | 21.117 | 7.006 | 67.847 | 1.00 34.23 | A | C |
| ATOM | 1146 | CD1 | ILE | A | 75 | 20.339 | 7.830 | 66.752 | 1.00 32.37 | A | C |
| ATOM | 1150 | CG2 | ILE | A | 75 | 19.414 | 5.109 | 67.601 | 1.00 31.33 | A | C |
| ATOM | 1154 | C | ILE | A | 75 | 23.057 | 4.933 | 69.035 | 1.00 33.28 | A | C |
| ATOM | 1155 | O | ILE | A | 75 | 23.727 | 5.030 | 68.004 | 1.00 34.45 | A | O |
| ATOM | 1157 | N | ASN | A | 76 | 23.598 | 5.017 | 70.252 | 1.00 33.03 | A | N |
| ATOM | 1158 | CA | ASN | A | 76 | 25.031 | 5.091 | 70.508 | 1.00 32.93 | A | C |
| ATOM | 1160 | CB | ASN | A | 76 | 25.679 | 3.732 | 70.190 | 1.00 33.54 | A | C |

Figure 8 – CONT.

```
ATOM   1163  CG   ASN A   76      26.860   3.419  71.089  1.00 32.89      A  C
ATOM   1164  OD1  ASN A   76      26.758   3.548  72.307  1.00 32.46      A  O
ATOM   1165  ND2  ASN A   76      28.014   3.032  70.490  1.00 30.43      A  N
ATOM   1168  C    ASN A   76      25.788   6.210  69.773  1.00 33.66      A  C
ATOM   1169  O    ASN A   76      26.962   6.028  69.393  1.00 35.07      A  O
ATOM   1171  N    THR A   77      25.156   7.373  69.630  1.00 32.33      A  N
ATOM   1172  CA   THR A   77      25.660   8.455  68.792  1.00 31.88      A  C
ATOM   1174  CB   THR A   77      24.724   8.645  67.571  1.00 32.12      A  C
ATOM   1176  OG1  THR A   77      24.682   7.416  66.808  1.00 31.80      A  O
ATOM   1178  CG2  THR A   77      25.171   9.814  66.675  1.00 31.37      A  C
ATOM   1182  C    THR A   77      25.817   9.742  69.603  1.00 31.75      A  C
ATOM   1183  O    THR A   77      24.911  10.109  70.363  1.00 31.65      A  O
ATOM   1185  N    ALA A   78      26.987  10.386  69.508  1.00 30.61      A  N
ATOM   1186  CA   ALA A   78      27.187  11.740  70.059  1.00 29.81      A  C
ATOM   1188  CB   ALA A   78      28.482  11.850  70.844  1.00 29.41      A  C
ATOM   1192  C    ALA A   78      27.177  12.760  68.939  1.00 29.38      A  C
ATOM   1193  O    ALA A   78      27.474  12.425  67.789  1.00 29.65      A  O
ATOM   1195  N    TYR A   79      26.823  14.011  69.268  1.00 28.24      A  N
ATOM   1196  CA   TYR A   79      26.671  15.023  68.261  1.00 27.58      A  C
ATOM   1198  CB   TYR A   79      25.220  15.306  67.953  1.00 27.23      A  C
ATOM   1201  CG   TYR A   79      24.348  14.144  67.592  1.00 27.91      A  C
ATOM   1202  CD1  TYR A   79      24.233  13.705  66.268  1.00 27.66      A  C
ATOM   1204  CE1  TYR A   79      23.393  12.662  65.947  1.00 29.08      A  C
ATOM   1206  CZ   TYR A   79      22.643  12.053  66.950  1.00 30.52      A  C
ATOM   1207  OH   TYR A   79      21.781  11.015  66.675  1.00 30.38      A  O
ATOM   1209  CE2  TYR A   79      22.718  12.506  68.245  1.00 28.75      A  C
ATOM   1211  CD2  TYR A   79      23.554  13.537  68.556  1.00 27.70      A  C
ATOM   1213  C    TYR A   79      27.334  16.360  68.633  1.00 27.75      A  C
ATOM   1214  O    TYR A   79      27.553  16.661  69.803  1.00 27.38      A  O
ATOM   1216  N    LEU A   80      27.646  17.144  67.598  1.00 27.53      A  N
ATOM   1217  CA   LEU A   80      28.156  18.496  67.734  1.00 27.88      A  C
ATOM   1219  CB   LEU A   80      29.608  18.552  67.311  1.00 28.35      A  C
ATOM   1222  CG   LEU A   80      30.520  19.725  67.688  1.00 29.17      A  C
ATOM   1224  CD1  LEU A   80      30.583  19.933  69.203  1.00 27.30      A  C
ATOM   1228  CD2  LEU A   80      31.902  19.420  67.122  1.00 26.46      A  C
ATOM   1232  C    LEU A   80      27.297  19.335  66.829  1.00 28.21      A  C
ATOM   1233  O    LEU A   80      27.001  18.938  65.684  1.00 27.75      A  O
ATOM   1235  N    GLN A   81      26.867  20.481  67.346  1.00 28.36      A  N
ATOM   1236  CA   GLN A   81      25.808  21.203  66.727  1.00 28.94      A  C
ATOM   1238  CB   GLN A   81      24.555  20.818  67.465  1.00 30.50      A  C
ATOM   1241  CG   GLN A   81      23.248  21.164  66.870  1.00 33.95      A  C
ATOM   1244  CD   GLN A   81      22.049  20.625  67.736  1.00 40.77      A  C
ATOM   1245  OE1  GLN A   81      20.878  20.817  67.374  1.00 45.24      A  O
ATOM   1246  NE2  GLN A   81      22.351  19.951  68.860  1.00 39.31      A  N
ATOM   1249  C    GLN A   81      26.026  22.709  66.805  1.00 27.75      A  C
ATOM   1250  O    GLN A   81      26.453  23.231  67.821  1.00 27.75      A  O
ATOM   1252  N    TRP A   82      25.679  23.390  65.730  1.00 26.47      A  N
ATOM   1253  CA   TRP A   82      25.816  24.818  65.632  1.00 26.71      A  C
ATOM   1255  CB   TRP A   82      26.853  25.167  64.575  1.00 26.51      A  C
ATOM   1258  CG   TRP A   82      28.266  24.933  64.949  1.00 24.55      A  C
ATOM   1259  CD1  TRP A   82      29.099  25.817  65.549  1.00 22.00      A  C
ATOM   1261  NE1  TRP A   82      30.325  25.266  65.698  1.00 22.96      A  N
ATOM   1263  CE2  TRP A   82      30.311  23.989  65.201  1.00 22.28      A  C
ATOM   1264  CD2  TRP A   82      29.035  23.756  64.697  1.00 22.62      A  C
ATOM   1265  CE3  TRP A   82      28.761  22.532  64.083  1.00 23.71      A  C
ATOM   1267  CZ3  TRP A   82      29.762  21.591  63.992  1.00 22.26      A  C
ATOM   1269  CH2  TRP A   82      31.034  21.854  64.491  1.00 23.34      A  C
ATOM   1271  CZ2  TRP A   82      31.332  23.054  65.104  1.00 23.33      A  C
```

Figure 8 – CONT.

```
ATOM   1273  C    TRP A  82      24.505  25.285  65.102  1.00 27.67       A  C
ATOM   1274  O    TRP A  82      23.977  24.676  64.176  1.00 27.76       A  O
ATOM   1276  N    SER A  82A     23.983  26.376  65.633  1.00 28.10       A  N
ATOM   1277  CA   SER A  82A     22.777  26.972  65.053  1.00 28.72       A  C
ATOM   1279  CB   SER A  82A     21.898  27.548  66.160  1.00 28.87       A  C
ATOM   1282  OG   SER A  82A     22.658  28.416  66.948  1.00 30.93       A  O
ATOM   1284  C    SER A  82A     23.092  28.059  64.007  1.00 28.34       A  C
ATOM   1285  O    SER A  82A     22.262  28.382  63.165  1.00 29.96       A  O
ATOM   1287  N    SER A  82B     24.276  28.622  64.062  1.00 28.05       A  N
ATOM   1288  CA   SER A  82B     24.690  29.675  63.116  1.00 27.99       A  C
ATOM   1290  CB   SER A  82B     24.282  31.055  63.637  1.00 28.00       A  C
ATOM   1293  OG   SER A  82B     24.578  32.089  62.717  1.00 29.16       A  O
ATOM   1295  C    SER A  82B     26.203  29.615  62.899  1.00 26.85       A  C
ATOM   1296  O    SER A  82B     26.977  30.113  63.723  1.00 27.31       A  O
ATOM   1298  N    LEU A  82C     26.608  28.944  61.815  1.00 24.83       A  N
ATOM   1299  CA   LEU A  82C     28.004  28.717  61.525  1.00 23.64       A  C
ATOM   1301  CB   LEU A  82C     28.156  27.690  60.389  1.00 23.36       A  C
ATOM   1304  CG   LEU A  82C     27.802  26.213  60.676  1.00 19.96       A  C
ATOM   1306  CD1  LEU A  82C     27.537  25.450  59.388  1.00 21.81       A  C
ATOM   1310  CD2  LEU A  82C     28.908  25.531  61.446  1.00 16.23       A  C
ATOM   1314  C    LEU A  82C     28.689  29.999  61.106  1.00 23.79       A  C
ATOM   1315  O    LEU A  82C     28.095  30.840  60.437  1.00 21.28       A  O
ATOM   1317  N    LYS A  83      29.968  30.083  61.451  1.00 24.55       A  N
ATOM   1318  CA   LYS A  83      30.841  31.152  61.007  1.00 26.23       A  C
ATOM   1320  CB   LYS A  83      31.591  31.783  62.196  1.00 27.12       A  C
ATOM   1323  CG   LYS A  83      30.743  32.167  63.389  1.00 30.85       A  C
ATOM   1326  CD   LYS A  83      31.635  32.621  64.588  1.00 33.74       A  C
ATOM   1329  CE   LYS A  83      30.809  32.888  65.859  1.00 36.36       A  C
ATOM   1332  NZ   LYS A  83      30.174  31.649  66.454  1.00 39.07       A  N
ATOM   1336  C    LYS A  83      31.898  30.555  60.107  1.00 26.07       A  C
ATOM   1337  O    LYS A  83      32.324  29.416  60.346  1.00 26.07       A  O
ATOM   1339  N    ALA A  84      32.385  31.338  59.140  1.00 26.68       A  N
ATOM   1340  CA   ALA A  84      33.484  30.897  58.233  1.00 27.36       A  C
ATOM   1342  CB   ALA A  84      33.997  32.037  57.327  1.00 27.24       A  C
ATOM   1346  C    ALA A  84      34.633  30.364  59.045  1.00 27.22       A  C
ATOM   1347  O    ALA A  84      35.317  29.374  58.651  1.00 26.83       A  O
ATOM   1349  N    SER A  85      34.855  31.013  60.178  1.00 26.67       A  N
ATOM   1350  CA   SER A  85      35.935  30.594  61.066  1.00 27.57       A  C
ATOM   1352  CB   SER A  85      36.237  31.671  62.108  1.00 27.49       A  C
ATOM   1355  OG   SER A  85      35.172  31.727  63.029  1.00 29.15       A  O
ATOM   1357  C    SER A  85      35.661  29.239  61.764  1.00 27.13       A  C
ATOM   1358  O    SER A  85      36.564  28.671  62.353  1.00 28.51       A  O
ATOM   1360  N    ASP A  86      34.458  28.691  61.682  1.00 27.17       A  N
ATOM   1361  CA   ASP A  86      34.261  27.290  62.133  1.00 27.30       A  C
ATOM   1363  CB   ASP A  86      32.784  27.006  62.365  1.00 27.34       A  C
ATOM   1366  CG   ASP A  86      32.221  27.807  63.529  1.00 27.89       A  C
ATOM   1367  OD1  ASP A  86      32.934  27.889  64.567  1.00 25.26       A  O
ATOM   1368  OD2  ASP A  86      31.087  28.345  63.382  1.00 25.55       A  O
ATOM   1369  C    ASP A  86      34.837  26.233  61.179  1.00 27.15       A  C
ATOM   1370  O    ASP A  86      34.691  25.023  61.432  1.00 27.64       A  O
ATOM   1372  N    THR A  87      35.501  26.675  60.102  1.00 26.60       A  N
ATOM   1373  CA   THR A  87      36.060  25.764  59.083  1.00 25.29       A  C
ATOM   1375  CB   THR A  87      36.599  26.532  57.838  1.00 25.27       A  C
ATOM   1377  OG1  THR A  87      35.499  27.193  57.205  1.00 22.56       A  O
ATOM   1379  CG2  THR A  87      37.225  25.525  56.803  1.00 26.27       A  C
ATOM   1383  C    THR A  87      37.138  24.951  59.699  1.00 24.58       A  C
ATOM   1384  O    THR A  87      38.128  25.492  60.136  1.00 25.12       A  O
ATOM   1386  N    ALA A  88      36.971  23.635  59.762  1.00 24.07       A  N
```

Figure 8 – CONT.

| | | | | | | | | | | | |
|---|---|---|---|---|---|---|---|---|---|---|---|
| ATOM | 1387 | CA | ALA | A | 88 | 37.949 | 22.845 | 60.496 | 1.00 | 23.53 | A C |
| ATOM | 1389 | CB | ALA | A | 88 | 37.940 | 23.237 | 62.026 | 1.00 | 23.75 | A C |
| ATOM | 1393 | C | ALA | A | 88 | 37.618 | 21.398 | 60.338 | 1.00 | 23.40 | A C |
| ATOM | 1394 | O | ALA | A | 88 | 36.570 | 21.068 | 59.813 | 1.00 | 22.83 | A O |
| ATOM | 1396 | N | ILE | A | 89 | 38.536 | 20.545 | 60.770 | 1.00 | 24.57 | A N |
| ATOM | 1397 | CA | ILE | A | 89 | 38.242 | 19.114 | 60.991 | 1.00 | 25.53 | A C |
| ATOM | 1399 | CB | ILE | A | 89 | 39.452 | 18.210 | 60.639 | 1.00 | 25.68 | A C |
| ATOM | 1401 | CG1 | ILE | A | 89 | 39.775 | 18.349 | 59.150 | 1.00 | 28.20 | A C |
| ATOM | 1404 | CD1 | ILE | A | 89 | 41.020 | 17.588 | 58.744 | 1.00 | 30.18 | A C |
| ATOM | 1408 | CG2 | ILE | A | 89 | 39.123 | 16.716 | 60.861 | 1.00 | 24.48 | A C |
| ATOM | 1412 | C | ILE | A | 89 | 37.846 | 18.959 | 62.446 | 1.00 | 25.04 | A C |
| ATOM | 1413 | O | ILE | A | 89 | 38.472 | 19.551 | 63.312 | 1.00 | 24.66 | A O |
| ATOM | 1415 | N | TYR | A | 90 | 36.780 | 18.203 | 62.696 | 1.00 | 26.11 | A N |
| ATOM | 1416 | CA | TYR | A | 90 | 36.273 | 17.932 | 64.058 | 1.00 | 26.13 | A C |
| ATOM | 1418 | CB | TYR | A | 90 | 34.826 | 18.392 | 64.202 | 1.00 | 25.90 | A C |
| ATOM | 1421 | CG | TYR | A | 90 | 34.698 | 19.895 | 64.141 | 1.00 | 25.39 | A C |
| ATOM | 1422 | CD1 | TYR | A | 90 | 34.491 | 20.543 | 62.928 | 1.00 | 23.85 | A C |
| ATOM | 1424 | CE1 | TYR | A | 90 | 34.407 | 21.925 | 62.850 | 1.00 | 24.38 | A C |
| ATOM | 1426 | CZ | TYR | A | 90 | 34.557 | 22.675 | 63.979 | 1.00 | 23.66 | A C |
| ATOM | 1427 | OH | TYR | A | 90 | 34.509 | 24.027 | 63.879 | 1.00 | 22.74 | A O |
| ATOM | 1429 | CE2 | TYR | A | 90 | 34.802 | 22.063 | 65.213 | 1.00 | 25.60 | A C |
| ATOM | 1431 | CD2 | TYR | A | 90 | 34.860 | 20.673 | 65.283 | 1.00 | 24.00 | A C |
| ATOM | 1433 | C | TYR | A | 90 | 36.402 | 16.439 | 64.331 | 1.00 | 26.99 | A C |
| ATOM | 1434 | O | TYR | A | 90 | 35.803 | 15.634 | 63.641 | 1.00 | 27.36 | A O |
| ATOM | 1436 | N | TYR | A | 91 | 37.225 | 16.091 | 65.309 | 1.00 | 27.77 | A N |
| ATOM | 1437 | CA | TYR | A | 91 | 37.429 | 14.720 | 65.709 | 1.00 | 28.43 | A C |
| ATOM | 1439 | CB | TYR | A | 91 | 38.881 | 14.461 | 66.074 | 1.00 | 27.77 | A C |
| ATOM | 1442 | CG | TYR | A | 91 | 39.868 | 14.759 | 64.971 | 1.00 | 28.69 | A C |
| ATOM | 1443 | CD1 | TYR | A | 91 | 40.061 | 13.867 | 63.922 | 1.00 | 28.54 | A C |
| ATOM | 1445 | CE1 | TYR | A | 91 | 40.957 | 14.151 | 62.895 | 1.00 | 28.98 | A C |
| ATOM | 1447 | CZ | TYR | A | 91 | 41.687 | 15.319 | 62.930 | 1.00 | 30.92 | A C |
| ATOM | 1448 | OH | TYR | A | 91 | 42.574 | 15.612 | 61.909 | 1.00 | 32.35 | A O |
| ATOM | 1450 | CE2 | TYR | A | 91 | 41.519 | 16.223 | 63.975 | 1.00 | 30.62 | A C |
| ATOM | 1452 | CD2 | TYR | A | 91 | 40.620 | 15.944 | 64.981 | 1.00 | 30.22 | A C |
| ATOM | 1454 | C | TYR | A | 91 | 36.562 | 14.379 | 66.922 | 1.00 | 30.62 | A C |
| ATOM | 1455 | O | TYR | A | 91 | 36.498 | 15.117 | 67.895 | 1.00 | 30.23 | A O |
| ATOM | 1457 | N | CYS | A | 92 | 35.901 | 13.237 | 66.791 | 1.00 | 32.19 | A N |
| ATOM | 1458 | CA | CYS | A | 92 | 35.229 | 12.505 | 67.835 | 1.00 | 34.04 | A C |
| ATOM | 1460 | CB | CYS | A | 92 | 34.272 | 11.481 | 67.139 | 1.00 | 34.17 | A C |
| ATOM | 1463 | SG | CYS | A | 92 | 33.400 | 10.741 | 68.304 | 1.00 | 43.42 | A S |
| ATOM | 1465 | C | CYS | A | 92 | 36.329 | 11.776 | 68.637 | 1.00 | 33.85 | A C |
| ATOM | 1466 | O | CYS | A | 92 | 37.218 | 11.166 | 68.058 | 1.00 | 33.88 | A O |
| ATOM | 1468 | N | VAL | A | 93 | 36.291 | 11.864 | 69.959 | 1.00 | 34.67 | A N |
| ATOM | 1469 | CA | VAL | A | 93 | 37.234 | 11.148 | 70.817 | 1.00 | 35.23 | A C |
| ATOM | 1471 | CB | VAL | A | 93 | 38.176 | 12.100 | 71.504 | 1.00 | 35.46 | A C |
| ATOM | 1473 | CG1 | VAL | A | 93 | 38.955 | 11.359 | 72.539 | 1.00 | 37.41 | A C |
| ATOM | 1477 | CG2 | VAL | A | 93 | 39.127 | 12.694 | 70.481 | 1.00 | 37.14 | A C |
| ATOM | 1481 | C | VAL | A | 93 | 36.517 | 10.298 | 71.900 | 1.00 | 35.34 | A C |
| ATOM | 1482 | O | VAL | A | 93 | 35.590 | 10.772 | 72.564 | 1.00 | 34.92 | A O |
| ATOM | 1484 | N | GLY | A | 94 | 36.948 | 9.048 | 72.046 | 1.00 | 34.89 | A N |
| ATOM | 1485 | CA | GLY | A | 94 | 36.369 | 8.114 | 73.006 | 1.00 | 35.14 | A C |
| ATOM | 1488 | C | GLY | A | 94 | 37.262 | 8.012 | 74.239 | 1.00 | 35.05 | A C |
| ATOM | 1489 | O | GLY | A | 94 | 38.458 | 7.744 | 74.113 | 1.00 | 35.02 | A O |
| ATOM | 1491 | N | LEU | A | 95 | 36.683 | 8.255 | 75.413 | 1.00 | 34.78 | A N |
| ATOM | 1492 | CA | LEU | A | 95 | 37.401 | 8.197 | 76.716 | 1.00 | 35.40 | A C |
| ATOM | 1494 | CB | LEU | A | 95 | 37.472 | 9.573 | 77.388 | 1.00 | 34.94 | A C |
| ATOM | 1497 | CG | LEU | A | 95 | 37.930 | 10.776 | 76.552 | 1.00 | 36.57 | A C |
| ATOM | 1499 | CD1 | LEU | A | 95 | 38.518 | 11.854 | 77.479 | 1.00 | 35.63 | A C |

Figure 8 – CONT.

```
ATOM   1503  CD2 LEU A  95      36.788  11.371  75.695  1.00 35.22      A    C
ATOM   1507  C   LEU A  95      36.683   7.229  77.667  1.00 35.40      A    C
ATOM   1508  O   LEU A  95      35.454   7.142  77.655  1.00 34.45      A    O
ATOM   1510  N   ASP A  96      37.458   6.517  78.494  1.00 36.80      A    N
ATOM   1511  CA  ASP A  96      36.908   5.516  79.435  1.00 37.42      A    C
ATOM   1513  CB  ASP A  96      38.034   4.734  80.092  1.00 37.47      A    C
ATOM   1516  CG  ASP A  96      38.862   3.928  79.097  1.00 38.55      A    C
ATOM   1517  OD1 ASP A  96      40.102   3.913  79.251  1.00 39.27      A    O
ATOM   1518  OD2 ASP A  96      38.296   3.323  78.174  1.00 39.34      A    O
ATOM   1519  C   ASP A  96      36.086   6.210  80.537  1.00 38.15      A    C
ATOM   1520  O   ASP A  96      35.105   5.659  81.067  1.00 37.85      A    O
ATOM   1522  N   TRP A  97      36.526   7.408  80.893  1.00 38.41      A    N
ATOM   1523  CA  TRP A  97      35.811   8.245  81.812  1.00 39.41      A    C
ATOM   1525  CB  TRP A  97      35.975   7.752  83.255  1.00 39.03      A    C
ATOM   1528  CG  TRP A  97      34.869   8.226  84.167  1.00 38.59      A    C
ATOM   1529  CD1 TRP A  97      34.938   9.251  85.064  1.00 38.82      A    C
ATOM   1531  NE1 TRP A  97      33.731   9.396  85.691  1.00 39.23      A    N
ATOM   1533  CE2 TRP A  97      32.849   8.470  85.199  1.00 37.11      A    C
ATOM   1534  CD2 TRP A  97      33.529   7.714  84.242  1.00 35.85      A    C
ATOM   1535  CE3 TRP A  97      32.845   6.689  83.586  1.00 39.57      A    C
ATOM   1537  CZ3 TRP A  97      31.522   6.449  83.913  1.00 40.31      A    C
ATOM   1539  CH2 TRP A  97      30.868   7.227  84.877  1.00 41.08      A    C
ATOM   1541  CZ2 TRP A  97      31.513   8.244  85.523  1.00 38.87      A    C
ATOM   1543  C   TRP A  97      36.392   9.639  81.651  1.00 40.74      A    C
ATOM   1544  O   TRP A  97      37.346   9.811  80.922  1.00 41.00      A    O
ATOM   1546  N   ASN A  98      35.810  10.620  82.336  1.00 42.17      A    N
ATOM   1547  CA  ASN A  98      36.349  11.975  82.418  1.00 43.06      A    C
ATOM   1549  CB  ASN A  98      35.430  12.827  83.305  1.00 43.42      A    C
ATOM   1552  CG  ASN A  98      35.356  14.295  82.881  1.00 44.11      A    C
ATOM   1553  OD1 ASN A  98      34.386  14.981  83.230  1.00 46.73      A    O
ATOM   1554  ND2 ASN A  98      36.351  14.779  82.143  1.00 39.76      A    N
ATOM   1557  C   ASN A  98      37.752  11.962  82.999  1.00 44.18      A    C
ATOM   1558  O   ASN A  98      38.092  11.065  83.771  1.00 44.47      A    O
ATOM   1560  N   TYR A  99      38.566  12.949  82.613  1.00 45.47      A    N
ATOM   1561  CA  TYR A  99      39.956  13.088  83.076  1.00 46.38      A    C
ATOM   1563  CB  TYR A  99      39.964  13.380  84.581  1.00 47.16      A    C
ATOM   1566  CG  TYR A  99      39.007  14.490  84.942  1.00 49.54      A    C
ATOM   1567  CD1 TYR A  99      39.167  15.760  84.394  1.00 53.72      A    C
ATOM   1569  CE1 TYR A  99      38.285  16.799  84.694  1.00 55.48      A    C
ATOM   1571  CZ  TYR A  99      37.232  16.577  85.556  1.00 55.37      A    C
ATOM   1572  OH  TYR A  99      36.382  17.619  85.835  1.00 56.89      A    O
ATOM   1574  CE2 TYR A  99      37.042  15.322  86.118  1.00 53.88      A    C
ATOM   1576  CD2 TYR A  99      37.930  14.276  85.796  1.00 51.82      A    C
ATOM   1578  C   TYR A  99      40.836  11.871  82.733  1.00 46.34      A    C
ATOM   1579  O   TYR A  99      41.816  11.584  83.445  1.00 47.97      A    O
ATOM   1581  N   ASN A 100      40.487  11.169  81.650  1.00 45.38      A    N
ATOM   1582  CA  ASN A 100      41.227   9.992  81.168  1.00 44.97      A    C
ATOM   1584  CB  ASN A 100      40.283   8.797  81.014  1.00 45.22      A    C
ATOM   1587  CG  ASN A 100      40.073   8.032  82.325  1.00 46.01      A    C
ATOM   1588  OD1 ASN A 100      39.792   8.629  83.375  1.00 46.33      A    O
ATOM   1589  ND2 ASN A 100      40.214   6.709  82.261  1.00 44.08      A    N
ATOM   1592  C   ASN A 100      41.914  10.292  79.831  1.00 44.70      A    C
ATOM   1593  O   ASN A 100      41.708  11.369  79.238  1.00 44.74      A    O
ATOM   1595  N   PRO A 100A     42.755   9.365  79.358  1.00 44.02      A    N
ATOM   1596  CA  PRO A 100A     43.421   9.681  78.103  1.00 43.60      A    C
ATOM   1598  CB  PRO A 100A     44.513   8.598  77.990  1.00 43.55      A    C
ATOM   1601  CG  PRO A 100A     44.156   7.542  78.930  1.00 43.58      A    C
ATOM   1604  CD  PRO A 100A     43.261   8.120  79.970  1.00 44.17      A    C
```

Figure 8 – CONT.

```
ATOM   1607  C   PRO A 100A     42.458   9.662  76.906  1.00 43.06      A    C
ATOM   1608  O   PRO A 100A     41.457   8.922  76.914  1.00 42.88      A    O
ATOM   1609  N   LEU A 100B     42.757  10.487  75.900  1.00 41.90      A    N
ATOM   1610  CA  LEU A 100B     41.974  10.512  74.672  1.00 41.09      A    C
ATOM   1612  CB  LEU A 100B     42.214  11.783  73.862  1.00 40.86      A    C
ATOM   1615  CG  LEU A 100B     42.253  13.133  74.584  1.00 40.65      A    C
ATOM   1617  CD1 LEU A 100B     41.662  14.192  73.686  1.00 40.25      A    C
ATOM   1621  CD2 LEU A 100B     41.519  13.115  75.919  1.00 42.40      A    C
ATOM   1625  C   LEU A 100B     42.398   9.293  73.892  1.00 41.02      A    C
ATOM   1626  O   LEU A 100B     43.342   9.327  73.092  1.00 40.83      A    O
ATOM   1628  N   ARG A 101      41.669   8.212  74.130  1.00 40.24      A    N
ATOM   1629  CA  ARG A 101      42.102   6.892  73.769  1.00 39.70      A    C
ATOM   1631  CB  ARG A 101      41.511   5.910  74.780  1.00 40.24      A    C
ATOM   1634  CG  ARG A 101      41.855   4.475  74.547  1.00 42.55      A    C
ATOM   1637  CD  ARG A 101      41.881   3.691  75.867  1.00 45.19      A    C
ATOM   1640  NE  ARG A 101      41.495   2.316  75.624  1.00 46.70      A    N
ATOM   1642  CZ  ARG A 101      42.025   1.262  76.229  1.00 50.81      A    C
ATOM   1643  NH1 ARG A 101      41.592   0.040  75.913  1.00 49.45      A    N
ATOM   1646  NH2 ARG A 101      42.996   1.416  77.142  1.00 54.96      A    N
ATOM   1649  C   ARG A 101      41.696   6.502  72.368  1.00 38.55      A    C
ATOM   1650  O   ARG A 101      42.484   5.899  71.652  1.00 39.34      A    O
ATOM   1652  N   TYR A 102      40.464   6.809  71.983  1.00 37.16      A    N
ATOM   1653  CA  TYR A 102      39.934   6.413  70.685  1.00 35.86      A    C
ATOM   1655  CB  TYR A 102      38.706   5.507  70.826  1.00 35.34      A    C
ATOM   1658  CG  TYR A 102      38.918   4.195  71.590  1.00 37.22      A    C
ATOM   1659  CD1 TYR A 102      39.592   3.129  71.024  1.00 37.21      A    C
ATOM   1661  CE1 TYR A 102      39.770   1.917  71.728  1.00 37.64      A    C
ATOM   1663  CZ  TYR A 102      39.249   1.784  73.018  1.00 39.53      A    C
ATOM   1664  OH  TYR A 102      39.416   0.618  73.743  1.00 36.66      A    O
ATOM   1666  CE2 TYR A 102      38.558   2.834  73.595  1.00 38.93      A    C
ATOM   1668  CD2 TYR A 102      38.390   4.023  72.887  1.00 38.50      A    C
ATOM   1670  C   TYR A 102      39.583   7.676  69.866  1.00 34.62      A    C
ATOM   1671  O   TYR A 102      39.012   8.643  70.364  1.00 34.31      A    O
ATOM   1673  N   TRP A 103      39.915   7.656  68.592  1.00 33.17      A    N
ATOM   1674  CA  TRP A 103      39.738   8.831  67.755  1.00 31.66      A    C
ATOM   1676  CB  TRP A 103      41.096   9.317  67.302  1.00 32.00      A    C
ATOM   1679  CG  TRP A 103      41.858   9.899  68.403  1.00 30.14      A    C
ATOM   1680  CD1 TRP A 103      42.482   9.235  69.395  1.00 31.06      A    C
ATOM   1682  NE1 TRP A 103      43.089  10.128  70.248  1.00 28.68      A    N
ATOM   1684  CE2 TRP A 103      42.834  11.394  69.814  1.00 25.92      A    C
ATOM   1685  CD2 TRP A 103      42.073  11.287  68.644  1.00 27.28      A    C
ATOM   1686  CE3 TRP A 103      41.715  12.448  67.968  1.00 27.73      A    C
ATOM   1688  CZ3 TRP A 103      42.100  13.687  68.505  1.00 25.84      A    C
ATOM   1690  CH2 TRP A 103      42.856  13.751  69.663  1.00 27.09      A    C
ATOM   1692  CZ2 TRP A 103      43.241  12.619  70.333  1.00 27.26      A    C
ATOM   1694  C   TRP A 103      38.907   8.453  66.561  1.00 30.98      A    C
ATOM   1695  O   TRP A 103      39.123   7.406  65.967  1.00 31.17      A    O
ATOM   1697  N   GLY A 104      37.919   9.272  66.239  1.00 29.29      A    N
ATOM   1698  CA  GLY A 104      37.275   9.164  64.958  1.00 29.48      A    C
ATOM   1701  C   GLY A 104      38.194   9.701  63.856  1.00 28.58      A    C
ATOM   1702  O   GLY A 104      39.226  10.270  64.147  1.00 28.16      A    O
ATOM   1704  N   PRO A 105      37.840   9.484  62.590  1.00 28.63      A    N
ATOM   1705  CA  PRO A 105      38.732   9.903  61.478  1.00 29.12      A    C
ATOM   1707  CB  PRO A 105      38.243   9.088  60.276  1.00 29.01      A    C
ATOM   1710  CG  PRO A 105      36.926   8.582  60.626  1.00 28.98      A    C
ATOM   1713  CD  PRO A 105      36.734   8.645  62.133  1.00 27.88      A    C
ATOM   1716  C   PRO A 105      38.611  11.374  61.152  1.00 29.49      A    C
ATOM   1717  O   PRO A 105      39.421  11.889  60.374  1.00 31.88      A    O
```

Figure 8 – CONT.

```
ATOM   1718  N    GLY A 106      37.594  12.036  61.693  1.00 28.76      A  N
ATOM   1719  CA   GLY A 106      37.430  13.449  61.505  1.00 27.46      A  C
ATOM   1722  C    GLY A 106      36.302  13.730  60.546  1.00 27.43      A  C
ATOM   1723  O    GLY A 106      36.019  12.940  59.643  1.00 27.18      A  O
ATOM   1725  N    THR A 107      35.609  14.842  60.791  1.00 27.31      A  N
ATOM   1726  CA   THR A 107      34.643  15.378  59.858  1.00 26.44      A  C
ATOM   1728  CB   THR A 107      33.261  15.465  60.504  1.00 26.68      A  C
ATOM   1730  OG1  THR A 107      32.768  14.142  60.756  1.00 25.37      A  O
ATOM   1732  CG2  THR A 107      32.318  16.216  59.609  1.00 28.54      A  C
ATOM   1736  C    THR A 107      35.097  16.770  59.456  1.00 25.74      A  C
ATOM   1737  O    THR A 107      35.194  17.675  60.319  1.00 25.40      A  O
ATOM   1739  N    LEU A 108      35.340  16.957  58.152  1.00 24.68      A  N
ATOM   1740  CA   LEU A 108      35.705  18.254  57.613  1.00 24.57      A  C
ATOM   1742  CB   LEU A 108      36.402  18.138  56.227  1.00 24.92      A  C
ATOM   1745  CG   LEU A 108      36.690  19.542  55.590  1.00 25.99      A  C
ATOM   1747  CD1  LEU A 108      37.297  19.429  54.159  1.00 29.31      A  C
ATOM   1751  CD2  LEU A 108      37.600  20.471  56.473  1.00 23.79      A  C
ATOM   1755  C    LEU A 108      34.453  19.074  57.471  1.00 23.74      A  C
ATOM   1756  O    LEU A 108      33.475  18.660  56.839  1.00 24.03      A  O
ATOM   1758  N    VAL A 109      34.478  20.257  58.031  1.00 23.35      A  N
ATOM   1759  CA   VAL A 109      33.363  21.176  57.901  1.00 22.89      A  C
ATOM   1761  CB   VAL A 109      32.718  21.505  59.273  1.00 22.83      A  C
ATOM   1763  CG1  VAL A 109      31.712  22.625  59.140  1.00 23.49      A  C
ATOM   1767  CG2  VAL A 109      32.040  20.300  59.837  1.00 19.85      A  C
ATOM   1771  C    VAL A 109      33.944  22.428  57.290  1.00 23.58      A  C
ATOM   1772  O    VAL A 109      34.855  23.049  57.877  1.00 23.81      A  O
ATOM   1774  N    THR A 110      33.440  22.768  56.101  1.00 23.92      A  N
ATOM   1775  CA   THR A 110      33.872  23.939  55.367  1.00 23.03      A  C
ATOM   1777  CB   THR A 110      34.177  23.634  53.849  1.00 24.19      A  C
ATOM   1779  OG1  THR A 110      35.261  22.692  53.722  1.00 24.94      A  O
ATOM   1781  CG2  THR A 110      34.471  24.949  53.078  1.00 21.39      A  C
ATOM   1785  C    THR A 110      32.718  24.841  55.397  1.00 23.60      A  C
ATOM   1786  O    THR A 110      31.640  24.447  54.972  1.00 24.16      A  O
ATOM   1788  N    VAL A 111      32.945  26.069  55.857  1.00 24.07      A  N
ATOM   1789  CA   VAL A 111      31.925  27.062  55.924  1.00 24.57      A  C
ATOM   1791  CB   VAL A 111      31.699  27.545  57.376  1.00 24.61      A  C
ATOM   1793  CG1  VAL A 111      30.514  28.480  57.431  1.00 22.21      A  C
ATOM   1797  CG2  VAL A 111      31.545  26.330  58.338  1.00 23.01      A  C
ATOM   1801  C    VAL A 111      32.419  28.217  55.113  1.00 25.98      A  C
ATOM   1802  O    VAL A 111      33.446  28.775  55.426  1.00 26.08      A  O
ATOM   1804  N    SER A 112      31.699  28.573  54.062  1.00 28.32      A  N
ATOM   1805  CA   SER A 112      32.051  29.770  53.268  1.00 30.32      A  C
ATOM   1807  CB   SER A 112      33.230  29.513  52.296  1.00 30.72      A  C
ATOM   1810  OG   SER A 112      32.778  28.842  51.111  1.00 31.46      A  O
ATOM   1812  C    SER A 112      30.868  30.187  52.479  1.00 31.00      A  C
ATOM   1813  O    SER A 112      29.893  29.458  52.363  1.00 30.87      A  O
ATOM   1815  N    SER A 113      30.980  31.365  51.893  1.00 33.92      A  N
ATOM   1816  CA   SER A 113      29.929  31.902  51.025  1.00 34.78      A  C
ATOM   1818  CB   SER A 113      30.209  33.369  50.748  1.00 35.72      A  C
ATOM   1821  OG   SER A 113      30.192  34.115  51.970  1.00 36.27      A  O
ATOM   1823  C    SER A 113      29.765  31.113  49.724  1.00 36.14      A  C
ATOM   1824  O    SER A 113      28.651  31.024  49.196  1.00 37.02      A  O
ATOM   1826  N    ALA A 114      30.819  30.466  49.233  1.00 37.15      A  N
ATOM   1827  CA   ALA A 114      30.698  29.714  47.967  1.00 37.89      A  C
ATOM   1829  CB   ALA A 114      32.049  29.654  47.251  1.00 37.91      A  C
ATOM   1833  C    ALA A 114      30.180  28.316  48.248  1.00 39.05      A  C
ATOM   1834  O    ALA A 114      30.503  27.732  49.286  1.00 40.56      A  O
ATOM   1836  N    SER A 115      29.353  27.749  47.375  1.00 39.67      A  N
```

Figure 8 – CONT.

```
ATOM   1837  CA   SER A 115      28.901  26.358  47.612  1.00 39.83      A  C
ATOM   1839  CB   SER A 115      27.409  26.155  47.312  1.00 40.04      A  C
ATOM   1842  OG   SER A 115      26.993  26.885  46.179  1.00 41.24      A  O
ATOM   1844  C    SER A 115      29.765  25.396  46.814  1.00 39.55      A  C
ATOM   1845  O    SER A 115      30.619  25.813  46.042  1.00 38.70      A  O
ATOM   1847  N    THR A 116      29.537  24.113  47.003  1.00 39.36      A  N
ATOM   1848  CA   THR A 116      30.349  23.129  46.334  1.00 40.65      A  C
ATOM   1850  CB   THR A 116      30.003  21.708  46.822  1.00 40.56      A  C
ATOM   1852  OG1  THR A 116      30.660  21.537  48.079  1.00 44.01      A  O
ATOM   1854  CG2  THR A 116      30.540  20.622  45.912  1.00 43.56      A  C
ATOM   1858  C    THR A 116      30.286  23.310  44.814  1.00 40.20      A  C
ATOM   1859  O    THR A 116      29.228  23.638  44.265  1.00 39.87      A  O
ATOM   1861  N    LYS A 117      31.458  23.168  44.180  1.00 39.61      A  N
ATOM   1862  CA   LYS A 117      31.609  23.147  42.732  1.00 39.11      A  C
ATOM   1864  CB   LYS A 117      32.273  24.438  42.215  1.00 39.92      A  C
ATOM   1867  CG   LYS A 117      32.261  24.516  40.672  1.00 40.13      A  C
ATOM   1870  CD   LYS A 117      33.175  25.589  40.089  1.00 40.87      A  C
ATOM   1873  CE   LYS A 117      33.307  25.416  38.542  1.00 39.90      A  C
ATOM   1876  NZ   LYS A 117      33.942  24.114  38.119  1.00 38.37      A  N
ATOM   1880  C    LYS A 117      32.454  21.938  42.305  1.00 38.16      A  C
ATOM   1881  O    LYS A 117      33.555  21.715  42.811  1.00 37.03      A  O
ATOM   1883  N    GLY A 118      31.912  21.157  41.383  1.00 36.96      A  N
ATOM   1884  CA   GLY A 118      32.651  20.104  40.746  1.00 36.67      A  C
ATOM   1887  C    GLY A 118      33.724  20.627  39.795  1.00 36.02      A  C
ATOM   1888  O    GLY A 118      33.675  21.777  39.341  1.00 36.53      A  O
ATOM   1890  N    PRO A 119      34.718  19.783  39.497  1.00 34.91      A  N
ATOM   1891  CA   PRO A 119      35.773  20.177  38.593  1.00 34.20      A  C
ATOM   1893  CB   PRO A 119      36.891  19.218  38.960  1.00 34.04      A  C
ATOM   1896  CG   PRO A 119      36.108  17.912  39.301  1.00 34.88      A  C
ATOM   1899  CD   PRO A 119      34.737  18.331  39.753  1.00 34.74      A  C
ATOM   1902  C    PRO A 119      35.370  19.942  37.146  1.00 33.37      A  C
ATOM   1903  O    PRO A 119      34.514  19.104  36.864  1.00 33.09      A  O
ATOM   1904  N    SER A 120      35.991  20.678  36.244  1.00 32.97      A  N
ATOM   1905  CA   SER A 120      36.067  20.277  34.847  1.00 32.61      A  C
ATOM   1907  CB   SER A 120      35.927  21.487  33.908  1.00 32.81      A  C
ATOM   1910  OG   SER A 120      34.777  22.278  34.203  1.00 33.20      A  O
ATOM   1912  C    SER A 120      37.444  19.650  34.678  1.00 32.07      A  C
ATOM   1913  O    SER A 120      38.450  20.125  35.213  1.00 31.82      A  O
ATOM   1915  N    VAL A 121      37.486  18.584  33.905  1.00 32.10      A  N
ATOM   1916  CA   VAL A 121      38.688  17.814  33.767  1.00 32.04      A  C
ATOM   1918  CB   VAL A 121      38.458  16.375  34.109  1.00 31.60      A  C
ATOM   1920  CG1  VAL A 121      39.802  15.631  34.023  1.00 32.48      A  C
ATOM   1924  CG2  VAL A 121      37.855  16.261  35.508  1.00 31.41      A  C
ATOM   1928  C    VAL A 121      39.188  17.887  32.349  1.00 31.75      A  C
ATOM   1929  O    VAL A 121      38.437  17.647  31.410  1.00 32.19      A  O
ATOM   1931  N    PHE A 122      40.466  18.205  32.210  1.00 30.71      A  N
ATOM   1932  CA   PHE A 122      41.055  18.404  30.898  1.00 30.31      A  C
ATOM   1934  CB   PHE A 122      41.496  19.854  30.736  1.00 29.67      A  C
ATOM   1937  CG   PHE A 122      40.388  20.845  30.813  1.00 29.85      A  C
ATOM   1938  CD1  PHE A 122      39.380  20.842  29.893  1.00 31.76      A  C
ATOM   1940  CE1  PHE A 122      38.364  21.794  29.951  1.00 32.41      A  C
ATOM   1942  CZ   PHE A 122      38.385  22.775  30.947  1.00 32.84      A  C
ATOM   1944  CE2  PHE A 122      39.389  22.814  31.848  1.00 29.89      A  C
ATOM   1946  CD2  PHE A 122      40.384  21.836  31.798  1.00 33.68      A  C
ATOM   1948  C    PHE A 122      42.239  17.454  30.727  1.00 30.21      A  C
ATOM   1949  O    PHE A 122      42.971  17.216  31.665  1.00 30.03      A  O
ATOM   1951  N    PRO A 123      42.415  16.890  29.524  1.00 30.69      A  N
ATOM   1952  CA   PRO A 123      43.562  16.014  29.286  1.00 30.93      A  C
```

Figure 8 – CONT.

```
ATOM   1954  CB   PRO A 123      43.202  15.364  27.952  1.00 31.10       A  C
ATOM   1957  CG   PRO A 123      42.531  16.489  27.206  1.00 30.26       A  C
ATOM   1960  CD   PRO A 123      41.739  17.245  28.264  1.00 30.62       A  C
ATOM   1963  C    PRO A 123      44.906  16.789  29.186  1.00 31.03       A  C
ATOM   1964  O    PRO A 123      44.941  17.917  28.710  1.00 30.52       A  O
ATOM   1965  N    LEU A 124      45.973  16.211  29.726  1.00 31.47       A  N
ATOM   1966  CA   LEU A 124      47.313  16.729  29.548  1.00 32.14       A  C
ATOM   1968  CB   LEU A 124      48.045  16.885  30.879  1.00 31.69       A  C
ATOM   1971  CG   LEU A 124      47.365  17.885  31.833  1.00 31.03       A  C
ATOM   1973  CD1  LEU A 124      48.056  17.917  33.148  1.00 28.70       A  C
ATOM   1977  CD2  LEU A 124      47.316  19.295  31.235  1.00 28.96       A  C
ATOM   1981  C    LEU A 124      47.975  15.724  28.607  1.00 33.30       A  C
ATOM   1982  O    LEU A 124      48.504  14.701  29.024  1.00 32.71       A  O
ATOM   1984  N    ALA A 125      47.870  16.021  27.320  1.00 34.64       A  N
ATOM   1985  CA   ALA A 125      48.202  15.059  26.280  1.00 36.33       A  C
ATOM   1987  CB   ALA A 125      47.691  15.561  24.925  1.00 36.13       A  C
ATOM   1991  C    ALA A 125      49.714  14.798  26.204  1.00 37.52       A  C
ATOM   1992  O    ALA A 125      50.503  15.736  26.265  1.00 36.34       A  O
ATOM   1994  N    PRO A 126      50.104  13.518  26.038  1.00 39.55       A  N
ATOM   1995  CA   PRO A 126      51.488  13.146  25.754  1.00 40.70       A  C
ATOM   1997  CB   PRO A 126      51.443  11.622  25.701  1.00 40.71       A  C
ATOM   2000  CG   PRO A 126      50.063  11.281  25.316  1.00 40.57       A  C
ATOM   2003  CD   PRO A 126      49.171  12.416  25.739  1.00 40.13       A  C
ATOM   2006  C    PRO A 126      51.931  13.715  24.419  1.00 41.71       A  C
ATOM   2007  O    PRO A 126      51.118  13.860  23.513  1.00 41.57       A  O
ATOM   2008  N    SER A 127      53.199  14.092  24.315  1.00 43.99       A  N
ATOM   2009  CA   SER A 127      53.703  14.708  23.070  1.00 45.68       A  C
ATOM   2011  CB   SER A 127      53.383  16.198  23.052  1.00 45.12       A  C
ATOM   2014  OG   SER A 127      54.308  16.880  23.856  1.00 44.45       A  O
ATOM   2016  C    SER A 127      55.200  14.512  22.952  1.00 47.25       A  C
ATOM   2017  O    SER A 127      55.790  13.893  23.820  1.00 48.05       A  O
ATOM   2019  N    SER A 128      55.821  15.039  21.895  1.00 49.42       A  N
ATOM   2020  CA   SER A 128      57.289  14.944  21.769  1.00 51.18       A  C
ATOM   2022  CB   SER A 128      57.788  15.264  20.344  1.00 51.30       A  C
ATOM   2025  OG   SER A 128      57.308  16.504  19.863  1.00 51.68       A  O
ATOM   2027  C    SER A 128      57.950  15.829  22.831  1.00 52.47       A  C
ATOM   2028  O    SER A 128      58.908  15.405  23.476  1.00 52.84       A  O
ATOM   2030  N    LYS A 129      57.394  17.025  23.060  1.00 53.97       A  N
ATOM   2031  CA   LYS A 129      57.843  17.907  24.167  1.00 54.90       A  C
ATOM   2033  CB   LYS A 129      57.132  19.286  24.114  1.00 55.14       A  C
ATOM   2036  CG   LYS A 129      57.840  20.358  23.253  1.00 55.12       A  C
ATOM   2042  C    LYS A 129      57.725  17.295  25.590  1.00 55.30       A  C
ATOM   2043  O    LYS A 129      58.434  17.741  26.514  1.00 55.79       A  O
ATOM   2045  N    SER A 130      56.872  16.282  25.771  1.00 55.74       A  N
ATOM   2046  CA   SER A 130      56.732  15.599  27.083  1.00 56.20       A  C
ATOM   2048  CB   SER A 130      55.242  15.552  27.509  1.00 56.35       A  C
ATOM   2051  OG   SER A 130      54.536  14.445  26.952  1.00 54.91       A  O
ATOM   2053  C    SER A 130      57.345  14.181  27.151  1.00 57.08       A  C
ATOM   2054  O    SER A 130      57.095  13.431  28.114  1.00 56.53       A  O
ATOM   2056  N    THR A 133      58.149  13.822  26.147  1.00 58.30       A  N
ATOM   2057  CA   THR A 133      58.665  12.454  26.005  1.00 59.19       A  C
ATOM   2059  CB   THR A 133      58.010  11.709  24.811  1.00 59.61       A  C
ATOM   2061  OG1  THR A 133      58.430  12.309  23.584  1.00 61.18       A  O
ATOM   2063  CG2  THR A 133      56.491  11.745  24.883  1.00 58.93       A  C
ATOM   2067  C    THR A 133      60.181  12.429  25.780  1.00 59.77       A  C
ATOM   2068  O    THR A 133      60.715  13.151  24.937  1.00 59.56       A  O
ATOM   2070  N    SER A 134      60.867  11.569  26.525  1.00 60.10       A  N
ATOM   2071  CA   SER A 134      62.303  11.473  26.418  1.00 60.32       A  C
```

Figure 8 – CONT.

```
ATOM   2073  CB   SER A 134      62.959  12.608  27.207  1.00 60.91           A    C
ATOM   2076  OG   SER A 134      62.522  13.879  26.750  1.00 61.32           A    O
ATOM   2078  C    SER A 134      62.782  10.129  26.950  1.00 59.85           A    C
ATOM   2079  O    SER A 134      62.249   9.616  27.943  1.00 59.63           A    O
ATOM   2081  N    GLY A 135      63.784   9.566  26.274  1.00 58.96           A    N
ATOM   2082  CA   GLY A 135      64.408   8.325  26.707  1.00 58.18           A    C
ATOM   2085  C    GLY A 135      63.431   7.183  26.835  1.00 57.49           A    C
ATOM   2086  O    GLY A 135      63.508   6.404  27.779  1.00 57.70           A    O
ATOM   2088  N    GLY A 136      62.486   7.101  25.904  1.00 56.86           A    N
ATOM   2089  CA   GLY A 136      61.599   5.942  25.815  1.00 56.44           A    C
ATOM   2092  C    GLY A 136      60.357   5.924  26.699  1.00 55.76           A    C
ATOM   2093  O    GLY A 136      59.509   5.038  26.541  1.00 56.25           A    O
ATOM   2095  N    THR A 137      60.236   6.850  27.649  1.00 54.54           A    N
ATOM   2096  CA   THR A 137      58.955   6.995  28.366  1.00 53.57           A    C
ATOM   2098  CB   THR A 137      59.077   6.644  29.867  1.00 53.90           A    C
ATOM   2100  OG1  THR A 137      60.078   7.457  30.482  1.00 53.59           A    O
ATOM   2102  CG2  THR A 137      59.413   5.122  30.053  1.00 54.05           A    C
ATOM   2106  C    THR A 137      58.308   8.377  28.144  1.00 51.96           A    C
ATOM   2107  O    THR A 137      58.987   9.359  27.885  1.00 51.65           A    O
ATOM   2109  N    ALA A 138      56.979   8.415  28.186  1.00 50.47           A    N
ATOM   2110  CA   ALA A 138      56.211   9.652  27.962  1.00 48.82           A    C
ATOM   2112  CB   ALA A 138      55.270   9.482  26.767  1.00 48.79           A    C
ATOM   2116  C    ALA A 138      55.415  10.055  29.216  1.00 46.92           A    C
ATOM   2117  O    ALA A 138      55.007   9.194  30.014  1.00 47.22           A    O
ATOM   2119  N    ALA A 139      55.214  11.363  29.382  1.00 44.56           A    N
ATOM   2120  CA   ALA A 139      54.370  11.919  30.454  1.00 42.81           A    C
ATOM   2122  CB   ALA A 139      55.072  13.098  31.140  1.00 42.04           A    C
ATOM   2126  C    ALA A 139      53.011  12.359  29.887  1.00 41.02           A    C
ATOM   2127  O    ALA A 139      52.947  13.069  28.894  1.00 40.89           A    O
ATOM   2129  N    LEU A 140      51.933  11.908  30.518  1.00 39.64           A    N
ATOM   2130  CA   LEU A 140      50.577  12.431  30.266  1.00 37.80           A    C
ATOM   2132  CB   LEU A 140      49.761  11.485  29.394  1.00 37.45           A    C
ATOM   2135  CG   LEU A 140      49.658  10.102  30.017  1.00 37.70           A    C
ATOM   2137  CD1  LEU A 140      48.291   9.506  29.868  1.00 38.85           A    C
ATOM   2141  CD2  LEU A 140      50.695   9.207  29.405  1.00 40.18           A    C
ATOM   2145  C    LEU A 140      49.884  12.581  31.604  1.00 36.42           A    C
ATOM   2146  O    LEU A 140      50.363  12.083  32.601  1.00 36.09           A    O
ATOM   2148  N    GLY A 141      48.747  13.265  31.614  1.00 34.99           A    N
ATOM   2149  CA   GLY A 141      48.017  13.511  32.854  1.00 33.65           A    C
ATOM   2152  C    GLY A 141      46.651  14.183  32.659  1.00 32.45           A    C
ATOM   2153  O    GLY A 141      46.170  14.375  31.519  1.00 29.54           A    O
ATOM   2155  N    CYS A 142      46.011  14.500  33.786  1.00 31.15           A    N
ATOM   2156  CA   CYS A 142      44.724  15.178  33.751  1.00 30.33           A    C
ATOM   2158  CB   CYS A 142      43.628  14.284  34.275  1.00 30.26           A    C
ATOM   2161  SG   CYS A 142      43.166  12.996  33.064  1.00 35.05           A    S
ATOM   2163  C    CYS A 142      44.835  16.394  34.590  1.00 28.59           A    C
ATOM   2164  O    CYS A 142      45.453  16.369  35.647  1.00 28.39           A    O
ATOM   2166  N    LEU A 143      44.244  17.461  34.102  1.00 27.31           A    N
ATOM   2167  CA   LEU A 143      44.138  18.696  34.829  1.00 26.81           A    C
ATOM   2169  CB   LEU A 143      44.347  19.862  33.883  1.00 25.52           A    C
ATOM   2172  CG   LEU A 143      44.089  21.265  34.435  1.00 25.10           A    C
ATOM   2174  CD1  LEU A 143      44.910  21.552  35.637  1.00 21.58           A    C
ATOM   2178  CD2  LEU A 143      44.324  22.307  33.370  1.00 21.21           A    C
ATOM   2182  C    LEU A 143      42.704  18.721  35.399  1.00 27.61           A    C
ATOM   2183  O    LEU A 143      41.730  18.670  34.650  1.00 27.90           A    O
ATOM   2185  N    VAL A 144      42.613  18.793  36.721  1.00 28.25           A    N
ATOM   2186  CA   VAL A 144      41.366  18.883  37.442  1.00 28.70           A    C
ATOM   2188  CB   VAL A 144      41.397  17.916  38.613  1.00 29.11           A    C
```

Figure 8 – CONT.

```
ATOM   2190  CG1 VAL A 144      40.052  17.904  39.310  1.00 28.72           A  C
ATOM   2194  CG2 VAL A 144      41.722  16.500  38.087  1.00 28.65           A  C
ATOM   2198  C   VAL A 144      41.178  20.314  37.901  1.00 28.97           A  C
ATOM   2199  O   VAL A 144      41.780  20.762  38.856  1.00 28.85           A  O
ATOM   2201  N   LYS A 145      40.335  21.040  37.184  1.00 30.50           A  N
ATOM   2202  CA  LYS A 145      40.277  22.489  37.275  1.00 31.55           A  C
ATOM   2204  CB  LYS A 145      40.287  23.053  35.860  1.00 32.31           A  C
ATOM   2207  CG  LYS A 145      40.551  24.520  35.786  1.00 35.59           A  C
ATOM   2210  CD  LYS A 145      42.044  24.796  35.726  1.00 39.98           A  C
ATOM   2213  CE  LYS A 145      42.350  26.288  35.893  1.00 42.00           A  C
ATOM   2216  NZ  LYS A 145      41.343  27.102  35.108  1.00 44.61           A  N
ATOM   2220  C   LYS A 145      39.014  23.008  38.003  1.00 31.76           A  C
ATOM   2221  O   LYS A 145      37.918  22.506  37.784  1.00 30.89           A  O
ATOM   2223  N   ASP A 146      39.219  24.032  38.828  1.00 32.28           A  N
ATOM   2224  CA  ASP A 146      38.157  24.823  39.486  1.00 34.30           A  C
ATOM   2226  CB  ASP A 146      37.449  25.715  38.449  1.00 34.78           A  C
ATOM   2229  CG  ASP A 146      38.368  26.766  37.863  1.00 35.72           A  C
ATOM   2230  OD1 ASP A 146      39.365  27.112  38.529  1.00 36.33           A  O
ATOM   2231  OD2 ASP A 146      38.102  27.233  36.726  1.00 43.62           A  O
ATOM   2232  C   ASP A 146      37.127  24.015  40.278  1.00 34.71           A  C
ATOM   2233  O   ASP A 146      35.957  23.980  39.921  1.00 35.87           A  O
ATOM   2235  N   TYR A 147      37.566  23.347  41.338  1.00 35.41           A  N
ATOM   2236  CA  TYR A 147      36.647  22.571  42.181  1.00 35.47           A  C
ATOM   2238  CB  TYR A 147      36.977  21.100  42.139  1.00 34.88           A  C
ATOM   2241  CG  TYR A 147      38.308  20.745  42.748  1.00 35.13           A  C
ATOM   2242  CD1 TYR A 147      39.449  20.621  41.958  1.00 34.68           A  C
ATOM   2244  CE1 TYR A 147      40.677  20.271  42.511  1.00 32.33           A  C
ATOM   2246  CZ  TYR A 147      40.763  20.042  43.863  1.00 33.42           A  C
ATOM   2247  OH  TYR A 147      41.970  19.690  44.417  1.00 34.96           A  O
ATOM   2249  CE2 TYR A 147      39.634  20.143  44.675  1.00 34.52           A  C
ATOM   2251  CD2 TYR A 147      38.420  20.480  44.112  1.00 34.98           A  C
ATOM   2253  C   TYR A 147      36.702  23.057  43.625  1.00 35.96           A  C
ATOM   2254  O   TYR A 147      37.668  23.710  44.024  1.00 35.60           A  O
ATOM   2256  N   PHE A 148      35.665  22.711  44.399  1.00 36.71           A  N
ATOM   2257  CA  PHE A 148      35.544  23.197  45.768  1.00 36.98           A  C
ATOM   2259  CB  PHE A 148      35.059  24.636  45.779  1.00 36.82           A  C
ATOM   2262  CG  PHE A 148      35.066  25.266  47.142  1.00 38.12           A  C
ATOM   2263  CD1 PHE A 148      36.248  25.742  47.697  1.00 38.90           A  C
ATOM   2265  CE1 PHE A 148      36.264  26.357  48.951  1.00 37.29           A  C
ATOM   2267  CZ  PHE A 148      35.086  26.496  49.650  1.00 38.80           A  C
ATOM   2269  CE2 PHE A 148      33.896  26.016  49.106  1.00 38.78           A  C
ATOM   2271  CD2 PHE A 148      33.889  25.410  47.864  1.00 37.90           A  C
ATOM   2273  C   PHE A 148      34.612  22.394  46.646  1.00 37.05           A  C
ATOM   2274  O   PHE A 148      33.580  21.893  46.181  1.00 37.39           A  O
ATOM   2276  N   PRO A 149      35.014  22.190  47.915  1.00 36.47           A  N
ATOM   2277  CA  PRO A 149      36.365  22.382  48.468  1.00 35.88           A  C
ATOM   2279  CB  PRO A 149      36.086  22.539  49.958  1.00 36.09           A  C
ATOM   2282  CG  PRO A 149      34.941  21.557  50.187  1.00 36.34           A  C
ATOM   2285  CD  PRO A 149      34.137  21.518  48.886  1.00 36.87           A  C
ATOM   2288  C   PRO A 149      37.149  21.090  48.204  1.00 34.64           A  C
ATOM   2289  O   PRO A 149      36.717  20.281  47.392  1.00 32.91           A  O
ATOM   2290  N   GLU A 150      38.266  20.892  48.888  1.00 34.28           A  N
ATOM   2291  CA  GLU A 150      38.988  19.625  48.840  1.00 34.72           A  C
ATOM   2293  CB  GLU A 150      40.297  19.741  49.619  1.00 35.20           A  C
ATOM   2296  CG  GLU A 150      41.300  20.700  48.984  1.00 36.93           A  C
ATOM   2299  CD  GLU A 150      42.307  19.980  48.108  1.00 37.86           A  C
ATOM   2300  OE1 GLU A 150      41.897  19.126  47.266  1.00 33.67           A  O
ATOM   2301  OE2 GLU A 150      43.516  20.267  48.308  1.00 39.30           A  O
```

Figure 8 – CONT.

```
ATOM   2302  C    GLU A 150      38.160  18.509  49.444  1.00 34.81      A    C
ATOM   2303  O    GLU A 150      37.239  18.767  50.208  1.00 35.34      A    O
ATOM   2305  N    PRO A 151      38.481  17.255  49.124  1.00 34.17      A    N
ATOM   2306  CA   PRO A 151      39.481  16.734  48.231  1.00 34.03      A    C
ATOM   2308  CB   PRO A 151      40.061  15.572  49.030  1.00 33.99      A    C
ATOM   2311  CG   PRO A 151      38.825  14.970  49.691  1.00 34.07      A    C
ATOM   2314  CD   PRO A 151      37.937  16.196  49.988  1.00 34.72      A    C
ATOM   2317  C    PRO A 151      38.956  16.140  46.927  1.00 34.11      A    C
ATOM   2318  O    PRO A 151      37.757  15.863  46.783  1.00 33.00      A    O
ATOM   2319  N    VAL A 152      39.915  15.867  46.036  1.00 33.93      A    N
ATOM   2320  CA   VAL A 152      39.700  15.119  44.842  1.00 34.62      A    C
ATOM   2322  CB   VAL A 152      39.997  15.993  43.594  1.00 34.98      A    C
ATOM   2324  CG1  VAL A 152      40.526  15.157  42.404  1.00 33.96      A    C
ATOM   2328  CG2  VAL A 152      38.779  16.768  43.211  1.00 34.31      A    C
ATOM   2332  C    VAL A 152      40.589  13.882  44.838  1.00 35.42      A    C
ATOM   2333  O    VAL A 152      41.704  13.918  45.283  1.00 36.57      A    O
ATOM   2335  N    THR A 153      40.083  12.814  44.267  1.00 36.25      A    N
ATOM   2336  CA   THR A 153      40.765  11.542  44.191  1.00 37.59      A    C
ATOM   2338  CB   THR A 153      39.832  10.452  44.818  1.00 37.54      A    C
ATOM   2340  OG1  THR A 153      40.297  10.161  46.141  1.00 42.31      A    O
ATOM   2342  CG2  THR A 153      39.788   9.177  44.018  1.00 38.59      A    C
ATOM   2346  C    THR A 153      41.017  11.276  42.710  1.00 37.26      A    C
ATOM   2347  O    THR A 153      40.096  11.453  41.915  1.00 37.23      A    O
ATOM   2349  N    VAL A 154      42.234  10.875  42.330  1.00 36.78      A    N
ATOM   2350  CA   VAL A 154      42.487  10.487  40.952  1.00 36.88      A    C
ATOM   2352  CB   VAL A 154      43.441  11.465  40.226  1.00 36.98      A    C
ATOM   2354  CG1  VAL A 154      43.552  11.118  38.731  1.00 34.44      A    C
ATOM   2358  CG2  VAL A 154      42.978  12.889  40.419  1.00 33.14      A    C
ATOM   2362  C    VAL A 154      43.051   9.086  40.915  1.00 38.30      A    C
ATOM   2363  O    VAL A 154      43.966   8.761  41.648  1.00 39.27      A    O
ATOM   2365  N    SER A 156      42.464   8.232  40.100  1.00 39.47      A    N
ATOM   2366  CA   SER A 156      43.099   6.986  39.769  1.00 40.52      A    C
ATOM   2368  CB   SER A 156      42.264   5.816  40.271  1.00 40.65      A    C
ATOM   2371  OG   SER A 156      40.958   5.848  39.723  1.00 42.45      A    O
ATOM   2373  C    SER A 156      43.237   6.959  38.258  1.00 41.24      A    C
ATOM   2374  O    SER A 156      42.651   7.798  37.561  1.00 41.08      A    O
ATOM   2376  N    TRP A 157      44.022   6.004  37.766  1.00 42.11      A    N
ATOM   2377  CA   TRP A 157      44.193   5.776  36.349  1.00 42.86      A    C
ATOM   2379  CB   TRP A 157      45.638   6.012  35.995  1.00 41.95      A    C
ATOM   2382  CG   TRP A 157      45.990   7.467  36.027  1.00 39.47      A    C
ATOM   2383  CD1  TRP A 157      46.431   8.188  37.096  1.00 36.37      A    C
ATOM   2385  NE1  TRP A 157      46.643   9.489  36.731  1.00 34.76      A    N
ATOM   2387  CE2  TRP A 157      46.342   9.632  35.406  1.00 34.24      A    C
ATOM   2388  CD2  TRP A 157      45.915   8.377  34.931  1.00 36.62      A    C
ATOM   2389  CE3  TRP A 157      45.560   8.243  33.575  1.00 35.48      A    C
ATOM   2391  CZ3  TRP A 157      45.629   9.374  32.753  1.00 36.47      A    C
ATOM   2393  CH2  TRP A 157      46.051  10.606  33.266  1.00 36.46      A    C
ATOM   2395  CZ2  TRP A 157      46.410  10.751  34.593  1.00 35.73      A    C
ATOM   2397  C    TRP A 157      43.760   4.361  35.953  1.00 45.14      A    C
ATOM   2398  O    TRP A 157      44.081   3.393  36.639  1.00 45.94      A    O
ATOM   2400  N    ASN A 162      43.024   4.258  34.852  1.00 47.51      A    N
ATOM   2401  CA   ASN A 162      42.470   2.993  34.389  1.00 49.57      A    C
ATOM   2403  CB   ASN A 162      43.551   2.152  33.694  1.00 50.11      A    C
ATOM   2406  CG   ASN A 162      44.105   2.818  32.449  1.00 51.69      A    C
ATOM   2407  OD1  ASN A 162      43.545   3.800  31.945  1.00 54.04      A    O
ATOM   2408  ND2  ASN A 162      45.204   2.274  31.929  1.00 52.87      A    N
ATOM   2411  C    ASN A 162      41.827   2.214  35.536  1.00 50.79      A    C
ATOM   2412  O    ASN A 162      42.047   1.007  35.693  1.00 51.11      A    O
```

Figure 8 – CONT.

```
ATOM   2414  N    SER A 163      41.040   2.940  36.329  1.00 52.02      A    N
ATOM   2415  CA   SER A 163      40.342   2.420  37.490  1.00 52.74      A    C
ATOM   2417  CB   SER A 163      39.136   1.609  37.034  1.00 52.90      A    C
ATOM   2420  OG   SER A 163      38.329   2.379  36.154  1.00 53.87      A    O
ATOM   2422  C    SER A 163      41.202   1.593  38.446  1.00 53.22      A    C
ATOM   2423  O    SER A 163      40.702   0.648  39.051  1.00 53.74      A    O
ATOM   2425  N    GLY A 164      42.474   1.948  38.598  1.00 53.50      A    N
ATOM   2426  CA   GLY A 164      43.360   1.250  39.545  1.00 53.85      A    C
ATOM   2429  C    GLY A 164      44.380   0.310  38.917  1.00 53.92      A    C
ATOM   2430  O    GLY A 164      45.428   0.050  39.500  1.00 54.12      A    O
ATOM   2432  N    ALA A 165      44.080  -0.190  37.723  1.00 54.40      A    N
ATOM   2433  CA   ALA A 165      45.012  -1.049  36.963  1.00 54.69      A    C
ATOM   2435  CB   ALA A 165      44.398  -1.431  35.600  1.00 54.50      A    C
ATOM   2439  C    ALA A 165      46.410  -0.444  36.755  1.00 54.81      A    C
ATOM   2440  O    ALA A 165      47.398  -1.179  36.652  1.00 54.89      A    O
ATOM   2442  N    LEU A 166      46.488   0.886  36.690  1.00 54.73      A    N
ATOM   2443  CA   LEU A 166      47.744   1.591  36.485  1.00 54.50      A    C
ATOM   2445  CB   LEU A 166      47.620   2.516  35.268  1.00 54.33      A    C
ATOM   2448  CG   LEU A 166      48.834   3.336  34.834  1.00 54.33      A    C
ATOM   2450  CD1  LEU A 166      50.050   2.441  34.597  1.00 54.69      A    C
ATOM   2454  CD2  LEU A 166      48.509   4.152  33.571  1.00 53.54      A    C
ATOM   2458  C    LEU A 166      48.046   2.390  37.737  1.00 54.62      A    C
ATOM   2459  O    LEU A 166      47.255   3.243  38.140  1.00 54.80      A    O
ATOM   2461  N    THR A 167      49.170   2.093  38.375  1.00 54.71      A    N
ATOM   2462  CA   THR A 167      49.584   2.810  39.587  1.00 54.59      A    C
ATOM   2464  CB   THR A 167      49.391   1.930  40.817  1.00 54.90      A    C
ATOM   2466  OG1  THR A 167      50.154   0.731  40.642  1.00 55.75      A    O
ATOM   2468  CG2  THR A 167      47.910   1.587  41.022  1.00 54.45      A    C
ATOM   2472  C    THR A 167      51.059   3.234  39.556  1.00 54.32      A    C
ATOM   2473  O    THR A 167      51.454   4.185  40.237  1.00 54.11      A    O
ATOM   2475  N    SER A 168      51.865   2.508  38.780  1.00 54.01      A    N
ATOM   2476  CA   SER A 168      53.307   2.774  38.632  1.00 53.44      A    C
ATOM   2478  CB   SER A 168      54.007   1.501  38.124  1.00 53.53      A    C
ATOM   2481  OG   SER A 168      54.972   1.807  37.133  1.00 54.95      A    O
ATOM   2483  C    SER A 168      53.604   3.958  37.693  1.00 52.26      A    C
ATOM   2484  O    SER A 168      53.119   4.018  36.573  1.00 51.99      A    O
ATOM   2486  N    GLY A 169      54.418   4.891  38.163  1.00 51.56      A    N
ATOM   2487  CA   GLY A 169      54.655   6.147  37.451  1.00 50.90      A    C
ATOM   2490  C    GLY A 169      53.600   7.220  37.687  1.00 49.91      A    C
ATOM   2491  O    GLY A 169      53.685   8.320  37.134  1.00 50.41      A    O
ATOM   2493  N    VAL A 171      52.606   6.918  38.506  1.00 48.81      A    N
ATOM   2494  CA   VAL A 171      51.508   7.837  38.726  1.00 48.16      A    C
ATOM   2496  CB   VAL A 171      50.244   7.124  39.190  1.00 47.77      A    C
ATOM   2498  CG1  VAL A 171      49.172   8.153  39.535  1.00 49.03      A    C
ATOM   2502  CG2  VAL A 171      49.765   6.188  38.115  1.00 48.21      A    C
ATOM   2506  C    VAL A 171      51.868   8.810  39.799  1.00 47.09      A    C
ATOM   2507  O    VAL A 171      52.269   8.422  40.877  1.00 47.04      A    O
ATOM   2509  N    HIS A 172      51.690  10.087  39.535  1.00 46.25      A    N
ATOM   2510  CA   HIS A 172      51.821  11.025  40.615  1.00 45.20      A    C
ATOM   2512  CB   HIS A 172      53.209  11.594  40.641  1.00 45.93      A    C
ATOM   2515  CG   HIS A 172      53.463  12.497  41.805  1.00 47.99      A    C
ATOM   2516  ND1  HIS A 172      54.593  13.283  41.896  1.00 50.65      A    N
ATOM   2518  CE1  HIS A 172      54.540  13.988  43.015  1.00 52.66      A    C
ATOM   2520  NE2  HIS A 172      53.426  13.676  43.659  1.00 51.76      A    N
ATOM   2522  CD2  HIS A 172      52.738  12.739  42.925  1.00 50.06      A    C
ATOM   2524  C    HIS A 172      50.769  12.113  40.540  1.00 43.87      A    C
ATOM   2525  O    HIS A 172      50.699  12.902  39.580  1.00 43.54      A    O
ATOM   2527  N    THR A 173      49.944  12.133  41.578  1.00 41.94      A    N
```

Figure 8 – CONT.

```
ATOM   2528  CA   THR A 173      48.924  13.136  41.744  1.00 40.21      A    C
ATOM   2530  CB   THR A 173      47.648  12.454  42.245  1.00 40.25      A    C
ATOM   2532  OG1  THR A 173      47.157  11.627  41.171  1.00 39.93      A    O
ATOM   2534  CG2  THR A 173      46.575  13.486  42.695  1.00 38.55      A    C
ATOM   2538  C    THR A 173      49.454  14.173  42.706  1.00 38.96      A    C
ATOM   2539  O    THR A 173      49.879  13.829  43.799  1.00 38.92      A    O
ATOM   2541  N    PHE A 174      49.420  15.433  42.290  1.00 37.48      A    N
ATOM   2542  CA   PHE A 174      50.044  16.520  43.015  1.00 37.25      A    C
ATOM   2544  CB   PHE A 174      50.565  17.597  42.053  1.00 37.16      A    C
ATOM   2547  CG   PHE A 174      51.789  17.182  41.248  1.00 36.29      A    C
ATOM   2548  CD1  PHE A 174      53.019  17.748  41.498  1.00 36.50      A    C
ATOM   2550  CE1  PHE A 174      54.137  17.386  40.757  1.00 37.79      A    C
ATOM   2552  CZ   PHE A 174      54.030  16.420  39.743  1.00 37.21      A    C
ATOM   2554  CE2  PHE A 174      52.821  15.861  39.480  1.00 37.15      A    C
ATOM   2556  CD2  PHE A 174      51.690  16.250  40.223  1.00 36.42      A    C
ATOM   2558  C    PHE A 174      49.087  17.172  43.982  1.00 37.44      A    C
ATOM   2559  O    PHE A 174      47.900  17.097  43.805  1.00 38.42      A    O
ATOM   2561  N    PRO A 175      49.611  17.821  45.022  1.00 37.95      A    N
ATOM   2562  CA   PRO A 175      48.822  18.696  45.876  1.00 37.88      A    C
ATOM   2564  CB   PRO A 175      49.847  19.180  46.910  1.00 37.69      A    C
ATOM   2567  CG   PRO A 175      50.771  18.032  47.064  1.00 38.02      A    C
ATOM   2570  CD   PRO A 175      50.858  17.391  45.692  1.00 38.34      A    C
ATOM   2573  C    PRO A 175      48.204  19.884  45.145  1.00 37.76      A    C
ATOM   2574  O    PRO A 175      48.892  20.584  44.403  1.00 38.15      A    O
ATOM   2575  N    ALA A 176      46.922  20.131  45.407  1.00 37.52      A    N
ATOM   2576  CA   ALA A 176      46.159  21.163  44.726  1.00 37.53      A    C
ATOM   2578  CB   ALA A 176      44.706  21.094  45.167  1.00 37.86      A    C
ATOM   2582  C    ALA A 176      46.703  22.541  45.004  1.00 37.66      A    C
ATOM   2583  O    ALA A 176      47.319  22.733  46.050  1.00 38.23      A    O
ATOM   2585  N    VAL A 177      46.508  23.467  44.054  1.00 37.71      A    N
ATOM   2586  CA   VAL A 177      46.691  24.894  44.275  1.00 38.64      A    C
ATOM   2588  CB   VAL A 177      47.132  25.735  43.006  1.00 38.04      A    C
ATOM   2590  CG1  VAL A 177      48.591  25.694  42.824  1.00 38.77      A    C
ATOM   2594  CG2  VAL A 177      46.397  25.344  41.754  1.00 36.42      A    C
ATOM   2598  C    VAL A 177      45.361  25.511  44.648  1.00 39.96      A    C
ATOM   2599  O    VAL A 177      44.329  25.111  44.116  1.00 40.05      A    O
ATOM   2601  N    LEU A 178      45.394  26.487  45.539  1.00 41.64      A    N
ATOM   2602  CA   LEU A 178      44.225  27.291  45.825  1.00 43.53      A    C
ATOM   2604  CB   LEU A 178      44.070  27.544  47.323  1.00 43.53      A    C
ATOM   2607  CG   LEU A 178      43.081  28.651  47.732  1.00 43.75      A    C
ATOM   2609  CD1  LEU A 178      41.694  28.474  47.116  1.00 39.85      A    C
ATOM   2613  CD2  LEU A 178      43.001  28.713  49.273  1.00 42.90      A    C
ATOM   2617  C    LEU A 178      44.440  28.587  45.090  1.00 44.81      A    C
ATOM   2618  O    LEU A 178      45.360  29.337  45.414  1.00 44.76      A    O
ATOM   2620  N    GLN A 179      43.612  28.836  44.081  1.00 46.73      A    N
ATOM   2621  CA   GLN A 179      43.785  30.020  43.234  1.00 48.30      A    C
ATOM   2623  CB   GLN A 179      43.097  29.819  41.889  1.00 48.66      A    C
ATOM   2626  CG   GLN A 179      43.510  28.540  41.169  1.00 51.00      A    C
ATOM   2629  CD   GLN A 179      42.339  27.879  40.458  1.00 55.23      A    C
ATOM   2630  OE1  GLN A 179      41.888  26.774  40.830  1.00 56.47      A    O
ATOM   2631  NE2  GLN A 179      41.819  28.563  39.441  1.00 58.08      A    N
ATOM   2634  C    GLN A 179      43.195  31.221  43.958  1.00 48.85      A    C
ATOM   2635  O    GLN A 179      42.700  31.071  45.073  1.00 49.39      A    O
ATOM   2637  N    SER A 180      43.260  32.398  43.328  1.00 49.37      A    N
ATOM   2638  CA   SER A 180      42.668  33.644  43.863  1.00 49.75      A    C
ATOM   2640  CB   SER A 180      43.221  34.880  43.129  1.00 50.42      A    C
ATOM   2643  OG   SER A 180      44.645  34.947  43.206  1.00 52.63      A    O
ATOM   2645  C    SER A 180      41.145  33.666  43.736  1.00 48.97      A    C
```

Figure 8 – CONT.

```
ATOM   2646  O    SER A 180      40.490  34.491  44.376  1.00 49.47      A    O
ATOM   2648  N    SER A 182      40.588  32.787  42.901  1.00 47.54      A    N
ATOM   2649  CA   SER A 182      39.134  32.627  42.807  1.00 46.42      A    C
ATOM   2651  CB   SER A 182      38.758  31.766  41.593  1.00 46.51      A    C
ATOM   2654  OG   SER A 182      39.272  30.437  41.709  1.00 45.25      A    O
ATOM   2656  C    SER A 182      38.531  31.970  44.056  1.00 45.51      A    C
ATOM   2657  O    SER A 182      37.325  32.045  44.271  1.00 45.61      A    O
ATOM   2659  N    GLY A 183      39.361  31.301  44.859  1.00 44.71      A    N
ATOM   2660  CA   GLY A 183      38.864  30.428  45.946  1.00 43.34      A    C
ATOM   2663  C    GLY A 183      38.599  28.998  45.485  1.00 42.18      A    C
ATOM   2664  O    GLY A 183      38.154  28.141  46.268  1.00 42.45      A    O
ATOM   2666  N    LEU A 184      38.848  28.723  44.206  1.00 40.25      A    N
ATOM   2667  CA   LEU A 184      38.690  27.367  43.717  1.00 37.85      A    C
ATOM   2669  CB   LEU A 184      38.110  27.332  42.322  1.00 38.11      A    C
ATOM   2672  CG   LEU A 184      36.645  27.633  42.022  1.00 38.11      A    C
ATOM   2674  CD1  LEU A 184      35.735  27.738  43.270  1.00 37.05      A    C
ATOM   2678  CD2  LEU A 184      36.570  28.860  41.150  1.00 38.91      A    C
ATOM   2682  C    LEU A 184      40.042  26.724  43.710  1.00 35.45      A    C
ATOM   2683  O    LEU A 184      41.055  27.402  43.658  1.00 33.45      A    O
ATOM   2685  N    TYR A 185      40.036  25.396  43.808  1.00 33.45      A    N
ATOM   2686  CA   TYR A 185      41.246  24.619  43.700  1.00 32.03      A    C
ATOM   2688  CB   TYR A 185      41.170  23.455  44.683  1.00 32.46      A    C
ATOM   2691  CG   TYR A 185      41.151  23.866  46.151  1.00 33.17      A    C
ATOM   2692  CD1  TYR A 185      42.328  24.053  46.855  1.00 33.88      A    C
ATOM   2694  CE1  TYR A 185      42.320  24.402  48.218  1.00 36.18      A    C
ATOM   2696  CZ   TYR A 185      41.106  24.558  48.880  1.00 36.80      A    C
ATOM   2697  OH   TYR A 185      41.084  24.926  50.202  1.00 40.44      A    O
ATOM   2699  CE2  TYR A 185      39.913  24.392  48.194  1.00 37.28      A    C
ATOM   2701  CD2  TYR A 185      39.941  24.031  46.836  1.00 36.55      A    C
ATOM   2703  C    TYR A 185      41.426  24.035  42.280  1.00 31.26      A    C
ATOM   2704  O    TYR A 185      40.449  23.833  41.550  1.00 29.05      A    O
ATOM   2706  N    SER A 186      42.677  23.713  41.935  1.00 30.50      A    N
ATOM   2707  CA   SER A 186      42.959  22.830  40.799  1.00 29.55      A    C
ATOM   2709  CB   SER A 186      43.330  23.643  39.551  1.00 29.57      A    C
ATOM   2712  OG   SER A 186      42.291  24.539  39.187  1.00 27.51      A    O
ATOM   2714  C    SER A 186      44.106  21.927  41.163  1.00 29.19      A    C
ATOM   2715  O    SER A 186      44.993  22.312  41.918  1.00 29.36      A    O
ATOM   2717  N    LEU A 187      44.088  20.711  40.648  1.00 27.91      A    N
ATOM   2718  CA   LEU A 187      45.257  19.900  40.753  1.00 28.25      A    C
ATOM   2720  CB   LEU A 187      45.159  18.923  41.947  1.00 27.44      A    C
ATOM   2723  CG   LEU A 187      44.172  17.784  41.956  1.00 27.26      A    C
ATOM   2725  CD1  LEU A 187      44.539  16.753  40.892  1.00 26.78      A    C
ATOM   2729  CD2  LEU A 187      44.078  17.122  43.406  1.00 23.16      A    C
ATOM   2733  C    LEU A 187      45.530  19.179  39.449  1.00 28.11      A    C
ATOM   2734  O    LEU A 187      44.697  19.177  38.551  1.00 28.57      A    O
ATOM   2736  N    SER A 188      46.705  18.563  39.366  1.00 28.53      A    N
ATOM   2737  CA   SER A 188      47.044  17.695  38.244  1.00 28.65      A    C
ATOM   2739  CB   SER A 188      48.149  18.320  37.398  1.00 28.14      A    C
ATOM   2742  OG   SER A 188      47.832  19.654  37.037  1.00 28.40      A    O
ATOM   2744  C    SER A 188      47.489  16.336  38.745  1.00 30.08      A    C
ATOM   2745  O    SER A 188      48.057  16.222  39.847  1.00 29.82      A    O
ATOM   2747  N    SER A 189      47.198  15.316  37.937  1.00 31.52      A    N
ATOM   2748  CA   SER A 189      47.718  13.974  38.114  1.00 33.54      A    C
ATOM   2750  CB   SER A 189      46.596  12.985  38.328  1.00 33.55      A    C
ATOM   2753  OG   SER A 189      47.099  11.699  38.677  1.00 33.88      A    O
ATOM   2755  C    SER A 189      48.467  13.605  36.846  1.00 35.34      A    C
ATOM   2756  O    SER A 189      47.986  13.883  35.744  1.00 36.52      A    O
ATOM   2758  N    VAL A 190      49.654  13.030  36.978  1.00 37.19      A    N
```

Figure 8 – CONT.

```
ATOM   2759  CA   VAL A 190     50.441  12.640  35.795  1.00 38.24      A  C
ATOM   2761  CB   VAL A 190     51.653  13.508  35.636  1.00 38.65      A  C
ATOM   2763  CG1  VAL A 190     51.244  14.944  35.367  1.00 38.57      A  C
ATOM   2767  CG2  VAL A 190     52.530  13.385  36.880  1.00 39.36      A  C
ATOM   2771  C    VAL A 190     50.949  11.207  35.862  1.00 39.50      A  C
ATOM   2772  O    VAL A 190     51.289  10.683  36.921  1.00 39.12      A  O
ATOM   2774  N    VAL A 191     51.011  10.575  34.709  1.00 41.42      A  N
ATOM   2775  CA   VAL A 191     51.619   9.271  34.628  1.00 43.23      A  C
ATOM   2777  CB   VAL A 191     50.650   8.152  34.197  1.00 43.54      A  C
ATOM   2779  CG1  VAL A 191     51.094   6.822  34.819  1.00 44.19      A  C
ATOM   2783  CG2  VAL A 191     49.232   8.476  34.548  1.00 44.73      A  C
ATOM   2787  C    VAL A 191     52.708   9.278  33.589  1.00 43.92      A  C
ATOM   2788  O    VAL A 191     52.539   9.860  32.508  1.00 44.20      A  O
ATOM   2790  N    THR A 192     53.803   8.591  33.920  1.00 44.90      A  N
ATOM   2791  CA   THR A 192     54.863   8.274  32.981  1.00 45.28      A  C
ATOM   2793  CB   THR A 192     56.221   8.500  33.628  1.00 45.44      A  C
ATOM   2795  OG1  THR A 192     56.178   7.948  34.939  1.00 47.35      A  O
ATOM   2797  CG2  THR A 192     56.533   9.987  33.737  1.00 44.13      A  C
ATOM   2801  C    THR A 192     54.690   6.811  32.532  1.00 45.78      A  C
ATOM   2802  O    THR A 192     54.502   5.893  33.342  1.00 45.42      A  O
ATOM   2804  N    VAL A 193     54.727   6.622  31.219  1.00 46.88      A  N
ATOM   2805  CA   VAL A 193     54.436   5.338  30.590  1.00 47.53      A  C
ATOM   2807  CB   VAL A 193     52.988   5.322  30.066  1.00 47.54      A  C
ATOM   2809  CG1  VAL A 193     52.028   5.683  31.188  1.00 45.97      A  C
ATOM   2813  CG2  VAL A 193     52.820   6.274  28.871  1.00 45.32      A  C
ATOM   2817  C    VAL A 193     55.411   5.126  29.431  1.00 48.94      A  C
ATOM   2818  O    VAL A 193     56.087   6.067  29.019  1.00 48.97      A  O
ATOM   2820  N    PRO A 194     55.501   3.897  28.897  1.00 50.66      A  N
ATOM   2821  CA   PRO A 194     56.483   3.761  27.822  1.00 51.51      A  C
ATOM   2823  CB   PRO A 194     56.672   2.247  27.688  1.00 51.67      A  C
ATOM   2826  CG   PRO A 194     56.054   1.648  28.934  1.00 51.74      A  C
ATOM   2829  CD   PRO A 194     54.936   2.596  29.296  1.00 50.85      A  C
ATOM   2832  C    PRO A 194     55.928   4.375  26.546  1.00 52.48      A  C
ATOM   2833  O    PRO A 194     54.757   4.181  26.229  1.00 52.57      A  O
ATOM   2834  N    SER A 195     56.765   5.117  25.833  1.00 53.46      A  N
ATOM   2835  CA   SER A 195     56.350   5.804  24.624  1.00 54.43      A  C
ATOM   2837  CB   SER A 195     57.506   6.657  24.067  1.00 54.68      A  C
ATOM   2840  OG   SER A 195     58.618   5.861  23.636  1.00 55.03      A  O
ATOM   2842  C    SER A 195     55.834   4.831  23.562  1.00 55.33      A  C
ATOM   2843  O    SER A 195     55.063   5.221  22.684  1.00 55.67      A  O
ATOM   2845  N    SER A 196     56.250   3.570  23.639  1.00 56.25      A  N
ATOM   2846  CA   SER A 196     55.779   2.549  22.704  1.00 57.19      A  C
ATOM   2848  CB   SER A 196     56.653   1.293  22.801  1.00 57.17      A  C
ATOM   2851  OG   SER A 196     56.632   0.752  24.117  1.00 58.27      A  O
ATOM   2853  C    SER A 196     54.308   2.179  22.932  1.00 57.70      A  C
ATOM   2854  O    SER A 196     53.650   1.701  22.018  1.00 58.48      A  O
ATOM   2856  N    SER A 197     53.792   2.399  24.140  1.00 57.95      A  N
ATOM   2857  CA   SER A 197     52.386   2.105  24.447  1.00 57.75      A  C
ATOM   2859  CB   SER A 197     52.172   2.099  25.970  1.00 58.04      A  C
ATOM   2862  OG   SER A 197     52.184   3.415  26.520  1.00 55.63      A  O
ATOM   2864  C    SER A 197     51.364   3.073  23.808  1.00 58.21      A  C
ATOM   2865  O    SER A 197     50.173   2.762  23.741  1.00 58.03      A  O
ATOM   2867  N    LEU A 198     51.817   4.238  23.347  1.00 58.57      A  N
ATOM   2868  CA   LEU A 198     50.905   5.359  23.126  1.00 58.78      A  C
ATOM   2870  CB   LEU A 198     51.670   6.630  22.759  1.00 58.34      A  C
ATOM   2873  CG   LEU A 198     52.376   7.299  23.940  1.00 58.43      A  C
ATOM   2875  CD1  LEU A 198     53.091   8.555  23.466  1.00 58.44      A  C
ATOM   2879  CD2  LEU A 198     51.405   7.636  25.085  1.00 58.02      A  C
```

Figure 8 – CONT.

```
ATOM   2883  C    LEU A 198      49.797   5.100  22.112  1.00 59.28      A  C
ATOM   2884  O    LEU A 198      48.676   5.564  22.299  1.00 59.87      A  O
ATOM   2886  N    GLY A 199      50.098   4.374  21.045  1.00 59.86      A  N
ATOM   2887  CA   GLY A 199      49.072   4.020  20.041  1.00 60.01      A  C
ATOM   2890  C    GLY A 199      48.116   2.900  20.456  1.00 59.84      A  C
ATOM   2891  O    GLY A 199      46.926   2.899  20.093  1.00 60.21      A  O
ATOM   2893  N    THR A 200      48.629   1.954  21.233  1.00 59.41      A  N
ATOM   2894  CA   THR A 200      47.884   0.759  21.572  1.00 59.01      A  C
ATOM   2896  CB   THR A 200      48.835  -0.455  21.619  1.00 59.18      A  C
ATOM   2898  OG1  THR A 200      49.855  -0.234  22.600  1.00 58.53      A  O
ATOM   2900  CG2  THR A 200      49.493  -0.653  20.244  1.00 59.07      A  C
ATOM   2904  C    THR A 200      47.131   0.879  22.893  1.00 58.54      A  C
ATOM   2905  O    THR A 200      45.987   0.441  22.996  1.00 58.94      A  O
ATOM   2907  N    GLN A 203      47.764   1.483  23.895  1.00 57.60      A  N
ATOM   2908  CA   GLN A 203      47.238   1.462  25.251  1.00 56.60      A  C
ATOM   2910  CB   GLN A 203      48.388   1.432  26.255  1.00 57.20      A  C
ATOM   2913  CG   GLN A 203      47.946   1.232  27.709  1.00 57.95      A  C
ATOM   2916  CD   GLN A 203      47.283  -0.110  27.933  1.00 59.41      A  C
ATOM   2917  OE1  GLN A 203      47.692  -1.120  27.346  1.00 60.68      A  O
ATOM   2918  NE2  GLN A 203      46.255  -0.133  28.781  1.00 58.11      A  N
ATOM   2921  C    GLN A 203      46.333   2.656  25.532  1.00 55.31      A  C
ATOM   2922  O    GLN A 203      46.639   3.788  25.149  1.00 54.76      A  O
ATOM   2924  N    THR A 205      45.219   2.376  26.206  1.00 53.59      A  N
ATOM   2925  CA   THR A 205      44.258   3.390  26.608  1.00 52.37      A  C
ATOM   2927  CB   THR A 205      42.806   2.851  26.603  1.00 52.38      A  C
ATOM   2929  OG1  THR A 205      42.426   2.514  25.264  1.00 53.77      A  O
ATOM   2931  CG2  THR A 205      41.820   3.889  27.135  1.00 51.79      A  C
ATOM   2935  C    THR A 205      44.581   3.847  28.007  1.00 50.81      A  C
ATOM   2936  O    THR A 205      44.770   3.034  28.904  1.00 51.51      A  O
ATOM   2938  N    TYR A 206      44.608   5.160  28.192  1.00 49.17      A  N
ATOM   2939  CA   TYR A 206      44.823   5.779  29.506  1.00 47.52      A  C
ATOM   2941  CB   TYR A 206      46.149   6.542  29.494  1.00 47.49      A  C
ATOM   2944  CG   TYR A 206      47.352   5.651  29.269  1.00 47.87      A  C
ATOM   2945  CD1  TYR A 206      47.869   4.880  30.310  1.00 49.10      A  C
ATOM   2947  CE1  TYR A 206      48.977   4.038  30.123  1.00 49.38      A  C
ATOM   2949  CZ   TYR A 206      49.584   3.974  28.895  1.00 49.15      A  C
ATOM   2950  OH   TYR A 206      50.679   3.153  28.741  1.00 50.12      A  O
ATOM   2952  CE2  TYR A 206      49.090   4.737  27.829  1.00 49.58      A  C
ATOM   2954  CD2  TYR A 206      47.974   5.575  28.026  1.00 47.62      A  C
ATOM   2956  C    TYR A 206      43.650   6.710  29.874  1.00 45.57      A  C
ATOM   2957  O    TYR A 206      43.301   7.624  29.118  1.00 45.93      A  O
ATOM   2959  N    ILE A 207      43.040   6.454  31.028  1.00 43.19      A  N
ATOM   2960  CA   ILE A 207      41.858   7.176  31.480  1.00 41.35      A  C
ATOM   2962  CB   ILE A 207      40.570   6.297  31.384  1.00 41.54      A  C
ATOM   2964  CG1  ILE A 207      40.376   5.740  29.966  1.00 42.09      A  C
ATOM   2967  CD1  ILE A 207      39.115   4.871  29.800  1.00 42.38      A  C
ATOM   2971  CG2  ILE A 207      39.333   7.091  31.795  1.00 40.33      A  C
ATOM   2975  C    ILE A 207      42.089   7.547  32.924  1.00 39.54      A  C
ATOM   2976  O    ILE A 207      42.430   6.689  33.730  1.00 38.87      A  O
ATOM   2978  N    CYS A 208      41.948   8.822  33.251  1.00 37.90      A  N
ATOM   2979  CA   CYS A 208      42.012   9.236  34.648  1.00 37.10      A  C
ATOM   2981  CB   CYS A 208      42.637  10.607  34.811  1.00 36.36      A  C
ATOM   2984  SG   CYS A 208      41.723  11.907  34.041  1.00 35.33      A  S
ATOM   2986  C    CYS A 208      40.596   9.229  35.191  1.00 36.90      A  C
ATOM   2987  O    CYS A 208      39.679   9.669  34.502  1.00 37.27      A  O
ATOM   2989  N    ASN A 209      40.420   8.677  36.386  1.00 36.32      A  N
ATOM   2990  CA   ASN A 209      39.114   8.621  37.041  1.00 36.32      A  C
ATOM   2992  CB   ASN A 209      38.764   7.196  37.533  1.00 35.75      A  C
```

Figure 8 – CONT.

```
ATOM   2995  CG   ASN A 209      39.364   6.096  36.681  1.00 37.43      A  C
ATOM   2996  OD1  ASN A 209      40.440   5.558  37.004  1.00 39.73      A  O
ATOM   2997  ND2  ASN A 209      38.690   5.758  35.575  1.00 38.53      A  N
ATOM   3000  C    ASN A 209      39.190   9.608  38.218  1.00 36.02      A  C
ATOM   3001  O    ASN A 209      39.915   9.365  39.199  1.00 36.41      A  O
ATOM   3003  N    VAL A 210      38.471  10.725  38.094  1.00 35.83      A  N
ATOM   3004  CA   VAL A 210      38.540  11.845  39.032  1.00 35.28      A  C
ATOM   3006  CB   VAL A 210      38.663  13.181  38.268  1.00 35.64      A  C
ATOM   3008  CG1  VAL A 210      38.638  14.353  39.190  1.00 34.63      A  C
ATOM   3012  CG2  VAL A 210      39.943  13.224  37.459  1.00 34.39      A  C
ATOM   3016  C    VAL A 210      37.253  11.837  39.859  1.00 36.73      A  C
ATOM   3017  O    VAL A 210      36.143  11.806  39.299  1.00 36.58      A  O
ATOM   3019  N    ASN A 211      37.395  11.824  41.184  1.00 36.90      A  N
ATOM   3020  CA   ASN A 211      36.247  11.765  42.089  1.00 37.19      A  C
ATOM   3022  CB   ASN A 211      36.229  10.424  42.871  1.00 38.09      A  C
ATOM   3025  CG   ASN A 211      34.922  10.213  43.700  1.00 41.74      A  C
ATOM   3026  OD1  ASN A 211      33.867  10.793  43.406  1.00 45.98      A  O
ATOM   3027  ND2  ASN A 211      35.009   9.379  44.748  1.00 45.29      A  N
ATOM   3030  C    ASN A 211      36.307  12.993  42.986  1.00 36.21      A  C
ATOM   3031  O    ASN A 211      37.356  13.301  43.591  1.00 35.01      A  O
ATOM   3033  N    HIS A 212      35.213  13.752  42.969  1.00 34.89      A  N
ATOM   3034  CA   HIS A 212      35.018  14.871  43.855  1.00 34.21      A  C
ATOM   3036  CB   HIS A 212      34.874  16.147  43.068  1.00 33.97      A  C
ATOM   3039  CG   HIS A 212      34.728  17.361  43.915  1.00 32.77      A  C
ATOM   3040  ND1  HIS A 212      33.667  18.230  43.787  1.00 30.85      A  N
ATOM   3042  CE1  HIS A 212      33.820  19.231  44.635  1.00 30.11      A  C
ATOM   3044  NE2  HIS A 212      34.938  19.044  45.311  1.00 30.56      A  N
ATOM   3046  CD2  HIS A 212      35.521  17.872  44.888  1.00 32.97      A  C
ATOM   3048  C    HIS A 212      33.759  14.638  44.674  1.00 35.00      A  C
ATOM   3049  O    HIS A 212      32.688  15.150  44.325  1.00 34.75      A  O
ATOM   3051  N    LYS A 213      33.911  13.884  45.775  1.00 35.75      A  N
ATOM   3052  CA   LYS A 213      32.805  13.533  46.687  1.00 36.62      A  C
ATOM   3054  CB   LYS A 213      33.301  12.824  47.974  1.00 37.38      A  C
ATOM   3057  CG   LYS A 213      33.755  11.354  47.801  1.00 38.37      A  C
ATOM   3063  C    LYS A 213      31.891  14.682  47.075  1.00 36.18      A  C
ATOM   3064  O    LYS A 213      30.685  14.533  46.954  1.00 36.26      A  O
ATOM   3066  N    PRO A 214      32.439  15.836  47.501  1.00 36.50      A  N
ATOM   3067  CA   PRO A 214      31.570  16.946  47.956  1.00 36.18      A  C
ATOM   3069  CB   PRO A 214      32.535  18.106  48.128  1.00 36.05      A  C
ATOM   3072  CG   PRO A 214      33.855  17.517  48.301  1.00 36.04      A  C
ATOM   3075  CD   PRO A 214      33.867  16.170  47.641  1.00 36.74      A  C
ATOM   3078  C    PRO A 214      30.456  17.359  46.978  1.00 37.17      A  C
ATOM   3079  O    PRO A 214      29.382  17.764  47.419  1.00 37.50      A  O
ATOM   3080  N    SER A 215      30.723  17.290  45.671  1.00 37.38      A  N
ATOM   3081  CA   SER A 215      29.761  17.682  44.626  1.00 36.92      A  C
ATOM   3083  CB   SER A 215      30.490  18.443  43.513  1.00 37.59      A  C
ATOM   3086  OG   SER A 215      31.327  17.564  42.757  1.00 32.55      A  O
ATOM   3088  C    SER A 215      29.130  16.441  43.994  1.00 37.81      A  C
ATOM   3089  O    SER A 215      28.434  16.538  43.002  1.00 38.49      A  O
ATOM   3091  N    ASN A 216      29.442  15.275  44.537  1.00 38.20      A  N
ATOM   3092  CA   ASN A 216      28.995  14.004  44.007  1.00 38.72      A  C
ATOM   3094  CB   ASN A 216      27.504  13.857  44.283  1.00 39.22      A  C
ATOM   3097  CG   ASN A 216      27.206  13.643  45.738  1.00 40.12      A  C
ATOM   3098  OD1  ASN A 216      27.595  12.624  46.337  1.00 40.63      A  O
ATOM   3099  ND2  ASN A 216      26.497  14.589  46.318  1.00 42.23      A  N
ATOM   3102  C    ASN A 216      29.307  13.793  42.524  1.00 38.81      A  C
ATOM   3103  O    ASN A 216      28.516  13.197  41.778  1.00 38.88      A  O
ATOM   3105  N    THR A 217      30.483  14.259  42.115  1.00 38.80      A  N
```

Figure 8 – CONT.

```
ATOM   3106  CA   THR A 217      30.899  14.228  40.728  1.00 37.87           A  C
ATOM   3108  CB   THR A 217      31.423  15.583  40.308  1.00 37.09           A  C
ATOM   3110  OG1  THR A 217      30.394  16.537  40.461  1.00 35.10           A  O
ATOM   3112  CG2  THR A 217      31.849  15.577  38.861  1.00 36.87           A  C
ATOM   3116  C    THR A 217      32.009  13.214  40.527  1.00 38.45           A  C
ATOM   3117  O    THR A 217      32.945  13.137  41.313  1.00 37.98           A  O
ATOM   3119  N    LYS A 218      31.908  12.448  39.458  1.00 38.91           A  N
ATOM   3120  CA   LYS A 218      32.979  11.548  39.085  1.00 40.05           A  C
ATOM   3122  CB   LYS A 218      32.606  10.113  39.421  1.00 40.89           A  C
ATOM   3125  CG   LYS A 218      33.752   9.259  39.913  1.00 44.54           A  C
ATOM   3128  CD   LYS A 218      33.300   7.867  40.424  1.00 47.50           A  C
ATOM   3131  CE   LYS A 218      32.157   7.974  41.469  1.00 50.32           A  C
ATOM   3134  NZ   LYS A 218      32.081   6.831  42.464  1.00 49.31           A  N
ATOM   3138  C    LYS A 218      33.159  11.754  37.597  1.00 40.02           A  C
ATOM   3139  O    LYS A 218      32.177  11.726  36.843  1.00 40.14           A  O
ATOM   3141  N    VAL A 219      34.389  12.034  37.177  1.00 39.58           A  N
ATOM   3142  CA   VAL A 219      34.676  12.264  35.768  1.00 38.80           A  C
ATOM   3144  CB   VAL A 219      35.149  13.679  35.522  1.00 38.41           A  C
ATOM   3146  CG1  VAL A 219      35.420  13.900  34.014  1.00 36.36           A  C
ATOM   3150  CG2  VAL A 219      34.138  14.654  36.046  1.00 37.51           A  C
ATOM   3154  C    VAL A 219      35.745  11.305  35.287  1.00 39.14           A  C
ATOM   3155  O    VAL A 219      36.779  11.201  35.915  1.00 39.93           A  O
ATOM   3157  N    ASP A 220      35.474  10.585  34.196  1.00 39.03           A  N
ATOM   3158  CA   ASP A 220      36.492   9.793  33.516  1.00 39.30           A  C
ATOM   3160  CB   ASP A 220      35.966   8.415  33.126  1.00 39.44           A  C
ATOM   3163  CG   ASP A 220      35.668   7.524  34.326  1.00 40.84           A  C
ATOM   3164  OD1  ASP A 220      34.724   6.710  34.211  1.00 43.99           A  O
ATOM   3165  OD2  ASP A 220      36.362   7.622  35.366  1.00 41.76           A  O
ATOM   3166  C    ASP A 220      36.914  10.519  32.231  1.00 39.45           A  C
ATOM   3167  O    ASP A 220      36.065  10.939  31.441  1.00 39.26           A  O
ATOM   3169  N    LYS A 221      38.223  10.621  32.013  1.00 39.11           A  N
ATOM   3170  CA   LYS A 221      38.775  11.329  30.868  1.00 39.15           A  C
ATOM   3172  CB   LYS A 221      39.438  12.622  31.318  1.00 39.33           A  C
ATOM   3175  CG   LYS A 221      39.665  13.604  30.220  1.00 41.19           A  C
ATOM   3178  CD   LYS A 221      38.336  14.233  29.812  1.00 43.37           A  C
ATOM   3181  CE   LYS A 221      38.454  15.074  28.592  1.00 43.33           A  C
ATOM   3184  NZ   LYS A 221      37.109  15.545  28.229  1.00 44.90           A  N
ATOM   3188  C    LYS A 221      39.794  10.469  30.172  1.00 39.04           A  C
ATOM   3189  O    LYS A 221      40.817  10.116  30.755  1.00 39.33           A  O
ATOM   3191  N    LYS A 222      39.505  10.111  28.933  1.00 39.29           A  N
ATOM   3192  CA   LYS A 222      40.488   9.451  28.087  1.00 40.11           A  C
ATOM   3194  CB   LYS A 222      39.838   8.770  26.872  1.00 40.66           A  C
ATOM   3197  CG   LYS A 222      40.741   7.758  26.169  1.00 42.54           A  C
ATOM   3200  CD   LYS A 222      39.955   6.800  25.257  1.00 46.18           A  C
ATOM   3203  CE   LYS A 222      40.887   6.033  24.286  1.00 47.18           A  C
ATOM   3206  NZ   LYS A 222      41.507   6.944  23.271  1.00 47.46           A  N
ATOM   3210  C    LYS A 222      41.527  10.491  27.665  1.00 39.30           A  C
ATOM   3211  O    LYS A 222      41.189  11.604  27.250  1.00 39.34           A  O
ATOM   3213  N    VAL A 225      42.790  10.146  27.860  1.00 38.84           A  N
ATOM   3214  CA   VAL A 225      43.887  11.008  27.459  1.00 38.59           A  C
ATOM   3216  CB   VAL A 225      44.891  11.208  28.587  1.00 37.98           A  C
ATOM   3218  CG1  VAL A 225      45.930  12.195  28.127  1.00 36.73           A  C
ATOM   3222  CG2  VAL A 225      44.194  11.671  29.875  1.00 36.08           A  C
ATOM   3226  C    VAL A 225      44.593  10.344  26.278  1.00 39.53           A  C
ATOM   3227  O    VAL A 225      45.068   9.223  26.382  1.00 38.94           A  O
ATOM   3229  N    GLU A 226      44.639  11.033  25.151  1.00 41.52           A  N
ATOM   3230  CA   GLU A 226      45.255  10.492  23.947  1.00 42.73           A  C
ATOM   3232  CB   GLU A 226      44.175  10.023  22.962  1.00 43.03           A  C
```

Figure 8 – CONT.

```
ATOM   3235  CG  GLU A 226      43.249  11.101  22.399  1.00 45.15      A  C
ATOM   3238  CD  GLU A 226      41.977  10.513  21.759  1.00 48.86      A  C
ATOM   3239  OE1 GLU A 226      41.684   9.314  21.987  1.00 50.60      A  O
ATOM   3240  OE2 GLU A 226      41.251  11.255  21.052  1.00 51.16      A  O
ATOM   3241  C   GLU A 226      46.226  11.530  23.371  1.00 43.43      A  C
ATOM   3242  O   GLU A 226      46.174  12.688  23.754  1.00 42.89      A  O
ATOM   3244  N   PRO A 227      47.141  11.104  22.471  1.00 44.31      A  N
ATOM   3245  CA  PRO A 227      48.228  11.956  21.987  1.00 44.04      A  C
ATOM   3247  CB  PRO A 227      48.986  11.018  21.047  1.00 44.16      A  C
ATOM   3250  CG  PRO A 227      48.797   9.688  21.643  1.00 44.05      A  C
ATOM   3253  CD  PRO A 227      47.345   9.700  22.051  1.00 44.59      A  C
ATOM   3256  C   PRO A 227      47.794  13.215  21.265  1.00 43.96      A  C
ATOM   3257  O   PRO A 227      46.753  13.184  20.632  1.00 44.44      A  O
TER
ATOM   3258  N   LEU B   4      49.940  24.507  76.812  1.00 48.76      B  N
ATOM   3259  CA  LEU B   4      51.276  23.846  76.911  1.00 49.16      B  C
ATOM   3261  CB  LEU B   4      51.151  22.322  76.877  1.00 48.29      B  C
ATOM   3264  CG  LEU B   4      50.109  21.688  77.794  1.00 48.03      B  C
ATOM   3266  CD1 LEU B   4      50.118  20.137  77.692  1.00 44.08      B  C
ATOM   3270  CD2 LEU B   4      50.326  22.148  79.244  1.00 47.12      B  C
ATOM   3274  C   LEU B   4      52.207  24.302  75.792  1.00 49.87      B  C
ATOM   3275  O   LEU B   4      51.745  24.739  74.727  1.00 50.29      B  O
ATOM   3279  N   THR B   5      53.518  24.179  76.030  1.00 50.57      B  N
ATOM   3280  CA  THR B   5      54.536  24.703  75.093  1.00 51.11      B  C
ATOM   3282  CB  THR B   5      55.298  25.902  75.687  1.00 51.06      B  C
ATOM   3284  OG1 THR B   5      54.360  26.926  76.033  1.00 51.02      B  O
ATOM   3286  CG2 THR B   5      56.274  26.455  74.684  1.00 50.93      B  C
ATOM   3290  C   THR B   5      55.540  23.642  74.661  1.00 51.31      B  C
ATOM   3291  O   THR B   5      56.221  23.040  75.483  1.00 51.33      B  O
ATOM   3293  N   GLN B   6      55.600  23.421  73.354  1.00 51.60      B  N
ATOM   3294  CA  GLN B   6      56.542  22.512  72.760  1.00 51.71      B  C
ATOM   3296  CB  GLN B   6      55.826  21.382  72.008  1.00 51.57      B  C
ATOM   3299  CG  GLN B   6      54.779  20.607  72.796  1.00 51.12      B  C
ATOM   3302  CD  GLN B   6      54.028  19.581  71.937  1.00 49.07      B  C
ATOM   3303  OE1 GLN B   6      52.792  19.601  71.863  1.00 48.04      B  O
ATOM   3304  NE2 GLN B   6      54.767  18.700  71.283  1.00 46.66      B  N
ATOM   3307  C   GLN B   6      57.357  23.332  71.789  1.00 52.16      B  C
ATOM   3308  O   GLN B   6      56.972  24.437  71.437  1.00 52.51      B  O
ATOM   3310  N   PRO B   7      58.504  22.809  71.361  1.00 52.87      B  N
ATOM   3311  CA  PRO B   7      59.194  23.458  70.250  1.00 53.41      B  C
ATOM   3313  CB  PRO B   7      60.546  22.741  70.215  1.00 53.38      B  C
ATOM   3316  CG  PRO B   7      60.294  21.413  70.868  1.00 52.89      B  C
ATOM   3319  CD  PRO B   7      59.233  21.637  71.878  1.00 52.88      B  C
ATOM   3322  C   PRO B   7      58.423  23.218  68.950  1.00 53.75      B  C
ATOM   3323  O   PRO B   7      57.823  22.147  68.801  1.00 53.64      B  O
ATOM   3324  N   PRO B   8      58.412  24.205  68.031  1.00 54.30      B  N
ATOM   3325  CA  PRO B   8      57.741  23.986  66.744  1.00 54.41      B  C
ATOM   3327  CB  PRO B   8      57.957  25.301  65.988  1.00 54.43      B  C
ATOM   3330  CG  PRO B   8      58.249  26.329  67.050  1.00 54.93      B  C
ATOM   3333  CD  PRO B   8      58.921  25.587  68.169  1.00 54.64      B  C
ATOM   3336  C   PRO B   8      58.332  22.825  65.953  1.00 54.73      B  C
ATOM   3337  O   PRO B   8      57.591  22.073  65.309  1.00 54.79      B  O
ATOM   3338  N   SER B   9      59.653  22.677  66.012  1.00 55.05      B  N
ATOM   3339  CA  SER B   9      60.348  21.728  65.163  1.00 55.23      B  C
ATOM   3341  CB  SER B   9      60.908  22.445  63.943  1.00 55.58      B  C
ATOM   3344  OG  SER B   9      62.253  22.822  64.185  1.00 56.74      B  O
ATOM   3346  C   SER B   9      61.499  21.015  65.867  1.00 55.11      B  C
ATOM   3347  O   SER B   9      62.083  21.532  66.801  1.00 54.24      B  O
```

Figure 8 – CONT.

```
ATOM   3349  N    VAL B  11      61.809  19.816  65.382  1.00 55.34      B  N
ATOM   3350  CA   VAL B  11      62.950  19.056  65.833  1.00 55.75      B  C
ATOM   3352  CB   VAL B  11      62.606  18.236  67.085  1.00 55.81      B  C
ATOM   3354  CG1  VAL B  11      63.687  17.225  67.374  1.00 56.17      B  C
ATOM   3358  CG2  VAL B  11      62.430  19.161  68.282  1.00 56.72      B  C
ATOM   3362  C    VAL B  11      63.406  18.139  64.695  1.00 56.19      B  C
ATOM   3363  O    VAL B  11      62.579  17.587  63.959  1.00 56.26      B  O
ATOM   3365  N    SER B  12      64.721  17.980  64.562  1.00 56.88      B  N
ATOM   3366  CA   SER B  12      65.336  17.314  63.404  1.00 57.56      B  C
ATOM   3368  CB   SER B  12      65.946  18.364  62.470  1.00 57.29      B  C
ATOM   3371  OG   SER B  12      65.160  19.539  62.465  1.00 58.47      B  O
ATOM   3373  C    SER B  12      66.435  16.374  63.853  1.00 57.73      B  C
ATOM   3374  O    SER B  12      67.095  16.645  64.842  1.00 57.98      B  O
ATOM   3376  N    ALA B  13      66.631  15.274  63.135  1.00 58.21      B  N
ATOM   3377  CA   ALA B  13      67.784  14.391  63.377  1.00 58.73      B  C
ATOM   3379  CB   ALA B  13      67.716  13.749  64.780  1.00 58.14      B  C
ATOM   3383  C    ALA B  13      67.902  13.319  62.290  1.00 59.00      B  C
ATOM   3384  O    ALA B  13      66.940  13.052  61.583  1.00 59.16      B  O
ATOM   3386  N    ALA B  14      69.093  12.733  62.159  1.00 59.55      B  N
ATOM   3387  CA   ALA B  14      69.353  11.669  61.187  1.00 60.03      B  C
ATOM   3389  CB   ALA B  14      70.856  11.429  61.053  1.00 60.06      B  C
ATOM   3393  C    ALA B  14      68.691  10.374  61.612  1.00 60.49      B  C
ATOM   3394  O    ALA B  14      68.527  10.133  62.813  1.00 60.54      B  O
ATOM   3396  N    PRO B  15      68.343   9.517  60.639  1.00 60.99      B  N
ATOM   3397  CA   PRO B  15      67.902   8.167  60.996  1.00 61.63      B  C
ATOM   3399  CB   PRO B  15      67.873   7.420  59.657  1.00 61.49      B  C
ATOM   3402  CG   PRO B  15      67.762   8.488  58.614  1.00 61.60      B  C
ATOM   3405  CD   PRO B  15      68.388   9.731  59.182  1.00 60.99      B  C
ATOM   3408  C    PRO B  15      68.899   7.520  61.945  1.00 62.31      B  C
ATOM   3409  O    PRO B  15      70.097   7.773  61.835  1.00 62.55      B  O
ATOM   3410  N    GLY B  16      68.405   6.722  62.886  1.00 62.99      B  N
ATOM   3411  CA   GLY B  16      69.259   6.045  63.850  1.00 63.27      B  C
ATOM   3414  C    GLY B  16      69.430   6.807  65.152  1.00 63.71      B  C
ATOM   3415  O    GLY B  16      69.493   6.186  66.219  1.00 64.37      B  O
ATOM   3417  N    GLN B  17      69.506   8.137  65.084  1.00 63.63      B  N
ATOM   3418  CA   GLN B  17      69.690   8.957  66.286  1.00 63.84      B  C
ATOM   3420  CB   GLN B  17      69.956  10.436  65.931  1.00 63.94      B  C
ATOM   3423  CG   GLN B  17      71.359  10.721  65.412  1.00 65.42      B  C
ATOM   3426  CD   GLN B  17      71.745  12.200  65.511  1.00 67.33      B  C
ATOM   3427  OE1  GLN B  17      70.974  13.087  65.129  1.00 68.04      B  O
ATOM   3428  NE2  GLN B  17      72.954  12.466  66.020  1.00 67.21      B  N
ATOM   3431  C    GLN B  17      68.500   8.881  67.242  1.00 63.49      B  C
ATOM   3432  O    GLN B  17      67.442   8.333  66.917  1.00 63.25      B  O
ATOM   3434  N    LYS B  18      68.713   9.441  68.430  1.00 63.45      B  N
ATOM   3435  CA   LYS B  18      67.699   9.562  69.459  1.00 63.18      B  C
ATOM   3437  CB   LYS B  18      68.270   9.140  70.827  1.00 63.24      B  C
ATOM   3440  CG   LYS B  18      67.478   9.625  72.045  1.00 63.34      B  C
ATOM   3446  C    LYS B  18      67.231  11.023  69.458  1.00 62.83      B  C
ATOM   3447  O    LYS B  18      68.046  11.935  69.292  1.00 62.68      B  O
ATOM   3449  N    VAL B  19      65.921  11.234  69.626  1.00 62.05      B  N
ATOM   3450  CA   VAL B  19      65.342  12.581  69.612  1.00 61.60      B  C
ATOM   3452  CB   VAL B  19      64.407  12.805  68.389  1.00 61.71      B  C
ATOM   3454  CG1  VAL B  19      64.481  14.260  67.942  1.00 61.90      B  C
ATOM   3458  CG2  VAL B  19      64.769  11.873  67.242  1.00 61.49      B  C
ATOM   3462  C    VAL B  19      64.528  12.841  70.877  1.00 60.79      B  C
ATOM   3463  O    VAL B  19      64.019  11.905  71.490  1.00 61.09      B  O
ATOM   3465  N    THR B  20      64.391  14.113  71.240  1.00 59.79      B  N
ATOM   3466  CA   THR B  20      63.705  14.489  72.463  1.00 59.07      B  C
```

Figure 8 – CONT.

```
ATOM   3468  CB   THR B  20      64.728  14.674  73.619  1.00 59.12      B  C
ATOM   3470  OG1  THR B  20      64.357  13.842  74.723  1.00 58.55      B  O
ATOM   3472  CG2  THR B  20      64.846  16.135  74.072  1.00 58.28      B  C
ATOM   3476  C    THR B  20      62.844  15.750  72.273  1.00 58.86      B  C
ATOM   3477  O    THR B  20      63.315  16.772  71.758  1.00 58.67      B  O
ATOM   3479  N    ILE B  21      61.583  15.670  72.710  1.00 58.34      B  N
ATOM   3480  CA   ILE B  21      60.621  16.762  72.551  1.00 57.78      B  C
ATOM   3482  CB   ILE B  21      59.389  16.323  71.686  1.00 57.84      B  C
ATOM   3484  CG1  ILE B  21      59.806  16.024  70.249  1.00 57.83      B  C
ATOM   3487  CD1  ILE B  21      58.654  15.547  69.375  1.00 58.60      B  C
ATOM   3491  CG2  ILE B  21      58.314  17.405  71.650  1.00 57.49      B  C
ATOM   3495  C    ILE B  21      60.137  17.185  73.922  1.00 57.44      B  C
ATOM   3496  O    ILE B  21      59.547  16.389  74.634  1.00 56.86      B  O
ATOM   3498  N    SER B  22      60.377  18.440  74.280  1.00 57.43      B  N
ATOM   3499  CA   SER B  22      59.965  18.943  75.574  1.00 57.52      B  C
ATOM   3501  CB   SER B  22      60.839  20.119  76.019  1.00 57.51      B  C
ATOM   3504  OG   SER B  22      60.305  21.346  75.533  1.00 58.29      B  O
ATOM   3506  C    SER B  22      58.519  19.399  75.500  1.00 57.60      B  C
ATOM   3507  O    SER B  22      58.041  19.807  74.442  1.00 57.66      B  O
ATOM   3509  N    CYS B  23      57.840  19.324  76.644  1.00 57.55      B  N
ATOM   3510  CA   CYS B  23      56.480  19.824  76.816  1.00 57.36      B  C
ATOM   3512  CB   CYS B  23      55.477  18.669  76.749  1.00 56.63      B  C
ATOM   3515  SG   CYS B  23      53.755  19.088  77.136  1.00 55.74      B  S
ATOM   3517  C    CYS B  23      56.451  20.462  78.190  1.00 58.01      B  C
ATOM   3518  O    CYS B  23      56.682  19.779  79.184  1.00 58.18      B  O
ATOM   3520  N    SER B  24      56.200  21.760  78.272  1.00 58.48      B  N
ATOM   3521  CA   SER B  24      56.177  22.399  79.580  1.00 59.09      B  C
ATOM   3523  CB   SER B  24      57.408  23.310  79.755  1.00 59.26      B  C
ATOM   3526  OG   SER B  24      57.203  24.608  79.227  1.00 58.27      B  O
ATOM   3528  C    SER B  24      54.858  23.148  79.807  1.00 59.66      B  C
ATOM   3529  O    SER B  24      54.408  23.924  78.960  1.00 59.89      B  O
ATOM   3531  N    GLY B  25      54.230  22.892  80.947  1.00 59.88      B  N
ATOM   3532  CA   GLY B  25      53.011  23.592  81.316  1.00 60.23      B  C
ATOM   3535  C    GLY B  25      53.185  24.268  82.656  1.00 60.58      B  C
ATOM   3536  O    GLY B  25      54.224  24.874  82.919  1.00 60.52      B  O
ATOM   3538  N    SER B  26      52.167  24.149  83.509  1.00 60.92      B  N
ATOM   3539  CA   SER B  26      52.178  24.761  84.837  1.00 60.96      B  C
ATOM   3541  CB   SER B  26      51.400  26.101  84.815  1.00 61.29      B  C
ATOM   3544  OG   SER B  26      50.019  25.924  84.547  1.00 61.74      B  O
ATOM   3546  C    SER B  26      51.657  23.773  85.898  1.00 60.90      B  C
ATOM   3547  O    SER B  26      51.589  22.556  85.650  1.00 60.67      B  O
ATOM   3549  N    SER B  27      51.324  24.287  87.080  1.00 60.80      B  N
ATOM   3550  CA   SER B  27      50.940  23.455  88.227  1.00 60.81      B  C
ATOM   3552  CB   SER B  27      51.184  24.241  89.526  1.00 61.06      B  C
ATOM   3555  OG   SER B  27      52.396  24.991  89.442  1.00 61.72      B  O
ATOM   3557  C    SER B  27      49.476  22.975  88.145  1.00 60.45      B  C
ATOM   3558  O    SER B  27      49.145  21.856  88.566  1.00 60.53      B  O
ATOM   3560  N    SER B  27A     48.610  23.838  87.621  1.00 60.09      B  N
ATOM   3561  CA   SER B  27A     47.243  23.464  87.236  1.00 59.71      B  C
ATOM   3563  CB   SER B  27A     46.613  24.584  86.388  1.00 59.77      B  C
ATOM   3566  OG   SER B  27A     47.326  25.811  86.523  1.00 60.50      B  O
ATOM   3568  C    SER B  27A     47.219  22.159  86.421  1.00 59.16      B  C
ATOM   3569  O    SER B  27A     46.450  21.234  86.722  1.00 58.99      B  O
ATOM   3571  N    ASP B  27B     48.078  22.086  85.404  1.00 58.35      B  N
ATOM   3572  CA   ASP B  27B     47.986  21.022  84.403  1.00 57.77      B  C
ATOM   3574  CB   ASP B  27B     48.006  21.590  82.959  1.00 57.48      B  C
ATOM   3577  CG   ASP B  27B     49.077  22.636  82.731  1.00 56.25      B  C
ATOM   3578  OD1  ASP B  27B     50.264  22.250  82.669  1.00 53.12      B  O
```

Figure 8 – CONT.

```
ATOM   3579  OD2 ASP B  27B     48.732  23.838  82.592  1.00 54.99       B  O
ATOM   3580  C   ASP B  27B     48.964  19.852  84.597  1.00 57.67       B  C
ATOM   3581  O   ASP B  27B     48.613  18.867  85.243  1.00 58.22       B  O
ATOM   3583  N   ILE B  28      50.170  19.936  84.049  1.00 57.85       B  N
ATOM   3584  CA  ILE B  28      51.109  18.810  84.125  1.00 58.15       B  C
ATOM   3586  CB  ILE B  28      52.361  19.034  83.239  1.00 58.20       B  C
ATOM   3588  CG1 ILE B  28      51.953  19.187  81.770  1.00 57.74       B  C
ATOM   3591  CD1 ILE B  28      53.120  19.391  80.839  1.00 56.74       B  C
ATOM   3595  CG2 ILE B  28      53.356  17.875  83.389  1.00 57.23       B  C
ATOM   3599  C   ILE B  28      51.527  18.544  85.579  1.00 58.39       B  C
ATOM   3600  O   ILE B  28      51.721  17.400  85.975  1.00 58.15       B  O
ATOM   3602  N   GLY B  29      51.643  19.610  86.365  1.00 59.02       B  N
ATOM   3603  CA  GLY B  29      51.890  19.503  87.812  1.00 59.34       B  C
ATOM   3606  C   GLY B  29      50.935  18.577  88.550  1.00 59.49       B  C
ATOM   3607  O   GLY B  29      51.353  17.802  89.424  1.00 59.84       B  O
ATOM   3609  N   SER B  30      49.657  18.638  88.189  1.00 59.30       B  N
ATOM   3610  CA  SER B  30      48.633  17.892  88.900  1.00 59.08       B  C
ATOM   3612  CB  SER B  30      47.441  18.812  89.225  1.00 59.31       B  C
ATOM   3615  OG  SER B  30      47.851  20.112  89.634  1.00 59.69       B  O
ATOM   3617  C   SER B  30      48.108  16.662  88.155  1.00 58.83       B  C
ATOM   3618  O   SER B  30      47.270  15.948  88.708  1.00 58.84       B  O
ATOM   3620  N   ASN B  31      48.561  16.404  86.922  1.00 58.47       B  N
ATOM   3621  CA  ASN B  31      47.862  15.424  86.069  1.00 58.04       B  C
ATOM   3623  CB  ASN B  31      46.824  16.140  85.204  1.00 57.83       B  C
ATOM   3626  CG  ASN B  31      45.654  16.661  86.010  1.00 57.28       B  C
ATOM   3627  OD1 ASN B  31      44.724  15.916  86.305  1.00 55.71       B  O
ATOM   3628  ND2 ASN B  31      45.691  17.955  86.365  1.00 55.50       B  N
ATOM   3631  C   ASN B  31      48.747  14.567  85.183  1.00 57.84       B  C
ATOM   3632  O   ASN B  31      49.911  14.861  84.991  1.00 58.03       B  O
ATOM   3634  N   TYR B  32      48.163  13.498  84.658  1.00 57.74       B  N
ATOM   3635  CA  TYR B  32      48.848  12.579  83.753  1.00 57.76       B  C
ATOM   3637  CB  TYR B  32      48.085  11.262  83.621  1.00 58.49       B  C
ATOM   3640  CG  TYR B  32      48.193  10.328  84.808  1.00 61.38       B  C
ATOM   3641  CD1 TYR B  32      49.439   9.910  85.286  1.00 64.01       B  C
ATOM   3643  CE1 TYR B  32      49.546   9.035  86.377  1.00 64.65       B  C
ATOM   3645  CZ  TYR B  32      48.398   8.567  86.987  1.00 65.78       B  C
ATOM   3646  OH  TYR B  32      48.493   7.702  88.053  1.00 68.07       B  O
ATOM   3648  CE2 TYR B  32      47.143   8.957  86.529  1.00 65.63       B  C
ATOM   3650  CD2 TYR B  32      47.046   9.832  85.437  1.00 64.18       B  C
ATOM   3652  C   TYR B  32      48.973  13.186  82.363  1.00 56.46       B  C
ATOM   3653  O   TYR B  32      48.049  13.828  81.866  1.00 56.58       B  O
ATOM   3655  N   VAL B  33      50.121  12.966  81.741  1.00 54.59       B  N
ATOM   3656  CA  VAL B  33      50.449  13.580  80.469  1.00 53.12       B  C
ATOM   3658  CB  VAL B  33      51.889  14.162  80.480  1.00 53.13       B  C
ATOM   3660  CG1 VAL B  33      52.303  14.657  79.088  1.00 51.95       B  C
ATOM   3664  CG2 VAL B  33      51.985  15.292  81.500  1.00 53.01       B  C
ATOM   3668  C   VAL B  33      50.311  12.506  79.402  1.00 51.66       B  C
ATOM   3669  O   VAL B  33      50.797  11.382  79.589  1.00 51.20       B  O
ATOM   3671  N   SER B  34      49.627  12.838  78.307  1.00 49.43       B  N
ATOM   3672  CA  SER B  34      49.552  11.936  77.169  1.00 47.95       B  C
ATOM   3674  CB  SER B  34      48.099  11.672  76.791  1.00 47.75       B  C
ATOM   3677  OG  SER B  34      47.438  10.935  77.809  1.00 46.65       B  O
ATOM   3679  C   SER B  34      50.309  12.552  75.992  1.00 47.07       B  C
ATOM   3680  O   SER B  34      50.522  13.760  75.951  1.00 46.69       B  O
ATOM   3682  N   TRP B  35      50.728  11.716  75.052  1.00 45.46       B  N
ATOM   3683  CA  TRP B  35      51.282  12.189  73.793  1.00 44.74       B  C
ATOM   3685  CB  TRP B  35      52.750  11.788  73.641  1.00 45.20       B  C
ATOM   3688  CG  TRP B  35      53.648  12.488  74.613  1.00 47.71       B  C
```

Figure 8 – CONT.

| | | | | | | | | | | | |
|---|---|---|---|---|---|---|---|---|---|---|---|
| ATOM | 3689 | CD1 | TRP | B | 35 | 53.916 | 12.107 | 75.907 | 1.00 48.41 | B | C |
| ATOM | 3691 | NE1 | TRP | B | 35 | 54.764 | 13.017 | 76.499 | 1.00 48.74 | B | N |
| ATOM | 3693 | CE2 | TRP | B | 35 | 55.089 | 13.988 | 75.592 | 1.00 49.39 | B | C |
| ATOM | 3694 | CD2 | TRP | B | 35 | 54.401 | 13.694 | 74.389 | 1.00 49.22 | B | C |
| ATOM | 3695 | CE3 | TRP | B | 35 | 54.564 | 14.547 | 73.294 | 1.00 50.62 | B | C |
| ATOM | 3697 | CZ3 | TRP | B | 35 | 55.398 | 15.639 | 73.423 | 1.00 51.20 | B | C |
| ATOM | 3699 | CH2 | TRP | B | 35 | 56.071 | 15.903 | 74.630 | 1.00 51.80 | B | C |
| ATOM | 3701 | CZ2 | TRP | B | 35 | 55.926 | 15.090 | 75.724 | 1.00 50.18 | B | C |
| ATOM | 3703 | C | TRP | B | 35 | 50.466 | 11.643 | 72.619 | 1.00 43.03 | B | C |
| ATOM | 3704 | O | TRP | B | 35 | 49.948 | 10.504 | 72.660 | 1.00 41.97 | B | O |
| ATOM | 3706 | N | TYR | B | 36 | 50.367 | 12.467 | 71.576 | 1.00 41.07 | B | N |
| ATOM | 3707 | CA | TYR | B | 36 | 49.605 | 12.108 | 70.399 | 1.00 40.16 | B | C |
| ATOM | 3709 | CB | TYR | B | 36 | 48.308 | 12.920 | 70.355 | 1.00 40.12 | B | C |
| ATOM | 3712 | CG | TYR | B | 36 | 47.491 | 12.731 | 71.609 | 1.00 37.82 | B | C |
| ATOM | 3713 | CD1 | TYR | B | 36 | 46.596 | 11.686 | 71.737 | 1.00 38.29 | B | C |
| ATOM | 3715 | CE1 | TYR | B | 36 | 45.849 | 11.525 | 72.908 | 1.00 39.22 | B | C |
| ATOM | 3717 | CZ | TYR | B | 36 | 46.045 | 12.397 | 73.970 | 1.00 38.29 | B | C |
| ATOM | 3718 | OH | TYR | B | 36 | 45.375 | 12.278 | 75.167 | 1.00 37.82 | B | O |
| ATOM | 3720 | CE2 | TYR | B | 36 | 46.957 | 13.414 | 73.858 | 1.00 38.82 | B | C |
| ATOM | 3722 | CD2 | TYR | B | 36 | 47.678 | 13.563 | 72.691 | 1.00 39.32 | B | C |
| ATOM | 3724 | C | TYR | B | 36 | 50.445 | 12.279 | 69.153 | 1.00 39.83 | B | C |
| ATOM | 3725 | O | TYR | B | 36 | 51.206 | 13.228 | 69.024 | 1.00 39.63 | B | O |
| ATOM | 3727 | N | GLN | B | 37 | 50.349 | 11.301 | 68.272 | 1.00 40.00 | B | N |
| ATOM | 3728 | CA | GLN | B | 37 | 51.105 | 11.272 | 67.033 | 1.00 39.70 | B | C |
| ATOM | 3730 | CB | GLN | B | 37 | 51.794 | 9.909 | 66.873 | 1.00 39.86 | B | C |
| ATOM | 3733 | CG | GLN | B | 37 | 52.621 | 9.750 | 65.579 | 1.00 40.84 | B | C |
| ATOM | 3736 | CD | GLN | B | 37 | 53.140 | 8.340 | 65.359 | 1.00 42.75 | B | C |
| ATOM | 3737 | OE1 | GLN | B | 37 | 54.322 | 8.143 | 65.079 | 1.00 44.67 | B | O |
| ATOM | 3738 | NE2 | GLN | B | 37 | 52.272 | 7.363 | 65.483 | 1.00 41.83 | B | N |
| ATOM | 3741 | C | GLN | B | 37 | 50.138 | 11.461 | 65.874 | 1.00 38.96 | B | C |
| ATOM | 3742 | O | GLN | B | 37 | 49.207 | 10.680 | 65.730 | 1.00 38.03 | B | O |
| ATOM | 3744 | N | GLN | B | 38 | 50.372 | 12.484 | 65.058 | 1.00 38.58 | B | N |
| ATOM | 3745 | CA | GLN | B | 38 | 49.545 | 12.743 | 63.873 | 1.00 38.27 | B | C |
| ATOM | 3747 | CB | GLN | B | 38 | 48.765 | 14.032 | 64.031 | 1.00 38.07 | B | C |
| ATOM | 3750 | CG | GLN | B | 38 | 47.849 | 14.368 | 62.827 | 1.00 36.38 | B | C |
| ATOM | 3753 | CD | GLN | B | 38 | 46.985 | 15.556 | 63.125 | 1.00 33.79 | B | C |
| ATOM | 3754 | OE1 | GLN | B | 38 | 47.439 | 16.502 | 63.771 | 1.00 31.70 | B | O |
| ATOM | 3755 | NE2 | GLN | B | 38 | 45.730 | 15.514 | 62.696 | 1.00 28.19 | B | N |
| ATOM | 3758 | C | GLN | B | 38 | 50.350 | 12.815 | 62.583 | 1.00 38.46 | B | C |
| ATOM | 3759 | O | GLN | B | 38 | 51.049 | 13.785 | 62.323 | 1.00 37.78 | B | O |
| ATOM | 3761 | N | PHE | B | 39 | 50.222 | 11.789 | 61.767 | 1.00 39.32 | B | N |
| ATOM | 3762 | CA | PHE | B | 39 | 50.751 | 11.839 | 60.410 | 1.00 40.54 | B | C |
| ATOM | 3764 | CB | PHE | B | 39 | 50.755 | 10.441 | 59.776 | 1.00 40.91 | B | C |
| ATOM | 3767 | CG | PHE | B | 39 | 51.562 | 9.409 | 60.552 | 1.00 41.80 | B | C |
| ATOM | 3768 | CD1 | PHE | B | 39 | 52.933 | 9.554 | 60.714 | 1.00 43.62 | B | C |
| ATOM | 3770 | CE1 | PHE | B | 39 | 53.682 | 8.595 | 61.414 | 1.00 43.97 | B | C |
| ATOM | 3772 | CZ | PHE | B | 39 | 53.061 | 7.490 | 61.958 | 1.00 43.71 | B | C |
| ATOM | 3774 | CE2 | PHE | B | 39 | 51.683 | 7.326 | 61.799 | 1.00 44.57 | B | C |
| ATOM | 3776 | CD2 | PHE | B | 39 | 50.947 | 8.285 | 61.097 | 1.00 44.12 | B | C |
| ATOM | 3778 | C | PHE | B | 39 | 49.868 | 12.783 | 59.586 | 1.00 41.16 | B | C |
| ATOM | 3779 | O | PHE | B | 39 | 48.683 | 12.970 | 59.918 | 1.00 40.98 | B | O |
| ATOM | 3781 | N | PRO | B | 40 | 50.433 | 13.387 | 58.511 | 1.00 41.43 | B | N |
| ATOM | 3782 | CA | PRO | B | 40 | 49.710 | 14.370 | 57.702 | 1.00 40.97 | B | C |
| ATOM | 3784 | CB | PRO | B | 40 | 50.706 | 14.724 | 56.587 | 1.00 41.56 | B | C |
| ATOM | 3787 | CG | PRO | B | 40 | 52.032 | 14.226 | 57.055 | 1.00 42.49 | B | C |
| ATOM | 3790 | CD | PRO | B | 40 | 51.726 | 13.023 | 57.898 | 1.00 41.87 | B | C |
| ATOM | 3793 | C | PRO | B | 40 | 48.470 | 13.752 | 57.099 | 1.00 40.47 | B | C |
| ATOM | 3794 | O | PRO | B | 40 | 48.505 | 12.585 | 56.735 | 1.00 40.37 | B | O |

Figure 8 – CONT.

```
ATOM   3795  N    GLY B  41      47.379  14.509  57.039  1.00 39.72           B  N
ATOM   3796  CA   GLY B  41      46.112  13.994  56.550  1.00 39.43           B  C
ATOM   3799  C    GLY B  41      45.521  12.826  57.343  1.00 39.20           B  C
ATOM   3800  O    GLY B  41      44.635  12.136  56.844  1.00 40.35           B  O
ATOM   3802  N    THR B  42      45.978  12.589  58.568  1.00 37.54           B  N
ATOM   3803  CA   THR B  42      45.410  11.517  59.379  1.00 36.48           B  C
ATOM   3805  CB   THR B  42      46.437  10.402  59.594  1.00 36.71           B  C
ATOM   3807  OG1  THR B  42      47.044  10.089  58.340  1.00 37.79           B  O
ATOM   3809  CG2  THR B  42      45.786   9.145  60.154  1.00 37.99           B  C
ATOM   3813  C    THR B  42      44.994  12.043  60.739  1.00 35.02           B  C
ATOM   3814  O    THR B  42      45.474  13.088  61.189  1.00 32.97           B  O
ATOM   3816  N    ALA B  43      44.107  11.289  61.384  1.00 34.44           B  N
ATOM   3817  CA   ALA B  43      43.676  11.560  62.746  1.00 33.90           B  C
ATOM   3819  CB   ALA B  43      42.528  10.643  63.123  1.00 33.47           B  C
ATOM   3823  C    ALA B  43      44.841  11.337  63.707  1.00 33.90           B  C
ATOM   3824  O    ALA B  43      45.607  10.394  63.550  1.00 34.57           B  O
ATOM   3826  N    PRO B  44      44.975  12.199  64.708  1.00 33.41           B  N
ATOM   3827  CA   PRO B  44      45.865  11.912  65.820  1.00 34.37           B  C
ATOM   3829  CB   PRO B  44      45.507  12.996  66.853  1.00 34.55           B  C
ATOM   3832  CG   PRO B  44      44.974  14.128  66.029  1.00 33.46           B  C
ATOM   3835  CD   PRO B  44      44.221  13.434  64.910  1.00 33.51           B  C
ATOM   3838  C    PRO B  44      45.608  10.546  66.418  1.00 35.29           B  C
ATOM   3839  O    PRO B  44      44.518   9.976  66.278  1.00 34.84           B  O
ATOM   3840  N    LYS B  45      46.629   9.997  67.050  1.00 36.58           B  N
ATOM   3841  CA   LYS B  45      46.424   8.814  67.833  1.00 37.72           B  C
ATOM   3843  CB   LYS B  45      46.640   7.553  67.006  1.00 38.16           B  C
ATOM   3846  CG   LYS B  45      47.977   6.916  67.106  1.00 39.84           B  C
ATOM   3849  CD   LYS B  45      48.099   5.745  66.089  1.00 42.74           B  C
ATOM   3852  CE   LYS B  45      49.506   5.107  66.162  1.00 44.78           B  C
ATOM   3855  NZ   LYS B  45      49.841   4.228  64.996  1.00 46.23           B  N
ATOM   3859  C    LYS B  45      47.271   8.835  69.080  1.00 38.34           B  C
ATOM   3860  O    LYS B  45      48.347   9.452  69.119  1.00 37.97           B  O
ATOM   3862  N    LEU B  46      46.734   8.175  70.101  1.00 38.88           B  N
ATOM   3863  CA   LEU B  46      47.376   8.068  71.381  1.00 40.00           B  C
ATOM   3865  CB   LEU B  46      46.447   7.379  72.390  1.00 39.76           B  C
ATOM   3868  CG   LEU B  46      46.967   7.299  73.834  1.00 40.52           B  C
ATOM   3870  CD1  LEU B  46      47.005   8.678  74.481  1.00 39.66           B  C
ATOM   3874  CD2  LEU B  46      46.115   6.310  74.663  1.00 40.14           B  C
ATOM   3878  C    LEU B  46      48.644   7.250  71.217  1.00 40.95           B  C
ATOM   3879  O    LEU B  46      48.587   6.116  70.726  1.00 41.18           B  O
ATOM   3881  N    LEU B  47      49.756   7.839  71.658  1.00 42.16           B  N
ATOM   3882  CA   LEU B  47      51.098   7.284  71.569  1.00 43.48           B  C
ATOM   3884  CB   LEU B  47      52.024   8.332  70.927  1.00 43.27           B  C
ATOM   3887  CG   LEU B  47      53.443   7.919  70.551  1.00 42.09           B  C
ATOM   3889  CD1  LEU B  47      53.411   6.906  69.437  1.00 42.25           B  C
ATOM   3893  CD2  LEU B  47      54.276   9.134  70.164  1.00 41.20           B  C
ATOM   3897  C    LEU B  47      51.679   6.938  72.942  1.00 44.79           B  C
ATOM   3898  O    LEU B  47      52.339   5.914  73.093  1.00 45.56           B  O
ATOM   3900  N    ILE B  48      51.489   7.837  73.904  1.00 46.00           B  N
ATOM   3901  CA   ILE B  48      51.882   7.639  75.298  1.00 47.15           B  C
ATOM   3903  CB   ILE B  48      53.124   8.437  75.697  1.00 46.74           B  C
ATOM   3905  CG1  ILE B  48      54.379   7.919  74.990  1.00 48.03           B  C
ATOM   3908  CD1  ILE B  48      54.670   6.432  75.195  1.00 46.46           B  C
ATOM   3912  CG2  ILE B  48      53.336   8.344  77.199  1.00 47.97           B  C
ATOM   3916  C    ILE B  48      50.772   8.136  76.208  1.00 47.84           B  C
ATOM   3917  O    ILE B  48      50.213   9.192  75.973  1.00 47.29           B  O
ATOM   3919  N    TYR B  49      50.469   7.365  77.246  1.00 49.09           B  N
ATOM   3920  CA   TYR B  49      49.495   7.760  78.256  1.00 50.25           B  C
```

Figure 8 – CONT.

```
ATOM   3922  CB   TYR B  49      48.165   7.042  78.018  1.00 50.46      B  C
ATOM   3925  CG   TYR B  49      48.155   5.564  78.330  1.00 51.06      B  C
ATOM   3926  CD1  TYR B  49      47.598   5.088  79.517  1.00 50.91      B  C
ATOM   3928  CE1  TYR B  49      47.576   3.752  79.802  1.00 50.99      B  C
ATOM   3930  CZ   TYR B  49      48.118   2.862  78.915  1.00 50.67      B  C
ATOM   3931  OH   TYR B  49      48.096   1.527  79.204  1.00 50.01      B  O
ATOM   3933  CE2  TYR B  49      48.666   3.304  77.731  1.00 51.09      B  C
ATOM   3935  CD2  TYR B  49      48.692   4.648  77.452  1.00 51.06      B  C
ATOM   3937  C    TYR B  49      50.044   7.454  79.640  1.00 51.06      B  C
ATOM   3938  O    TYR B  49      50.967   6.639  79.778  1.00 51.15      B  O
ATOM   3940  N    ASP B  50      49.477   8.110  80.651  1.00 52.17      B  N
ATOM   3941  CA   ASP B  50      49.977   8.040  82.046  1.00 53.00      B  C
ATOM   3943  CB   ASP B  50      49.624   6.694  82.703  1.00 52.96      B  C
ATOM   3946  CG   ASP B  50      48.122   6.529  82.982  1.00 54.23      B  C
ATOM   3947  OD1  ASP B  50      47.321   7.434  82.651  1.00 55.45      B  O
ATOM   3948  OD2  ASP B  50      47.742   5.469  83.543  1.00 54.90      B  O
ATOM   3949  C    ASP B  50      51.493   8.302  82.127  1.00 53.34      B  C
ATOM   3950  O    ASP B  50      52.250   7.533  82.717  1.00 53.00      B  O
ATOM   3952  N    ASN B  51      51.928   9.387  81.505  1.00 53.69      B  N
ATOM   3953  CA   ASN B  51      53.328   9.793  81.515  1.00 54.47      B  C
ATOM   3955  CB   ASN B  51      53.870   9.881  82.942  1.00 54.75      B  C
ATOM   3958  CG   ASN B  51      52.953  10.645  83.849  1.00 56.45      B  C
ATOM   3959  OD1  ASN B  51      52.650  10.214  84.971  1.00 59.00      B  O
ATOM   3960  ND2  ASN B  51      52.478  11.786  83.363  1.00 56.20      B  N
ATOM   3963  C    ASN B  51      54.246   8.919  80.688  1.00 54.42      B  C
ATOM   3964  O    ASN B  51      54.999   9.446  79.875  1.00 54.79      B  O
ATOM   3966  N    ASN B  52      54.183   7.601  80.881  1.00 54.44      B  N
ATOM   3967  CA   ASN B  52      55.189   6.702  80.315  1.00 54.54      B  C
ATOM   3969  CB   ASN B  52      56.296   6.503  81.356  1.00 54.83      B  C
ATOM   3972  CG   ASN B  52      55.780   5.884  82.644  1.00 55.37      B  C
ATOM   3973  OD1  ASN B  52      54.928   4.992  82.619  1.00 57.24      B  O
ATOM   3974  ND2  ASN B  52      56.270   6.379  83.779  1.00 56.23      B  N
ATOM   3977  C    ASN B  52      54.710   5.325  79.826  1.00 54.45      B  C
ATOM   3978  O    ASN B  52      55.537   4.496  79.455  1.00 54.41      B  O
ATOM   3980  N    LYS B  53      53.406   5.074  79.815  1.00 54.28      B  N
ATOM   3981  CA   LYS B  53      52.892   3.794  79.318  1.00 54.67      B  C
ATOM   3983  CB   LYS B  53      51.607   3.386  80.061  1.00 54.83      B  C
ATOM   3986  CG   LYS B  53      51.688   3.598  81.586  1.00 55.69      B  C
ATOM   3989  CD   LYS B  53      50.584   2.869  82.345  1.00 57.43      B  C
ATOM   3992  CE   LYS B  53      50.622   3.171  83.857  1.00 58.16      B  C
ATOM   3995  NZ   LYS B  53      49.368   2.699  84.547  1.00 57.62      B  N
ATOM   3999  C    LYS B  53      52.642   3.903  77.810  1.00 54.74      B  C
ATOM   4000  O    LYS B  53      52.401   5.002  77.290  1.00 54.52      B  O
ATOM   4002  N    ARG B  54      52.712   2.764  77.126  1.00 54.33      B  N
ATOM   4003  CA   ARG B  54      52.455   2.679  75.693  1.00 54.55      B  C
ATOM   4005  CB   ARG B  54      53.653   2.060  74.979  1.00 55.00      B  C
ATOM   4008  CG   ARG B  54      54.792   3.021  74.643  1.00 56.53      B  C
ATOM   4011  CD   ARG B  54      55.874   2.267  73.926  1.00 58.36      B  C
ATOM   4014  NE   ARG B  54      56.455   1.228  74.782  1.00 60.98      B  N
ATOM   4016  CZ   ARG B  54      57.470   1.409  75.633  1.00 61.84      B  C
ATOM   4017  NH1  ARG B  54      58.058   2.604  75.772  1.00 60.97      B  N
ATOM   4020  NH2  ARG B  54      57.911   0.374  76.349  1.00 61.83      B  N
ATOM   4023  C    ARG B  54      51.272   1.776  75.403  1.00 54.03      B  C
ATOM   4024  O    ARG B  54      51.142   0.742  76.022  1.00 54.23      B  O
ATOM   4026  N    PRO B  55      50.421   2.143  74.434  1.00 53.78      B  N
ATOM   4027  CA   PRO B  55      49.473   1.160  73.948  1.00 54.07      B  C
ATOM   4029  CB   PRO B  55      48.578   1.958  72.997  1.00 54.08      B  C
ATOM   4032  CG   PRO B  55      48.803   3.379  73.360  1.00 53.60      B  C
```

Figure 8 – CONT.

```
ATOM   4035  CD   PRO B  55      50.226   3.444  73.782  1.00 53.65      B    C
ATOM   4038  C    PRO B  55      50.225   0.061  73.216  1.00 54.46      B    C
ATOM   4039  O    PRO B  55      51.367   0.265  72.783  1.00 53.63      B    O
ATOM   4040  N    SER B  56      49.596  -1.101  73.100  1.00 55.41      B    N
ATOM   4041  CA   SER B  56      50.327  -2.318  72.733  1.00 56.32      B    C
ATOM   4043  CB   SER B  56      49.516  -3.562  73.092  1.00 56.58      B    C
ATOM   4046  OG   SER B  56      48.366  -3.671  72.281  1.00 55.99      B    O
ATOM   4048  C    SER B  56      50.740  -2.368  71.262  1.00 56.75      B    C
ATOM   4049  O    SER B  56      51.609  -3.158  70.901  1.00 57.11      B    O
ATOM   4051  N    ALA B  57      50.109  -1.539  70.428  1.00 57.18      B    N
ATOM   4052  CA   ALA B  57      50.496  -1.402  69.017  1.00 57.50      B    C
ATOM   4054  CB   ALA B  57      49.318  -0.897  68.193  1.00 57.47      B    C
ATOM   4058  C    ALA B  57      51.709  -0.476  68.825  1.00 57.60      B    C
ATOM   4059  O    ALA B  57      52.304  -0.459  67.756  1.00 57.82      B    O
ATOM   4061  N    ILE B  58      52.066   0.291  69.852  1.00 57.79      B    N
ATOM   4062  CA   ILE B  58      53.176   1.228  69.755  1.00 57.68      B    C
ATOM   4064  CB   ILE B  58      52.984   2.435  70.710  1.00 57.26      B    C
ATOM   4066  CG1  ILE B  58      51.667   3.165  70.388  1.00 56.54      B    C
ATOM   4069  CD1  ILE B  58      51.424   3.462  68.897  1.00 54.02      B    C
ATOM   4073  CG2  ILE B  58      54.145   3.418  70.623  1.00 56.58      B    C
ATOM   4077  C    ILE B  58      54.477   0.497  70.053  1.00 58.63      B    C
ATOM   4078  O    ILE B  58      54.541  -0.309  70.986  1.00 59.29      B    O
ATOM   4080  N    PRO B  59      55.522   0.756  69.250  1.00 59.14      B    N
ATOM   4081  CA   PRO B  59      56.801   0.108  69.511  1.00 59.40      B    C
ATOM   4083  CB   PRO B  59      57.551   0.286  68.193  1.00 59.74      B    C
ATOM   4086  CG   PRO B  59      57.038   1.589  67.683  1.00 60.08      B    C
ATOM   4089  CD   PRO B  59      55.576   1.613  68.053  1.00 59.16      B    C
ATOM   4092  C    PRO B  59      57.574   0.758  70.655  1.00 59.40      B    C
ATOM   4093  O    PRO B  59      57.453   1.965  70.899  1.00 59.43      B    O
ATOM   4094  N    ASP B  60      58.379  -0.062  71.323  1.00 59.19      B    N
ATOM   4095  CA   ASP B  60      59.184   0.341  72.493  1.00 59.21      B    C
ATOM   4097  CB   ASP B  60      59.978  -0.877  73.019  1.00 59.40      B    C
ATOM   4100  CG   ASP B  60      60.578  -1.733  71.881  1.00 60.98      B    C
ATOM   4101  OD1  ASP B  60      61.622  -1.325  71.312  1.00 63.05      B    O
ATOM   4102  OD2  ASP B  60      59.990  -2.795  71.542  1.00 61.10      B    O
ATOM   4103  C    ASP B  60      60.132   1.527  72.251  1.00 58.56      B    C
ATOM   4104  O    ASP B  60      60.594   2.169  73.196  1.00 58.71      B    O
ATOM   4106  N    ARG B  61      60.418   1.815  70.990  1.00 58.09      B    N
ATOM   4107  CA   ARG B  61      61.279   2.940  70.624  1.00 57.52      B    C
ATOM   4109  CB   ARG B  61      61.384   3.043  69.094  1.00 57.80      B    C
ATOM   4112  CG   ARG B  61      61.912   1.796  68.414  1.00 57.40      B    C
ATOM   4115  CD   ARG B  61      62.309   2.052  66.965  1.00 56.92      B    C
ATOM   4118  NE   ARG B  61      61.169   2.251  66.056  1.00 54.72      B    N
ATOM   4120  CZ   ARG B  61      60.749   3.428  65.583  1.00 52.29      B    C
ATOM   4121  NH1  ARG B  61      61.343   4.577  65.940  1.00 51.21      B    N
ATOM   4124  NH2  ARG B  61      59.708   3.453  64.753  1.00 50.92      B    N
ATOM   4127  C    ARG B  61      60.794   4.283  71.180  1.00 56.95      B    C
ATOM   4128  O    ARG B  61      61.600   5.179  71.457  1.00 56.79      B    O
ATOM   4130  N    PHE B  62      59.476   4.428  71.316  1.00 56.30      B    N
ATOM   4131  CA   PHE B  62      58.895   5.641  71.891  1.00 55.75      B    C
ATOM   4133  CB   PHE B  62      57.483   5.900  71.354  1.00 55.49      B    C
ATOM   4136  CG   PHE B  62      57.417   6.060  69.858  1.00 53.95      B    C
ATOM   4137  CD1  PHE B  62      57.587   7.307  69.274  1.00 52.57      B    C
ATOM   4139  CE1  PHE B  62      57.521   7.462  67.901  1.00 52.81      B    C
ATOM   4141  CZ   PHE B  62      57.283   6.363  67.092  1.00 53.10      B    C
ATOM   4143  CE2  PHE B  62      57.111   5.099  67.664  1.00 53.27      B    C
ATOM   4145  CD2  PHE B  62      57.173   4.960  69.043  1.00 53.17      B    C
ATOM   4147  C    PHE B  62      58.826   5.492  73.394  1.00 55.84      B    C
```

Figure 8 – CONT.

```
ATOM   4148  O    PHE B  62      58.400   4.458  73.901  1.00 55.51           B  O
ATOM   4150  N    SER B  63      59.241   6.540  74.093  1.00 55.95           B  N
ATOM   4151  CA   SER B  63      59.196   6.573  75.541  1.00 56.11           B  C
ATOM   4153  CB   SER B  63      60.595   6.314  76.125  1.00 56.18           B  C
ATOM   4156  OG   SER B  63      61.461   7.432  75.955  1.00 55.61           B  O
ATOM   4158  C    SER B  63      58.692   7.937  75.976  1.00 56.15           B  C
ATOM   4159  O    SER B  63      58.807   8.911  75.236  1.00 56.18           B  O
ATOM   4161  N    GLY B  64      58.130   7.999  77.173  1.00 56.48           B  N
ATOM   4162  CA   GLY B  64      57.707   9.259  77.745  1.00 57.27           B  C
ATOM   4165  C    GLY B  64      58.026   9.361  79.226  1.00 57.87           B  C
ATOM   4166  O    GLY B  64      58.047   8.355  79.946  1.00 57.71           B  O
ATOM   4168  N    SER B  65      58.261  10.580  79.686  1.00 58.39           B  N
ATOM   4169  CA   SER B  65      58.447  10.810  81.099  1.00 59.25           B  C
ATOM   4171  CB   SER B  65      59.924  10.745  81.435  1.00 59.14           B  C
ATOM   4174  OG   SER B  65      60.611  11.750  80.722  1.00 59.39           B  O
ATOM   4176  C    SER B  65      57.910  12.173  81.485  1.00 60.04           B  C
ATOM   4177  O    SER B  65      57.940  13.113  80.685  1.00 60.20           B  O
ATOM   4179  N    LYS B  66      57.432  12.255  82.726  1.00 60.91           B  N
ATOM   4180  CA   LYS B  66      56.992  13.493  83.344  1.00 61.47           B  C
ATOM   4182  CB   LYS B  66      55.549  13.326  83.843  1.00 61.72           B  C
ATOM   4185  CG   LYS B  66      55.032  14.463  84.716  1.00 61.99           B  C
ATOM   4188  CD   LYS B  66      53.676  14.138  85.337  1.00 62.27           B  C
ATOM   4191  CE   LYS B  66      53.436  14.953  86.591  1.00 61.98           B  C
ATOM   4194  NZ   LYS B  66      52.004  14.932  87.005  1.00 62.66           B  N
ATOM   4198  C    LYS B  66      57.934  13.816  84.513  1.00 61.89           B  C
ATOM   4199  O    LYS B  66      58.391  12.908  85.212  1.00 61.75           B  O
ATOM   4201  N    SER B  67      58.211  15.110  84.706  1.00 62.33           B  N
ATOM   4202  CA   SER B  67      58.997  15.622  85.838  1.00 62.36           B  C
ATOM   4204  CB   SER B  67      60.504  15.572  85.537  1.00 62.68           B  C
ATOM   4207  OG   SER B  67      60.973  14.239  85.379  1.00 63.67           B  O
ATOM   4209  C    SER B  67      58.615  17.073  86.161  1.00 62.21           B  C
ATOM   4210  O    SER B  67      58.954  18.003  85.415  1.00 61.91           B  O
ATOM   4212  N    GLY B  68      57.940  17.273  87.288  1.00 62.07           B  N
ATOM   4213  CA   GLY B  68      57.567  18.618  87.715  1.00 61.84           B  C
ATOM   4216  C    GLY B  68      56.503  19.154  86.777  1.00 61.48           B  C
ATOM   4217  O    GLY B  68      55.528  18.450  86.491  1.00 61.48           B  O
ATOM   4219  N    THR B  69      56.716  20.371  86.268  1.00 60.90           B  N
ATOM   4220  CA   THR B  69      55.764  21.034  85.375  1.00 60.25           B  C
ATOM   4222  CB   THR B  69      55.760  22.552  85.610  1.00 60.40           B  C
ATOM   4224  OG1  THR B  69      57.028  23.096  85.226  1.00 60.13           B  O
ATOM   4226  CG2  THR B  69      55.474  22.878  87.068  1.00 60.27           B  C
ATOM   4230  C    THR B  69      56.103  20.792  83.901  1.00 59.84           B  C
ATOM   4231  O    THR B  69      55.692  21.557  83.025  1.00 59.59           B  O
ATOM   4233  N    SER B  70      56.848  19.723  83.638  1.00 59.09           B  N
ATOM   4234  CA   SER B  70      57.364  19.441  82.317  1.00 58.46           B  C
ATOM   4236  CB   SER B  70      58.792  19.993  82.202  1.00 58.66           B  C
ATOM   4239  OG   SER B  70      59.722  18.986  81.821  1.00 59.26           B  O
ATOM   4241  C    SER B  70      57.302  17.941  82.008  1.00 57.79           B  C
ATOM   4242  O    SER B  70      57.195  17.107  82.913  1.00 57.46           B  O
ATOM   4244  N    ALA B  71      57.323  17.609  80.715  1.00 57.10           B  N
ATOM   4245  CA   ALA B  71      57.371  16.215  80.269  1.00 56.35           B  C
ATOM   4247  CB   ALA B  71      55.986  15.647  80.025  1.00 56.19           B  C
ATOM   4251  C    ALA B  71      58.186  16.153  79.017  1.00 55.83           B  C
ATOM   4252  O    ALA B  71      58.498  17.175  78.395  1.00 55.87           B  O
ATOM   4254  N    THR B  72      58.555  14.941  78.660  1.00 55.16           B  N
ATOM   4255  CA   THR B  72      59.428  14.745  77.538  1.00 54.76           B  C
ATOM   4257  CB   THR B  72      60.921  14.720  77.972  1.00 54.98           B  C
ATOM   4259  OG1  THR B  72      61.325  16.032  78.388  1.00 55.34           B  O
```

Figure 8 – CONT.

```
ATOM   4261  CG2 THR B  72      61.808  14.305  76.820  1.00 55.40      B  C
ATOM   4265  C   THR B  72      59.042  13.456  76.863  1.00 53.75      B  C
ATOM   4266  O   THR B  72      58.774  12.464  77.524  1.00 53.50      B  O
ATOM   4268  N   LEU B  73      58.972  13.520  75.542  1.00 52.92      B  N
ATOM   4269  CA  LEU B  73      58.847  12.361  74.694  1.00 52.39      B  C
ATOM   4271  CB  LEU B  73      57.820  12.615  73.572  1.00 52.00      B  C
ATOM   4274  CG  LEU B  73      57.642  11.531  72.504  1.00 51.26      B  C
ATOM   4276  CD1 LEU B  73      56.975  10.319  73.096  1.00 47.55      B  C
ATOM   4280  CD2 LEU B  73      56.833  12.064  71.320  1.00 49.84      B  C
ATOM   4284  C   LEU B  73      60.222  12.169  74.091  1.00 52.35      B  C
ATOM   4285  O   LEU B  73      60.887  13.146  73.743  1.00 51.85      B  O
ATOM   4287  N   GLY B  74      60.633  10.907  73.971  1.00 52.76      B  N
ATOM   4288  CA  GLY B  74      61.907  10.536  73.367  1.00 52.60      B  C
ATOM   4291  C   GLY B  74      61.672   9.425  72.378  1.00 52.96      B  C
ATOM   4292  O   GLY B  74      60.834   8.546  72.603  1.00 52.64      B  O
ATOM   4294  N   ILE B  75      62.395   9.487  71.265  1.00 53.79      B  N
ATOM   4295  CA  ILE B  75      62.270   8.514  70.186  1.00 54.34      B  C
ATOM   4297  CB  ILE B  75      61.645   9.138  68.898  1.00 54.68      B  C
ATOM   4299  CG1 ILE B  75      60.440  10.017  69.244  1.00 54.95      B  C
ATOM   4302  CD1 ILE B  75      60.168  11.069  68.214  1.00 56.22      B  C
ATOM   4306  CG2 ILE B  75      61.218   8.048  67.899  1.00 53.39      B  C
ATOM   4310  C   ILE B  75      63.676   8.033  69.880  1.00 55.20      B  C
ATOM   4311  O   ILE B  75      64.608   8.832  69.761  1.00 55.26      B  O
ATOM   4313  N   THR B  76      63.805   6.720  69.751  1.00 55.96      B  N
ATOM   4314  CA  THR B  76      65.073   6.048  69.582  1.00 56.56      B  C
ATOM   4316  CB  THR B  76      65.349   5.129  70.787  1.00 56.46      B  C
ATOM   4318  OG1 THR B  76      66.114   5.858  71.750  1.00 57.27      B  O
ATOM   4320  CG2 THR B  76      66.106   3.855  70.375  1.00 57.18      B  C
ATOM   4324  C   THR B  76      64.964   5.216  68.332  1.00 57.06      B  C
ATOM   4325  O   THR B  76      63.880   4.727  68.006  1.00 57.58      B  O
ATOM   4327  N   GLY B  77      66.082   5.036  67.639  1.00 57.19      B  N
ATOM   4328  CA  GLY B  77      66.082   4.275  66.396  1.00 57.31      B  C
ATOM   4331  C   GLY B  77      65.297   5.037  65.342  1.00 57.23      B  C
ATOM   4332  O   GLY B  77      64.597   4.443  64.515  1.00 56.64      B  O
ATOM   4334  N   LEU B  78      65.433   6.360  65.383  1.00 57.22      B  N
ATOM   4335  CA  LEU B  78      64.690   7.243  64.509  1.00 57.33      B  C
ATOM   4337  CB  LEU B  78      65.334   8.619  64.499  1.00 57.18      B  C
ATOM   4340  CG  LEU B  78      64.555   9.743  63.827  1.00 57.95      B  C
ATOM   4342  CD1 LEU B  78      65.191  11.072  64.157  1.00 58.02      B  C
ATOM   4346  CD2 LEU B  78      64.527   9.550  62.339  1.00 59.37      B  C
ATOM   4350  C   LEU B  78      64.615   6.667  63.101  1.00 57.55      B  C
ATOM   4351  O   LEU B  78      65.635   6.260  62.522  1.00 57.90      B  O
ATOM   4353  N   GLN B  79      63.389   6.604  62.582  1.00 57.55      B  N
ATOM   4354  CA  GLN B  79      63.102   6.110  61.242  1.00 57.47      B  C
ATOM   4356  CB  GLN B  79      62.206   4.872  61.303  1.00 57.65      B  C
ATOM   4359  CG  GLN B  79      62.820   3.681  62.022  1.00 58.68      B  C
ATOM   4362  CD  GLN B  79      61.911   2.458  62.022  1.00 60.02      B  C
ATOM   4363  OE1 GLN B  79      60.869   2.446  61.369  1.00 62.22      B  O
ATOM   4364  NE2 GLN B  79      62.305   1.427  62.757  1.00 58.95      B  N
ATOM   4367  C   GLN B  79      62.394   7.190  60.424  1.00 57.13      B  C
ATOM   4368  O   GLN B  79      61.836   8.151  60.968  1.00 56.93      B  O
ATOM   4370  N   THR B  80      62.409   7.008  59.109  1.00 56.55      B  N
ATOM   4371  CA  THR B  80      61.717   7.905  58.209  1.00 56.23      B  C
ATOM   4373  CB  THR B  80      61.987   7.534  56.737  1.00 56.29      B  C
ATOM   4375  OG1 THR B  80      61.626   8.647  55.913  1.00 57.61      B  O
ATOM   4377  CG2 THR B  80      61.187   6.292  56.320  1.00 56.10      B  C
ATOM   4381  C   THR B  80      60.203   7.893  58.501  1.00 55.29      B  C
ATOM   4382  O   THR B  80      59.554   8.934  58.467  1.00 54.94      B  O
```

Figure 8 – CONT.

```
ATOM   4384  N    GLY B  81      59.669   6.712  58.822  1.00 54.38      B   N
ATOM   4385  CA   GLY B  81      58.264   6.541  59.174  1.00 53.37      B   C
ATOM   4388  C    GLY B  81      57.784   7.275  60.425  1.00 52.48      B   C
ATOM   4389  O    GLY B  81      56.575   7.296  60.678  1.00 51.95      B   O
ATOM   4391  N    ASP B  82      58.717   7.861  61.193  1.00 51.40      B   N
ATOM   4392  CA   ASP B  82      58.428   8.626  62.423  1.00 50.58      B   C
ATOM   4394  CB   ASP B  82      59.618   8.548  63.390  1.00 50.53      B   C
ATOM   4397  CG   ASP B  82      59.930   7.130  63.832  1.00 50.71      B   C
ATOM   4398  OD1  ASP B  82      59.067   6.234  63.681  1.00 50.21      B   O
ATOM   4399  OD2  ASP B  82      61.054   6.911  64.335  1.00 50.56      B   O
ATOM   4400  C    ASP B  82      58.105  10.112  62.222  1.00 49.95      B   C
ATOM   4401  O    ASP B  82      57.706  10.797  63.183  1.00 49.20      B   O
ATOM   4403  N    GLU B  83      58.318  10.607  60.998  1.00 49.24      B   N
ATOM   4404  CA   GLU B  83      57.978  11.983  60.600  1.00 48.67      B   C
ATOM   4406  CB   GLU B  83      58.254  12.203  59.105  1.00 49.01      B   C
ATOM   4409  CG   GLU B  83      59.723  12.332  58.727  1.00 51.56      B   C
ATOM   4412  CD   GLU B  83      59.921  13.035  57.387  1.00 53.83      B   C
ATOM   4413  OE1  GLU B  83      59.249  12.656  56.392  1.00 55.88      B   O
ATOM   4414  OE2  GLU B  83      60.757  13.959  57.342  1.00 54.34      B   O
ATOM   4415  C    GLU B  83      56.505  12.253  60.823  1.00 47.08      B   C
ATOM   4416  O    GLU B  83      55.674  11.614  60.209  1.00 47.04      B   O
ATOM   4418  N    ALA B  84      56.182  13.207  61.682  1.00 45.51      B   N
ATOM   4419  CA   ALA B  84      54.788  13.458  62.057  1.00 44.26      B   C
ATOM   4421  CB   ALA B  84      54.180  12.237  62.776  1.00 43.27      B   C
ATOM   4425  C    ALA B  84      54.773  14.651  62.970  1.00 43.21      B   C
ATOM   4426  O    ALA B  84      55.832  15.119  63.378  1.00 42.60      B   O
ATOM   4428  N    ASP B  85      53.574  15.132  63.286  1.00 42.27      B   N
ATOM   4429  CA   ASP B  85      53.388  16.107  64.349  1.00 41.75      B   C
ATOM   4431  CB   ASP B  85      52.251  17.095  64.025  1.00 41.95      B   C
ATOM   4434  CG   ASP B  85      52.567  18.003  62.820  1.00 43.36      B   C
ATOM   4435  OD1  ASP B  85      53.759  18.179  62.495  1.00 44.74      B   O
ATOM   4436  OD2  ASP B  85      51.621  18.555  62.207  1.00 44.21      B   O
ATOM   4437  C    ASP B  85      53.104  15.332  65.652  1.00 40.69      B   C
ATOM   4438  O    ASP B  85      52.291  14.406  65.680  1.00 40.02      B   O
ATOM   4440  N    TYR B  86      53.799  15.722  66.712  1.00 39.70      B   N
ATOM   4441  CA   TYR B  86      53.648  15.109  68.009  1.00 39.38      B   C
ATOM   4443  CB   TYR B  86      54.992  14.580  68.534  1.00 38.66      B   C
ATOM   4446  CG   TYR B  86      55.458  13.390  67.746  1.00 37.96      B   C
ATOM   4447  CD1  TYR B  86      55.150  12.117  68.152  1.00 37.28      B   C
ATOM   4449  CE1  TYR B  86      55.537  11.026  67.421  1.00 38.35      B   C
ATOM   4451  CZ   TYR B  86      56.246  11.188  66.250  1.00 37.20      B   C
ATOM   4452  OH   TYR B  86      56.618  10.074  65.534  1.00 36.51      B   O
ATOM   4454  CE2  TYR B  86      56.545  12.449  65.800  1.00 37.21      B   C
ATOM   4456  CD2  TYR B  86      56.158  13.547  66.553  1.00 37.83      B   C
ATOM   4458  C    TYR B  86      53.070  16.157  68.929  1.00 39.68      B   C
ATOM   4459  O    TYR B  86      53.600  17.268  69.012  1.00 39.45      B   O
ATOM   4461  N    TYR B  87      51.969  15.804  69.596  1.00 40.17      B   N
ATOM   4462  CA   TYR B  87      51.296  16.722  70.523  1.00 40.76      B   C
ATOM   4464  CB   TYR B  87      49.832  16.952  70.135  1.00 40.20      B   C
ATOM   4467  CG   TYR B  87      49.609  17.748  68.867  1.00 39.48      B   C
ATOM   4468  CD1  TYR B  87      49.506  19.127  68.905  1.00 39.12      B   C
ATOM   4470  CE1  TYR B  87      49.310  19.850  67.763  1.00 38.71      B   C
ATOM   4472  CZ   TYR B  87      49.197  19.207  66.566  1.00 38.03      B   C
ATOM   4473  OH   TYR B  87      48.990  19.954  65.428  1.00 38.62      B   O
ATOM   4475  CE2  TYR B  87      49.290  17.839  66.508  1.00 37.19      B   C
ATOM   4477  CD2  TYR B  87      49.490  17.124  67.638  1.00 36.20      B   C
ATOM   4479  C    TYR B  87      51.329  16.147  71.940  1.00 42.30      B   C
ATOM   4480  O    TYR B  87      51.026  14.950  72.164  1.00 42.11      B   O
```

Figure 8 – CONT.

```
ATOM   4482  N    CYS B  88      51.674  16.997  72.898  1.00 43.70           B  N
ATOM   4483  CA   CYS B  88      51.474  16.638  74.286  1.00 45.63           B  C
ATOM   4485  CB   CYS B  88      52.622  17.125  75.174  1.00 45.94           B  C
ATOM   4488  SG   CYS B  88      52.728  18.878  75.341  1.00 48.52           B  S
ATOM   4490  C    CYS B  88      50.139  17.185  74.752  1.00 46.04           B  C
ATOM   4491  O    CYS B  88      49.657  18.224  74.261  1.00 46.57           B  O
ATOM   4493  N    GLY B  89      49.549  16.477  75.707  1.00 46.75           B  N
ATOM   4494  CA   GLY B  89      48.287  16.878  76.291  1.00 47.25           B  C
ATOM   4497  C    GLY B  89      48.110  16.351  77.699  1.00 47.91           B  C
ATOM   4498  O    GLY B  89      48.752  15.384  78.107  1.00 47.22           B  O
ATOM   4500  N    THR B  90      47.219  17.012  78.423  1.00 48.96           B  N
ATOM   4501  CA   THR B  90      46.920  16.685  79.803  1.00 50.01           B  C
ATOM   4503  CB   THR B  90      48.033  17.196  80.806  1.00 50.37           B  C
ATOM   4505  OG1  THR B  90      47.857  16.582  82.100  1.00 50.29           B  O
ATOM   4507  CG2  THR B  90      48.013  18.701  80.954  1.00 49.15           B  C
ATOM   4511  C    THR B  90      45.578  17.304  80.143  1.00 50.80           B  C
ATOM   4512  O    THR B  90      44.831  17.722  79.251  1.00 50.76           B  O
ATOM   4514  N    TRP B  91      45.278  17.346  81.437  1.00 51.84           B  N
ATOM   4515  CA   TRP B  91      44.065  17.956  81.947  1.00 52.22           B  C
ATOM   4517  CB   TRP B  91      43.228  16.906  82.665  1.00 52.26           B  C
ATOM   4520  CG   TRP B  91      42.725  15.842  81.756  1.00 51.33           B  C
ATOM   4521  CD1  TRP B  91      43.367  14.688  81.394  1.00 51.08           B  C
ATOM   4523  NE1  TRP B  91      42.578  13.958  80.538  1.00 50.13           B  N
ATOM   4525  CE2  TRP B  91      41.411  14.646  80.322  1.00 49.09           B  C
ATOM   4526  CD2  TRP B  91      41.472  15.839  81.077  1.00 49.33           B  C
ATOM   4527  CE3  TRP B  91      40.389  16.724  81.042  1.00 48.26           B  C
ATOM   4529  CZ3  TRP B  91      39.298  16.404  80.278  1.00 47.68           B  C
ATOM   4531  CH2  TRP B  91      39.257  15.203  79.541  1.00 48.60           B  C
ATOM   4533  CZ2  TRP B  91      40.306  14.314  79.546  1.00 48.00           B  C
ATOM   4535  C    TRP B  91      44.438  19.050  82.911  1.00 53.00           B  C
ATOM   4536  O    TRP B  91      45.499  18.996  83.522  1.00 53.26           B  O
ATOM   4538  N    ASP B  92      43.558  20.034  83.048  1.00 53.98           B  N
ATOM   4539  CA   ASP B  92      43.760  21.126  83.968  1.00 54.79           B  C
ATOM   4541  CB   ASP B  92      43.579  22.458  83.253  1.00 55.10           B  C
ATOM   4544  CG   ASP B  92      43.613  23.631  84.208  1.00 55.49           B  C
ATOM   4545  OD1  ASP B  92      44.528  24.472  84.104  1.00 55.40           B  O
ATOM   4546  OD2  ASP B  92      42.726  23.691  85.081  1.00 56.62           B  O
ATOM   4547  C    ASP B  92      42.764  20.986  85.107  1.00 55.44           B  C
ATOM   4548  O    ASP B  92      41.562  20.930  84.876  1.00 55.38           B  O
ATOM   4550  N    SER B  93      43.277  20.963  86.339  1.00 56.49           B  N
ATOM   4551  CA   SER B  93      42.463  20.674  87.538  1.00 56.84           B  C
ATOM   4553  CB   SER B  93      43.365  20.341  88.733  1.00 57.06           B  C
ATOM   4556  OG   SER B  93      44.285  19.304  88.410  1.00 58.31           B  O
ATOM   4558  C    SER B  93      41.480  21.786  87.934  1.00 56.81           B  C
ATOM   4559  O    SER B  93      40.403  21.485  88.466  1.00 57.15           B  O
ATOM   4561  N    ARG B  94      41.842  23.050  87.684  1.00 56.69           B  N
ATOM   4562  CA   ARG B  94      40.945  24.190  87.967  1.00 56.65           B  C
ATOM   4564  CB   ARG B  94      41.724  25.522  87.961  1.00 56.98           B  C
ATOM   4573  C    ARG B  94      39.731  24.282  87.003  1.00 56.53           B  C
ATOM   4574  O    ARG B  94      38.594  24.471  87.464  1.00 56.66           B  O
ATOM   4576  N    LEU B  95      39.977  24.161  85.686  1.00 55.95           B  N
ATOM   4577  CA   LEU B  95      38.917  24.241  84.640  1.00 55.24           B  C
ATOM   4579  CB   LEU B  95      39.466  24.838  83.352  1.00 55.37           B  C
ATOM   4582  CG   LEU B  95      40.018  26.256  83.405  1.00 55.89           B  C
ATOM   4584  CD1  LEU B  95      40.779  26.546  82.098  1.00 55.61           B  C
ATOM   4588  CD2  LEU B  95      38.887  27.244  83.653  1.00 54.91           B  C
ATOM   4592  C    LEU B  95      38.292  22.894  84.275  1.00 54.35           B  C
ATOM   4593  O    LEU B  95      37.221  22.852  83.668  1.00 54.33           B  O
```

Figure 8 – CONT.

```
ATOM   4595  N    GLY B  95A     38.970  21.804  84.617  1.00 53.33      B  N
ATOM   4596  CA   GLY B  95A     38.443  20.461  84.387  1.00 52.79      B  C
ATOM   4599  C    GLY B  95A     38.312  20.128  82.908  1.00 52.14      B  C
ATOM   4600  O    GLY B  95A     37.469  19.306  82.515  1.00 51.68      B  O
ATOM   4602  N    ILE B  95B     39.159  20.765  82.096  1.00 50.97      B  N
ATOM   4603  CA   ILE B  95B     39.175  20.547  80.658  1.00 50.13      B  C
ATOM   4605  CB   ILE B  95B     38.934  21.873  79.876  1.00 49.77      B  C
ATOM   4607  CG1  ILE B  95B     40.102  22.836  80.014  1.00 50.47      B  C
ATOM   4610  CD1  ILE B  95B     39.903  24.134  79.229  1.00 50.70      B  C
ATOM   4614  CG2  ILE B  95B     37.657  22.543  80.344  1.00 50.36      B  C
ATOM   4618  C    ILE B  95B     40.485  19.890  80.221  1.00 48.98      B  C
ATOM   4619  O    ILE B  95B     41.504  19.988  80.901  1.00 48.50      B  O
ATOM   4621  N    ALA B  96      40.454  19.200  79.085  1.00 47.98      B  N
ATOM   4622  CA   ALA B  96      41.688  18.678  78.508  1.00 46.70      B  C
ATOM   4624  CB   ALA B  96      41.414  17.566  77.538  1.00 46.36      B  C
ATOM   4628  C    ALA B  96      42.406  19.834  77.843  1.00 45.45      B  C
ATOM   4629  O    ALA B  96      41.816  20.857  77.557  1.00 45.26      B  O
ATOM   4631  N    VAL B  97      43.697  19.663  77.618  1.00 44.85      B  N
ATOM   4632  CA   VAL B  97      44.585  20.781  77.293  1.00 44.17      B  C
ATOM   4634  CB   VAL B  97      45.048  21.491  78.631  1.00 44.38      B  C
ATOM   4636  CG1  VAL B  97      46.524  21.654  78.714  1.00 45.55      B  C
ATOM   4640  CG2  VAL B  97      44.343  22.821  78.800  1.00 43.63      B  C
ATOM   4644  C    VAL B  97      45.718  20.236  76.431  1.00 43.15      B  C
ATOM   4645  O    VAL B  97      46.091  19.073  76.563  1.00 43.30      B  O
ATOM   4647  N    PHE B  98      46.220  21.048  75.513  1.00 42.40      B  N
ATOM   4648  CA   PHE B  98      47.217  20.590  74.544  1.00 41.72      B  C
ATOM   4650  CB   PHE B  98      46.594  20.404  73.156  1.00 41.26      B  C
ATOM   4653  CG   PHE B  98      45.600  19.276  73.041  1.00 39.62      B  C
ATOM   4654  CD1  PHE B  98      46.017  17.958  73.026  1.00 37.45      B  C
ATOM   4656  CE1  PHE B  98      45.106  16.927  72.865  1.00 37.73      B  C
ATOM   4658  CZ   PHE B  98      43.764  17.207  72.681  1.00 37.31      B  C
ATOM   4660  CE2  PHE B  98      43.341  18.517  72.670  1.00 37.38      B  C
ATOM   4662  CD2  PHE B  98      44.255  19.545  72.845  1.00 37.68      B  C
ATOM   4664  C    PHE B  98      48.367  21.581  74.348  1.00 41.90      B  C
ATOM   4665  O    PHE B  98      48.208  22.802  74.525  1.00 41.10      B  O
ATOM   4667  N    GLY B  99      49.511  21.030  73.940  1.00 42.03      B  N
ATOM   4668  CA   GLY B  99      50.594  21.823  73.358  1.00 42.35      B  C
ATOM   4671  C    GLY B  99      50.375  22.144  71.894  1.00 42.41      B  C
ATOM   4672  O    GLY B  99      49.561  21.507  71.231  1.00 42.31      B  O
ATOM   4674  N    GLY B 100      51.102  23.146  71.393  1.00 42.83      B  N
ATOM   4675  CA   GLY B 100      50.977  23.596  70.005  1.00 42.69      B  C
ATOM   4678  C    GLY B 100      51.488  22.601  68.979  1.00 43.13      B  C
ATOM   4679  O    GLY B 100      51.326  22.808  67.777  1.00 43.24      B  O
ATOM   4681  N    GLY B 101      52.135  21.529  69.432  1.00 43.43      B  N
ATOM   4682  CA   GLY B 101      52.633  20.491  68.521  1.00 43.57      B  C
ATOM   4685  C    GLY B 101      54.047  20.753  68.044  1.00 43.65      B  C
ATOM   4686  O    GLY B 101      54.479  21.904  67.938  1.00 43.13      B  O
ATOM   4688  N    THR B 102      54.772  19.667  67.789  1.00 43.77      B  N
ATOM   4689  CA   THR B 102      56.134  19.732  67.310  1.00 44.12      B  C
ATOM   4691  CB   THR B 102      57.111  19.125  68.339  1.00 44.36      B  C
ATOM   4693  OG1  THR B 102      56.974  19.799  69.599  1.00 43.89      B  O
ATOM   4695  CG2  THR B 102      58.570  19.236  67.837  1.00 43.26      B  C
ATOM   4699  C    THR B 102      56.243  18.935  66.030  1.00 45.17      B  C
ATOM   4700  O    THR B 102      55.891  17.751  66.010  1.00 45.07      B  O
ATOM   4702  N    GLN B 103      56.708  19.569  64.957  1.00 46.36      B  N
ATOM   4703  CA   GLN B 103      56.944  18.829  63.718  1.00 47.64      B  C
ATOM   4705  CB   GLN B 103      56.899  19.731  62.480  1.00 47.96      B  C
ATOM   4708  CG   GLN B 103      57.203  18.939  61.197  1.00 49.71      B  C
```

Figure 8 – CONT.

```
ATOM   4711  CD   GLN B 103      56.951  19.719  59.914  1.00 53.71      B  C
ATOM   4712  OE1  GLN B 103      56.555  20.892  59.949  1.00 55.64      B  O
ATOM   4713  NE2  GLN B 103      57.182  19.065  58.764  1.00 53.38      B  N
ATOM   4716  C    GLN B 103      58.285  18.107  63.779  1.00 48.13      B  C
ATOM   4717  O    GLN B 103      59.328  18.733  64.020  1.00 48.13      B  O
ATOM   4719  N    LEU B 104      58.251  16.798  63.548  1.00 48.96      B  N
ATOM   4720  CA   LEU B 104      59.465  15.972  63.510  1.00 49.87      B  C
ATOM   4722  CB   LEU B 104      59.293  14.667  64.298  1.00 49.84      B  C
ATOM   4725  CG   LEU B 104      60.609  13.911  64.570  1.00 50.64      B  C
ATOM   4727  CD1  LEU B 104      61.133  14.293  65.957  1.00 52.09      B  C
ATOM   4731  CD2  LEU B 104      60.456  12.388  64.457  1.00 49.06      B  C
ATOM   4735  C    LEU B 104      59.864  15.649  62.060  1.00 50.32      B  C
ATOM   4736  O    LEU B 104      59.148  14.938  61.341  1.00 49.50      B  O
ATOM   4738  N    THR B 105      61.021  16.182  61.666  1.00 51.45      B  N
ATOM   4739  CA   THR B 105      61.653  15.893  60.373  1.00 52.35      B  C
ATOM   4741  CB   THR B 105      62.121  17.205  59.741  1.00 52.53      B  C
ATOM   4743  OG1  THR B 105      60.963  17.995  59.433  1.00 52.54      B  O
ATOM   4745  CG2  THR B 105      62.949  16.955  58.465  1.00 53.23      B  C
ATOM   4749  C    THR B 105      62.842  14.929  60.511  1.00 52.60      B  C
ATOM   4750  O    THR B 105      63.708  15.128  61.356  1.00 53.10      B  O
ATOM   4752  N    VAL B 106      62.870  13.888  59.682  1.00 53.08      B  N
ATOM   4753  CA   VAL B 106      63.975  12.940  59.648  1.00 53.68      B  C
ATOM   4755  CB   VAL B 106      63.478  11.495  59.374  1.00 53.86      B  C
ATOM   4757  CG1  VAL B 106      64.662  10.522  59.212  1.00 53.25      B  C
ATOM   4761  CG2  VAL B 106      62.524  11.029  60.476  1.00 53.40      B  C
ATOM   4765  C    VAL B 106      64.932  13.365  58.521  1.00 54.57      B  C
ATOM   4766  O    VAL B 106      64.580  13.237  57.350  1.00 55.08      B  O
ATOM   4768  N    LEU B 106A     66.128  13.850  58.876  1.00 54.88      B  N
ATOM   4769  CA   LEU B 106A     67.103  14.365  57.905  1.00 55.30      B  C
ATOM   4771  CB   LEU B 106A     68.085  15.319  58.609  1.00 55.07      B  C
ATOM   4774  CG   LEU B 106A     67.422  16.537  59.273  1.00 54.77      B  C
ATOM   4776  CD1  LEU B 106A     68.386  17.250  60.216  1.00 54.17      B  C
ATOM   4780  CD2  LEU B 106A     66.881  17.491  58.215  1.00 52.39      B  C
ATOM   4784  C    LEU B 106A     67.852  13.240  57.155  1.00 56.11      B  C
ATOM   4785  O    LEU B 106A     67.386  12.097  57.098  1.00 56.21      B  O
ATOM   4787  N    GLY B 107      68.979  13.592  56.524  1.00 56.88      B  N
ATOM   4788  CA   GLY B 107      69.847  12.623  55.861  1.00 56.78      B  C
ATOM   4791  C    GLY B 107      69.558  12.269  54.406  1.00 56.54      B  C
ATOM   4792  O    GLY B 107      70.319  11.493  53.829  1.00 57.41      B  O
ATOM   4794  N    GLN B 108      68.478  12.784  53.805  1.00 55.51      B  N
ATOM   4795  CA   GLN B 108      68.172  12.476  52.380  1.00 54.74      B  C
ATOM   4797  CB   GLN B 108      66.775  12.990  51.938  1.00 55.20      B  C
ATOM   4800  CG   GLN B 108      65.656  11.919  51.833  1.00 57.23      B  C
ATOM   4803  CD   GLN B 108      65.594  11.157  50.479  1.00 59.15      B  C
ATOM   4804  OE1  GLN B 108      65.992  11.666  49.417  1.00 58.61      B  O
ATOM   4805  NE2  GLN B 108      65.063   9.930  50.530  1.00 60.03      B  N
ATOM   4808  C    GLN B 108      69.252  13.110  51.483  1.00 52.71      B  C
ATOM   4809  O    GLN B 108      69.687  14.228  51.747  1.00 51.86      B  O
ATOM   4811  N    PRO B 109      69.687  12.385  50.434  1.00 51.12      B  N
ATOM   4812  CA   PRO B 109      70.643  12.960  49.493  1.00 50.49      B  C
ATOM   4814  CB   PRO B 109      71.049  11.762  48.628  1.00 50.42      B  C
ATOM   4817  CG   PRO B 109      69.885  10.809  48.721  1.00 50.78      B  C
ATOM   4820  CD   PRO B 109      69.312  11.000  50.073  1.00 50.90      B  C
ATOM   4823  C    PRO B 109      69.974  14.027  48.634  1.00 49.73      B  C
ATOM   4824  O    PRO B 109      68.760  13.944  48.410  1.00 49.70      B  O
ATOM   4825  N    LYS B 110      70.747  15.020  48.185  1.00 48.80      B  N
ATOM   4826  CA   LYS B 110      70.258  15.994  47.211  1.00 48.13      B  C
ATOM   4828  CB   LYS B 110      71.390  16.894  46.681  1.00 48.25      B  C
```

Figure 8 – CONT.

```
ATOM   4835  C    LYS B 110      69.607  15.196  46.085  1.00 47.19      B  C
ATOM   4836  O    LYS B 110      70.096  14.123  45.755  1.00 48.20      B  O
ATOM   4838  N    ALA B 111      68.456  15.656  45.583  1.00 45.73      B  N
ATOM   4839  CA   ALA B 111      67.861  15.134  44.349  1.00 44.50      B  C
ATOM   4841  CB   ALA B 111      66.719  14.222  44.643  1.00 44.76      B  C
ATOM   4845  C    ALA B 111      67.412  16.307  43.463  1.00 43.93      B  C
ATOM   4846  O    ALA B 111      66.815  17.294  43.938  1.00 43.35      B  O
ATOM   4848  N    ALA B 112      67.758  16.218  42.179  1.00 43.05      B  N
ATOM   4849  CA   ALA B 112      67.404  17.238  41.201  1.00 41.97      B  C
ATOM   4851  CB   ALA B 112      68.366  17.176  39.977  1.00 42.24      B  C
ATOM   4855  C    ALA B 112      65.950  17.010  40.769  1.00 40.69      B  C
ATOM   4856  O    ALA B 112      65.508  15.864  40.645  1.00 40.28      B  O
ATOM   4858  N    PRO B 113      65.202  18.097  40.549  1.00 39.39      B  N
ATOM   4859  CA   PRO B 113      63.789  17.967  40.180  1.00 38.89      B  C
ATOM   4861  CB   PRO B 113      63.261  19.399  40.343  1.00 39.18      B  C
ATOM   4864  CG   PRO B 113      64.449  20.258  40.210  1.00 38.97      B  C
ATOM   4867  CD   PRO B 113      65.573  19.500  40.803  1.00 39.07      B  C
ATOM   4870  C    PRO B 113      63.578  17.494  38.754  1.00 38.47      B  C
ATOM   4871  O    PRO B 113      64.376  17.814  37.900  1.00 38.19      B  O
ATOM   4872  N    SER B 114      62.543  16.680  38.537  1.00 38.22      B  N
ATOM   4873  CA   SER B 114      61.973  16.440  37.211  1.00 38.09      B  C
ATOM   4875  CB   SER B 114      61.188  15.129  37.154  1.00 38.42      B  C
ATOM   4878  OG   SER B 114      62.062  14.032  37.145  1.00 40.70      B  O
ATOM   4880  C    SER B 114      60.988  17.548  36.979  1.00 37.29      B  C
ATOM   4881  O    SER B 114      60.254  17.919  37.895  1.00 37.90      B  O
ATOM   4883  N    VAL B 115      60.970  18.080  35.774  1.00 36.03      B  N
ATOM   4884  CA   VAL B 115      60.092  19.186  35.426  1.00 35.03      B  C
ATOM   4886  CB   VAL B 115      60.883  20.466  35.193  1.00 35.13      B  C
ATOM   4888  CG1  VAL B 115      59.973  21.576  34.730  1.00 35.86      B  C
ATOM   4892  CG2  VAL B 115      61.621  20.889  36.463  1.00 34.21      B  C
ATOM   4896  C    VAL B 115      59.356  18.800  34.170  1.00 34.59      B  C
ATOM   4897  O    VAL B 115      59.985  18.417  33.166  1.00 34.77      B  O
ATOM   4899  N    THR B 116      58.025  18.822  34.242  1.00 33.58      B  N
ATOM   4900  CA   THR B 116      57.174  18.608  33.076  1.00 32.47      B  C
ATOM   4902  CB   THR B 116      56.311  17.371  33.251  1.00 33.27      B  C
ATOM   4904  OG1  THR B 116      57.128  16.278  33.672  1.00 32.18      B  O
ATOM   4906  CG2  THR B 116      55.618  16.999  31.939  1.00 33.41      B  C
ATOM   4910  C    THR B 116      56.277  19.830  32.906  1.00 31.65      B  C
ATOM   4911  O    THR B 116      55.634  20.285  33.858  1.00 31.63      B  O
ATOM   4913  N    LEU B 117      56.231  20.369  31.697  1.00 30.08      B  N
ATOM   4914  CA   LEU B 117      55.371  21.487  31.396  1.00 29.80      B  C
ATOM   4916  CB   LEU B 117      56.189  22.672  30.929  1.00 29.38      B  C
ATOM   4919  CG   LEU B 117      55.451  23.932  30.451  1.00 30.41      B  C
ATOM   4921  CD1  LEU B 117      54.718  24.586  31.590  1.00 29.69      B  C
ATOM   4925  CD2  LEU B 117      56.441  24.915  29.859  1.00 30.40      B  C
ATOM   4929  C    LEU B 117      54.370  21.070  30.331  1.00 29.32      B  C
ATOM   4930  O    LEU B 117      54.779  20.555  29.288  1.00 30.05      B  O
ATOM   4932  N    PHE B 118      53.077  21.303  30.590  1.00 28.64      B  N
ATOM   4933  CA   PHE B 118      52.013  21.120  29.597  1.00 28.88      B  C
ATOM   4935  CB   PHE B 118      50.902  20.220  30.118  1.00 28.77      B  C
ATOM   4938  CG   PHE B 118      51.351  18.792  30.383  1.00 29.52      B  C
ATOM   4939  CD1  PHE B 118      51.410  17.870  29.341  1.00 29.74      B  C
ATOM   4941  CE1  PHE B 118      51.792  16.559  29.565  1.00 30.24      B  C
ATOM   4943  CZ   PHE B 118      52.127  16.150  30.862  1.00 31.72      B  C
ATOM   4945  CE2  PHE B 118      52.074  17.085  31.916  1.00 31.26      B  C
ATOM   4947  CD2  PHE B 118      51.694  18.388  31.666  1.00 27.58      B  C
ATOM   4949  C    PHE B 118      51.404  22.439  29.164  1.00 29.07      B  C
ATOM   4950  O    PHE B 118      51.197  23.331  29.994  1.00 27.95      B  O
```

Figure 8 – CONT.

```
ATOM   4952  N    PRO B 119      51.110  22.563  27.846  1.00 28.85           B    N
ATOM   4953  CA   PRO B 119      50.370  23.689  27.357  1.00 29.08           B    C
ATOM   4955  CB   PRO B 119      50.581  23.610  25.828  1.00 29.47           B    C
ATOM   4958  CG   PRO B 119      50.825  22.173  25.551  1.00 27.59           B    C
ATOM   4961  CD   PRO B 119      51.535  21.655  26.748  1.00 28.76           B    C
ATOM   4964  C    PRO B 119      48.905  23.523  27.676  1.00 29.41           B    C
ATOM   4965  O    PRO B 119      48.489  22.445  28.012  1.00 28.81           B    O
ATOM   4966  N    PRO B 120      48.112  24.571  27.481  1.00 30.58           B    N
ATOM   4967  CA   PRO B 120      46.667  24.402  27.534  1.00 31.63           B    C
ATOM   4969  CB   PRO B 120      46.140  25.736  27.012  1.00 31.81           B    C
ATOM   4972  CG   PRO B 120      47.285  26.697  27.119  1.00 31.37           B    C
ATOM   4975  CD   PRO B 120      48.497  25.885  26.947  1.00 30.69           B    C
ATOM   4978  C    PRO B 120      46.177  23.297  26.609  1.00 32.75           B    C
ATOM   4979  O    PRO B 120      46.730  23.117  25.535  1.00 32.30           B    O
ATOM   4980  N    SER B 121      45.128  22.588  27.008  1.00 33.58           B    N
ATOM   4981  CA   SER B 121      44.468  21.639  26.116  1.00 34.68           B    C
ATOM   4983  CB   SER B 121      43.703  20.572  26.941  1.00 34.99           B    C
ATOM   4986  OG   SER B 121      42.631  21.129  27.682  1.00 33.73           B    O
ATOM   4988  C    SER B 121      43.524  22.392  25.166  1.00 35.61           B    C
ATOM   4989  O    SER B 121      43.052  23.508  25.469  1.00 34.23           B    O
ATOM   4991  N    SER B 122      43.255  21.795  24.002  1.00 37.23           B    N
ATOM   4992  CA   SER B 122      42.310  22.414  23.043  1.00 38.71           B    C
ATOM   4994  CB   SER B 122      42.265  21.648  21.714  1.00 39.38           B    C
ATOM   4997  OG   SER B 122      42.325  20.241  21.915  1.00 42.79           B    O
ATOM   4999  C    SER B 122      40.923  22.528  23.666  1.00 39.02           B    C
ATOM   5000  O    SER B 122      40.256  23.571  23.551  1.00 39.37           B    O
ATOM   5002  N    GLU B 123      40.514  21.471  24.366  1.00 39.29           B    N
ATOM   5003  CA   GLU B 123      39.284  21.479  25.159  1.00 39.64           B    C
ATOM   5005  CB   GLU B 123      39.170  20.215  26.024  1.00 40.21           B    C
ATOM   5008  CG   GLU B 123      38.434  19.081  25.404  1.00 42.36           B    C
ATOM   5011  CD   GLU B 123      38.516  17.826  26.248  1.00 47.11           B    C
ATOM   5012  OE1  GLU B 123      37.957  17.844  27.384  1.00 45.43           B    O
ATOM   5013  OE2  GLU B 123      39.137  16.831  25.771  1.00 49.13           B    O
ATOM   5014  C    GLU B 123      39.193  22.683  26.074  1.00 39.30           B    C
ATOM   5015  O    GLU B 123      38.186  23.380  26.062  1.00 39.84           B    O
ATOM   5017  N    GLU B 124      40.224  22.944  26.872  1.00 39.19           B    N
ATOM   5018  CA   GLU B 124      40.133  24.079  27.793  1.00 39.19           B    C
ATOM   5020  CB   GLU B 124      41.328  24.137  28.741  1.00 38.76           B    C
ATOM   5023  CG   GLU B 124      41.245  25.283  29.723  1.00 35.14           B    C
ATOM   5026  CD   GLU B 124      42.464  25.423  30.584  1.00 34.43           B    C
ATOM   5027  OE1  GLU B 124      43.587  24.965  30.197  1.00 30.32           B    O
ATOM   5028  OE2  GLU B 124      42.294  26.018  31.674  1.00 32.82           B    O
ATOM   5029  C    GLU B 124      39.988  25.383  27.023  1.00 40.51           B    C
ATOM   5030  O    GLU B 124      39.249  26.260  27.425  1.00 41.00           B    O
ATOM   5032  N    LEU B 125      40.705  25.527  25.917  1.00 43.02           B    N
ATOM   5033  CA   LEU B 125      40.477  26.688  25.022  1.00 44.42           B    C
ATOM   5035  CB   LEU B 125      41.364  26.604  23.783  1.00 44.01           B    C
ATOM   5038  CG   LEU B 125      42.843  26.492  24.111  1.00 43.03           B    C
ATOM   5040  CD1  LEU B 125      43.670  26.444  22.861  1.00 43.29           B    C
ATOM   5044  CD2  LEU B 125      43.278  27.621  25.012  1.00 40.88           B    C
ATOM   5048  C    LEU B 125      38.997  26.813  24.623  1.00 45.91           B    C
ATOM   5049  O    LEU B 125      38.411  27.893  24.748  1.00 46.71           B    O
ATOM   5051  N    GLN B 126      38.375  25.696  24.239  1.00 47.41           B    N
ATOM   5052  CA   GLN B 126      36.972  25.706  23.784  1.00 48.25           B    C
ATOM   5054  CB   GLN B 126      36.480  24.305  23.403  1.00 48.49           B    C
ATOM   5061  C    GLN B 126      36.084  26.265  24.860  1.00 49.05           B    C
ATOM   5062  O    GLN B 126      35.061  26.894  24.564  1.00 50.24           B    O
ATOM   5064  N    ALA B 127      36.482  26.034  26.113  1.00 49.04           B    N
```

Figure 8 – CONT.

```
ATOM   5065  CA   ALA B 127      35.796  26.571  27.277  1.00 48.64      B    C
ATOM   5067  CB   ALA B 127      35.953  25.605  28.465  1.00 49.33      B    C
ATOM   5071  C    ALA B 127      36.292  27.967  27.660  1.00 48.29      B    C
ATOM   5072  O    ALA B 127      35.993  28.457  28.770  1.00 48.47      B    O
ATOM   5074  N    ASN B 128      37.016  28.625  26.751  1.00 47.24      B    N
ATOM   5075  CA   ASN B 128      37.485  30.003  26.974  1.00 46.66      B    C
ATOM   5077  CB   ASN B 128      36.303  30.950  27.090  1.00 47.30      B    C
ATOM   5080  CG   ASN B 128      36.169  31.831  25.876  1.00 50.69      B    C
ATOM   5081  OD1  ASN B 128      36.862  32.865  25.766  1.00 50.19      B    O
ATOM   5082  ND2  ASN B 128      35.281  31.425  24.936  1.00 51.95      B    N
ATOM   5085  C    ASN B 128      38.437  30.243  28.131  1.00 44.76      B    C
ATOM   5086  O    ASN B 128      38.410  31.285  28.746  1.00 44.52      B    O
ATOM   5088  N    LYS B 129      39.311  29.279  28.383  1.00 43.77      B    N
ATOM   5089  CA   LYS B 129      40.338  29.396  29.414  1.00 42.68      B    C
ATOM   5091  CB   LYS B 129      39.928  28.633  30.677  1.00 43.16      B    C
ATOM   5094  CG   LYS B 129      38.716  29.189  31.450  1.00 44.82      B    C
ATOM   5097  CD   LYS B 129      37.757  28.051  31.878  1.00 46.72      B    C
ATOM   5100  CE   LYS B 129      38.442  26.841  32.576  1.00 46.89      B    C
ATOM   5103  NZ   LYS B 129      37.569  25.616  32.504  1.00 45.62      B    N
ATOM   5107  C    LYS B 129      41.625  28.783  28.896  1.00 40.13      B    C
ATOM   5108  O    LYS B 129      41.605  28.000  27.961  1.00 38.90      B    O
ATOM   5110  N    ALA B 130      42.736  29.114  29.545  1.00 37.07      B    N
ATOM   5111  CA   ALA B 130      44.010  28.516  29.194  1.00 34.91      B    C
ATOM   5113  CB   ALA B 130      44.703  29.344  28.106  1.00 34.50      B    C
ATOM   5117  C    ALA B 130      44.882  28.434  30.422  1.00 32.48      B    C
ATOM   5118  O    ALA B 130      45.194  29.458  31.023  1.00 32.68      B    O
ATOM   5120  N    THR B 131      45.306  27.223  30.759  1.00 29.90      B    N
ATOM   5121  CA   THR B 131      46.216  27.004  31.854  1.00 28.77      B    C
ATOM   5123  CB   THR B 131      45.572  26.140  32.942  1.00 28.26      B    C
ATOM   5125  OG1  THR B 131      44.206  26.555  33.152  1.00 27.37      B    O
ATOM   5127  CG2  THR B 131      46.385  26.242  34.209  1.00 25.68      B    C
ATOM   5131  C    THR B 131      47.487  26.300  31.434  1.00 28.37      B    C
ATOM   5132  O    THR B 131      47.436  25.233  30.839  1.00 28.94      B    O
ATOM   5134  N    LEU B 132      48.627  26.876  31.775  1.00 28.03      B    N
ATOM   5135  CA   LEU B 132      49.893  26.201  31.610  1.00 28.70      B    C
ATOM   5137  CB   LEU B 132      50.988  27.180  31.197  1.00 28.66      B    C
ATOM   5140  CG   LEU B 132      50.944  27.714  29.765  1.00 29.66      B    C
ATOM   5142  CD1  LEU B 132      49.823  28.659  29.629  1.00 27.92      B    C
ATOM   5146  CD2  LEU B 132      52.277  28.384  29.378  1.00 29.05      B    C
ATOM   5150  C    LEU B 132      50.224  25.541  32.946  1.00 29.06      B    C
ATOM   5151  O    LEU B 132      50.110  26.178  34.014  1.00 29.78      B    O
ATOM   5153  N    VAL B 133      50.587  24.266  32.897  1.00 29.37      B    N
ATOM   5154  CA   VAL B 133      50.880  23.475  34.093  1.00 29.13      B    C
ATOM   5156  CB   VAL B 133      50.056  22.166  34.098  1.00 29.87      B    C
ATOM   5158  CG1  VAL B 133      50.393  21.309  35.325  1.00 28.21      B    C
ATOM   5162  CG2  VAL B 133      48.537  22.485  34.038  1.00 31.34      B    C
ATOM   5166  C    VAL B 133      52.340  23.095  34.088  1.00 29.42      B    C
ATOM   5167  O    VAL B 133      52.801  22.469  33.146  1.00 29.30      B    O
ATOM   5169  N    CYS B 134      53.064  23.483  35.132  1.00 29.29      B    N
ATOM   5170  CA   CYS B 134      54.452  23.145  35.296  1.00 29.34      B    C
ATOM   5172  CB   CYS B 134      55.289  24.409  35.336  1.00 29.13      B    C
ATOM   5175  SG   CYS B 134      57.098  24.151  35.333  1.00 29.97      B    S
ATOM   5177  C    CYS B 134      54.607  22.306  36.586  1.00 29.28      B    C
ATOM   5178  O    CYS B 134      54.474  22.834  37.677  1.00 28.99      B    O
ATOM   5180  N    LEU B 135      54.875  21.013  36.411  1.00 29.23      B    N
ATOM   5181  CA   LEU B 135      54.994  20.044  37.484  1.00 30.31      B    C
ATOM   5183  CB   LEU B 135      54.263  18.779  37.082  1.00 30.20      B    C
ATOM   5186  CG   LEU B 135      52.844  19.148  36.640  1.00 31.16      B    C
```

Figure 8 – CONT.

```
ATOM   5188  CD1 LEU B 135      52.150  17.981  36.015  1.00 29.38      B  C
ATOM   5192  CD2 LEU B 135      52.027  19.749  37.823  1.00 27.60      B  C
ATOM   5196  C   LEU B 135      56.454  19.711  37.809  1.00 31.16      B  C
ATOM   5197  O   LEU B 135      57.252  19.341  36.937  1.00 30.32      B  O
ATOM   5199  N   VAL B 136      56.791  19.863  39.089  1.00 31.55      B  N
ATOM   5200  CA  VAL B 136      58.120  19.650  39.584  1.00 31.27      B  C
ATOM   5202  CB  VAL B 136      58.613  20.933  40.182  1.00 31.12      B  C
ATOM   5204  CG1 VAL B 136      60.137  20.867  40.439  1.00 29.99      B  C
ATOM   5208  CG2 VAL B 136      58.219  22.087  39.268  1.00 29.83      B  C
ATOM   5212  C   VAL B 136      58.087  18.573  40.644  1.00 32.87      B  C
ATOM   5213  O   VAL B 136      57.399  18.712  41.658  1.00 32.71      B  O
ATOM   5215  N   SER B 137      58.824  17.494  40.435  1.00 34.81      B  N
ATOM   5216  CA  SER B 137      58.807  16.423  41.423  1.00 36.46      B  C
ATOM   5218  CB  SER B 137      57.894  15.318  40.913  1.00 37.08      B  C
ATOM   5221  OG  SER B 137      58.410  14.841  39.703  1.00 39.60      B  O
ATOM   5223  C   SER B 137      60.171  15.820  41.733  1.00 37.09      B  C
ATOM   5224  O   SER B 137      61.166  16.101  41.048  1.00 36.35      B  O
ATOM   5226  N   ASP B 138      60.172  14.980  42.775  1.00 38.38      B  N
ATOM   5227  CA  ASP B 138      61.293  14.138  43.185  1.00 39.25      B  C
ATOM   5229  CB  ASP B 138      61.579  13.076  42.126  1.00 40.36      B  C
ATOM   5232  CG  ASP B 138      60.402  12.124  41.942  1.00 43.81      B  C
ATOM   5233  OD1 ASP B 138      60.046  11.448  42.938  1.00 46.17      B  O
ATOM   5234  OD2 ASP B 138      59.832  12.052  40.819  1.00 48.58      B  O
ATOM   5235  C   ASP B 138      62.517  14.968  43.469  1.00 39.42      B  C
ATOM   5236  O   ASP B 138      63.614  14.654  43.024  1.00 39.90      B  O
ATOM   5238  N   PHE B 139      62.329  16.047  44.221  1.00 39.40      B  N
ATOM   5239  CA  PHE B 139      63.454  16.869  44.588  1.00 38.84      B  C
ATOM   5241  CB  PHE B 139      63.360  18.221  43.887  1.00 38.73      B  C
ATOM   5244  CG  PHE B 139      62.259  19.102  44.360  1.00 37.86      B  C
ATOM   5245  CD1 PHE B 139      62.479  20.009  45.386  1.00 37.21      B  C
ATOM   5247  CE1 PHE B 139      61.501  20.866  45.809  1.00 35.89      B  C
ATOM   5249  CZ  PHE B 139      60.266  20.844  45.187  1.00 37.19      B  C
ATOM   5251  CE2 PHE B 139      60.028  19.946  44.144  1.00 35.88      B  C
ATOM   5253  CD2 PHE B 139      61.032  19.099  43.725  1.00 38.06      B  C
ATOM   5255  C   PHE B 139      63.692  16.992  46.103  1.00 38.94      B  C
ATOM   5256  O   PHE B 139      62.774  16.800  46.909  1.00 38.19      B  O
ATOM   5258  N   TYR B 140      64.954  17.260  46.457  1.00 38.69      B  N
ATOM   5259  CA  TYR B 140      65.400  17.416  47.849  1.00 38.87      B  C
ATOM   5261  CB  TYR B 140      65.667  16.053  48.509  1.00 38.64      B  C
ATOM   5264  CG  TYR B 140      65.840  16.259  49.975  1.00 39.71      B  C
ATOM   5265  CD1 TYR B 140      64.733  16.192  50.836  1.00 40.11      B  C
ATOM   5267  CE1 TYR B 140      64.861  16.417  52.192  1.00 41.41      B  C
ATOM   5269  CZ  TYR B 140      66.111  16.754  52.728  1.00 42.56      B  C
ATOM   5270  OH  TYR B 140      66.225  17.001  54.093  1.00 42.55      B  O
ATOM   5272  CE2 TYR B 140      67.224  16.854  51.881  1.00 41.65      B  C
ATOM   5274  CD2 TYR B 140      67.077  16.613  50.509  1.00 39.71      B  C
ATOM   5276  C   TYR B 140      66.690  18.246  47.887  1.00 38.73      B  C
ATOM   5277  O   TYR B 140      67.644  17.901  47.182  1.00 38.34      B  O
ATOM   5279  N   PRO B 141      66.758  19.301  48.723  1.00 38.58      B  N
ATOM   5280  CA  PRO B 141      65.806  19.775  49.738  1.00 38.84      B  C
ATOM   5282  CB  PRO B 141      66.551  20.911  50.469  1.00 38.35      B  C
ATOM   5285  CG  PRO B 141      67.879  21.049  49.847  1.00 38.48      B  C
ATOM   5288  CD  PRO B 141      67.977  20.125  48.662  1.00 38.82      B  C
ATOM   5291  C   PRO B 141      64.491  20.297  49.154  1.00 39.02      B  C
ATOM   5292  O   PRO B 141      64.356  20.404  47.922  1.00 38.51      B  O
ATOM   5293  N   GLY B 142      63.544  20.617  50.036  1.00 38.81      B  N
ATOM   5294  CA  GLY B 142      62.183  21.010  49.642  1.00 39.10      B  C
ATOM   5297  C   GLY B 142      62.057  22.504  49.497  1.00 39.64      B  C
```

Figure 8 – CONT.

```
ATOM   5298  O    GLY B 142      61.333  23.151  50.269  1.00 40.67           B  O
ATOM   5300  N    ALA B 143      62.775  23.054  48.520  1.00 39.66           B  N
ATOM   5301  CA   ALA B 143      62.779  24.481  48.217  1.00 39.56           B  C
ATOM   5303  CB   ALA B 143      63.810  25.234  49.104  1.00 39.91           B  C
ATOM   5307  C    ALA B 143      63.133  24.638  46.728  1.00 39.33           B  C
ATOM   5308  O    ALA B 143      64.197  24.199  46.294  1.00 39.51           B  O
ATOM   5310  N    VAL B 144      62.209  25.199  45.951  1.00 38.72           B  N
ATOM   5311  CA   VAL B 144      62.446  25.521  44.562  1.00 38.17           B  C
ATOM   5313  CB   VAL B 144      61.696  24.615  43.567  1.00 38.59           B  C
ATOM   5315  CG1  VAL B 144      62.308  23.209  43.482  1.00 39.08           B  C
ATOM   5319  CG2  VAL B 144      60.199  24.571  43.914  1.00 38.38           B  C
ATOM   5323  C    VAL B 144      61.899  26.895  44.322  1.00 37.45           B  C
ATOM   5324  O    VAL B 144      61.046  27.371  45.050  1.00 36.68           B  O
ATOM   5326  N    THR B 145      62.395  27.519  43.274  1.00 37.61           B  N
ATOM   5327  CA   THR B 145      61.813  28.732  42.754  1.00 38.07           B  C
ATOM   5329  CB   THR B 145      62.852  29.820  42.669  1.00 38.08           B  C
ATOM   5331  OG1  THR B 145      63.285  30.130  44.002  1.00 40.40           B  O
ATOM   5333  CG2  THR B 145      62.260  31.082  41.988  1.00 39.07           B  C
ATOM   5337  C    THR B 145      61.305  28.392  41.369  1.00 37.84           B  C
ATOM   5338  O    THR B 145      61.972  27.672  40.628  1.00 37.63           B  O
ATOM   5340  N    VAL B 146      60.118  28.891  41.031  1.00 37.94           B  N
ATOM   5341  CA   VAL B 146      59.553  28.710  39.693  1.00 36.89           B  C
ATOM   5343  CB   VAL B 146      58.250  27.942  39.778  1.00 36.61           B  C
ATOM   5345  CG1  VAL B 146      57.671  27.717  38.395  1.00 36.06           B  C
ATOM   5349  CG2  VAL B 146      58.473  26.634  40.507  1.00 35.72           B  C
ATOM   5353  C    VAL B 146      59.284  30.095  39.128  1.00 36.84           B  C
ATOM   5354  O    VAL B 146      58.672  30.898  39.810  1.00 35.92           B  O
ATOM   5356  N    ALA B 147      59.766  30.375  37.911  1.00 36.67           B  N
ATOM   5357  CA   ALA B 147      59.489  31.633  37.226  1.00 36.88           B  C
ATOM   5359  CB   ALA B 147      60.723  32.471  37.151  1.00 36.32           B  C
ATOM   5363  C    ALA B 147      58.952  31.335  35.825  1.00 37.33           B  C
ATOM   5364  O    ALA B 147      59.281  30.300  35.244  1.00 38.09           B  O
ATOM   5366  N    TRP B 148      58.111  32.225  35.292  1.00 37.60           B  N
ATOM   5367  CA   TRP B 148      57.531  32.044  33.965  1.00 37.08           B  C
ATOM   5369  CB   TRP B 148      56.002  32.059  34.004  1.00 36.67           B  C
ATOM   5372  CG   TRP B 148      55.391  30.916  34.702  1.00 34.79           B  C
ATOM   5373  CD1  TRP B 148      55.182  30.811  36.039  1.00 31.59           B  C
ATOM   5375  NE1  TRP B 148      54.592  29.618  36.330  1.00 32.26           B  N
ATOM   5377  CE2  TRP B 148      54.391  28.913  35.174  1.00 32.20           B  C
ATOM   5378  CD2  TRP B 148      54.867  29.713  34.114  1.00 32.25           B  C
ATOM   5379  CE3  TRP B 148      54.781  29.229  32.812  1.00 32.19           B  C
ATOM   5381  CZ3  TRP B 148      54.213  27.953  32.607  1.00 33.91           B  C
ATOM   5383  CH2  TRP B 148      53.728  27.189  33.698  1.00 33.41           B  C
ATOM   5385  CZ2  TRP B 148      53.819  27.651  34.979  1.00 31.18           B  C
ATOM   5387  C    TRP B 148      57.994  33.137  33.031  1.00 37.97           B  C
ATOM   5388  O    TRP B 148      58.302  34.244  33.455  1.00 38.59           B  O
ATOM   5390  N    LYS B 149      58.031  32.829  31.745  1.00 38.55           B  N
ATOM   5391  CA   LYS B 149      58.363  33.828  30.739  1.00 39.18           B  C
ATOM   5393  CB   LYS B 149      59.815  33.701  30.318  1.00 39.83           B  C
ATOM   5396  CG   LYS B 149      60.807  34.144  31.386  1.00 43.10           B  C
ATOM   5399  CD   LYS B 149      62.219  33.750  31.010  1.00 47.23           B  C
ATOM   5402  CE   LYS B 149      63.229  34.110  32.111  1.00 50.42           B  C
ATOM   5405  NZ   LYS B 149      63.034  35.457  32.722  1.00 50.83           B  N
ATOM   5409  C    LYS B 149      57.462  33.674  29.526  1.00 38.50           B  C
ATOM   5410  O    LYS B 149      57.044  32.559  29.177  1.00 37.90           B  O
ATOM   5412  N    ALA B 150      57.142  34.813  28.916  1.00 38.20           B  N
ATOM   5413  CA   ALA B 150      56.412  34.866  27.663  1.00 38.10           B  C
ATOM   5415  CB   ALA B 150      55.112  35.647  27.831  1.00 37.51           B  C
```

Figure 8 – CONT.

```
ATOM   5419  C    ALA B 150      57.331  35.543  26.662  1.00 38.24           B  C
ATOM   5420  O    ALA B 150      57.658  36.729  26.827  1.00 38.25           B  O
ATOM   5422  N    ASP B 151      57.762  34.789  25.647  1.00 38.58           B  N
ATOM   5423  CA   ASP B 151      58.694  35.291  24.634  1.00 39.34           B  C
ATOM   5425  CB   ASP B 151      58.002  36.342  23.749  1.00 39.38           B  C
ATOM   5428  CG   ASP B 151      56.932  35.748  22.856  1.00 38.28           B  C
ATOM   5429  OD1  ASP B 151      57.105  34.619  22.345  1.00 37.99           B  O
ATOM   5430  OD2  ASP B 151      55.907  36.422  22.654  1.00 40.49           B  O
ATOM   5431  C    ASP B 151      59.941  35.897  25.263  1.00 40.78           B  C
ATOM   5432  O    ASP B 151      60.359  36.997  24.884  1.00 41.31           B  O
ATOM   5434  N    GLY B 152      60.513  35.197  26.244  1.00 42.22           B  N
ATOM   5435  CA   GLY B 152      61.663  35.692  26.999  1.00 43.63           B  C
ATOM   5438  C    GLY B 152      61.417  36.807  28.019  1.00 44.79           B  C
ATOM   5439  O    GLY B 152      62.353  37.212  28.712  1.00 46.34           B  O
ATOM   5441  N    SER B 153      60.196  37.324  28.128  1.00 44.97           B  N
ATOM   5442  CA   SER B 153      59.892  38.335  29.146  1.00 45.44           B  C
ATOM   5444  CB   SER B 153      58.984  39.412  28.577  1.00 45.53           B  C
ATOM   5447  OG   SER B 153      59.726  40.243  27.711  1.00 47.92           B  O
ATOM   5449  C    SER B 153      59.203  37.712  30.366  1.00 45.45           B  C
ATOM   5450  O    SER B 153      58.322  36.877  30.200  1.00 44.92           B  O
ATOM   5452  N    PRO B 154      59.590  38.133  31.591  1.00 45.21           B  N
ATOM   5453  CA   PRO B 154      58.983  37.548  32.782  1.00 44.79           B  C
ATOM   5455  CB   PRO B 154      59.753  38.214  33.930  1.00 45.09           B  C
ATOM   5458  CG   PRO B 154      61.071  38.637  33.301  1.00 45.28           B  C
ATOM   5461  CD   PRO B 154      60.652  39.095  31.944  1.00 45.11           B  C
ATOM   5464  C    PRO B 154      57.490  37.838  32.908  1.00 44.72           B  C
ATOM   5465  O    PRO B 154      57.037  38.931  32.614  1.00 44.69           B  O
ATOM   5466  N    VAL B 155      56.734  36.847  33.351  1.00 44.39           B  N
ATOM   5467  CA   VAL B 155      55.303  36.980  33.523  1.00 44.14           B  C
ATOM   5469  CB   VAL B 155      54.560  35.939  32.663  1.00 44.34           B  C
ATOM   5471  CG1  VAL B 155      53.080  36.251  32.611  1.00 43.73           B  C
ATOM   5475  CG2  VAL B 155      55.157  35.886  31.252  1.00 43.97           B  C
ATOM   5479  C    VAL B 155      55.038  36.681  34.980  1.00 44.31           B  C
ATOM   5480  O    VAL B 155      55.504  35.659  35.462  1.00 43.71           B  O
ATOM   5482  N    LYS B 156      54.317  37.566  35.675  1.00 44.58           B  N
ATOM   5483  CA   LYS B 156      54.007  37.392  37.112  1.00 44.90           B  C
ATOM   5485  CB   LYS B 156      54.625  38.535  37.933  1.00 45.11           B  C
ATOM   5488  CG   LYS B 156      56.155  38.676  37.780  1.00 46.55           B  C
ATOM   5491  CD   LYS B 156      56.848  39.245  39.049  1.00 47.64           B  C
ATOM   5496  C    LYS B 156      52.490  37.316  37.360  1.00 44.50           B  C
ATOM   5497  O    LYS B 156      51.995  36.530  38.195  1.00 44.84           B  O
ATOM   5499  N    VAL B 157      51.763  38.148  36.629  1.00 43.41           B  N
ATOM   5500  CA   VAL B 157      50.314  38.140  36.635  1.00 42.53           B  C
ATOM   5502  CB   VAL B 157      49.793  39.249  35.678  1.00 42.60           B  C
ATOM   5504  CG1  VAL B 157      48.348  38.998  35.298  1.00 42.53           B  C
ATOM   5508  CG2  VAL B 157      50.026  40.661  36.305  1.00 41.89           B  C
ATOM   5512  C    VAL B 157      49.763  36.772  36.205  1.00 41.68           B  C
ATOM   5513  O    VAL B 157      50.118  36.264  35.155  1.00 42.12           B  O
ATOM   5515  N    GLY B 158      48.905  36.179  37.027  1.00 40.39           B  N
ATOM   5516  CA   GLY B 158      48.251  34.919  36.683  1.00 39.40           B  C
ATOM   5519  C    GLY B 158      48.990  33.667  37.118  1.00 38.51           B  C
ATOM   5520  O    GLY B 158      48.563  32.553  36.799  1.00 38.15           B  O
ATOM   5522  N    VAL B 159      50.087  33.842  37.854  1.00 37.92           B  N
ATOM   5523  CA   VAL B 159      50.917  32.719  38.334  1.00 36.78           B  C
ATOM   5525  CB   VAL B 159      52.385  33.137  38.413  1.00 36.34           B  C
ATOM   5527  CG1  VAL B 159      53.249  32.062  39.042  1.00 33.56           B  C
ATOM   5531  CG2  VAL B 159      52.877  33.485  37.001  1.00 35.87           B  C
ATOM   5535  C    VAL B 159      50.466  32.279  39.705  1.00 36.78           B  C
```

Figure 8 – CONT.

```
ATOM   5536  O    VAL B 159      50.287  33.104  40.580  1.00 35.71      B    O
ATOM   5538  N    GLU B 160      50.275  30.971  39.885  1.00 37.09      B    N
ATOM   5539  CA   GLU B 160      49.961  30.414  41.196  1.00 37.61      B    C
ATOM   5541  CB   GLU B 160      48.479  30.077  41.334  1.00 38.24      B    C
ATOM   5544  CG   GLU B 160      47.508  31.177  40.949  1.00 41.95      B    C
ATOM   5547  CD   GLU B 160      46.950  31.985  42.141  1.00 48.01      B    C
ATOM   5548  OE1  GLU B 160      47.725  32.317  43.098  1.00 47.23      B    O
ATOM   5549  OE2  GLU B 160      45.720  32.303  42.071  1.00 49.63      B    O
ATOM   5550  C    GLU B 160      50.787  29.168  41.409  1.00 37.03      B    C
ATOM   5551  O    GLU B 160      50.680  28.201  40.656  1.00 36.74      B    O
ATOM   5553  N    THR B 161      51.618  29.199  42.442  1.00 36.75      B    N
ATOM   5554  CA   THR B 161      52.545  28.116  42.705  1.00 36.96      B    C
ATOM   5556  CB   THR B 161      53.985  28.620  42.599  1.00 37.07      B    C
ATOM   5558  OG1  THR B 161      54.204  29.087  41.275  1.00 37.64      B    O
ATOM   5560  CG2  THR B 161      54.985  27.513  42.926  1.00 37.00      B    C
ATOM   5564  C    THR B 161      52.304  27.547  44.089  1.00 36.23      B    C
ATOM   5565  O    THR B 161      52.199  28.300  45.036  1.00 36.28      B    O
ATOM   5567  N    THR B 162      52.219  26.225  44.182  1.00 36.70      B    N
ATOM   5568  CA   THR B 162      52.089  25.530  45.450  1.00 37.11      B    C
ATOM   5570  CB   THR B 162      51.730  24.035  45.295  1.00 37.26      B    C
ATOM   5572  OG1  THR B 162      52.830  23.303  44.724  1.00 34.85      B    O
ATOM   5574  CG2  THR B 162      50.471  23.863  44.473  1.00 35.96      B    C
ATOM   5578  C    THR B 162      53.396  25.578  46.226  1.00 38.42      B    C
ATOM   5579  O    THR B 162      54.473  25.707  45.641  1.00 37.97      B    O
ATOM   5581  N    LYS B 163      53.285  25.455  47.553  1.00 39.22      B    N
ATOM   5582  CA   LYS B 163      54.446  25.267  48.423  1.00 39.56      B    C
ATOM   5584  CB   LYS B 163      54.077  25.486  49.916  1.00 40.66      B    C
ATOM   5587  CG   LYS B 163      53.484  26.891  50.276  1.00 39.70      B    C
ATOM   5593  C    LYS B 163      54.902  23.835  48.192  1.00 39.65      B    C
ATOM   5594  O    LYS B 163      54.091  22.978  47.872  1.00 38.93      B    O
ATOM   5596  N    PRO B 164      56.202  23.559  48.357  1.00 40.07      B    N
ATOM   5597  CA   PRO B 164      56.575  22.169  48.168  1.00 40.62      B    C
ATOM   5599  CB   PRO B 164      58.095  22.168  48.377  1.00 40.78      B    C
ATOM   5602  CG   PRO B 164      58.522  23.659  48.259  1.00 40.86      B    C
ATOM   5605  CD   PRO B 164      57.325  24.387  48.824  1.00 39.70      B    C
ATOM   5608  C    PRO B 164      55.906  21.283  49.205  1.00 41.42      B    C
ATOM   5609  O    PRO B 164      55.646  21.727  50.319  1.00 41.50      B    O
ATOM   5610  N    SER B 165      55.656  20.039  48.841  1.00 42.24      B    N
ATOM   5611  CA   SER B 165      55.031  19.093  49.735  1.00 43.51      B    C
ATOM   5613  CB   SER B 165      53.538  19.008  49.408  1.00 43.76      B    C
ATOM   5616  OG   SER B 165      53.110  17.665  49.289  1.00 46.75      B    O
ATOM   5618  C    SER B 165      55.732  17.728  49.625  1.00 44.15      B    C
ATOM   5619  O    SER B 165      56.188  17.335  48.552  1.00 43.12      B    O
ATOM   5621  N    LYS B 166      55.842  17.029  50.751  1.00 45.13      B    N
ATOM   5622  CA   LYS B 166      56.591  15.783  50.822  1.00 46.50      B    C
ATOM   5624  CB   LYS B 166      56.911  15.414  52.287  1.00 46.47      B    C
ATOM   5627  CG   LYS B 166      57.761  14.144  52.454  1.00 47.06      B    C
ATOM   5633  C    LYS B 166      55.765  14.713  50.177  1.00 47.30      B    C
ATOM   5634  O    LYS B 166      54.626  14.523  50.541  1.00 48.32      B    O
ATOM   5636  N    GLN B 167      56.309  14.038  49.186  1.00 48.90      B    N
ATOM   5637  CA   GLN B 167      55.594  12.923  48.591  1.00 50.78      B    C
ATOM   5639  CB   GLN B 167      55.890  12.812  47.080  1.00 51.03      B    C
ATOM   5642  CG   GLN B 167      57.326  12.520  46.683  1.00 52.14      B    C
ATOM   5645  CD   GLN B 167      57.732  13.092  45.293  1.00 52.29      B    C
ATOM   5646  OE1  GLN B 167      57.390  14.222  44.926  1.00 52.37      B    O
ATOM   5647  NE2  GLN B 167      58.490  12.307  44.547  1.00 50.67      B    N
ATOM   5650  C    GLN B 167      55.908  11.642  49.394  1.00 52.15      B    C
ATOM   5651  O    GLN B 167      56.601  11.692  50.421  1.00 51.99      B    O
```

Figure 8 – CONT.

```
ATOM   5653  N    SER B 168      55.376  10.509  48.948  1.00 53.70      B  N
ATOM   5654  CA   SER B 168      55.536   9.252  49.675  1.00 54.82      B  C
ATOM   5656  CB   SER B 168      54.660   8.147  49.057  1.00 54.87      B  C
ATOM   5659  OG   SER B 168      55.053   7.863  47.720  1.00 56.89      B  O
ATOM   5661  C    SER B 168      57.009   8.802  49.733  1.00 55.31      B  C
ATOM   5662  O    SER B 168      57.455   8.237  50.745  1.00 56.02      B  O
ATOM   5664  N    ASN B 170      57.776   9.055  48.671  1.00 55.04      B  N
ATOM   5665  CA   ASN B 170      59.156   8.582  48.637  1.00 54.59      B  C
ATOM   5667  CB   ASN B 170      59.598   8.252  47.196  1.00 54.95      B  C
ATOM   5670  CG   ASN B 170      59.884   9.495  46.343  1.00 55.81      B  C
ATOM   5671  OD1  ASN B 170      59.817  10.627  46.819  1.00 56.28      B  O
ATOM   5672  ND2  ASN B 170      60.233   9.270  45.073  1.00 56.82      B  N
ATOM   5675  C    ASN B 170      60.098   9.553  49.338  1.00 53.91      B  C
ATOM   5676  O    ASN B 170      61.303   9.478  49.166  1.00 54.00      B  O
ATOM   5678  N    ASN B 171      59.527  10.470  50.120  1.00 53.33      B  N
ATOM   5679  CA   ASN B 171      60.267  11.404  50.981  1.00 52.76      B  C
ATOM   5681  CB   ASN B 171      61.198  10.649  51.950  1.00 53.39      B  C
ATOM   5684  CG   ASN B 171      60.419   9.875  52.994  1.00 55.56      B  C
ATOM   5685  OD1  ASN B 171      59.451  10.391  53.571  1.00 57.85      B  O
ATOM   5686  ND2  ASN B 171      60.817   8.623  53.228  1.00 58.68      B  N
ATOM   5689  C    ASN B 171      61.008  12.527  50.276  1.00 51.09      B  C
ATOM   5690  O    ASN B 171      61.681  13.307  50.924  1.00 49.37      B  O
ATOM   5692  N    LYS B 172      60.852  12.614  48.952  1.00 50.53      B  N
ATOM   5693  CA   LYS B 172      61.253  13.806  48.177  1.00 49.50      B  C
ATOM   5695  CB   LYS B 172      61.724  13.406  46.774  1.00 49.90      B  C
ATOM   5698  CG   LYS B 172      62.912  12.447  46.784  1.00 51.54      B  C
ATOM   5701  CD   LYS B 172      63.163  11.827  45.417  1.00 52.55      B  C
ATOM   5704  CE   LYS B 172      64.266  10.780  45.475  1.00 53.48      B  C
ATOM   5707  NZ   LYS B 172      64.724  10.400  44.118  1.00 53.77      B  N
ATOM   5711  C    LYS B 172      60.068  14.771  48.103  1.00 47.67      B  C
ATOM   5712  O    LYS B 172      59.006  14.486  48.649  1.00 47.85      B  O
ATOM   5714  N    TYR B 173      60.269  15.916  47.458  1.00 45.35      B  N
ATOM   5715  CA   TYR B 173      59.280  16.963  47.405  1.00 43.81      B  C
ATOM   5717  CB   TYR B 173      59.888  18.272  47.885  1.00 43.88      B  C
ATOM   5720  CG   TYR B 173      60.085  18.278  49.379  1.00 46.42      B  C
ATOM   5721  CD1  TYR B 173      59.120  18.850  50.230  1.00 46.48      B  C
ATOM   5723  CE1  TYR B 173      59.285  18.840  51.595  1.00 48.53      B  C
ATOM   5725  CZ   TYR B 173      60.417  18.242  52.134  1.00 48.27      B  C
ATOM   5726  OH   TYR B 173      60.581  18.219  53.478  1.00 49.67      B  O
ATOM   5728  CE2  TYR B 173      61.377  17.664  51.325  1.00 47.26      B  C
ATOM   5730  CD2  TYR B 173      61.205  17.680  49.954  1.00 46.35      B  C
ATOM   5732  C    TYR B 173      58.704  17.156  46.014  1.00 42.25      B  C
ATOM   5733  O    TYR B 173      59.372  16.924  44.998  1.00 42.60      B  O
ATOM   5735  N    ALA B 174      57.462  17.613  45.986  1.00 40.04      B  N
ATOM   5736  CA   ALA B 174      56.792  17.988  44.756  1.00 38.72      B  C
ATOM   5738  CB   ALA B 174      55.662  17.005  44.415  1.00 38.56      B  C
ATOM   5742  C    ALA B 174      56.247  19.385  44.927  1.00 37.30      B  C
ATOM   5743  O    ALA B 174      56.001  19.846  46.043  1.00 36.61      B  O
ATOM   5745  N    ALA B 175      56.078  20.056  43.803  1.00 35.50      B  N
ATOM   5746  CA   ALA B 175      55.457  21.357  43.755  1.00 33.86      B  C
ATOM   5748  CB   ALA B 175      56.461  22.449  44.047  1.00 33.14      B  C
ATOM   5752  C    ALA B 175      54.854  21.511  42.364  1.00 33.20      B  C
ATOM   5753  O    ALA B 175      55.210  20.761  41.442  1.00 32.44      B  O
ATOM   5755  N    SER B 176      53.936  22.466  42.244  1.00 32.17      B  N
ATOM   5756  CA   SER B 176      53.152  22.721  41.045  1.00 31.72      B  C
ATOM   5758  CB   SER B 176      51.708  22.274  41.248  1.00 31.34      B  C
ATOM   5761  OG   SER B 176      51.592  20.900  41.064  1.00 34.38      B  O
ATOM   5763  C    SER B 176      53.118  24.233  40.845  1.00 31.33      B  C
```

Figure 8 – CONT.

```
ATOM   5764  O    SER B 176      53.034  24.973  41.837  1.00 31.20      B  O
ATOM   5766  N    SER B 177      53.189  24.683  39.589  1.00 30.08      B  N
ATOM   5767  CA   SER B 177      52.874  26.065  39.235  1.00 29.65      B  C
ATOM   5769  CB   SER B 177      54.113  26.879  38.922  1.00 29.22      B  C
ATOM   5772  OG   SER B 177      53.784  28.259  38.851  1.00 29.12      B  O
ATOM   5774  C    SER B 177      51.912  26.095  38.062  1.00 29.83      B  C
ATOM   5775  O    SER B 177      52.058  25.298  37.127  1.00 30.25      B  O
ATOM   5777  N    TYR B 178      50.934  27.002  38.142  1.00 29.13      B  N
ATOM   5778  CA   TYR B 178      49.906  27.175  37.139  1.00 28.97      B  C
ATOM   5780  CB   TYR B 178      48.518  26.948  37.738  1.00 28.43      B  C
ATOM   5783  CG   TYR B 178      48.301  25.510  38.112  1.00 28.69      B  C
ATOM   5784  CD1  TYR B 178      47.701  24.636  37.233  1.00 29.90      B  C
ATOM   5786  CE1  TYR B 178      47.525  23.275  37.561  1.00 30.52      B  C
ATOM   5788  CZ   TYR B 178      47.984  22.785  38.776  1.00 28.98      B  C
ATOM   5789  OH   TYR B 178      47.824  21.457  39.060  1.00 28.34      B  O
ATOM   5791  CE2  TYR B 178      48.604  23.635  39.675  1.00 28.91      B  C
ATOM   5793  CD2  TYR B 178      48.756  25.001  39.340  1.00 30.23      B  C
ATOM   5795  C    TYR B 178      50.017  28.582  36.613  1.00 29.76      B  C
ATOM   5796  O    TYR B 178      50.111  29.518  37.394  1.00 29.41      B  O
ATOM   5798  N    LEU B 179      50.068  28.727  35.290  1.00 30.41      B  N
ATOM   5799  CA   LEU B 179      49.954  30.037  34.664  1.00 31.13      B  C
ATOM   5801  CB   LEU B 179      51.123  30.332  33.700  1.00 30.39      B  C
ATOM   5804  CG   LEU B 179      51.066  31.662  32.920  1.00 30.45      B  C
ATOM   5806  CD1  LEU B 179      50.772  32.823  33.840  1.00 29.09      B  C
ATOM   5810  CD2  LEU B 179      52.376  31.962  32.128  1.00 28.46      B  C
ATOM   5814  C    LEU B 179      48.614  30.040  33.956  1.00 31.80      B  C
ATOM   5815  O    LEU B 179      48.389  29.260  33.010  1.00 32.23      B  O
ATOM   5817  N    SER B 180      47.730  30.903  34.436  1.00 32.55      B  N
ATOM   5818  CA   SER B 180      46.399  31.039  33.897  1.00 33.30      B  C
ATOM   5820  CB   SER B 180      45.420  31.208  35.047  1.00 33.56      B  C
ATOM   5823  OG   SER B 180      45.383  29.998  35.816  1.00 36.31      B  O
ATOM   5825  C    SER B 180      46.368  32.243  32.948  1.00 33.77      B  C
ATOM   5826  O    SER B 180      46.902  33.304  33.251  1.00 34.62      B  O
ATOM   5828  N    LEU B 181      45.781  32.061  31.782  1.00 33.76      B  N
ATOM   5829  CA   LEU B 181      45.821  33.085  30.740  1.00 34.18      B  C
ATOM   5831  CB   LEU B 181      46.951  32.786  29.739  1.00 34.13      B  C
ATOM   5834  CG   LEU B 181      48.397  32.741  30.193  1.00 35.50      B  C
ATOM   5836  CD1  LEU B 181      49.265  32.022  29.111  1.00 35.57      B  C
ATOM   5840  CD2  LEU B 181      48.928  34.136  30.493  1.00 33.08      B  C
ATOM   5844  C    LEU B 181      44.523  32.992  29.982  1.00 33.46      B  C
ATOM   5845  O    LEU B 181      43.880  31.928  29.979  1.00 33.70      B  O
ATOM   5847  N    THR B 182      44.154  34.076  29.310  1.00 33.04      B  N
ATOM   5848  CA   THR B 182      43.058  34.009  28.305  1.00 33.22      B  C
ATOM   5850  CB   THR B 182      42.600  35.394  27.802  1.00 33.17      B  C
ATOM   5852  OG1  THR B 182      43.702  36.027  27.128  1.00 32.74      B  O
ATOM   5854  CG2  THR B 182      42.107  36.320  28.978  1.00 34.24      B  C
ATOM   5858  C    THR B 182      43.611  33.257  27.091  1.00 33.14      B  C
ATOM   5859  O    THR B 182      44.851  33.263  26.862  1.00 31.32      B  O
ATOM   5861  N    PRO B 183      42.711  32.592  26.320  1.00 34.14      B  N
ATOM   5862  CA   PRO B 183      43.150  31.903  25.089  1.00 35.02      B  C
ATOM   5864  CB   PRO B 183      41.848  31.355  24.513  1.00 35.21      B  C
ATOM   5867  CG   PRO B 183      40.951  31.146  25.742  1.00 34.73      B  C
ATOM   5870  CD   PRO B 183      41.307  32.261  26.675  1.00 33.86      B  C
ATOM   5873  C    PRO B 183      43.862  32.869  24.114  1.00 35.90      B  C
ATOM   5874  O    PRO B 183      44.804  32.475  23.420  1.00 35.75      B  O
ATOM   5875  N    GLU B 184      43.449  34.135  24.155  1.00 36.58      B  N
ATOM   5876  CA   GLU B 184      44.033  35.211  23.366  1.00 37.86      B  C
ATOM   5878  CB   GLU B 184      43.224  36.525  23.522  1.00 38.24      B  C
```

Figure 8 – CONT.

```
ATOM   5881  CG   GLU B 184      41.713  36.359  23.231  1.00 41.38      B  C
ATOM   5884  CD   GLU B 184      40.892  36.073  24.511  1.00 43.97      B  C
ATOM   5885  OE1  GLU B 184      40.234  35.007  24.572  1.00 44.52      B  O
ATOM   5886  OE2  GLU B 184      40.934  36.922  25.445  1.00 46.83      B  O
ATOM   5887  C    GLU B 184      45.482  35.465  23.754  1.00 38.25      B  C
ATOM   5888  O    GLU B 184      46.357  35.499  22.867  1.00 38.71      B  O
ATOM   5890  N    GLN B 185      45.731  35.667  25.057  1.00 37.86      B  N
ATOM   5891  CA   GLN B 185      47.100  35.863  25.578  1.00 37.73      B  C
ATOM   5893  CB   GLN B 185      47.072  36.055  27.101  1.00 38.45      B  C
ATOM   5896  CG   GLN B 185      46.594  37.430  27.532  1.00 40.63      B  C
ATOM   5899  CD   GLN B 185      46.125  37.503  28.994  1.00 43.11      B  C
ATOM   5900  OE1  GLN B 185      46.165  36.528  29.754  1.00 42.38      B  O
ATOM   5901  NE2  GLN B 185      45.640  38.676  29.373  1.00 45.76      B  N
ATOM   5904  C    GLN B 185      48.006  34.673  25.252  1.00 36.56      B  C
ATOM   5905  O    GLN B 185      49.184  34.825  24.939  1.00 37.45      B  O
ATOM   5907  N    TRP B 186      47.451  33.481  25.320  1.00 34.93      B  N
ATOM   5908  CA   TRP B 186      48.206  32.274  24.993  1.00 34.36      B  C
ATOM   5910  CB   TRP B 186      47.342  31.028  25.313  1.00 33.41      B  C
ATOM   5913  CG   TRP B 186      47.794  29.730  24.651  1.00 31.33      B  C
ATOM   5914  CD1  TRP B 186      47.081  28.961  23.771  1.00 28.85      B  C
ATOM   5916  NE1  TRP B 186      47.814  27.838  23.412  1.00 28.77      B  N
ATOM   5918  CE2  TRP B 186      49.017  27.879  24.070  1.00 30.64      B  C
ATOM   5919  CD2  TRP B 186      49.041  29.066  24.845  1.00 28.60      B  C
ATOM   5920  CE3  TRP B 186      50.168  29.334  25.630  1.00 30.65      B  C
ATOM   5922  CZ3  TRP B 186      51.238  28.441  25.590  1.00 29.81      B  C
ATOM   5924  CH2  TRP B 186      51.194  27.289  24.776  1.00 28.09      B  C
ATOM   5926  CZ2  TRP B 186      50.102  26.991  24.022  1.00 27.61      B  C
ATOM   5928  C    TRP B 186      48.620  32.290  23.498  1.00 34.54      B  C
ATOM   5929  O    TRP B 186      49.764  31.999  23.167  1.00 33.63      B  O
ATOM   5931  N    LYS B 187      47.674  32.637  22.620  1.00 35.69      B  N
ATOM   5932  CA   LYS B 187      47.873  32.530  21.143  1.00 36.42      B  C
ATOM   5934  CB   LYS B 187      46.522  32.364  20.433  1.00 36.06      B  C
ATOM   5937  CG   LYS B 187      45.924  30.978  20.614  1.00 39.16      B  C
ATOM   5940  CD   LYS B 187      44.501  30.849  19.995  1.00 42.57      B  C
ATOM   5943  CE   LYS B 187      43.911  29.445  20.162  1.00 44.52      B  C
ATOM   5946  NZ   LYS B 187      42.493  29.338  19.621  1.00 44.29      B  N
ATOM   5950  C    LYS B 187      48.666  33.692  20.550  1.00 35.99      B  C
ATOM   5951  O    LYS B 187      49.250  33.581  19.461  1.00 36.39      B  O
ATOM   5953  N    SER B 188      48.702  34.798  21.286  1.00 36.61      B  N
ATOM   5954  CA   SER B 188      49.411  36.014  20.860  1.00 36.32      B  C
ATOM   5956  CB   SER B 188      48.874  37.259  21.603  1.00 36.60      B  C
ATOM   5959  OG   SER B 188      47.503  37.484  21.296  1.00 35.90      B  O
ATOM   5961  C    SER B 188      50.908  35.942  21.067  1.00 36.33      B  C
ATOM   5962  O    SER B 188      51.614  36.811  20.589  1.00 36.91      B  O
ATOM   5964  N    HIS B 189      51.407  34.923  21.763  1.00 35.84      B  N
ATOM   5965  CA   HIS B 189      52.835  34.817  22.001  1.00 36.16      B  C
ATOM   5967  CB   HIS B 189      53.138  34.774  23.512  1.00 36.13      B  C
ATOM   5970  CG   HIS B 189      52.914  36.092  24.176  1.00 36.40      B  C
ATOM   5971  ND1  HIS B 189      53.874  37.080  24.194  1.00 37.23      B  N
ATOM   5973  CE1  HIS B 189      53.388  38.149  24.799  1.00 39.63      B  C
ATOM   5975  NE2  HIS B 189      52.136  37.900  25.143  1.00 39.70      B  N
ATOM   5977  CD2  HIS B 189      51.814  36.622  24.755  1.00 36.20      B  C
ATOM   5979  C    HIS B 189      53.352  33.605  21.292  1.00 36.78      B  C
ATOM   5980  O    HIS B 189      52.567  32.721  20.937  1.00 37.32      B  O
ATOM   5982  N    ARG B 190      54.660  33.546  21.071  1.00 36.82      B  N
ATOM   5983  CA   ARG B 190      55.211  32.394  20.357  1.00 37.28      B  C
ATOM   5985  CB   ARG B 190      56.061  32.858  19.169  1.00 37.96      B  C
ATOM   5988  CG   ARG B 190      55.065  33.269  18.052  1.00 39.08      B  C
```

Figure 8 – CONT.

```
ATOM   5991  CD   ARG B 190      55.634  33.508  16.769  1.00 38.39      B  C
ATOM   5994  NE   ARG B 190      56.079  32.320  16.047  1.00 38.45      B  N
ATOM   5996  CZ   ARG B 190      55.318  31.475  15.348  1.00 36.90      B  C
ATOM   5997  NH1  ARG B 190      53.988  31.577  15.313  1.00 36.30      B  N
ATOM   6000  NH2  ARG B 190      55.923  30.487  14.694  1.00 34.47      B  N
ATOM   6003  C    ARG B 190      55.881  31.341  21.206  1.00 37.06      B  C
ATOM   6004  O    ARG B 190      55.950  30.167  20.779  1.00 36.40      B  O
ATOM   6006  N    SER B 191      56.324  31.741  22.402  1.00 36.92      B  N
ATOM   6007  CA   SER B 191      56.817  30.792  23.422  1.00 37.50      B  C
ATOM   6009  CB   SER B 191      58.342  30.680  23.460  1.00 37.32      B  C
ATOM   6012  OG   SER B 191      58.891  30.584  22.169  1.00 44.45      B  O
ATOM   6014  C    SER B 191      56.422  31.225  24.816  1.00 35.89      B  C
ATOM   6015  O    SER B 191      56.374  32.409  25.111  1.00 35.06      B  O
ATOM   6017  N    TYR B 192      56.201  30.230  25.666  1.00 35.30      B  N
ATOM   6018  CA   TYR B 192      56.140  30.420  27.112  1.00 34.75      B  C
ATOM   6020  CB   TYR B 192      54.750  30.131  27.656  1.00 34.04      B  C
ATOM   6023  CG   TYR B 192      53.771  31.243  27.465  1.00 33.21      B  C
ATOM   6024  CD1  TYR B 192      53.628  32.225  28.432  1.00 35.70      B  C
ATOM   6026  CE1  TYR B 192      52.728  33.247  28.282  1.00 35.74      B  C
ATOM   6028  CZ   TYR B 192      51.930  33.306  27.149  1.00 36.52      B  C
ATOM   6029  OH   TYR B 192      51.041  34.349  27.034  1.00 39.07      B  O
ATOM   6031  CE2  TYR B 192      52.034  32.342  26.171  1.00 35.10      B  C
ATOM   6033  CD2  TYR B 192      52.966  31.310  26.336  1.00 35.29      B  C
ATOM   6035  C    TYR B 192      57.146  29.474  27.714  1.00 34.60      B  C
ATOM   6036  O    TYR B 192      57.353  28.381  27.190  1.00 34.60      B  O
ATOM   6038  N    SER B 193      57.780  29.902  28.804  1.00 34.49      B  N
ATOM   6039  CA   SER B 193      58.704  29.039  29.513  1.00 34.69      B  C
ATOM   6041  CB   SER B 193      60.134  29.515  29.305  1.00 34.58      B  C
ATOM   6044  OG   SER B 193      60.392  29.575  27.911  1.00 37.42      B  O
ATOM   6046  C    SER B 193      58.392  28.923  31.002  1.00 34.50      B  C
ATOM   6047  O    SER B 193      57.982  29.882  31.648  1.00 33.08      B  O
ATOM   6049  N    CYS B 194      58.558  27.710  31.504  1.00 34.35      B  N
ATOM   6050  CA   CYS B 194      58.617  27.455  32.918  1.00 35.40      B  C
ATOM   6052  CB   CYS B 194      57.848  26.176  33.285  1.00 34.79      B  C
ATOM   6055  SG   CYS B 194      57.775  26.010  35.046  1.00 37.55      B  S
ATOM   6057  C    CYS B 194      60.079  27.281  33.324  1.00 35.78      B  C
ATOM   6058  O    CYS B 194      60.776  26.402  32.798  1.00 34.81      B  O
ATOM   6060  N    ARG B 195      60.526  28.071  34.301  1.00 36.72      B  N
ATOM   6061  CA   ARG B 195      61.925  28.017  34.763  1.00 37.48      B  C
ATOM   6063  CB   ARG B 195      62.586  29.353  34.479  1.00 38.48      B  C
ATOM   6066  CG   ARG B 195      63.882  29.595  35.174  1.00 42.76      B  C
ATOM   6069  CD   ARG B 195      64.449  30.984  34.802  1.00 47.68      B  C
ATOM   6072  NE   ARG B 195      65.401  30.831  33.707  1.00 52.31      B  N
ATOM   6074  CZ   ARG B 195      66.728  30.821  33.825  1.00 54.93      B  C
ATOM   6075  NH1  ARG B 195      67.342  31.044  34.986  1.00 55.43      B  N
ATOM   6078  NH2  ARG B 195      67.451  30.618  32.732  1.00 58.03      B  N
ATOM   6081  C    ARG B 195      61.975  27.680  36.243  1.00 37.12      B  C
ATOM   6082  O    ARG B 195      61.473  28.442  37.090  1.00 37.42      B  O
ATOM   6084  N    VAL B 196      62.567  26.528  36.539  1.00 36.50      B  N
ATOM   6085  CA   VAL B 196      62.633  25.979  37.869  1.00 36.09      B  C
ATOM   6087  CB   VAL B 196      62.004  24.602  37.886  1.00 36.09      B  C
ATOM   6089  CG1  VAL B 196      62.115  23.975  39.265  1.00 32.48      B  C
ATOM   6093  CG2  VAL B 196      60.535  24.717  37.427  1.00 34.70      B  C
ATOM   6097  C    VAL B 196      64.072  25.901  38.389  1.00 37.11      B  C
ATOM   6098  O    VAL B 196      64.907  25.171  37.843  1.00 36.57      B  O
ATOM   6100  N    THR B 197      64.340  26.659  39.451  1.00 37.65      B  N
ATOM   6101  CA   THR B 197      65.652  26.694  40.063  1.00 38.90      B  C
ATOM   6103  CB   THR B 197      66.087  28.124  40.354  1.00 38.78      B  C
```

Figure 8 – CONT.

```
ATOM   6105  OG1 THR B 197      66.017  28.872  39.137  1.00 41.53      B  O
ATOM   6107  CG2 THR B 197      67.543  28.173  40.888  1.00 38.69      B  C
ATOM   6111  C   THR B 197      65.663  25.854  41.349  1.00 39.44      B  C
ATOM   6112  O   THR B 197      64.822  26.036  42.238  1.00 39.56      B  O
ATOM   6114  N   HIS B 198      66.598  24.917  41.411  1.00 39.91      B  N
ATOM   6115  CA  HIS B 198      66.818  24.102  42.596  1.00 41.16      B  C
ATOM   6117  CB  HIS B 198      66.277  22.700  42.363  1.00 40.74      B  C
ATOM   6120  CG  HIS B 198      66.543  21.752  43.490  1.00 42.35      B  C
ATOM   6121  ND1 HIS B 198      65.785  21.726  44.644  1.00 44.35      B  N
ATOM   6123  CE1 HIS B 198      66.233  20.768  45.435  1.00 43.74      B  C
ATOM   6125  NE2 HIS B 198      67.242  20.166  44.835  1.00 42.92      B  N
ATOM   6127  CD2 HIS B 198      67.458  20.766  43.621  1.00 43.20      B  C
ATOM   6129  C   HIS B 198      68.314  24.040  42.907  1.00 41.81      B  C
ATOM   6130  O   HIS B 198      69.101  23.540  42.082  1.00 41.20      B  O
ATOM   6132  N   GLU B 199      68.690  24.563  44.073  1.00 42.98      B  N
ATOM   6133  CA  GLU B 199      70.065  24.472  44.591  1.00 44.62      B  C
ATOM   6135  CB  GLU B 199      70.441  23.009  44.959  1.00 45.16      B  C
ATOM   6138  CG  GLU B 199      69.746  22.459  46.238  1.00 47.65      B  C
ATOM   6141  CD  GLU B 199      69.904  23.398  47.429  1.00 50.51      B  C
ATOM   6142  OE1 GLU B 199      71.068  23.717  47.776  1.00 51.48      B  O
ATOM   6143  OE2 GLU B 199      68.869  23.857  47.988  1.00 52.74      B  O
ATOM   6144  C   GLU B 199      71.037  25.036  43.569  1.00 44.77      B  C
ATOM   6145  O   GLU B 199      71.950  24.334  43.112  1.00 45.16      B  O
ATOM   6147  N   GLY B 200      70.807  26.292  43.179  1.00 44.59      B  N
ATOM   6148  CA  GLY B 200      71.661  26.966  42.198  1.00 44.59      B  C
ATOM   6151  C   GLY B 200      71.662  26.403  40.782  1.00 44.38      B  C
ATOM   6152  O   GLY B 200      72.353  26.922  39.928  1.00 44.65      B  O
ATOM   6154  N   SER B 203      70.875  25.362  40.531  1.00 43.68      B  N
ATOM   6155  CA  SER B 203      70.771  24.742  39.218  1.00 43.73      B  C
ATOM   6157  CB  SER B 203      71.254  23.304  39.348  1.00 43.17      B  C
ATOM   6160  OG  SER B 203      70.400  22.478  38.625  1.00 46.02      B  O
ATOM   6162  C   SER B 203      69.329  24.872  38.578  1.00 43.07      B  C
ATOM   6163  O   SER B 203      68.313  24.776  39.274  1.00 43.36      B  O
ATOM   6165  N   THR B 204      69.244  25.118  37.267  1.00 42.24      B  N
ATOM   6166  CA  THR B 204      67.967  25.515  36.634  1.00 41.20      B  C
ATOM   6168  CB  THR B 204      67.986  26.993  36.234  1.00 41.12      B  C
ATOM   6170  OG1 THR B 204      68.118  27.801  37.408  1.00 40.14      B  O
ATOM   6172  CG2 THR B 204      66.699  27.374  35.474  1.00 40.09      B  C
ATOM   6176  C   THR B 204      67.593  24.747  35.383  1.00 41.34      B  C
ATOM   6177  O   THR B 204      68.393  24.641  34.461  1.00 41.39      B  O
ATOM   6179  N   VAL B 205      66.367  24.227  35.357  1.00 41.15      B  N
ATOM   6180  CA  VAL B 205      65.788  23.605  34.176  1.00 40.79      B  C
ATOM   6182  CB  VAL B 205      65.084  22.266  34.473  1.00 41.37      B  C
ATOM   6184  CG1 VAL B 205      64.595  21.641  33.162  1.00 41.56      B  C
ATOM   6188  CG2 VAL B 205      65.991  21.297  35.227  1.00 41.71      B  C
ATOM   6192  C   VAL B 205      64.709  24.515  33.638  1.00 40.79      B  C
ATOM   6193  O   VAL B 205      63.903  25.060  34.391  1.00 40.71      B  O
ATOM   6195  N   GLU B 206      64.644  24.632  32.327  1.00 40.35      B  N
ATOM   6196  CA  GLU B 206      63.698  25.535  31.719  1.00 40.17      B  C
ATOM   6198  CB  GLU B 206      64.462  26.756  31.259  1.00 40.52      B  C
ATOM   6201  CG  GLU B 206      63.661  27.939  30.825  1.00 41.87      B  C
ATOM   6204  CD  GLU B 206      64.515  29.213  30.763  1.00 43.69      B  C
ATOM   6205  OE1 GLU B 206      65.577  29.287  31.451  1.00 44.40      B  O
ATOM   6206  OE2 GLU B 206      64.102  30.163  30.060  1.00 46.22      B  O
ATOM   6207  C   GLU B 206      63.028  24.792  30.573  1.00 39.62      B  C
ATOM   6208  O   GLU B 206      63.702  24.335  29.641  1.00 39.38      B  O
ATOM   6210  N   LYS B 207      61.712  24.588  30.670  1.00 38.20      B  N
ATOM   6211  CA  LYS B 207      60.989  23.958  29.582  1.00 36.90      B  C
```

Figure 8 – CONT.

```
ATOM   6213  CB   LYS B 207      60.129  22.798  30.063  1.00 36.28      B  C
ATOM   6216  CG   LYS B 207      60.812  21.763  30.917  1.00 36.84      B  C
ATOM   6219  CD   LYS B 207      61.744  20.894  30.135  1.00 37.68      B  C
ATOM   6222  CE   LYS B 207      61.711  19.448  30.541  1.00 38.95      B  C
ATOM   6225  NZ   LYS B 207      62.685  19.157  31.581  1.00 40.55      B  N
ATOM   6229  C    LYS B 207      60.134  25.012  28.909  1.00 36.63      B  C
ATOM   6230  O    LYS B 207      59.797  26.037  29.505  1.00 36.62      B  O
ATOM   6232  N    THR B 208      59.742  24.722  27.682  1.00 36.28      B  N
ATOM   6233  CA   THR B 208      59.089  25.683  26.827  1.00 36.93      B  C
ATOM   6235  CB   THR B 208      60.131  26.233  25.828  1.00 38.08      B  C
ATOM   6237  OG1  THR B 208      61.026  27.122  26.532  1.00 39.48      B  O
ATOM   6239  CG2  THR B 208      59.448  26.988  24.697  1.00 38.01      B  C
ATOM   6243  C    THR B 208      57.928  25.036  26.064  1.00 36.11      B  C
ATOM   6244  O    THR B 208      57.965  23.838  25.777  1.00 35.70      B  O
ATOM   6246  N    VAL B 209      56.910  25.829  25.731  1.00 35.31      B  N
ATOM   6247  CA   VAL B 209      55.811  25.351  24.892  1.00 34.99      B  C
ATOM   6249  CB   VAL B 209      54.556  24.916  25.709  1.00 34.80      B  C
ATOM   6251  CG1  VAL B 209      54.832  23.594  26.417  1.00 34.26      B  C
ATOM   6255  CG2  VAL B 209      54.124  26.011  26.689  1.00 32.24      B  C
ATOM   6259  C    VAL B 209      55.406  26.445  23.926  1.00 35.83      B  C
ATOM   6260  O    VAL B 209      55.488  27.625  24.260  1.00 35.71      B  O
ATOM   6262  N    ALA B 210      54.979  26.039  22.730  1.00 36.68      B  N
ATOM   6263  CA   ALA B 210      54.562  26.979  21.671  1.00 37.51      B  C
ATOM   6265  CB   ALA B 210      55.493  26.885  20.444  1.00 37.92      B  C
ATOM   6269  C    ALA B 210      53.138  26.676  21.282  1.00 37.57      B  C
ATOM   6270  O    ALA B 210      52.788  25.522  21.128  1.00 37.93      B  O
ATOM   6272  N    PRO B 211      52.297  27.705  21.177  1.00 37.94      B  N
ATOM   6273  CA   PRO B 211      50.956  27.567  20.626  1.00 39.01      B  C
ATOM   6275  CB   PRO B 211      50.501  29.008  20.509  1.00 39.30      B  C
ATOM   6278  CG   PRO B 211      51.197  29.657  21.644  1.00 39.75      B  C
ATOM   6281  CD   PRO B 211      52.528  29.043  21.725  1.00 37.72      B  C
ATOM   6284  C    PRO B 211      50.882  26.898  19.257  1.00 39.43      B  C
ATOM   6285  O    PRO B 211      50.107  25.945  19.099  1.00 40.89      B  O
TER
ATOM   6286  N    GLN C   1      22.240  -8.732  -0.994  1.00 40.01      C  N
ATOM   6287  CA   GLN C   1      23.641  -8.863  -1.516  1.00 39.17      C  C
ATOM   6289  CB   GLN C   1      23.692  -9.908  -2.629  1.00 39.27      C  C
ATOM   6296  C    GLN C   1      24.253  -7.509  -1.986  1.00 37.68      C  C
ATOM   6297  O    GLN C   1      25.443  -7.272  -1.758  1.00 38.53      C  O
ATOM   6301  N    VAL C   2      23.484  -6.627  -2.622  1.00 35.82      G  N
ATOM   6302  CA   VAL C   2      24.023  -5.293  -2.934  1.00 34.05      G  C
ATOM   6304  CB   VAL C   2      23.261  -4.535  -4.026  1.00 34.18      C  C
ATOM   6306  CG1  VAL C   2      23.774  -3.064  -4.119  1.00 31.13      C  C
ATOM   6310  CG2  VAL C   2      23.374  -5.249  -5.394  1.00 32.74      C  C
ATOM   6314  C    VAL C   2      24.011  -4.452  -1.670  1.00 34.23      G  C
ATOM   6315  O    VAL C   2      22.959  -4.258  -1.070  1.00 33.78      G  O
ATOM   6317  N    GLN C   3      25.177  -3.958  -1.257  1.00 33.68      G  N
ATOM   6318  CA   GLN C   3      25.241  -3.052  -0.122  1.00 33.28      G  C
ATOM   6320  CB   GLN C   3      25.667  -3.829   1.116  1.00 34.38      G  C
ATOM   6323  CG   GLN C   3      25.429  -3.100   2.419  1.00 38.11      G  C
ATOM   6326  CD   GLN C   3      25.739  -3.981   3.636  1.00 44.27      G  C
ATOM   6327  OE1  GLN C   3      26.587  -3.634   4.476  1.00 46.34      G  O
ATOM   6328  NE2  GLN C   3      25.083  -5.148   3.710  1.00 46.46      G  N
ATOM   6331  C    GLN C   3      26.192  -1.888  -0.341  1.00 32.44      G  C
ATOM   6332  O    GLN C   3      27.312  -2.048  -0.858  1.00 30.81      G  O
ATOM   6334  N    LEU C   4      25.751  -0.714   0.101  1.00 32.01      G  N
ATOM   6335  CA   LEU C   4      26.562   0.481   0.055  1.00 31.02      G  C
ATOM   6337  CB   LEU C   4      25.788   1.573  -0.671  1.00 31.11      G  C
```

Figure 8 – CONT.

```
ATOM   6340  CG   LEU C   4      25.392    1.244   -2.125  1.00 31.06           G  C
ATOM   6342  CD1  LEU C   4      24.632    2.409   -2.699  1.00 30.40           G  C
ATOM   6346  CD2  LEU C   4      26.598    0.926   -2.991  1.00 28.03           G  C
ATOM   6350  C    LEU C   4      26.978    0.913    1.468  1.00 31.40           G  C
ATOM   6351  O    LEU C   4      26.153    1.250    2.308  1.00 32.57           G  O
ATOM   6353  N    VAL C   5      28.270    0.910    1.723  1.00 30.81           G  N
ATOM   6354  CA   VAL C   5      28.800    1.230    3.023  1.00 31.05           G  C
ATOM   6356  CB   VAL C   5      29.824    0.138    3.450  1.00 31.75           C  C
ATOM   6358  CG1  VAL C   5      30.421    0.395    4.849  1.00 32.33           C  C
ATOM   6362  CG2  VAL C   5      29.144   -1.265    3.418  1.00 33.05           C  C
ATOM   6366  C    VAL C   5      29.412    2.644    2.959  1.00 30.04           G  C
ATOM   6367  O    VAL C   5      30.319    2.938    2.134  1.00 30.14           G  O
ATOM   6369  N    GLN C   6      28.868    3.522    3.794  1.00 28.57           G  N
ATOM   6370  CA   GLN C   6      29.280    4.912    3.876  1.00 27.64           G  C
ATOM   6372  CB   GLN C   6      28.069    5.830    3.786  1.00 27.21           G  C
ATOM   6375  CG   GLN C   6      27.380    5.786    2.443  1.00 23.97           G  C
ATOM   6378  CD   GLN C   6      26.408    6.888    2.218  1.00 21.40           G  C
ATOM   6379  OE1  GLN C   6      25.224    6.642    2.011  1.00 21.28           G  O
ATOM   6380  NE2  GLN C   6      26.900    8.138    2.197  1.00 23.05           G  N
ATOM   6383  C    GLN C   6      30.082    5.232    5.141  1.00 28.59           G  C
ATOM   6384  O    GLN C   6      29.841    4.697    6.228  1.00 29.46           G  O
ATOM   6386  N    SER C   7      31.026    6.152    4.998  1.00 28.75           G  N
ATOM   6387  CA   SER C   7      31.914    6.504    6.083  1.00 28.22           G  C
ATOM   6389  CB   SER C   7      33.066    7.391    5.578  1.00 27.87           G  C
ATOM   6392  OG   SER C   7      32.581    8.452    4.782  1.00 28.45           G  O
ATOM   6394  C    SER C   7      31.119    7.187    7.187  1.00 27.27           G  C
ATOM   6395  O    SER C   7      29.977    7.621    6.988  1.00 27.51           G  O
ATOM   6397  N    GLY C   8      31.732    7.279    8.352  1.00 26.52           G  N
ATOM   6398  CA   GLY C   8      31.019    7.703    9.552  1.00 26.68           G  C
ATOM   6401  C    GLY C   8      30.811    9.203    9.627  1.00 25.66           G  C
ATOM   6402  O    GLY C   8      31.327    9.972    8.801  1.00 25.82           G  O
ATOM   6404  N    ALA C   9      30.091    9.599   10.653  1.00 24.38           G  N
ATOM   6405  CA   ALA C   9      29.665   10.964   10.852  1.00 24.24           G  C
ATOM   6407  CB   ALA C   9      28.754   11.050   12.072  1.00 24.33           G  C
ATOM   6411  C    ALA C   9      30.848   11.901   11.000  1.00 23.93           G  C
ATOM   6412  O    ALA C   9      31.864   11.535   11.548  1.00 23.40           G  O
ATOM   6414  N    GLU C  10      30.704   13.117   10.485  1.00 23.72           G  N
ATOM   6415  CA   GLU C  10      31.801   14.048   10.460  1.00 23.73           G  C
ATOM   6417  CB   GLU C  10      32.243   14.342    9.007  1.00 23.72           G  C
ATOM   6420  CG   GLU C  10      32.788   13.153    8.237  1.00 25.88           G  C
ATOM   6423  CD   GLU C  10      34.219   12.871    8.573  1.00 27.28           G  C
ATOM   6424  OE1  GLU C  10      34.843   13.623    9.355  1.00 31.67           G  O
ATOM   6425  OE2  GLU C  10      34.721   11.883    8.071  1.00 28.36           G  O
ATOM   6426  C    GLU C  10      31.353   15.347   11.055  1.00 23.09           G  C
ATOM   6427  O    GLU C  10      30.248   15.816   10.769  1.00 22.39           G  O
ATOM   6429  N    VAL C  11      32.266   15.946   11.817  1.00 23.93           G  N
ATOM   6430  CA   VAL C  11      32.069   17.244   12.404  1.00 24.65           G  C
ATOM   6432  CB   VAL C  11      31.909   17.142   13.928  1.00 25.12           G  C
ATOM   6434  CG1  VAL C  11      31.491   18.499   14.512  1.00 23.58           G  C
ATOM   6438  CG2  VAL C  11      30.844   16.053   14.257  1.00 26.06           G  C
ATOM   6442  C    VAL C  11      33.295   18.055   12.067  1.00 24.66           G  C
ATOM   6443  O    VAL C  11      34.409   17.648   12.347  1.00 24.79           G  O
ATOM   6445  N    LYS C  12      33.072   19.219   11.484  1.00 24.72           G  N
ATOM   6446  CA   LYS C  12      34.153   20.047   10.968  1.00 25.75           G  C
ATOM   6448  CB   LYS C  12      34.288   19.833    9.457  1.00 25.55           G  C
ATOM   6451  CG   LYS C  12      34.600   18.428    9.049  1.00 26.14           G  C
ATOM   6454  CD   LYS C  12      35.850   17.887    9.657  1.00 28.05           G  C
ATOM   6457  CE   LYS C  12      36.932   17.602    8.663  1.00 32.41           G  C
```

Figure 8 – CONT.

```
ATOM   6460  NZ   LYS C  12      38.107  16.922   9.357  1.00 32.11       G  N
ATOM   6464  C    LYS C  12      33.811  21.494  11.168  1.00 25.25       G  C
ATOM   6465  O    LYS C  12      32.657  21.821  11.313  1.00 24.35       G  O
ATOM   6467  N    LYS C  13      34.819  22.353  11.082  1.00 26.49       G  N
ATOM   6468  CA   LYS C  13      34.625  23.808  11.051  1.00 27.08       G  C
ATOM   6470  CB   LYS C  13      35.777  24.496  11.778  1.00 28.06       G  C
ATOM   6473  CG   LYS C  13      35.892  24.000  13.209  1.00 31.43       G  C
ATOM   6476  CD   LYS C  13      36.977  24.639  14.033  1.00 34.60       G  C
ATOM   6479  CE   LYS C  13      36.501  24.749  15.501  1.00 36.83       G  C
ATOM   6482  NZ   LYS C  13      37.543  25.229  16.455  1.00 36.99       G  N
ATOM   6486  C    LYS C  13      34.555  24.320   9.628  1.00 26.82       G  C
ATOM   6487  O    LYS C  13      35.166  23.756   8.729  1.00 25.97       G  O
ATOM   6489  N    PRO C  14      33.873  25.448   9.416  1.00 27.45       G  N
ATOM   6490  CA   PRO C  14      33.893  26.026   8.074  1.00 27.10       G  C
ATOM   6492  CB   PRO C  14      33.177  27.364   8.251  1.00 27.77       C  C
ATOM   6495  CG   PRO C  14      32.267  27.163   9.468  1.00 27.33       C  C
ATOM   6498  CD   PRO C  14      33.115  26.289  10.367  1.00 28.03       C  C
ATOM   6501  C    PRO C  14      35.313  26.221   7.572  1.00 27.26       G  C
ATOM   6502  O    PRO C  14      36.206  26.565   8.350  1.00 27.12       G  O
ATOM   6503  N    GLY C  15      35.532  25.966   6.280  1.00 27.31       G  N
ATOM   6504  CA   GLY C  15      36.866  26.118   5.679  1.00 27.14       G  C
ATOM   6507  C    GLY C  15      37.723  24.857   5.705  1.00 27.35       G  C
ATOM   6508  O    GLY C  15      38.726  24.773   4.978  1.00 27.95       G  O
ATOM   6510  N    GLN C  16      37.349  23.854   6.497  1.00 26.51       G  N
ATOM   6511  CA   GLN C  16      38.095  22.579   6.462  1.00 27.16       G  C
ATOM   6513  CB   GLN C  16      37.847  21.729   7.703  1.00 27.13       C  C
ATOM   6516  CG   GLN C  16      38.353  22.440   8.952  1.00 28.97       C  C
ATOM   6519  CD   GLN C  16      38.337  21.570  10.190  1.00 29.54       C  C
ATOM   6520  OE1  GLN C  16      37.295  21.097  10.591  1.00 32.99       C  O
ATOM   6521  NE2  GLN C  16      39.491  21.366  10.795  1.00 29.88       C  N
ATOM   6524  C    GLN C  16      37.733  21.802   5.226  1.00 26.85       G  C
ATOM   6525  O    GLN C  16      36.637  21.944   4.704  1.00 26.64       G  O
ATOM   6527  N    SER C  17      38.659  20.993   4.758  1.00 27.50       G  N
ATOM   6528  CA   SER C  17      38.376  20.106   3.680  1.00 29.18       G  C
ATOM   6530  CB   SER C  17      39.637  19.845   2.844  1.00 29.84       G  C
ATOM   6533  OG   SER C  17      40.535  19.010   3.549  1.00 32.90       G  O
ATOM   6535  C    SER C  17      37.854  18.817   4.274  1.00 28.72       G  C
ATOM   6536  O    SER C  17      38.002  18.580   5.454  1.00 30.57       G  O
ATOM   6538  N    LEU C  18      37.253  17.987   3.430  1.00 28.24       G  N
ATOM   6539  CA   LEU C  18      36.592  16.781   3.833  1.00 26.79       G  C
ATOM   6541  CB   LEU C  18      35.258  17.088   4.529  1.00 25.88       G  C
ATOM   6544  CG   LEU C  18      34.325  15.916   4.861  1.00 26.64       G  C
ATOM   6546  CD1  LEU C  18      34.888  14.986   5.938  1.00 23.57       G  C
ATOM   6550  CD2  LEU C  18      32.901  16.445   5.236  1.00 23.70       G  C
ATOM   6554  C    LEU C  18      36.312  15.945   2.608  1.00 27.03       G  C
ATOM   6555  O    LEU C  18      35.787  16.444   1.600  1.00 26.32       G  O
ATOM   6557  N    LYS C  19      36.580  14.656   2.766  1.00 26.59       G  N
ATOM   6558  CA   LYS C  19      36.321  13.645   1.773  1.00 27.36       G  C
ATOM   6560  CB   LYS C  19      37.671  13.135   1.228  1.00 27.68       G  C
ATOM   6563  CG   LYS C  19      37.596  12.292  -0.034  1.00 31.52       G  C
ATOM   6566  CD   LYS C  19      39.034  12.170  -0.679  1.00 35.65       G  C
ATOM   6569  CE   LYS C  19      39.029  11.546  -2.083  1.00 38.23       G  C
ATOM   6572  NZ   LYS C  19      40.432  11.331  -2.620  1.00 39.21       G  N
ATOM   6576  C    LYS C  19      35.575  12.492   2.462  1.00 26.45       G  C
ATOM   6577  O    LYS C  19      36.054  11.958   3.450  1.00 25.38       G  O
ATOM   6579  N    ILE C  20      34.381  12.179   1.982  1.00 26.27       G  N
ATOM   6580  CA   ILE C  20      33.612  11.069   2.496  1.00 26.97       G  C
ATOM   6582  CB   ILE C  20      32.223  11.482   3.028  1.00 26.60       G  C
```

Figure 8 – CONT.

```
ATOM   6584  CG1 ILE C   20      31.302  11.969   1.934  1.00 26.82      G  C
ATOM   6587  CD1 ILE C   20      29.932  12.467   2.485  1.00 27.19      G  C
ATOM   6591  CG2 ILE C   20      32.367  12.519   4.171  1.00 26.13      G  C
ATOM   6595  C   ILE C   20      33.509   9.992   1.411  1.00 27.34      G  C
ATOM   6596  O   ILE C   20      33.725  10.276   0.222  1.00 27.42      G  O
ATOM   6598  N   SER C   21      33.174   8.780   1.835  1.00 27.34      G  N
ATOM   6599  CA  SER C   21      33.315   7.599   0.998  1.00 27.71      G  C
ATOM   6601  CB  SER C   21      34.538   6.817   1.461  1.00 28.12      G  C
ATOM   6604  OG  SER C   21      34.254   6.061   2.628  1.00 31.21      G  O
ATOM   6606  C   SER C   21      32.082   6.719   0.982  1.00 26.65      G  C
ATOM   6607  O   SER C   21      31.331   6.639   1.963  1.00 27.47      G  O
ATOM   6609  N   CYS C   22      31.865   6.092  -0.156  1.00 25.90      G  N
ATOM   6610  CA  CYS C   22      30.827   5.121  -0.365  1.00 27.13      G  C
ATOM   6612  CB  CYS C   22      29.760   5.702  -1.220  1.00 27.40      G  C
ATOM   6615  SG  CYS C   22      28.448   4.622  -1.826  1.00 27.41      G  S
ATOM   6617  C   CYS C   22      31.447   3.942  -1.067  1.00 28.61      G  C
ATOM   6618  O   CYS C   22      31.966   4.086  -2.194  1.00 30.76      G  O
ATOM   6620  N   LYS C   23      31.458   2.797  -0.389  1.00 28.60      G  N
ATOM   6621  CA  LYS C   23      31.993   1.570  -0.926  1.00 28.82      G  C
ATOM   6623  CB  LYS C   23      32.981   0.994   0.075  1.00 30.17      C  C
ATOM   6626  CG  LYS C   23      33.546  -0.365  -0.360  1.00 32.06      C  C
ATOM   6629  CD  LYS C   23      34.945  -0.585   0.210  1.00 34.96      C  C
ATOM   6632  CE  LYS C   23      35.226  -2.061   0.478  1.00 38.70      C  C
ATOM   6635  NZ  LYS C   23      34.822  -2.494   1.849  1.00 42.70      C  N
ATOM   6639  C   LYS C   23      30.900   0.536  -1.183  1.00 28.02      G  C
ATOM   6640  O   LYS C   23      30.109   0.256  -0.303  1.00 27.61      G  O
ATOM   6642  N   ALA C   24      30.829   0.009  -2.401  1.00 26.56      G  N
ATOM   6643  CA  ALA C   24      29.800  -0.964  -2.746  1.00 25.85      G  C
ATOM   6645  CB  ALA C   24      29.268  -0.759  -4.192  1.00 24.27      C  C
ATOM   6649  C   ALA C   24      30.347  -2.377  -2.570  1.00 25.33      G  C
ATOM   6650  O   ALA C   24      31.530  -2.607  -2.793  1.00 25.25      G  O
ATOM   6652  N   SER C   25      29.448  -3.280  -2.176  1.00 25.75      G  N
ATOM   6653  CA  SER C   25      29.668  -4.727  -1.938  1.00 25.78      G  C
ATOM   6655  CB  SER C   25      29.317  -5.053  -0.500  1.00 25.68      G  C
ATOM   6658  OG  SER C   25      30.441  -4.868   0.310  1.00 28.66      G  O
ATOM   6660  C   SER C   25      28.665  -5.465  -2.752  1.00 25.43      G  C
ATOM   6661  O   SER C   25      27.527  -5.011  -2.782  1.00 25.04      G  O
ATOM   6663  N   GLY C   26      29.023  -6.626  -3.326  1.00 25.96      G  N
ATOM   6664  CA  GLY C   26      28.144  -7.367  -4.264  1.00 25.86      G  C
ATOM   6667  C   GLY C   26      27.633  -6.506  -5.429  1.00 26.29      G  C
ATOM   6668  O   GLY C   26      26.497  -6.640  -5.884  1.00 26.27      G  O
ATOM   6670  N   TYR C   27      28.472  -5.604  -5.903  1.00 26.67      G  N
ATOM   6671  CA  TYR C   27      28.033  -4.542  -6.850  1.00 26.87      G  C
ATOM   6673  CB  TYR C   27      27.124  -3.529  -6.115  1.00 26.11      G  C
ATOM   6676  CG  TYR C   27      26.290  -2.617  -6.982  1.00 24.77      G  C
ATOM   6677  CD1 TYR C   27      25.321  -3.123  -7.828  1.00 25.78      G  C
ATOM   6679  CE1 TYR C   27      24.528  -2.281  -8.609  1.00 26.52      G  C
ATOM   6681  CZ  TYR C   27      24.715  -0.907  -8.532  1.00 25.34      G  C
ATOM   6682  OH  TYR C   27      23.931  -0.072  -9.302  1.00 30.88      G  O
ATOM   6684  CE2 TYR C   27      25.675  -0.386  -7.725  1.00 23.58      G  C
ATOM   6686  CD2 TYR C   27      26.453  -1.233  -6.933  1.00 24.38      G  C
ATOM   6688  C   TYR C   27      29.272  -3.847  -7.333  1.00 26.46      G  C
ATOM   6689  O   TYR C   27      29.926  -3.175  -6.548  1.00 28.38      G  O
ATOM   6691  N   SER C   28      29.643  -4.057  -8.584  1.00 26.71      G  N
ATOM   6692  CA  SER C   28      30.868  -3.498  -9.119  1.00 26.94      G  C
ATOM   6694  CB  SER C   28      31.441  -4.370 -10.254  1.00 27.55      G  C
ATOM   6697  OG  SER C   28      32.737  -3.884 -10.597  1.00 27.28      G  O
ATOM   6699  C   SER C   28      30.607  -2.139  -9.694  1.00 27.30      G  C
```

Figure 8 – CONT.

```
ATOM   6700  O    SER C  28      29.732  -1.971 -10.556  1.00 27.23      G  O
ATOM   6702  N    LEU C  29      31.387  -1.167  -9.252  1.00 28.24      G  N
ATOM   6703  CA   LEU C  29      31.287   0.183  -9.804  1.00 29.01      G  C
ATOM   6705  CB   LEU C  29      31.770   1.196  -8.793  1.00 29.04      C  C
ATOM   6708  CG   LEU C  29      31.094   1.247  -7.422  1.00 28.87      C  C
ATOM   6710  CD1  LEU C  29      31.566   2.499  -6.743  1.00 27.96      C  C
ATOM   6714  CD2  LEU C  29      29.605   1.237  -7.525  1.00 26.44      C  C
ATOM   6718  C    LEU C  29      32.078   0.336 -11.104  1.00 29.90      G  C
ATOM   6719  O    LEU C  29      32.230   1.450 -11.629  1.00 30.31      G  O
ATOM   6721  N    THR C  30      32.582  -0.782 -11.625  1.00 30.73      G  N
ATOM   6722  CA   THR C  30      33.092  -0.831 -12.988  1.00 31.31      G  C
ATOM   6724  CB   THR C  30      33.985  -2.052 -13.190  1.00 31.80      C  C
ATOM   6726  OG1  THR C  30      35.059  -1.990 -12.241  1.00 33.18      C  O
ATOM   6728  CG2  THR C  30      34.579  -2.099 -14.650  1.00 32.42      C  C
ATOM   6732  C    THR C  30      31.933  -0.880 -13.966  1.00 31.44      G  C
ATOM   6733  O    THR C  30      32.064  -0.449 -15.117  1.00 31.43      G  O
ATOM   6735  N    ASP C  31      30.795  -1.407 -13.513  1.00 31.07      G  N
ATOM   6736  CA   ASP C  31      29.631  -1.597 -14.366  1.00 31.16      G  C
ATOM   6738  CB   ASP C  31      29.201  -3.056 -14.296  1.00 31.79      G  C
ATOM   6741  CG   ASP C  31      30.292  -4.006 -14.735  1.00 32.33      G  C
ATOM   6742  OD1  ASP C  31      31.173  -3.584 -15.503  1.00 35.84      G  O
ATOM   6743  OD2  ASP C  31      30.256  -5.174 -14.318  1.00 33.39      G  O
ATOM   6744  C    ASP C  31      28.411  -0.746 -13.999  1.00 30.81      G  C
ATOM   6745  O    ASP C  31      27.397  -0.844 -14.667  1.00 30.99      G  O
ATOM   6747  N    ASN C  32      28.484   0.023 -12.914  1.00 29.63      G  N
ATOM   6748  CA   ASN C  32      27.324   0.727 -12.377  1.00 28.61      G  C
ATOM   6750  CB   ASN C  32      26.684  -0.026 -11.187  1.00 28.90      C  C
ATOM   6753  CG   ASN C  32      26.068  -1.365 -11.584  1.00 29.04      C  C
ATOM   6754  OD1  ASN C  32      24.997  -1.419 -12.171  1.00 33.06      C  O
ATOM   6755  ND2  ASN C  32      26.744  -2.449 -11.249  1.00 30.54      C  N
ATOM   6758  C    ASN C  32      27.746   2.125 -11.955  1.00 27.62      G  C
ATOM   6759  O    ASN C  32      28.924   2.395 -11.746  1.00 26.77      G  O
ATOM   6761  N    TRP C  33      26.771   3.012 -11.841  1.00 27.02      G  N
ATOM   6762  CA   TRP C  33      27.037   4.384 -11.482  1.00 27.33      G  C
ATOM   6764  CB   TRP C  33      26.232   5.293 -12.409  1.00 27.55      G  C
ATOM   6767  CG   TRP C  33      26.654   5.200 -13.835  1.00 30.35      G  C
ATOM   6768  CD1  TRP C  33      26.853   4.043 -14.596  1.00 33.03      G  C
ATOM   6770  NE1  TRP C  33      27.228   4.384 -15.875  1.00 31.47      G  N
ATOM   6772  CE2  TRP C  33      27.292   5.749 -15.968  1.00 33.34      G  C
ATOM   6773  CD2  TRP C  33      26.938   6.293 -14.696  1.00 31.27      G  C
ATOM   6774  CE3  TRP C  33      26.933   7.680 -14.526  1.00 27.96      G  C
ATOM   6776  CZ3  TRP C  33      27.302   8.483 -15.589  1.00 30.90      G  C
ATOM   6778  CH2  TRP C  33      27.648   7.925 -16.855  1.00 31.98      G  C
ATOM   6780  CZ2  TRP C  33      27.649   6.563 -17.058  1.00 33.09      G  C
ATOM   6782  C    TRP C  33      26.680   4.688 -10.013  1.00 26.76      G  C
ATOM   6783  O    TRP C  33      25.830   4.068  -9.436  1.00 25.95      G  O
ATOM   6785  N    ILE C  34      27.311   5.702  -9.443  1.00 27.56      G  N
ATOM   6786  CA   ILE C  34      26.981   6.192  -8.099  1.00 26.77      G  C
ATOM   6788  CB   ILE C  34      28.191   6.074  -7.172  1.00 27.10      G  C
ATOM   6790  CG1  ILE C  34      28.501   4.581  -6.934  1.00 27.00      G  C
ATOM   6793  CD1  ILE C  34      27.632   3.914  -5.933  1.00 24.42      G  C
ATOM   6797  CG2  ILE C  34      27.983   6.876  -5.843  1.00 24.82      G  C
ATOM   6801  C    ILE C  34      26.516   7.650  -8.171  1.00 27.08      G  C
ATOM   6802  O    ILE C  34      27.212   8.506  -8.720  1.00 26.82      G  O
ATOM   6804  N    GLY C  35      25.324   7.904  -7.637  1.00 27.28      G  N
ATOM   6805  CA   GLY C  35      24.838   9.239  -7.415  1.00 27.29      G  C
ATOM   6808  C    GLY C  35      25.000   9.653  -5.941  1.00 27.40      G  C
ATOM   6809  O    GLY C  35      25.124   8.796  -5.054  1.00 26.66      G  O
```

Figure 8 – CONT.

```
ATOM   6811  N    TRP C  36      24.981  10.973  -5.718  1.00 27.05       G  N
ATOM   6812  CA   TRP C  36      24.976  11.583  -4.414  1.00 27.40       G  C
ATOM   6814  CB   TRP C  36      26.262  12.358  -4.178  1.00 27.07       G  C
ATOM   6817  CG   TRP C  36      27.496  11.488  -4.028  1.00 28.27       G  C
ATOM   6818  CD1  TRP C  36      28.372  11.123  -5.011  1.00 26.37       G  C
ATOM   6820  NE1  TRP C  36      29.361  10.321  -4.497  1.00 26.22       G  N
ATOM   6822  CE2  TRP C  36      29.151  10.148  -3.157  1.00 26.64       G  C
ATOM   6823  CD2  TRP C  36      27.979  10.858  -2.820  1.00 29.45       G  C
ATOM   6824  CE3  TRP C  36      27.554  10.845  -1.503  1.00 25.66       G  C
ATOM   6826  CZ3  TRP C  36      28.301  10.131  -0.560  1.00 26.97       G  C
ATOM   6828  CH2  TRP C  36      29.442   9.452  -0.918  1.00 27.83       G  C
ATOM   6830  CZ2  TRP C  36      29.902   9.470  -2.213  1.00 29.02       G  C
ATOM   6832  C    TRP C  36      23.761  12.521  -4.234  1.00 27.39       G  C
ATOM   6833  O    TRP C  36      23.467  13.364  -5.080  1.00 27.06       G  O
ATOM   6835  N    VAL C  37      23.074  12.322  -3.112  1.00 26.89       G  N
ATOM   6836  CA   VAL C  37      21.905  13.062  -2.721  1.00 26.74       G  C
ATOM   6838  CB   VAL C  37      20.693  12.170  -2.656  1.00 27.37       G  C
ATOM   6840  CG1  VAL C  37      19.460  12.993  -2.207  1.00 26.09       G  C
ATOM   6844  CG2  VAL C  37      20.461  11.516  -4.017  1.00 25.82       G  C
ATOM   6848  C    VAL C  37      22.114  13.695  -1.348  1.00 27.03       G  C
ATOM   6849  O    VAL C  37      22.555  13.038  -0.405  1.00 26.54       G  O
ATOM   6851  N    ARG C  38      21.843  14.999  -1.286  1.00 27.29       G  N
ATOM   6852  CA   ARG C  38      21.965  15.775  -0.070  1.00 28.10       G  C
ATOM   6854  CB   ARG C  38      22.577  17.151  -0.380  1.00 27.96       G  C
ATOM   6857  CG   ARG C  38      22.672  18.081   0.834  1.00 28.38       G  C
ATOM   6860  CD   ARG C  38      23.424  19.373   0.527  1.00 28.65       G  C
ATOM   6863  NE   ARG C  38      22.587  20.419  -0.061  1.00 30.40       G  N
ATOM   6865  CZ   ARG C  38      22.992  21.660  -0.367  1.00 32.08       G  C
ATOM   6866  NH1  ARG C  38      24.249  22.032  -0.197  1.00 34.78       G  N
ATOM   6869  NH2  ARG C  38      22.141  22.528  -0.897  1.00 33.81       G  N
ATOM   6872  C    ARG C  38      20.581  15.913   0.549  1.00 28.54       G  C
ATOM   6873  O    ARG C  38      19.582  16.012  -0.178  1.00 28.27       G  O
ATOM   6875  N    GLN C  39      20.533  15.870   1.884  1.00 28.37       G  N
ATOM   6876  CA   GLN C  39      19.303  16.139   2.637  1.00 28.88       G  C
ATOM   6878  CB   GLN C  39      18.567  14.858   3.011  1.00 28.96       G  C
ATOM   6881  CG   GLN C  39      17.205  15.116   3.703  1.00 28.56       G  C
ATOM   6884  CD   GLN C  39      16.390  13.870   3.900  1.00 27.18       G  C
ATOM   6885  OE1  GLN C  39      16.915  12.840   4.313  1.00 28.56       G  O
ATOM   6886  NE2  GLN C  39      15.099  13.943   3.588  1.00 26.26       G  N
ATOM   6889  C    GLN C  39      19.632  16.939   3.896  1.00 29.38       G  C
ATOM   6890  O    GLN C  39      20.141  16.412   4.885  1.00 28.48       G  O
ATOM   6892  N    LYS C  40      19.384  18.230   3.831  1.00 30.59       G  N
ATOM   6893  CA   LYS C  40      19.669  19.081   4.955  1.00 31.84       G  C
ATOM   6895  CB   LYS C  40      19.718  20.538   4.498  1.00 31.85       C  C
ATOM   6898  CG   LYS C  40      20.888  20.819   3.599  1.00 33.26       C  C
ATOM   6901  CD   LYS C  40      20.681  22.008   2.684  1.00 36.81       C  C
ATOM   6904  CE   LYS C  40      21.096  23.305   3.282  1.00 37.69       C  C
ATOM   6907  NZ   LYS C  40      21.470  24.276   2.219  1.00 41.50       C  N
ATOM   6911  C    LYS C  40      18.587  18.815   6.025  1.00 32.48       G  C
ATOM   6912  O    LYS C  40      17.500  18.351   5.712  1.00 31.60       G  O
ATOM   6914  N    PRO C  41      18.889  19.101   7.299  1.00 33.77       G  N
ATOM   6915  CA   PRO C  41      17.987  18.654   8.365  1.00 34.04       G  C
ATOM   6917  CB   PRO C  41      18.661  19.151   9.656  1.00 34.24       G  C
ATOM   6920  CG   PRO C  41      19.985  19.620   9.256  1.00 35.15       G  C
ATOM   6923  CD   PRO C  41      19.924  20.001   7.807  1.00 33.43       G  C
ATOM   6926  C    PRO C  41      16.610  19.238   8.218  1.00 33.83       G  C
ATOM   6927  O    PRO C  41      16.449  20.433   7.970  1.00 33.25       G  O
ATOM   6928  N    GLY C  42      15.628  18.360   8.315  1.00 34.90       G  N
```

Figure 8 – CONT.

```
ATOM   6929  CA   GLY C  42      14.234  18.717   8.095  1.00 35.20       G  C
ATOM   6932  C    GLY C  42      13.822  19.029   6.670  1.00 35.99       G  C
ATOM   6933  O    GLY C  42      12.672  19.448   6.460  1.00 36.92       G  O
ATOM   6935  N    LYS C  43      14.703  18.847   5.674  1.00 35.09       G  N
ATOM   6936  CA   LYS C  43      14.332  19.221   4.314  1.00 35.02       G  C
ATOM   6938  CB   LYS C  43      15.334  20.224   3.745  1.00 36.06       G  C
ATOM   6941  CG   LYS C  43      15.396  21.598   4.451  1.00 39.16       G  C
ATOM   6944  CD   LYS C  43      14.036  22.302   4.611  1.00 44.48       G  C
ATOM   6947  CE   LYS C  43      13.217  22.443   3.285  1.00 47.97       G  C
ATOM   6950  NZ   LYS C  43      12.220  23.583   3.332  1.00 51.00       G  N
ATOM   6954  C    LYS C  43      14.220  18.020   3.375  1.00 33.79       G  C
ATOM   6955  O    LYS C  43      14.395  16.869   3.770  1.00 32.32       G  O
ATOM   6957  N    GLY C  44      13.926  18.316   2.117  1.00 33.29       G  N
ATOM   6958  CA   GLY C  44      13.862  17.308   1.078  1.00 33.13       G  C
ATOM   6961  C    GLY C  44      15.193  16.806   0.502  1.00 32.15       G  C
ATOM   6962  O    GLY C  44      16.277  17.227   0.892  1.00 31.49       G  O
ATOM   6964  N    LEU C  45      15.071  15.913  -0.476  1.00 31.99       G  N
ATOM   6965  CA   LEU C  45      16.222  15.319  -1.161  1.00 31.01       G  C
ATOM   6967  CB   LEU C  45      15.842  13.958  -1.712  1.00 31.18       G  C
ATOM   6970  CG   LEU C  45      15.210  12.979  -0.746  1.00 30.21       G  C
ATOM   6972  CD1  LEU C  45      14.672  11.756  -1.528  1.00 29.57       G  C
ATOM   6976  CD2  LEU C  45      16.196  12.592   0.325  1.00 26.90       G  C
ATOM   6980  C    LEU C  45      16.672  16.187  -2.309  1.00 30.56       G  C
ATOM   6981  O    LEU C  45      15.847  16.636  -3.104  1.00 29.91       G  O
ATOM   6983  N    GLU C  46      17.987  16.388  -2.419  1.00 29.82       G  N
ATOM   6984  CA   GLU C  46      18.528  17.115  -3.520  1.00 29.71       G  C
ATOM   6986  CB   GLU C  46      19.178  18.400  -3.042  1.00 29.77       G  C
ATOM   6989  CG   GLU C  46      18.317  19.338  -2.252  1.00 30.60       G  C
ATOM   6992  CD   GLU C  46      19.182  20.295  -1.519  1.00 31.95       G  C
ATOM   6993  OE1  GLU C  46      19.588  19.953  -0.379  1.00 28.00       G  O
ATOM   6994  OE2  GLU C  46      19.530  21.358  -2.114  1.00 36.27       G  O
ATOM   6995  C    GLU C  46      19.575  16.278  -4.262  1.00 29.67       G  C
ATOM   6996  O    GLU C  46      20.464  15.679  -3.651  1.00 29.91       G  O
ATOM   6998  N    TRP C  47      19.487  16.267  -5.585  1.00 29.61       G  N
ATOM   6999  CA   TRP C  47      20.426  15.525  -6.419  1.00 29.06       G  C
ATOM   7001  CB   TRP C  47      19.815  15.284  -7.785  1.00 29.66       G  C
ATOM   7004  CG   TRP C  47      20.670  14.502  -8.740  1.00 28.84       G  C
ATOM   7005  CD1  TRP C  47      21.303  14.978  -9.830  1.00 27.40       G  C
ATOM   7007  NE1  TRP C  47      21.963  13.953 -10.488  1.00 26.99       G  N
ATOM   7009  CE2  TRP C  47      21.739  12.784  -9.810  1.00 28.64       G  C
ATOM   7010  CD2  TRP C  47      20.932  13.093  -8.697  1.00 27.66       G  C
ATOM   7011  CE3  TRP C  47      20.568  12.072  -7.825  1.00 28.38       G  C
ATOM   7013  CZ3  TRP C  47      21.000  10.802  -8.069  1.00 29.60       G  C
ATOM   7015  CH2  TRP C  47      21.808  10.508  -9.195  1.00 29.42       G  C
ATOM   7017  CZ2  TRP C  47      22.198  11.485 -10.065  1.00 28.00       G  C
ATOM   7019  C    TRP C  47      21.677  16.341  -6.573  1.00 28.38       G  C
ATOM   7020  O    TRP C  47      21.613  17.514  -6.935  1.00 27.70       G  O
ATOM   7022  N    MET C  48      22.824  15.747  -6.267  1.00 28.02       G  N
ATOM   7023  CA   MET C  48      24.064  16.488  -6.391  1.00 28.83       G  C
ATOM   7025  CB   MET C  48      25.022  16.148  -5.258  1.00 28.89       G  C
ATOM   7028  CG   MET C  48      24.415  16.469  -3.899  1.00 27.73       G  C
ATOM   7031  SD   MET C  48      25.480  16.059  -2.594  1.00 24.08       G  S
ATOM   7032  CE   MET C  48      26.791  17.266  -2.802  1.00 21.60       G  C
ATOM   7036  C    MET C  48      24.744  16.226  -7.708  1.00 29.23       G  C
ATOM   7037  O    MET C  48      25.331  17.127  -8.263  1.00 30.53       G  O
ATOM   7039  N    GLY C  49      24.690  14.986  -8.173  1.00 29.12       G  N
ATOM   7040  CA   GLY C  49      25.426  14.576  -9.339  1.00 29.37       G  C
ATOM   7043  C    GLY C  49      25.726  13.101  -9.328  1.00 29.31       G  C
```

Figure 8 – CONT.

```
ATOM   7044  O    GLY C  49      25.259  12.372  -8.444  1.00 29.58     G  O
ATOM   7046  N    ILE C  50      26.556  12.668 -10.273  1.00 29.20     G  N
ATOM   7047  CA   ILE C  50      26.721  11.257 -10.540  1.00 29.32     G  C
ATOM   7049  CB   ILE C  50      25.576  10.748 -11.468  1.00 29.89     G  C
ATOM   7051  CG1  ILE C  50      25.351   9.251 -11.288  1.00 29.01     G  C
ATOM   7054  CD1  ILE C  50      24.255   8.675 -12.141  1.00 28.52     G  C
ATOM   7058  CG2  ILE C  50      25.883  11.060 -12.945  1.00 31.49     G  C
ATOM   7062  C    ILE C  50      28.091  10.979 -11.148  1.00 29.88     G  C
ATOM   7063  O    ILE C  50      28.696  11.859 -11.763  1.00 30.79     G  O
ATOM   7065  N    ILE C  51      28.591   9.755 -10.956  1.00 28.88     G  N
ATOM   7066  CA   ILE C  51      29.908   9.358 -11.433  1.00 27.64     G  C
ATOM   7068  CB   ILE C  51      31.064   9.580 -10.392  1.00 27.42     C  C
ATOM   7070  CG1  ILE C  51      32.443   9.379 -11.069  1.00 26.87     C  C
ATOM   7073  CD1  ILE C  51      33.635   9.940 -10.361  1.00 23.47     C  C
ATOM   7077  CG2  ILE C  51      30.908   8.636  -9.160  1.00 25.39     C  C
ATOM   7081  C    ILE C  51      29.872   7.888 -11.892  1.00 28.35     G  C
ATOM   7082  O    ILE C  51      29.209   7.015 -11.276  1.00 27.27     G  O
ATOM   7084  N    TYR C  52      30.551   7.635 -13.007  1.00 29.14     G  N
ATOM   7085  CA   TYR C  52      30.740   6.281 -13.519  1.00 30.05     G  C
ATOM   7087  CB   TYR C  52      30.443   6.198 -15.013  1.00 30.54     G  C
ATOM   7090  CG   TYR C  52      30.648   4.782 -15.578  1.00 31.98     G  C
ATOM   7091  CD1  TYR C  52      30.424   3.650 -14.779  1.00 32.10     G  C
ATOM   7093  CE1  TYR C  52      30.621   2.401 -15.263  1.00 32.51     G  C
ATOM   7095  CZ   TYR C  52      31.061   2.229 -16.551  1.00 34.48     G  C
ATOM   7096  OH   TYR C  52      31.251   0.955 -16.999  1.00 34.52     G  O
ATOM   7098  CE2  TYR C  52      31.292   3.311 -17.383  1.00 32.26     G  C
ATOM   7100  CD2  TYR C  52      31.089   4.584 -16.888  1.00 32.98     G  C
ATOM   7102  C    TYR C  52      32.187   5.920 -13.263  1.00 29.81     G  C
ATOM   7103  O    TYR C  52      33.055   6.439 -13.941  1.00 29.22     G  O
ATOM   7105  N    PRO C  52A     32.454   5.084 -12.236  1.00 30.18     G  N
ATOM   7106  CA   PRO C  52A     33.846   4.862 -11.889  1.00 30.06     G  C
ATOM   7108  CB   PRO C  52A     33.755   4.121 -10.547  1.00 29.78     G  C
ATOM   7111  CG   PRO C  52A     32.423   4.544 -10.003  1.00 30.55     G  C
ATOM   7114  CD   PRO C  52A     31.551   4.575 -11.181  1.00 30.25     G  C
ATOM   7117  C    PRO C  52A     34.600   4.047 -12.944  1.00 30.81     G  C
ATOM   7118  O    PRO C  52A     35.811   3.974 -12.901  1.00 30.53     G  O
ATOM   7119  N    GLY C  53      33.870   3.421 -13.856  1.00 32.00     G  N
ATOM   7120  CA   GLY C  53      34.469   2.681 -14.930  1.00 33.17     G  C
ATOM   7123  C    GLY C  53      35.319   3.588 -15.790  1.00 34.06     G  C
ATOM   7124  O    GLY C  53      36.364   3.182 -16.230  1.00 34.62     G  O
ATOM   7126  N    ASP C  54      34.874   4.810 -16.048  1.00 34.85     G  N
ATOM   7127  CA   ASP C  54      35.684   5.691 -16.875  1.00 35.89     G  C
ATOM   7129  CB   ASP C  54      35.167   5.643 -18.314  1.00 35.62     G  C
ATOM   7132  CG   ASP C  54      33.781   6.181 -18.440  1.00 37.04     G  C
ATOM   7133  OD1  ASP C  54      33.133   5.893 -19.465  1.00 40.07     G  O
ATOM   7134  OD2  ASP C  54      33.335   6.897 -17.511  1.00 36.97     G  O
ATOM   7135  C    ASP C  54      35.767   7.108 -16.333  1.00 36.67     G  C
ATOM   7136  O    ASP C  54      36.302   7.987 -16.997  1.00 36.83     G  O
ATOM   7138  N    SER C  55      35.265   7.314 -15.111  1.00 37.18     G  N
ATOM   7139  CA   SER C  55      35.390   8.586 -14.389  1.00 37.61     G  C
ATOM   7141  CB   SER C  55      36.838   9.089 -14.361  1.00 37.92     G  C
ATOM   7144  OG   SER C  55      37.681   8.161 -13.695  1.00 39.54     G  O
ATOM   7146  C    SER C  55      34.492   9.671 -14.923  1.00 37.43     G  C
ATOM   7147  O    SER C  55      34.662  10.840 -14.574  1.00 37.51     G  O
ATOM   7149  N    ASP C  56      33.515   9.290 -15.731  1.00 37.34     G  N
ATOM   7150  CA   ASP C  56      32.591  10.247 -16.317  1.00 37.85     G  C
ATOM   7152  CB   ASP C  56      31.782   9.524 -17.399  1.00 38.54     G  C
ATOM   7155  CG   ASP C  56      30.835  10.437 -18.189  1.00 41.30     G  C
```

Figure 8 – CONT.

```
ATOM   7156  OD1 ASP C  56      30.756  11.668 -17.958  1.00 47.25      G  O
ATOM   7157  OD2 ASP C  56      30.145   9.888 -19.067  1.00 43.59      G  O
ATOM   7158  C   ASP C  56      31.696  10.780 -15.184  1.00 38.24      G  C
ATOM   7159  O   ASP C  56      30.966  10.014 -14.515  1.00 37.62      G  O
ATOM   7161  N   THR C  57      31.781  12.075 -14.928  1.00 37.96      G  N
ATOM   7162  CA  THR C  57      30.997  12.668 -13.857  1.00 38.58      G  C
ATOM   7164  CB  THR C  57      31.871  13.120 -12.633  1.00 38.46      C  C
ATOM   7166  OG1 THR C  57      32.107  14.517 -12.706  1.00 41.37      C  O
ATOM   7168  CG2 THR C  57      33.205  12.405 -12.577  1.00 36.81      C  C
ATOM   7172  C   THR C  57      30.133  13.807 -14.415  1.00 38.21      G  C
ATOM   7173  O   THR C  57      30.597  14.580 -15.252  1.00 38.13      G  O
ATOM   7175  N   ARG C  58      28.864  13.864 -13.980  1.00 37.45      G  N
ATOM   7176  CA  ARG C  58      27.945  14.935 -14.374  1.00 36.90      G  C
ATOM   7178  CB  ARG C  58      26.839  14.416 -15.311  1.00 36.54      G  C
ATOM   7187  C   ARG C  58      27.324  15.539 -13.126  1.00 36.64      G  C
ATOM   7188  O   ARG C  58      26.609  14.869 -12.385  1.00 35.96      G  O
ATOM   7190  N   TYR C  59      27.564  16.826 -12.916  1.00 36.55      G  N
ATOM   7191  CA  TYR C  59      27.021  17.497 -11.740  1.00 36.20      G  C
ATOM   7193  CB  TYR C  59      27.973  18.576 -11.269  1.00 35.46      G  C
ATOM   7196  CG  TYR C  59      29.292  18.080 -10.790  1.00 33.49      G  C
ATOM   7197  CD1 TYR C  59      30.327  17.874 -11.673  1.00 32.28      G  C
ATOM   7199  CE1 TYR C  59      31.553  17.410 -11.230  1.00 31.99      G  C
ATOM   7201  CZ  TYR C  59      31.754  17.162  -9.888  1.00 30.16      G  C
ATOM   7202  OH  TYR C  59      32.994  16.743  -9.464  1.00 28.30      G  O
ATOM   7204  CE2 TYR C  59      30.732  17.359  -8.991  1.00 30.40      G  C
ATOM   7206  CD2 TYR C  59      29.513  17.815  -9.438  1.00 31.48      G  C
ATOM   7208  C   TYR C  59      25.693  18.133 -12.022  1.00 36.80      G  C
ATOM   7209  O   TYR C  59      25.437  18.578 -13.134  1.00 38.18      G  O
ATOM   7211  N   SER C  60      24.845  18.208 -11.008  1.00 37.42      G  N
ATOM   7212  CA  SER C  60      23.745  19.173 -11.039  1.00 38.28      G  C
ATOM   7214  CB  SER C  60      22.813  18.998  -9.854  1.00 38.33      G  C
ATOM   7217  OG  SER C  60      21.961  20.116  -9.752  1.00 40.21      G  O
ATOM   7219  C   SER C  60      24.351  20.575 -11.045  1.00 38.32      G  C
ATOM   7220  O   SER C  60      25.361  20.801 -10.410  1.00 38.00      G  O
ATOM   7222  N   PRO C  61      23.768  21.507 -11.809  1.00 39.82      G  N
ATOM   7223  CA  PRO C  61      24.273  22.886 -11.863  1.00 40.50      G  C
ATOM   7225  CB  PRO C  61      23.235  23.609 -12.726  1.00 40.79      G  C
ATOM   7228  CG  PRO C  61      22.580  22.521 -13.518  1.00 41.43      G  C
ATOM   7231  CD  PRO C  61      22.568  21.327 -12.645  1.00 39.88      G  C
ATOM   7234  C   PRO C  61      24.338  23.575 -10.507  1.00 40.88      G  C
ATOM   7235  O   PRO C  61      25.206  24.392 -10.308  1.00 41.63      G  O
ATOM   7236  N   SER C  62      23.420  23.261  -9.592  1.00 41.24      G  N
ATOM   7237  CA  SER C  62      23.451  23.841  -8.240  1.00 41.47      G  C
ATOM   7239  CB  SER C  62      22.246  23.398  -7.423  1.00 41.65      G  C
ATOM   7242  OG  SER C  62      21.123  23.159  -8.250  1.00 43.12      G  O
ATOM   7244  C   SER C  62      24.695  23.435  -7.459  1.00 41.42      G  C
ATOM   7245  O   SER C  62      25.058  24.110  -6.485  1.00 41.56      G  O
ATOM   7247  N   PHE C  63      25.346  22.340  -7.876  1.00 40.56      G  N
ATOM   7248  CA  PHE C  63      26.514  21.826  -7.154  1.00 39.80      G  C
ATOM   7250  CB  PHE C  63      26.242  20.407  -6.717  1.00 39.54      G  C
ATOM   7253  CG  PHE C  63      25.154  20.316  -5.730  1.00 38.29      G  C
ATOM   7254  CD1 PHE C  63      25.423  20.451  -4.376  1.00 36.44      G  C
ATOM   7256  CE1 PHE C  63      24.431  20.407  -3.470  1.00 34.23      G  C
ATOM   7258  CZ  PHE C  63      23.125  20.233  -3.876  1.00 35.17      G  C
ATOM   7260  CE2 PHE C  63      22.827  20.124  -5.205  1.00 36.77      G  C
ATOM   7262  CD2 PHE C  63      23.848  20.179  -6.139  1.00 37.83      G  C
ATOM   7264  C   PHE C  63      27.811  21.903  -7.907  1.00 39.75      G  C
ATOM   7265  O   PHE C  63      28.869  21.690  -7.330  1.00 38.80      G  O
```

Figure 8 – CONT.

```
ATOM   7267  N    GLN C  64      27.717  22.227  -9.196  1.00 40.90           G  N
ATOM   7268  CA   GLN C  64      28.880  22.389 -10.068  1.00 41.14           G  C
ATOM   7270  CB   GLN C  64      28.431  22.854 -11.466  1.00 41.68           C  C
ATOM   7273  CG   GLN C  64      29.558  23.025 -12.502  1.00 43.10           C  C
ATOM   7276  CD   GLN C  64      30.083  21.695 -13.058  1.00 46.85           C  C
ATOM   7277  OE1  GLN C  64      31.261  21.330 -12.843  1.00 50.46           C  O
ATOM   7278  NE2  GLN C  64      29.226  20.972 -13.783  1.00 44.04           C  N
ATOM   7281  C    GLN C  64      29.804  23.404  -9.430  1.00 40.75           G  C
ATOM   7282  O    GLN C  64      29.383  24.508  -9.106  1.00 41.26           G  O
ATOM   7284  N    GLY C  65      31.048  23.005  -9.202  1.00 40.26           G  N
ATOM   7285  CA   GLY C  65      32.016  23.855  -8.569  1.00 39.83           G  C
ATOM   7288  C    GLY C  65      31.978  23.964  -7.054  1.00 39.73           G  C
ATOM   7289  O    GLY C  65      32.894  24.525  -6.473  1.00 39.98           G  O
ATOM   7291  N    GLN C  66      30.936  23.473  -6.400  1.00 39.75           G  N
ATOM   7292  CA   GLN C  66      30.863  23.528  -4.926  1.00 40.23           G  C
ATOM   7294  CB   GLN C  66      29.418  23.722  -4.463  1.00 40.68           G  C
ATOM   7297  CG   GLN C  66      28.743  24.971  -5.026  1.00 45.02           G  C
ATOM   7300  CD   GLN C  66      29.417  26.224  -4.517  1.00 48.81           G  C
ATOM   7301  OE1  GLN C  66      29.625  26.361  -3.314  1.00 52.74           G  O
ATOM   7302  NE2  GLN C  66      29.809  27.118  -5.424  1.00 50.81           G  N
ATOM   7305  C    GLN C  66      31.428  22.255  -4.270  1.00 39.30           G  C
ATOM   7306  O    GLN C  66      31.732  22.245  -3.083  1.00 41.28           G  O
ATOM   7308  N    VAL C  67      31.577  21.194  -5.044  1.00 37.53           G  N
ATOM   7309  CA   VAL C  67      31.927  19.899  -4.503  1.00 36.13           G  C
ATOM   7311  CB   VAL C  67      30.655  19.186  -3.961  1.00 35.93           G  C
ATOM   7313  CG1  VAL C  67      29.765  18.720  -5.103  1.00 34.00           G  C
ATOM   7317  CG2  VAL C  67      31.043  18.047  -3.024  1.00 36.38           G  C
ATOM   7321  C    VAL C  67      32.577  19.096  -5.610  1.00 35.08           G  C
ATOM   7322  O    VAL C  67      32.370  19.387  -6.781  1.00 34.93           G  O
ATOM   7324  N    THR C  68      33.398  18.116  -5.248  1.00 33.58           G  N
ATOM   7325  CA   THR C  68      33.989  17.240  -6.239  1.00 31.97           G  C
ATOM   7327  CB   THR C  68      35.479  17.330  -6.241  1.00 31.77           G  C
ATOM   7329  OG1  THR C  68      35.851  18.658  -6.600  1.00 31.06           G  O
ATOM   7331  CG2  THR C  68      36.079  16.363  -7.261  1.00 32.91           G  C
ATOM   7335  C    THR C  68      33.556  15.826  -5.982  1.00 31.35           G  C
ATOM   7336  O    THR C  68      33.733  15.308  -4.878  1.00 31.36           G  O
ATOM   7338  N    ILE C  69      32.932  15.223  -6.983  1.00 30.28           G  N
ATOM   7339  CA   ILE C  69      32.627  13.808  -6.937  1.00 29.58           G  C
ATOM   7341  CB   ILE C  69      31.344  13.516  -7.639  1.00 28.99           C  C
ATOM   7343  CG1  ILE C  69      30.169  14.160  -6.906  1.00 28.50           C  C
ATOM   7346  CD1  ILE C  69      28.957  14.308  -7.808  1.00 28.18           C  C
ATOM   7350  CG2  ILE C  69      31.133  12.028  -7.752  1.00 27.59           C  C
ATOM   7354  C    ILE C  69      33.764  13.022  -7.592  1.00 29.96           G  C
ATOM   7355  O    ILE C  69      34.265  13.410  -8.648  1.00 29.95           G  O
ATOM   7357  N    SER C  70      34.207  11.947  -6.957  1.00 29.86           G  N
ATOM   7358  CA   SER C  70      35.340  11.196  -7.497  1.00 30.38           G  C
ATOM   7360  CB   SER C  70      36.690  11.800  -7.078  1.00 30.64           G  C
ATOM   7363  OG   SER C  70      37.068  11.512  -5.747  1.00 34.10           G  O
ATOM   7365  C    SER C  70      35.188   9.718  -7.165  1.00 30.39           G  C
ATOM   7366  O    SER C  70      34.205   9.305  -6.526  1.00 29.50           G  O
ATOM   7368  N    ALA C  71      36.068   8.901  -7.721  1.00 30.03           G  N
ATOM   7369  CA   ALA C  71      35.960   7.455  -7.508  1.00 30.17           G  C
ATOM   7371  CB   ALA C  71      34.842   6.849  -8.337  1.00 28.80           G  C
ATOM   7375  C    ALA C  71      37.278   6.787  -7.806  1.00 30.43           G  C
ATOM   7376  O    ALA C  71      38.120   7.368  -8.472  1.00 30.30           G  O
ATOM   7378  N    ASP C  72      37.422   5.570  -7.282  1.00 31.02           G  N
ATOM   7379  CA   ASP C  72      38.566   4.720  -7.499  1.00 31.53           G  C
ATOM   7381  CB   ASP C  72      39.521   4.807  -6.286  1.00 32.02           G  C
```

Figure 8 – CONT.

```
ATOM   7384  CG  ASP C  72      40.684   3.799  -6.341  1.00 33.55      G  C
ATOM   7385  OD1 ASP C  72      41.612   3.950  -5.520  1.00 34.26      G  O
ATOM   7386  OD2 ASP C  72      40.665   2.841  -7.149  1.00 34.06      G  O
ATOM   7387  C   ASP C  72      38.018   3.311  -7.700  1.00 31.67      G  C
ATOM   7388  O   ASP C  72      37.773   2.615  -6.733  1.00 31.91      G  O
ATOM   7390  N   LYS C  73      37.796   2.941  -8.965  1.00 31.45      G  N
ATOM   7391  CA  LYS C  73      37.481   1.574  -9.429  1.00 31.52      G  C
ATOM   7393  CB  LYS C  73      38.103   1.333 -10.805  1.00 33.18      C  C
ATOM   7396  CG  LYS C  73      37.305   1.665 -11.932  1.00 36.77      C  C
ATOM   7399  CD  LYS C  73      37.897   1.022 -13.171  1.00 39.36      C  C
ATOM   7402  CE  LYS C  73      39.314   1.504 -13.498  1.00 40.65      C  C
ATOM   7405  NZ  LYS C  73      39.555   1.228 -14.921  1.00 41.04      C  N
ATOM   7409  C   LYS C  73      38.148   0.473  -8.706  1.00 29.76      G  C
ATOM   7410  O   LYS C  73      37.563  -0.584  -8.516  1.00 29.75      G  O
ATOM   7412  N   SER C  74      39.435   0.655  -8.452  1.00 28.45      G  N
ATOM   7413  CA  SER C  74      40.242  -0.472  -7.969  1.00 28.32      G  C
ATOM   7415  CB  SER C  74      41.737  -0.141  -8.023  1.00 27.79      G  C
ATOM   7418  OG  SER C  74      42.110   0.792  -7.042  1.00 29.51      G  O
ATOM   7420  C   SER C  74      39.786  -0.990  -6.585  1.00 28.16      G  C
ATOM   7421  O   SER C  74      39.973  -2.175  -6.286  1.00 27.49      G  O
ATOM   7423  N   ILE C  75      39.162  -0.114  -5.783  1.00 27.07      G  N
ATOM   7424  CA  ILE C  75      38.647  -0.466  -4.441  1.00 26.79      G  C
ATOM   7426  CB  ILE C  75      39.446   0.266  -3.348  1.00 27.00      C  C
ATOM   7428  CG1 ILE C  75      39.265   1.815  -3.443  1.00 27.33      C  C
ATOM   7431  CD1 ILE C  75      39.914   2.617  -2.305  1.00 29.89      C  C
ATOM   7435  CG2 ILE C  75      40.894  -0.071  -3.543  1.00 26.93      C  C
ATOM   7439  C   ILE C  75      37.148  -0.206  -4.329  1.00 26.35      G  C
ATOM   7440  O   ILE C  75      36.617   0.001  -3.226  1.00 27.72      G  O
ATOM   7442  N   ASN C  76      36.475  -0.190  -5.491  1.00 25.84      G  N
ATOM   7443  CA  ASN C  76      35.018  -0.062  -5.629  1.00 24.71      G  C
ATOM   7445  CB  ASN C  76      34.355  -1.425  -5.442  1.00 24.53      G  C
ATOM   7448  CG  ASN C  76      33.101  -1.579  -6.241  1.00 22.36      G  C
ATOM   7449  OD1 ASN C  76      33.144  -1.488  -7.455  1.00 22.64      G  O
ATOM   7450  ND2 ASN C  76      31.956  -1.825  -5.573  1.00 21.83      G  N
ATOM   7453  C   ASN C  76      34.376   1.005  -4.724  1.00 26.07      G  C
ATOM   7454  O   ASN C  76      33.349   0.757  -4.094  1.00 26.38      G  O
ATOM   7456  N   THR C  77      34.990   2.198  -4.717  1.00 26.43      G  N
ATOM   7457  CA  THR C  77      34.641   3.284  -3.813  1.00 26.51      G  C
ATOM   7459  CB  THR C  77      35.737   3.430  -2.721  1.00 26.37      G  C
ATOM   7461  OG1 THR C  77      35.923   2.161  -2.086  1.00 26.05      G  O
ATOM   7463  CG2 THR C  77      35.371   4.479  -1.656  1.00 25.39      G  C
ATOM   7467  C   THR C  77      34.464   4.611  -4.584  1.00 26.41      G  C
ATOM   7468  O   THR C  77      35.264   4.936  -5.441  1.00 26.59      G  O
ATOM   7470  N   ALA C  78      33.366   5.313  -4.308  1.00 26.47      G  N
ATOM   7471  CA  ALA C  78      33.129   6.675  -4.768  1.00 26.27      G  C
ATOM   7473  CB  ALA C  78      31.744   6.806  -5.408  1.00 25.34      G  C
ATOM   7477  C   ALA C  78      33.264   7.640  -3.589  1.00 26.70      G  C
ATOM   7478  O   ALA C  78      33.140   7.257  -2.429  1.00 26.69      G  O
ATOM   7480  N   TYR C  79      33.528   8.903  -3.897  1.00 27.43      G  N
ATOM   7481  CA  TYR C  79      33.786   9.897  -2.894  1.00 26.97      G  C
ATOM   7483  CB  TYR C  79      35.267  10.223  -2.818  1.00 27.10      C  C
ATOM   7486  CG  TYR C  79      36.178   9.046  -2.585  1.00 28.15      C  C
ATOM   7487  CD1 TYR C  79      36.463   8.587  -1.296  1.00 28.56      C  C
ATOM   7489  CE1 TYR C  79      37.356   7.483  -1.096  1.00 29.16      C  C
ATOM   7491  CZ  TYR C  79      37.948   6.869  -2.204  1.00 29.37      C  C
ATOM   7492  OH  TYR C  79      38.830   5.795  -2.091  1.00 29.80      C  O
ATOM   7494  CE2 TYR C  79      37.670   7.335  -3.469  1.00 29.24      C  C
ATOM   7496  CD2 TYR C  79      36.815   8.427  -3.656  1.00 30.10      C  C
```

Figure 8 – CONT.

```
ATOM   7498  C    TYR C   79      33.058  11.186  -3.207  1.00 27.48      G  C
ATOM   7499  O    TYR C   79      32.735  11.488  -4.378  1.00 27.98      G  O
ATOM   7501  N    LEU C   80      32.826  11.948  -2.146  1.00 26.06      G  N
ATOM   7502  CA   LEU C   80      32.368  13.291  -2.244  1.00 26.26      G  C
ATOM   7504  CB   LEU C   80      30.995  13.369  -1.597  1.00 26.73      G  C
ATOM   7507  CG   LEU C   80      30.001  14.406  -2.010  1.00 26.61      G  C
ATOM   7509  CD1  LEU C   80      29.730  14.283  -3.524  1.00 29.48      G  C
ATOM   7513  CD2  LEU C   80      28.743  14.203  -1.161  1.00 21.40      G  C
ATOM   7517  C    LEU C   80      33.399  14.122  -1.501  1.00 26.06      G  C
ATOM   7518  O    LEU C   80      33.868  13.715  -0.431  1.00 26.00      G  O
ATOM   7520  N    GLN C   81      33.767  15.266  -2.067  1.00 25.75      G  N
ATOM   7521  CA   GLN C   81      34.901  16.006  -1.586  1.00 27.06      G  C
ATOM   7523  CB   GLN C   81      36.077  15.693  -2.501  1.00 28.72      G  C
ATOM   7526  CG   GLN C   81      37.391  16.249  -2.118  1.00 32.69      G  C
ATOM   7529  CD   GLN C   81      38.581  15.567  -2.842  1.00 41.81      G  C
ATOM   7530  OE1  GLN C   81      39.744  15.942  -2.605  1.00 45.73      G  O
ATOM   7531  NE2  GLN C   81      38.299  14.563  -3.721  1.00 43.01      G  N
ATOM   7534  C    GLN C   81      34.641  17.513  -1.599  1.00 26.48      G  C
ATOM   7535  O    GLN C   81      34.102  18.079  -2.549  1.00 26.00      G  O
ATOM   7537  N    TRP C   82      35.112  18.161  -0.558  1.00 26.70      G  N
ATOM   7538  CA   TRP C   82      34.920  19.590  -0.378  1.00 26.39      G  C
ATOM   7540  CB   TRP C   82      33.960  19.853   0.770  1.00 26.56      G  C
ATOM   7543  CG   TRP C   82      32.578  19.560   0.541  1.00 23.29      G  C
ATOM   7544  CD1  TRP C   82      31.642  20.402   0.057  1.00 25.47      G  C
ATOM   7546  NE1  TRP C   82      30.406  19.786   0.040  1.00 26.51      G  N
ATOM   7548  CE2  TRP C   82      30.549  18.520   0.552  1.00 25.94      G  C
ATOM   7549  CD2  TRP C   82      31.905  18.357   0.894  1.00 25.28      G  C
ATOM   7550  CE3  TRP C   82      32.321  17.141   1.454  1.00 26.63      G  C
ATOM   7552  CZ3  TRP C   82      31.393  16.148   1.643  1.00 25.87      G  C
ATOM   7554  CH2  TRP C   82      30.053  16.339   1.307  1.00 23.45      G  C
ATOM   7556  CZ2  TRP C   82      29.617  17.519   0.740  1.00 25.29      G  C
ATOM   7558  C    TRP C   82      36.251  20.099   0.050  1.00 26.65      G  C
ATOM   7559  O    TRP C   82      36.891  19.489   0.907  1.00 26.70      G  O
ATOM   7561  N    SER C   82A     36.679  21.205  -0.521  1.00 26.58      G  N
ATOM   7562  CA   SER C   82A     37.953  21.787  -0.135  1.00 27.09      G  C
ATOM   7564  CB   SER C   82A     38.599  22.399  -1.390  1.00 27.79      G  C
ATOM   7567  OG   SER C   82A     37.763  23.404  -1.956  1.00 27.84      G  O
ATOM   7569  C    SER C   82A     37.796  22.856   0.995  1.00 27.24      G  C
ATOM   7570  O    SER C   82A     38.714  23.073   1.777  1.00 27.69      G  O
ATOM   7572  N    SER C   82B     36.639  23.510   1.056  1.00 27.25      G  N
ATOM   7573  CA   SER C   82B     36.349  24.569   2.039  1.00 27.29      G  C
ATOM   7575  CB   SER C   82B     36.584  25.938   1.383  1.00 26.88      G  C
ATOM   7578  OG   SER C   82B     36.417  27.017   2.302  1.00 30.00      G  O
ATOM   7580  C    SER C   82B     34.891  24.460   2.479  1.00 26.70      G  C
ATOM   7581  O    SER C   82B     33.992  24.995   1.835  1.00 26.34      G  O
ATOM   7583  N    LEU C   82C     34.627  23.732   3.552  1.00 26.46      G  N
ATOM   7584  CA   LEU C   82C     33.228  23.519   3.949  1.00 25.58      G  C
ATOM   7586  CB   LEU C   82C     33.124  22.528   5.093  1.00 25.31      G  C
ATOM   7589  CG   LEU C   82C     33.356  21.038   4.778  1.00 24.46      G  C
ATOM   7591  CD1  LEU C   82C     33.720  20.271   6.064  1.00 23.38      G  C
ATOM   7595  CD2  LEU C   82C     32.198  20.381   4.051  1.00 18.90      G  C
ATOM   7599  C    LEU C   82C     32.556  24.819   4.360  1.00 26.15      G  C
ATOM   7600  O    LEU C   82C     33.218  25.701   4.916  1.00 25.06      G  O
ATOM   7602  N    LYS C   83      31.253  24.919   4.061  1.00 26.40      G  N
ATOM   7603  CA   LYS C   83      30.377  25.932   4.614  1.00 27.16      G  C
ATOM   7605  CB   LYS C   83      29.511  26.518   3.515  1.00 27.97      G  C
ATOM   7608  CG   LYS C   83      30.289  27.030   2.319  1.00 30.71      G  C
ATOM   7611  CD   LYS C   83      29.411  27.275   1.110  1.00 34.25      G  C
```

Figure 8 – CONT.

| | | | | | | | | | | | |
|---|---|---|---|---|---|---|---|---|---|---|---|
| ATOM | 7614 | CE | LYS | C | 83 | 30.268 | 27.121 | -0.186 | 1.00 | 37.96 | G C |
| ATOM | 7617 | NZ | LYS | C | 83 | 29.706 | 27.889 | -1.295 | 1.00 | 38.79 | G N |
| ATOM | 7621 | C | LYS | C | 83 | 29.453 | 25.306 | 5.692 | 1.00 | 27.88 | G C |
| ATOM | 7622 | O | LYS | C | 83 | 29.127 | 24.085 | 5.635 | 1.00 | 28.20 | G O |
| ATOM | 7624 | N | ALA | C | 84 | 29.061 | 26.135 | 6.664 | 1.00 | 26.50 | G N |
| ATOM | 7625 | CA | ALA | C | 84 | 27.984 | 25.830 | 7.614 | 1.00 | 27.19 | G C |
| ATOM | 7627 | CB | ALA | C | 84 | 27.496 | 27.121 | 8.349 | 1.00 | 26.15 | C C |
| ATOM | 7631 | C | ALA | C | 84 | 26.816 | 25.181 | 6.902 | 1.00 | 27.03 | G C |
| ATOM | 7632 | O | ALA | C | 84 | 26.327 | 24.117 | 7.341 | 1.00 | 26.72 | G O |
| ATOM | 7634 | N | SER | C | 85 | 26.419 | 25.810 | 5.786 | 1.00 | 26.61 | G N |
| ATOM | 7635 | CA | SER | C | 85 | 25.268 | 25.401 | 4.989 | 1.00 | 26.44 | G C |
| ATOM | 7637 | CB | SER | C | 85 | 24.973 | 26.456 | 3.903 | 1.00 | 27.80 | G C |
| ATOM | 7640 | OG | SER | C | 85 | 26.101 | 26.654 | 3.026 | 1.00 | 28.40 | G O |
| ATOM | 7642 | C | SER | C | 85 | 25.414 | 24.034 | 4.332 | 1.00 | 26.07 | G C |
| ATOM | 7643 | O | SER | C | 85 | 24.446 | 23.511 | 3.813 | 1.00 | 25.95 | G O |
| ATOM | 7645 | N | ASP | C | 86 | 26.609 | 23.441 | 4.376 | 1.00 | 26.53 | G N |
| ATOM | 7646 | CA | ASP | C | 86 | 26.817 | 22.046 | 3.918 | 1.00 | 25.45 | G C |
| ATOM | 7648 | CB | ASP | C | 86 | 28.278 | 21.791 | 3.563 | 1.00 | 24.76 | G C |
| ATOM | 7651 | CG | ASP | C | 86 | 28.757 | 22.602 | 2.379 | 1.00 | 24.35 | G C |
| ATOM | 7652 | OD1 | ASP | C | 86 | 28.019 | 22.719 | 1.379 | 1.00 | 24.74 | G O |
| ATOM | 7653 | OD2 | ASP | C | 86 | 29.927 | 23.054 | 2.416 | 1.00 | 22.99 | G O |
| ATOM | 7654 | C | ASP | C | 86 | 26.430 | 21.029 | 4.964 | 1.00 | 24.96 | G C |
| ATOM | 7655 | O | ASP | C | 86 | 26.569 | 19.812 | 4.732 | 1.00 | 24.09 | G O |
| ATOM | 7657 | N | THR | C | 87 | 26.013 | 21.500 | 6.144 | 1.00 | 24.33 | G N |
| ATOM | 7658 | CA | THR | C | 87 | 25.459 | 20.586 | 7.175 | 1.00 | 23.50 | G C |
| ATOM | 7660 | CB | THR | C | 87 | 25.105 | 21.352 | 8.458 | 1.00 | 23.88 | G C |
| ATOM | 7662 | OG1 | THR | C | 87 | 26.315 | 21.894 | 8.996 | 1.00 | 23.20 | G O |
| ATOM | 7664 | CG2 | THR | C | 87 | 24.405 | 20.421 | 9.520 | 1.00 | 21.55 | G C |
| ATOM | 7668 | C | THR | C | 87 | 24.235 | 19.836 | 6.637 | 1.00 | 22.70 | G C |
| ATOM | 7669 | O | THR | C | 87 | 23.268 | 20.434 | 6.230 | 1.00 | 22.40 | G O |
| ATOM | 7671 | N | ALA | C | 88 | 24.314 | 18.513 | 6.609 | 1.00 | 23.01 | G N |
| ATOM | 7672 | CA | ALA | C | 88 | 23.295 | 17.696 | 6.002 | 1.00 | 22.41 | G C |
| ATOM | 7674 | CB | ALA | C | 88 | 23.151 | 18.050 | 4.528 | 1.00 | 23.66 | G C |
| ATOM | 7678 | C | ALA | C | 88 | 23.693 | 16.257 | 6.117 | 1.00 | 23.78 | G C |
| ATOM | 7679 | O | ALA | C | 88 | 24.795 | 15.942 | 6.547 | 1.00 | 23.79 | G O |
| ATOM | 7681 | N | ILE | C | 89 | 22.801 | 15.367 | 5.711 | 1.00 | 24.47 | G N |
| ATOM | 7682 | CA | ILE | C | 89 | 23.178 | 13.976 | 5.539 | 1.00 | 25.37 | G C |
| ATOM | 7684 | CB | ILE | C | 89 | 22.116 | 13.084 | 6.138 | 1.00 | 26.03 | C C |
| ATOM | 7686 | CG1 | ILE | C | 89 | 22.531 | 11.623 | 6.116 | 1.00 | 30.07 | C C |
| ATOM | 7689 | CD1 | ILE | C | 89 | 21.855 | 10.814 | 7.303 | 1.00 | 35.70 | C C |
| ATOM | 7693 | CG2 | ILE | C | 89 | 20.838 | 13.230 | 5.383 | 1.00 | 27.94 | C C |
| ATOM | 7697 | C | ILE | C | 89 | 23.391 | 13.743 | 4.035 | 1.00 | 25.29 | G C |
| ATOM | 7698 | O | ILE | C | 89 | 22.680 | 14.320 | 3.211 | 1.00 | 25.65 | G O |
| ATOM | 7700 | N | TYR | C | 90 | 24.426 | 12.974 | 3.683 | 1.00 | 25.40 | G N |
| ATOM | 7701 | CA | TYR | C | 90 | 24.770 | 12.684 | 2.289 | 1.00 | 24.84 | G C |
| ATOM | 7703 | CB | TYR | C | 90 | 26.201 | 13.119 | 1.950 | 1.00 | 24.31 | G C |
| ATOM | 7706 | CG | TYR | C | 90 | 26.312 | 14.614 | 2.056 | 1.00 | 24.46 | G C |
| ATOM | 7707 | CD1 | TYR | C | 90 | 26.549 | 15.251 | 3.291 | 1.00 | 22.89 | G C |
| ATOM | 7709 | CE1 | TYR | C | 90 | 26.556 | 16.636 | 3.375 | 1.00 | 23.13 | G C |
| ATOM | 7711 | CZ | TYR | C | 90 | 26.327 | 17.379 | 2.238 | 1.00 | 23.22 | G C |
| ATOM | 7712 | OH | TYR | C | 90 | 26.314 | 18.759 | 2.250 | 1.00 | 22.93 | G O |
| ATOM | 7714 | CE2 | TYR | C | 90 | 26.089 | 16.752 | 1.031 | 1.00 | 23.74 | G C |
| ATOM | 7716 | CD2 | TYR | C | 90 | 26.055 | 15.405 | 0.958 | 1.00 | 24.66 | G C |
| ATOM | 7718 | C | TYR | C | 90 | 24.550 | 11.225 | 2.069 | 1.00 | 25.16 | G C |
| ATOM | 7719 | O | TYR | C | 90 | 25.147 | 10.393 | 2.759 | 1.00 | 25.50 | G O |
| ATOM | 7721 | N | TYR | C | 91 | 23.678 | 10.916 | 1.116 | 1.00 | 25.30 | G N |
| ATOM | 7722 | CA | TYR | C | 91 | 23.440 | 9.535 | 0.709 | 1.00 | 26.15 | G C |
| ATOM | 7724 | CB | TYR | C | 91 | 21.959 | 9.260 | 0.562 | 1.00 | 25.68 | G C |

Figure 8 – CONT.

```
ATOM   7727  CG   TYR C   91      21.089    9.529    1.780  1.00 26.79      G  C
ATOM   7728  CD1  TYR C   91      20.978    8.603    2.816  1.00 28.37      G  C
ATOM   7730  CE1  TYR C   91      20.137    8.838    3.940  1.00 28.93      G  C
ATOM   7732  CZ   TYR C   91      19.406   10.024    3.978  1.00 30.71      G  C
ATOM   7733  OH   TYR C   91      18.578   10.324    5.014  1.00 31.81      G  O
ATOM   7735  CE2  TYR C   91      19.496   10.939    2.940  1.00 29.79      G  C
ATOM   7737  CD2  TYR C   91      20.324   10.686    1.853  1.00 28.44      G  C
ATOM   7739  C    TYR C   91      24.084    9.280   -0.658  1.00 27.10      G  C
ATOM   7740  O    TYR C   91      23.967   10.095   -1.585  1.00 26.88      G  O
ATOM   7742  N    CYS C   92      24.770    8.151   -0.773  1.00 27.84      G  N
ATOM   7743  CA   CYS C   92      25.237    7.686   -2.057  1.00 28.21      G  C
ATOM   7745  CB   CYS C   92      26.614    7.018   -1.954  1.00 28.08      G  C
ATOM   7748  SG   CYS C   92      26.720    5.510   -1.062  1.00 28.09      G  S
ATOM   7750  C    CYS C   92      24.167    6.735   -2.559  1.00 29.25      G  C
ATOM   7751  O    CYS C   92      23.486    6.102   -1.776  1.00 29.32      G  O
ATOM   7753  N    VAL C   93      23.996    6.693   -3.869  1.00 29.73      G  N
ATOM   7754  CA   VAL C   93      22.944    5.928   -4.496  1.00 30.02      G  C
ATOM   7756  CB   VAL C   93      21.865    6.829   -5.054  1.00 30.39      C  C
ATOM   7758  CG1  VAL C   93      20.853    6.018   -5.877  1.00 29.82      C  C
ATOM   7762  CG2  VAL C   93      21.168    7.585   -3.909  1.00 29.75      C  C
ATOM   7766  C    VAL C   93      23.561    5.121   -5.638  1.00 30.93      G  C
ATOM   7767  O    VAL C   93      24.383    5.631   -6.414  1.00 30.29      G  O
ATOM   7769  N    GLY C   94      23.178    3.858   -5.700  1.00 31.17      G  N
ATOM   7770  CA   GLY C   94      23.707    2.941   -6.688  1.00 32.18      G  C
ATOM   7773  C    GLY C   94      22.705    2.862   -7.813  1.00 32.31      G  C
ATOM   7774  O    GLY C   94      21.551    2.565   -7.566  1.00 31.95      G  O
ATOM   7776  N    LEU C   95      23.135    3.176   -9.036  1.00 32.46      G  N
ATOM   7777  CA   LEU C   95      22.257    3.025  -10.196  1.00 33.05      G  C
ATOM   7779  CB   LEU C   95      21.650    4.335  -10.714  1.00 32.71      G  C
ATOM   7782  CG   LEU C   95      22.092    5.794  -10.507  1.00 33.37      G  C
ATOM   7784  CD1  LEU C   95      22.732    6.077   -9.163  1.00 32.33      G  C
ATOM   7788  CD2  LEU C   95      20.861    6.703  -10.726  1.00 29.16      G  C
ATOM   7792  C    LEU C   95      22.931    2.249  -11.317  1.00 33.60      G  C
ATOM   7793  O    LEU C   95      24.142    2.379  -11.574  1.00 33.68      G  O
ATOM   7795  N    ASP C   96      22.108    1.459  -11.978  1.00 34.18      G  N
ATOM   7796  CA   ASP C   96      22.546    0.570  -13.018  1.00 35.15      G  C
ATOM   7798  CB   ASP C   96      21.373   -0.253  -13.498  1.00 35.66      C  C
ATOM   7801  CG   ASP C   96      20.900   -1.177  -12.460  1.00 36.62      C  C
ATOM   7802  OD1  ASP C   96      21.732   -1.637  -11.643  1.00 43.92      C  O
ATOM   7803  OD2  ASP C   96      19.704   -1.434  -12.437  1.00 41.23      C  O
ATOM   7804  C    ASP C   96      23.177    1.317  -14.166  1.00 35.23      G  C
ATOM   7805  O    ASP C   96      24.181    0.875  -14.714  1.00 35.12      G  O
ATOM   7807  N    TRP C   97      22.608    2.455  -14.519  1.00 34.98      G  N
ATOM   7808  CA   TRP C   97      23.292    3.337  -15.427  1.00 35.31      G  C
ATOM   7810  CB   TRP C   97      23.066    2.912  -16.891  1.00 35.05      C  C
ATOM   7813  CG   TRP C   97      24.110    3.450  -17.806  1.00 33.98      C  C
ATOM   7814  CD1  TRP C   97      24.000    4.548  -18.607  1.00 33.95      C  C
ATOM   7816  NE1  TRP C   97      25.166    4.763  -19.280  1.00 33.93      C  N
ATOM   7818  CE2  TRP C   97      26.069    3.797  -18.930  1.00 34.40      C  C
ATOM   7819  CD2  TRP C   97      25.442    2.959  -17.987  1.00 34.31      C  C
ATOM   7820  CE3  TRP C   97      26.172    1.887  -17.444  1.00 34.20      C  C
ATOM   7822  CZ3  TRP C   97      27.478    1.683  -17.877  1.00 35.16      C  C
ATOM   7824  CH2  TRP C   97      28.081    2.540  -18.821  1.00 34.31      C  C
ATOM   7826  CZ2  TRP C   97      27.400    3.605  -19.349  1.00 34.51      C  C
ATOM   7828  C    TRP C   97      22.807    4.740  -15.201  1.00 35.76      G  C
ATOM   7829  O    TRP C   97      21.795    4.952  -14.513  1.00 35.39      G  O
ATOM   7831  N    ASN C   98      23.528    5.705  -15.760  1.00 36.07      C  N
ATOM   7832  CA   ASN C   98      22.997    7.053  -15.834  1.00 37.46      C  C
```

Figure 8 – CONT.

```
ATOM   7834  CB   ASN C  98      23.841   7.968 -16.761  1.00 37.50           C   C
ATOM   7837  CG   ASN C  98      23.579   9.457 -16.494  1.00 38.37           C   C
ATOM   7838  OD1  ASN C  98      22.922   9.803 -15.501  1.00 38.86           C   O
ATOM   7839  ND2  ASN C  98      24.084  10.332 -17.363  1.00 35.74           C   N
ATOM   7842  C    ASN C  98      21.555   6.958 -16.311  1.00 38.29           C   C
ATOM   7843  O    ASN C  98      21.205   6.003 -17.034  1.00 38.36           C   O
ATOM   7845  N    TYR C  99      20.715   7.892 -15.864  1.00 39.09           C   N
ATOM   7846  CA   TYR C  99      19.305   7.978 -16.299  1.00 40.49           C   C
ATOM   7848  CB   TYR C  99      19.196   8.003 -17.827  1.00 41.32           C   C
ATOM   7851  CG   TYR C  99      19.499   9.330 -18.462  1.00 46.56           C   C
ATOM   7852  CD1  TYR C  99      18.469  10.245 -18.715  1.00 51.64           C   C
ATOM   7854  CE1  TYR C  99      18.721  11.485 -19.327  1.00 53.91           C   C
ATOM   7856  CZ   TYR C  99      20.017  11.818 -19.711  1.00 55.38           C   C
ATOM   7857  OH   TYR C  99      20.230  13.052 -20.319  1.00 57.45           C   O
ATOM   7859  CE2  TYR C  99      21.076  10.924 -19.468  1.00 53.26           C   C
ATOM   7861  CD2  TYR C  99      20.799   9.667 -18.856  1.00 51.37           C   C
ATOM   7863  C    TYR C  99      18.381   6.880 -15.801  1.00 40.20           C   C
ATOM   7864  O    TYR C  99      17.200   6.876 -16.133  1.00 40.60           C   O
ATOM   7866  N    ASN C 100      18.897   5.940 -15.027  1.00 39.92           G   N
ATOM   7867  CA   ASN C 100      18.077   4.835 -14.534  1.00 39.25           G   C
ATOM   7869  CB   ASN C 100      18.892   3.532 -14.591  1.00 39.25           C   C
ATOM   7872  CG   ASN C 100      19.041   3.002 -16.025  1.00 37.78           C   C
ATOM   7873  OD1  ASN C 100      19.642   3.648 -16.871  1.00 37.76           C   O
ATOM   7874  ND2  ASN C 100      18.473   1.849 -16.289  1.00 36.56           C   N
ATOM   7877  C    ASN C 100      17.559   5.149 -13.120  1.00 39.40           G   C
ATOM   7878  O    ASN C 100      17.832   6.233 -12.591  1.00 39.47           G   O
ATOM   7880  N    PRO C 100A     16.773   4.236 -12.529  1.00 38.81           G   N
ATOM   7881  CA   PRO C 100A     16.198   4.526 -11.211  1.00 38.95           G   C
ATOM   7883  CB   PRO C 100A     15.211   3.364 -10.984  1.00 38.71           C   C
ATOM   7886  CG   PRO C 100A     14.978   2.774 -12.338  1.00 39.46           C   C
ATOM   7889  CD   PRO C 100A     16.267   2.963 -13.074  1.00 39.23           C   C
ATOM   7892  C    PRO C 100A     17.250   4.559 -10.086  1.00 38.07           G   C
ATOM   7893  O    PRO C 100A     18.222   3.813 -10.134  1.00 38.78           G   O
ATOM   7894  N    LEU C 100B     17.057   5.433  -9.105  1.00 36.95           G   N
ATOM   7895  CA   LEU C 100B     17.923   5.477  -7.919  1.00 36.15           G   C
ATOM   7897  CB   LEU C 100B     17.697   6.768  -7.117  1.00 36.32           C   C
ATOM   7900  CG   LEU C 100B     17.565   8.122  -7.831  1.00 36.33           C   C
ATOM   7902  CD1  LEU C 100B     17.968   9.274  -6.878  1.00 36.13           C   C
ATOM   7906  CD2  LEU C 100B     18.323   8.193  -9.091  1.00 36.14           C   C
ATOM   7910  C    LEU C 100B     17.627   4.220  -7.079  1.00 34.96           G   C
ATOM   7911  O    LEU C 100B     16.764   4.211  -6.201  1.00 33.32           G   O
ATOM   7913  N    ARG C 101      18.335   3.147  -7.389  1.00 34.34           G   N
ATOM   7914  CA   ARG C 101      17.897   1.817  -6.980  1.00 34.45           G   C
ATOM   7916  CB   ARG C 101      18.273   0.774  -8.069  1.00 35.27           C   C
ATOM   7919  CG   ARG C 101      18.262  -0.692  -7.567  1.00 38.36           C   C
ATOM   7922  CD   ARG C 101      17.341  -1.601  -8.366  1.00 44.96           C   C
ATOM   7925  NE   ARG C 101      17.980  -2.201  -9.532  1.00 47.96           C   N
ATOM   7927  CZ   ARG C 101      17.949  -3.505  -9.865  1.00 50.57           C   C
ATOM   7928  NH1  ARG C 101      17.311  -4.426  -9.139  1.00 49.87           C   N
ATOM   7931  NH2  ARG C 101      18.581  -3.896 -10.966  1.00 50.72           C   N
ATOM   7934  C    ARG C 101      18.415   1.408  -5.603  1.00 32.80           G   C
ATOM   7935  O    ARG C 101      17.674   0.828  -4.805  1.00 32.38           G   O
ATOM   7937  N    TYR C 102      19.686   1.658  -5.335  1.00 31.35           G   N
ATOM   7938  CA   TYR C 102      20.262   1.228  -4.055  1.00 31.67           G   C
ATOM   7940  CB   TYR C 102      21.452   0.287  -4.235  1.00 31.60           C   C
ATOM   7943  CG   TYR C 102      21.141  -0.929  -5.048  1.00 32.92           C   C
ATOM   7944  CD1  TYR C 102      20.548  -2.044  -4.456  1.00 35.41           C   C
ATOM   7946  CE1  TYR C 102      20.250  -3.173  -5.192  1.00 36.85           C   C
```

Figure 8 – CONT.

```
ATOM   7948  CZ   TYR C 102      20.569  -3.213  -6.552  1.00 36.79      C  C
ATOM   7949  OH   TYR C 102      20.253  -4.335  -7.260  1.00 39.93      C  O
ATOM   7951  CE2  TYR C 102      21.157  -2.126  -7.182  1.00 35.07      C  C
ATOM   7953  CD2  TYR C 102      21.430  -0.971  -6.423  1.00 34.76      C  C
ATOM   7955  C    TYR C 102      20.698   2.459  -3.298  1.00 30.94      G  C
ATOM   7956  O    TYR C 102      21.264   3.399  -3.875  1.00 31.81      G  O
ATOM   7958  N    TRP C 103      20.415   2.473  -2.008  1.00 29.81      G  N
ATOM   7959  CA   TRP C 103      20.705   3.661  -1.195  1.00 28.37      G  C
ATOM   7961  CB   TRP C 103      19.407   4.207  -0.655  1.00 28.53      G  C
ATOM   7964  CG   TRP C 103      18.584   4.880  -1.686  1.00 27.25      G  C
ATOM   7965  CD1  TRP C 103      17.859   4.285  -2.657  1.00 27.43      G  C
ATOM   7967  NE1  TRP C 103      17.251   5.231  -3.431  1.00 29.46      G  N
ATOM   7969  CE2  TRP C 103      17.585   6.473  -2.972  1.00 26.95      G  C
ATOM   7970  CD2  TRP C 103      18.410   6.294  -1.862  1.00 28.24      G  C
ATOM   7971  CE3  TRP C 103      18.886   7.424  -1.188  1.00 27.83      G  C
ATOM   7973  CZ3  TRP C 103      18.504   8.655  -1.634  1.00 26.85      G  C
ATOM   7975  CH2  TRP C 103      17.674   8.800  -2.731  1.00 25.38      G  C
ATOM   7977  CZ2  TRP C 103      17.192   7.714  -3.406  1.00 28.02      G  C
ATOM   7979  C    TRP C 103      21.665   3.265  -0.080  1.00 27.86      G  C
ATOM   7980  O    TRP C 103      21.528   2.185   0.512  1.00 28.12      G  O
ATOM   7982  N    GLY C 104      22.692   4.077   0.153  1.00 26.62      G  N
ATOM   7983  CA   GLY C 104      23.535   3.894   1.343  1.00 27.19      G  C
ATOM   7986  C    GLY C 104      22.788   4.428   2.570  1.00 26.63      G  C
ATOM   7987  O    GLY C 104      21.719   4.988   2.406  1.00 25.36      G  O
ATOM   7989  N    PRO C 105      23.321   4.217   3.787  1.00 27.23      G  N
ATOM   7990  CA   PRO C 105      22.611   4.672   4.997  1.00 27.97      G  C
ATOM   7992  CB   PRO C 105      23.208   3.819   6.128  1.00 28.10      C  C
ATOM   7995  CG   PRO C 105      24.490   3.340   5.630  1.00 28.11      C  C
ATOM   7998  CD   PRO C 105      24.352   3.219   4.120  1.00 28.46      C  C
ATOM   8001  C    PRO C 105      22.777   6.153   5.275  1.00 27.92      G  C
ATOM   8002  O    PRO C 105      22.010   6.714   6.060  1.00 28.03      G  O
ATOM   8003  N    GLY C 106      23.719   6.790   4.587  1.00 27.48      G  N
ATOM   8004  CA   GLY C 106      23.894   8.236   4.690  1.00 26.28      G  C
ATOM   8007  C    GLY C 106      25.098   8.529   5.561  1.00 25.73      G  C
ATOM   8008  O    GLY C 106      25.491   7.714   6.410  1.00 25.41      G  O
ATOM   8010  N    THR C 107      25.703   9.690   5.343  1.00 25.11      G  N
ATOM   8011  CA   THR C 107      26.810  10.152   6.187  1.00 24.75      G  C
ATOM   8013  CB   THR C 107      28.151  10.216   5.371  1.00 25.07      G  C
ATOM   8015  OG1  THR C 107      28.634   8.894   5.163  1.00 24.03      G  O
ATOM   8017  CG2  THR C 107      29.222  11.014   6.142  1.00 27.91      G  C
ATOM   8021  C    THR C 107      26.410  11.524   6.671  1.00 24.23      G  C
ATOM   8022  O    THR C 107      26.136  12.374   5.850  1.00 22.36      G  O
ATOM   8024  N    LEU C 108      26.308  11.706   7.997  1.00 24.22      G  N
ATOM   8025  CA   LEU C 108      25.956  12.975   8.580  1.00 24.74      G  C
ATOM   8027  CB   LEU C 108      25.507  12.885  10.080  1.00 26.35      G  C
ATOM   8030  CG   LEU C 108      24.374  13.810  10.581  1.00 27.84      G  C
ATOM   8032  CD1  LEU C 108      24.482  14.089  12.098  1.00 30.69      G  C
ATOM   8036  CD2  LEU C 108      24.200  15.110   9.866  1.00 27.39      G  C
ATOM   8040  C    LEU C 108      27.190  13.789   8.557  1.00 23.49      G  C
ATOM   8041  O    LEU C 108      28.242  13.340   8.985  1.00 22.18      G  O
ATOM   8043  N    VAL C 109      27.044  14.999   8.076  1.00 22.84      G  N
ATOM   8044  CA   VAL C 109      28.115  15.948   8.105  1.00 23.30      G  C
ATOM   8046  CB   VAL C 109      28.612  16.323   6.684  1.00 23.61      G  C
ATOM   8048  CG1  VAL C 109      29.733  17.416   6.766  1.00 20.71      G  C
ATOM   8052  CG2  VAL C 109      29.097  15.046   5.981  1.00 22.35      G  C
ATOM   8056  C    VAL C 109      27.605  17.193   8.814  1.00 23.83      G  C
ATOM   8057  O    VAL C 109      26.628  17.789   8.389  1.00 23.29      G  O
ATOM   8059  N    THR C 110      28.303  17.553   9.889  1.00 25.43      G  N
```

Figure 8 – CONT.

```
ATOM   8060  CA   THR C 110      27.940  18.702  10.737  1.00 25.96      G  C
ATOM   8062  CB   THR C 110      27.778  18.320  12.243  1.00 25.77      G  C
ATOM   8064  OG1  THR C 110      26.816  17.290  12.364  1.00 26.90      G  O
ATOM   8066  CG2  THR C 110      27.288  19.540  13.049  1.00 26.85      G  C
ATOM   8070  C    THR C 110      29.030  19.696  10.615  1.00 25.23      G  C
ATOM   8071  O    THR C 110      30.159  19.405  10.958  1.00 25.07      G  O
ATOM   8073  N    VAL C 111      28.698  20.862  10.086  1.00 26.98      G  N
ATOM   8074  CA   VAL C 111      29.702  21.879   9.869  1.00 27.93      G  C
ATOM   8076  CB   VAL C 111      29.741  22.337   8.398  1.00 28.46      G  C
ATOM   8078  CG1  VAL C 111      30.868  23.365   8.199  1.00 27.63      G  C
ATOM   8082  CG2  VAL C 111      29.920  21.119   7.419  1.00 26.38      G  C
ATOM   8086  C    VAL C 111      29.357  23.042  10.799  1.00 28.74      G  C
ATOM   8087  O    VAL C 111      28.296  23.635  10.685  1.00 29.40      G  O
ATOM   8089  N    SER C 112      30.242  23.360  11.730  1.00 28.82      C  N
ATOM   8090  CA   SER C 112      29.938  24.472  12.622  1.00 29.77      C  C
ATOM   8092  CB   SER C 112      29.017  23.969  13.759  1.00 30.04      C  C
ATOM   8095  OG   SER C 112      29.189  24.718  14.947  1.00 31.35      C  O
ATOM   8097  C    SER C 112      31.207  25.089  13.186  1.00 29.44      C  C
ATOM   8098  O    SER C 112      32.223  24.416  13.335  1.00 27.44      C  O
ATOM   8100  N    SER C 113      31.115  26.370  13.520  1.00 30.82      C  N
ATOM   8101  CA   SER C 113      32.244  27.072  14.121  1.00 32.05      C  C
ATOM   8103  CB   SER C 113      32.046  28.581  14.006  1.00 32.71      C  C
ATOM   8106  OG   SER C 113      32.034  28.971  12.632  1.00 31.62      C  O
ATOM   8108  C    SER C 113      32.502  26.655  15.577  1.00 32.69      C  C
ATOM   8109  O    SER C 113      33.592  26.865  16.079  1.00 34.04      C  O
ATOM   8111  N    ALA C 114      31.542  25.998  16.233  1.00 32.97      C  N
ATOM   8112  CA   ALA C 114      31.722  25.567  17.619  1.00 31.96      C  C
ATOM   8114  CB   ALA C 114      30.422  24.898  18.172  1.00 31.54      C  C
ATOM   8118  C    ALA C 114      32.865  24.602  17.658  1.00 32.25      C  C
ATOM   8119  O    ALA C 114      33.146  23.943  16.649  1.00 31.77      C  O
ATOM   8121  N    SER C 115      33.534  24.524  18.808  1.00 31.90      C  N
ATOM   8122  CA   SER C 115      34.638  23.581  19.003  1.00 32.64      C  C
ATOM   8124  CB   SER C 115      35.875  24.339  19.551  1.00 33.46      C  C
ATOM   8127  OG   SER C 115      36.172  25.505  18.765  1.00 35.92      C  O
ATOM   8129  C    SER C 115      34.251  22.469  19.972  1.00 32.30      C  C
ATOM   8130  O    SER C 115      33.405  22.683  20.852  1.00 31.01      C  O
ATOM   8132  N    THR C 116      34.866  21.299  19.847  1.00 32.42      C  N
ATOM   8133  CA   THR C 116      34.535  20.239  20.793  1.00 33.85      C  C
ATOM   8135  CB   THR C 116      35.039  18.797  20.438  1.00 34.15      C  C
ATOM   8137  OG1  THR C 116      35.548  18.160  21.622  1.00 37.17      C  O
ATOM   8139  CG2  THR C 116      36.032  18.733  19.351  1.00 35.06      C  C
ATOM   8143  C    THR C 116      34.773  20.575  22.299  1.00 33.55      C  C
ATOM   8144  O    THR C 116      35.767  21.199  22.689  1.00 33.29      C  O
ATOM   8146  N    LYS C 117      33.785  20.195  23.113  1.00 32.98      C  N
ATOM   8147  CA   LYS C 117      33.680  20.616  24.498  1.00 32.12      C  C
ATOM   8149  CB   LYS C 117      33.060  22.001  24.541  1.00 32.51      C  C
ATOM   8152  CG   LYS C 117      33.011  22.612  25.954  1.00 32.13      C  C
ATOM   8155  CD   LYS C 117      32.069  23.787  26.031  1.00 32.99      C  C
ATOM   8158  CE   LYS C 117      31.919  24.279  27.485  1.00 34.64      C  C
ATOM   8161  NZ   LYS C 117      31.413  23.199  28.449  1.00 38.23      C  N
ATOM   8165  C    LYS C 117      32.824  19.639  25.284  1.00 32.27      C  C
ATOM   8166  O    LYS C 117      31.668  19.402  24.936  1.00 31.28      C  O
ATOM   8168  N    GLY C 118      33.404  19.031  26.320  1.00 32.86      C  N
ATOM   8169  CA   GLY C 118      32.663  18.111  27.225  1.00 32.50      C  C
ATOM   8172  C    GLY C 118      31.586  18.862  27.995  1.00 31.89      C  C
ATOM   8173  O    GLY C 118      31.673  20.054  28.171  1.00 31.48      C  O
ATOM   8175  N    PRO C 119      30.524  18.171  28.415  1.00 32.73      G  N
ATOM   8176  CA   PRO C 119      29.430  18.850  29.105  1.00 32.72      G  C
```

Figure 8 – CONT.

```
ATOM   8178  CB   PRO C 119      28.321  17.819  29.063  1.00 32.80           G  C
ATOM   8181  CG   PRO C 119      29.042  16.546  29.189  1.00 32.91           G  C
ATOM   8184  CD   PRO C 119      30.326  16.715  28.410  1.00 32.83           G  C
ATOM   8187  C    PRO C 119      29.772  19.152  30.553  1.00 32.81           G  C
ATOM   8188  O    PRO C 119      30.628  18.493  31.129  1.00 32.32           G  O
ATOM   8189  N    SER C 120      29.136  20.184  31.093  1.00 33.70           G  N
ATOM   8190  CA   SER C 120      28.948  20.314  32.537  1.00 34.56           G  C
ATOM   8192  CB   SER C 120      28.944  21.780  32.952  1.00 34.54           G  C
ATOM   8195  OG   SER C 120      30.218  22.342  32.781  1.00 36.56           G  O
ATOM   8197  C    SER C 120      27.588  19.692  32.915  1.00 33.97           G  C
ATOM   8198  O    SER C 120      26.579  20.016  32.315  1.00 34.87           G  O
ATOM   8200  N    VAL C 121      27.584  18.843  33.930  1.00 34.12           G  N
ATOM   8201  CA   VAL C 121      26.387  18.153  34.404  1.00 34.35           G  C
ATOM   8203  CB   VAL C 121      26.644  16.654  34.563  1.00 34.05           G  C
ATOM   8205  CG1  VAL C 121      25.350  15.926  34.938  1.00 35.46           G  C
ATOM   8209  CG2  VAL C 121      27.201  16.081  33.302  1.00 31.53           G  C
ATOM   8213  C    VAL C 121      25.891  18.714  35.746  1.00 34.63           G  C
ATOM   8214  O    VAL C 121      26.615  18.761  36.737  1.00 34.78           G  O
ATOM   8216  N    PHE C 122      24.639  19.155  35.764  1.00 35.09           G  N
ATOM   8217  CA   PHE C 122      24.048  19.652  36.980  1.00 34.53           G  C
ATOM   8219  CB   PHE C 122      23.650  21.067  36.757  1.00 34.55           G  C
ATOM   8222  CG   PHE C 122      24.806  21.949  36.478  1.00 35.92           G  C
ATOM   8223  CD1  PHE C 122      25.773  22.150  37.445  1.00 38.08           G  C
ATOM   8225  CE1  PHE C 122      26.881  22.946  37.196  1.00 38.13           G  C
ATOM   8227  CZ   PHE C 122      27.025  23.562  35.964  1.00 38.12           G  C
ATOM   8229  CE2  PHE C 122      26.071  23.360  34.983  1.00 38.95           G  C
ATOM   8231  CD2  PHE C 122      24.968  22.541  35.241  1.00 37.95           G  C
ATOM   8233  C    PHE C 122      22.880  18.779  37.412  1.00 35.17           G  C
ATOM   8234  O    PHE C 122      22.124  18.282  36.571  1.00 36.46           G  O
ATOM   8236  N    PRO C 123      22.755  18.528  38.730  1.00 34.89           G  N
ATOM   8237  CA   PRO C 123      21.650  17.664  39.169  1.00 33.77           G  C
ATOM   8239  CB   PRO C 123      22.014  17.363  40.630  1.00 33.92           G  C
ATOM   8242  CG   PRO C 123      22.724  18.615  41.090  1.00 33.48           G  C
ATOM   8245  CD   PRO C 123      23.504  19.101  39.877  1.00 34.30           G  C
ATOM   8248  C    PRO C 123      20.351  18.437  39.067  1.00 32.88           G  C
ATOM   8249  O    PRO C 123      20.360  19.641  39.277  1.00 32.99           G  O
ATOM   8250  N    LEU C 124      19.262  17.785  38.678  1.00 32.38           G  N
ATOM   8251  CA   LEU C 124      17.932  18.426  38.744  1.00 32.81           G  C
ATOM   8253  CB   LEU C 124      17.165  18.308  37.423  1.00 32.17           G  C
ATOM   8256  CG   LEU C 124      17.909  19.001  36.246  1.00 31.24           G  C
ATOM   8258  CD1  LEU C 124      17.375  18.571  34.903  1.00 28.25           G  C
ATOM   8262  CD2  LEU C 124      17.879  20.526  36.367  1.00 28.75           G  C
ATOM   8266  C    LEU C 124      17.202  17.769  39.929  1.00 33.68           G  C
ATOM   8267  O    LEU C 124      16.676  16.658  39.825  1.00 32.67           G  O
ATOM   8269  N    ALA C 125      17.263  18.449  41.071  1.00 35.33           G  N
ATOM   8270  CA   ALA C 125      16.900  17.840  42.378  1.00 37.19           G  C
ATOM   8272  CB   ALA C 125      17.390  18.748  43.563  1.00 36.92           G  C
ATOM   8276  C    ALA C 125      15.385  17.592  42.510  1.00 38.27           G  C
ATOM   8277  O    ALA C 125      14.575  18.441  42.136  1.00 38.48           G  O
ATOM   8279  N    PRO C 126      15.001  16.431  43.035  1.00 40.09           G  N
ATOM   8280  CA   PRO C 126      13.580  16.272  43.357  1.00 41.47           G  C
ATOM   8282  CB   PRO C 126      13.464  14.814  43.776  1.00 41.13           G  C
ATOM   8285  CG   PRO C 126      14.829  14.493  44.367  1.00 41.37           G  C
ATOM   8288  CD   PRO C 126      15.817  15.301  43.523  1.00 40.76           G  C
ATOM   8291  C    PRO C 126      13.193  17.178  44.502  1.00 42.80           G  C
ATOM   8292  O    PRO C 126      13.944  17.297  45.474  1.00 43.39           G  O
ATOM   8293  N    SER C 127      12.056  17.847  44.348  1.00 44.90           G  N
ATOM   8294  CA   SER C 127      11.495  18.719  45.381  1.00 46.56           G  C
```

Figure 8 – CONT.

```
ATOM   8296  CB   SER C 127      11.709  20.196  45.023  1.00 46.14           G  C
ATOM   8299  OG   SER C 127      10.735  20.608  44.087  1.00 45.21           G  O
ATOM   8301  C    SER C 127       9.993  18.448  45.491  1.00 48.16           G  C
ATOM   8302  O    SER C 127       9.458  17.595  44.786  1.00 48.60           G  O
ATOM   8304  N    SER C 128       9.312  19.210  46.341  1.00 49.81           G  N
ATOM   8305  CA   SER C 128       7.871  19.080  46.481  1.00 51.03           G  C
ATOM   8307  CB   SER C 128       7.371  19.759  47.765  1.00 51.34           G  C
ATOM   8310  OG   SER C 128       7.545  21.165  47.728  1.00 50.88           G  O
ATOM   8312  C    SER C 128       7.170  19.638  45.239  1.00 51.99           G  C
ATOM   8313  O    SER C 128       6.039  19.263  44.976  1.00 52.67           G  O
ATOM   8315  N    LYS C 129       7.842  20.500  44.464  1.00 52.66           G  N
ATOM   8316  CA   LYS C 129       7.302  20.955  43.165  1.00 53.03           G  C
ATOM   8318  CB   LYS C 129       7.979  22.249  42.694  1.00 53.54           G  C
ATOM   8321  CG   LYS C 129       7.507  23.524  43.413  1.00 54.83           G  C
ATOM   8324  CD   LYS C 129       6.136  24.030  42.902  1.00 55.80           G  C
ATOM   8327  CE   LYS C 129       6.076  25.568  42.889  1.00 55.77           G  C
ATOM   8330  NZ   LYS C 129       4.873  26.120  43.552  1.00 55.96           G  N
ATOM   8334  C    LYS C 129       7.443  19.894  42.074  1.00 52.94           G  C
ATOM   8335  O    LYS C 129       6.698  19.907  41.110  1.00 52.70           G  O
ATOM   8337  N    SER C 130       8.399  18.984  42.214  1.00 53.02           G  N
ATOM   8338  CA   SER C 130       8.575  17.908  41.223  1.00 53.23           G  C
ATOM   8340  CB   SER C 130      10.078  17.682  40.945  1.00 52.99           G  C
ATOM   8343  OG   SER C 130      10.660  16.803  41.909  1.00 52.84           G  O
ATOM   8345  C    SER C 130       7.917  16.570  41.639  1.00 53.25           G  C
ATOM   8346  O    SER C 130       8.006  15.587  40.900  1.00 52.18           G  O
ATOM   8348  N    THR C 133       7.286  16.525  42.819  1.00 54.01           G  N
ATOM   8349  CA   THR C 133       6.717  15.261  43.328  1.00 54.59           G  C
ATOM   8351  CB   THR C 133       7.363  14.779  44.669  1.00 54.74           G  C
ATOM   8353  OG1  THR C 133       6.517  15.103  45.783  1.00 55.66           G  O
ATOM   8355  CG2  THR C 133       8.752  15.371  44.887  1.00 53.40           G  C
ATOM   8359  C    THR C 133       5.187  15.353  43.474  1.00 54.96           G  C
ATOM   8360  O    THR C 133       4.640  16.386  43.883  1.00 54.81           G  O
ATOM   8362  N    SER C 134       4.508  14.268  43.116  1.00 54.72           G  N
ATOM   8363  CA   SER C 134       3.060  14.242  43.149  1.00 54.58           G  C
ATOM   8365  CB   SER C 134       2.476  15.051  41.980  1.00 54.99           G  C
ATOM   8368  OG   SER C 134       1.139  15.465  42.255  1.00 56.46           G  O
ATOM   8370  C    SER C 134       2.573  12.805  43.075  1.00 54.20           G  C
ATOM   8371  O    SER C 134       3.199  11.959  42.416  1.00 53.03           G  O
ATOM   8373  N    GLY C 135       1.452  12.539  43.758  1.00 53.98           G  N
ATOM   8374  CA   GLY C 135       0.819  11.214  43.740  1.00 53.45           G  C
ATOM   8377  C    GLY C 135       1.774  10.118  44.159  1.00 52.95           G  C
ATOM   8378  O    GLY C 135       1.740   9.020  43.619  1.00 53.15           G  O
ATOM   8380  N    GLY C 136       2.647  10.428  45.109  1.00 52.57           G  N
ATOM   8381  CA   GLY C 136       3.661   9.471  45.536  1.00 52.53           G  C
ATOM   8384  C    GLY C 136       4.766   9.139  44.521  1.00 52.27           G  C
ATOM   8385  O    GLY C 136       5.442   8.108  44.648  1.00 52.47           G  O
ATOM   8387  N    THR C 137       4.971   9.997  43.524  1.00 51.49           G  N
ATOM   8388  CA   THR C 137       6.078   9.811  42.595  1.00 50.91           G  C
ATOM   8390  CB   THR C 137       5.665   9.052  41.286  1.00 51.04           G  C
ATOM   8392  OG1  THR C 137       6.201   9.719  40.138  1.00 52.71           G  O
ATOM   8394  CG2  THR C 137       4.169   8.938  41.135  1.00 51.63           G  C
ATOM   8398  C    THR C 137       6.767  11.154  42.349  1.00 49.81           G  C
ATOM   8399  O    THR C 137       6.110  12.188  42.152  1.00 49.86           G  O
ATOM   8401  N    ALA C 138       8.100  11.133  42.412  1.00 48.43           G  N
ATOM   8402  CA   ALA C 138       8.914  12.346  42.257  1.00 47.33           G  C
ATOM   8404  CB   ALA C 138       9.796  12.547  43.496  1.00 47.81           G  C
ATOM   8408  C    ALA C 138       9.773  12.332  40.982  1.00 45.78           G  C
ATOM   8409  O    ALA C 138      10.365  11.301  40.628  1.00 44.62           G  O
```

Figure 8 – CONT.

```
ATOM   8411  N    ALA C 139       9.812  13.477  40.294  1.00 44.31      G  N
ATOM   8412  CA   ALA C 139      10.689  13.665  39.111  1.00 43.42      G  C
ATOM   8414  CB   ALA C 139      10.037  14.565  38.068  1.00 42.71      G  C
ATOM   8418  C    ALA C 139      12.013  14.269  39.569  1.00 42.25      G  C
ATOM   8419  O    ALA C 139      12.022  15.294  40.264  1.00 42.47      G  O
ATOM   8421  N    LEU C 140      13.107  13.600  39.215  1.00 40.47      G  N
ATOM   8422  CA   LEU C 140      14.464  14.114  39.388  1.00 39.35      G  C
ATOM   8424  CB   LEU C 140      15.210  13.366  40.503  1.00 39.33      G  C
ATOM   8427  CG   LEU C 140      15.409  11.846  40.346  1.00 38.53      G  C
ATOM   8429  CD1  LEU C 140      16.840  11.495  40.065  1.00 36.20      G  C
ATOM   8433  CD2  LEU C 140      14.953  11.098  41.617  1.00 40.61      G  C
ATOM   8437  C    LEU C 140      15.206  13.939  38.069  1.00 38.58      G  C
ATOM   8438  O    LEU C 140      14.815  13.109  37.227  1.00 38.02      G  O
ATOM   8440  N    GLY C 141      16.277  14.708  37.885  1.00 37.60      G  N
ATOM   8441  CA   GLY C 141      17.032  14.615  36.623  1.00 37.23      G  C
ATOM   8444  C    GLY C 141      18.496  15.014  36.652  1.00 36.12      G  C
ATOM   8445  O    GLY C 141      19.081  15.282  37.731  1.00 33.67      G  O
ATOM   8447  N    CYS C 142      19.058  15.029  35.432  1.00 35.21      G  N
ATOM   8448  CA   CYS C 142      20.380  15.566  35.137  1.00 34.17      G  C
ATOM   8450  CB   CYS C 142      21.364  14.442  34.897  1.00 35.16      G  C
ATOM   8453  SG   CYS C 142      22.161  13.915  36.424  1.00 37.24      G  S
ATOM   8455  C    CYS C 142      20.317  16.491  33.931  1.00 33.56      G  C
ATOM   8456  O    CYS C 142      19.780  16.125  32.878  1.00 32.39      G  O
ATOM   8458  N    LEU C 143      20.808  17.718  34.138  1.00 32.37      G  N
ATOM   8459  CA   LEU C 143      21.032  18.699  33.089  1.00 32.21      G  C
ATOM   8461  CB   LEU C 143      20.870  20.111  33.659  1.00 31.74      G  C
ATOM   8464  CG   LEU C 143      21.177  21.329  32.794  1.00 32.26      G  C
ATOM   8466  CD1  LEU C 143      20.352  21.365  31.516  1.00 27.85      G  C
ATOM   8470  CD2  LEU C 143      20.919  22.608  33.602  1.00 29.15      G  C
ATOM   8474  C    LEU C 143      22.454  18.493  32.564  1.00 31.74      G  C
ATOM   8475  O    LEU C 143      23.424  18.560  33.309  1.00 32.18      G  O
ATOM   8477  N    VAL C 144      22.560  18.156  31.292  1.00 32.17      G  N
ATOM   8478  CA   VAL C 144      23.849  18.023  30.604  1.00 31.46      G  C
ATOM   8480  CB   VAL C 144      23.846  16.763  29.767  1.00 31.63      G  C
ATOM   8482  CG1  VAL C 144      25.209  16.526  29.182  1.00 32.33      G  C
ATOM   8486  CG2  VAL C 144      23.415  15.557  30.632  1.00 28.59      G  C
ATOM   8490  C    VAL C 144      24.025  19.272  29.753  1.00 31.43      G  C
ATOM   8491  O    VAL C 144      23.366  19.415  28.738  1.00 32.24      G  O
ATOM   8493  N    LYS C 145      24.899  20.181  30.186  1.00 31.78      G  N
ATOM   8494  CA   LYS C 145      24.949  21.563  29.650  1.00 33.09      G  C
ATOM   8496  CB   LYS C 145      24.882  22.561  30.815  1.00 33.79      G  C
ATOM   8499  CG   LYS C 145      24.345  24.028  30.487  1.00 37.70      G  C
ATOM   8502  CD   LYS C 145      24.900  25.054  31.550  1.00 41.11      G  C
ATOM   8505  CE   LYS C 145      24.713  26.540  31.171  1.00 44.39      G  C
ATOM   8508  NZ   LYS C 145      25.695  27.098  30.124  1.00 46.51      G  N
ATOM   8512  C    LYS C 145      26.194  21.870  28.787  1.00 32.27      G  C
ATOM   8513  O    LYS C 145      27.325  21.557  29.144  1.00 32.13      G  O
ATOM   8515  N    ASP C 146      25.948  22.495  27.646  1.00 32.72      G  N
ATOM   8516  CA   ASP C 146      26.986  23.126  26.829  1.00 32.44      G  C
ATOM   8518  CB   ASP C 146      27.570  24.334  27.566  1.00 33.15      G  C
ATOM   8521  CG   ASP C 146      26.636  25.493  27.576  1.00 33.01      G  C
ATOM   8522  OD1  ASP C 146      25.626  25.465  26.859  1.00 38.84      G  O
ATOM   8523  OD2  ASP C 146      26.895  26.447  28.313  1.00 38.44      G  O
ATOM   8524  C    ASP C 146      28.097  22.201  26.394  1.00 31.92      G  C
ATOM   8525  O    ASP C 146      29.253  22.367  26.745  1.00 33.07      G  O
ATOM   8527  N    TYR C 147      27.735  21.214  25.622  1.00 31.01      G  N
ATOM   8528  CA   TYR C 147      28.703  20.317  25.033  1.00 30.71      G  C
ATOM   8530  CB   TYR C 147      28.424  18.886  25.462  1.00 29.76      G  C
```

Figure 8 – CONT.

```
ATOM   8533  CG   TYR C 147      27.102  18.367  24.959  1.00 30.83      G  C
ATOM   8534  CD1  TYR C 147      25.925  18.531  25.695  1.00 31.36      G  C
ATOM   8536  CE1  TYR C 147      24.712  18.042  25.212  1.00 30.62      G  C
ATOM   8538  CZ   TYR C 147      24.668  17.376  24.004  1.00 29.92      G  C
ATOM   8539  OH   TYR C 147      23.488  16.884  23.517  1.00 28.04      G  O
ATOM   8541  CE2  TYR C 147      25.808  17.213  23.262  1.00 29.94      G  C
ATOM   8543  CD2  TYR C 147      27.014  17.698  23.741  1.00 31.78      G  C
ATOM   8545  C    TYR C 147      28.614  20.432  23.492  1.00 30.44      G  C
ATOM   8546  O    TYR C 147      27.641  20.964  22.927  1.00 29.58      G  O
ATOM   8548  N    PHE C 148      29.643  19.926  22.835  1.00 30.51      G  N
ATOM   8549  CA   PHE C 148      29.702  19.929  21.381  1.00 30.20      G  C
ATOM   8551  CB   PHE C 148      30.093  21.302  20.785  1.00 29.90      G  C
ATOM   8554  CG   PHE C 148      30.200  21.276  19.283  1.00 30.30      G  C
ATOM   8555  CD1  PHE C 148      29.106  21.573  18.491  1.00 29.11      G  C
ATOM   8557  CE1  PHE C 148      29.191  21.477  17.101  1.00 31.35      G  C
ATOM   8559  CZ   PHE C 148      30.377  21.076  16.478  1.00 27.25      G  C
ATOM   8561  CE2  PHE C 148      31.452  20.769  17.235  1.00 30.79      G  C
ATOM   8563  CD2  PHE C 148      31.365  20.854  18.661  1.00 30.21      G  C
ATOM   8565  C    PHE C 148      30.711  18.881  21.005  1.00 30.13      G  C
ATOM   8566  O    PHE C 148      31.771  18.806  21.589  1.00 30.96      G  O
ATOM   8568  N    PRO C 149      30.392  18.040  20.031  1.00 30.49      G  N
ATOM   8569  CA   PRO C 149      29.179  17.922  19.265  1.00 30.58      G  C
ATOM   8571  CB   PRO C 149      29.698  17.465  17.898  1.00 31.17      G  C
ATOM   8574  CG   PRO C 149      30.839  16.630  18.203  1.00 31.10      G  C
ATOM   8577  CD   PRO C 149      31.444  17.157  19.504  1.00 31.29      G  C
ATOM   8580  C    PRO C 149      28.274  16.854  19.868  1.00 29.81      G  C
ATOM   8581  O    PRO C 149      28.677  16.218  20.827  1.00 28.68      G  O
ATOM   8582  N    GLU C 150      27.074  16.676  19.300  1.00 28.93      G  N
ATOM   8583  CA   GLU C 150      26.295  15.434  19.512  1.00 29.26      G  C
ATOM   8585  CB   GLU C 150      25.056  15.388  18.631  1.00 28.49      G  C
ATOM   8588  CG   GLU C 150      24.027  16.380  19.001  1.00 29.12      G  C
ATOM   8591  CD   GLU C 150      23.110  15.866  20.074  1.00 27.80      G  C
ATOM   8592  OE1  GLU C 150      23.599  15.375  21.117  1.00 28.93      G  O
ATOM   8593  OE2  GLU C 150      21.889  15.951  19.851  1.00 30.10      G  O
ATOM   8594  C    GLU C 150      27.138  14.238  19.157  1.00 29.01      G  C
ATOM   8595  O    GLU C 150      28.039  14.357  18.375  1.00 29.31      G  O
ATOM   8597  N    PRO C 151      26.836  13.077  19.715  1.00 29.94      G  N
ATOM   8598  CA   PRO C 151      25.791  12.741  20.666  1.00 30.70      G  C
ATOM   8600  CB   PRO C 151      25.386  11.333  20.207  1.00 30.58      G  C
ATOM   8603  CG   PRO C 151      26.716  10.719  19.851  1.00 30.88      G  C
ATOM   8606  CD   PRO C 151      27.606  11.874  19.354  1.00 29.86      G  C
ATOM   8609  C    PRO C 151      26.306  12.634  22.103  1.00 31.06      G  C
ATOM   8610  O    PRO C 151      27.508  12.410  22.353  1.00 30.86      G  O
ATOM   8611  N    VAL C 152      25.376  12.763  23.036  1.00 32.42      G  N
ATOM   8612  CA   VAL C 152      25.565  12.286  24.390  1.00 33.57      G  C
ATOM   8614  CB   VAL C 152      25.325  13.393  25.389  1.00 33.61      G  C
ATOM   8616  CG1  VAL C 152      24.768  12.829  26.712  1.00 33.36      G  C
ATOM   8620  CG2  VAL C 152      26.613  14.153  25.589  1.00 34.19      G  C
ATOM   8624  C    VAL C 152      24.588  11.162  24.653  1.00 34.71      G  C
ATOM   8625  O    VAL C 152      23.457  11.218  24.184  1.00 35.71      G  O
ATOM   8627  N    THR C 153      25.030  10.148  25.389  1.00 35.58      G  N
ATOM   8628  CA   THR C 153      24.127   9.157  25.952  1.00 36.23      G  C
ATOM   8630  CB   THR C 153      24.544   7.709  25.592  1.00 36.72      G  C
ATOM   8632  OG1  THR C 153      25.850   7.425  26.097  1.00 37.45      G  O
ATOM   8634  CG2  THR C 153      24.590   7.545  24.090  1.00 37.52      G  C
ATOM   8638  C    THR C 153      24.070   9.338  27.463  1.00 36.61      G  C
ATOM   8639  O    THR C 153      25.050   9.742  28.095  1.00 35.53      G  O
ATOM   8641  N    VAL C 154      22.890   9.075  28.031  1.00 37.46      G  N
```

Figure 8 – CONT.

```
ATOM   8642  CA   VAL C 154      22.692    9.079   29.469  1.00 37.71          G  C
ATOM   8644  CB   VAL C 154      21.761   10.201   29.920  1.00 38.02          G  C
ATOM   8646  CG1  VAL C 154      21.683   10.219   31.455  1.00 37.71          G  C
ATOM   8650  CG2  VAL C 154      22.214   11.549   29.370  1.00 35.07          G  C
ATOM   8654  C    VAL C 154      22.053    7.776   29.908  1.00 39.34          G  C
ATOM   8655  O    VAL C 154      21.145    7.266   29.261  1.00 39.59          G  O
ATOM   8657  N    SER C 156      22.539    7.243   31.017  1.00 40.64          G  N
ATOM   8658  CA   SER C 156      21.877    6.157   31.723  1.00 40.81          G  C
ATOM   8660  CB   SER C 156      22.620    4.850   31.505  1.00 40.84          G  C
ATOM   8663  OG   SER C 156      23.857    4.875   32.181  1.00 40.66          G  O
ATOM   8665  C    SER C 156      21.816    6.503   33.210  1.00 41.37          G  C
ATOM   8666  O    SER C 156      22.319    7.543   33.645  1.00 40.15          G  O
ATOM   8668  N    TRP C 157      21.159    5.636   33.980  1.00 42.46          G  N
ATOM   8669  CA   TRP C 157      20.983    5.850   35.424  1.00 42.73          G  C
ATOM   8671  CB   TRP C 157      19.553    6.270   35.725  1.00 42.25          G  C
ATOM   8674  CG   TRP C 157      19.176    7.638   35.270  1.00 39.71          G  C
ATOM   8675  CD1  TRP C 157      18.704    7.984   34.049  1.00 38.52          G  C
ATOM   8677  NE1  TRP C 157      18.419    9.326   34.009  1.00 36.23          G  N
ATOM   8679  CE2  TRP C 157      18.709    9.870   35.231  1.00 36.12          G  C
ATOM   8680  CD2  TRP C 157      19.178    8.838   36.051  1.00 36.99          G  C
ATOM   8681  CE3  TRP C 157      19.542    9.136   37.363  1.00 38.38          G  C
ATOM   8683  CZ3  TRP C 157      19.419   10.429   37.805  1.00 37.75          G  C
ATOM   8685  CH2  TRP C 157      18.949   11.442   36.956  1.00 38.54          G  C
ATOM   8687  CZ2  TRP C 157      18.594   11.176   35.671  1.00 36.31          G  C
ATOM   8689  C    TRP C 157      21.358    4.597   36.223  1.00 44.03          G  C
ATOM   8690  O    TRP C 157      21.138    3.475   35.777  1.00 43.81          G  O
ATOM   8692  N    ASN C 162      21.970    4.808   37.387  1.00 45.91          G  N
ATOM   8693  CA   ASN C 162      22.531    3.715   38.193  1.00 47.32          G  C
ATOM   8695  CB   ASN C 162      21.463    3.204   39.169  1.00 47.15          G  C
ATOM   8698  CG   ASN C 162      21.038    4.282   40.174  1.00 48.12          G  C
ATOM   8699  OD1  ASN C 162      21.680    5.338   40.283  1.00 46.79          G  O
ATOM   8700  ND2  ASN C 162      19.966    4.018   40.916  1.00 48.98          G  N
ATOM   8703  C    ASN C 162      23.140    2.611   37.320  1.00 48.53          G  C
ATOM   8704  O    ASN C 162      22.791    1.443   37.423  1.00 49.11          G  O
ATOM   8706  N    SER C 163      24.054    3.037   36.448  1.00 50.24          G  N
ATOM   8707  CA   SER C 163      24.724    2.203   35.428  1.00 51.15          G  C
ATOM   8709  CB   SER C 163      25.829    1.361   36.071  1.00 51.23          G  C
ATOM   8712  OG   SER C 163      26.806    2.213   36.652  1.00 52.68          G  O
ATOM   8714  C    SER C 163      23.815    1.325   34.559  1.00 52.12          G  C
ATOM   8715  O    SER C 163      24.208    0.227   34.139  1.00 52.57          G  O
ATOM   8717  N    GLY C 164      22.620    1.814   34.254  1.00 52.73          G  N
ATOM   8718  CA   GLY C 164      21.689    1.064   33.417  1.00 53.40          G  C
ATOM   8721  C    GLY C 164      20.784    0.109   34.179  1.00 53.64          G  C
ATOM   8722  O    GLY C 164      19.956   -0.558   33.576  1.00 53.89          G  O
ATOM   8724  N    ALA C 165      20.927    0.049   35.500  1.00 54.07          G  N
ATOM   8725  CA   ALA C 165      20.068   -0.790   36.323  1.00 54.18          G  C
ATOM   8727  CB   ALA C 165      20.680   -0.975   37.715  1.00 54.10          G  C
ATOM   8731  C    ALA C 165      18.657   -0.184   36.424  1.00 54.39          G  C
ATOM   8732  O    ALA C 165      17.662   -0.912   36.533  1.00 54.77          G  O
ATOM   8734  N    LEU C 166      18.577    1.146   36.383  1.00 54.07          G  N
ATOM   8735  CA   LEU C 166      17.308    1.860   36.471  1.00 53.73          G  C
ATOM   8737  CB   LEU C 166      17.427    3.016   37.475  1.00 53.37          G  C
ATOM   8740  CG   LEU C 166      16.248    3.979   37.616  1.00 53.31          G  C
ATOM   8742  CD1  LEU C 166      14.967    3.221   37.983  1.00 53.53          G  C
ATOM   8746  CD2  LEU C 166      16.537    5.093   38.641  1.00 52.02          G  C
ATOM   8750  C    LEU C 166      16.929    2.368   35.079  1.00 54.11          G  C
ATOM   8751  O    LEU C 166      17.544    3.314   34.550  1.00 54.32          G  O
ATOM   8753  N    THR C 167      15.938    1.723   34.474  1.00 54.11          G  N
```

Figure 8 – CONT.

```
ATOM   8754  CA   THR C 167      15.485    2.093   33.142  1.00 54.28          G  C
ATOM   8756  CB   THR C 167      15.739    0.946   32.145  1.00 54.62          G  C
ATOM   8758  OG1  THR C 167      15.127   -0.255   32.629  1.00 56.47          G  O
ATOM   8760  CG2  THR C 167      17.238    0.708   31.981  1.00 54.32          G  C
ATOM   8764  C    THR C 167      14.010    2.511   33.117  1.00 54.10          G  C
ATOM   8765  O    THR C 167      13.591    3.317   32.278  1.00 54.05          G  O
ATOM   8767  N    SER C 168      13.232    1.977   34.055  1.00 53.81          G  N
ATOM   8768  CA   SER C 168      11.817    2.241   34.123  1.00 53.26          G  C
ATOM   8770  CB   SER C 168      11.161    1.216   35.070  1.00 53.85          G  C
ATOM   8773  OG   SER C 168       9.781    1.056   34.781  1.00 56.05          G  O
ATOM   8775  C    SER C 168      11.608    3.680   34.607  1.00 52.04          G  C
ATOM   8776  O    SER C 168      12.177    4.087   35.627  1.00 52.18          G  O
ATOM   8778  N    GLY C 169      10.809    4.444   33.867  1.00 50.44          G  N
ATOM   8779  CA   GLY C 169      10.526    5.857   34.188  1.00 49.64          G  C
ATOM   8782  C    GLY C 169      11.527    6.895   33.661  1.00 48.22          G  C
ATOM   8783  O    GLY C 169      11.381    8.098   33.911  1.00 47.47          G  O
ATOM   8785  N    VAL C 171      12.529    6.431   32.919  1.00 46.75          G  N
ATOM   8786  CA   VAL C 171      13.609    7.292   32.433  1.00 45.40          G  C
ATOM   8788  CB   VAL C 171      14.927    6.485   32.272  1.00 45.40          G  C
ATOM   8790  CG1  VAL C 171      15.989    7.279   31.481  1.00 43.58          G  C
ATOM   8794  CG2  VAL C 171      15.442    6.103   33.636  1.00 45.03          G  C
ATOM   8798  C    VAL C 171      13.240    7.890   31.099  1.00 44.03          G  C
ATOM   8799  O    VAL C 171      12.911    7.154   30.176  1.00 44.42          G  O
ATOM   8801  N    HIS C 172      13.274    9.220   31.015  1.00 42.72          G  N
ATOM   8802  CA  AHIS C 172      13.117    9.942   29.756  0.50 42.38          G  C
ATOM   8803  CA  BHIS C 172      13.160    9.906   29.730  0.50 41.67          G  C
ATOM   8806  CB  AHIS C 172      11.853   10.831   29.787  0.50 42.55          G  C
ATOM   8807  CB  BHIS C 172      11.854   10.698   29.616  0.50 41.37          G  C
ATOM   8812  CG  AHIS C 172      10.574   10.095   30.083  0.50 44.32          G  C
ATOM   8813  CG  BHIS C 172      11.470   11.019   28.201  0.50 39.94          G  C
ATOM   8814  ND1 AHIS C 172       9.908    9.339   29.140  0.50 45.48          G  N
ATOM   8815  ND1 BHIS C 172      12.327   10.838   27.136  0.50 36.38          G  N
ATOM   8818  CE1 AHIS C 172       8.815    8.827   29.680  0.50 45.87          G  C
ATOM   8819  CE1 BHIS C 172      11.730   11.214   26.023  0.50 36.08          G  C
ATOM   8822  NE2 AHIS C 172       8.741    9.232   30.936  0.50 45.53          G  N
ATOM   8823  NE2 BHIS C 172      10.521   11.653   26.327  0.50 37.45          G  N
ATOM   8826  CD2 AHIS C 172       9.823   10.031   31.212  0.50 45.03          G  C
ATOM   8827  CD2 BHIS C 172      10.331   11.536   27.681  0.50 38.58          G  C
ATOM   8830  C    HIS C 172      14.366   10.828   29.509  1.00 41.58          G  C
ATOM   8831  O    HIS C 172      14.599   11.801   30.244  1.00 40.35          G  O
ATOM   8833  N    THR C 173      15.164   10.498   28.489  1.00 40.76          G  N
ATOM   8834  CA   THR C 173      16.277   11.340   28.079  1.00 39.37          G  C
ATOM   8836  CB   THR C 173      17.520   10.507   27.772  1.00 39.36          G  C
ATOM   8838  OG1  THR C 173      17.992    9.950   28.988  1.00 41.04          G  O
ATOM   8840  CG2  THR C 173      18.637   11.357   27.178  1.00 40.10          G  C
ATOM   8844  C    THR C 173      15.805   12.077   26.856  1.00 37.98          G  C
ATOM   8845  O    THR C 173      15.479   11.446   25.862  1.00 37.49          G  O
ATOM   8847  N    PHE C 174      15.776   13.405   26.929  1.00 36.44          G  N
ATOM   8848  CA   PHE C 174      15.227   14.231   25.881  1.00 36.10          G  C
ATOM   8850  CB   PHE C 174      14.682   15.538   26.469  1.00 36.32          G  C
ATOM   8853  CG   PHE C 174      13.439   15.341   27.295  1.00 37.48          G  C
ATOM   8854  CD1  PHE C 174      12.212   15.815   26.848  1.00 39.31          G  C
ATOM   8856  CE1  PHE C 174      11.070   15.629   27.582  1.00 38.18          G  C
ATOM   8858  CZ   PHE C 174      11.126   14.921   28.754  1.00 38.86          G  C
ATOM   8860  CE2  PHE C 174      12.337   14.408   29.199  1.00 38.94          G  C
ATOM   8862  CD2  PHE C 174      13.483   14.619   28.472  1.00 36.98          G  C
ATOM   8864  C    PHE C 174      16.286   14.550   24.828  1.00 36.47          G  C
ATOM   8865  O    PHE C 174      17.474   14.517   25.145  1.00 36.33          G  O
```

Figure 8 – CONT.

```
ATOM   8867  N    PRO C 175      15.854  14.844  23.578  1.00 36.43       G  N
ATOM   8868  CA   PRO C 175      16.713  15.370  22.523  1.00 36.83       G  C
ATOM   8870  CB   PRO C 175      15.770  15.474  21.300  1.00 36.81       G  C
ATOM   8873  CG   PRO C 175      14.733  14.456  21.540  1.00 37.76       G  C
ATOM   8876  CD   PRO C 175      14.562  14.379  23.035  1.00 37.07       G  C
ATOM   8879  C    PRO C 175      17.255  16.755  22.866  1.00 36.28       G  C
ATOM   8880  O    PRO C 175      16.527  17.598  23.407  1.00 36.42       G  O
ATOM   8881  N    ALA C 176      18.507  16.999  22.500  1.00 35.16       G  N
ATOM   8882  CA   ALA C 176      19.179  18.244  22.860  1.00 34.15       G  C
ATOM   8884  CB   ALA C 176      20.647  18.168  22.441  1.00 33.66       G  C
ATOM   8888  C    ALA C 176      18.531  19.446  22.213  1.00 33.77       G  C
ATOM   8889  O    ALA C 176      17.873  19.316  21.218  1.00 33.59       G  O
ATOM   8891  N    VAL C 177      18.701  20.620  22.806  1.00 34.25       G  N
ATOM   8892  CA   VAL C 177      18.559  21.898  22.094  1.00 34.60       G  C
ATOM   8894  CB   VAL C 177      18.099  23.071  23.015  1.00 34.52       G  C
ATOM   8896  CG1  VAL C 177      16.635  23.084  23.191  1.00 36.30       G  C
ATOM   8900  CG2  VAL C 177      18.775  23.009  24.359  1.00 33.62       G  C
ATOM   8904  C    VAL C 177      19.926  22.339  21.580  1.00 34.90       G  C
ATOM   8905  O    VAL C 177      20.953  22.106  22.215  1.00 35.27       G  O
ATOM   8907  N    LEU C 178      19.936  23.026  20.458  1.00 35.82       G  N
ATOM   8908  CA   LEU C 178      21.158  23.618  19.957  1.00 35.50       G  C
ATOM   8910  CB   LEU C 178      21.261  23.385  18.458  1.00 35.36       G  C
ATOM   8913  CG   LEU C 178      22.394  24.161  17.774  1.00 34.89       G  C
ATOM   8915  CD1  LEU C 178      23.707  23.841  18.473  1.00 30.35       G  C
ATOM   8919  CD2  LEU C 178      22.404  23.833  16.284  1.00 31.34       G  C
ATOM   8923  C    LEU C 178      21.053  25.099  20.283  1.00 36.18       G  C
ATOM   8924  O    LEU C 178      20.140  25.761  19.852  1.00 35.24       G  O
ATOM   8926  N    GLN C 179      21.966  25.620  21.079  1.00 37.63       G  N
ATOM   8927  CA   GLN C 179      21.839  27.017  21.481  1.00 39.16       G  C
ATOM   8929  CB   GLN C 179      22.471  27.214  22.865  1.00 39.73       G  C
ATOM   8932  CG   GLN C 179      21.965  26.193  23.949  1.00 42.76       G  C
ATOM   8935  CD   GLN C 179      23.036  25.881  24.998  1.00 47.10       G  C
ATOM   8936  OE1  GLN C 179      23.526  24.746  25.114  1.00 46.66       G  O
ATOM   8937  NE2  GLN C 179      23.434  26.912  25.742  1.00 51.15       G  N
ATOM   8940  C    GLN C 179      22.485  27.940  20.438  1.00 39.59       G  C
ATOM   8941  O    GLN C 179      23.245  27.488  19.589  1.00 38.11       G  O
ATOM   8943  N    SER C 180      22.190  29.242  20.543  1.00 40.27       G  N
ATOM   8944  CA   SER C 180      22.787  30.275  19.693  1.00 40.54       G  C
ATOM   8946  CB   SER C 180      22.200  31.663  20.033  1.00 41.25       G  C
ATOM   8949  OG   SER C 180      20.899  31.802  19.476  1.00 43.24       G  O
ATOM   8951  C    SER C 180      24.307  30.348  19.810  1.00 39.77       G  C
ATOM   8952  O    SER C 180      24.956  30.945  18.971  1.00 39.71       G  O
ATOM   8954  N    SER C 182      24.851  29.777  20.875  1.00 38.64       G  N
ATOM   8955  CA   SER C 182      26.290  29.678  21.085  1.00 37.71       G  C
ATOM   8957  CB   SER C 182      26.536  29.312  22.550  1.00 37.87       G  C
ATOM   8960  OG   SER C 182      26.092  27.981  22.807  1.00 34.88       G  O
ATOM   8962  C    SER C 182      26.968  28.587  20.246  1.00 37.42       G  C
ATOM   8963  O    SER C 182      28.191  28.508  20.234  1.00 37.30       G  O
ATOM   8965  N    GLY C 183      26.167  27.708  19.625  1.00 36.83       G  N
ATOM   8966  CA   GLY C 183      26.665  26.532  18.912  1.00 35.69       G  C
ATOM   8969  C    GLY C 183      26.782  25.282  19.763  1.00 34.66       G  C
ATOM   8970  O    GLY C 183      27.122  24.210  19.271  1.00 34.92       G  O
ATOM   8972  N    LEU C 184      26.494  25.402  21.045  1.00 33.49       G  N
ATOM   8973  CA   LEU C 184      26.641  24.279  21.967  1.00 32.48       G  C
ATOM   8975  CB   LEU C 184      27.256  24.747  23.284  1.00 32.31       G  C
ATOM   8978  CG   LEU C 184      28.764  24.912  23.480  1.00 34.73       G  C
ATOM   8980  CD1  LEU C 184      29.605  24.873  22.203  1.00 34.30       G  C
ATOM   8984  CD2  LEU C 184      29.031  26.157  24.322  1.00 32.85       G  C
```

Figure 8 – CONT.

```
ATOM   8988  C    LEU C 184      25.267  23.682  22.227  1.00 31.11       G  C
ATOM   8989  O    LEU C 184      24.250  24.354  22.084  1.00 30.75       G  O
ATOM   8991  N    TYR C 185      25.261  22.402  22.586  1.00 29.81       G  N
ATOM   8992  CA   TYR C 185      24.036  21.694  22.901  1.00 29.39       G  C
ATOM   8994  CB   TYR C 185      24.106  20.272  22.366  1.00 28.51       G  C
ATOM   8997  CG   TYR C 185      24.195  20.206  20.857  1.00 28.08       G  C
ATOM   8998  CD1  TYR C 185      23.041  20.163  20.083  1.00 25.38       G  C
ATOM   9000  CE1  TYR C 185      23.111  20.111  18.706  1.00 29.39       G  C
ATOM   9002  CZ   TYR C 185      24.369  20.087  18.080  1.00 27.73       G  C
ATOM   9003  OH   TYR C 185      24.438  20.011  16.715  1.00 29.22       G  O
ATOM   9005  CE2  TYR C 185      25.526  20.127  18.823  1.00 25.90       G  C
ATOM   9007  CD2  TYR C 185      25.441  20.166  20.206  1.00 26.78       G  C
ATOM   9009  C    TYR C 185      23.825  21.594  24.413  1.00 28.72       G  C
ATOM   9010  O    TYR C 185      24.772  21.474  25.162  1.00 27.66       G  O
ATOM   9012  N    SER C 186      22.571  21.573  24.835  1.00 29.43       G  N
ATOM   9013  CA   SER C 186      22.238  21.043  26.150  1.00 30.16       G  C
ATOM   9015  CB   SER C 186      21.852  22.191  27.067  1.00 30.44       G  C
ATOM   9018  OG   SER C 186      22.997  23.015  27.351  1.00 29.21       G  O
ATOM   9020  C    SER C 186      21.117  20.001  26.023  1.00 31.34       G  C
ATOM   9021  O    SER C 186      20.241  20.120  25.163  1.00 31.06       G  O
ATOM   9023  N    LEU C 187      21.134  18.996  26.898  1.00 31.87       G  N
ATOM   9024  CA   LEU C 187      19.978  18.124  27.036  1.00 31.92       G  C
ATOM   9026  CB   LEU C 187      20.130  16.872  26.168  1.00 31.56       G  C
ATOM   9029  CG   LEU C 187      21.156  15.781  26.470  1.00 31.50       G  C
ATOM   9031  CD1  LEU C 187      20.846  15.087  27.799  1.00 29.61       G  C
ATOM   9035  CD2  LEU C 187      21.174  14.744  25.287  1.00 28.55       G  C
ATOM   9039  C    LEU C 187      19.707  17.773  28.502  1.00 32.15       G  C
ATOM   9040  O    LEU C 187      20.504  18.119  29.392  1.00 32.37       G  O
ATOM   9042  N    SER C 188      18.566  17.125  28.741  1.00 31.55       G  N
ATOM   9043  CA   SER C 188      18.178  16.689  30.078  1.00 31.66       G  C
ATOM   9045  CB   SER C 188      17.055  17.546  30.582  1.00 31.36       G  C
ATOM   9048  OG   SER C 188      17.513  18.882  30.776  1.00 30.72       G  O
ATOM   9050  C    SER C 188      17.744  15.253  30.071  1.00 33.08       G  C
ATOM   9051  O    SER C 188      17.169  14.790  29.079  1.00 33.87       G  O
ATOM   9053  N    SER C 189      18.075  14.524  31.134  1.00 33.83       G  N
ATOM   9054  CA   SER C 189      17.480  13.220  31.385  1.00 34.88       G  C
ATOM   9056  CB   SER C 189      18.517  12.126  31.407  1.00 34.86       G  C
ATOM   9059  OG   SER C 189      17.896  10.853  31.404  1.00 36.04       G  O
ATOM   9061  C    SER C 189      16.737  13.285  32.720  1.00 36.00       G  C
ATOM   9062  O    SER C 189      17.232  13.892  33.672  1.00 36.08       G  O
ATOM   9064  N    VAL C 190      15.537  12.694  32.780  1.00 36.85       G  N
ATOM   9065  CA   VAL C 190      14.751  12.692  34.020  1.00 37.49       G  C
ATOM   9067  CB   VAL C 190      13.528  13.609  33.904  1.00 37.67       G  C
ATOM   9069  CG1  VAL C 190      13.971  15.038  33.718  1.00 37.79       G  C
ATOM   9073  CG2  VAL C 190      12.659  13.157  32.772  1.00 37.84       G  C
ATOM   9077  C    VAL C 190      14.242  11.316  34.386  1.00 37.55       G  C
ATOM   9078  O    VAL C 190      13.821  10.579  33.506  1.00 37.73       G  O
ATOM   9080  N    VAL C 191      14.260  10.983  35.681  1.00 38.32       G  N
ATOM   9081  CA   VAL C 191      13.597   9.753  36.176  1.00 38.67       G  C
ATOM   9083  CB   VAL C 191      14.481   8.823  37.076  1.00 38.92       G  C
ATOM   9085  CG1  VAL C 191      14.329   7.336  36.658  1.00 38.51       G  C
ATOM   9089  CG2  VAL C 191      15.918   9.245  37.123  1.00 38.87       G  C
ATOM   9093  C    VAL C 191      12.434  10.150  37.089  1.00 38.81       G  C
ATOM   9094  O    VAL C 191      12.555  11.058  37.919  1.00 37.29       G  O
ATOM   9096  N    THR C 192      11.336   9.420  36.936  1.00 39.58       G  N
ATOM   9097  CA   THR C 192      10.223   9.408  37.888  1.00 40.10       G  C
ATOM   9099  CB   THR C 192       8.880   9.386  37.159  1.00 40.24       G  C
ATOM   9101  OG1  THR C 192       8.837   8.258  36.273  1.00 41.43       G  O
```

Figure 8 – CONT.

```
ATOM   9103  CG2 THR C 192       8.698  10.657  36.331  1.00 39.66      G  C
ATOM   9107  C   THR C 192      10.367   8.169  38.793  1.00 40.54      G  C
ATOM   9108  O   THR C 192      10.437   7.035  38.313  1.00 39.91      G  O
ATOM   9110  N   VAL C 193      10.437   8.408  40.104  1.00 41.17      G  N
ATOM   9111  CA  VAL C 193      10.668   7.354  41.096  1.00 42.03      G  C
ATOM   9113  CB  VAL C 193      12.112   7.415  41.638  1.00 41.92      G  C
ATOM   9115  CG1 VAL C 193      13.139   7.301  40.493  1.00 42.48      G  C
ATOM   9119  CG2 VAL C 193      12.327   8.720  42.454  1.00 41.17      G  C
ATOM   9123  C   VAL C 193       9.723   7.527  42.308  1.00 43.25      G  C
ATOM   9124  O   VAL C 193       9.219   8.633  42.540  1.00 42.96      G  O
ATOM   9126  N   PRO C 194       9.505   6.446  43.096  1.00 44.80      G  N
ATOM   9127  CA  PRO C 194       8.653   6.557  44.303  1.00 46.15      G  C
ATOM   9129  CB  PRO C 194       8.782   5.168  44.976  1.00 46.41      G  C
ATOM   9132  CG  PRO C 194       9.131   4.221  43.845  1.00 46.23      G  C
ATOM   9135  CD  PRO C 194       9.940   5.052  42.843  1.00 44.67      G  C
ATOM   9138  C   PRO C 194       9.162   7.637  45.226  1.00 47.31      G  C
ATOM   9139  O   PRO C 194      10.360   7.691  45.482  1.00 47.66      G  O
ATOM   9140  N   SER C 195       8.284   8.517  45.698  1.00 48.94      G  N
ATOM   9141  CA  SER C 195       8.739   9.604  46.574  1.00 50.41      G  C
ATOM   9143  CB  SER C 195       7.694  10.733  46.689  1.00 50.47      G  C
ATOM   9146  OG  SER C 195       6.372  10.233  46.843  1.00 51.21      G  O
ATOM   9148  C   SER C 195       9.192   9.085  47.950  1.00 51.48      G  C
ATOM   9149  O   SER C 195       9.992   9.744  48.634  1.00 51.47      G  O
ATOM   9151  N   SER C 196       8.702   7.895  48.325  1.00 52.96      G  N
ATOM   9152  CA  SER C 196       9.082   7.214  49.578  1.00 53.59      G  C
ATOM   9154  CB  SER C 196       8.286   5.906  49.737  1.00 53.56      G  C
ATOM   9157  OG  SER C 196       8.529   5.007  48.658  1.00 52.65      G  O
ATOM   9159  C   SER C 196      10.565   6.875  49.641  1.00 54.46      G  C
ATOM   9160  O   SER C 196      11.144   6.850  50.725  1.00 54.52      G  O
ATOM   9162  N   SER C 197      11.157   6.613  48.470  1.00 55.48      G  N
ATOM   9163  CA  SER C 197      12.544   6.128  48.344  1.00 55.91      G  C
ATOM   9165  CB  SER C 197      12.677   5.358  47.029  1.00 56.25      G  C
ATOM   9168  OG  SER C 197      12.734   6.266  45.931  1.00 56.59      G  O
ATOM   9170  C   SER C 197      13.633   7.223  48.368  1.00 55.94      G  C
ATOM   9171  O   SER C 197      14.835   6.915  48.351  1.00 55.76      G  O
ATOM   9173  N   LEU C 198      13.225   8.489  48.390  1.00 56.08      G  N
ATOM   9174  CA  LEU C 198      14.170   9.594  48.252  1.00 56.39      G  C
ATOM   9176  CB  LEU C 198      13.424  10.927  48.119  1.00 56.43      G  C
ATOM   9179  CG  LEU C 198      12.598  11.152  46.850  1.00 55.05      G  C
ATOM   9181  CD1 LEU C 198      11.987  12.531  46.919  1.00 53.85      G  C
ATOM   9185  CD2 LEU C 198      13.454  11.012  45.589  1.00 54.98      G  C
ATOM   9189  C   LEU C 198      15.171   9.666  49.413  1.00 57.12      G  C
ATOM   9190  O   LEU C 198      16.353   9.943  49.205  1.00 57.72      G  O
ATOM   9192  N   GLY C 199      14.704   9.412  50.634  1.00 57.39      G  N
ATOM   9193  CA  GLY C 199      15.600   9.318  51.787  1.00 57.36      G  C
ATOM   9196  C   GLY C 199      16.593   8.155  51.751  1.00 57.24      G  C
ATOM   9197  O   GLY C 199      17.618   8.205  52.430  1.00 57.67      G  O
ATOM   9199  N   THR C 200      16.308   7.124  50.960  1.00 56.79      G  N
ATOM   9200  CA  THR C 200      17.057   5.873  51.030  1.00 56.65      G  C
ATOM   9202  CB  THR C 200      16.134   4.799  51.573  1.00 56.91      G  C
ATOM   9204  OG1 THR C 200      15.119   4.523  50.601  1.00 56.87      G  O
ATOM   9206  CG2 THR C 200      15.475   5.286  52.876  1.00 57.50      G  C
ATOM   9210  C   THR C 200      17.699   5.352  49.711  1.00 56.05      G  C
ATOM   9211  O   THR C 200      18.746   4.699  49.765  1.00 56.71      G  O
ATOM   9213  N   GLN C 203      17.094   5.594  48.545  1.00 54.78      G  N
ATOM   9214  CA  GLN C 203      17.702   5.124  47.265  1.00 53.79      G  C
ATOM   9216  CB  GLN C 203      16.641   4.723  46.218  1.00 54.24      G  C
ATOM   9219  CG  GLN C 203      16.527   3.195  45.944  1.00 56.06      G  C
```

Figure 8 – CONT.

```
ATOM   9222  CD   GLN C 203      17.551    2.659   44.933  1.00 57.90           G  C
ATOM   9223  OE1  GLN C 203      17.371    1.574   44.364  1.00 59.62           G  O
ATOM   9224  NE2  GLN C 203      18.624    3.406   44.717  1.00 58.73           G  N
ATOM   9227  C    GLN C 203      18.658    6.155   46.661  1.00 51.75           G  C
ATOM   9228  O    GLN C 203      18.351    7.351   46.587  1.00 51.33           G  O
ATOM   9230  N    THR C 205      19.813    5.669   46.225  1.00 49.75           G  N
ATOM   9231  CA   THR C 205      20.801    6.498   45.530  1.00 48.21           G  C
ATOM   9233  CB   THR C 205      22.240    5.971   45.794  1.00 48.14           G  C
ATOM   9235  OG1  THR C 205      22.752    6.626   46.965  1.00 48.66           G  O
ATOM   9237  CG2  THR C 205      23.172    6.226   44.619  1.00 47.28           G  C
ATOM   9241  C    THR C 205      20.502    6.593   44.016  1.00 46.80           G  C
ATOM   9242  O    THR C 205      20.339    5.570   43.319  1.00 46.54           G  O
ATOM   9244  N    TYR C 206      20.437    7.826   43.519  1.00 44.54           G  N
ATOM   9245  CA   TYR C 206      20.211    8.059   42.083  1.00 43.41           G  C
ATOM   9247  CB   TYR C 206      18.881    8.822   41.880  1.00 43.26           G  C
ATOM   9250  CG   TYR C 206      17.673    8.057   42.426  1.00 43.70           G  C
ATOM   9251  CD1  TYR C 206      17.251    6.877   41.820  1.00 43.13           G  C
ATOM   9253  CE1  TYR C 206      16.177    6.149   42.326  1.00 45.12           G  C
ATOM   9255  CZ   TYR C 206      15.501    6.606   43.450  1.00 44.89           G  C
ATOM   9256  OH   TYR C 206      14.438    5.877   43.914  1.00 46.70           G  O
ATOM   9258  CE2  TYR C 206      15.902    7.779   44.092  1.00 43.25           G  C
ATOM   9260  CD2  TYR C 206      16.990    8.495   43.581  1.00 43.37           G  C
ATOM   9262  C    TYR C 206      21.412    8.751   41.371  1.00 41.58           G  C
ATOM   9263  O    TYR C 206      21.744    9.905   41.620  1.00 41.34           G  O
ATOM   9265  N    ILE C 207      22.050    8.025   40.476  1.00 40.24           G  N
ATOM   9266  CA   ILE C 207      23.229    8.528   39.757  1.00 39.58           G  C
ATOM   9268  CB   ILE C 207      24.472    7.678   40.114  1.00 39.36           G  C
ATOM   9270  CG1  ILE C 207      24.829    7.833   41.600  1.00 40.90           G  C
ATOM   9273  CD1  ILE C 207      26.051    6.996   42.051  1.00 40.43           G  C
ATOM   9277  CG2  ILE C 207      25.673    8.092   39.297  1.00 40.16           G  C
ATOM   9281  C    ILE C 207      22.999    8.510   38.236  1.00 38.12           G  C
ATOM   9282  O    ILE C 207      22.801    7.453   37.651  1.00 37.03           G  O
ATOM   9284  N    CYS C 208      23.028    9.676   37.596  1.00 37.80           G  N
ATOM   9285  CA   CYS C 208      23.040    9.709   36.120  1.00 37.89           G  C
ATOM   9287  CB   CYS C 208      22.401   10.993   35.591  1.00 38.12           G  C
ATOM   9290  SG   CYS C 208      23.404   12.453   35.809  1.00 40.14           G  S
ATOM   9292  C    CYS C 208      24.465    9.496   35.579  1.00 37.54           G  C
ATOM   9293  O    CYS C 208      25.423   10.095   36.072  1.00 37.82           G  O
ATOM   9295  N    ASN C 209      24.602    8.598   34.611  1.00 37.03           G  N
ATOM   9296  CA   ASN C 209      25.862    8.339   33.935  1.00 36.95           G  C
ATOM   9298  CB   ASN C 209      26.103    6.848   33.785  1.00 36.76           G  C
ATOM   9301  CG   ASN C 209      25.574    6.069   34.959  1.00 39.32           G  C
ATOM   9302  OD1  ASN C 209      26.219    5.998   36.007  1.00 41.88           G  O
ATOM   9303  ND2  ASN C 209      24.367    5.516   34.811  1.00 38.75           G  N
ATOM   9306  C    ASN C 209      25.821    8.960   32.546  1.00 36.69           G  C
ATOM   9307  O    ASN C 209      25.095    8.468   31.679  1.00 37.20           G  O
ATOM   9309  N    VAL C 210      26.597   10.025   32.347  1.00 35.74           G  N
ATOM   9310  CA   VAL C 210      26.588   10.809   31.112  1.00 35.84           G  C
ATOM   9312  CB   VAL C 210      26.567   12.297   31.411  1.00 35.42           G  C
ATOM   9314  CG1  VAL C 210      26.430   13.110   30.123  1.00 35.78           G  C
ATOM   9318  CG2  VAL C 210      25.433   12.647   32.367  1.00 34.36           G  C
ATOM   9322  C    VAL C 210      27.846   10.498   30.289  1.00 36.43           G  C
ATOM   9323  O    VAL C 210      28.954   10.562   30.803  1.00 37.62           G  O
ATOM   9325  N    ASN C 211      27.678   10.119   29.033  1.00 36.42           G  N
ATOM   9326  CA   ASN C 211      28.814    9.800   28.179  1.00 37.19           G  C
ATOM   9328  CB   ASN C 211      28.770    8.327   27.760  1.00 37.04           G  C
ATOM   9331  CG   ASN C 211      30.103    7.831   27.190  1.00 41.43           G  C
ATOM   9332  OD1  ASN C 211      31.027    8.616   26.903  1.00 44.33           G  O
```

Figure 8 – CONT.

```
ATOM   9333  ND2 ASN C 211      30.200    6.512   27.006  1.00 44.14          G  N
ATOM   9336  C   ASN C 211      28.837   10.706   26.953  1.00 36.48          G  C
ATOM   9337  O   ASN C 211      27.855   10.765   26.198  1.00 36.26          G  O
ATOM   9339  N   HIS C 212      29.957   11.397   26.771  1.00 35.92          G  N
ATOM   9340  CA  HIS C 212      30.207   12.240   25.589  1.00 36.28          G  C
ATOM   9342  CB  HIS C 212      30.354   13.694   26.026  1.00 35.39          G  C
ATOM   9345  CG  HIS C 212      30.446   14.664   24.897  1.00 35.58          G  C
ATOM   9346  ND1 HIS C 212      31.418   15.632   24.829  1.00 35.76          G  N
ATOM   9348  CE1 HIS C 212      31.231   16.366   23.750  1.00 35.79          G  C
ATOM   9350  NE2 HIS C 212      30.182   15.898   23.105  1.00 33.86          G  N
ATOM   9352  CD2 HIS C 212      29.686   14.821   23.789  1.00 36.13          G  C
ATOM   9354  C   HIS C 212      31.486   11.769   24.863  1.00 37.11          G  C
ATOM   9355  O   HIS C 212      32.572   12.365   25.006  1.00 36.48          G  O
ATOM   9357  N   LYS C 213      31.351   10.688   24.091  1.00 38.33          G  N
ATOM   9358  CA  LYS C 213      32.495   10.084   23.410  1.00 39.27          G  C
ATOM   9360  CB  LYS C 213      32.064    8.947   22.478  1.00 39.94          G  C
ATOM   9363  CG  LYS C 213      31.614    7.678   23.209  1.00 43.36          G  C
ATOM   9366  CD  LYS C 213      31.034    6.665   22.217  1.00 47.65          G  C
ATOM   9369  CE  LYS C 213      30.600    5.340   22.880  1.00 50.36          G  C
ATOM   9372  NZ  LYS C 213      31.746    4.361   23.060  1.00 53.67          G  N
ATOM   9376  C   LYS C 213      33.375   11.122   22.675  1.00 38.37          G  C
ATOM   9377  O   LYS C 213      34.575   11.131   22.865  1.00 38.36          G  O
ATOM   9379  N   PRO C 214      32.776   12.026   21.899  1.00 38.02          G  N
ATOM   9380  CA  PRO C 214      33.597   12.962   21.116  1.00 38.24          G  C
ATOM   9382  CB  PRO C 214      32.556   13.875   20.479  1.00 37.98          G  C
ATOM   9385  CG  PRO C 214      31.341   12.995   20.375  1.00 37.97          G  C
ATOM   9388  CD  PRO C 214      31.340   12.226   21.638  1.00 37.72          G  C
ATOM   9391  C   PRO C 214      34.604   13.797   21.902  1.00 38.52          G  C
ATOM   9392  O   PRO C 214      35.596   14.229   21.321  1.00 39.02          G  O
ATOM   9393  N   SER C 215      34.353   14.051   23.188  1.00 38.28          G  N
ATOM   9394  CA  SER C 215      35.320   14.769   24.023  1.00 38.23          G  C
ATOM   9396  CB  SER C 215      34.666   15.935   24.758  1.00 38.47          G  C
ATOM   9399  OG  SER C 215      33.981   15.495   25.933  1.00 39.53          G  O
ATOM   9401  C   SER C 215      35.939   13.836   25.034  1.00 37.80          G  C
ATOM   9402  O   SER C 215      36.554   14.277   25.999  1.00 37.73          G  O
ATOM   9404  N   ASN C 216      35.792   12.543   24.814  1.00 37.67          G  N
ATOM   9405  CA  ASN C 216      36.305   11.567   25.749  1.00 38.41          G  C
ATOM   9407  CB  ASN C 216      37.824   11.510   25.601  1.00 39.27          G  C
ATOM   9410  CG  ASN C 216      38.258   10.997   24.247  1.00 39.99          G  C
ATOM   9411  OD1 ASN C 216      37.789    9.956   23.793  1.00 39.18          G  O
ATOM   9412  ND2 ASN C 216      39.178   11.725   23.600  1.00 41.98          G  N
ATOM   9415  C   ASN C 216      35.958   11.832   27.225  1.00 38.54          G  C
ATOM   9416  O   ASN C 216      36.807   11.617   28.095  1.00 39.25          G  O
ATOM   9418  N   THR C 217      34.734   12.296   27.506  1.00 37.80          G  N
ATOM   9419  CA  THR C 217      34.303   12.637   28.867  1.00 37.73          G  C
ATOM   9421  CB  THR C 217      33.931   14.131   28.962  1.00 37.92          G  C
ATOM   9423  OG1 THR C 217      34.942   14.906   28.309  1.00 36.44          G  O
ATOM   9425  CG2 THR C 217      33.807   14.587   30.426  1.00 36.80          G  C
ATOM   9429  C   THR C 217      33.105   11.788   29.288  1.00 37.63          G  C
ATOM   9430  O   THR C 217      32.095   11.797   28.600  1.00 37.98          G  O
ATOM   9432  N   LYS C 218      33.248   11.015   30.374  1.00 37.58          G  N
ATOM   9433  CA  LYS C 218      32.109   10.362   31.075  1.00 37.05          G  C
ATOM   9435  CB  LYS C 218      32.263    8.845   31.195  1.00 36.10          G  C
ATOM   9442  C   LYS C 218      31.972   10.969   32.464  1.00 37.29          G  C
ATOM   9443  O   LYS C 218      32.964   11.075   33.211  1.00 37.13          G  O
ATOM   9445  N   VAL C 219      30.749   11.361   32.817  1.00 37.57          G  N
ATOM   9446  CA  VAL C 219      30.482   11.978   34.115  1.00 38.05          G  C
ATOM   9448  CB  VAL C 219      30.156   13.471   33.973  1.00 37.84          G  C
```

Figure 8 – CONT.

```
ATOM   9450  CG1 VAL C 219      29.973  14.099  35.326  1.00 37.56          G  C
ATOM   9454  CG2 VAL C 219      31.255  14.209  33.155  1.00 37.80          G  C
ATOM   9458  C   VAL C 219      29.323  11.262  34.851  1.00 39.14          G  C
ATOM   9459  O   VAL C 219      28.248  11.026  34.285  1.00 39.52          G  O
ATOM   9461  N   ASP C 220      29.575  10.908  36.105  1.00 39.60          G  N
ATOM   9462  CA  ASP C 220      28.574  10.386  37.005  1.00 40.14          G  C
ATOM   9464  CB  ASP C 220      29.119   9.153  37.740  1.00 40.81          G  C
ATOM   9467  CG  ASP C 220      29.350   7.988  36.810  1.00 42.53          G  C
ATOM   9468  OD1 ASP C 220      29.050   8.119  35.610  1.00 46.72          G  O
ATOM   9469  OD2 ASP C 220      29.824   6.936  37.258  1.00 45.89          G  O
ATOM   9470  C   ASP C 220      28.220  11.490  37.980  1.00 39.88          G  C
ATOM   9471  O   ASP C 220      29.105  12.156  38.527  1.00 39.81          G  O
ATOM   9473  N   LYS C 221      26.919  11.699  38.166  1.00 40.18          G  N
ATOM   9474  CA  LYS C 221      26.401  12.734  39.029  1.00 40.27          G  C
ATOM   9476  CB  LYS C 221      25.921  13.925  38.226  1.00 40.01          G  C
ATOM   9479  CG  LYS C 221      25.669  15.152  39.072  1.00 40.48          G  C
ATOM   9482  CD  LYS C 221      27.003  15.645  39.656  1.00 41.86          G  C
ATOM   9485  CE  LYS C 221      26.961  17.061  40.098  1.00 42.21          G  C
ATOM   9488  NZ  LYS C 221      28.255  17.707  39.855  1.00 44.38          G  N
ATOM   9492  C   LYS C 221      25.247  12.185  39.874  1.00 41.70          G  C
ATOM   9493  O   LYS C 221      24.148  11.903  39.369  1.00 41.85          G  O
ATOM   9495  N   LYS C 222      25.509  12.030  41.169  1.00 42.78          G  N
ATOM   9496  CA  LYS C 222      24.488  11.595  42.108  1.00 43.28          G  C
ATOM   9498  CB  LYS C 222      25.140  11.116  43.423  1.00 44.13          G  C
ATOM   9501  CG  LYS C 222      24.209  10.648  44.556  1.00 46.48          G  C
ATOM   9504  CD  LYS C 222      25.000  10.572  45.905  1.00 48.69          G  C
ATOM   9507  CE  LYS C 222      24.312   9.680  46.951  1.00 50.48          G  C
ATOM   9510  NZ  LYS C 222      23.172  10.320  47.687  1.00 50.58          G  N
ATOM   9514  C   LYS C 222      23.592  12.799  42.310  1.00 42.19          G  C
ATOM   9515  O   LYS C 222      24.067  13.927  42.426  1.00 41.19          G  O
ATOM   9517  N   VAL C 225      22.295  12.539  42.326  1.00 41.85          G  N
ATOM   9518  CA  VAL C 225      21.280  13.582  42.430  1.00 42.27          G  C
ATOM   9520  CB  VAL C 225      20.338  13.524  41.222  1.00 41.93          G  C
ATOM   9522  CG1 VAL C 225      19.222  14.558  41.353  1.00 41.42          G  C
ATOM   9526  CG2 VAL C 225      21.132  13.719  39.922  1.00 42.66          G  C
ATOM   9530  C   VAL C 225      20.460  13.369  43.712  1.00 43.37          G  C
ATOM   9531  O   VAL C 225      19.848  12.307  43.915  1.00 42.62          G  O
ATOM   9533  N   GLU C 226      20.443  14.370  44.571  1.00 44.25          G  N
ATOM   9534  CA  GLU C 226      19.795  14.207  45.848  1.00 45.58          G  C
ATOM   9536  CB  GLU C 226      20.807  13.869  46.972  1.00 46.05          G  C
ATOM   9539  CG  GLU C 226      22.197  14.446  46.807  1.00 47.53          G  C
ATOM   9542  CD  GLU C 226      23.196  14.070  47.915  1.00 48.27          G  C
ATOM   9543  OE1 GLU C 226      23.356  12.863  48.226  1.00 49.13          G  O
ATOM   9544  OE2 GLU C 226      23.858  15.002  48.441  1.00 48.05          G  O
ATOM   9545  C   GLU C 226      18.912  15.421  46.149  1.00 46.16          G  C
ATOM   9546  O   GLU C 226      19.087  16.478  45.551  1.00 45.77          G  O
ATOM   9548  N   PRO C 227      17.907  15.235  47.034  1.00 46.82          G  N
ATOM   9549  CA  PRO C 227      16.871  16.217  47.335  1.00 47.19          G  C
ATOM   9551  CB  PRO C 227      16.204  15.630  48.574  1.00 47.75          G  C
ATOM   9554  CG  PRO C 227      16.393  14.116  48.433  1.00 47.28          G  C
ATOM   9557  CD  PRO C 227      17.563  13.886  47.546  1.00 46.87          G  C
ATOM   9560  C   PRO C 227      17.339  17.662  47.574  1.00 47.42          G  C
ATOM   9561  O   PRO C 227      18.002  17.951  48.559  1.00 48.31          G  O
TER
ATOM   9562  N   SER D   2      12.430  23.465  -5.562  1.00 56.31          D  N
ATOM   9563  CA  SER D   2      12.061  22.023  -5.755  1.00 56.53          D  C
ATOM   9565  CB  SER D   2      11.112  21.546  -4.655  1.00 56.98          D  C
ATOM   9568  OG  SER D   2      10.355  20.419  -5.089  1.00 57.69          D  O
```

Figure 8 – CONT.

```
ATOM   9570  C    SER D   2      11.408  21.822  -7.123  1.00 56.09      D C
ATOM   9571  O    SER D   2      10.284  22.280  -7.357  1.00 55.90      D O
ATOM   9575  N    VAL D   3      12.106  21.105  -8.005  1.00 55.32      D N
ATOM   9576  CA   VAL D   3      11.759  21.063  -9.424  1.00 54.58      D C
ATOM   9578  CB   VAL D   3      12.940  20.472 -10.252  1.00 54.69      D C
ATOM   9580  CG1  VAL D   3      12.527  20.243 -11.705  1.00 54.06      D C
ATOM   9584  CG2  VAL D   3      14.170  21.410 -10.163  1.00 53.86      D C
ATOM   9588  C    VAL D   3      10.404  20.364  -9.710  1.00 53.86      D C
ATOM   9589  O    VAL D   3       9.676  20.774 -10.617  1.00 53.54      D O
ATOM   9591  N    LEU D   4      10.067  19.334  -8.932  1.00 52.87      D N
ATOM   9592  CA   LEU D   4       8.737  18.682  -8.998  1.00 52.18      D C
ATOM   9594  CB   LEU D   4       8.866  17.158  -8.902  1.00 51.65      D C
ATOM   9597  CG   LEU D   4       9.161  16.342 -10.164  1.00 51.65      D C
ATOM   9599  CD1  LEU D   4       9.574  14.941  -9.795  1.00 49.63      D C
ATOM   9603  CD2  LEU D   4      10.213  16.985 -11.034  1.00 51.19      D C
ATOM   9607  C    LEU D   4       7.884  19.206  -7.838  1.00 51.77      D C
ATOM   9608  O    LEU D   4       8.432  19.519  -6.785  1.00 51.94      D O
ATOM   9610  N    THR D   5       6.561  19.294  -8.017  1.00 51.25      D N
ATOM   9611  CA   THR D   5       5.680  19.872  -6.981  1.00 50.49      D C
ATOM   9613  CB   THR D   5       4.849  21.051  -7.521  1.00 50.60      D C
ATOM   9615  OG1  THR D   5       5.727  22.116  -7.910  1.00 50.20      D O
ATOM   9617  CG2  THR D   5       3.901  21.569  -6.461  1.00 50.55      D C
ATOM   9621  C    THR D   5       4.748  18.837  -6.405  1.00 49.99      D C
ATOM   9622  O    THR D   5       3.944  18.263  -7.125  1.00 50.19      D O
ATOM   9624  N    GLN D   6       4.887  18.589  -5.106  1.00 49.34      D N
ATOM   9625  CA   GLN D   6       3.999  17.724  -4.355  1.00 49.05      D C
ATOM   9627  CB   GLN D   6       4.776  16.617  -3.653  1.00 49.11      D C
ATOM   9630  CG   GLN D   6       5.631  15.730  -4.547  1.00 47.70      D C
ATOM   9633  CD   GLN D   6       6.434  14.725  -3.733  1.00 44.66      D C
ATOM   9634  OE1  GLN D   6       5.884  13.994  -2.906  1.00 41.87      D O
ATOM   9635  NE2  GLN D   6       7.744  14.699  -3.961  1.00 39.42      D N
ATOM   9638  C    GLN D   6       3.304  18.543  -3.271  1.00 49.62      D C
ATOM   9639  O    GLN D   6       3.728  19.673  -2.958  1.00 49.48      D O
ATOM   9641  N    PRO D   7       2.231  17.985  -2.695  1.00 49.98      D N
ATOM   9642  CA   PRO D   7       1.593  18.592  -1.526  1.00 50.51      D C
ATOM   9644  CB   PRO D   7       0.199  17.940  -1.498  1.00 50.26      D C
ATOM   9647  CG   PRO D   7       0.357  16.664  -2.234  1.00 50.46      D C
ATOM   9650  CD   PRO D   7       1.377  16.950  -3.305  1.00 50.23      D C
ATOM   9653  C    PRO D   7       2.360  18.291  -0.231  1.00 51.10      D C
ATOM   9654  O    PRO D   7       2.773  17.142  -0.019  1.00 50.66      D O
ATOM   9655  N    PRO D   8       2.536  19.314   0.638  1.00 51.71      D N
ATOM   9656  CA   PRO D   8       3.321  19.153   1.870  1.00 52.10      D C
ATOM   9658  CB   PRO D   8       3.094  20.478   2.609  1.00 52.02      D C
ATOM   9661  CG   PRO D   8       2.869  21.467   1.521  1.00 51.89      D C
ATOM   9664  CD   PRO D   8       2.149  20.724   0.422  1.00 51.83      D C
ATOM   9667  C    PRO D   8       2.886  17.983   2.737  1.00 52.45      D C
ATOM   9668  O    PRO D   8       3.717  17.364   3.393  1.00 52.79      D O
ATOM   9669  N    SER D   9       1.599  17.686   2.747  1.00 53.05      D N
ATOM   9670  CA   SER D   9       1.102  16.625   3.592  1.00 54.08      D C
ATOM   9672  CB   SER D   9       0.987  17.088   5.071  1.00 54.96      D C
ATOM   9675  OG   SER D   9       0.613  18.461   5.165  1.00 55.03      D O
ATOM   9677  C    SER D   9      -0.231  16.085   3.111  1.00 54.47      D C
ATOM   9678  O    SER D   9      -0.887  16.652   2.230  1.00 54.26      D O
ATOM   9680  N    VAL D  11      -0.596  14.970   3.727  1.00 54.87      D N
ATOM   9681  CA   VAL D  11      -1.723  14.182   3.338  1.00 55.34      D C
ATOM   9683  CB   VAL D  11      -1.414  13.398   2.036  1.00 55.68      D C
ATOM   9685  CG1  VAL D  11      -2.003  12.012   2.073  1.00 54.96      D C
ATOM   9689  CG2  VAL D  11      -1.884  14.196   0.803  1.00 55.54      D C
```

Figure 8 – CONT.

```
ATOM    9693  C    VAL D  11      -2.008  13.261   4.517  1.00 55.94           D  C
ATOM    9694  O    VAL D  11      -1.106  12.889   5.275  1.00 55.38           D  O
ATOM    9696  N    SER D  12      -3.282  12.920   4.672  1.00 56.71           D  N
ATOM    9697  CA   SER D  12      -3.782  12.323   5.901  1.00 56.84           D  C
ATOM    9699  CB   SER D  12      -4.050  13.433   6.917  1.00 56.91           D  C
ATOM    9702  OG   SER D  12      -4.072  14.701   6.269  1.00 56.01           D  O
ATOM    9704  C    SER D  12      -5.045  11.540   5.617  1.00 56.95           D  C
ATOM    9705  O    SER D  12      -5.842  11.935   4.770  1.00 57.42           D  O
ATOM    9707  N    ALA D  13      -5.211  10.421   6.314  1.00 57.04           D  N
ATOM    9708  CA   ALA D  13      -6.389   9.572   6.157  1.00 56.97           D  C
ATOM    9710  CB   ALA D  13      -6.454   8.988   4.744  1.00 56.94           D  C
ATOM    9714  C    ALA D  13      -6.391   8.454   7.209  1.00 57.01           D  C
ATOM    9715  O    ALA D  13      -5.338   8.091   7.751  1.00 56.86           D  O
ATOM    9717  N    ALA D  14      -7.582   7.920   7.493  1.00 56.74           D  N
ATOM    9718  CA   ALA D  14      -7.774   6.976   8.591  1.00 56.47           D  C
ATOM    9720  CB   ALA D  14      -9.255   6.859   8.934  1.00 56.34           D  C
ATOM    9724  C    ALA D  14      -7.239   5.644   8.149  1.00 56.01           D  C
ATOM    9725  O    ALA D  14      -7.096   5.430   6.962  1.00 56.16           D  O
ATOM    9727  N    PRO D  15      -6.934   4.740   9.089  1.00 55.98           D  N
ATOM    9728  CA   PRO D  15      -6.551   3.422   8.603  1.00 56.10           D  C
ATOM    9730  CB   PRO D  15      -6.389   2.593   9.877  1.00 56.15           D  C
ATOM    9733  CG   PRO D  15      -6.072   3.577  10.942  1.00 56.51           D  C
ATOM    9736  CD   PRO D  15      -6.651   4.914  10.522  1.00 56.07           D  C
ATOM    9739  C    PRO D  15      -7.624   2.832   7.689  1.00 56.35           D  C
ATOM    9740  O    PRO D  15      -8.811   3.152   7.829  1.00 56.11           D  O
ATOM    9741  N    GLY D  16      -7.185   1.999   6.749  1.00 56.55           D  N
ATOM    9742  CA   GLY D  16      -8.061   1.346   5.804  1.00 56.57           D  C
ATOM    9745  C    GLY D  16      -8.251   2.149   4.536  1.00 56.65           D  C
ATOM    9746  O    GLY D  16      -8.371   1.572   3.470  1.00 57.46           D  O
ATOM    9748  N    GLN D  17      -8.282   3.474   4.632  1.00 56.47           D  N
ATOM    9749  CA   GLN D  17      -8.659   4.291   3.483  1.00 56.37           D  C
ATOM    9751  CB   GLN D  17      -8.898   5.754   3.883  1.00 56.53           D  C
ATOM    9758  C    GLN D  17      -7.628   4.211   2.361  1.00 56.37           D  C
ATOM    9759  O    GLN D  17      -6.617   3.508   2.460  1.00 56.82           D  O
ATOM    9761  N    LYS D  18      -7.938   4.898   1.271  1.00 55.96           D  N
ATOM    9762  CA   LYS D  18      -7.043   5.041   0.164  1.00 55.75           D  C
ATOM    9764  CB   LYS D  18      -7.774   4.798  -1.166  1.00 55.88           D  C
ATOM    9771  C    LYS D  18      -6.563   6.472   0.242  1.00 55.60           D  C
ATOM    9772  O    LYS D  18      -7.351   7.391   0.496  1.00 56.12           D  O
ATOM    9774  N    VAL D  19      -5.267   6.679   0.062  1.00 54.96           D  N
ATOM    9775  CA   VAL D  19      -4.786   8.030  -0.092  1.00 54.40           D  C
ATOM    9777  CB   VAL D  19      -3.880   8.488   1.075  1.00 54.42           D  C
ATOM    9779  CG1  VAL D  19      -2.428   8.205   0.791  1.00 54.17           D  C
ATOM    9783  CG2  VAL D  19      -4.091   9.987   1.329  1.00 54.61           D  C
ATOM    9787  C    VAL D  19      -4.082   8.067  -1.414  1.00 53.81           D  C
ATOM    9788  O    VAL D  19      -3.734   7.028  -1.952  1.00 53.05           D  O
ATOM    9790  N    THR D  20      -3.903   9.279  -1.918  1.00 53.52           D  N
ATOM    9791  CA   THR D  20      -3.408   9.536  -3.255  1.00 53.84           D  C
ATOM    9793  CB   THR D  20      -4.603   9.832  -4.229  1.00 53.91           D  C
ATOM    9795  OG1  THR D  20      -4.383  11.059  -4.946  1.00 54.22           D  O
ATOM    9797  CG2  THR D  20      -5.922   9.975  -3.447  1.00 54.18           D  C
ATOM    9801  C    THR D  20      -2.451  10.743  -3.146  1.00 53.86           D  C
ATOM    9802  O    THR D  20      -2.762  11.730  -2.474  1.00 53.60           D  O
ATOM    9804  N    ILE D  21      -1.279  10.653  -3.768  1.00 53.80           D  N
ATOM    9805  CA   ILE D  21      -0.315  11.745  -3.686  1.00 53.53           D  C
ATOM    9807  CB   ILE D  21       0.935  11.380  -2.856  1.00 53.59           D  C
ATOM    9809  CG1  ILE D  21       0.538  10.939  -1.452  1.00 53.41           D  C
ATOM    9812  CD1  ILE D  21       1.721  10.469  -0.621  1.00 54.20           D  C
```

Figure 8 – CONT.

```
ATOM   9816  CG2 ILE D  21       1.887  12.585  -2.759  1.00 52.72           D  C
ATOM   9820  C   ILE D  21       0.090  12.143  -5.081  1.00 53.71           D  C
ATOM   9821  O   ILE D  21       0.567  11.315  -5.867  1.00 54.06           D  O
ATOM   9823  N   SER D  22      -0.103  13.420  -5.375  1.00 53.32           D  N
ATOM   9824  CA  SER D  22       0.130  13.948  -6.695  1.00 53.46           D  C
ATOM   9826  CB  SER D  22      -0.837  15.105  -6.963  1.00 53.50           D  C
ATOM   9829  OG  SER D  22      -0.284  16.335  -6.511  1.00 55.11           D  O
ATOM   9831  C   SER D  22       1.573  14.448  -6.823  1.00 53.00           D  C
ATOM   9832  O   SER D  22       2.185  14.879  -5.839  1.00 52.89           D  O
ATOM   9834  N   CYS D  23       2.098  14.390  -8.045  1.00 52.17           D  N
ATOM   9835  CA  CYS D  23       3.399  14.957  -8.381  1.00 51.41           D  C
ATOM   9837  CB  CYS D  23       4.475  13.851  -8.426  1.00 51.07           D  C
ATOM   9840  SG  CYS D  23       6.129  14.394  -8.887  1.00 50.70           D  S
ATOM   9842  C   CYS D  23       3.248  15.641  -9.737  1.00 51.25           D  C
ATOM   9843  O   CYS D  23       2.809  15.023 -10.712  1.00 51.15           D  O
ATOM   9845  N   SER D  24       3.627  16.906  -9.793  1.00 50.86           D  N
ATOM   9846  CA  SER D  24       3.351  17.725 -10.935  1.00 51.34           D  C
ATOM   9848  CB  SER D  24       2.374  18.835 -10.533  1.00 51.51           D  C
ATOM   9851  OG  SER D  24       2.509  19.953 -11.386  1.00 52.85           D  O
ATOM   9853  C   SER D  24       4.632  18.334 -11.443  1.00 51.11           D  C
ATOM   9854  O   SER D  24       5.368  18.956 -10.683  1.00 51.65           D  O
ATOM   9856  N   GLY D  25       4.875  18.196 -12.738  1.00 50.97           D  N
ATOM   9857  CA  GLY D  25       6.147  18.591 -13.308  1.00 51.04           D  C
ATOM   9860  C   GLY D  25       6.042  19.393 -14.582  1.00 50.91           D  C
ATOM   9861  O   GLY D  25       5.145  20.216 -14.742  1.00 50.88           D  O
ATOM   9863  N   SER D  26       6.983  19.161 -15.485  1.00 50.83           D  N
ATOM   9864  CA  SER D  26       7.054  19.907 -16.721  1.00 50.83           D  C
ATOM   9866  CB  SER D  26       8.139  20.997 -16.638  1.00 50.79           D  C
ATOM   9869  OG  SER D  26       9.422  20.506 -16.990  1.00 52.39           D  O
ATOM   9871  C   SER D  26       7.307  18.964 -17.886  1.00 50.69           D  C
ATOM   9872  O   SER D  26       7.469  17.744 -17.708  1.00 50.61           D  O
ATOM   9874  N   SER D  27       7.317  19.552 -19.078  1.00 50.05           D  N
ATOM   9875  CA  SER D  27       7.468  18.822 -20.331  1.00 49.96           D  C
ATOM   9877  CB  SER D  27       7.292  19.821 -21.495  1.00 50.16           D  C
ATOM   9880  OG  SER D  27       7.669  19.279 -22.740  1.00 51.09           D  O
ATOM   9882  C   SER D  27       8.811  18.074 -20.412  1.00 49.00           D  C
ATOM   9883  O   SER D  27       8.866  16.913 -20.792  1.00 48.94           D  O
ATOM   9885  N   SER D  27A      9.879  18.754 -20.014  1.00 48.71           D  N
ATOM   9886  CA  SER D  27A     11.245  18.220 -20.067  1.00 47.91           D  C
ATOM   9888  CB  SER D  27A     12.251  19.377 -20.003  1.00 47.92           D  C
ATOM   9891  OG  SER D  27A     12.216  20.022 -18.735  1.00 47.58           D  O
ATOM   9893  C   SER D  27A     11.568  17.197 -18.967  1.00 47.42           D  C
ATOM   9894  O   SER D  27A     12.520  16.426 -19.111  1.00 47.01           D  O
ATOM   9896  N   ASP D  27B     10.809  17.197 -17.868  1.00 46.84           D  N
ATOM   9897  CA  ASP D  27B     11.018  16.190 -16.826  1.00 46.25           D  C
ATOM   9899  CB  ASP D  27B     11.193  16.796 -15.418  1.00 46.39           D  C
ATOM   9902  CG  ASP D  27B     10.057  17.724 -14.988  1.00 45.80           D  C
ATOM   9903  OD1 ASP D  27B     10.304  18.945 -14.859  1.00 44.75           D  O
ATOM   9904  OD2 ASP D  27B      8.941  17.227 -14.734  1.00 45.26           D  O
ATOM   9905  C   ASP D  27B     10.006  15.037 -16.906  1.00 45.78           D  C
ATOM   9906  O   ASP D  27B     10.218  14.140 -17.701  1.00 45.41           D  O
ATOM   9908  N   ILE D  28       8.941  15.040 -16.109  1.00 45.40           D  N
ATOM   9909  CA  ILE D  28       7.910  13.973 -16.159  1.00 45.96           D  C
ATOM   9911  CB  ILE D  28       6.705  14.274 -15.222  1.00 46.02           D  C
ATOM   9913  CG1 ILE D  28       7.146  14.339 -13.761  1.00 46.87           D  C
ATOM   9916  CD1 ILE D  28       5.958  14.544 -12.788  1.00 48.33           D  C
ATOM   9920  CG2 ILE D  28       5.577  13.239 -15.387  1.00 44.78           D  C
ATOM   9924  C   ILE D  28       7.340  13.801 -17.559  1.00 46.00           D  C
```

Figure 8 – CONT.

```
ATOM   9925  O    ILE D  28       6.969  12.694 -17.962  1.00 45.81      D  O
ATOM   9927  N    GLY D  29       7.271  14.906 -18.293  1.00 46.19      D  N
ATOM   9928  CA   GLY D  29       6.775  14.879 -19.669  1.00 46.83      D  C
ATOM   9931  C    GLY D  29       7.575  13.966 -20.581  1.00 46.82      D  C
ATOM   9932  O    GLY D  29       7.018  13.374 -21.519  1.00 47.01      D  O
ATOM   9934  N    SER D  30       8.865  13.809 -20.280  1.00 45.93      D  N
ATOM   9935  CA   SER D  30       9.761  13.102 -21.169  1.00 45.48      D  C
ATOM   9937  CB   SER D  30      10.889  14.037 -21.580  1.00 45.46      D  C
ATOM   9940  OG   SER D  30      10.391  15.257 -22.096  1.00 46.68      D  O
ATOM   9942  C    SER D  30      10.373  11.829 -20.590  1.00 44.72      D  C
ATOM   9943  O    SER D  30      11.154  11.169 -21.286  1.00 44.18      D  O
ATOM   9945  N    ASN D  31      10.027  11.482 -19.346  1.00 43.43      D  N
ATOM   9946  CA   ASN D  31      10.816  10.510 -18.593  1.00 42.43      D  C
ATOM   9948  CB   ASN D  31      11.926  11.219 -17.811  1.00 42.32      D  C
ATOM   9951  CG   ASN D  31      13.045  11.754 -18.719  1.00 41.41      D  C
ATOM   9952  OD1  ASN D  31      13.852  10.980 -19.243  1.00 43.36      D  O
ATOM   9953  ND2  ASN D  31      13.083  13.068 -18.921  1.00 38.48      D  N
ATOM   9956  C    ASN D  31       9.979   9.684 -17.652  1.00 42.13      D  C
ATOM   9957  O    ASN D  31       8.853  10.043 -17.337  1.00 42.26      D  O
ATOM   9959  N    TYR D  32      10.524   8.548 -17.233  1.00 41.63      D  N
ATOM   9960  CA   TYR D  32       9.852   7.694 -16.274  1.00 41.65      D  C
ATOM   9962  CB   TYR D  32      10.537   6.351 -16.186  1.00 42.36      D  C
ATOM   9965  CG   TYR D  32      10.392   5.484 -17.408  1.00 44.43      D  C
ATOM   9966  CD1  TYR D  32       9.254   4.688 -17.586  1.00 46.05      D  C
ATOM   9968  CE1  TYR D  32       9.121   3.861 -18.694  1.00 47.28      D  C
ATOM   9970  CZ   TYR D  32      10.130   3.820 -19.640  1.00 48.66      D  C
ATOM   9971  OH   TYR D  32       9.988   3.002 -20.753  1.00 53.24      D  O
ATOM   9973  CE2  TYR D  32      11.269   4.609 -19.494  1.00 46.65      D  C
ATOM   9975  CD2  TYR D  32      11.402   5.429 -18.374  1.00 44.79      D  C
ATOM   9977  C    TYR D  32       9.871   8.352 -14.893  1.00 40.51      D  C
ATOM   9978  O    TYR D  32      10.692   9.203 -14.633  1.00 39.89      D  O
ATOM   9980  N    VAL D  33       8.941   7.960 -14.038  1.00 39.86      D  N
ATOM   9981  CA   VAL D  33       8.742   8.607 -12.743  1.00 39.60      D  C
ATOM   9983  CB   VAL D  33       7.314   9.199 -12.603  1.00 39.51      D  C
ATOM   9985  CG1  VAL D  33       6.983   9.533 -11.122  1.00 38.31      D  C
ATOM   9989  CG2  VAL D  33       7.163  10.435 -13.494  1.00 37.88      D  C
ATOM   9993  C    VAL D  33       8.960   7.570 -11.676  1.00 39.68      D  C
ATOM   9994  O    VAL D  33       8.496   6.466 -11.814  1.00 40.19      D  O
ATOM   9996  N    SER D  34       9.677   7.941 -10.619  1.00 39.91      D  N
ATOM   9997  CA   SER D  34       9.919   7.067  -9.486  1.00 40.05      D  C
ATOM   9999  CB   SER D  34      11.432   6.848  -9.333  1.00 40.49      D  C
ATOM  10002  OG   SER D  34      11.918   5.905 -10.266  1.00 41.02      D  O
ATOM  10004  C    SER D  34       9.376   7.708  -8.203  1.00 39.59      D  C
ATOM  10005  O    SER D  34       9.238   8.933  -8.112  1.00 39.15      D  O
ATOM  10007  N    TRP D  35       9.119   6.864  -7.216  1.00 39.67      D  N
ATOM  10008  CA   TRP D  35       8.735   7.283  -5.873  1.00 39.75      D  C
ATOM  10010  CB   TRP D  35       7.293   6.885  -5.576  1.00 40.39      D  C
ATOM  10013  CG   TRP D  35       6.310   7.603  -6.430  1.00 42.98      D  C
ATOM  10014  CD1  TRP D  35       5.846   7.211  -7.662  1.00 42.31      D  C
ATOM  10016  NE1  TRP D  35       4.985   8.144  -8.150  1.00 44.65      D  N
ATOM  10018  CE2  TRP D  35       4.850   9.161  -7.244  1.00 44.85      D  C
ATOM  10019  CD2  TRP D  35       5.683   8.859  -6.147  1.00 44.94      D  C
ATOM  10020  CE3  TRP D  35       5.736   9.753  -5.071  1.00 47.22      D  C
ATOM  10022  CZ3  TRP D  35       4.957  10.904  -5.125  1.00 47.98      D  C
ATOM  10024  CH2  TRP D  35       4.138  11.167  -6.238  1.00 47.51      D  C
ATOM  10026  CZ2  TRP D  35       4.082  10.310  -7.303  1.00 45.81      D  C
ATOM  10028  C    TRP D  35       9.631   6.634  -4.836  1.00 39.20      D  C
ATOM  10029  O    TRP D  35      10.003   5.459  -4.990  1.00 38.14      D  O
```

Figure 8 – CONT.

| | | | | | | | | | | | |
|---|---|---|---|---|---|---|---|---|---|---|---|
| ATOM | 10031 | N | TYR | D | 36 | 9.949 | 7.403 | -3.781 | 1.00 38.36 | D | N |
| ATOM | 10032 | CA | TYR | D | 36 | 10.785 | 6.940 | -2.684 | 1.00 38.14 | D | C |
| ATOM | 10034 | CB | TYR | D | 36 | 12.120 | 7.687 | -2.714 | 1.00 38.60 | D | C |
| ATOM | 10037 | CG | TYR | D | 36 | 12.787 | 7.620 | -4.064 | 1.00 38.04 | D | C |
| ATOM | 10038 | CD1 | TYR | D | 36 | 13.596 | 6.557 | -4.394 | 1.00 38.96 | D | C |
| ATOM | 10040 | CE1 | TYR | D | 36 | 14.180 | 6.451 | -5.633 | 1.00 38.28 | D | C |
| ATOM | 10042 | CZ | TYR | D | 36 | 13.953 | 7.403 | -6.578 | 1.00 36.78 | D | C |
| ATOM | 10043 | OH | TYR | D | 36 | 14.568 | 7.261 | -7.823 | 1.00 39.74 | D | O |
| ATOM | 10045 | CE2 | TYR | D | 36 | 13.132 | 8.466 | -6.292 | 1.00 36.81 | D | C |
| ATOM | 10047 | CD2 | TYR | D | 36 | 12.548 | 8.571 | -5.036 | 1.00 38.19 | D | C |
| ATOM | 10049 | C | TYR | D | 36 | 10.087 | 7.115 | -1.324 | 1.00 37.91 | D | C |
| ATOM | 10050 | O | TYR | D | 36 | 9.446 | 8.120 | -1.065 | 1.00 38.73 | D | O |
| ATOM | 10052 | N | GLN | D | 37 | 10.202 | 6.115 | -0.475 | 1.00 37.14 | D | N |
| ATOM | 10053 | CA | GLN | D | 37 | 9.647 | 6.146 | 0.869 | 1.00 37.47 | D | C |
| ATOM | 10055 | CB | GLN | D | 37 | 8.973 | 4.810 | 1.197 | 1.00 37.13 | D | C |
| ATOM | 10058 | CG | GLN | D | 37 | 8.288 | 4.793 | 2.545 | 1.00 38.71 | D | C |
| ATOM | 10061 | CD | GLN | D | 37 | 7.711 | 3.433 | 2.914 | 1.00 41.31 | D | C |
| ATOM | 10062 | OE1 | GLN | D | 37 | 6.513 | 3.315 | 3.176 | 1.00 43.96 | D | O |
| ATOM | 10063 | NE2 | GLN | D | 37 | 8.556 | 2.412 | 2.950 | 1.00 41.14 | D | N |
| ATOM | 10066 | C | GLN | D | 37 | 10.753 | 6.344 | 1.898 | 1.00 37.46 | D | C |
| ATOM | 10067 | O | GLN | D | 37 | 11.642 | 5.505 | 2.000 | 1.00 37.62 | D | O |
| ATOM | 10069 | N | GLN | D | 38 | 10.655 | 7.395 | 2.700 | 1.00 37.29 | D | N |
| ATOM | 10070 | CA | GLN | D | 38 | 11.616 | 7.636 | 3.789 | 1.00 37.51 | D | C |
| ATOM | 10072 | CB | GLN | D | 38 | 12.337 | 8.964 | 3.573 | 1.00 37.07 | D | C |
| ATOM | 10075 | CG | GLN | D | 38 | 13.515 | 9.179 | 4.550 | 1.00 36.00 | D | C |
| ATOM | 10078 | CD | GLN | D | 38 | 14.295 | 10.438 | 4.269 | 1.00 31.81 | D | C |
| ATOM | 10079 | OE1 | GLN | D | 38 | 13.760 | 11.433 | 3.768 | 1.00 29.78 | D | O |
| ATOM | 10080 | NE2 | GLN | D | 38 | 15.566 | 10.413 | 4.620 | 1.00 31.14 | D | N |
| ATOM | 10083 | C | GLN | D | 38 | 10.953 | 7.651 | 5.182 | 1.00 38.30 | D | C |
| ATOM | 10084 | O | GLN | D | 38 | 10.288 | 8.593 | 5.550 | 1.00 37.27 | D | O |
| ATOM | 10086 | N | PHE | D | 39 | 11.164 | 6.591 | 5.941 | 1.00 39.63 | D | N |
| ATOM | 10087 | CA | PHE | D | 39 | 10.840 | 6.587 | 7.340 | 1.00 40.57 | D | C |
| ATOM | 10089 | CB | PHE | D | 39 | 11.031 | 5.192 | 7.896 | 1.00 40.45 | D | C |
| ATOM | 10092 | CG | PHE | D | 39 | 10.101 | 4.191 | 7.301 | 1.00 43.78 | D | C |
| ATOM | 10093 | CD1 | PHE | D | 39 | 8.729 | 4.350 | 7.423 | 1.00 45.92 | D | C |
| ATOM | 10095 | CE1 | PHE | D | 39 | 7.854 | 3.416 | 6.868 | 1.00 46.30 | D | C |
| ATOM | 10097 | CZ | PHE | D | 39 | 8.352 | 2.315 | 6.191 | 1.00 47.45 | D | C |
| ATOM | 10099 | CE2 | PHE | D | 39 | 9.722 | 2.137 | 6.064 | 1.00 46.96 | D | C |
| ATOM | 10101 | CD2 | PHE | D | 39 | 10.589 | 3.070 | 6.623 | 1.00 46.61 | D | C |
| ATOM | 10103 | C | PHE | D | 39 | 11.729 | 7.593 | 8.074 | 1.00 40.37 | D | C |
| ATOM | 10104 | O | PHE | D | 39 | 12.720 | 8.032 | 7.517 | 1.00 40.22 | D | O |
| ATOM | 10106 | N | PRO | D | 40 | 11.345 | 8.003 | 9.301 | 1.00 41.00 | D | N |
| ATOM | 10107 | CA | PRO | D | 40 | 12.158 | 9.018 | 9.992 | 1.00 41.24 | D | C |
| ATOM | 10109 | CB | PRO | D | 40 | 11.268 | 9.442 | 11.183 | 1.00 41.65 | D | C |
| ATOM | 10112 | CG | PRO | D | 40 | 9.874 | 9.152 | 10.732 | 1.00 41.44 | D | C |
| ATOM | 10115 | CD | PRO | D | 40 | 10.004 | 7.876 | 9.918 | 1.00 41.56 | D | C |
| ATOM | 10118 | C | PRO | D | 40 | 13.468 | 8.435 | 10.460 | 1.00 40.74 | D | C |
| ATOM | 10119 | O | PRO | D | 40 | 13.510 | 7.258 | 10.845 | 1.00 41.35 | D | O |
| ATOM | 10120 | N | GLY | D | 41 | 14.541 | 9.223 | 10.389 | 1.00 40.26 | D | N |
| ATOM | 10121 | CA | GLY | D | 41 | 15.882 | 8.701 | 10.694 | 1.00 39.76 | D | C |
| ATOM | 10124 | C | GLY | D | 41 | 16.360 | 7.514 | 9.839 | 1.00 39.73 | D | C |
| ATOM | 10125 | O | GLY | D | 41 | 17.242 | 6.753 | 10.268 | 1.00 40.13 | D | O |
| ATOM | 10127 | N | THR | D | 42 | 15.798 | 7.353 | 8.636 | 1.00 38.47 | D | N |
| ATOM | 10128 | CA | THR | D | 42 | 16.148 | 6.245 | 7.743 | 1.00 37.93 | D | C |
| ATOM | 10130 | CB | THR | D | 42 | 14.996 | 5.185 | 7.707 | 1.00 38.20 | D | C |
| ATOM | 10132 | OG1 | THR | D | 42 | 14.886 | 4.585 | 9.003 | 1.00 41.96 | D | O |
| ATOM | 10134 | CG2 | THR | D | 42 | 15.281 | 4.061 | 6.745 | 1.00 39.42 | D | C |
| ATOM | 10138 | C | THR | D | 42 | 16.482 | 6.760 | 6.332 | 1.00 36.13 | D | C |

Figure 8 – CONT.

```
ATOM  10139  O    THR D  42      16.037   7.836   5.913  1.00 35.78      D  O
ATOM  10141  N    ALA D  43      17.302   6.006   5.616  1.00 34.70      D  N
ATOM  10142  CA   ALA D  43      17.574   6.289   4.214  1.00 34.32      D  C
ATOM  10144  CB   ALA D  43      18.661   5.352   3.661  1.00 33.79      D  C
ATOM  10148  C    ALA D  43      16.287   6.114   3.428  1.00 33.54      D  C
ATOM  10149  O    ALA D  43      15.439   5.306   3.775  1.00 32.65      D  O
ATOM  10151  N    PRO D  44      16.129   6.894   2.371  1.00 33.53      D  N
ATOM  10152  CA   PRO D  44      15.053   6.633   1.466  1.00 33.84      D  C
ATOM  10154  CB   PRO D  44      15.225   7.700   0.400  1.00 33.39      D  C
ATOM  10157  CG   PRO D  44      15.989   8.739   1.014  1.00 33.57      D  C
ATOM  10160  CD   PRO D  44      16.932   8.032   1.918  1.00 34.07      D  C
ATOM  10163  C    PRO D  44      15.214   5.277   0.835  1.00 34.34      D  C
ATOM  10164  O    PRO D  44      16.308   4.719   0.825  1.00 33.88      D  O
ATOM  10165  N    LYS D  45      14.120   4.793   0.273  1.00 35.80      D  N
ATOM  10166  CA   LYS D  45      14.049   3.490  -0.355  1.00 36.72      D  C
ATOM  10168  CB   LYS D  45      13.396   2.518   0.603  1.00 37.26      D  C
ATOM  10171  CG   LYS D  45      13.419   1.074   0.126  1.00 40.39      D  C
ATOM  10174  CD   LYS D  45      12.937   0.113   1.237  1.00 41.56      D  C
ATOM  10177  CE   LYS D  45      11.504   0.378   1.621  1.00 42.39      D  C
ATOM  10180  NZ   LYS D  45      10.886  -0.852   2.187  1.00 44.14      D  N
ATOM  10184  C    LYS D  45      13.199   3.637  -1.595  1.00 37.23      D  C
ATOM  10185  O    LYS D  45      12.151   4.284  -1.576  1.00 37.15      D  O
ATOM  10187  N    LEU D  46      13.665   3.051  -2.688  1.00 38.23      D  N
ATOM  10188  CA   LEU D  46      12.901   3.010  -3.935  1.00 37.85      D  C
ATOM  10190  CB   LEU D  46      13.712   2.306  -5.042  1.00 37.11      D  C
ATOM  10193  CG   LEU D  46      13.054   2.297  -6.439  1.00 37.00      D  C
ATOM  10195  CD1  LEU D  46      12.719   3.740  -6.900  1.00 31.89      D  C
ATOM  10199  CD2  LEU D  46      13.904   1.552  -7.488  1.00 34.56      D  C
ATOM  10203  C    LEU D  46      11.577   2.276  -3.707  1.00 37.55      D  C
ATOM  10204  O    LEU D  46      11.584   1.136  -3.289  1.00 37.79      D  O
ATOM  10206  N    LEU D  47      10.466   2.943  -4.012  1.00 37.91      D  N
ATOM  10207  CA   LEU D  47       9.123   2.415  -3.777  1.00 38.12      D  C
ATOM  10209  CB   LEU D  47       8.320   3.513  -3.122  1.00 38.36      D  C
ATOM  10212  CG   LEU D  47       6.884   3.226  -2.726  1.00 37.64      D  C
ATOM  10214  CD1  LEU D  47       6.869   2.239  -1.606  1.00 36.60      D  C
ATOM  10218  CD2  LEU D  47       6.215   4.545  -2.360  1.00 37.84      D  C
ATOM  10222  C    LEU D  47       8.397   1.997  -5.062  1.00 38.67      D  C
ATOM  10223  O    LEU D  47       7.765   0.936  -5.129  1.00 37.80      D  O
ATOM  10225  N    ILE D  48       8.444   2.899  -6.037  1.00 38.93      D  N
ATOM  10226  CA   ILE D  48       7.924   2.684  -7.374  1.00 39.31      D  C
ATOM  10228  CB   ILE D  48       6.648   3.522  -7.642  1.00 39.47      D  C
ATOM  10230  CG1  ILE D  48       5.467   3.075  -6.779  1.00 39.00      D  C
ATOM  10233  CD1  ILE D  48       4.875   1.751  -7.186  1.00 38.14      D  C
ATOM  10237  CG2  ILE D  48       6.252   3.457  -9.153  1.00 40.77      D  C
ATOM  10241  C    ILE D  48       8.969   3.200  -8.372  1.00 39.08      D  C
ATOM  10242  O    ILE D  48       9.589   4.263  -8.150  1.00 39.19      D  O
ATOM  10244  N    TYR D  49       9.143   2.450  -9.461  1.00 38.58      D  N
ATOM  10245  CA   TYR D  49       9.913   2.893 -10.624  1.00 38.87      D  C
ATOM  10247  CB   TYR D  49      11.293   2.227 -10.622  1.00 39.46      D  C
ATOM  10250  CG   TYR D  49      11.277   0.730 -10.862  1.00 39.35      D  C
ATOM  10251  CD1  TYR D  49      11.636   0.195 -12.106  1.00 40.77      D  C
ATOM  10253  CE1  TYR D  49      11.618  -1.183 -12.327  1.00 39.42      D  C
ATOM  10255  CZ   TYR D  49      11.230  -2.013 -11.300  1.00 39.01      D  C
ATOM  10256  OH   TYR D  49      11.211  -3.367 -11.471  1.00 36.37      D  O
ATOM  10258  CE2  TYR D  49      10.872  -1.491 -10.068  1.00 39.21      D  C
ATOM  10260  CD2  TYR D  49      10.890  -0.137  -9.867  1.00 38.29      D  C
ATOM  10262  C    TYR D  49       9.215   2.611 -11.974  1.00 39.16      D  C
ATOM  10263  O    TYR D  49       8.307   1.769 -12.085  1.00 38.19      D  O
```

Figure 8 – CONT.

```
ATOM  10265  N    ASP D  50      9.691   3.307 -13.002  1.00 39.95      D  N
ATOM  10266  CA   ASP D  50      9.200   3.136 -14.374  1.00 40.67      D  C
ATOM  10268  CB   ASP D  50      9.581   1.746 -14.962  1.00 40.10      D  C
ATOM  10271  CG   ASP D  50     11.072   1.630 -15.342  1.00 39.83      D  C
ATOM  10272  OD1  ASP D  50     11.810   2.629 -15.338  1.00 35.53      D  O
ATOM  10273  OD2  ASP D  50     11.522   0.513 -15.690  1.00 41.41      D  O
ATOM  10274  C    ASP D  50      7.690   3.351 -14.304  1.00 41.09      D  C
ATOM  10275  O    ASP D  50      6.896   2.508 -14.723  1.00 40.89      D  O
ATOM  10277  N    ASN D  51      7.326   4.484 -13.712  1.00 42.12      D  N
ATOM  10278  CA   ASN D  51      5.931   4.918 -13.528  1.00 42.57      D  C
ATOM  10280  CB   ASN D  51      5.215   5.044 -14.880  1.00 42.83      D  C
ATOM  10283  CG   ASN D  51      5.888   6.034 -15.807  1.00 43.52      D  C
ATOM  10284  OD1  ASN D  51      6.705   6.847 -15.388  1.00 45.31      D  O
ATOM  10285  ND2  ASN D  51      5.515   5.990 -17.076  1.00 43.78      D  N
ATOM  10288  C    ASN D  51      5.072   4.066 -12.608  1.00 42.74      D  C
ATOM  10289  O    ASN D  51      4.343   4.605 -11.785  1.00 42.92      D  O
ATOM  10291  N    ASN D  52      5.115   2.753 -12.751  1.00 43.52      D  N
ATOM  10292  CA   ASN D  52      4.125   1.912 -12.082  1.00 44.51      D  C
ATOM  10294  CB   ASN D  52      2.902   1.709 -13.004  1.00 44.52      D  C
ATOM  10297  CG   ASN D  52      3.281   1.179 -14.376  1.00 45.48      D  C
ATOM  10298  OD1  ASN D  52      4.069   0.247 -14.501  1.00 43.30      D  O
ATOM  10299  ND2  ASN D  52      2.720   1.794 -15.420  1.00 47.50      D  N
ATOM  10302  C    ASN D  52      4.584   0.567 -11.577  1.00 45.03      D  C
ATOM  10303  O    ASN D  52      3.751  -0.222 -11.130  1.00 44.77      D  O
ATOM  10305  N    LYS D  53      5.884   0.291 -11.623  1.00 46.42      D  N
ATOM  10306  CA   LYS D  53      6.386  -1.003 -11.158  1.00 47.74      D  C
ATOM  10308  CB   LYS D  53      7.549  -1.482 -12.032  1.00 47.77      D  C
ATOM  10311  CG   LYS D  53      7.232  -1.638 -13.520  1.00 48.16      D  C
ATOM  10314  CD   LYS D  53      8.377  -2.381 -14.274  1.00 48.37      D  C
ATOM  10317  CE   LYS D  53      8.482  -1.969 -15.758  1.00 49.03      D  C
ATOM  10320  NZ   LYS D  53      9.871  -2.203 -16.330  1.00 49.85      D  N
ATOM  10324  C    LYS D  53      6.836  -0.951  -9.695  1.00 48.95      D  C
ATOM  10325  O    LYS D  53      7.266   0.101  -9.182  1.00 49.29      D  O
ATOM  10327  N    ARG D  54      6.764  -2.110  -9.046  1.00 49.97      D  N
ATOM  10328  CA   ARG D  54      7.192  -2.276  -7.667  1.00 50.91      D  C
ATOM  10330  CB   ARG D  54      6.090  -2.926  -6.837  1.00 51.34      D  C
ATOM  10333  CG   ARG D  54      5.062  -1.959  -6.309  1.00 53.56      D  C
ATOM  10336  CD   ARG D  54      3.996  -2.696  -5.555  1.00 55.85      D  C
ATOM  10339  NE   ARG D  54      3.463  -3.791  -6.362  1.00 59.35      D  N
ATOM  10341  CZ   ARG D  54      2.582  -3.656  -7.354  1.00 60.82      D  C
ATOM  10342  NH1  ARG D  54      2.184  -4.739  -8.017  1.00 61.25      D  N
ATOM  10345  NH2  ARG D  54      2.086  -2.460  -7.685  1.00 60.25      D  N
ATOM  10348  C    ARG D  54      8.391  -3.184  -7.555  1.00 51.15      D  C
ATOM  10349  O    ARG D  54      8.361  -4.303  -8.068  1.00 50.99      D  O
ATOM  10351  N    PRO D  55      9.426  -2.739  -6.823  1.00 51.35      D  N
ATOM  10352  CA   PRO D  55     10.425  -3.678  -6.313  1.00 51.48      D  C
ATOM  10354  CB   PRO D  55     11.265  -2.814  -5.369  1.00 51.43      D  C
ATOM  10357  CG   PRO D  55     11.142  -1.441  -5.906  1.00 51.10      D  C
ATOM  10360  CD   PRO D  55      9.759  -1.341  -6.491  1.00 51.41      D  C
ATOM  10363  C    PRO D  55      9.763  -4.837  -5.567  1.00 51.85      D  C
ATOM  10364  O    PRO D  55      8.657  -4.673  -5.058  1.00 50.75      D  O
ATOM  10365  N    SER D  56     10.446  -5.983  -5.521  1.00 52.96      D  N
ATOM  10366  CA   SER D  56      9.900  -7.247  -4.973  1.00 53.80      D  C
ATOM  10368  CB   SER D  56     10.995  -8.333  -4.874  1.00 53.95      D  C
ATOM  10371  OG   SER D  56     11.925  -8.273  -5.943  1.00 54.80      D  O
ATOM  10373  C    SER D  56      9.305  -7.096  -3.587  1.00 54.35      D  C
ATOM  10374  O    SER D  56      8.216  -7.597  -3.307  1.00 54.14      D  O
ATOM  10376  N    ALA D  57     10.058  -6.428  -2.716  1.00 54.97      D  N
```

Figure 8 – CONT.

```
ATOM  10377  CA   ALA D  57       9.701  -6.323  -1.313  1.00 55.49      D C
ATOM  10379  CB   ALA D  57      10.908  -5.857  -0.489  1.00 55.73      D C
ATOM  10383  C    ALA D  57       8.520  -5.391  -1.096  1.00 55.86      D C
ATOM  10384  O    ALA D  57       7.861  -5.481  -0.064  1.00 56.55      D O
ATOM  10386  N    ILE D  58       8.245  -4.507  -2.055  1.00 56.26      D N
ATOM  10387  CA   ILE D  58       7.140  -3.552  -1.930  1.00 56.81      D C
ATOM  10389  CB   ILE D  58       7.307  -2.366  -2.907  1.00 56.63      D C
ATOM  10391  CG1  ILE D  58       8.672  -1.695  -2.709  1.00 57.32      D C
ATOM  10394  CD1  ILE D  58       9.083  -1.468  -1.244  1.00 56.86      D C
ATOM  10398  CG2  ILE D  58       6.176  -1.354  -2.748  1.00 55.95      D C
ATOM  10402  C    ILE D  58       5.778  -4.242  -2.156  1.00 57.41      D C
ATOM  10403  O    ILE D  58       5.572  -4.865  -3.205  1.00 58.33      D O
ATOM  10405  N    PRO D  59       4.859  -4.160  -1.165  1.00 57.52      D N
ATOM  10406  CA   PRO D  59       3.544  -4.796  -1.332  1.00 57.42      D C
ATOM  10408  CB   PRO D  59       2.946  -4.779   0.092  1.00 57.70      D C
ATOM  10411  CG   PRO D  59       3.685  -3.700   0.823  1.00 57.32      D C
ATOM  10414  CD   PRO D  59       5.067  -3.669   0.216  1.00 57.54      D C
ATOM  10417  C    PRO D  59       2.603  -4.088  -2.299  1.00 57.40      D C
ATOM  10418  O    PRO D  59       2.780  -2.915  -2.608  1.00 57.14      D O
ATOM  10419  N    ASP D  60       1.568  -4.820  -2.694  1.00 57.50      D N
ATOM  10420  CA   ASP D  60       0.619  -4.439  -3.743  1.00 57.75      D C
ATOM  10422  CB   ASP D  60      -0.443  -5.538  -3.918  1.00 58.29      D C
ATOM  10425  CG   ASP D  60       0.110  -6.955  -3.692  1.00 60.37      D C
ATOM  10426  OD1  ASP D  60       1.144  -7.100  -2.985  1.00 62.26      D O
ATOM  10427  OD2  ASP D  60      -0.509  -7.926  -4.209  1.00 62.89      D O
ATOM  10428  C    ASP D  60      -0.115  -3.135  -3.458  1.00 57.23      D C
ATOM  10429  O    ASP D  60      -0.544  -2.444  -4.378  1.00 57.16      D O
ATOM  10431  N    ARG D  61      -0.261  -2.821  -2.174  1.00 56.70      D N
ATOM  10432  CA   ARG D  61      -1.005  -1.654  -1.703  1.00 55.89      D C
ATOM  10434  CB   ARG D  61      -0.994  -1.635  -0.170  1.00 56.32      D C
ATOM  10437  CG   ARG D  61      -1.623  -2.888   0.454  1.00 57.52      D C
ATOM  10440  CD   ARG D  61      -1.668  -2.848   1.984  1.00 58.67      D C
ATOM  10443  NE   ARG D  61      -0.346  -2.756   2.622  1.00 58.67      D N
ATOM  10445  CZ   ARG D  61       0.184  -1.643   3.144  1.00 58.38      D C
ATOM  10446  NH1  ARG D  61      -0.454  -0.470   3.114  1.00 56.72      D N
ATOM  10449  NH2  ARG D  61       1.380  -1.703   3.707  1.00 59.71      D N
ATOM  10452  C    ARG D  61      -0.483  -0.329  -2.262  1.00 54.56      D C
ATOM  10453  O    ARG D  61      -1.233   0.640  -2.389  1.00 54.41      D O
ATOM  10455  N    PHE D  62       0.798  -0.301  -2.613  1.00 53.31      D N
ATOM  10456  CA   PHE D  62       1.410   0.877  -3.232  1.00 52.29      D C
ATOM  10458  CB   PHE D  62       2.872   1.004  -2.803  1.00 52.41      D C
ATOM  10461  CG   PHE D  62       3.045   1.260  -1.337  1.00 51.94      D C
ATOM  10462  CD1  PHE D  62       3.094   2.556  -0.849  1.00 51.72      D C
ATOM  10464  CE1  PHE D  62       3.234   2.793   0.513  1.00 52.62      D C
ATOM  10466  CZ   PHE D  62       3.324   1.731   1.398  1.00 51.35      D C
ATOM  10468  CE2  PHE D  62       3.279   0.454   0.927  1.00 53.01      D C
ATOM  10470  CD2  PHE D  62       3.130   0.216  -0.448  1.00 52.36      D C
ATOM  10472  C    PHE D  62       1.346   0.766  -4.740  1.00 51.73      D C
ATOM  10473  O    PHE D  62       1.578  -0.294  -5.299  1.00 50.85      D O
ATOM  10475  N    SER D  63       1.039   1.869  -5.400  1.00 50.98      D N
ATOM  10476  CA   SER D  63       0.918   1.855  -6.832  1.00 50.81      D C
ATOM  10478  CB   SER D  63      -0.509   1.431  -7.227  1.00 51.26      D C
ATOM  10481  OG   SER D  63      -1.485   2.385  -6.799  1.00 51.55      D O
ATOM  10483  C    SER D  63       1.250   3.229  -7.369  1.00 50.42      D C
ATOM  10484  O    SER D  63       1.283   4.204  -6.611  1.00 49.66      D O
ATOM  10486  N    GLY D  64       1.507   3.302  -8.672  1.00 50.14      D N
ATOM  10487  CA   GLY D  64       1.803   4.571  -9.328  1.00 50.31      D C
ATOM  10490  C    GLY D  64       1.255   4.662 -10.740  1.00 50.55      D C
```

Figure 8 – CONT.

```
ATOM  10491  O    GLY D  64       1.005   3.648 -11.394  1.00 50.80        D  O
ATOM  10493  N    SER D  65       1.069   5.887 -11.210  1.00 50.65        D  N
ATOM  10494  CA   SER D  65       0.684   6.126 -12.584  1.00 50.86        D  C
ATOM  10496  CB   SER D  65      -0.841   6.150 -12.718  1.00 50.88        D  C
ATOM  10499  OG   SER D  65      -1.431   7.097 -11.850  1.00 50.60        D  O
ATOM  10501  C    SER D  65       1.282   7.449 -13.013  1.00 51.09        D  C
ATOM  10502  O    SER D  65       1.672   8.250 -12.177  1.00 50.81        D  O
ATOM  10504  N    LYS D  66       1.379   7.655 -14.322  1.00 51.45        D  N
ATOM  10505  CA   LYS D  66       1.837   8.915 -14.881  1.00 51.52        D  C
ATOM  10507  CB   LYS D  66       3.257   8.793 -15.444  1.00 51.27        D  C
ATOM  10510  CG   LYS D  66       3.750  10.025 -16.218  1.00 50.67        D  C
ATOM  10513  CD   LYS D  66       5.094   9.775 -16.915  1.00 50.91        D  C
ATOM  10516  CE   LYS D  66       5.087  10.256 -18.368  1.00 50.43        D  C
ATOM  10519  NZ   LYS D  66       6.337   9.903 -19.103  1.00 48.61        D  N
ATOM  10523  C    LYS D  66       0.871   9.296 -15.982  1.00 52.00        D  C
ATOM  10524  O    LYS D  66       0.419   8.443 -16.747  1.00 52.37        D  O
ATOM  10526  N    SER D  67       0.551  10.582 -16.056  1.00 52.49        D  N
ATOM  10527  CA   SER D  67      -0.269  11.094 -17.136  1.00 52.62        D  C
ATOM  10529  CB   SER D  67      -1.744  11.077 -16.743  1.00 52.95        D  C
ATOM  10532  OG   SER D  67      -2.515  11.877 -17.634  1.00 54.93        D  O
ATOM  10534  C    SER D  67       0.180  12.503 -17.440  1.00 52.25        D  C
ATOM  10535  O    SER D  67       0.063  13.384 -16.597  1.00 52.40        D  O
ATOM  10537  N    GLY D  68       0.692  12.698 -18.653  1.00 51.73        D  N
ATOM  10538  CA   GLY D  68       1.186  13.982 -19.092  1.00 51.36        D  C
ATOM  10541  C    GLY D  68       2.406  14.357 -18.274  1.00 51.49        D  C
ATOM  10542  O    GLY D  68       3.398  13.598 -18.208  1.00 51.55        D  O
ATOM  10544  N    THR D  69       2.318  15.524 -17.642  1.00 51.16        D  N
ATOM  10545  CA   THR D  69       3.369  16.064 -16.790  1.00 50.70        D  C
ATOM  10547  CB   THR D  69       3.491  17.571 -17.019  1.00 50.77        D  C
ATOM  10549  OG1  THR D  69       2.200  18.166 -16.866  1.00 51.14        D  O
ATOM  10551  CG2  THR D  69       4.029  17.862 -18.427  1.00 51.43        D  C
ATOM  10555  C    THR D  69       3.063  15.786 -15.312  1.00 50.13        D  C
ATOM  10556  O    THR D  69       3.629  16.417 -14.422  1.00 49.97        D  O
ATOM  10558  N    SER D  70       2.174  14.828 -15.056  1.00 49.69        D  N
ATOM  10559  CA   SER D  70       1.795  14.488 -13.700  1.00 49.28        D  C
ATOM  10561  CB   SER D  70       0.343  14.868 -13.425  1.00 49.59        D  C
ATOM  10564  OG   SER D  70       0.158  16.248 -13.637  1.00 50.20        D  O
ATOM  10566  C    SER D  70       1.926  13.010 -13.462  1.00 48.48        D  C
ATOM  10567  O    SER D  70       1.836  12.200 -14.377  1.00 48.48        D  O
ATOM  10569  N    ALA D  71       2.109  12.676 -12.196  1.00 47.46        D  N
ATOM  10570  CA   ALA D  71       2.071  11.308 -11.743  1.00 46.99        D  C
ATOM  10572  CB   ALA D  71       3.496  10.709 -11.680  1.00 46.96        D  C
ATOM  10576  C    ALA D  71       1.436  11.336 -10.379  1.00 46.14        D  C
ATOM  10577  O    ALA D  71       1.313  12.396  -9.764  1.00 46.02        D  O
ATOM  10579  N    THR D  72       1.006  10.183  -9.916  1.00 45.53        D  N
ATOM  10580  CA   THR D  72       0.430  10.107  -8.606  1.00 45.63        D  C
ATOM  10582  CB   THR D  72      -1.130  10.368  -8.606  1.00 46.04        D  C
ATOM  10584  OG1  THR D  72      -1.831   9.205  -8.155  1.00 45.80        D  O
ATOM  10586  CG2  THR D  72      -1.640  10.820  -9.976  1.00 45.08        D  C
ATOM  10590  C    THR D  72       0.759   8.746  -8.033  1.00 45.80        D  C
ATOM  10591  O    THR D  72       0.808   7.750  -8.750  1.00 45.32        D  O
ATOM  10593  N    LEU D  73       1.020   8.732  -6.737  1.00 45.70        D  N
ATOM  10594  CA   LEU D  73       1.279   7.522  -6.011  1.00 45.69        D  C
ATOM  10596  CB   LEU D  73       2.373   7.744  -4.956  1.00 45.23        D  C
ATOM  10599  CG   LEU D  73       2.531   6.679  -3.871  1.00 43.28        D  C
ATOM  10601  CD1  LEU D  73       3.279   5.488  -4.357  1.00 42.17        D  C
ATOM  10605  CD2  LEU D  73       3.269   7.281  -2.703  1.00 45.50        D  C
ATOM  10609  C    LEU D  73      -0.016   7.142  -5.339  1.00 46.38        D  C
```

Figure 8 – CONT.

```
ATOM  10610  O    LEU D  73    -0.769   8.004  -4.917  1.00 47.36      D  O
ATOM  10612  N    GLY D  74    -0.261   5.847  -5.229  1.00 47.11      D  N
ATOM  10613  CA   GLY D  74    -1.442   5.350  -4.565  1.00 47.75      D  C
ATOM  10616  C    GLY D  74    -1.059   4.389  -3.477  1.00 48.35      D  C
ATOM  10617  O    GLY D  74    -0.175   3.546  -3.679  1.00 47.97      D  O
ATOM  10619  N    ILE D  75    -1.707   4.545  -2.322  1.00 49.18      D  N
ATOM  10620  CA   ILE D  75    -1.532   3.664  -1.184  1.00 50.25      D  C
ATOM  10622  CB   ILE D  75    -0.765   4.358  -0.019  1.00 50.62      D  C
ATOM  10624  CG1  ILE D  75     0.500   5.074  -0.531  1.00 50.39      D  C
ATOM  10627  CD1  ILE D  75     1.217   5.925   0.512  1.00 50.03      D  C
ATOM  10631  CG2  ILE D  75    -0.434   3.344   1.080  1.00 49.20      D  C
ATOM  10635  C    ILE D  75    -2.933   3.315  -0.713  1.00 51.54      D  C
ATOM  10636  O    ILE D  75    -3.761   4.210  -0.519  1.00 52.06      D  O
ATOM  10638  N    THR D  76    -3.200   2.029  -0.542  1.00 52.92      D  N
ATOM  10639  CA   THR D  76    -4.520   1.546  -0.137  1.00 54.18      D  C
ATOM  10641  CB   THR D  76    -5.197   0.646  -1.227  1.00 54.40      D  C
ATOM  10643  OG1  THR D  76    -4.729  -0.707  -1.092  1.00 53.25      D  O
ATOM  10645  CG2  THR D  76    -4.940   1.178  -2.658  1.00 53.63      D  C
ATOM  10649  C    THR D  76    -4.344   0.704   1.106  1.00 55.14      D  C
ATOM  10650  O    THR D  76    -3.248   0.238   1.380  1.00 55.35      D  O
ATOM  10652  N    GLY D  77    -5.430   0.488   1.841  1.00 56.48      D  N
ATOM  10653  CA   GLY D  77    -5.362  -0.239   3.105  1.00 57.16      D  C
ATOM  10656  C    GLY D  77    -4.323   0.369   4.028  1.00 57.68      D  C
ATOM  10657  O    GLY D  77    -3.451  -0.346   4.536  1.00 58.02      D  O
ATOM  10659  N    LEU D  78    -4.409   1.688   4.224  1.00 58.32      D  N
ATOM  10660  CA   LEU D  78    -3.471   2.426   5.096  1.00 58.74      D  C
ATOM  10662  CB   LEU D  78    -3.956   3.831   5.408  1.00 58.75      D  C
ATOM  10665  CG   LEU D  78    -3.441   4.959   4.534  1.00 59.84      D  C
ATOM  10667  CD1  LEU D  78    -3.954   4.778   3.103  1.00 60.30      D  C
ATOM  10671  CD2  LEU D  78    -3.875   6.305   5.121  1.00 58.71      D  C
ATOM  10675  C    LEU D  78    -3.296   1.743   6.421  1.00 59.11      D  C
ATOM  10676  O    LEU D  78    -4.262   1.245   7.010  1.00 59.21      D  O
ATOM  10678  N    GLN D  79    -2.056   1.728   6.885  1.00 59.08      D  N
ATOM  10679  CA   GLN D  79    -1.748   1.217   8.193  1.00 59.22      D  C
ATOM  10681  CB   GLN D  79    -0.954  -0.069   8.103  1.00 59.31      D  C
ATOM  10684  CG   GLN D  79    -1.463  -1.061   7.100  1.00 60.09      D  C
ATOM  10687  CD   GLN D  79    -0.530  -2.225   7.013  1.00 60.47      D  C
ATOM  10688  OE1  GLN D  79     0.531  -2.210   7.643  1.00 60.66      D  O
ATOM  10689  NE2  GLN D  79    -0.894  -3.237   6.226  1.00 59.85      D  N
ATOM  10692  C    GLN D  79    -0.905   2.243   8.918  1.00 59.06      D  C
ATOM  10693  O    GLN D  79    -0.465   3.248   8.334  1.00 59.37      D  O
ATOM  10695  N    THR D  80    -0.673   1.957  10.193  1.00 58.27      D  N
ATOM  10696  CA   THR D  80     0.179   2.778  11.016  1.00 57.65      D  C
ATOM  10698  CB   THR D  80     0.189   2.264  12.487  1.00 57.69      D  C
ATOM  10700  OG1  THR D  80     0.794   3.255  13.327  1.00 60.07      D  O
ATOM  10702  CG2  THR D  80     0.949   0.929  12.630  1.00 57.43      D  C
ATOM  10706  C    THR D  80     1.594   2.786  10.415  1.00 56.30      D  C
ATOM  10707  O    THR D  80     2.224   3.841  10.317  1.00 56.19      D  O
ATOM  10709  N    GLY D  81     2.052   1.612   9.972  1.00 54.82      D  N
ATOM  10710  CA   GLY D  81     3.373   1.448   9.377  1.00 53.48      D  C
ATOM  10713  C    GLY D  81     3.749   2.390   8.237  1.00 51.96      D  C
ATOM  10714  O    GLY D  81     4.928   2.645   8.034  1.00 52.16      D  O
ATOM  10716  N    ASP D  82     2.773   2.918   7.505  1.00 50.08      D  N
ATOM  10717  CA   ASP D  82     3.056   3.681   6.277  1.00 48.87      D  C
ATOM  10719  CB   ASP D  82     1.860   3.626   5.313  1.00 48.71      D  C
ATOM  10722  CG   ASP D  82     1.385   2.198   5.013  1.00 49.11      D  C
ATOM  10723  OD1  ASP D  82     2.096   1.219   5.314  1.00 49.49      D  O
ATOM  10724  OD2  ASP D  82     0.267   2.067   4.473  1.00 51.18      D  O
```

Figure 8 – CONT.

```
ATOM  10725  C    ASP D  82      3.409   5.154   6.522  1.00 48.00      D  C
ATOM  10726  O    ASP D  82      3.697   5.904   5.567  1.00 46.89      D  O
ATOM  10728  N    GLU D  83      3.364   5.565   7.791  1.00 46.73      D  N
ATOM  10729  CA   GLU D  83      3.661   6.944   8.196  1.00 46.05      D  C
ATOM  10731  CB   GLU D  83      3.398   7.105   9.708  1.00 46.66      D  C
ATOM  10734  CG   GLU D  83      2.831   8.463  10.147  1.00 49.27      D  C
ATOM  10737  CD   GLU D  83      2.023   8.384  11.468  1.00 51.64      D  C
ATOM  10738  OE1  GLU D  83      2.273   7.464  12.286  1.00 53.81      D  O
ATOM  10739  OE2  GLU D  83      1.115   9.230  11.660  1.00 53.28      D  O
ATOM  10740  C    GLU D  83      5.127   7.258   7.846  1.00 43.83      D  C
ATOM  10741  O    GLU D  83      6.022   6.556   8.273  1.00 42.86      D  O
ATOM  10743  N    ALA D  84      5.342   8.294   7.037  1.00 42.35      D  N
ATOM  10744  CA   ALA D  84      6.627   8.506   6.365  1.00 41.46      D  C
ATOM  10746  CB   ALA D  84      7.054   7.246   5.616  1.00 40.92      D  C
ATOM  10750  C    ALA D  84      6.572   9.670   5.401  1.00 40.52      D  C
ATOM  10751  O    ALA D  84      5.527  10.266   5.176  1.00 40.52      D  O
ATOM  10753  N    ASP D  85      7.723   9.987   4.830  1.00 39.43      D  N
ATOM  10754  CA   ASP D  85      7.806  10.990   3.808  1.00 38.55      D  C
ATOM  10756  CB   ASP D  85      9.018  11.883   4.065  1.00 38.42      D  C
ATOM  10759  CG   ASP D  85      8.794  12.879   5.204  1.00 39.98      D  C
ATOM  10760  OD1  ASP D  85      7.620  13.244   5.459  1.00 42.64      D  O
ATOM  10761  OD2  ASP D  85      9.788  13.322   5.812  1.00 37.53      D  O
ATOM  10762  C    ASP D  85      7.923  10.289   2.456  1.00 37.58      D  C
ATOM  10763  O    ASP D  85      8.678   9.335   2.310  1.00 37.32      D  O
ATOM  10765  N    TYR D  86      7.204  10.812   1.474  1.00 36.66      D  N
ATOM  10766  CA   TYR D  86      7.125  10.244   0.156  1.00 36.06      D  C
ATOM  10768  CB   TYR D  86      5.691   9.787  -0.117  1.00 36.39      D  C
ATOM  10771  CG   TYR D  86      5.305   8.623   0.748  1.00 35.96      D  C
ATOM  10772  CD1  TYR D  86      5.659   7.352   0.392  1.00 33.69      D  C
ATOM  10774  CE1  TYR D  86      5.325   6.273   1.171  1.00 36.08      D  C
ATOM  10776  CZ   TYR D  86      4.639   6.455   2.364  1.00 34.99      D  C
ATOM  10777  OH   TYR D  86      4.339   5.346   3.115  1.00 34.59      D  O
ATOM  10779  CE2  TYR D  86      4.280   7.719   2.769  1.00 34.41      D  C
ATOM  10781  CD2  TYR D  86      4.623   8.807   1.961  1.00 37.03      D  C
ATOM  10783  C    TYR D  86      7.523  11.276  -0.850  1.00 35.89      D  C
ATOM  10784  O    TYR D  86      6.965  12.365  -0.876  1.00 35.81      D  O
ATOM  10786  N    TYR D  87      8.476  10.899  -1.696  1.00 35.68      D  N
ATOM  10787  CA   TYR D  87      9.048  11.769  -2.693  1.00 35.58      D  C
ATOM  10789  CB   TYR D  87     10.547  11.900  -2.429  1.00 34.87      D  C
ATOM  10792  CG   TYR D  87     10.918  12.637  -1.161  1.00 31.39      D  C
ATOM  10793  CD1  TYR D  87     11.160  14.010  -1.179  1.00 29.39      D  C
ATOM  10795  CE1  TYR D  87     11.524  14.694  -0.011  1.00 31.27      D  C
ATOM  10797  CZ   TYR D  87     11.653  13.989   1.173  1.00 30.60      D  C
ATOM  10798  OH   TYR D  87     12.013  14.634   2.340  1.00 35.88      D  O
ATOM  10800  CE2  TYR D  87     11.450  12.622   1.193  1.00 31.25      D  C
ATOM  10802  CD2  TYR D  87     11.083  11.956   0.031  1.00 29.33      D  C
ATOM  10804  C    TYR D  87      8.889  11.163  -4.096  1.00 36.66      D  C
ATOM  10805  O    TYR D  87      9.072   9.963  -4.281  1.00 35.17      D  O
ATOM  10807  N    CYS D  88      8.583  11.999  -5.076  1.00 37.88      D  N
ATOM  10808  CA   CYS D  88      8.621  11.552  -6.452  1.00 39.63      D  C
ATOM  10810  CB   CYS D  88      7.456  12.091  -7.295  1.00 40.24      D  C
ATOM  10813  SG   CYS D  88      7.301  13.896  -7.274  1.00 43.57      D  S
ATOM  10815  C    CYS D  88      9.916  12.066  -6.995  1.00 39.60      D  C
ATOM  10816  O    CYS D  88     10.494  13.006  -6.461  1.00 39.61      D  O
ATOM  10818  N    GLY D  89     10.372  11.418  -8.057  1.00 40.26      D  N
ATOM  10819  CA   GLY D  89     11.554  11.841  -8.775  1.00 40.16      D  C
ATOM  10822  C    GLY D  89     11.483  11.380 -10.200  1.00 39.68      D  C
ATOM  10823  O    GLY D  89     10.719  10.500 -10.525  1.00 40.12      D  O
```

Figure 8 – CONT.

```
ATOM  10825  N    THR D  90      12.274  12.005 -11.051  1.00 39.91      D  N
ATOM  10826  CA   THR D  90      12.352  11.618 -12.440  1.00 40.09      D  C
ATOM  10828  CB   THR D  90      11.149  12.195 -13.285  1.00 40.47      D  C
ATOM  10830  OG1  THR D  90      11.174  11.643 -14.611  1.00 40.57      D  O
ATOM  10832  CG2  THR D  90      11.205  13.741 -13.380  1.00 39.21      D  C
ATOM  10836  C    THR D  90      13.685  12.136 -12.927  1.00 40.28      D  C
ATOM  10837  O    THR D  90      14.548  12.471 -12.092  1.00 39.63      D  O
ATOM  10839  N    TRP D  91      13.846  12.188 -14.261  1.00 39.91      D  N
ATOM  10840  CA   TRP D  91      15.007  12.800 -14.914  1.00 40.08      D  C
ATOM  10842  CB   TRP D  91      15.707  11.737 -15.780  1.00 40.09      D  C
ATOM  10845  CG   TRP D  91      16.276  10.647 -14.909  1.00 38.30      D  C
ATOM  10846  CD1  TRP D  91      15.606   9.574 -14.370  1.00 36.20      D  C
ATOM  10848  NE1  TRP D  91      16.447   8.832 -13.603  1.00 35.63      D  N
ATOM  10850  CE2  TRP D  91      17.684   9.427 -13.607  1.00 35.47      D  C
ATOM  10851  CD2  TRP D  91      17.600  10.579 -14.419  1.00 35.46      D  C
ATOM  10852  CE3  TRP D  91      18.741  11.354 -14.618  1.00 34.42      D  C
ATOM  10854  CZ3  TRP D  91      19.908  10.964 -14.007  1.00 35.37      D  C
ATOM  10856  CH2  TRP D  91      19.952   9.819 -13.192  1.00 31.90      D  C
ATOM  10858  CZ2  TRP D  91      18.857   9.044 -12.982  1.00 31.29      D  C
ATOM  10860  C    TRP D  91      14.593  14.015 -15.747  1.00 40.89      D  C
ATOM  10861  O    TRP D  91      13.426  14.133 -16.144  1.00 41.10      D  O
ATOM  10863  N    ASP D  92      15.522  14.939 -15.973  1.00 41.87      D  N
ATOM  10864  CA   ASP D  92      15.261  16.041 -16.872  1.00 43.13      D  C
ATOM  10866  CB   ASP D  92      15.504  17.391 -16.221  1.00 43.85      D  C
ATOM  10869  CG   ASP D  92      15.237  18.545 -17.191  1.00 45.28      D  C
ATOM  10870  OD1  ASP D  92      14.092  19.059 -17.198  1.00 47.08      D  O
ATOM  10871  OD2  ASP D  92      16.157  18.897 -17.975  1.00 48.00      D  O
ATOM  10872  C    ASP D  92      16.100  15.937 -18.139  1.00 43.83      D  C
ATOM  10873  O    ASP D  92      17.334  15.940 -18.086  1.00 43.72      D  O
ATOM  10875  N    SER D  93      15.411  15.905 -19.279  1.00 44.46      D  N
ATOM  10876  CA   SER D  93      16.047  15.695 -20.574  1.00 45.28      D  C
ATOM  10878  CB   SER D  93      15.003  15.339 -21.631  1.00 45.26      D  C
ATOM  10881  OG   SER D  93      14.554  14.001 -21.426  1.00 46.87      D  O
ATOM  10883  C    SER D  93      16.857  16.885 -21.036  1.00 45.64      D  C
ATOM  10884  O    SER D  93      17.827  16.706 -21.754  1.00 46.24      D  O
ATOM  10886  N    ARG D  94      16.480  18.095 -20.632  1.00 46.04      D  N
ATOM  10887  CA   ARG D  94      17.248  19.277 -21.028  1.00 46.36      D  C
ATOM  10889  CB   ARG D  94      16.445  20.580 -20.837  1.00 46.66      D  C
ATOM  10898  C    ARG D  94      18.568  19.325 -20.255  1.00 46.19      D  C
ATOM  10899  O    ARG D  94      19.625  19.579 -20.845  1.00 46.59      D  O
ATOM  10901  N    LEU D  95      18.518  19.072 -18.944  1.00 46.06      D  N
ATOM  10902  CA   LEU D  95      19.718  19.207 -18.073  1.00 45.31      D  C
ATOM  10904  CB   LEU D  95      19.309  19.735 -16.695  1.00 45.55      D  C
ATOM  10907  CG   LEU D  95      19.267  21.234 -16.312  1.00 45.87      D  C
ATOM  10909  CD1  LEU D  95      19.556  22.193 -17.450  1.00 46.37      D  C
ATOM  10913  CD2  LEU D  95      17.920  21.540 -15.653  1.00 45.57      D  C
ATOM  10917  C    LEU D  95      20.483  17.877 -17.934  1.00 44.71      D  C
ATOM  10918  O    LEU D  95      21.694  17.860 -17.769  1.00 45.54      D  O
ATOM  10920  N    GLY D  95A     19.775  16.762 -18.002  1.00 43.80      D  N
ATOM  10921  CA   GLY D  95A     20.420  15.461 -17.974  1.00 42.96      D  C
ATOM  10924  C    GLY D  95A     20.815  15.017 -16.580  1.00 42.36      D  C
ATOM  10925  O    GLY D  95A     21.826  14.315 -16.413  1.00 42.49      D  O
ATOM  10927  N    ILE D  95B     20.013  15.412 -15.586  1.00 41.07      D  N
ATOM  10928  CA   ILE D  95B     20.213  15.028 -14.194  1.00 39.41      D  C
ATOM  10930  CB   ILE D  95B     20.728  16.227 -13.373  1.00 39.90      D  C
ATOM  10932  CG1  ILE D  95B     19.626  17.306 -13.219  1.00 39.80      D  C
ATOM  10935  CD1  ILE D  95B     20.100  18.638 -12.620  1.00 38.35      D  C
ATOM  10939  CG2  ILE D  95B     22.051  16.744 -14.017  1.00 39.84      D  C
```

Figure 8 – CONT.

```
ATOM  10943  C    ILE D  95B   18.899  14.539 -13.631  1.00 38.30      D C
ATOM  10944  O    ILE D  95B   17.866  14.754 -14.246  1.00 37.72      D O
ATOM  10946  N    ALA D  96    18.946  13.862 -12.482  1.00 37.03      D N
ATOM  10947  CA   ALA D  96    17.739  13.473 -11.742  1.00 36.26      D C
ATOM  10949  CB   ALA D  96    18.073  12.449 -10.692  1.00 36.15      D C
ATOM  10953  C    ALA D  96    17.122  14.676 -11.059  1.00 35.64      D C
ATOM  10954  O    ALA D  96    17.816  15.609 -10.745  1.00 34.12      D O
ATOM  10956  N    VAL D  97    15.820  14.615 -10.796  1.00 35.97      D N
ATOM  10957  CA   VAL D  97    15.128  15.637 -10.032  1.00 36.36      D C
ATOM  10959  CB   VAL D  97    14.381  16.667 -10.923  1.00 36.79      D C
ATOM  10961  CG1  VAL D  97    15.371  17.600 -11.629  1.00 36.74      D C
ATOM  10965  CG2  VAL D  97    13.467  15.966 -11.928  1.00 37.40      D C
ATOM  10969  C    VAL D  97    14.170  15.002  -9.051  1.00 36.98      D C
ATOM  10970  O    VAL D  97    13.774  13.852  -9.203  1.00 36.89      D O
ATOM  10972  N    PHE D  98    13.819  15.751  -8.009  1.00 37.80      D N
ATOM  10973  CA   PHE D  98    12.932  15.239  -6.985  1.00 37.95      D C
ATOM  10975  CB   PHE D  98    13.639  15.134  -5.631  1.00 37.94      D C
ATOM  10978  CG   PHE D  98    14.642  14.012  -5.540  1.00 34.68      D C
ATOM  10979  CD1  PHE D  98    14.225  12.706  -5.430  1.00 32.27      D C
ATOM  10981  CE1  PHE D  98    15.124  11.689  -5.326  1.00 31.34      D C
ATOM  10983  CZ   PHE D  98    16.474  11.964  -5.342  1.00 31.68      D C
ATOM  10985  CE2  PHE D  98    16.905  13.254  -5.433  1.00 32.93      D C
ATOM  10987  CD2  PHE D  98    15.986  14.277  -5.530  1.00 33.15      D C
ATOM  10989  C    PHE D  98    11.795  16.192  -6.799  1.00 38.99      D C
ATOM  10990  O    PHE D  98    11.911  17.380  -7.091  1.00 39.22      D O
ATOM  10992  N    GLY D  99    10.707  15.670  -6.250  1.00 39.52      D N
ATOM  10993  CA   GLY D  99     9.702  16.534  -5.657  1.00 40.03      D C
ATOM  10996  C    GLY D  99    10.124  16.906  -4.256  1.00 39.81      D C
ATOM  10997  O    GLY D  99    11.142  16.451  -3.773  1.00 39.12      D O
ATOM  10999  N    GLY D 100     9.305  17.719  -3.605  1.00 40.22      D N
ATOM  11000  CA   GLY D 100     9.651  18.325  -2.328  1.00 40.25      D C
ATOM  11003  C    GLY D 100     9.257  17.501  -1.126  1.00 40.59      D C
ATOM  11004  O    GLY D 100     9.504  17.903  -0.001  1.00 41.29      D O
ATOM  11006  N    GLY D 101     8.639  16.354  -1.349  1.00 40.51      D N
ATOM  11007  CA   GLY D 101     8.241  15.479  -0.259  1.00 40.56      D C
ATOM  11010  C    GLY D 101     6.798  15.693   0.160  1.00 41.03      D C
ATOM  11011  O    GLY D 101     6.263  16.807   0.074  1.00 40.76      D O
ATOM  11013  N    THR D 102     6.170  14.619   0.613  1.00 41.27      D N
ATOM  11014  CA   THR D 102     4.858  14.698   1.204  1.00 42.08      D C
ATOM  11016  CB   THR D 102     3.784  14.105   0.300  1.00 41.86      D C
ATOM  11018  OG1  THR D 102     3.777  14.805  -0.947  1.00 41.36      D O
ATOM  11020  CG2  THR D 102     2.443  14.222   0.968  1.00 40.10      D C
ATOM  11024  C    THR D 102     4.851  13.884   2.470  1.00 43.45      D C
ATOM  11025  O    THR D 102     5.117  12.681   2.436  1.00 43.03      D O
ATOM  11027  N    GLN D 103     4.542  14.544   3.583  1.00 44.87      D N
ATOM  11028  CA   GLN D 103     4.424  13.852   4.860  1.00 46.57      D C
ATOM  11030  CB   GLN D 103     4.654  14.788   6.062  1.00 46.87      D C
ATOM  11033  CG   GLN D 103     4.774  14.022   7.408  1.00 49.00      D C
ATOM  11036  CD   GLN D 103     4.721  14.918   8.652  1.00 52.25      D C
ATOM  11037  OE1  GLN D 103     4.056  15.962   8.665  1.00 55.91      D O
ATOM  11038  NE2  GLN D 103     5.413  14.499   9.709  1.00 53.97      D N
ATOM  11041  C    GLN D 103     3.041  13.232   4.935  1.00 46.85      D C
ATOM  11042  O    GLN D 103     2.042  13.880   4.663  1.00 45.84      D O
ATOM  11044  N    LEU D 104     3.010  11.961   5.294  1.00 48.40      D N
ATOM  11045  CA   LEU D 104     1.772  11.226   5.390  1.00 49.61      D C
ATOM  11047  CB   LEU D 104     1.868   9.909   4.622  1.00 49.50      D C
ATOM  11050  CG   LEU D 104     0.633   8.980   4.597  1.00 50.41      D C
ATOM  11052  CD1  LEU D 104     0.630   8.101   3.335  1.00 49.62      D C
```

Figure 8 – CONT.

```
ATOM  11056  CD2  LEU  D  104     0.543   8.083   5.855  1.00  49.72      D  C
ATOM  11060  C    LEU  D  104     1.494  10.983   6.859  1.00  50.28      D  C
ATOM  11061  O    LEU  D  104     2.316  10.400   7.560  1.00  50.71      D  O
ATOM  11063  N    THR  D  105     0.342  11.449   7.321  1.00  51.48      D  N
ATOM  11064  CA   THR  D  105    -0.090  11.217   8.691  1.00  52.38      D  C
ATOM  11066  CB   THR  D  105    -0.592  12.515   9.334  1.00  52.75      D  C
ATOM  11068  OG1  THR  D  105     0.386  13.546   9.130  1.00  52.70      D  O
ATOM  11070  CG2  THR  D  105    -0.837  12.311  10.835  1.00  53.13      D  C
ATOM  11074  C    THR  D  105    -1.216  10.214   8.640  1.00  52.91      D  C
ATOM  11075  O    THR  D  105    -2.144  10.361   7.838  1.00  52.87      D  O
ATOM  11077  N    VAL  D  106    -1.129   9.187   9.476  1.00  53.93      D  N
ATOM  11078  CA   VAL  D  106    -2.203   8.205   9.595  1.00  54.84      D  C
ATOM  11080  CB   VAL  D  106    -1.635   6.795   9.803  1.00  54.87      D  C
ATOM  11082  CG1  VAL  D  106    -2.714   5.856  10.319  1.00  55.86      D  C
ATOM  11086  CG2  VAL  D  106    -1.029   6.279   8.494  1.00  55.85      D  C
ATOM  11090  C    VAL  D  106    -3.118   8.621  10.763  1.00  55.52      D  C
ATOM  11091  O    VAL  D  106    -2.719   8.535  11.937  1.00  55.41      D  O
ATOM  11093  N    LEU  D  106A   -4.334   9.071  10.431  1.00  56.04      D  N
ATOM  11094  CA   LEU  D  106A   -5.261   9.653  11.429  1.00  56.61      D  C
ATOM  11096  CB   LEU  D  106A   -6.431  10.400  10.739  1.00  56.67      D  C
ATOM  11099  CG   LEU  D  106A   -6.049  11.714  10.026  1.00  57.60      D  C
ATOM  11101  CD1  LEU  D  106A   -7.233  12.344   9.261  1.00  57.67      D  C
ATOM  11105  CD2  LEU  D  106A   -5.434  12.740  10.995  1.00  57.57      D  C
ATOM  11109  C    LEU  D  106A   -5.810   8.672  12.472  1.00  56.47      D  C
ATOM  11110  O    LEU  D  106A   -5.662   7.448  12.362  1.00  56.34      D  O
ATOM  11112  N    GLY  D  107    -6.402   9.253  13.519  1.00  56.89      D  N
ATOM  11113  CA   GLY  D  107    -7.136   8.509  14.537  1.00  56.71      D  C
ATOM  11116  C    GLY  D  107    -6.304   7.822  15.601  1.00  56.68      D  C
ATOM  11117  O    GLY  D  107    -6.835   6.982  16.339  1.00  57.54      D  O
ATOM  11119  N    GLN  D  108    -5.012   8.143  15.699  1.00  56.26      D  N
ATOM  11120  CA   GLN  D  108    -4.237   7.697  16.859  1.00  55.43      D  C
ATOM  11122  CB   GLN  D  108    -2.729   7.855  16.643  1.00  55.87      D  C
ATOM  11129  C    GLN  D  108    -4.740   8.541  18.043  1.00  54.62      D  C
ATOM  11130  O    GLN  D  108    -5.111   9.714  17.860  1.00  53.34      D  O
ATOM  11132  N    PRO  D  109    -4.768   7.937  19.245  1.00  53.46      D  N
ATOM  11133  CA   PRO  D  109    -5.449   8.503  20.409  1.00  53.31      D  C
ATOM  11135  CB   PRO  D  109    -5.500   7.323  21.395  1.00  53.58      D  C
ATOM  11138  CG   PRO  D  109    -4.298   6.487  21.049  1.00  53.76      D  C
ATOM  11141  CD   PRO  D  109    -4.073   6.673  19.563  1.00  54.30      D  C
ATOM  11144  C    PRO  D  109    -4.732   9.698  21.037  1.00  52.06      D  C
ATOM  11145  O    PRO  D  109    -3.516   9.665  21.213  1.00  51.73      D  O
ATOM  11146  N    LYS  D  110    -5.486  10.740  21.370  1.00  50.71      D  N
ATOM  11147  CA   LYS  D  110    -4.898  11.900  22.037  1.00  50.05      D  C
ATOM  11149  CB   LYS  D  110    -5.923  12.999  22.291  1.00  50.22      D  C
ATOM  11152  CG   LYS  D  110    -6.203  13.863  21.069  1.00  52.22      D  C
ATOM  11155  CD   LYS  D  110    -7.372  14.824  21.305  1.00  54.89      D  C
ATOM  11158  CE   LYS  D  110    -7.031  15.913  22.343  1.00  56.16      D  C
ATOM  11161  NZ   LYS  D  110    -8.155  16.878  22.536  1.00  54.50      D  N
ATOM  11165  C    LYS  D  110    -4.218  11.514  23.341  1.00  48.52      D  C
ATOM  11166  O    LYS  D  110    -4.646  10.597  24.033  1.00  48.37      D  O
ATOM  11168  N    ALA  D  111    -3.108  12.190  23.623  1.00  47.23      D  N
ATOM  11169  CA   ALA  D  111    -2.424  12.084  24.905  1.00  46.10      D  C
ATOM  11171  CB   ALA  D  111    -1.226  11.179  24.797  1.00  46.02      D  C
ATOM  11175  C    ALA  D  111    -2.024  13.509  25.346  1.00  45.04      D  C
ATOM  11176  O    ALA  D  111    -1.507  14.317  24.544  1.00  44.69      D  O
ATOM  11178  N    ALA  D  112    -2.321  13.842  26.598  1.00  43.09      D  N
ATOM  11179  CA   ALA  D  112    -2.012  15.179  27.112  1.00  41.82      D  C
ATOM  11181  CB   ALA  D  112    -2.995  15.578  28.252  1.00  41.48      D  C
```

Figure 8 – CONT.

```
ATOM  11185  C    ALA D 112    -0.553  15.228  27.596  1.00 40.49    D  C
ATOM  11186  O    ALA D 112    -0.037  14.259  28.175  1.00 39.93    D  O
ATOM  11188  N    PRO D 113     0.112  16.368  27.381  1.00 39.14    D  N
ATOM  11189  CA   PRO D 113     1.514  16.437  27.776  1.00 39.29    D  C
ATOM  11191  CB   PRO D 113     1.978  17.797  27.226  1.00 38.90    D  C
ATOM  11194  CG   PRO D 113     0.735  18.603  27.095  1.00 39.72    D  C
ATOM  11197  CD   PRO D 113    -0.387  17.643  26.845  1.00 39.13    D  C
ATOM  11200  C    PRO D 113     1.698  16.397  29.272  1.00 38.53    D  C
ATOM  11201  O    PRO D 113     1.023  17.126  29.983  1.00 38.87    D  O
ATOM  11202  N    SER D 114     2.612  15.567  29.740  1.00 37.69    D  N
ATOM  11203  CA   SER D 114     3.089  15.691  31.103  1.00 37.63    D  C
ATOM  11205  CB   SER D 114     3.540  14.354  31.637  1.00 37.90    D  C
ATOM  11208  OG   SER D 114     4.349  14.585  32.768  1.00 41.57    D  O
ATOM  11210  C    SER D 114     4.226  16.738  31.151  1.00 36.68    D  C
ATOM  11211  O    SER D 114     5.068  16.796  30.244  1.00 37.42    D  O
ATOM  11213  N    VAL D 115     4.234  17.584  32.181  1.00 34.76    D  N
ATOM  11214  CA   VAL D 115     5.118  18.734  32.213  1.00 33.30    D  C
ATOM  11216  CB   VAL D 115     4.336  20.037  32.010  1.00 32.67    D  C
ATOM  11218  CG1  VAL D 115     5.254  21.234  32.016  1.00 31.42    D  C
ATOM  11222  CG2  VAL D 115     3.581  19.986  30.705  1.00 32.08    D  C
ATOM  11226  C    VAL D 115     5.879  18.802  33.518  1.00 33.83    D  C
ATOM  11227  O    VAL D 115     5.285  18.833  34.592  1.00 32.91    D  O
ATOM  11229  N    THR D 116     7.207  18.850  33.411  1.00 34.09    D  N
ATOM  11230  CA   THR D 116     8.074  18.978  34.563  1.00 33.79    D  C
ATOM  11232  CB   THR D 116     8.881  17.736  34.729  1.00 33.81    D  C
ATOM  11234  OG1  THR D 116     8.008  16.614  34.631  1.00 33.78    D  O
ATOM  11236  CG2  THR D 116     9.572  17.745  36.092  1.00 35.09    D  C
ATOM  11240  C    THR D 116     9.010  20.154  34.387  1.00 33.88    D  C
ATOM  11241  O    THR D 116     9.677  20.282  33.353  1.00 34.24    D  O
ATOM  11243  N    LEU D 117     9.082  20.995  35.408  1.00 32.87    D  N
ATOM  11244  CA   LEU D 117     9.832  22.228  35.357  1.00 31.90    D  C
ATOM  11246  CB   LEU D 117     8.875  23.385  35.460  1.00 31.65    D  C
ATOM  11249  CG   LEU D 117     9.503  24.749  35.689  1.00 32.32    D  C
ATOM  11251  CD1  LEU D 117    10.403  25.077  34.460  1.00 32.64    D  C
ATOM  11255  CD2  LEU D 117     8.430  25.826  35.919  1.00 32.81    D  C
ATOM  11259  C    LEU D 117    10.803  22.271  36.524  1.00 32.23    D  C
ATOM  11260  O    LEU D 117    10.376  22.183  37.672  1.00 32.51    D  O
ATOM  11262  N    PHE D 118    12.097  22.397  36.238  1.00 31.99    D  N
ATOM  11263  CA   PHE D 118    13.111  22.477  37.266  1.00 32.19    D  C
ATOM  11265  CB   PHE D 118    14.216  21.446  37.065  1.00 31.62    D  C
ATOM  11268  CG   PHE D 118    13.780  20.022  37.212  1.00 31.42    D  C
ATOM  11269  CD1  PHE D 118    13.688  19.432  38.476  1.00 32.57    D  C
ATOM  11271  CE1  PHE D 118    13.305  18.127  38.619  1.00 32.84    D  C
ATOM  11273  CZ   PHE D 118    13.022  17.363  37.483  1.00 34.39    D  C
ATOM  11275  CE2  PHE D 118    13.126  17.952  36.214  1.00 31.51    D  C
ATOM  11277  CD2  PHE D 118    13.488  19.262  36.100  1.00 30.25    D  C
ATOM  11279  C    PHE D 118    13.745  23.873  37.218  1.00 33.19    D  C
ATOM  11280  O    PHE D 118    14.007  24.386  36.130  1.00 33.74    D  O
ATOM  11282  N    PRO D 119    14.000  24.489  38.400  1.00 33.14    D  N
ATOM  11283  CA   PRO D 119    14.833  25.679  38.518  1.00 33.41    D  C
ATOM  11285  CB   PRO D 119    14.490  26.206  39.936  1.00 33.56    D  C
ATOM  11288  CG   PRO D 119    14.186  24.988  40.713  1.00 33.95    D  C
ATOM  11291  CD   PRO D 119    13.558  23.997  39.720  1.00 33.70    D  C
ATOM  11294  C    PRO D 119    16.336  25.370  38.427  1.00 33.13    D  C
ATOM  11295  O    PRO D 119    16.740  24.211  38.405  1.00 32.34    D  O
ATOM  11296  N    PRO D 120    17.173  26.408  38.450  1.00 33.80    D  N
ATOM  11297  CA   PRO D 120    18.614  26.164  38.392  1.00 34.31    D  C
ATOM  11299  CB   PRO D 120    19.196  27.560  38.243  1.00 34.10    D  C
```

Figure 8 – CONT.

```
ATOM  11302  CG   PRO D 120     18.119  28.502  38.470  1.00 33.62      D  C
ATOM  11305  CD   PRO D 120     16.832  27.828  38.315  1.00 33.62      D  C
ATOM  11308  C    PRO D 120     19.146  25.470  39.639  1.00 35.15      D  C
ATOM  11309  O    PRO D 120     18.731  25.809  40.715  1.00 35.74      D  O
ATOM  11310  N    SER D 121     20.024  24.484  39.494  1.00 36.06      D  N
ATOM  11311  CA   SER D 121     20.700  23.887  40.640  1.00 37.19      D  C
ATOM  11313  CB   SER D 121     21.553  22.718  40.181  1.00 37.36      D  C
ATOM  11316  OG   SER D 121     22.553  23.154  39.252  1.00 36.99      D  O
ATOM  11318  C    SER D 121     21.606  24.901  41.356  1.00 38.58      D  C
ATOM  11319  O    SER D 121     22.028  25.914  40.766  1.00 39.51      D  O
ATOM  11321  N    SER D 122     21.951  24.644  42.613  1.00 39.15      D  N
ATOM  11322  CA   SER D 122     22.922  25.538  43.271  1.00 39.73      D  C
ATOM  11324  CB   SER D 122     22.958  25.343  44.802  1.00 39.96      D  C
ATOM  11327  OG   SER D 122     22.954  23.976  45.159  1.00 41.00      D  O
ATOM  11329  C    SER D 122     24.323  25.443  42.629  1.00 39.70      D  C
ATOM  11330  O    SER D 122     25.008  26.460  42.493  1.00 39.22      D  O
ATOM  11332  N    GLU D 123     24.729  24.247  42.200  1.00 40.25      D  N
ATOM  11333  CA   GLU D 123     26.008  24.080  41.482  1.00 41.17      D  C
ATOM  11335  CB   GLU D 123     26.150  22.681  40.879  1.00 41.59      D  C
ATOM  11338  CG   GLU D 123     26.512  21.625  41.880  1.00 44.20      D  C
ATOM  11341  CD   GLU D 123     26.927  20.295  41.277  1.00 45.58      D  C
ATOM  11342  OE1  GLU D 123     26.441  19.280  41.835  1.00 49.93      D  O
ATOM  11343  OE2  GLU D 123     27.750  20.259  40.319  1.00 44.71      D  O
ATOM  11344  C    GLU D 123     26.178  25.064  40.348  1.00 40.95      D  C
ATOM  11345  O    GLU D 123     27.252  25.651  40.199  1.00 40.94      D  O
ATOM  11347  N    GLU D 124     25.123  25.212  39.546  1.00 40.90      D  N
ATOM  11348  CA   GLU D 124     25.154  26.038  38.356  1.00 40.88      D  C
ATOM  11350  CB   GLU D 124     23.913  25.813  37.457  1.00 40.80      D  C
ATOM  11353  CG   GLU D 124     24.021  26.458  36.052  1.00 39.08      D  C
ATOM  11356  CD   GLU D 124     22.733  26.391  35.220  1.00 38.89      D  C
ATOM  11357  OE1  GLU D 124     21.672  25.995  35.753  1.00 33.93      D  O
ATOM  11358  OE2  GLU D 124     22.781  26.786  34.027  1.00 38.32      D  O
ATOM  11359  C    GLU D 124     25.204  27.486  38.734  1.00 41.26      D  C
ATOM  11360  O    GLU D 124     25.869  28.269  38.076  1.00 41.90      D  O
ATOM  11362  N    LEU D 125     24.450  27.867  39.743  1.00 41.84      D  N
ATOM  11363  CA   LEU D 125     24.531  29.237  40.244  1.00 42.79      D  C
ATOM  11365  CB   LEU D 125     23.459  29.520  41.293  1.00 42.48      D  C
ATOM  11368  CG   LEU D 125     22.022  29.403  40.771  1.00 41.95      D  C
ATOM  11370  CD1  LEU D 125     21.024  29.341  41.937  1.00 39.50      D  C
ATOM  11374  CD2  LEU D 125     21.676  30.510  39.797  1.00 39.21      D  C
ATOM  11378  C    LEU D 125     25.935  29.567  40.769  1.00 43.54      D  C
ATOM  11379  O    LEU D 125     26.375  30.688  40.596  1.00 44.07      D  O
ATOM  11381  N    GLN D 126     26.655  28.606  41.351  1.00 44.85      D  N
ATOM  11382  CA   GLN D 126     28.076  28.839  41.703  1.00 46.31      D  C
ATOM  11384  CB   GLN D 126     28.691  27.701  42.545  1.00 46.63      D  C
ATOM  11387  CG   GLN D 126     28.856  28.019  44.068  1.00 48.55      D  C
ATOM  11390  CD   GLN D 126     29.699  29.279  44.376  1.00 47.46      D  C
ATOM  11391  OE1  GLN D 126     30.892  29.354  44.067  1.00 48.49      D  O
ATOM  11392  NE2  GLN D 126     29.066  30.258  44.988  1.00 47.38      D  N
ATOM  11395  C    GLN D 126     28.972  29.065  40.463  1.00 47.23      D  C
ATOM  11396  O    GLN D 126     30.009  29.728  40.564  1.00 47.67      D  O
ATOM  11398  N    ALA D 127     28.581  28.529  39.305  1.00 47.01      D  N
ATOM  11399  CA   ALA D 127     29.283  28.819  38.055  1.00 47.00      D  C
ATOM  11401  CB   ALA D 127     29.153  27.627  37.077  1.00 46.85      D  C
ATOM  11405  C    ALA D 127     28.799  30.124  37.411  1.00 47.05      D  C
ATOM  11406  O    ALA D 127     29.186  30.444  36.283  1.00 48.37      D  O
ATOM  11408  N    ASN D 128     27.982  30.873  38.147  1.00 46.54      D  N
ATOM  11409  CA   ASN D 128     27.329  32.114  37.695  1.00 46.73      D  C
```

Figure 8 – CONT.

```
ATOM  11411  CB   ASN D 128      28.323  33.271  37.559  1.00 47.32      D  C
ATOM  11414  CG   ASN D 128      27.663  34.640  37.833  1.00 50.17      D  C
ATOM  11415  OD1  ASN D 128      27.003  34.838  38.864  1.00 55.62      D  O
ATOM  11416  ND2  ASN D 128      27.823  35.578  36.903  1.00 54.72      D  N
ATOM  11419  C    ASN D 128      26.406  32.016  36.454  1.00 45.83      D  C
ATOM  11420  O    ASN D 128      26.216  32.989  35.692  1.00 45.97      D  O
ATOM  11422  N    LYS D 129      25.755  30.862  36.323  1.00 44.41      D  N
ATOM  11423  CA   LYS D 129      24.772  30.629  35.278  1.00 42.39      D  C
ATOM  11425  CB   LYS D 129      25.321  29.541  34.359  1.00 42.66      D  C
ATOM  11428  CG   LYS D 129      26.567  29.946  33.499  1.00 42.10      D  C
ATOM  11431  CD   LYS D 129      27.721  28.858  33.559  1.00 42.79      D  C
ATOM  11434  CE   LYS D 129      27.306  27.375  33.189  1.00 41.94      D  C
ATOM  11437  NZ   LYS D 129      28.259  26.313  33.676  1.00 37.35      D  N
ATOM  11441  C    LYS D 129      23.466  30.186  35.931  1.00 41.43      D  C
ATOM  11442  O    LYS D 129      23.486  29.599  37.012  1.00 41.89      D  O
ATOM  11444  N    ALA D 130      22.336  30.481  35.286  1.00 39.79      D  N
ATOM  11445  CA   ALA D 130      21.023  29.992  35.710  1.00 38.00      D  C
ATOM  11447  CB   ALA D 130      20.267  31.098  36.385  1.00 37.82      D  C
ATOM  11451  C    ALA D 130      20.212  29.454  34.512  1.00 36.36      D  C
ATOM  11452  O    ALA D 130      19.899  30.184  33.596  1.00 35.68      D  O
ATOM  11454  N    THR D 131      19.877  28.171  34.524  1.00 35.17      D  N
ATOM  11455  CA   THR D 131      18.989  27.615  33.492  1.00 33.26      D  C
ATOM  11457  CB   THR D 131      19.700  26.511  32.695  1.00 33.20      D  C
ATOM  11459  OG1  THR D 131      20.971  26.974  32.243  1.00 30.97      D  O
ATOM  11461  CG2  THR D 131      18.841  26.044  31.504  1.00 30.92      D  C
ATOM  11465  C    THR D 131      17.718  26.987  34.096  1.00 32.72      D  C
ATOM  11466  O    THR D 131      17.814  26.082  34.945  1.00 31.76      D  O
ATOM  11468  N    LEU D 132      16.545  27.429  33.628  1.00 31.79      D  N
ATOM  11469  CA   LEU D 132      15.286  26.759  33.958  1.00 31.57      D  C
ATOM  11471  CB   LEU D 132      14.135  27.748  34.030  1.00 31.61      D  C
ATOM  11474  CG   LEU D 132      14.019  28.633  35.290  1.00 33.15      D  C
ATOM  11476  CD1  LEU D 132      15.283  29.348  35.516  1.00 32.29      D  C
ATOM  11480  CD2  LEU D 132      12.889  29.627  35.112  1.00 30.76      D  C
ATOM  11484  C    LEU D 132      14.983  25.739  32.868  1.00 31.50      D  C
ATOM  11485  O    LEU D 132      15.060  26.063  31.682  1.00 31.63      D  O
ATOM  11487  N    VAL D 133      14.603  24.538  33.273  1.00 30.95      D  N
ATOM  11488  CA   VAL D 133      14.424  23.395  32.388  1.00 31.08      D  C
ATOM  11490  CB   VAL D 133      15.300  22.262  32.858  1.00 30.69      D  C
ATOM  11492  CG1  VAL D 133      15.172  21.070  31.941  1.00 30.13      D  C
ATOM  11496  CG2  VAL D 133      16.746  22.745  32.967  1.00 32.01      D  C
ATOM  11500  C    VAL D 133      12.954  22.913  32.380  1.00 31.46      D  C
ATOM  11501  O    VAL D 133      12.453  22.381  33.385  1.00 31.87      D  O
ATOM  11503  N    CYS D 134      12.250  23.158  31.279  1.00 31.37      D  N
ATOM  11504  CA   CYS D 134      10.866  22.714  31.120  1.00 30.92      D  C
ATOM  11506  CB   CYS D 134      10.009  23.839  30.570  1.00 31.21      D  C
ATOM  11509  SG   CYS D 134       8.166  23.524  30.709  1.00 29.39      D  S
ATOM  11511  C    CYS D 134      10.817  21.519  30.187  1.00 31.27      D  C
ATOM  11512  O    CYS D 134      11.042  21.676  28.987  1.00 31.91      D  O
ATOM  11514  N    LEU D 135      10.524  20.344  30.748  1.00 30.86      D  N
ATOM  11515  CA   LEU D 135      10.408  19.098  30.023  1.00 30.75      D  C
ATOM  11517  CB   LEU D 135      11.149  18.021  30.792  1.00 30.32      D  C
ATOM  11520  CG   LEU D 135      12.563  18.459  31.156  1.00 28.97      D  C
ATOM  11522  CD1  LEU D 135      13.190  17.361  31.936  1.00 32.37      D  C
ATOM  11526  CD2  LEU D 135      13.399  18.810  29.927  1.00 27.45      D  C
ATOM  11530  C    LEU D 135       8.938  18.682  29.780  1.00 32.28      D  C
ATOM  11531  O    LEU D 135       8.120  18.667  30.713  1.00 32.86      D  O
ATOM  11533  N    VAL D 136       8.624  18.331  28.531  1.00 32.61      D  N
ATOM  11534  CA   VAL D 136       7.283  18.041  28.092  1.00 33.55      D  C
```

Figure 8 – CONT.

```
ATOM  11536  CB   VAL D 136      6.799  19.077  27.077  1.00 33.45      D  C
ATOM  11538  CG1  VAL D 136      5.295  18.956  26.871  1.00 32.49      D  C
ATOM  11542  CG2  VAL D 136      7.194  20.485  27.505  1.00 31.23      D  C
ATOM  11546  C    VAL D 136      7.235  16.674  27.422  1.00 35.80      D  C
ATOM  11547  O    VAL D 136      7.898  16.471  26.392  1.00 36.79      D  O
ATOM  11549  N    SER D 137      6.466  15.728  27.966  1.00 37.09      D  N
ATOM  11550  CA   SER D 137      6.488  14.389  27.398  1.00 38.98      D  C
ATOM  11552  CB   SER D 137      7.437  13.496  28.187  1.00 39.08      D  C
ATOM  11555  OG   SER D 137      6.979  13.276  29.500  1.00 41.74      D  O
ATOM  11557  C    SER D 137      5.154  13.695  27.264  1.00 40.55      D  C
ATOM  11558  O    SER D 137      4.171  14.026  27.943  1.00 41.63      D  O
ATOM  11560  N    ASP D 138      5.152  12.705  26.374  1.00 41.94      D  N
ATOM  11561  CA   ASP D 138      4.076  11.740  26.215  1.00 42.94      D  C
ATOM  11563  CB   ASP D 138      3.802  11.002  27.544  1.00 43.73      D  C
ATOM  11566  CG   ASP D 138      4.811   9.889  27.803  1.00 47.39      D  C
ATOM  11567  OD1  ASP D 138      5.098   9.135  26.838  1.00 51.98      D  O
ATOM  11568  OD2  ASP D 138      5.290   9.736  28.958  1.00 52.60      D  O
ATOM  11569  C    ASP D 138      2.823  12.363  25.649  1.00 42.76      D  C
ATOM  11570  O    ASP D 138      1.737  11.960  25.993  1.00 43.16      D  O
ATOM  11572  N    PHE D 139      2.987  13.323  24.746  1.00 42.98      D  N
ATOM  11573  CA   PHE D 139      1.856  13.971  24.136  1.00 43.17      D  C
ATOM  11575  CB   PHE D 139      1.941  15.488  24.266  1.00 42.85      D  C
ATOM  11578  CG   PHE D 139      3.132  16.126  23.593  1.00 42.67      D  C
ATOM  11579  CD1  PHE D 139      4.331  16.288  24.280  1.00 42.33      D  C
ATOM  11581  CE1  PHE D 139      5.421  16.904  23.692  1.00 41.73      D  C
ATOM  11583  CZ   PHE D 139      5.323  17.420  22.400  1.00 43.07      D  C
ATOM  11585  CE2  PHE D 139      4.114  17.297  21.702  1.00 44.76      D  C
ATOM  11587  CD2  PHE D 139      3.021  16.659  22.310  1.00 43.21      D  C
ATOM  11589  C    PHE D 139      1.623  13.543  22.671  1.00 44.39      D  C
ATOM  11590  O    PHE D 139      2.559  13.151  21.949  1.00 43.52      D  O
ATOM  11592  N    TYR D 140      0.351  13.608  22.270  1.00 45.00      D  N
ATOM  11593  CA   TYR D 140     -0.074  13.280  20.912  1.00 46.04      D  C
ATOM  11595  CB   TYR D 140     -0.306  11.777  20.705  1.00 45.71      D  C
ATOM  11598  CG   TYR D 140     -0.513  11.501  19.234  1.00 49.04      D  C
ATOM  11599  CD1  TYR D 140      0.554  11.127  18.418  1.00 51.02      D  C
ATOM  11601  CE1  TYR D 140      0.364  10.917  17.038  1.00 53.13      D  C
ATOM  11603  CZ   TYR D 140     -0.900  11.101  16.473  1.00 53.35      D  C
ATOM  11604  OH   TYR D 140     -1.102  10.917  15.124  1.00 54.96      D  O
ATOM  11606  CE2  TYR D 140     -1.965  11.494  17.268  1.00 52.48      D  C
ATOM  11608  CD2  TYR D 140     -1.766  11.703  18.632  1.00 50.61      D  C
ATOM  11610  C    TYR D 140     -1.344  14.064  20.556  1.00 46.36      D  C
ATOM  11611  O    TYR D 140     -2.297  14.080  21.326  1.00 46.13      D  O
ATOM  11613  N    PRO D 141     -1.369  14.693  19.375  1.00 47.10      D  N
ATOM  11614  CA   PRO D 141     -0.335  14.728  18.325  1.00 47.85      D  C
ATOM  11616  CB   PRO D 141     -1.077  15.316  17.119  1.00 47.97      D  C
ATOM  11619  CG   PRO D 141     -2.158  16.166  17.720  1.00 48.27      D  C
ATOM  11622  CD   PRO D 141     -2.574  15.442  18.990  1.00 47.55      D  C
ATOM  11625  C    PRO D 141      0.877  15.591  18.697  1.00 48.31      D  C
ATOM  11626  O    PRO D 141      0.905  16.192  19.770  1.00 48.54      D  O
ATOM  11627  N    GLY D 142      1.882  15.634  17.826  1.00 48.65      D  N
ATOM  11628  CA   GLY D 142      3.167  16.259  18.152  1.00 48.40      D  C
ATOM  11631  C    GLY D 142      3.240  17.718  17.769  1.00 48.52      D  C
ATOM  11632  O    GLY D 142      4.099  18.119  16.968  1.00 49.95      D  O
ATOM  11634  N    ALA D 143      2.351  18.513  18.334  1.00 48.03      D  N
ATOM  11635  CA   ALA D 143      2.329  19.936  18.095  1.00 47.74      D  C
ATOM  11637  CB   ALA D 143      1.282  20.277  17.043  1.00 47.87      D  C
ATOM  11641  C    ALA D 143      2.002  20.628  19.418  1.00 47.39      D  C
ATOM  11642  O    ALA D 143      0.904  20.452  19.951  1.00 47.07      D  O
```

Figure 8 – CONT.

```
ATOM  11644  N    VAL D 144    2.968  21.383  19.946  1.00  46.73    D  N
ATOM  11645  CA   VAL D 144    2.798  22.137  21.183  1.00  46.17    D  C
ATOM  11647  CB   VAL D 144    3.530  21.507  22.406  1.00  45.78    D  C
ATOM  11649  CG1  VAL D 144    2.630  20.605  23.159  1.00  46.40    D  C
ATOM  11653  CG2  VAL D 144    4.790  20.783  22.003  1.00  45.77    D  C
ATOM  11657  C    VAL D 144    3.364  23.506  21.018  1.00  45.76    D  C
ATOM  11658  O    VAL D 144    4.300  23.698  20.251  1.00  46.66    D  O
ATOM  11660  N    THR D 145    2.802  24.458  21.748  1.00  44.72    D  N
ATOM  11661  CA   THR D 145    3.426  25.751  21.936  1.00  44.18    D  C
ATOM  11663  CB   THR D 145    2.431  26.877  21.678  1.00  44.22    D  C
ATOM  11665  OG1  THR D 145    2.264  27.007  20.265  1.00  46.91    D  O
ATOM  11667  CG2  THR D 145    2.912  28.196  22.232  1.00  44.98    D  C
ATOM  11671  C    THR D 145    3.950  25.776  23.373  1.00  43.14    D  C
ATOM  11672  O    THR D 145    3.262  25.301  24.297  1.00  42.39    D  O
ATOM  11674  N    VAL D 146    5.180  26.271  23.534  1.00  41.41    D  N
ATOM  11675  CA   VAL D 146    5.760  26.518  24.842  1.00  40.56    D  C
ATOM  11677  CB   VAL D 146    7.055  25.725  25.073  1.00  40.40    D  C
ATOM  11679  CG1  VAL D 146    7.545  25.950  26.497  1.00  39.03    D  C
ATOM  11683  CG2  VAL D 146    6.849  24.233  24.803  1.00  39.09    D  C
ATOM  11687  C    VAL D 146    6.070  28.003  24.982  1.00  40.30    D  C
ATOM  11688  O    VAL D 146    6.724  28.569  24.121  1.00  39.97    D  O
ATOM  11690  N    ALA D 147    5.610  28.606  26.076  1.00  40.27    D  N
ATOM  11691  CA   ALA D 147    5.889  30.005  26.398  1.00  40.69    D  C
ATOM  11693  CB   ALA D 147    4.630  30.846  26.179  1.00  40.33    D  C
ATOM  11697  C    ALA D 147    6.366  30.143  27.850  1.00  41.20    D  C
ATOM  11698  O    ALA D 147    6.047  29.292  28.693  1.00  41.22    D  O
ATOM  11700  N    TRP D 148    7.074  31.238  28.146  1.00  41.39    D  N
ATOM  11701  CA   TRP D 148    7.609  31.491  29.466  1.00  41.82    D  C
ATOM  11703  CB   TRP D 148    9.129  31.505  29.432  1.00  41.79    D  C
ATOM  11706  CG   TRP D 148    9.782  30.188  29.214  1.00  39.07    D  C
ATOM  11707  CD1  TRP D 148   10.084  29.624  28.015  1.00  37.53    D  C
ATOM  11709  NE1  TRP D 148   10.722  28.431  28.198  1.00  37.41    D  N
ATOM  11711  CE2  TRP D 148   10.864  28.205  29.538  1.00  37.15    D  C
ATOM  11712  CD2  TRP D 148   10.280  29.297  30.213  1.00  37.74    D  C
ATOM  11713  CE3  TRP D 148   10.299  29.315  31.610  1.00  36.33    D  C
ATOM  11715  CZ3  TRP D 148   10.872  28.262  32.276  1.00  36.22    D  C
ATOM  11717  CH2  TRP D 148   11.431  27.175  31.574  1.00  37.61    D  C
ATOM  11719  CZ2  TRP D 148   11.437  27.133  30.208  1.00  37.27    D  C
ATOM  11721  C    TRP D 148    7.157  32.815  30.032  1.00  43.46    D  C
ATOM  11722  O    TRP D 148    7.007  33.795  29.303  1.00  43.86    D  O
ATOM  11724  N    LYS D 149    6.945  32.848  31.344  1.00  45.33    D  N
ATOM  11725  CA   LYS D 149    6.592  34.093  32.022  1.00  47.13    D  C
ATOM  11727  CB   LYS D 149    5.122  34.102  32.464  1.00  47.72    D  C
ATOM  11730  CG   LYS D 149    4.155  34.509  31.362  1.00  49.60    D  C
ATOM  11733  CD   LYS D 149    2.797  33.815  31.471  1.00  52.03    D  C
ATOM  11736  CE   LYS D 149    1.966  34.014  30.177  1.00  53.37    D  C
ATOM  11739  NZ   LYS D 149    1.371  35.400  30.039  1.00  53.10    D  N
ATOM  11743  C    LYS D 149    7.502  34.364  33.210  1.00  47.80    D  C
ATOM  11744  O    LYS D 149    8.092  33.442  33.765  1.00  47.66    D  O
ATOM  11746  N    ALA D 150    7.647  35.651  33.529  1.00  49.21    D  N
ATOM  11747  CA   ALA D 150    8.294  36.129  34.755  1.00  50.47    D  C
ATOM  11749  CB   ALA D 150    9.552  36.893  34.432  1.00  50.11    D  C
ATOM  11753  C    ALA D 150    7.283  37.032  35.464  1.00  51.82    D  C
ATOM  11754  O    ALA D 150    6.924  38.092  34.940  1.00  52.25    D  O
ATOM  11756  N    ASP D 151    6.783  36.585  36.617  1.00  53.10    D  N
ATOM  11757  CA   ASP D 151    5.736  37.303  37.342  1.00  54.38    D  C
ATOM  11759  CB   ASP D 151    6.306  38.545  38.026  1.00  54.91    D  C
ATOM  11762  CG   ASP D 151    7.469  38.224  38.905  1.00  56.72    D  C
```

Figure 8 – CONT.

```
ATOM  11763  OD1  ASP  D  151      7.559  37.063  39.370  1.00  59.24      D  O
ATOM  11764  OD2  ASP  D  151      8.296  39.133  39.119  1.00  60.32      D  O
ATOM  11765  C    ASP  D  151      4.616  37.732  36.431  1.00  54.75      D  C
ATOM  11766  O    ASP  D  151      4.236  38.901  36.431  1.00  54.23      D  O
ATOM  11768  N    GLY  D  152      4.118  36.790  35.633  1.00  55.83      D  N
ATOM  11769  CA   GLY  D  152      2.956  37.032  34.787  1.00  56.50      D  C
ATOM  11772  C    GLY  D  152      3.241  37.625  33.423  1.00  57.41      D  C
ATOM  11773  O    GLY  D  152      2.380  37.538  32.544  1.00  58.35      D  O
ATOM  11775  N    SER  D  153      4.431  38.216  33.237  1.00  57.81      D  N
ATOM  11776  CA   SER  D  153      4.826  38.864  31.970  1.00  57.75      D  C
ATOM  11778  CB   SER  D  153      5.798  40.014  32.238  1.00  57.94      D  C
ATOM  11781  OG   SER  D  153      5.180  41.063  32.945  1.00  58.44      D  O
ATOM  11783  C    SER  D  153      5.555  37.884  31.063  1.00  57.61      D  C
ATOM  11784  O    SER  D  153      6.392  37.131  31.549  1.00  57.85      D  O
ATOM  11786  N    PRO  D  154      5.291  37.924  29.739  1.00  57.13      D  N
ATOM  11787  CA   PRO  D  154      6.001  37.016  28.839  1.00  56.38      D  C
ATOM  11789  CB   PRO  D  154      5.364  37.286  27.472  1.00  56.53      D  C
ATOM  11792  CG   PRO  D  154      4.115  38.049  27.754  1.00  56.73      D  C
ATOM  11795  CD   PRO  D  154      4.399  38.830  28.994  1.00  57.24      D  C
ATOM  11798  C    PRO  D  154      7.479  37.331  28.780  1.00  55.85      D  C
ATOM  11799  O    PRO  D  154      7.866  38.501  28.861  1.00  56.07      D  O
ATOM  11800  N    VAL  D  155      8.289  36.283  28.680  1.00  54.95      D  N
ATOM  11801  CA   VAL  D  155      9.725  36.396  28.512  1.00  54.25      D  C
ATOM  11803  CB   VAL  D  155     10.490  35.686  29.658  1.00  54.25      D  C
ATOM  11805  CG1  VAL  D  155     11.984  35.711  29.410  1.00  54.24      D  C
ATOM  11809  CG2  VAL  D  155     10.173  36.318  30.996  1.00  54.06      D  C
ATOM  11813  C    VAL  D  155     10.064  35.708  27.194  1.00  53.87      D  C
ATOM  11814  O    VAL  D  155      9.688  34.558  26.986  1.00  53.16      D  O
ATOM  11816  N    LYS  D  156     10.764  36.424  26.316  1.00  53.51      D  N
ATOM  11817  CA   LYS  D  156     11.229  35.898  25.019  1.00  53.17      D  C
ATOM  11819  CB   LYS  D  156     10.771  36.830  23.885  1.00  52.94      D  C
ATOM  11826  C    LYS  D  156     12.762  35.717  24.971  1.00  52.44      D  C
ATOM  11827  O    LYS  D  156     13.271  34.753  24.369  1.00  52.57      D  O
ATOM  11829  N    VAL  D  157     13.497  36.626  25.601  1.00  51.40      D  N
ATOM  11830  CA   VAL  D  157     14.961  36.577  25.558  1.00  50.97      D  C
ATOM  11832  CB   VAL  D  157     15.587  37.951  25.935  1.00  51.18      D  C
ATOM  11834  CG1  VAL  D  157     15.244  38.348  27.377  1.00  52.05      D  C
ATOM  11838  CG2  VAL  D  157     17.081  37.936  25.723  1.00  52.02      D  C
ATOM  11842  C    VAL  D  157     15.489  35.452  26.454  1.00  50.04      D  C
ATOM  11843  O    VAL  D  157     15.064  35.314  27.605  1.00  50.98      D  O
ATOM  11845  N    GLY  D  158     16.378  34.625  25.914  1.00  48.43      D  N
ATOM  11846  CA   GLY  D  158     16.991  33.533  26.669  1.00  46.90      D  C
ATOM  11849  C    GLY  D  158     16.320  32.193  26.476  1.00  46.10      D  C
ATOM  11850  O    GLY  D  158     16.789  31.182  26.999  1.00  44.86      D  O
ATOM  11852  N    VAL  D  159     15.232  32.180  25.707  1.00  45.57      D  N
ATOM  11853  CA   VAL  D  159     14.479  30.964  25.458  1.00  45.25      D  C
ATOM  11855  CB   VAL  D  159     12.989  31.272  25.262  1.00  45.36      D  C
ATOM  11857  CG1  VAL  D  159     12.202  29.970  25.055  1.00  44.29      D  C
ATOM  11861  CG2  VAL  D  159     12.449  32.065  26.443  1.00  43.92      D  C
ATOM  11865  C    VAL  D  159     14.981  30.172  24.235  1.00  45.37      D  C
ATOM  11866  O    VAL  D  159     15.159  30.714  23.139  1.00  46.10      D  O
ATOM  11868  N    GLU  D  160     15.192  28.881  24.430  1.00  44.90      D  N
ATOM  11869  CA   GLU  D  160     15.515  27.979  23.339  1.00  44.76      D  C
ATOM  11871  CB   GLU  D  160     17.041  27.709  23.268  1.00  44.85      D  C
ATOM  11874  CG   GLU  D  160     17.824  28.803  22.408  1.00  46.95      D  C
ATOM  11877  CD   GLU  D  160     19.250  29.165  22.916  1.00  48.91      D  C
ATOM  11878  OE1  GLU  D  160     19.644  28.764  24.051  1.00  49.03      D  O
ATOM  11879  OE2  GLU  D  160     19.984  29.866  22.166  1.00  45.52      D  O
```

Figure 8 – CONT.

```
ATOM  11880  C    GLU D 160     14.654  26.718  23.503  1.00 44.15      D  C
ATOM  11881  O    GLU D 160     14.757  25.991  24.485  1.00 43.22      D  O
ATOM  11883  N    THR D 161     13.761  26.504  22.545  1.00 43.89      D  N
ATOM  11884  CA   THR D 161     12.822  25.398  22.593  1.00 43.94      D  C
ATOM  11886  CB   THR D 161     11.407  25.908  22.439  1.00 44.31      D  C
ATOM  11888  OG1  THR D 161     11.112  26.777  23.537  1.00 44.51      D  O
ATOM  11890  CG2  THR D 161     10.427  24.734  22.375  1.00 44.26      D  C
ATOM  11894  C    THR D 161     13.061  24.408  21.473  1.00 43.43      D  C
ATOM  11895  O    THR D 161     13.263  24.780  20.338  1.00 43.26      D  O
ATOM  11897  N    THR D 162     13.011  23.146  21.837  1.00 43.89      D  N
ATOM  11898  CA   THR D 162     13.176  22.019  20.954  1.00 44.40      D  C
ATOM  11900  CB   THR D 162     13.340  20.776  21.836  1.00 44.47      D  C
ATOM  11902  OG1  THR D 162     14.726  20.399  21.898  1.00 45.68      D  O
ATOM  11904  CG2  THR D 162     12.491  19.653  21.408  1.00 43.46      D  C
ATOM  11908  C    THR D 162     11.949  21.887  20.066  1.00 45.57      D  C
ATOM  11909  O    THR D 162     10.840  22.177  20.496  1.00 44.65      D  O
ATOM  11911  N    LYS D 163     12.146  21.491  18.811  1.00 46.84      D  N
ATOM  11912  CA   LYS D 163     11.022  21.010  18.001  1.00 47.85      D  C
ATOM  11914  CB   LYS D 163     11.417  20.815  16.523  1.00 48.63      D  C
ATOM  11917  CG   LYS D 163     11.811  22.109  15.762  1.00 51.65      D  C
ATOM  11920  CD   LYS D 163     12.546  21.778  14.432  1.00 54.63      D  C
ATOM  11923  CE   LYS D 163     13.274  23.004  13.837  1.00 56.90      D  C
ATOM  11926  NZ   LYS D 163     14.467  23.498  14.646  1.00 58.35      D  N
ATOM  11930  C    LYS D 163     10.559  19.671  18.601  1.00 47.28      D  C
ATOM  11931  O    LYS D 163     11.368  18.922  19.128  1.00 46.00      D  O
ATOM  11933  N    PRO D 164      9.256  19.369  18.513  1.00 47.97      D  N
ATOM  11934  CA   PRO D 164      8.740  18.074  18.984  1.00 48.60      D  C
ATOM  11936  CB   PRO D 164      7.262  18.111  18.590  1.00 48.36      D  C
ATOM  11939  CG   PRO D 164      6.928  19.576  18.396  1.00 48.47      D  C
ATOM  11942  CD   PRO D 164      8.197  20.237  17.960  1.00 48.06      D  C
ATOM  11945  C    PRO D 164      9.410  16.910  18.285  1.00 49.59      D  C
ATOM  11946  O    PRO D 164      9.644  16.999  17.090  1.00 49.42      D  O
ATOM  11947  N    SER D 165      9.697  15.834  19.009  1.00 50.77      D  N
ATOM  11948  CA   SER D 165     10.291  14.656  18.406  1.00 52.35      D  C
ATOM  11950  CB   SER D 165     11.785  14.590  18.729  1.00 52.51      D  C
ATOM  11953  OG   SER D 165     12.021  13.713  19.821  1.00 54.94      D  O
ATOM  11955  C    SER D 165      9.612  13.380  18.896  1.00 53.17      D  C
ATOM  11956  O    SER D 165      9.382  13.212  20.086  1.00 52.77      D  O
ATOM  11958  N    LYS D 166      9.336  12.462  17.972  1.00 54.50      D  N
ATOM  11959  CA   LYS D 166      8.606  11.236  18.293  1.00 55.49      D  C
ATOM  11961  CB   LYS D 166      8.335  10.421  17.021  1.00 55.97      D  C
ATOM  11964  CG   LYS D 166      7.283   9.329  17.170  1.00 57.10      D  C
ATOM  11967  CD   LYS D 166      6.788   8.816  15.807  1.00 59.01      D  C
ATOM  11970  CE   LYS D 166      7.683   7.711  15.230  1.00 60.22      D  C
ATOM  11973  NZ   LYS D 166      6.909   6.791  14.323  1.00 61.04      D  N
ATOM  11977  C    LYS D 166      9.378  10.392  19.277  1.00 55.72      D  C
ATOM  11978  O    LYS D 166     10.546  10.131  19.070  1.00 56.27      D  O
ATOM  11980  N    GLN D 167      8.719   9.970  20.349  1.00 56.45      D  N
ATOM  11981  CA   GLN D 167      9.323   9.094  21.340  1.00 56.84      D  C
ATOM  11983  CB   GLN D 167      8.602   9.188  22.692  1.00 56.98      D  C
ATOM  11986  CG   GLN D 167      8.611  10.576  23.361  1.00 57.36      D  C
ATOM  11989  CD   GLN D 167      7.815  10.615  24.679  1.00 56.67      D  C
ATOM  11990  OE1  GLN D 167      7.314   9.593  25.158  1.00 55.70      D  O
ATOM  11991  NE2  GLN D 167      7.713  11.797  25.265  1.00 54.10      D  N
ATOM  11994  C    GLN D 167      9.261   7.652  20.865  1.00 57.49      D  C
ATOM  11995  O    GLN D 167      8.640   7.345  19.851  1.00 57.52      D  O
ATOM  11997  N    SER D 168      9.927   6.795  21.633  1.00 58.28      D  N
ATOM  11998  CA   SER D 168      9.928   5.341  21.504  1.00 58.93      D  C
```

Figure 8 – CONT.

```
ATOM  12000  CB   SER D 168     10.552    4.774   22.797  1.00 58.99      D  C
ATOM  12003  OG   SER D 168     10.626    3.367   22.818  1.00 60.16      D  O
ATOM  12005  C    SER D 168      8.520    4.772   21.297  1.00 59.60      D  C
ATOM  12006  O    SER D 168      8.298    3.904   20.429  1.00 59.79      D  O
ATOM  12008  N    ASN D 170      7.573    5.298   22.084  1.00 59.67      D  N
ATOM  12009  CA   ASN D 170      6.199    4.802   22.158  1.00 59.16      D  C
ATOM  12011  CB   ASN D 170      5.712    4.947   23.600  1.00 59.57      D  C
ATOM  12014  CG   ASN D 170      5.478    6.412   24.000  1.00 60.29      D  C
ATOM  12015  OD1  ASN D 170      5.609    7.333   23.187  1.00 60.37      D  O
ATOM  12016  ND2  ASN D 170      5.116    6.619   25.254  1.00 62.07      D  N
ATOM  12019  C    ASN D 170      5.221    5.528   21.246  1.00 58.51      D  C
ATOM  12020  O    ASN D 170      4.019    5.496   21.489  1.00 58.49      D  O
ATOM  12022  N    ASN D 171      5.734    6.224   20.236  1.00 57.66      D  N
ATOM  12023  CA   ASN D 171      4.915    6.995   19.274  1.00 57.01      D  C
ATOM  12025  CB   ASN D 171      3.898    6.104   18.561  1.00 57.59      D  C
ATOM  12028  CG   ASN D 171      4.558    4.978   17.785  1.00 60.12      D  C
ATOM  12029  OD1  ASN D 171      5.150    5.192   16.715  1.00 64.15      D  O
ATOM  12030  ND2  ASN D 171      4.454    3.766   18.317  1.00 61.69      D  N
ATOM  12033  C    ASN D 171      4.218    8.265   19.799  1.00 55.54      D  C
ATOM  12034  O    ASN D 171      3.606    9.001   19.018  1.00 54.88      D  O
ATOM  12036  N    LYS D 172      4.317    8.537   21.097  1.00 54.12      D  N
ATOM  12037  CA   LYS D 172      3.952    9.855   21.613  1.00 52.94      D  C
ATOM  12039  CB   LYS D 172      3.468    9.742   23.066  1.00 52.82      D  C
ATOM  12046  C    LYS D 172      5.189   10.763   21.453  1.00 51.63      D  C
ATOM  12047  O    LYS D 172      6.292   10.270   21.234  1.00 51.75      D  O
ATOM  12049  N    TYR D 173      5.004   12.074   21.530  1.00 49.83      D  N
ATOM  12050  CA   TYR D 173      6.084   13.034   21.305  1.00 48.52      D  C
ATOM  12052  CB   TYR D 173      5.563   14.190   20.451  1.00 48.93      D  C
ATOM  12055  CG   TYR D 173      5.411   13.834   18.980  1.00 52.15      D  C
ATOM  12056  CD1  TYR D 173      6.440   14.109   18.061  1.00 54.32      D  C
ATOM  12058  CE1  TYR D 173      6.308   13.792   16.702  1.00 56.71      D  C
ATOM  12060  CZ   TYR D 173      5.126   13.188   16.246  1.00 57.96      D  C
ATOM  12061  OH   TYR D 173      4.985   12.861   14.921  1.00 58.69      D  O
ATOM  12063  CE2  TYR D 173      4.091   12.904   17.139  1.00 57.15      D  C
ATOM  12065  CD2  TYR D 173      4.239   13.232   18.501  1.00 55.10      D  C
ATOM  12067  C    TYR D 173      6.718   13.595   22.593  1.00 46.53      D  C
ATOM  12068  O    TYR D 173      6.110   13.547   23.676  1.00 45.78      D  O
ATOM  12070  N    ALA D 174      7.945   14.119   22.456  1.00 43.83      D  N
ATOM  12071  CA   ALA D 174      8.632   14.858   23.538  1.00 41.88      D  C
ATOM  12073  CB   ALA D 174      9.702   14.020   24.201  1.00 41.08      D  C
ATOM  12077  C    ALA D 174      9.203   16.182   23.028  1.00 40.23      D  C
ATOM  12078  O    ALA D 174      9.412   16.375   21.829  1.00 40.66      D  O
ATOM  12080  N    ALA D 175      9.396   17.112   23.947  1.00 37.82      D  N
ATOM  12081  CA   ALA D 175     10.030   18.396   23.654  1.00 36.65      D  C
ATOM  12083  CB   ALA D 175      9.060   19.348   22.987  1.00 35.92      D  C
ATOM  12087  C    ALA D 175     10.584   19.015   24.948  1.00 35.67      D  C
ATOM  12088  O    ALA D 175     10.236   18.556   26.044  1.00 35.62      D  O
ATOM  12090  N    SER D 176     11.423   20.044   24.804  1.00 34.20      D  N
ATOM  12091  CA   SER D 176     12.150   20.654   25.916  1.00 33.76      D  C
ATOM  12093  CB   SER D 176     13.575   20.151   25.996  1.00 33.90      D  C
ATOM  12096  OG   SER D 176     13.657   18.767   26.182  1.00 37.95      D  O
ATOM  12098  C    SER D 176     12.229   22.127   25.603  1.00 33.49      D  C
ATOM  12099  O    SER D 176     12.349   22.486   24.422  1.00 33.36      D  O
ATOM  12101  N    SER D 177     12.171   22.962   26.640  1.00 32.74      D  N
ATOM  12102  CA   SER D 177     12.469   24.390   26.530  1.00 32.58      D  C
ATOM  12104  CB   SER D 177     11.222   25.217   26.545  1.00 32.36      D  C
ATOM  12107  OG   SER D 177     11.505   26.574   26.261  1.00 34.79      D  O
ATOM  12109  C    SER D 177     13.381   24.774   27.679  1.00 33.21      D  C
```

Figure 8 – CONT.

```
ATOM  12110  O    SER D 177      13.381  24.141  28.756  1.00 33.36      D  O
ATOM  12112  N    TYR D 178      14.214  25.771  27.425  1.00 32.74      D  N
ATOM  12113  CA   TYR D 178      15.252  26.151  28.343  1.00 32.69      D  C
ATOM  12115  CB   TYR D 178      16.585  25.660  27.813  1.00 32.53      D  C
ATOM  12118  CG   TYR D 178      16.801  24.173  27.913  1.00 31.05      D  C
ATOM  12119  CD1  TYR D 178      17.414  23.623  29.030  1.00 29.97      D  C
ATOM  12121  CE1  TYR D 178      17.650  22.254  29.122  1.00 30.03      D  C
ATOM  12123  CZ   TYR D 178      17.243  21.410  28.103  1.00 28.47      D  C
ATOM  12124  OH   TYR D 178      17.483  20.058  28.228  1.00 27.38      D  O
ATOM  12126  CE2  TYR D 178      16.631  21.932  26.979  1.00 28.84      D  C
ATOM  12128  CD2  TYR D 178      16.430  23.325  26.887  1.00 30.12      D  C
ATOM  12130  C    TYR D 178      15.254  27.659  28.430  1.00 33.35      D  C
ATOM  12131  O    TYR D 178      15.254  28.299  27.392  1.00 34.52      D  O
ATOM  12133  N    LEU D 179      15.188  28.216  29.636  1.00 33.82      D  N
ATOM  12134  CA   LEU D 179      15.346  29.675  29.868  1.00 35.35      D  C
ATOM  12136  CB   LEU D 179      14.212  30.256  30.712  1.00 35.27      D  C
ATOM  12139  CG   LEU D 179      14.240  31.759  31.057  1.00 36.37      D  C
ATOM  12141  CD1  LEU D 179      14.476  32.644  29.806  1.00 36.69      D  C
ATOM  12145  CD2  LEU D 179      12.959  32.183  31.748  1.00 32.79      D  C
ATOM  12149  C    LEU D 179      16.698  29.934  30.555  1.00 36.44      D  C
ATOM  12150  O    LEU D 179      16.995  29.369  31.624  1.00 36.04      D  O
ATOM  12152  N    SER D 180      17.531  30.729  29.886  1.00 37.72      D  N
ATOM  12153  CA   SER D 180      18.853  31.041  30.359  1.00 38.93      D  C
ATOM  12155  CB   SER D 180      19.843  31.004  29.210  1.00 38.65      D  C
ATOM  12158  OG   SER D 180      19.946  29.685  28.714  1.00 39.89      D  O
ATOM  12160  C    SER D 180      18.774  32.425  30.981  1.00 40.04      D  C
ATOM  12161  O    SER D 180      18.109  33.317  30.457  1.00 40.07      D  O
ATOM  12163  N    LEU D 181      19.420  32.591  32.122  1.00 41.31      D  N
ATOM  12164  CA   LEU D 181      19.303  33.839  32.887  1.00 41.95      D  C
ATOM  12166  CB   LEU D 181      18.173  33.737  33.918  1.00 42.36      D  C
ATOM  12169  CG   LEU D 181      16.743  33.526  33.479  1.00 41.07      D  C
ATOM  12171  CD1  LEU D 181      15.907  33.441  34.726  1.00 40.77      D  C
ATOM  12175  CD2  LEU D 181      16.284  34.649  32.571  1.00 41.79      D  C
ATOM  12179  C    LEU D 181      20.558  34.011  33.654  1.00 42.12      D  C
ATOM  12180  O    LEU D 181      21.181  33.016  33.986  1.00 42.53      D  O
ATOM  12182  N    THR D 182      20.918  35.256  33.965  1.00 43.83      D  N
ATOM  12183  CA   THR D 182      21.993  35.533  34.951  1.00 44.97      D  C
ATOM  12185  CB   THR D 182      22.450  37.002  35.003  1.00 45.29      D  C
ATOM  12187  OG1  THR D 182      21.334  37.839  35.365  1.00 47.80      D  O
ATOM  12189  CG2  THR D 182      23.018  37.448  33.654  1.00 46.09      D  C
ATOM  12193  C    THR D 182      21.415  35.215  36.314  1.00 45.24      D  C
ATOM  12194  O    THR D 182      20.179  35.256  36.502  1.00 45.07      D  O
ATOM  12196  N    PRO D 183      22.291  34.899  37.273  1.00 46.00      D  N
ATOM  12197  CA   PRO D 183      21.733  34.669  38.596  1.00 46.99      D  C
ATOM  12199  CB   PRO D 183      22.957  34.277  39.417  1.00 47.11      D  C
ATOM  12202  CG   PRO D 183      23.795  33.538  38.416  1.00 46.40      D  C
ATOM  12205  CD   PRO D 183      23.655  34.368  37.160  1.00 45.50      D  C
ATOM  12208  C    PRO D 183      21.003  35.870  39.152  1.00 47.41      D  C
ATOM  12209  O    PRO D 183      19.998  35.694  39.828  1.00 48.22      D  O
ATOM  12210  N    GLU D 184      21.443  37.078  38.823  1.00 48.38      D  N
ATOM  12211  CA   GLU D 184      20.732  38.276  39.274  1.00 48.99      D  C
ATOM  12213  CB   GLU D 184      21.479  39.576  38.895  1.00 49.01      D  C
ATOM  12220  C    GLU D 184      19.283  38.243  38.758  1.00 49.18      D  C
ATOM  12221  O    GLU D 184      18.353  38.302  39.556  1.00 49.89      D  O
ATOM  12223  N    GLN D 185      19.076  38.077  37.451  1.00 49.35      D  N
ATOM  12224  CA   GLN D 185      17.692  38.006  36.908  1.00 48.70      D  C
ATOM  12226  CB   GLN D 185      17.692  37.745  35.413  1.00 49.41      D  C
ATOM  12229  CG   GLN D 185      18.379  38.781  34.539  1.00 51.29      D  C
```

Figure 8 – CONT.

```
ATOM  12232  CD   GLN D 185     19.042  38.134  33.340  1.00 51.64     D   C
ATOM  12233  OE1  GLN D 185     18.576  37.118  32.820  1.00 48.59     D   O
ATOM  12234  NE2  GLN D 185     20.166  38.692  32.932  1.00 54.14     D   N
ATOM  12237  C    GLN D 185     16.854  36.888  37.519  1.00 47.67     D   C
ATOM  12238  O    GLN D 185     15.659  37.031  37.689  1.00 46.95     D   O
ATOM  12240  N    TRP D 186     17.457  35.741  37.791  1.00 47.16     D   N
ATOM  12241  CA   TRP D 186     16.686  34.641  38.393  1.00 46.72     D   C
ATOM  12243  CB   TRP D 186     17.560  33.416  38.536  1.00 46.03     D   C
ATOM  12246  CG   TRP D 186     17.122  32.363  39.529  1.00 44.74     D   C
ATOM  12247  CD1  TRP D 186     17.866  31.868  40.566  1.00 44.40     D   C
ATOM  12249  NE1  TRP D 186     17.171  30.878  41.225  1.00 43.48     D   N
ATOM  12251  CE2  TRP D 186     15.965  30.699  40.607  1.00 42.01     D   C
ATOM  12252  CD2  TRP D 186     15.898  31.613  39.530  1.00 42.71     D   C
ATOM  12253  CE3  TRP D 186     14.754  31.619  38.726  1.00 41.97     D   C
ATOM  12255  CZ3  TRP D 186     13.722  30.738  39.036  1.00 41.75     D   C
ATOM  12257  CH2  TRP D 186     13.818  29.864  40.118  1.00 39.93     D   C
ATOM  12259  CZ2  TRP D 186     14.930  29.825  40.910  1.00 40.24     D   C
ATOM  12261  C    TRP D 186     16.131  35.077  39.757  1.00 47.68     D   C
ATOM  12262  O    TRP D 186     14.914  35.041  39.974  1.00 46.70     D   O
ATOM  12264  N    LYS D 187     17.038  35.510  40.645  1.00 48.40     D   N
ATOM  12265  CA   LYS D 187     16.695  35.848  42.038  1.00 49.14     D   C
ATOM  12267  CB   LYS D 187     17.955  36.032  42.900  1.00 48.68     D   C
ATOM  12270  CG   LYS D 187     18.781  34.753  43.136  1.00 48.91     D   C
ATOM  12273  CD   LYS D 187     18.387  33.996  44.416  1.00 48.78     D   C
ATOM  12278  C    LYS D 187     15.831  37.099  42.132  1.00 49.74     D   C
ATOM  12279  O    LYS D 187     15.143  37.296  43.125  1.00 50.12     D   O
ATOM  12281  N    SER D 188     15.831  37.922  41.088  1.00 50.58     D   N
ATOM  12282  CA   SER D 188     15.156  39.214  41.155  1.00 51.07     D   C
ATOM  12284  CB   SER D 188     15.909  40.225  40.281  1.00 51.52     D   C
ATOM  12287  OG   SER D 188     15.764  39.883  38.912  1.00 52.85     D   O
ATOM  12289  C    SER D 188     13.669  39.198  40.771  1.00 50.81     D   C
ATOM  12290  O    SER D 188     13.057  40.271  40.670  1.00 51.42     D   O
ATOM  12292  N    HIS D 189     13.085  38.020  40.549  1.00 50.20     D   N
ATOM  12293  CA   HIS D 189     11.628  37.903  40.326  1.00 49.84     D   C
ATOM  12295  CB   HIS D 189     11.303  37.502  38.883  1.00 50.71     D   C
ATOM  12298  CG   HIS D 189     11.635  38.548  37.868  1.00 53.06     D   C
ATOM  12299  ND1  HIS D 189     10.792  39.602  37.583  1.00 57.11     D   N
ATOM  12301  CE1  HIS D 189     11.336  40.361  36.647  1.00 57.54     D   C
ATOM  12303  NE2  HIS D 189     12.504  39.837  36.316  1.00 57.63     D   N
ATOM  12305  CD2  HIS D 189     12.710  38.697  37.059  1.00 55.78     D   C
ATOM  12307  C    HIS D 189     11.010  36.867  41.279  1.00 48.63     D   C
ATOM  12308  O    HIS D 189     11.698  35.972  41.778  1.00 47.50     D   O
ATOM  12310  N    ARG D 190      9.709  37.002  41.517  1.00 47.17     D   N
ATOM  12311  CA   ARG D 190      9.028  36.219  42.538  1.00 46.92     D   C
ATOM  12313  CB   ARG D 190      7.709  36.893  42.969  1.00 46.62     D   C
ATOM  12322  C    ARG D 190      8.732  34.823  42.034  1.00 46.26     D   C
ATOM  12323  O    ARG D 190      8.583  33.897  42.814  1.00 45.98     D   O
ATOM  12325  N    SER D 191      8.649  34.680  40.721  1.00 45.96     D   N
ATOM  12326  CA   SER D 191      8.066  33.505  40.115  1.00 45.44     D   C
ATOM  12328  CB   SER D 191      6.549  33.618  40.241  1.00 45.52     D   C
ATOM  12331  OG   SER D 191      5.887  32.757  39.346  1.00 47.64     D   O
ATOM  12333  C    SER D 191      8.446  33.458  38.637  1.00 44.67     D   C
ATOM  12334  O    SER D 191      8.533  34.495  37.989  1.00 44.91     D   O
ATOM  12336  N    TYR D 192      8.677  32.256  38.120  1.00 43.05     D   N
ATOM  12337  CA   TYR D 192      8.727  32.038  36.690  1.00 42.53     D   C
ATOM  12339  CB   TYR D 192     10.134  31.664  36.247  1.00 42.53     D   C
ATOM  12342  CG   TYR D 192     11.109  32.807  36.213  1.00 44.43     D   C
ATOM  12343  CD1  TYR D 192     11.364  33.481  35.028  1.00 44.79     D   C
```

Figure 8 – CONT.

```
ATOM  12345  CE1  TYR D 192      12.276  34.521  34.981  1.00 46.29      D  C
ATOM  12347  CZ   TYR D 192      12.950  34.894  36.127  1.00 45.99      D  C
ATOM  12348  OH   TYR D 192      13.844  35.932  36.060  1.00 48.64      D  O
ATOM  12350  CE2  TYR D 192      12.731  34.228  37.322  1.00 45.25      D  C
ATOM  12352  CD2  TYR D 192      11.816  33.193  37.365  1.00 44.51      D  C
ATOM  12354  C    TYR D 192       7.780  30.899  36.337  1.00 41.45      D  C
ATOM  12355  O    TYR D 192       7.592  29.975  37.116  1.00 39.70      D  O
ATOM  12357  N    SER D 193       7.225  30.933  35.136  1.00 40.41      D  N
ATOM  12358  CA   SER D 193       6.399  29.832  34.722  1.00 40.18      D  C
ATOM  12360  CB   SER D 193       4.942  30.227  34.857  1.00 40.16      D  C
ATOM  12363  OG   SER D 193       4.757  31.453  34.222  1.00 43.26      D  O
ATOM  12365  C    SER D 193       6.718  29.329  33.318  1.00 39.45      D  C
ATOM  12366  O    SER D 193       7.060  30.098  32.427  1.00 39.36      D  O
ATOM  12368  N    CYS D 194       6.623  28.021  33.158  1.00 38.90      D  N
ATOM  12369  CA   CYS D 194       6.616  27.381  31.872  1.00 39.36      D  C
ATOM  12371  CB   CYS D 194       7.515  26.160  31.861  1.00 38.92      D  C
ATOM  12374  SG   CYS D 194       7.468  25.294  30.297  1.00 38.33      D  S
ATOM  12376  C    CYS D 194       5.185  26.976  31.535  1.00 40.29      D  C
ATOM  12377  O    CYS D 194       4.556  26.225  32.273  1.00 40.39      D  O
ATOM  12379  N    ARG D 195       4.700  27.462  30.399  1.00 40.97      D  N
ATOM  12380  CA   ARG D 195       3.319  27.305  29.997  1.00 42.00      D  C
ATOM  12382  CB   ARG D 195       2.680  28.688  29.986  1.00 42.61      D  C
ATOM  12385  CG   ARG D 195       1.346  28.828  29.278  1.00 47.40      D  C
ATOM  12388  CD   ARG D 195       0.872  30.300  29.361  1.00 53.15      D  C
ATOM  12391  NE   ARG D 195      -0.279  30.559  28.498  1.00 58.12      D  N
ATOM  12393  CZ   ARG D 195      -1.554  30.317  28.825  1.00 62.91      D  C
ATOM  12394  NH1  ARG D 195      -1.875  29.806  30.012  1.00 64.34      D  N
ATOM  12397  NH2  ARG D 195      -2.527  30.584  27.952  1.00 64.38      D  N
ATOM  12400  C    ARG D 195       3.237  26.590  28.637  1.00 41.41      D  C
ATOM  12401  O    ARG D 195       3.657  27.121  27.595  1.00 41.72      D  O
ATOM  12403  N    VAL D 196       2.678  25.390  28.662  1.00 40.62      D  N
ATOM  12404  CA   VAL D 196       2.621  24.515  27.508  1.00 40.49      D  C
ATOM  12406  CB   VAL D 196       3.165  23.138  27.882  1.00 40.41      D  C
ATOM  12408  CG1  VAL D 196       3.026  22.172  26.707  1.00 40.35      D  C
ATOM  12412  CG2  VAL D 196       4.623  23.244  28.359  1.00 39.06      D  C
ATOM  12416  C    VAL D 196       1.183  24.347  27.001  1.00 41.18      D  C
ATOM  12417  O    VAL D 196       0.324  23.821  27.721  1.00 41.23      D  O
ATOM  12419  N    THR D 197       0.908  24.794  25.776  1.00 41.50      D  N
ATOM  12420  CA   THR D 197      -0.425  24.610  25.180  1.00 41.73      D  C
ATOM  12422  CB   THR D 197      -0.892  25.880  24.477  1.00 41.81      D  C
ATOM  12424  OG1  THR D 197      -0.832  26.983  25.390  1.00 41.23      D  O
ATOM  12426  CG2  THR D 197      -2.320  25.736  23.999  1.00 42.52      D  C
ATOM  12430  C    THR D 197      -0.456  23.402  24.206  1.00 42.41      D  C
ATOM  12431  O    THR D 197       0.383  23.310  23.305  1.00 42.31      D  O
ATOM  12433  N    HIS D 198      -1.407  22.483  24.414  1.00 42.79      D  N
ATOM  12434  CA   HIS D 198      -1.596  21.303  23.560  1.00 44.10      D  C
ATOM  12436  CB   HIS D 198      -1.004  20.070  24.229  1.00 43.83      D  C
ATOM  12439  CG   HIS D 198      -1.189  18.787  23.459  1.00 44.73      D  C
ATOM  12440  ND1  HIS D 198      -0.501  18.501  22.295  1.00 44.77      D  N
ATOM  12442  CE1  HIS D 198      -0.823  17.287  21.884  1.00 43.76      D  C
ATOM  12444  NE2  HIS D 198      -1.680  16.764  22.743  1.00 44.22      D  N
ATOM  12446  CD2  HIS D 198      -1.922  17.681  23.738  1.00 43.54      D  C
ATOM  12448  C    HIS D 198      -3.080  21.044  23.273  1.00 45.45      D  C
ATOM  12449  O    HIS D 198      -3.867  20.774  24.208  1.00 45.08      D  O
ATOM  12451  N    GLU D 199      -3.445  21.117  21.987  1.00 46.36      D  N
ATOM  12452  CA   GLU D 199      -4.816  20.900  21.542  1.00 47.79      D  C
ATOM  12454  CB   GLU D 199      -5.167  19.398  21.586  1.00 48.43      D  C
ATOM  12457  CG   GLU D 199      -4.371  18.510  20.588  1.00 50.76      D  C
```

Figure 8 – CONT.

```
ATOM  12460  CD   GLU D 199      -4.585  18.918  19.131  1.00 52.67      D  C
ATOM  12461  OE1  GLU D 199      -5.767  19.078  18.746  1.00 56.09      D  O
ATOM  12462  OE2  GLU D 199      -3.585  19.082  18.382  1.00 51.68      D  O
ATOM  12463  C    GLU D 199      -5.790  21.696  22.410  1.00 47.83      D  C
ATOM  12464  O    GLU D 199      -6.659  21.122  23.067  1.00 48.55      D  O
ATOM  12466  N    GLY D 200      -5.607  23.009  22.468  1.00 47.81      D  N
ATOM  12467  CA   GLY D 200      -6.545  23.869  23.177  1.00 48.10      D  C
ATOM  12470  C    GLY D 200      -6.363  23.956  24.677  1.00 48.26      D  C
ATOM  12471  O    GLY D 200      -6.686  24.980  25.273  1.00 49.17      D  O
ATOM  12473  N    SER D 203      -5.837  22.913  25.305  1.00 47.94      D  N
ATOM  12474  CA   SER D 203      -5.622  22.956  26.736  1.00 47.96      D  C
ATOM  12476  CB   SER D 203      -6.106  21.645  27.378  1.00 47.81      D  C
ATOM  12479  OG   SER D 203      -5.035  20.768  27.612  1.00 51.20      D  O
ATOM  12481  C    SER D 203      -4.149  23.322  27.077  1.00 47.51      D  C
ATOM  12482  O    SER D 203      -3.208  22.964  26.364  1.00 47.50      D  O
ATOM  12484  N    THR D 204      -3.987  24.081  28.156  1.00 46.64      D  N
ATOM  12485  CA   THR D 204      -2.709  24.623  28.599  1.00 45.65      D  C
ATOM  12487  CB   THR D 204      -2.782  26.138  28.685  1.00 45.40      D  C
ATOM  12489  OG1  THR D 204      -2.722  26.722  27.379  1.00 44.50      D  O
ATOM  12491  CG2  THR D 204      -1.649  26.665  29.522  1.00 45.84      D  C
ATOM  12495  C    THR D 204      -2.342  24.119  30.004  1.00 45.52      D  C
ATOM  12496  O    THR D 204      -3.115  24.288  30.954  1.00 45.03      D  O
ATOM  12498  N    VAL D 205      -1.162  23.517  30.132  1.00 45.34      D  N
ATOM  12499  CA   VAL D 205      -0.585  23.164  31.426  1.00 44.99      D  C
ATOM  12501  CB   VAL D 205      -0.022  21.764  31.414  1.00 44.91      D  C
ATOM  12503  CG1  VAL D 205       0.590  21.450  32.740  1.00 44.97      D  C
ATOM  12507  CG2  VAL D 205      -1.086  20.777  31.066  1.00 45.39      D  C
ATOM  12511  C    VAL D 205       0.570  24.108  31.764  1.00 45.13      D  C
ATOM  12512  O    VAL D 205       1.516  24.274  30.974  1.00 44.93      D  O
ATOM  12514  N    GLU D 206       0.513  24.686  32.959  1.00 44.54      D  N
ATOM  12515  CA   GLU D 206       1.449  25.690  33.362  1.00 44.59      D  C
ATOM  12517  CB   GLU D 206       0.722  27.027  33.396  1.00 45.06      D  C
ATOM  12520  CG   GLU D 206       1.356  28.067  34.284  1.00 47.42      D  C
ATOM  12523  CD   GLU D 206       0.928  29.474  33.904  1.00 50.28      D  C
ATOM  12524  OE1  GLU D 206      -0.195  29.633  33.348  1.00 50.11      D  O
ATOM  12525  OE2  GLU D 206       1.742  30.409  34.130  1.00 52.94      D  O
ATOM  12526  C    GLU D 206       2.065  25.361  34.718  1.00 44.07      D  C
ATOM  12527  O    GLU D 206       1.346  25.188  35.710  1.00 44.87      D  O
ATOM  12529  N    LYS D 207       3.391  25.293  34.770  1.00 42.68      D  N
ATOM  12530  CA   LYS D 207       4.100  24.991  36.013  1.00 41.74      D  C
ATOM  12532  CB   LYS D 207       4.983  23.765  35.869  1.00 40.89      D  C
ATOM  12535  CG   LYS D 207       4.244  22.548  35.468  1.00 40.76      D  C
ATOM  12538  CD   LYS D 207       3.792  21.691  36.658  1.00 39.60      D  C
ATOM  12541  CE   LYS D 207       2.851  20.586  36.156  1.00 39.02      D  C
ATOM  12544  NZ   LYS D 207       3.296  19.207  36.592  1.00 39.28      D  N
ATOM  12548  C    LYS D 207       4.936  26.172  36.442  1.00 41.46      D  C
ATOM  12549  O    LYS D 207       5.328  26.999  35.619  1.00 41.28      D  O
ATOM  12551  N    THR D 208       5.188  26.263  37.747  1.00 40.96      D  N
ATOM  12552  CA   THR D 208       5.826  27.429  38.300  1.00 40.93      D  C
ATOM  12554  CB   THR D 208       4.790  28.369  38.978  1.00 41.32      D  C
ATOM  12556  OG1  THR D 208       3.700  28.647  38.064  1.00 42.13      D  O
ATOM  12558  CG2  THR D 208       5.409  29.688  39.313  1.00 40.95      D  C
ATOM  12562  C    THR D 208       6.989  27.051  39.221  1.00 41.01      D  C
ATOM  12563  O    THR D 208       7.052  25.972  39.835  1.00 40.80      D  O
ATOM  12565  N    VAL D 209       7.944  27.953  39.267  1.00 40.96      D  N
ATOM  12566  CA   VAL D 209       9.111  27.769  40.064  1.00 41.48      D  C
ATOM  12568  CB   VAL D 209      10.230  27.194  39.164  1.00 41.27      D  C
ATOM  12570  CG1  VAL D 209      11.131  28.296  38.608  1.00 39.44      D
```

Figure 8 – CONT.

```
ATOM     12574  CG2 VAL D 209      10.991   26.133   39.897  1.00 41.52       D   C
ATOM     12578  C   VAL D 209       9.418   29.142   40.688  1.00 42.15       D   C
ATOM     12579  O   VAL D 209       9.230   30.162   40.038  1.00 42.03       D   O
ATOM     12581  N   ALA D 210       9.855   29.151   41.946  1.00 43.26       D   N
ATOM     12582  CA  ALA D 210      10.060   30.379   42.720  1.00 43.96       D   C
ATOM     12584  CB  ALA D 210       8.978   30.520   43.752  1.00 44.60       D   C
ATOM     12588  C   ALA D 210      11.435   30.353   43.388  1.00 44.83       D   C
ATOM     12589  O   ALA D 210      11.779   29.393   44.085  1.00 44.93       D   O
ATOM     12591  N   PRO D 211      12.243   31.397   43.154  1.00 45.74       D   N
ATOM     12592  CA  PRO D 211      13.605   31.450   43.662  1.00 46.72       D   C
ATOM     12594  CB  PRO D 211      14.206   32.660   42.941  1.00 46.85       D   C
ATOM     12597  CG  PRO D 211      13.096   33.432   42.466  1.00 46.21       D   C
ATOM     12600  CD  PRO D 211      11.953   32.522   42.250  1.00 45.68       D   C
ATOM     12603  C   PRO D 211      13.759   31.638   45.166  1.00 47.93       D   C
ATOM     12604  O   PRO D 211      14.873   31.494   45.667  1.00 47.80       D   O
ATOM     12605  N   ALA D 212      12.675   31.968   45.876  1.00 49.38       D   N
ATOM     12606  CA  ALA D 212      12.686   32.004   47.356  1.00 50.03       D   C
ATOM     12608  CB  ALA D 212      11.503   32.817   47.875  1.00 50.26       D   C
ATOM     12612  C   ALA D 212      12.667   30.596   47.957  1.00 50.62       D   C
ATOM     12613  O   ALA D 212      11.831   29.757   47.591  1.00 52.02       D   O
TER
HETATM12615  O   HOH W    1       8.499    8.717  -20.872  1.00 54.80       W   O
HETATM12618  O   HOH W    2      37.448    9.905  -10.211  1.00 25.85       W   O
HETATM12621  O   HOH W    3      29.708   29.260   11.327  1.00 27.99       W   O
HETATM12624  O   HOH W    4      63.316   17.379   33.894  1.00 37.34       W   O
HETATM12627  O   HOH W    5      36.314   20.342   -4.375  1.00 44.17       W   O
HETATM12630  O   HOH W    6      35.007   29.277   69.872  1.00 58.84       W   O
HETATM12633  O   HOH W    7      44.071   22.582   29.748  1.00 23.48       W   O
HETATM12636  O   HOH W    8      34.312    6.070    8.656  1.00 43.31       W   O
HETATM12639  O   HOH W    9      59.638   31.927   26.532  1.00 32.96       W   O
HETATM12642  O   HOH W   10      27.115   11.253   56.356  1.00 38.81       W   O
HETATM12645  O   HOH W   11      28.294   -6.137  -10.164  1.00 31.54       W   O
HETATM12648  O   HOH W   12      34.818   16.225  -11.086  1.00 33.68       W   O
HETATM12651  O   HOH W   13      47.769   37.345   39.862  1.00 50.62       W   O
HETATM12654  O   HOH W   14      18.469   23.752   36.003  1.00 29.88       W   O
HETATM12657  O   HOH W   15      30.267   23.685   80.641  1.00 34.93       W   O
HETATM12660  O   HOH W   16      17.046   17.680   -6.893  1.00 30.90       W   O
HETATM12663  O   HOH W   17      22.819   19.161   59.741  1.00 29.98       W   O
HETATM12666  O   HOH W   18      44.724   11.382   81.514  1.00 27.92       W   O
HETATM12669  O   HOH W   19      61.537   10.174   22.001  1.00 43.13       W   O
HETATM12672  O   HOH W   20      26.557   23.517   44.888  1.00 40.68       W   O
HETATM12675  O   HOH W   21      33.514   25.296   21.920  1.00 42.47       W   O
HETATM12678  O   HOH W   22      45.098   23.719   75.029  1.00 42.10       W   O
HETATM12681  O   HOH W   23      22.326   14.765   75.026  1.00 32.89       W   O
HETATM12684  O   HOH W   24      19.144   26.752   63.928  1.00 48.17       W   O
HETATM12687  O   HOH W   25      43.593    7.634   65.187  1.00 31.66       W   O
HETATM12690  O   HOH W   26      20.716   15.939   69.752  1.00 34.66       W   O
HETATM12693  O   HOH W   27      22.712   -0.187    0.996  1.00 33.05       W   O
HETATM12696  O   HOH W   28      20.770    9.753   75.577  1.00 47.55       W   O
HETATM12699  O   HOH W   29      29.522    7.212   12.652  1.00 35.83       W   O
HETATM12702  O   HOH W   30      32.325   20.205   -9.402  1.00 42.82       W   O
HETATM12705  O   HOH W   31      33.175   12.637   53.403  1.00 41.33       W   O
HETATM12708  O   HOH W   32      36.513   13.681   46.869  1.00 32.99       W   O
HETATM12711  O   HOH W   33      38.942    5.050    0.309  1.00 35.93       W   O
HETATM12714  O   HOH W   34      34.100   20.006   53.810  1.00 36.76       W   O
HETATM12717  O   HOH W   35       5.326   33.632   36.271  1.00 41.06       W   O
HETATM12720  O   HOH W   36      23.279   21.733   42.977  1.00 38.08       W   O
HETATM12723  O   HOH W   37       6.776   -6.427   -7.418  1.00 57.94       W   O
```

Figure 8 – CONT.

```
HETATM12726  O    HOH W  38       1.077    4.801  -15.716  1.00 45.59           W   O
HETATM12729  O    HOH W  39      65.931   12.105   27.759  1.00 53.27           W   O
HETATM12732  O    HOH W  40      20.842    8.323   26.257  1.00 28.44           W   O
HETATM12735  O    HOH W  41      38.625   14.048    4.947  1.00 32.67           W   O
HETATM12738  O    HOH W  42      28.579   10.282   23.151  1.00 31.23           W   O
HETATM12741  O    HOH W  43      31.755   24.040    0.417  1.00 36.84           W   O
HETATM12744  O    HOH W  44      15.072   20.966   17.849  1.00 29.23           W   O
HETATM12747  O    HOH W  45      44.349    6.057   69.623  1.00 36.20           W   O
HETATM12750  O    HOH W  46      36.793   -0.115  -16.795  1.00 41.09           W   O
HETATM12753  O    HOH W  47      39.617    5.353   84.589  1.00 43.83           W   O
HETATM12756  O    HOH W  48      23.570   25.025    0.081  1.00 41.75           W   O
HETATM12759  O    HOH W  49      41.095   13.478   25.345  1.00 38.24           W   O
HETATM12762  O    HOH W  50      29.038   29.312   65.036  1.00 38.19           W   O
HETATM12765  O    HOH W  51      47.562   25.843   21.241  1.00 39.82           W   O
HETATM12768  O    HOH W  52      14.555   19.039   -7.350  1.00 47.21           W   O
HETATM12771  O    HOH W  53      23.973   14.109  -12.665  1.00 27.75           W   O
HETATM12774  O    HOH W  54      39.736   29.832   39.102  1.00 39.96           W   O
HETATM12777  O    HOH W  55      46.857   30.068   37.735  1.00 30.68           W   O
HETATM12780  O    HOH W  56      44.275    0.662   79.441  1.00 49.95           W   O
HETATM12783  O    HOH W  57      36.070   17.880   30.052  1.00 52.65           W   O
HETATM12786  O    HOH W  58      69.397   13.883   41.355  1.00 38.05           W   O
HETATM12789  O    HOH W  59      44.282    8.836   84.222  1.00 50.89           W   O
HETATM12792  O    HOH W  60      19.863   14.967   20.860  1.00 32.92           W   O
HETATM12795  O    HOH W  61      22.267   23.144    6.068  1.00 34.05           W   O
HETATM12798  O    HOH W  62      34.189   33.876   60.427  1.00 32.90           W   O
HETATM12801  O    HOH W  63      15.845    1.130   -2.723  1.00 30.02           W   O
HETATM12804  O    HOH W  64      43.467    2.746   71.761  1.00 54.18           W   O
HETATM12807  O    HOH W  65      38.773    3.393  -18.299  1.00 50.52           W   O
HETATM12810  O    HOH W  66      27.075   19.459   53.431  1.00 38.24           W   O
HETATM12813  O    HOH W  67      28.870   26.769   51.401  1.00 34.72           W   O
HETATM12816  O    HOH W  68      13.371   28.745   20.458  1.00 40.66           W   O
HETATM12819  O    HOH W  69      41.636   10.410   59.405  1.00 41.53           W   O
HETATM12822  O    HOH W  70      26.590    9.160    9.621  1.00 31.13           W   O
HETATM12825  O    HOH W  71      41.581   13.691   -3.357  1.00 43.03           W   O
HETATM12828  O    HOH W  72      14.821   20.798   41.625  1.00 30.01           W   O
HETATM12831  O    HOH W  73      26.262    4.254   38.332  1.00 42.12           W   O
HETATM12834  O    HOH W  74      27.479   11.760  -18.915  1.00 55.62           W   O
HETATM12837  O    HOH W  75      41.226    9.385   -1.031  1.00 42.86           W   O
HETATM12840  O    HOH W  76      34.334   23.532   -1.043  1.00 29.93           W   O
HETATM12843  O    HOH W  77       2.309   17.723   34.408  1.00 44.11           W   O
HETATM12846  O    HOH W  78      31.455   28.397   66.670  1.00 41.63           W   O
HETATM12849  O    HOH W  79      63.618   29.904   38.501  1.00 39.06           W   O
HETATM12852  O    HOH W  80      36.420   12.120  -11.305  1.00 43.01           W   O
HETATM12855  O    HOH W  81      22.273    4.873   81.281  1.00 39.77           W   O
HETATM12858  O    HOH W  82      35.640   14.837   56.431  1.00 35.41           W   O
HETATM12861  O    HOH W  83      24.778   21.217   76.560  1.00 37.29           W   O
HETATM12864  O    HOH W  84      55.535   23.856   61.149  1.00 58.84           W   O
HETATM12867  O    HOH W  85      24.224   18.712   69.596  1.00 34.76           W   O
HETATM12870  O    HOH W  86      27.039    4.310    7.910  1.00 51.25           W   O
HETATM12873  O    HOH W  87      32.930   22.041   14.455  1.00 31.02           W   O
HETATM12876  O    HOH W  88      33.662    8.919   26.695  1.00 39.91           W   O
HETATM12879  O    HOH W  89      53.135   14.621   46.280  1.00 52.45           W   O
HETATM12882  O    HOH W  90      45.277    4.200   39.474  1.00 47.20           W   O
HETATM12885  O    HOH W  91       2.897   18.910   39.485  1.00 48.52           W   O
HETATM12888  O    HOH W  92      27.999   15.072   11.945  1.00 29.07           W   O
HETATM12891  O    HOH W  93      42.039   30.938   31.576  1.00 54.70           W   O
HETATM12894  O    HOH W  94      22.713   24.460   -3.405  1.00 59.56           W   O
HETATM12897  O    HOH W  95      26.490   20.865    0.388  1.00 24.68           W   O
```

Figure 8 – CONT.

```
HETATM12900  O   HOH W  96     11.929  10.404  17.110  1.00 48.87      W  O
HETATM12903  O   HOH W  97     50.590  25.095  48.654  1.00 38.98      W  O
HETATM12906  O   HOH W  98     36.736   7.493 -11.448  1.00 29.60      W  O
HETATM12909  O   HOH W  99     24.959  -1.505 -15.524  1.00 40.10      W  O
HETATM12912  O   HOH W 100     34.813  14.581  51.040  1.00 35.62      W  O
HETATM12915  O   HOH W 101     29.060  23.482  -0.894  1.00 33.54      W  O
HETATM12918  O   HOH W 102     28.273   8.795  62.221  1.00 33.24      W  O
HETATM12921  O   HOH W 103      8.261  32.675  25.988  1.00 37.09      W  O
HETATM12924  O   HOH W 104     47.189  22.289  69.915  1.00 34.59      W  O
HETATM12927  O   HOH W 105     47.303  25.688  66.663  1.00 43.74      W  O
HETATM12930  O   HOH W 106     46.241  18.321  26.378  1.00 25.44      W  O
HETATM12933  O   HOH W 107     28.649  18.493 -14.805  1.00 36.16      W  O
HETATM12936  O   HOH W 108     32.733  10.315   6.456  1.00 30.75      W  O
HETATM12939  O   HOH W 109      8.116  -0.071   2.569  1.00 47.27      W  O
HETATM12942  O   HOH W 110     16.974  22.896  19.017  1.00 43.46      W  O
HETATM12945  O   HOH W 111     33.952   7.842  59.493  1.00 41.83      W  O
HETATM12948  O   HOH W 112     18.225  28.742  26.922  1.00 30.17      W  O
HETATM12951  O   HOH W 113     28.786  15.405  58.888  1.00 33.82      W  O
HETATM12954  O   HOH W 114      1.703  10.486  14.020  1.00 55.58      W  O
HETATM12957  O   HOH W 115     35.195  17.046  51.749  1.00 42.18      W  O
HETATM12960  O   HOH W 116      7.468  11.951  13.160  1.00 47.98      W  O
HETATM12963  O   HOH W 117     34.311  25.896  65.642  1.00 22.19      W  O
HETATM12966  O   HOH W 118     37.229  30.306  65.813  1.00 49.82      W  O
HETATM12969  O   HOH W 119     57.092  26.796  70.768  1.00 52.51      W  O
HETATM12972  O   HOH W 120      1.029  18.937  -6.903  1.00 49.85      W  O
HETATM12975  O   HOH W 121     21.871  23.307  66.081  1.00 46.42      W  O
HETATM12978  O   HOH W 122     52.669   4.847  64.738  1.00 61.08      W  O
HETATM12981  O   HOH W 123     17.884  19.234   1.672  1.00 31.80      W  O
HETATM12984  O   HOH W 124      9.457   4.037  31.649  1.00 50.32      W  O
HETATM12987  O   HOH W 125     10.344  18.337   8.751  1.00 56.85      W  O
HETATM12990  O   HOH W 126     50.808   7.227  18.692  1.00 58.78      W  O
HETATM12993  O   HOH W 127     72.592  26.019  46.425  1.00 50.44      W  O
HETATM12996  O   HOH W 128      0.442  14.595  33.847  1.00 46.64      W  O
HETATM12999  O   HOH W 129     43.773   4.694  -7.777  1.00 62.49      W  O
HETATM13002  O   HOH W 130     20.496   9.909  45.114  1.00 38.47      W  O
HETATM13005  O   HOH W 131     50.298  18.101  25.912  1.00 30.67      W  O
HETATM13008  O   HOH W 132     33.785  28.021   2.902  1.00 32.49      W  O
HETATM13011  O   HOH W 133     27.271  28.580   5.200  1.00 33.21      W  O
HETATM13014  O   HOH W 134     48.265   9.766  62.966  1.00 37.46      W  O
HETATM13017  O   HOH W 135     37.021   2.431   0.305  1.00 36.52      W  O
HETATM13020  O   HOH W 136     58.329  30.019  43.124  1.00 34.03      W  O
HETATM13023  O   HOH W 137     18.872  21.057  41.323  1.00 32.97      W  O
HETATM13026  O   HOH W 138     57.704  18.806  29.741  1.00 37.32      W  O
HETATM13029  O   HOH W 139     16.331  18.568  26.230  1.00 31.09      W  O
HETATM13032  O   HOH W 140     52.236  31.737  43.552  1.00 46.38      W  O
HETATM13035  O   HOH W 141     47.863   8.758  25.332  1.00 41.57      W  O
HETATM13038  O   HOH W 142     39.004   3.296  33.589  1.00 45.97      W  O
HETATM13041  O   HOH W 143     41.129   1.331  31.049  1.00 49.57      W  O
HETATM13044  O   HOH W 144     12.199  11.241  22.745  1.00 52.88      W  O
HETATM13047  O   HOH W 145     46.878   4.444  70.328  1.00 36.97      W  O
HETATM13050  O   HOH W 146     25.678  28.153  25.562  1.00 39.98      W  O
HETATM13053  O   HOH W 147     35.532  31.966  19.304  1.00 48.23      W  O
HETATM13056  O   HOH W 148     10.826  20.707 -23.109  1.00 50.27      W  O
HETATM13059  O   HOH W 149     20.700  17.253  17.915  1.00 43.86      W  O
HETATM13062  O   HOH W 150     24.013  19.699 -16.290  1.00 55.10      W  O
HETATM13065  O   HOH W 151     41.955  19.032  24.546  1.00 40.60      W  O
HETATM13068  O   HOH W 152     35.497  18.957  79.079  1.00 37.13      W  O
HETATM13071  O   HOH W 153     26.573  17.885  16.613  1.00 38.56      W  O
```

Figure 8 – CONT.

```
HETATM13074  O    HOH W 154      11.748    4.410   37.962  1.00 43.54           W  O
HETATM13077  O    HOH W 155      -4.172   18.122   25.333  1.00 40.85           W  O
HETATM13080  O    HOH W 156       5.790    2.201   16.874  1.00 63.13           W  O
HETATM13083  O    HOH W 157      -8.987    9.924    1.682  1.00 60.14           W  O
HETATM13086  O    HOH W 158      -2.664   14.790   31.938  1.00 50.82           W  O
HETATM13089  O    HOH W 159      29.505   31.854   41.404  1.00 54.03           W  O
HETATM13092  O    HOH W 160      54.018   14.562   19.190  1.00 46.93           W  O
HETATM13095  O    HOH W 161      32.869   -0.254   77.655  1.00 53.38           W  O
HETATM13098  O    HOH W 162      34.858   -1.063   -9.543  1.00 39.16           W  O
HETATM13101  O    HOH W 163      42.941   24.392   65.791  1.00 22.64           W  O
HETATM13104  O    HOH W 164      12.950   27.417   43.218  1.00 48.59           W  O
HETATM13107  O    HOH W 165      13.759   17.726   23.762  1.00 30.05           W  O
HETATM13110  O    HOH W 166      26.137   29.393    2.666  1.00 43.49           W  O
HETATM13113  O    HOH W 167      26.164   18.591   82.779  1.00 51.62           W  O
HETATM13116  O    HOH W 168      42.496   22.888   74.171  1.00 42.18           W  O
HETATM13119  O    HOH W 169      41.308    7.385   64.288  1.00 41.53           W  O
HETATM13122  O    HOH W 170      29.598    8.899    2.504  1.00 28.64           W  O
HETATM13125  O    HOH W 171      21.364   16.942   43.864  1.00 42.77           W  O
HETATM13128  O    HOH W 172      23.413   19.047   75.386  1.00 46.27           W  O
HETATM13131  O    HOH W 173      61.987   35.026   35.208  1.00 54.60           W  O
HETATM13134  O    HOH W 174      17.504    0.546   -0.587  1.00 41.34           W  O
HETATM13137  O    HOH W 175      14.169    0.090   36.572  1.00 45.83           W  O
HETATM13140  O    HOH W 176      33.952   12.061   58.319  1.00 39.34           W  O
HETATM13143  O    HOH W 177      -1.095    9.644  -12.829  1.00 54.40           W  O
HETATM13146  O    HOH W 178       1.974   28.087   25.746  1.00 42.14           W  O
HETATM13149  O    HOH W 179       9.522    2.376   18.092  1.00 56.59           W  O
HETATM13152  O    HOH W 180      43.576   13.688   25.135  1.00 38.37           W  O
HETATM13155  O    HOH W 181      56.933   34.309   36.994  1.00 34.14           W  O
HETATM13158  O    HOH W 182      24.881    3.851   74.243  1.00 43.80           W  O
HETATM13161  O    HOH W 183      60.883   19.217   61.842  1.00 55.47           W  O
HETATM13164  O    HOH W 184      27.188   33.044   61.924  1.00 36.12           W  O
HETATM13167  O    HOH W 185      35.035   14.216   11.761  1.00 38.83           W  O
HETATM13170  O    HOH W 186       5.187   21.392  -19.097  1.00 54.47           W  O
HETATM13173  O    HOH W 187      41.205    3.919    0.968  1.00 47.36           W  O
HETATM13176  O    HOH W 188      53.372   26.330   78.972  1.00 58.68           W  O
HETATM13179  O    HOH W 189      62.735    3.195   73.452  1.00 53.71           W  O
HETATM13182  O    HOH W 190      60.387   15.071   81.554  1.00 62.79           W  O
HETATM13185  O    HOH W 191      54.796   24.202   69.273  1.00 47.77           W  O
HETATM13188  O    HOH W 192      26.097    7.024  -20.722  1.00 41.55           W  O
HETATM13191  O    HOH W 193      35.939   13.422  -15.584  1.00 55.86           W  O
HETATM13194  O    HOH W 194      14.386   11.198    8.905  1.00 69.27           W  O
HETATM13197  O    HOH W 195      35.727    9.704   10.011  1.00 56.20           W  O
HETATM13200  O    HOH W 196      25.920    6.986   29.435  1.00 55.85           W  O
HETATM13203  O    HOH W 197      35.662    8.906   28.712  1.00 61.97           W  O
HETATM13206  O    HOH W 198      26.351   -5.162  -11.568  1.00 42.69           W  O
HETATM13209  O    HOH W 199      40.930    6.899   -9.162  1.00 56.25           W  O
HETATM13212  O    HOH W 200      39.054    4.494  -15.378  1.00 59.13           W  O
HETATM13215  O    HOH W 201      69.554    3.510   65.950  1.00 66.41           W  O
HETATM13218  O    HOH W 202      53.576   24.614   71.550  1.00 40.01           W  O
HETATM13221  O    HOH W 203      48.954   20.598   41.453  1.00 28.69           W  O
HETATM13224  O    HOH W 204      21.520   -4.294   -9.976  1.00 49.20           W  O
HETATM13227  O    HOH W 205      40.444    6.819   78.202  1.00 37.87           W  O
HETATM13230  O    HOH W 206      16.878   21.956   39.905  1.00 33.54           W  O
HETATM13233  O    HOH W 207       9.310   28.289   23.064  1.00 36.86           W  O
HETATM13236  O    HOH W 208      38.852    7.415   85.809  1.00 49.26           W  O
HETATM13239  O    HOH W 209      26.082   25.051    0.943  1.00 36.23           W  O
HETATM13242  O    HOH W 210      49.127   18.465   63.114  1.00 33.90           W  O
HETATM13245  O    HOH W 211      17.833   22.833    7.609  1.00 38.97           W  O
```

Figure 8 – CONT.

```
HETATM13248  O    HOH W 212      53.019   39.558   34.389  1.00 45.17           W  O
HETATM13251  O    HOH W 213      44.294    6.598   25.802  1.00 46.90           W  O
HETATM13254  O    HOH W 214      52.129   31.440   18.663  1.00 35.79           W  O
HETATM13257  O    HOH W 215      39.799   24.425   74.498  1.00 45.45           W  O
HETATM13260  O    HOH W 216       7.617   16.477   31.612  1.00 40.00           W  O
HETATM13263  O    HOH W 217      27.286   23.255   48.836  1.00 34.86           W  O
HETATM13266  O    HOH W 218      45.520   18.723   47.786  1.00 31.88           W  O
HETATM13269  O    HOH W 219       6.153   19.056   -0.800  1.00 43.25           W  O
HETATM13272  O    HOH W 220      38.075   18.606   -8.258  1.00 65.29           W  O
HETATM13275  O    HOH W 221      16.138   15.511    7.854  1.00 39.86           W  O
HETATM13278  O    HOH W 222      31.345   14.315   63.218  1.00 29.83           W  O
HETATM13281  O    HOH W 223      21.677   23.411   57.573  1.00 31.12           W  O
HETATM13284  O    HOH W 224      41.674   21.953    0.552  1.00 38.62           W  O
HETATM13287  O    HOH W 225      25.022   -8.952   -4.794  1.00 44.03           W  O
HETATM13290  O    HOH W 226      44.653   10.838   44.361  1.00 36.27           W  O
HETATM13293  O    HOH W 227      37.644   23.555   53.304  1.00 33.36           W  O
HETATM13296  O    HOH W 228      49.393   30.317   45.055  1.00 50.55           W  O
HETATM13299  O    HOH W 229      20.873   21.520   63.477  1.00 43.41           W  O
HETATM13302  O    HOH W 230      12.528   -5.563   -3.548  1.00 51.28           W  O
HETATM13305  O    HOH W 231      27.498    7.051    8.155  1.00 39.44           W  O
HETATM13308  O    HOH W 232       9.952   31.704   23.588  1.00 61.76           W  O
HETATM13311  O    HOH W 233      35.663   17.209   14.711  1.00 47.40           W  O
HETATM13314  O    HOH W 234      35.363   10.043  -18.715  1.00 53.17           W  O
HETATM13317  O    HOH W 235      54.420   29.372   18.428  1.00 50.27           W  O
HETATM13320  O    HOH W 236      47.495    5.978   24.430  1.00 46.00           W  O
HETATM13323  O    HOH W 237      17.223    2.553    1.613  1.00 32.10           W  O
HETATM13326  O    HOH W 238      43.086   16.769   46.994  1.00 39.24           W  O
HETATM13329  O    HOH W 239       1.646    0.597   -9.743  1.00 46.45           W  O
HETATM13332  O    HOH W 240      22.641   13.095   22.274  1.00 39.55           W  O
HETATM13335  O    HOH W 241      19.111   18.774   67.607  1.00 50.47           W  O
HETATM13338  O    HOH W 242      28.922   18.621   49.902  1.00 46.77           W  O
HETATM13341  O    HOH W 243      12.052   -4.049  -14.944  1.00 60.17           W  O
HETATM13344  O    HOH W 244      34.986   20.682   14.955  1.00 37.24           W  O
HETATM13347  O    HOH W 245      32.599   31.315   26.856  1.00 60.88           W  O
HETATM13350  O    HOH W 246      26.708   13.944   55.450  1.00 50.41           W  O
HETATM13353  O    HOH W 247      48.007   20.471   61.655  1.00 39.05           W  O
HETATM13356  O    HOH W 248      30.082   17.946   35.051  1.00 33.73           W  O
HETATM13359  O    HOH W 249      -0.199   -1.680  -10.444  1.00 55.46           W  O
HETATM13362  O    HOH W 250      73.782   13.682   48.272  1.00 50.41           W  O
HETATM13365  O    HOH W 251      36.508   21.154   17.443  1.00 33.16           W  O
HETATM13368  O    HOH W 252      14.507   -2.860   -7.946  1.00 48.06           W  O
HETATM13371  O    HOH W 253       5.330   18.078   14.743  1.00 54.35           W  O
HETATM13374  O    HOH W 254      24.667   24.836   52.199  1.00 41.21           W  O
HETATM13377  O    HOH W 255      30.813    9.200   56.747  1.00 50.99           W  O
HETATM13380  O    HOH W 256       9.116   20.719  -13.254  1.00 38.69           W  O
HETATM13383  O    HOH W 257      66.753   24.921   46.310  1.00 50.35           W  O
HETATM13386  O    HOH W 258      40.947    6.010   -3.390  1.00 54.55           W  O
HETATM13389  O    HOH W 259      45.481   22.402   21.009  1.00 54.16           W  O
HETATM13392  O    HOH W 260      33.871    6.641   12.221  1.00 49.10           W  O
HETATM13395  O    HOH W 261      58.206   18.850   55.241  1.00 50.68           W  O
HETATM13398  O    HOH W 262      34.490   30.044   65.088  1.00 33.32           W  O
HETATM13401  O    HOH W 263       7.339   20.632   37.593  1.00 43.07           W  O
HETATM13404  O    HOH W 264      68.985   28.058   44.005  1.00 49.79           W  O
HETATM13407  O    HOH W 265      43.530   -0.357   25.493  1.00 51.46           W  O
HETATM13410  O    HOH W 266      25.233    8.905   12.400  1.00 49.12           W  O
HETATM13413  O    HOH W 267      15.451   19.773   15.069  1.00 54.64           W  O
HETATM13416  O    HOH W 268      27.804   13.841   14.599  1.00 25.88           W  O
HETATM13419  O    HOH W 269      26.020   11.800   14.851  1.00 50.63           W  O
```

Figure 8 – CONT.

```
HETATM13422  O   HOH W 270      20.288  21.837  43.617  1.00 33.97           W  O
HETATM13425  O   HOH W 271      35.227   2.506   2.531  1.00 37.05           W  O
HETATM13428  O   HOH W 272      40.312   4.872 -12.008  1.00 43.59           W  O
HETATM13431  O   HOH W 273      21.243  19.206  74.266  1.00 37.94           W  O
HETATM13434  O   HOH W 274      15.114  19.518  12.264  1.00 54.52           W  O
HETATM13437  O   HOH W 275      38.526   0.128   0.704  1.00 30.62           W  O
HETATM13440  O   HOH W 276      11.339  24.847  43.134  1.00 49.71           W  O
HETATM13443  O   HOH W 277      44.832  18.711  23.887  1.00 41.06           W  O
HETATM13446  O   HOH W 278      25.616   7.716  62.404  1.00 43.55           W  O
HETATM13449  O   HOH W 279      38.328  17.331  15.548  1.00 49.19           W  O
HETATM13452  O   HOH W 280      38.135  25.991  53.111  1.00 38.86           W  O
HETATM13455  O   HOH W 281      13.491  -5.811  -7.223  1.00 56.79           W  O
HETATM13458  O   HOH W 282      39.829  26.600  55.087  1.00 48.43           W  O
HETATM13461  O   HOH W 283      34.225  16.042  16.700  1.00 50.88           W  O
HETATM13464  O   HOH W 284      68.897   2.089  67.883  1.00 57.28           W  O
HETATM13467  O   HOH W 285      23.172  24.777  69.352  1.00 39.00           W  O
HETATM13470  O   HOH W 286      37.687   5.150  65.275  1.00 34.97           W  O
HETATM13473  O   HOH W 287      25.875  21.851  15.223  1.00 27.72           W  O
HETATM13476  O   HOH W 288      26.945  24.110  16.597  1.00 31.48           W  O
HETATM13479  O   HOH W 289      24.350  26.910  72.951  1.00 52.83           W  O
HETATM13482  O   HOH W 290      26.309  15.941  14.678  1.00 27.95           W  O
HETATM13485  O   HOH W 291      26.117  28.539  66.258  1.00 35.02           W  O
HETATM13488  O   HOH W 292      39.156  18.090  -0.671  1.00 50.30           W  O
HETATM13491  O   HOH W 293      28.407  27.834  12.913  1.00 37.67           W  O
HETATM13494  O   HOH W 294      29.583  13.171  16.181  1.00 32.50           W  O
HETATM13497  O   HOH W 295      39.584  -1.886  70.145  1.00 38.79           W  O
HETATM13500  O   HOH W 296      31.165  -0.828  75.815  1.00 33.82           W  O
HETATM13503  O   HOH W 297      39.551  10.039  -5.579  1.00 48.79           W  O
HETATM13506  O   HOH W 298      27.343  25.683  74.918  1.00 37.84           W  O
HETATM13509  O   HOH W 299      50.292  10.273  43.723  1.00 46.48           W  O
HETATM13512  O   HOH W 300      75.684  11.955  66.594  1.00 61.93           W  O
HETATM13515  O   HOH W 301      20.975  23.880  36.704  1.00 31.31           W  O
HETATM13518  O   HOH W 302      32.921   3.899   2.917  1.00 32.70           W  O
HETATM13521  O   HOH W 303      46.916  22.566  30.447  1.00 24.61           W  O
HETATM13524  O   HOH W 304      37.413  29.458  69.887  1.00 60.20           W  O
HETATM13527  O   HOH W 305       9.882  33.249  44.962  1.00 42.97           W  O
HETATM13530  O   HOH W 306      53.398  10.967  46.392  1.00 51.81           W  O
HETATM13533  O   HOH W 307      44.010   2.442  -4.760  1.00 47.20           W  O
HETATM13536  O   HOH W 308      37.802   5.098 -11.011  1.00 35.78           W  O
HETATM13539  O   HOH W 309      20.340   5.115   7.733  1.00 47.00           W  O
HETATM13542  O   HOH W 310      18.846   3.711   6.523  1.00 39.88           W  O
HETATM13545  O   HOH W 311      32.943   5.685  36.049  1.00 60.24           W  O
HETATM13548  O   HOH W 312      10.229  12.834  15.255  1.00 59.00           W  O
HETATM13551  O   HOH W 313      26.326  29.124  77.222  1.00 51.16           W  O
HETATM13554  O   HOH W 314      32.643  24.044 -12.221  1.00 49.49           W  O
HETATM13557  O   HOH W 315      17.710  34.398  22.977  1.00 60.44           W  O
HETATM13560  O   HOH W 316      52.804  25.552  17.953  1.00 52.57           W  O
HETATM13563  O   HOH W 317      56.529  10.546  43.008  1.00 57.50           W  O
HETATM13566  O   HOH W 318      21.995  10.253  64.317  1.00 36.37           W  O
HETATM13569  O   HOH W 319      22.711  12.565  76.552  1.00 40.48           W  O
HETATM13572  O   HOH W 320      29.939  10.635  16.308  1.00 41.25           W  O
HETATM13575  O   HOH W 321      11.963  33.143  22.437  1.00 53.86           W  O
HETATM13578  O   HOH W 322      57.503  16.661  37.041  1.00 48.80           W  O
HETATM13581  O   HOH W 323      26.078  15.356  49.969  1.00 63.05           W  O
HETATM13584  O   HOH W 324      33.999   8.882  11.833  1.00 52.96           W  O
HETATM13587  O   HOH W 325      46.549  34.186  39.426  1.00 57.86           W  O
HETATM13590  O   HOH W 326      19.510  11.663  82.345  1.00 55.17           W  O
HETATM13593  O   HOH W 327      32.348  13.618  16.161  1.00 44.89           W  O
```

Figure 8 – CONT.

```
HETATM13596  O   HOH W 328      35.787  28.989  37.222  1.00 56.27          W   O
HETATM13599  O   HOH W 329      13.754   4.520 -15.135  1.00 37.01          W   O
HETATM13602  O   HOH W 330      56.620  12.938  36.580  1.00 54.48          W   O
HETATM13605  O   HOH W 331       7.424  19.035   2.916  1.00 48.53          W   O
HETATM13608  O   HOH W 332      10.325  15.240   8.222  1.00 55.26          W   O
HETATM13611  O   HOH W 333      28.815 -10.109  -6.736  1.00 24.77          W   O
HETATM13614  O   HOH W 334      28.130  -8.302  -9.093  1.00 37.30          W   O
HETATM13617  O   HOH W 335      20.573  -7.027  -3.479  1.00 41.58          W   O
HETATM13620  O   HOH W 336       9.311  17.249   4.241  1.00 54.20          W   O
HETATM13623  O   HOH W 337      31.134  -5.136  71.708  1.00 23.44          W   O
HETATM13626  O   HOH W 338      31.988  -3.920  73.912  1.00 43.99          W   O
HETATM13629  O   HOH W 339      34.354   3.477  80.976  1.00 35.34          W   O
HETATM13632  O   HOH W 340      40.007   3.137  84.507  1.00 61.88          W   O
HETATM13635  O   HOH W 341      25.706  25.953  15.235  1.00 42.51          W   O
HETATM13638  O   HOH W 342      29.239  29.638  16.700  1.00 45.16          W   O
HETATM13641  O   HOH W 343      24.445  22.926  13.349  1.00 44.13          W   O
HETATM13644  O   HOH W 344      23.910  12.531  16.405  1.00 43.84          W   O
HETATM13647  O   HOH W 345      20.214  15.656   9.349  1.00 49.51          W   O
HETATM13650  O   HOH W 346      12.177  13.389   4.668  1.00 35.16          W   O
HETATM13653  O   HOH W 347      36.141  19.193  27.635  1.00 34.78          W   O
HETATM13656  O   HOH W 348      44.000  15.949  58.466  1.00 44.92          W   O
HETATM13659  O   HOH W 349      37.611  11.312  56.206  1.00 50.63          W   O
HETATM13662  O   HOH W 350      40.807   4.407  67.716  1.00 51.05          W   O
HETATM13665  O   HOH W 351      27.686  32.142  65.492  1.00 32.43          W   O
HETATM13668  O   HOH W 352      28.494  34.547  64.050  1.00 43.73          W   O
HETATM13671  O   HOH W 353      29.365  36.266  65.838  1.00 29.00          W   O
HETATM13674  O   HOH W 354      41.221   9.733 -12.445  1.00 50.02          W   O
HETATM13677  O   HOH W 355      18.955   2.971  75.403  1.00 40.59          W   O
HETATM13680  O   HOH W 356      19.397  14.578  65.553  1.00 45.45          W   O
HETATM13683  O   HOH W 357      51.200  13.105  88.192  1.00 52.01          W   O
HETATM13686  O   HOH W 358      35.910  21.816  87.123  1.00 50.82          W   O
HETATM13689  O   HOH W 359      31.737  17.297  84.947  1.00 41.46          W   O
HETATM13692  O   HOH W 360      13.466  37.940  32.697  1.00 47.66          W   O
HETATM13695  O   HOH W 361      61.915  11.485  30.317  1.00 54.44          W   O
HETATM13698  O   HOH W 362      60.285  16.233  29.215  1.00 58.14          W   O
HETATM13701  O   HOH W 363      61.941   8.797  23.833  1.00 51.29          W   O
TER
END
```

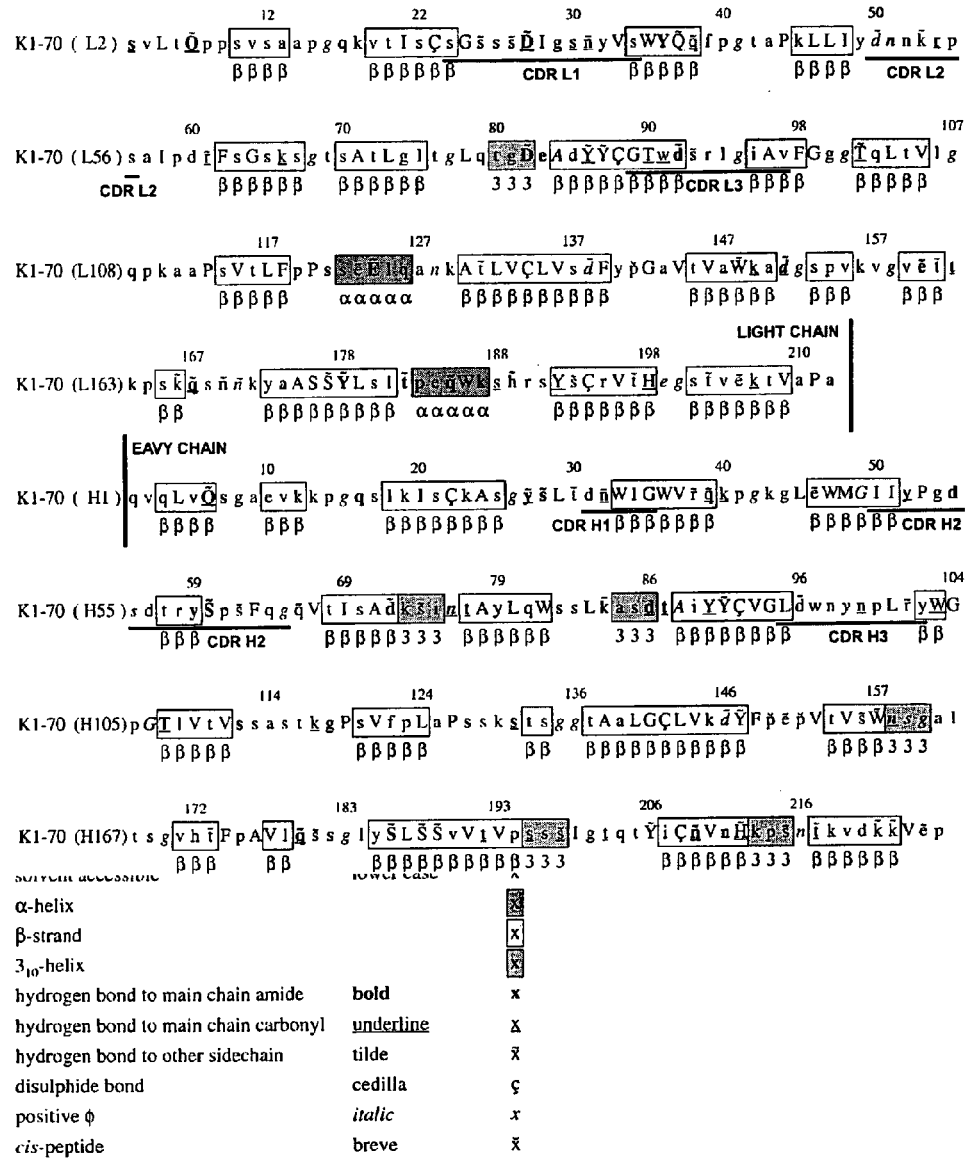
Figure 9a  Representation of K1-70 Fab structure in JOY format
The residues are numbered according to Kabat's system (Kabat E et al 1991 supra) as shown in Figure 8.

Figure 9b    Electrostatic potential of the combining site of K1-70
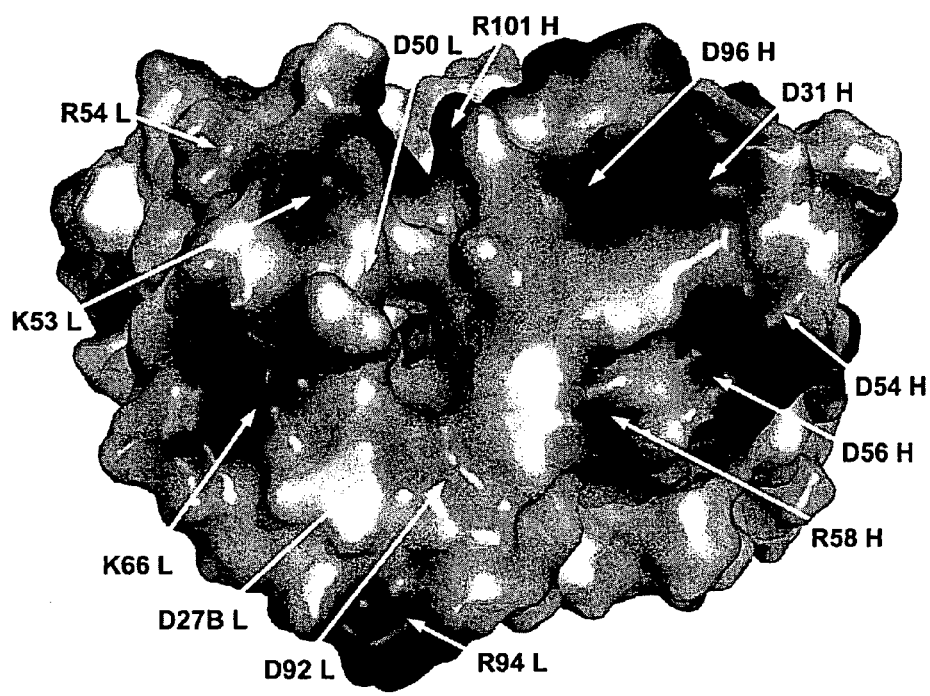
The residues are numbered according to Kabat's system (Kabat E *et al* 1991 *supra*) as shown in Figures 8 and 9a Figure 9c  Aromatic amino acids of the combining site of K1-70
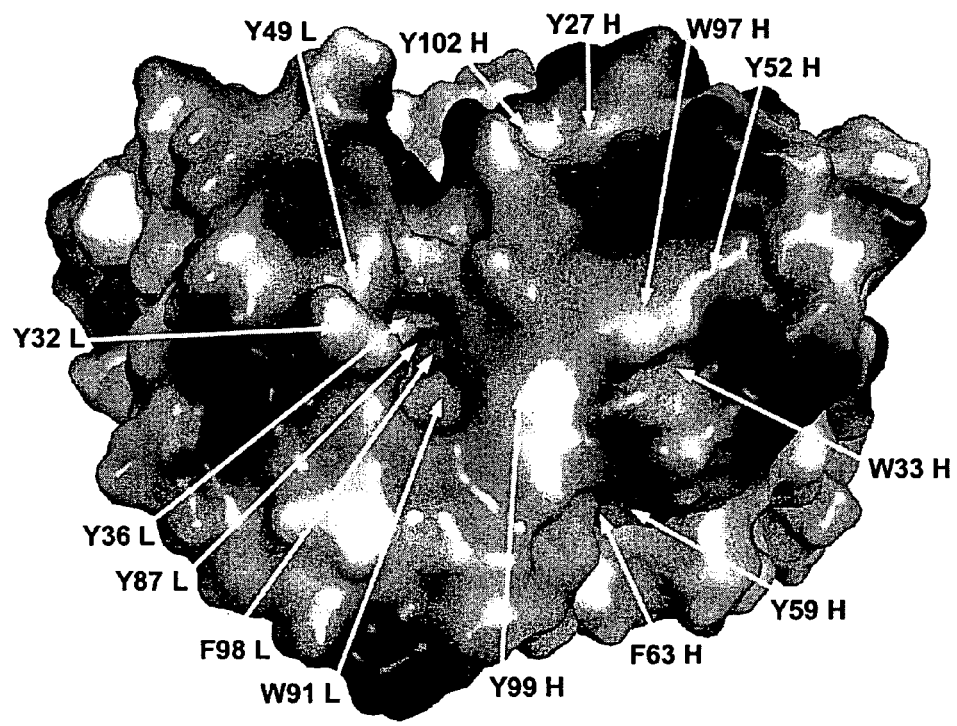
The residues are numbered according to Kabat's system (Kabat E *et al* 1991 *supra*) as shown in Figures 8 and 9a.

HUMAN ANTI TSHR ANTIBODIES

CROSS-REFERENCE TO RELATED APPLICATIONS

This application is a National Stage application under 35 U.S.C. §371 and claims benefit under 35 U.S.C. §119(a) of International Application No. PCT/GB2009/002946 having an International Filing Date of Dec. 23, 2009, which claims the benefit of priority of GB 0908945.9 having a filing date of May 22, 2009 and GB 0823562.4 having a filing date of Dec. 24, 2008.

FIELD OF THE INVENTION

The present invention relates to human monoclonal autoantibodies (MAbs) reactive with the thyroid stimulating hormone (TSH) receptor (TSHR). One of the human MAbs (K1-18) has the ability to bind to the TSHR and to stimulate TSHR cyclic AMP activity. The other human MAb (K1-70) has the ability to bind to the TSHR and to block stimulation of cyclic AMP mediated by TSH and TSHR stimulating antibodies. Both human MAbs were isolated from the peripheral lymphocytes of a patient who presented with clinical symptoms of hypothyroidism.

BACKGROUND

Thyroid function is regulated by TSH secreted by the pituitary (Szkudlinski M W, et al 2002. Physiological Reviews 82: 473-502). TSH binds to the TSHR on the surface of thyrocytes and this is the first step in initiating the TSHR signalling cascade. Binding of TSH to the TSHR leads to stimulation of formation and release of thyroid hormones; thyroxine (T4) and tri-iodothyronine (T3). A feedback mechanism involving the levels of T4 and T3 in the circulation and thyrotropin releasing hormone (TRH) secreted by the hypothalamus controls the release of TSH that in turn controls thyroid stimulation and the levels of thyroid hormones in serum (Szkudlinski M W, et al, 2002 supra). The TSHR is a G-protein coupled receptor and is composed of three domains:—a leucine rich repeat domain (LRD), a cleavage domain (CD) and a transmembrane domain (TMD) (Núñez Miguel R, et al 2004. Thyroid 14: 991-1011). It is well documented in the art that some patients with autoimmune thyroid disease (AITD) develop autoantibodies which are reactive with the TSHR (Rees Smith B, et al 1988. Endocrine Reviews 9: 106-121). There are two main types of TSHR autoantibodies (TRAbs); a stimulating type and a blocking type. Thyroid stimulating type autoantibodies bind to the TSHR and mimic the actions of TSH thereby stimulating the thyroid to produce high levels of T4 and T3; these autoantibodies are also described as TRAbs with stimulating activity or TSH agonist activity (Rees Smith B, et al 2007. Thyroid 17: 923-938). The feedback control mechanism of thyroid function is no longer effective in the presence of thyroid stimulating autoantibodies and patients present with the clinical symptoms of a hyperactive thyroid characterised by an excess of thyroid hormones in serum and its metabolic consequences. This condition is known as Graves' disease. TRAbs with stimulating activity may also interact with the TSHRs in retroorbital tissue and contribute to the development of the eye signs of Graves' disease. A human monoclonal autoantibody which acts as a powerful thyroid stimulator (hMAb TSHR1; also referred to as M22) has been described in detail in WO 2004/050708A2. The structure of the complex of M22 Fab bound to the TSHR LRD has been solved by x-ray crystallography at 2.55 Å resolution as described in WO2008/025991A1. Analysis of the structure of the TSHR-M22 complex provides detailed information about the receptor residues and the stimulating autoantibody residues involved in interactions with each other.

M22 has been used in ELISA for TSHR antibody measurement (Zöphel, K et al, Clinica Chimica Acta 2009 and Zöphel, K et al, Clinica Chimica Acta 2008.

Blocking type TRAbs occur less frequently in patients with AITD than stimulating autoantibodies. Blocking type autoantibodies bind to the TSHR, prevent TSH from binding to the receptor but have no ability to stimulate TSHR activity. Consequently formation and secretion of thyroid hormones (T4 and T3) is greatly reduced and the patients with this type of TRAb can present with clinical symptoms of an under-active thyroid (hypothyroidism). Blocking type autoantibodies are known as TRAbs with blocking activity or TSH antagonist activity (Rees Smith B, at al 1988 supra and Rees Smith B, 2007 at al supra). TRAbs with blocking activity when present in serum of pregnant women cross the placenta and may block the TSHRs in the foetal thyroid leading to neonatal hypothyroidism and serious consequences for development. Furthermore, TRAbs with blocking activity can be found in breast milk of affected mothers and may cause clinical hypothyroidism in the baby (Evans C, et al 2004 European Journal of Endocrinology 150: 265-268). A human autoantibody to the TSHR with TSH antagonist activity (5C9) has been described in detail in WO 2008/099185A1. Clinical symptoms in patients with AITD and circulating TRAbs are related to the effect of autoantibodies on TSHR activity i.e. whether the TRAbs cause stimulation or blocking. It has been proposed, however, that in some patients a mixture of stimulating and blocking TRAbs may be present simultaneously with the overall clinical presentation related to higher concentration and/or activity of one type of the TRAbs (Rees Smith B et al 1988 supra; Furmaniak J et al 1993 Springer Seminars in Immunopathology 14: 309-321 and Schott M et al 2005 Trends in Endocrinology and Metabolism 16: 243-248). Furthermore, the concentrations and/or activities of stimulating or blocking TRAb may vary in the same patient during the course of the disease and indeed fluctuation of symptoms from hypo- to hyperthyroidism in the same patient over time has been reported (Rees Smith B et al 1988 supra; Furmaniak J and Rees Smith B 1993 supra and Schott M et al 2005 supra). However, attempts to separate the TRAbs with different bioactivity or to differentiate between these TRAbs in serum samples using currently available bioassays is difficult. More recently, the invention described in WO2006/016121A1 provides a means to discriminate between stimulating and blocking types of TRAbs using bioassays that employ TSHR mutated at R255.

Human recombinant TSH (Thyrogen®) is a preparation of human TSH produced under cGMP regulations as a recombinant protein and approved by the US FDA as an aid in the diagnosis of residual or recurrent thyroid cancer (Duntas L H, Cooper D S 2008 Thyroid 18: 509-516). Monitoring of thyroid cancer patients after treatment includes stimulation of thyroid remnants or metastases with recombinant human TSH followed by a thyroid scan and/or measurement of serum thyroglobulin levels (Duntas L H and Cooper D S 2008 supra). Human chorionic gonadotropin is a hormone produced during pregnancy which has mild thyroid stimulating effects (Grossmann M at al 1997 Endocrine Reviews 18: 476-501). Characterisation of stimulating or blocking types of TRAbs and how they interact with the TSHR is of critical importance for development of improved methods to diagnose and manage different forms of AITD. In addition these studies are critical for developing new strategies for the management of diseases associated with an autoimmune response to the TSHR. The availability of potent thyroid stimulators other than recombinant human TSH provides new alternatives for monitoring and managing thyroid cancer patients.

RELATED PREVIOUS PATENT APPLICATIONS

The invention described in WO2004/050708A2 provides details of the properties of a human monoclonal autoantibody (MAb) with powerful stimulating activity and its interaction with the TSHR. The interactions between this autoantibody (M22) and the TSHR LRD have been solved at the molecular level from an X-ray diffraction analysis (2.55 Å resolution) of a complex between the two molecules as described in WO2008/025991A1. WO2006/016121A1 discloses a mutated TSHR preparation including at least one point mutation which can be used in the differential screening and identification of patient serum stimulating TSHR autoantibodies, patient serum blocking TSHR autoantibodies and TSH in a sample of body fluid from a patient being screened. Generation and characterisation of a mouse MAb (9D33) with TSHR blocking activity is also described in WO2004/050708A2. 9D33 binds to the TSHR with high affinity ($2 \times 10^{10}$ L/mol) and is an effective antagonist of TSH, hMAb TSHR1 (M22) and patient serum TRAbs with stimulating or blocking activities. WO2008/099185A1 discloses the isolation and characterisation of human MAb (5C9) to the TSHR that is an effective antagonist of TSH and of stimulating TRAbs in patient sera. 5C9 has been found unexpectedly to inhibit TSHR constitutive activity (also referred to as the TSHR basal activity), that is to say the production of cyclic AMP in a test system in the absence of TSH or M22. Furthermore, 5C9 has been found to inhibit TSHR cyclic AMP activity associated with TSHR activating mutations. WO2008/091981A2 describes a mouse MAb that has the ability to suppress the constitutive activity of TSHR and the methods of using the MAb to treat thyroid diseases including hyperthyroidism and thyroid cancer. The properties of the MAb described in WO2008/091981A2 are also disclosed in Chen C R et al 2007 Endocrinology 148: 2375-2382.

PRESENT INVENTION

Antibodies K1-18 and K1-70 have been isolated from the peripheral blood lymphocytes of a 54 year old female patient with hypothyroidism and high levels of TSHR autoantibodies. The patient had an 8 year history of AITD and first presented with hyperthyroidism and responded to treatment with methimazole which continued for 3 years. However, approximately 10 months after reaching the euthyroid state (i.e. having normal function) the patient developed hypothyroidism and was treated with thyroxine. The patient had been hypothyroid for approximately 4.5 years at the time of blood collection. At the time of lymphocyte isolation serum TRAb levels were 160 Units/L measured by TSH binding inhibition assay. The serum also showed an ability to block TSH stimulation of the TSHR (cyclic AMP based assay). Serum autoantibodies to thyroid peroxidase were positive at >500 Units/mL (Units are of the reference preparation 66/387 from National Institute for Standards and Control (NIBSC) Potters Bar, UK). The patient's lymphocytes were immortalised by infection with Epstein Barr virus (EBV) and supernatants of cultures of the infected cells screened for their ability to inhibit $^{125}$I-TSH binding to TSHR coated tubes. Cells from positive cell cultures were fused with a mouse/human cell line and screened as above. 2 stable clones secreting TSHR autoantibodies were obtained. IgGs were purified from supernatants of the clone cultures and the ability of the 2 MAbs (K1-18 and K1-70) IgGs to bind to the TSHR and influence TSHR activity assessed. In particular, the ability of K1-18 or K1-70 to inhibit TSH binding to the TSHR was studied. The ability of K1-18 to stimulate the TSHR was also studied and compared to the activity of various other thyroid stimulators. The ability of K1-70 to inhibit the ability of TSH to stimulate the TSHR was studied and compared to the activities of other TSH antagonists. Furthermore, the ability of stimulating or blocking patient serum TRAbs to inhibit TSHR binding and biological activity of K1-18 and K1-70 was assessed. In addition, the use of K1-18 and K1-70 in assays for TSHR antibodies, TSH and related compounds was investigated. Variable region (V region) genes of the heavy (HC) and light chains (LC) of K1-18 and K1-70 were sequenced and the complementarity determining regions (CDRs) assigned. Furthermore, purified preparations of K1-70 Fab were crystallised and analysed using X-ray diffraction methods. These analyses provided molecular level details about the overall structure of K1-70 Fab and the topography of the antigen binding site of K1-70.

SUMMARY OF THE INVENTION

According to one aspect of the invention there is provided an isolated human antibody molecule which binds to a TSHR and which reduces ligand induced stimulation of said TSHR but has no effect on constitutive activity of said TSHR.

Preferably, there is provided an isolated human antibody molecule or fragment thereof which binds to the TSHR and which reduces ligand-induced stimulation of the TSHR but has no effect on said TSHR constitutive activity wherein said human antibody or fragment thereof has the characteristics of patient serum TSH receptor autoantibodies of inhibiting TSH and M22 binding to the TSHR. More preferably the isolated human antibody molecule or fragment thereof has at least one further characteristic of patient serum TSH receptor autoantibodies selected from having a binding affinity for the TSHR of at least $10^8$ L/mol and the ability to cause detectable blocking of ligand-induced TSHR stimulation at an antibody concentration of less than 10 µg/mL. Even more preferably the further characteristics of patient serum TSH receptor autoantibodies are selected from having a binding affinity for the TSHR of at least $10^9$ L/mol and the ability to cause detectable blocking of ligand-induced TSHR stimulation at an antibody concentration of less than 1 µg/mL, preferably less than 0.1 µg/mL. The isolated human antibody may be an antagonist of TSH and/or thyroid stimulating autoantibodies, and/or thyroid stimulating animal antibodies and/or of human chorionic gonadotropin.

The isolated antibody molecule may be an inhibitor of TSH receptor binding by at least one of TSH, M22 or K1-18.

The isolated antibody molecule may comprise an antibody VH domain selected from the amino acid sequence of FIGS. 5b and 5d (SEQ ID No 41 and 51, respectively). The isolated antibody molecule may comprise an antibody VH domain consisting preferably of the amino acid sequence of FIGS. 5b and 5d (SEQ ID No 41 and 51, respectively). The isolated antibody molecule may comprise a CDR selected from CDR I (SEQ ID No 42 and 52), II (SEQ ID No 43 and 53) and III (SEQ ID No 44 and 54) of FIGS. 5b and 5d respectively. An antibody molecule according to the invention may comprise a VH region which comprises one or more amino acid sequences having substantial homology to those CDRs. Preferably an antibody according to the invention shows 70-99.9% amino acid homology to the CDRs shown in FIG.

5*d* (SEQ ID No 52, 53 and 54). Preferably, the isolated antibody molecule comprises CDR I, II and III of FIG. 5*d* (SEQ ID No 52, 53 and 54). In preferred embodiments a corresponding portion of the isolated antibody molecule is at least 70% identical, more preferably at least 80% identical, highly preferably at least 90% identical, particularly preferred at least 95% identical and especially preferred 99.9% identical to one of those CDRs. The isolated antibody molecule may comprise an antibody VL domain selected preferably from an amino acid sequence of FIG. 6*d* (SEQ ID No 69). The isolated antibody molecule may comprise an antibody VL domain consisting preferably of an amino acid sequence of FIG. 6*d* (SEQ ID No 69). The isolated antibody molecule thereof may comprise a CDR selected from CDR I (SEQ ID No 70), II (SEQ ID No 71) or III (SEQ ID No 72) of FIG. 6*d*. Additionally or alternatively, an isolated antibody molecule according to the invention may comprise one or more amino acid sequences having substantial homology to those CDRs. Preferably the CDRs of an isolated antibody molecule according to the invention shows 70-99.9% amino acid homology to the CDRs shown in FIG. 6*d* (SEQ ID No 70, 71 and 72). In preferred embodiments the isolated antibody molecule is at least 70% identical, more preferably at least 80% identical, highly preferably at least 90% identical, particularly preferred at least 95% identical and especially preferred 99.9% identical.

Preferably, the isolated antibody molecule comprises CDR I, II and III of FIG. 6*d* (SEQ ID No 70, 71 and 72).

The isolated antibody molecule may have a molecular structure as shown in FIG. 9*a* with the distribution of charged and aromatic residues in the antigen binding site as shown in FIGS. 9*b* and 9*c*. According to another aspect of the invention there is provided an isolated antibody molecule which binds to the TSHR so as to stimulate the TSHR, the antibody molecule comprising an antibody VL domain selected from the amino acid sequences of FIGS. 4*b* and 4*d* (SEQ ID No 23 and 33, respectively) and/or comprising one or more CDRs selected from CDR I (SEQ ID No 24 and 34), II (SEQ ID No 25 and 35) and III (SEQ ID No 26 and 36) of FIGS. 4*b* and 4*d* respectively, and/or an antibody VH domain selected from the amino acid sequences of FIGS. 3*b* and 3*d* (SEQ ID No 5 and 15, respectively) and/or comprising one or more CDRs selected from CDR I (SEQ ID No 6 and 16), II (SEQ ID No 7 and 17) and III (SEQ ID No 8 and 18) of FIGS. 3*b* and 3*d* respectively. Preferably the antibody molecule comprises: (i) an antibody VL domain comprising one or more CDRs selected from CDR I (SEQ ID No 24 and 34), II (SEQ ID No 25 and 35) and III (SEQ ID No 26 and 36) of FIGS. 4*b* and 4*d* respectively; and/or (ii) an antibody VH domain comprising one or more CDRs selected from CDR I (SEQ ID No 6 and 16), II (SEQ ID No 7 and 17) and III (SEQ ID No 8 and 18) of FIGS. 3*b* and 3*d* respectively.

Binding of the isolated antibody molecule to the TSHR may be inhibited by patient serum TSHR antibodies with thyroid stimulating or blocking activities.

Binding of the isolated antibody molecule to the TSHR may be inhibited by at least one of M22, K1-70, 5C9, 9D33 and thyroid stimulating mouse monoclonal antibodies.

The isolated antibody molecule may comprise an antibody VL domain selected from the amino acid sequences of FIGS. 4*b* and 4*d* (SEQ ID No 23 and 33, respectively) and an antibody VH domain selected from the amino acid sequences of FIGS. 3*b* and 3*d* (SEQ ID No 5 and 15, respectively). Preferably, the isolated antibody molecule comprises CDR I (SEQ ID No 6 and 16), II (SEQ ID No 7 and 17) and III (SEQ ID No 8 and 18) of FIGS. 3*b* and 3*d* respectively. An antibody according to the invention may comprise a VH region which comprises one or more amino acid sequences having substantial homology to those CDRs. Preferably an antibody molecule according to the invention shows 70-99.9% amino acid homology to the CDRs (SEQ ID No 6-8 and 16-18) shown in FIGS. 3*b* and 3*d* respectively. In preferred embodiments the isolated antibody molecule is at least 70% identical, more preferably at least 80% identical, highly preferably at least 90% identical, particularly preferred at least 95% identical and especially preferred 99.9% identical.

The isolated antibody molecule may comprise an antibody VL domain consisting of an amino acid sequence of FIG. 4*b* or 4*d* (SEQ ID No 23 and 33, respectively). The isolated antibody molecule may comprise an antibody VH domain consisting of an amino acid sequence of FIG. 3*b* or 3*d* (SEQ ID No 5 and 15, respectively). Preferably, the isolated antibody molecule comprises CDR I (SEQ ID No 24 and 34), II (SEQ ID No 25 and 35) and III (SEQ ID No 26 and 36) of FIG. 4*b* and 4*d* respectively.

Additionally or alternatively, an antibody according to the invention may comprise one or more amino acid sequences having substantial homology to those CDRs. Preferably the antibody shows 70-99.9% amino acid homology to the CDRs (SEQ ID No 24-26 and 34-36) shown in FIGS. 4*b* and 4*d* respectively. In preferred embodiments the isolated antibody molecule is at least 70% identical, more preferably at least 80% identical, highly preferably at least 90% identical, particularly preferred at least 95% identical and especially preferred 99.9% identical.

In most applications a VH domain in an antibody molecule according to the invention will be arranged with a VL domain to provide a TSHR binding site. In some applications a VH domain alone may be provided to bind a TSHR.

Methods of grafting antibody domains are well known in the art such that an antibody molecule in accordance with the invention can be constructed using VH and VL domains or portions thereof from different sources.

The term "antibody molecule" and cognate terms, such as "antibody molecules", used herein in relation to antibody molecules of the invention embraces, according to context, immunoglobulin-based binding moieties such as monoclonal, recombinant, synthetic and polyclonal antibodies, single chain antibodies, multi-specific antibodies and also binding moieties, which may be substituted by the skilled addressee for such immunoglobulin-based binding moieties, such as domain antibodies, diabodies, as well as IgG[Delta] CH2, F(ab')$_2$, Fab, scFv, VL, VH, dsFv, Minibody, Triabody, Tetrabody, (scFv)$_2$, scFv-Fc, F(ab')$_3$ moieties (Holliger P, et al 1993 Proc Natl Acad Sci USA 90: 6444-6448.), (Carter P J 2006 Nat Rev Immunol 6: 343-357). The term also embraces fragments of such entities, preferably fragments which bind TSHRs, and more preferably have the effects of K1-18 or K1-70.

The terms "thyroid stimulating hormone receptor" and "TSHR" refer to full length human TSHR having the amino acid sequence shown in FIG. 7*a* (SEQ ID No 74) or variants or fragments thereof having high homology with such TSHR. Preferably, such variants and fragments have 70 to 99.9% homology with the amino acid sequence shown in FIG. 7*a* (SEQ ID No 74). In preferred embodiments such variants or fragments are at least 70% identical, more preferably at least 80% identical, highly preferably at least 90% identical, particularly preferred at least 95% identical and especially preferred 99.9% identical to that sequence.

The isolated antibody of the invention may preferably be in the form of a monoclonal antibody, a recombinant antibody or a synthetic antibody. CDRs I, II or III from the K1-18 or K1-70 VH or VL domains may be incorporated into a suitable framework. Variants of the K1-18 and K1-70 VH and VL domains and their CDRs can be produced by modifications using methods well known to those skilled in the field.

Such variants may comprise one or more amino acid sequence variations, including the addition, deletion, substitution or insertion mutations. The framework of K1-18 or K1-70 may also be modified in antibody molecules according to the invention. The isolated antibody according to the invention may have a framework which is human or non-human.

According to another aspect of the invention there is provided an isolated nucleotide encoding an isolated antibody molecule or fragment thereof according to the invention, comprising an antibody VL domain comprising an amino acid sequence of FIGS. 4b (SEQ ID No 23) or 4d (SEQ ID No 33) or 6d (SEQ ID No 69), an antibody VH domain comprising an amino acid sequence of FIGS. 3b (SEQ ID No 5), 3d (SEQ ID No 15) or 5b (SEQ ID No 41) and 5d (SEQ ID No 51), or CDR I, II or III of FIGS. 3b (SEQ ID No 6-8), 3d (SEQ ID No 16-18), 4b (SEQ ID No 24-26), 4d (SEQ ID No 34-36), 5b (SEQ ID No 42-44), 5d (SEQ ID No 52-54) or 6d (SEQ ID No 70-72), or a combination thereof.

The isolated nucleotide may comprise a nucleotide sequence of FIGS. 3a (SEQ ID No 1) 3c (SEQ ID No 10), 4a (SEQ ID No 19), 4c (SEQ ID No 28), 5a (SEQ ID No 37), 5c (SEQ ID No 46) or 6c (SEQ ID No 64).

A plurality of such nucleotides may be provided, for example in a bacteriophage display library. Such bacteriophage display libraries may be used to express a variety of antibody molecules or fragments thereof such as isolated domains.

The invention also provides a vector including an isolated nucleotide according to the invention, or a host cell including such a vector or a nucleotide according to the invention. The vector may be a plasmid, virus or fragment thereof. Many different types of vectors are known to the skilled addressee. The isolated cell may express an antibody according to the invention. Preferably, the isolated cell secretes an antibody according to the invention. Preferably an isolated cell according to the invention is from a stable hetero-hybridoma cell line.

Another aspect of the invention provides a method of producing an isolated antibody molecule or a fragment thereof such as an isolated domain in accordance with the invention, the method comprising expressing a nucleotide encoding such an antibody molecule, or a fragment thereof.

According to a further aspect of the invention there is provided a method of producing an antibody according to the invention, the method comprising culturing one or more isolated host cells according to the invention whereby the antibody is expressed by the cell. Preferably, the antibody is secreted by the cell, According to another aspect of the invention there is provided a pharmaceutical composition comprising an isolated antibody molecule according to the invention, and a carrier.

A pharmaceutical composition according to the invention may be suitable for human administration. Preferably a pharmaceutical composition according to the invention has no significant adverse effect on the immune system of the subject.

Various formats are contemplated for pharmaceutical compositions according to the invention. A pharmaceutical composition according to the invention for use in the treatment of a thyroid-related condition may be in an injectable format. A pharmaceutical composition according to the invention for use in the treatment of ophthalmic Graves' disease is preferably in the form of eye drops. Pharmaceutical compositions of this invention comprise an isolated antibody in accordance with the invention, with a pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. The pharmaceutical compositions of the invention may be administered orally, parenterally, by inhalation spray, topically, by eyedrops, rectally, nasally, buccally, vaginally or via an implanted reservoir. We prefer oral administration or administration by injection. The term "parenteral" as used herein includes subcutaneous, intracutaneous, intravenous, intramuscular, intra-articular, intrasynovial, intrasternal, intrathecal, intralesional and intracranial injection or infusion techniques. The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, TWEEN™ 80(a solution of Polysorbate 80)) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol. The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added. The pharmaceutical compositions of this invention may also be provided in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols. Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention. The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

Antibodies according to the first mentioned aspect of the invention such as K1-70 have potential applications for management and control of conditions associated with TSHR activation for example: Graves' disease, Graves' opthalmopathy or hyperthyroidism due to abnormal levels of TSH or hCG. Antibodies according to the second mentioned aspect of the invention such as K1-18 have applications for stimulating the TSHR in different clinical conditions and treatment situations. These conditions include diagnosis and management of thyroid cancer and its metastases, multinodular goitre or congenital hypothyroidism.

According to another aspect of the invention there is provided the use of an isolated antibody molecule or a pharmaceutical composition according to the invention in therapy. The invention also provides an isolated antibody molecule or a pharmaceutical composition according to the invention for use in therapy. According to another aspect of the invention there is provided a method of characterising the activity of TSHR antibodies, TSH or human chorionic gonadotropin, the method comprising a step including the use of an isolated antibody molecule according to the invention.

According to another aspect of the invention there is provided an in vitro method of stimulating the TSHR in mammalian cells, the method comprising contacting the cells with an isolated antibody molecule according to the invention.

According to another aspect of the invention there is provided an in vivo method of stimulating the TSHR in mammalian cells, the method comprising contacting the cells with an isolated antibody molecule according to the invention. Preferably, cells of a subject with thyroid cancer and its metastases, multinodular goitre and/or congenital hypothyroidism are contacted with an isolated antibody according to the invention.

According to another aspect of the invention there is provided an in vivo method of preventing ligand induced stimulation of TSHRs in mammalian cells, the method comprising contacting a TSHR with an isolated antibody molecule according to the invention. The ligand may be a thyroid stimulating autoantibody, TSH or human chorionic gonadotropin. The mammalian cells may be thyroid cells or extra-thyroidal cells. Mammalian extra-thyroidal cells may be in retro-orbital tissue or pre-tibial tissue.

In methods according to this aspect of the invention the isolated antibody molecule may be used in combination with another TSHR binding antibody such as 5C9 or 9D33 referred to above.

The thyroid-related condition may be selected from hyperthyroidism, Graves' disease, ophthalmic Graves' disease and neonatal hyperthyroidism. Alternatively, the thyroid-related condition may be hypothyroidism related to the presence of TRAbs with blocking activity in patients with AITD, neonatal hypothyroidism due to transfer of maternal TRAbs (via placenta or breast milk).

The subject treated in the various methods of the invention described above is preferably human. According to another aspect of the invention there is provided a diagnostic method for detecting autoantibodies to TSHRs, the method comprising contacting a sample, which has been isolated from a subject believed to contain such autoantibodies, and an antibody molecule according to the invention with a TSHR.

According to another aspect of the invention there is provided a diagnostic method for detecting an antibody in accordance with the invention, preferably a human antibody, to the TSHR or antibodies to the TSHR in human serum comprising contacting any one of the antibodies to the TSHR with a TSHR fragment comprising amino acids 22-260 of the TSHR (TSHR260) (FIG. 7b; SEQ ID No 75).

A suitable detectable label that can be employed in a method according to the present invention can be selected from the group consisting of enzymic labels, isotopic labels, chemiluminescent labels, fluorescent, dyes and the like.

In the case where an isotopic label (such as $^{125}I$, $^{14}C$, $^{3}H$ or $^{35}S$) is employed, monitoring may therefore comprise measuring radioactivity dependent on binding of an antibody molecule according to the present invention. Radioactivity is generally measured using a gamma counter, or liquid scintillation counter. According to another aspect of the invention there is provided a method of identifying small molecules that bind to TSHR260 (SEQ ID No 75), the method comprising contacting a candidate small molecule with TSHR260 for example in an ELISA and selecting small molecules that bind to TSHR260. Further, there is provided a method of identifying small molecules that have the ability to prevent TSHR autoantibody binding to TSHR260, the method comprising determining inhibition of binding of TSHR autoantibody (stimulating or blocking) to TSHR260 in the presence of a candidate small molecule and selecting small molecules that inhibit TSHR autoantibody binding. Small molecules identified in this way may be developed to provide new drugs to control autoimmune thyroid disease caused by TSHR autoantibodies (stimulating or blocking).

The present invention provides new and/or improved means to:

1 Stimulate the TSHR in the thyroid or tissues expressing the TSHR such as thyroid cancer and thyroid cancer metastases.
2 Prevent thyroid stimulating autoantibodies binding to the TSHR in the thyroid and thereby providing a new treatment for Graves' disease.
3 Prevent TSHR autoantibodies binding to the extra-thyroidal TSHRs (for example in retro-orbital tissue or pre-tibial tissue) and thereby providing improved opportunities for the management of Graves' ophthalmopathy and pre-tibial myxoedema.
4 Determine TSHR amino acids critical for binding TRAbs with stimulating activities.
5 Determine TSHR amino acids critical for binding TRAbs with blocking activities.

6 Compare the TSHR amino acids critical for binding of TRAbs with stimulating and blocking activities.
7 Develop new assays for TRAbs that differentiate between blocking and stimulating antibodies.

8 Develop new assays for TRAb based on using thermostable TSHR fragments.

9 Determine TSHR amino acids critical for ligand-induced TSHR activation.

10 Determine TSHR amino acids critical for ligand-induced TSHR inactivation.

11 Determine the blocking autoantibody amino acids critical for binding to the TSHR.

12 Determine the blocking autoantibody amino acids critical for affecting TSH or thyroid stimulating antibody-mediated TSHR activation.

13 Control hyperthyroidism of Graves' disease, neonatal hyperthyroidism and the eye signs of Graves' disease. Alternatively, the thyroid-related condition may be hypothyroidism related to the presence of TRAbs with blocking activity in patients with AITD, or neonatal hypothyroidism due to transfer of maternal blocking type TRAbs (via placenta or breast milk).

14 Develop means to screen for small molecule drug candidates to control thyroid disease caused by the autoantibodies that bind to the TSHR.

15 Understand molecular differences between TSHR autoantibodies with thyroid stimulating or blocking activity produced by the immune system of the same patient and by the immune system of different patients.

16 Understand the immunological mechanisms involved in development and production of stimulating and blocking TSHR autoantibodies.

17 Understand the mechanisms including evolutionary driving forces which are the basis of the molecular mimicry between TSH and TSHR autoantibodies.

BRIEF DESCRIPTION OF THE DRAWINGS

Antibody molecules and methods in accordance with the invention will now be described, by way of example only, with reference to the accompanying drawings, FIGS. 1 to 9, in which:

FIG. 1 shows association and dissociation characteristics of binding of $^{125}$I-labelled K1-70 or $^{125}$I-labelled K1-18 to the TSHR: (a) the time course of binding of $^{125}$I-labelled K1-70 IgG and Fab to full length TSHR; (b) the time course of binding of $^{125}$I-labelled K1-70 IgG to TSHR260; (c) the time course of $^{125}$I-labelled K1-70 Fab to TSHR260; (d) the dissociation of $^{125}$I-labelled K1-70 IgG from the TSHR (full length) in the presence of various ligands; (e) the dissociation of $^{125}$I-labelled K1-70 IgG from TSHR (full length) in the presence of K1-18 Fab; (f) the dissociation $^{125}$I-labelled K1-70 Fab from the TSHR (full length) in the presence of various ligands; (g) the dissociation of $^{125}$I-labelled K1-70 IgG from TSHR260 in the presence of various ligands; (h) the dissociation of $^{125}$I-labelled K1-70 IgG from TSHR260 in the presence of K1-18 Fab; (i) the dissociation of $^{125}$I-labelled K1-70 Fab from the TSHR260 in the presence of various ligands; (j) the time course of binding of $^{125}$I-labelled K1-18 IgG to full length TSHR and TSHR260; (k) the dissociation of $^{125}$I-labelled K1-18 IgG from full length TSHR in the presence of various ligands; and (l) the dissociation of $^{125}$I-labelled K1-18 IgG from TSHR260 in the presence of various ligands;

FIG. 2 shows the results of measurements of TSHR autoantibodies in patient sera: (a) comparison of the measurements in a TRAb coated tube assay (based on inhibition of TSH binding) and in a TSHR260-AP ELISA; (b) comparison of measurements by ELISAs based on inhibition of M22 binding to full length TSHR and by inhibition of M22 Fab binding to TSHR260 in the ELISA; (c) comparison of measurements in a TRAb coated tube assay (based on inhibition of TSH binding) and by inhibition of M22 Fab binding to TSHR260 coated plates in an ELISA; and (d) comparison of the measurements in a TRAb ELISA (based on inhibition of M22 binding) and in a TSHR260-AP ELISA;

FIG. 3 gives the variable region sequences of K1-18 heavy chain (HC): (a) the oligonucleotide sequence of K1-18 HC (SEQ ID No 1) shown in unannotated and annotated forms. In the annotated forms, sequences used for PCR primers are underlined; for individual Complementarity Determining Regions (CDRs) are boxed; and constant regions are in bold; (b) the amino acid sequence of K1-18 HC (SEQ ID No 5) derived from the oligonucleotide sequence shown in (FIG. 3*a*) in unannotated and annotated forms; (c) the preferred oligonucleotide sequence of K1-18 HC (SEQ ID No 10) with the actual N-terminal sequence (the leader sequence) shown in unannotated and annotated forms. In the annotated forms, sequences used for PCR primers are underlined, the leader sequence is shown in lowercase letters; individual CDRs are boxed; and constant regions are in bold; and (d) the preferred amino acid sequence of K1-18 HC (SEQ ID No 15) with the leader sequence derived from the oligonucleotide sequence shown in FIG. 3*c* in unannotated and annotated forms;

FIG. 4 gives the variable region sequences of K1-18 light chain (LC): (a) the oligonucleotide sequence of K1-18 LC (SEQ ID No 19) shown in unannotated and annotated forms. In the annotated forms, sequences used for PCR primers are underlined; individual CDRs are boxed; and constant regions are in bold; (b) the amino acid sequence of K1-18 LC (SEQ ID No 23) derived from the oligonucleotide sequence shown in FIG. 4*a* in unannotated and annotated forms; (c) the preferred oligonucleotide sequence of K1-18 LC (SEQ ID No 28) with the actual N-terminal sequence (the leader sequence) shown in unannotated and annotated forms. In the annotated forms, sequences used for PCR primers are underlined, the leader sequence is shown in lowercase letters; individual CDRs are boxed; and constant regions are in bold; and (d) the preferred amino acid sequence of K1-18 LC (SEQ ID No 33) with the leader sequence derived from the oligonucleotide sequence shown in FIG. 4*c* in unannotated and annotated forms;

FIG. 5 gives the variable region sequences of K1-70 heavy chain (HC): (a) the oligonucleotide sequence of K1-70 HC (SEQ ID No 37) shown in unannotated and annotated forms. In the annotated forms, sequences used for PCR primers are underlined; individual CDRs are boxed; and constant regions are in bold; (b) the amino acid sequence of K1-70 HC (SEQ ID No 41) derived from the oligonucleotide sequence shown in FIG. 5*a* in unannotated and annotated forms; (c) the preferred oligonucleotide sequence of K1-70 HC (SEQ ID No 46) with the actual N-terminal sequence (the leader sequence) shown in unannotated and annotated forms. In the annotated forms, sequences used for PCR primers are underlined, the leader sequence is shown in lowercase letters; individual CDRs are boxed; and constant regions are in bold; and (d) the preferred amino acid sequence of K1-70 HC (SEQ ID No 51) with the leader sequence derived from the oligonucleotide sequence shown in FIG. 5*c* in unannotated and annotated forms;

FIG. 6 gives the variable region sequences of K1-70 light chain (LC): (a) the oligonucleotide sequence of K1-70 LC (SEQ ID No 55) shown in unannotated and annotated forms. In the annotated forms, sequences used for PCR primers are underlined; individual CDRs are boxed; and constant regions are in bold; (b) the amino acid sequence of K1-70 LC (SEQ ID No 59) derived from the oligonucleotide sequence shown in FIG. 6a in unannotated and annotated forms; (c) the preferred oligonucleotide sequence of K1-70 LC (SEQ ID No 64) with the actual N-terminal sequence (the leader sequence) shown in unannotated and annotated forms. In the annotated forms, sequences used for PCR primers are underlined, the leader sequence is shown in lowercase letters; individual CDRs are boxed; and constant regions are in bold; (d) the preferred amino acid sequence of K1-70 LC (SEQ ID No 69) with the leader sequence derived from the oligonucleotide sequence shown in FIG. 6c in unannotated and annotated forms; and (e) the actual N-terminal amino acid sequence (amino acids 2-21) (SEQ ID No 73) determined by Edman degradation reaction;

FIG. 7 gives the amino acid sequence of the human TSHR: (a) illustrates the consensus amino acid sequence of the human TSHR (amino acids 1-764 (SEQ ID No 74) (accession no. P16473, http://www.ncbi.nlm.nih.gov/entrez/viewer.fcgi?db=protein&val=62298994); (b) illustrates the consensus amino acid sequence of the human TSHR amino acids 1-260. The leader sequence (amino acids 1-21) is shown in lowercase and the histidine sequence added for purification purposes is shown at the C-terminus in bold (SEQ ID No 75); and (c) illustrates the amino acid sequence of the human TSHR LRD C-CAP. The leader sequence (amino acids 1-21) is shown in lowercase and the histidine sequence added for purification purposes is shown at the C-terminus in bold (SEQ ID No 76);

FIG. 8 gives the coordinates of K1-70 Fab at 2.22 Å resolution.

FIG. 9 shows the: (a) Structure of K1-70 Fab—representation of structure in Joy format; (b) Electrostatic potential of the combining site of K1-70 Fab; and (c) Aromatic amino acids of the combining site of K1-70 Fab.

METHODS

Lymphocyte Isolation and Cloning of Human Monoclonal TSHR Autoantibodies

The monoclonal autoantibodies K1-18 and K1-70 were isolated using the procedure described in WO2004/050708A2. Lymphocytes were isolated from a blood sample collected from a patient with an 8 year clinical history of AITD and high levels of TRAbs. Patient consent and Local Ethical Committee approval were obtained. The patient was first diagnosed with hyperthyroidism, reached the euthyroid state after treatment with methimazole, however, approximately 4.5 years prior to blood collection she developed hypothyroidism. At the time of blood collection the patient was being treated with thyroxine (50 µg daily). The lymphocytes were infected with Epstein Barr Virus (EBV) (European Collection of Cell Cultures—ECACC; Porton Down, SP4 0 JG, UK) and cultured on mouse macrophage feeder layers as described in WO2004/050708A2. Immortalised lymphocytes secreting TSHR autoantibodies were fused with a mouse/human hybrid cell line K6H6/B5 (ECACC) and cloned four times by limiting dilution to obtain a single colony. The presence of TSHR autoantibody in cell culture supernatants at different stages of cloning was detected by inhibition of labelled TSH binding to the TSHR (WO2004/050708A2). Two single clones producing the TSHR autoantibodies were expanded and supernatants from the cultures were harvested for autoantibody purification. One clone was designated as K1-18 and the other as K1-70.

Purification, Characterisation and Labelling of K1-18 and K1-70

TSHR human MAbs IgGs were purified from culture supernatants using protein A affinity chromatography on MABSELECT™ (GE Healthcare, UK (protein A-derived medium)) as described in Sanders J et at 2004. Thyroid 2004 14: 560-570) and purity assessed by SDS-polyacrylamide gel electrophoresis (PAGE). The heavy chain isotype was determined using a radial diffusion assay (The Binding Site; Birmingham, B29 6AT, UK), and the light chain isotype was determined by Western blotting with anti-human kappa chain and anti-human lambda chain specific mouse monoclonal antibodies (Sigma-Aldrich Company Ltd, Poole, UK). Purified K1-18 IgG was treated with mercuripapain (Sigma Aldrich, Poole, UK) at a IgG/enzyme ratio of 100:1 in phosphate buffered saline (PBS; 137 mmol/L NaCl, 8.1 mmol/L $Na_2HPO_4$, 2.7 mmol/L KCL, 1.47 mmol/L $KH_2PO_4$, pH 7.4 containing cysteine at final concentration of 1 mmol/L and EDTA at final concentration of 2 mmol/L) for 4 hours at 37° C. The reaction was stopped by addition of iodoacetamide (final concentration of 50 mmol/L) for 30 minutes at room temperature. The reaction mixture was then passed through a MABSELECT™ column to remove any intact IgG or Fc fragments from the Fab preparation. The Fab containing solution was dialysed into PBS containing 3.1 mmol/L $NaN_3$ and concentrated using a CENTRIPREP™ concentrator (Millipore, Watford, WD18 8YH, UK (centrifugal filter unit with ultracel-10 membrane)) when appropriate. K1-70 Fab were obtained using similar method except that an IgG/enzyme ratio of 200:1 was used and the digestion with enzyme was for 1 hour at 37° C. Analysis by SDS-PAGE indicated that intact IgG was undetectable in the Fab preparations. IgG preparations were labelled with $^{125}I$ as described in Sanders J et at 1999. Journal of Clinical Endocrinology and Metabolism. 1999 84: 3797-3802) or with biotin hydrazide (Perbio Science, Cramlington, UK) (Rees Smith et at 2004. Thyroid 14: 830-835).

Inhibition of $^{125}I$-TSH or $^{125}I$-Labelled Human MAbs Binding to the TSHR Binding inhibition assays were carried out using TSHR coated tubes as described in WO2004/050708A2. In the assay, 100 µL of test sample (MAb preparation, patient serum or unlabelled TSH) and 50 µL of start buffer (RSR Ltd) were incubated in TSHR coated tubes for 2 hours at room temperature with gentle shaking. After aspiration, the tubes were washed and 100 µL of $^{125}I$-labelled protein ($5 \times 10^4$ cpm) added and incubated for 1 hour at room temperature with shaking. The tubes were then aspirated, washed and counted in a gamma counter. Inhibition of labelled protein binding was calculated as $100 \times [1-($cpm bound in the presence of test material/cpm bound in the presence of control material$)]$. MAb preparations used in these experiments were K1-18, K1-70, M22, 5C9, 9D33 described above. TSMAbs 1-7 are mouse thyroid stimulating MAbs (WO 03/01863 and Sanders J et al 2002 supra). Control material was a pool of healthy blood donor sera or individual healthy blood donor sera or other materials as indicated in the results of various experiments.

Scatchard Analysis of Human MAb IgG Binding to the TSHR

Unlabelled K1-18 or K1-70 IgG in 50 µL of assay buffer (50 mmol/L NaCl, 10 mmol/L Tris pH 7.8 and 0.1% Triton X-100) and 50 µL start buffer (RSR Ltd) and 50 µL of $^{125}I$-labelled K1-18 or K1-70 IgG respectively (30,000 cpm in assay buffer) were incubated in TSHR coated tubes for 2 hours at room temperature with shaking (maximum binding occurred under these conditions), aspirated, washed twice with 1 mL of assay buffer and counted in a gamma counter.

The concentration of IgG bound vs bound/free was plotted (Scatchard G 1949. Annals of the New York Academy of Sciences 51: 660-672) to derive the association constant.

Inhibition of TSH Binding to the TSHR Measured by ELISA

A TRAb ELISA based on TSH-biotin binding to TSHR coated ELISA wells was used as described previously (Bolton J, et al 1999 Clinical Chemistry 45: 2285-2287). In the assay 75 µL of test sample was added to 75 µL of start buffer in the plate wells and incubated for 2 hours at room temperature with shaking at about 500 shakes/minute. After washing 100 µL of TSH-biotin was added and incubation continued for 25 minutes without shaking. The wells were washed again, the reaction developed using described standard procedures and the absorbance of each well read at 450 nm.

Inhibition of TSH-biotin binding was calculated as: 100×[1–(test sample absorbance at 450 nm/negative control sample absorbance at 450 nm)]. MAb preparations used in these experiments were K1-18, K1-70, M22, 5C9, 9D33 described above. TSMAbs 1-7 are mouse thyroid stimulating MAbs (WO03/01863 and Sanders J, et al 2002 supra). Control sample material was a pool of healthy blood donor sera or other materials as indicated in the results of various experiments.

Inhibition of M22 Binding to the TSHR in ELISA

A TRAb ELISA based on labelled M22 (M22 Fab-POD) binding to TSHR coated ELISA wells was used (Rees Smith B, et al 2004 supra). The assay was carried out as the TSH-biotin based ELISA except the first incubation was for 1 hour. Results were expressed as inhibition of M22 binding using the formula: 100×[1–(test sample absorbance at 450 nm/negative control sample absorbance at 450 nm)]. MAb preparations used in these experiments were K1-18, K1-70, M22, 5C9, 9D33 described above. TSMAbs 1-7 are mouse thyroid stimulating MAbs (Patent application number WO03/01863 and Sanders J, 2002 supra). Control material was a pool of healthy blood donor sera or other materials as indicated in the results of various experiments.

Analysis of TSHR Stimulation

The ability of K1-18 or K1-70 IgG and other preparations to stimulate production of cyclic AMP in Chinese hamster ovary (CHO) cells transfected with the human TSHR was tested as described in WO2004/050708A2. CHO cells expressing either approximately $5 \times 10^4$ or approximately $5 \times 10^5$ TSHR per cell were seeded into 96-well plates at $3 \times 10^4$ cells per well, adapted into DMEM (Invitrogen Ltd, Paisley, UK) without foetal calf serum and then test samples (TSH, IgG or patient serum) added (1004 diluted in cyclic AMP assay buffer i.e. NaCl free Hank's Buffered Salts solution containing 1 g/L glucose, 20 mmol/L HEPES, 222 mmol/L sucrose, 15 g/L bovine serum albumin and 0.5 mmol/L 3 isobutyl-1-methylxanthine pH 7.4; cyclic AMP assay hypotonic buffer) and incubated for 1 hour at 37° C. After removal of test solutions, cells were lysed and cyclic AMP concentration in the lysates assayed using Direct Cyclic AMP Correlate—EIA kits from Assay Designs; Cambridge Bioscience, UK. Results are expressed as pmol/mL of cyclic AMP in the cell lysate (200 µL). Some experiments were carried out under isotonic buffer condition. In these experiments Krebs Ringer Hepes buffer (KRH buffer) was used (124 mmol/L NaCl, 5 mmol/L KCl, 1.25 mmol/L $MgSO_4$, 1.45 mmol/L $CaCl_2$, 1.25 mmol/L $KH_2PO_4$, 25 mmol/L HEPES, 8 mmol/L glucose, 0.5 g/L bovine serum albumin, 0.5 mmol/L 3 isobutyl-1-methylxanthine, pH 7.4). Cells were allowed to reach the required density, the culture medium removed and the cells washed with 1 mL of KRH buffer. Fresh KRH buffer was then added and the cells incubated for 30 minutes at 37° C. The buffer was then removed and replaced with fresh KRH buffer containing test sample (TSH, MAb preparations, serum samples etc). The next steps were then carried out as described above for the experiments under the hypotonic conditions (i.e. in cyclic AMP assay buffer). In some experiments the effect of various MAbs on the TSHR stimulating activity of various preparations (for example, TSH, human MAbs, patient sera) measured as described above was assessed. This was carried out by comparing (a) the stimulating activity of the sample alone with (b) stimulating activity in the presence of various MAbs.

Measurement of Antagonist (Blocking) Activity

The ability of K1-70 IgG and other preparations to inhibit the stimulating activity of porcine (p) TSH, native human (h) TSH and recombinant human (rh) TSH, MAb M22, MAb K1-18 and patient serum TRAbs in CHO cells expressing TSHRs was assessed. This was carried out by comparing the stimulatory effect of TSH, M22, K1-18 or TRAbs in the absence and in the presence of K1-70 IgG (or other preparations being tested). The assay was carried out as described above except 50 µL of K1-70 (or other preparations being tested) diluted in cyclic AMP assay buffer was added to the cell wells followed by 50 µL of TSH or M22 or K1-18 or patient serum (diluted as appropriate in cyclic AMP assay buffer) and incubated and tested as for the stimulating assay described above. Other MAbs and sera from patients with blocking type TRAbs were tested in this assay in addition to K1-70.

Association and Dissociation of K1-18 and K1-70 Binding to the TSHR

The association and dissociation of K1-18 IgG, K1-18 Fab, K1-70 IgG and K1-70 Fab binding to the full length TSHR and the TSHR260 was studied using the method as described in: Nakatake N, et al Thyroid 2006, 16; 1077-1084. The full length TSHR or TSHR260 were coated onto plastic tubes which had been pre-coated with an appropriate mouse MAb to the TSHR. In association experiments 100 µL of $^{125}$I-labelled IgG or Fab were incubated in the TSHR coated tubes at room temperature for 5-180 min. The tubes were then aspirated, washed with assay buffer and counted in a gamma counter. In the dissociation experiments 100 µL of $^{125}$I-labelled IgG or Fab were incubated in TSHR coated tubes for 180 min at room temperature followed by the addition of 10 µL of 1 mg/mL of various MAb IgG or Fab preparations and incubation for 0-180 min at room temperature. At different time points the tubes were aspirated, washed and counted. In some experiments TSH or buffer was added instead of a MAb preparation.

Amino Acid Mutations in the TSHR

The methods used to introduce specific mutations into the TSHR sequence have been described in patent application WO2006/016121A. Furthermore, transfection of mutated TSHR constructs into CHO cells using the Flp-In system is also described in WO2006/016121A. Flp-In-CHO cells expressing either wild type or mutated TSHRs were seeded into 96 well plates and used to test the ability of various preparations to stimulate cyclic AMP activity in the CHO cells expressing the TSHR containing amino acid mutations. These experiments were compared to similar experiments carried out using CHO cells expressing wild type TSHR. Flp-In-CHO cells expressing either wild type or mutated TSHRs were also used in experiments to study the ability of various preparations to block the stimulating activity of TSH, stimulating antibodies or patient serum TRAbs as described above.

Production of TSHR260-Alkaline Phosphatase (TSHR260-AP) Construct

The TSHR 260 construct (coding amino acids 1-260 of the human TSHR; amino acids 1-21 being the leader sequence) was amplified using full length human TSHR as the template (Oda Y, et al 1998. Journal of Molecular Endocrinology 20: 233-244) and joined to the coding sequence of a secreted alkaline phosphatase (minus the 17 amino acid alkaline phosphatase leader sequence) using the cloning vector pSEAP2-basic (Clontech) as the template. Two PCR reactions were carried out, the first used the full length TSHR amplified with specific primers SEQ ID No 77 and SEQ ID No 78 primers (Sigma Genosys) which added an EcoRI restriction site at the N-terminus, and a 1 amino acid linker (Asparagine) and the first 8 amino acids (excluding the 17 amino acid leader sequence) of the secreted alkaline phosphatase at the C terminus. The second PCR was carried out using the cloning vector pSEAP2-basic amplified with the primers SEQ ID No 79 and SEQ ID No 80 which adds amino acids 254-260 of the TSHR and a 1 amino acid linker (Asparagine) to the N terminus of the secreted alkaline phosphatase and a 6 histidine tag, a stop codon and an XhoI restriction site at the C-terminus of the secreted alkaline phosphatase gene. The PCR reactions were carried out for 30 cycles of 1 minute at 94° C., 1 minute at 40° C. and 1 minute at 72° C. followed by 7 minutes at 72° C. The PCR products were run on 1% agarose gels and the DNA extracted using a geneclean II kit (Anachem Ltd, Luton) following the manufacturer's instructions. Purified PCR products 1 and 2 were then used to set up a third PCR to construct the whole TSHR 260-alkaline phosphatase gene. The PCR 3 reaction contained 200 ng of PCR 1 and 200 ng of PCR 2 product and PCR 3 was carried out for 7 cycles at 94° C. for 1.5 minutes, 65° C. for 1.5 minutes and 72° C. for 1.5 minutes. The temperature was then increased to 94° C. again for 2 minutes and primers SEQ ID No 77 and 80 added followed by 30 cycles of 94° C. for 1 minute, 52° C. for 1 minute and 72° C. for 2 minutes. The PCR 3 product was cloned into pFastBac1 using EcoRI and XhoI restriction sites and the presence of the mutation was verified using sequencing by the Sanger-Coulson method (Sanger F et al 1997. Proceedings of the National Academy of Sciences of the USA 74: 5463-5467). Recombinant DNA was made using the Bac to Bac Baculovirus expression system (Invitrogen, UK) and transfected into Sf-9 cells to obtain and amplify recombinant baculovirus stock as described in WO2008/025991A1. TSHR260-AP was expressed in insect cells as described in WO2008/025991A1.

ELISA Based on TSHR260-AP

An ELISA was established based on the ability of divalent TSHR antibodies to bind with one antigen binding site to TSHR coated onto an ELISA plate well and with the other antigen binding site to TSHR260-AP in a liquid phase i.e. forming a bridge. TSHR in the form of full length detergent-solubilised receptor expressed in CHO cells was coated onto ELISA plate wells via a C-terminal antibody as described previously (Bolton J et al 1999 supra). In the assay 75 μL of start buffer (as described for TRAb ELISA; Bolton J, et al 1999 supra) and 75 μL of test sample (patient sera or monoclonal antibodies) were added to the ELISA plate wells coated with the full length detergent solubilised TSHR and incubated for 2 hours at room temperature with shaking (500 rpm). Then the contents of the wells were removed, the wells washed 3 times with wash buffer (50 mmol/L NaCl, 20 mmol/L Tris pH 7.8, 1% Triton X-100) followed by addition of 100 μL of TSHR260-AP (diluted in wash buffer containing 0.2 g/L MgCl$_2$-6H$_2$O and 2 g/L BSA). After incubation for 1 hour at room temperature with shaking (500 rpm) the wells were emptied, washed (3 times) and 100 μL of p-nitrophenyl phosphate (pNpp) substrate (Europa Bioproducts Ltd, Ely, Cambridge UK) added and the plate incubated in the dark for 45 minutes. Thereafter 100 μL of stop solution (1 mol/L NaOH) was added and the absorbance read at 405 nm in an ELISA plate reader. The results were expressed as OD$_{405}$ nm absorbance values, values higher than those observed with a panel of healthy blood donor (HBD) sera indicated the presence of TSHR autoantibodies in the sample. In some experiments solubilised preparations of recombinant TSHR containing mutation R255D expressed in CHO cells were used to coat the ELISA plate wells.

Production of TSHR LRD C-CAP Construct

The TSHR LRD C-CAP construct coding amino acids 1-409 of the human TSHR with amino acids 306-384 removed, was amplified using full length human TSHR as the template (Oda Y, et al 1998. Journal of Molecular Endocrinology 20: 233-244). Two PCR reactions were carried out, the first used the full length TSHR amplified with T7 primer (SEQ ID No 81) and specific primer SEQ ID No 82 (Sigma Genosys, Gillingham, Dorset, UK) which added amino acids 385-342 of the TSHR to the C terminus of amino acid 305 of the TSHR. The second PCR was carried out using the full length TSHR amplified with BGH reverse primer SEQ ID No 83 and the specific primer (SEQ ID No 84), which adds amino acids 298-305 of the TSHR to the N terminus of amino acid 385 of the TSHR. The PCR reactions were carried out for 30 cycles of 1 minute at 94° C., 1 minute at 40° C. and 2 minutes at 72° C. followed by 7 minutes at 72° C. The PCR products were run on 1% agarose gels and the DNA extracted using a Geneclean II kit (Anachem Ltd, Luton, UK) following the manufacturers instructions. Purified PCR products 1 and 2 were then used to set up a third PCR to construct a continuous TSHR sequence joining Ser305 to Tyr385 with amino acids 306-384 removed. The PCR 3 reaction which contained 200 ng of PCR 1 and 200 ng of PCR 2 product and PCR 3 was carried out for 7 cycles at 94° C. for 1.5 minutes, 65° C. for 1.5 minutes and 72° C. for 1.5 minutes. The temperature was then increased to 94° C. again for 2 minutes and T7 primer (SEQ ID No 81) and BGHR primer (SEQ ID No 83) were added followed by 30 cycles of 94° C. for 1 minute, 52° C. for 1 minute and 72° C. for 2 minutes. The PCR 3 product containing TSHR sequence omitting amino acids 306-384 was then run on a 1% agarose gel and the DNA extracted using a Geneclean II kit (Anachem Ltd) following the manufacturer's instructions. Purified PCR3 product was used as the template for construction of the TSHR LRD C-CAP gene in PCR 4. The PCR 4 reaction contained 200 ng of PCR 3 as template DNA and was amplified with T7 primer (SEQ ID No 81) and the specific primer (SEQ ID No 85) which adds a 6 histidine tag, a stop codon and an XhoI restriction site to the C-terminus of amino acid 409 of the TSHR sequence (1-409 with amino acids 306-384 deleted). PCR 4 was carried out for 30 cycles of 1 minute at 94° C., 1 minute at 40° C. and 1 minute at 72° C., followed by 10 minutes at 72° C. The PCR 4 product was cloned into pFastBac1 using BamHI and XhoI restriction sites and the presence of the mutation was verified using sequencing by the Sanger-Coulson method (Sanger F. et al 1997. Proceedings of the National Academy of Sciences of the USA 74: 5463-5467). Recombinant DNA was made using the Bac to Bac Baculovirus expression system (Invitrogen, Paisley, UK) and transfected into Sf-9 cells to obtain and amplify recombinant baculovirus stock as described in WO2008/025991A1. TSHR LRD C-CAP (FIG. 7c; SEQ ID No 76) was expressed in insect cells using the procedure described in WO2008/025991A1.

Comparison of Stability of Different TSHR Preparations

Temperature stability of different preparations of recombinant TSHR was compared. Full length solubilised TSHR expressed in CHO cells, TSHR260 expressed in insect cells, TSHR260-AP expressed in insect cells and TSHR. LRD C-CAP expressed in insect cells were tested. An aliquot of each of the above listed preparations was removed from −80° C. storage, thawed on ice, a sample returned to −80° C. as a control while the bulk was stored at room temperature (20-25° C.) for 24 or 48 hours. After 24 or 48 hours at room temperature the TSHR preparations were stored at −80° C. and then tested as described below. ELISA plate wells were coated with a F(ab')$_2$ preparation of the mouse TSHR MAb 14C4 (Jeffreys J et al 2002, Thyroid 12: 1051-1061 and Sanders J et al 2007 Thyroid 17: 395-410) at 1 µg/mL in coating buffer (Bolton J et al 1999 supra). TSHR preparations under investigation were diluted in 20 mmol/L NaCl, 10 mmol/L Tris pH7.8, 1% v/v Triton X-100, 1 g/L BSA, 200 mg/L NaN3 and 150 µL added to ELISA plate wells (in quadruplicate). After incubation overnight at 4° C. to allow the TSHR preparations to bind to the antibody (14C4 F(ab')2) coated wells, the wells were washed and incubated with 75 µL of assay buffer (50 mmol/L NaCl, 20 mmol/L Tris pH7.8, 1% v/v Triton X-100, 1 g/L BSA) and 754 of healthy blood donor serum for 1 hour at room temperature at 500 shakes per minute on an ELISA plate shaker. Thereafter the contents of the wells were emptied, the wells washed and 100 µL of M22 Fab-peroxidase conjugate (see above) added to each well. After 25 minutes incubation at room temp without shaking the plate wells were washed again followed by addition of 100 µL of tetramethylbenzidine and a further incubation of 25 minutes at room temperature without shaking. The reaction was stopped by addition of 50 µL of 0.5 mol/L $H_2SO_4$ and the absorbance of each well read at 450 nm on an ELISA plate reader.

Variable Region Gene Analysis

The variable (V) region genes of K1-18 or K1-70 heavy and light chains were determined as described in WO2004/050708A2, using total RNA prepared from 1×10$^7$ heterohybridoma cells (secreting K1-18 IgG or K1-70 IgG) to produce mRNA for RT-PCR (reverse transcriptase PCR) reactions. Specific IgG1 HC and kappa LC sense and antisense strand oligonucleotide primers designed using the Medical Research Council's V-base (http://vbase.mrc-cpe.cam.ac.uk/) and synthesised by Invitrogen (Paisley, PA4 9RF, UK) were used in RT-PCR reactions with K1-18 mRNA. Specific IgG1 HC and lambda LC primers prepared as described above were used in RT-PCR reactions with K1-70 mRNA. The RT reaction was carried out at 50° C. for 15 minutes followed by 40 cycles of PCR at 94° C. for 15 seconds, 50° C. for 30 seconds and 72° C. for 30 seconds. DNA products were cloned into pUC18 and sequenced by the Sanger-Coulson method (Sanger F, et al 1977 supra). V region sequences were compared with available sequences of human Ig genes using Ig blast (http://www.ncbi.nlm.nih.gov/igblast/). The CDRs were assigned by the method of Kabat (Kabat E et al 1991 Sequences of proteins of immunological interest (US Public Health service, Bethesda, Md.) Fifth edition) and Ig blast (http://www.ncbi.nlm.nih.gov/igblast/). A second round of mRNA isolation was carried out from both the K1-70 and K1-18 hybridoma cell lines that had undergone further recloning by limiting dilution. The V-region sequences (K1-18 HC, K1-18 LC, K1-70 HC and K1-70 LC) were obtained by RT-PCR from the mRNA followed by cloning and sequencing as described above. In addition the RT-PCR reactions were also carried out using specifically designed PCR primers corresponding to the 5' end of the respective leader sequences for each of the V regions. This allowed the identification of the actual oligonucleotide sequences (and derived amino acid sequences) at the N-termini of the HC and LC V regions of K1-18 and K1-70. In addition, the N-terminal amino acid sequence of K1-70 LC protein was analysed by Edman degradation reaction by Alta Bioscience (Birmingham, UK). This was possible after the N-terminal "deblocking" of the K1-70 LC protein preparation with pyroglutamate aminopeptidase. Purified K1-70 Fab (10 µg) was treated with 2.5 mU of pyroglutamate aminopeptidase (in 50 mmol/L $Na_2HPO_4$ pH 7.0; 10 mmol/L dithiothreitol and 1 mmol/L EDTA) for 6 hours at 75° C. An equal volume of SDS-PAGE sample buffer was added and after heating at 100° C. for 5 minutes, K1-70 Fab was resolved into the HC (Fd part) and the LC on 15% SDS-PAGE. The LC band was carefully cut out of the gel and the N-terminal protein sequence determined. Repeat rounds of RT-PCR and sequencing of K1-18 HC, K1-18 LC and K1-70 HC confirmed the V region sequences were the same as obtained before while the K1-70 LC V region sequence differed. The K1-70 LC sequence obtained in the repeat round of experiments was consistent with the protein sequence of the 2-21 consecutive N-terminal amino acids obtained by Edman reaction (FIG. 6e; SEQ ID No 73) and the electron density of the LC amino acids in the crystal structure of K1-70 Fab (FIG. 8) and consequently concluded as the preferred K1-70 LC sequence (FIGS. 6c and 6d; (SEQ ID No 64 and 69, respectively).

X-Ray Diffraction Analysis of K1-70 Fab

K1-70 Fab solutions prepared as described above were concentrated to 15.5 mg/mL using ICON concentrators (ThermoFisher Scientific, Loughborough, UK) with a 9000 Da cut off and stored at −20° C. in aliquots. Crystals of K1-70 Fab were grown using the hanging drop method of vapour diffusion using the Structure Screen 1 sparse matrix screen from Molecular Dimensions (Newmarket, UK). Several crystals were obtained in a number of conditions and all were screened to identify the crystal most suitable for the X-ray diffraction analysis at Biofocus DPI (Saffron Walden, UK). A crystal grown in 30% PEG 400, 0.1 M sodium Hepes pH 7.5, 0.2 M magnesium chloride was chosen. It was washed in well solution and flash frozen by plunging into liquid nitrogen. The data set was collected on a Rigaku R-Axis IV image plate detector and was indexed, integrated and scaled using MOSFLM and SCALA (from CCP4 program suite (Collaborative computational project, number 4. 1994. "The CCP4 Suite: Programs for Protein Crystallography". Acta Cryst. D50, 760-763). Three structures from the Protein Data Bank (http://www.rcsb.org/pdb/home/home.do) 1 LIL (VL and CL domains), 2B0S (VH domain) and 2EH7 (VL domain) were chosen for use in molecular replacement, based on sequence alignment. There were two complete Fab K1-70 molecules in the asymmetric unit and the resulting model was given ten cycles of atomic refinement with tight geometric weights using REFMAC5 (CCP4). The electron density maps calculated after molecular replacement and initial refinement were examined in the model building program COOT (Emsley P, Cowtan K 2004. Nature 355: 472-475) and automated model rebuilding was performed using BUCCANEER(CCP4). The model was reexamined and any remaining missing features were built by hand and the model was refined using REFMAC5 (CCP4). Water molecules were then added using the water placement option in COOT and refined using REFMAC5 (CCP4). The structural geometry of Fab K1-70 was checked using PROCHECK (CCP4) and RAMPAGE (CCP4). Finally, the residues in the model were renumbered in accordance with the Kabat numbering system (Kabat E et al 1991 supra).

Cloning and Expression of Recombinant K1-70 Fab in *E. coli*

The K1-70 HC RT-PCR product was cut with XhoI and SpeI restriction endonucleases and the K1-70 LC PCR product was cut with SacI and XbaI restriction endonucleases and both HC and LC cDNAs cloned into the Immunozap H/L vector (Stratagene Europe; Amsterdam, Netherlands) (Matthews I, et al 2002 Laboratory Investigation 82: 1-11) under the control of the lacZ promoter. Plasmid DNA was prepared using the Qiagen midi plasmid purification kit (Qiagen Ltd, Crawley, UK) and the presence of K1-70 HC and LC cDNAs confirmed by sequencing using the Sanger-Coulson method (Sanger F, et al 1977 supra). Plasmid DNA was transformed into the *E coli* strain HB2151 (GE Life Sciences, Little Chalfont, UK) and grown overnight at 37° C. on LB ampicillin (Tryptone 10 g/L, Yeast Extract 5 g/L, NaCl 10 g/L, 100 µg/mL final concentration ampicillin) agar plates (15 g/L agar). Precultures (one colony in 3 mL LB ampicillin +1% glucose) were grown overnight at 30° C. with shaking. Production of the recombinant Fab is inhibited in the presence of glucose. Precultures after overnight incubation were diluted 1/100 (0.5 mL in 50 mL LB ampicillin) and grown at 30° C. until the $OD_{600}$ was 1.2 followed by addition of sucrose (final concentration 0.3 mol/L) and culture grown at 30° C. until $OD_{600}$ returned to 1.2. Thereafter isopropyl-β-D thiogalactoside (IPTG) was added to a final concentration of 1 mmol/L and cultures continued to be incubated for 24 hours at 23° C. with shaking. The cultures were then centrifuged at 3000 rpm for 30 minutes at 4° C. and the culture supernatants recovered. The culture supernatants were filtered through a 0.45 µm filter and dialysed overnight into PBS (8.1 mmol/L $Na_2HPO_4$, 1.5 mmol/L $KH_2PO_4$, 2.7 mmol/L KCl, 137 mmol/L NaCl pH 7.4). Culture supernatant from HB2151 cells transformed with K1-70 plasmid (HB2151/K1-70) grown with glucose without IPTG ie non-induced were used as negative controls. The culture supernatants were assayed for (a) their ability to inhibit TSH binding to the TSHR and (b) their ability to inhibit TSH mediated stimulation of cyclic AMP production in CHO cells expressing TSHR.

Results

Isolation and Cloning of Stable Cell Lines Secreting K1-18 or K1-70

Lymphocytes ($26\times10^6$) obtained from 20 mL of patient's blood were infected with EBV and plated out at $1\times10^6$ cells per well in a 48 well plate on feeder layers of mouse macrophages. On day 13 post EBV infection the plate well supernatants were monitored for inhibition of $^{125}$I-TSH binding. Positive clones were tested further for their effects (stimulating or blocking) on the TSHR. Cells from positive wells (positive in any of the assays used) were expanded and fused with the K6H6/B5 hybridoma cell line and plated out in 96 well plates. Two clones stably producing antibodies with $^{125}$I-TSH binding inhibiting activity were obtained and re-cloned 4 times. One of the clones secreted a human MAb designated as K1-18 that had TSHR stimulating activity. K1-18 antibody purified from the hetero-hybridoma culture supernatants was subclass IgG1 with kappa light chains. The other stable clone secreted a human MAb designated as K1-70 that had the ability to block TSH stimulation of cyclic AMP production in TSHR transfected CHO cells. K1-70 antibody purified from hetero-hybridoma culture supernatants was subclass IgG1 with lambda light chains.

Inhibition of $^{125}$I-TSH Binding to TSHR Coated Tubes

The ability of different concentrations of K1-18 or K1-70 IgGs to inhibit binding of labelled TSH to TSHR coated tubes is shown in Tables 1a and 1b. As shown in Table 1a, K1-18 IgG diluted in healthy blood donor (HBD) serum showed maximum inhibition of $^{125}$I-TSH binding of approx 95% at 1 µg/mL concentrations. The inhibiting effect of K1-18 IgG at concentrations between 1-0.001 µg/mL was dose dependent. The inhibiting effect of K1-18 was comparable to the effect of M22 IgG at the same concentrations. K1-18 IgG at 1 µg/mL is a more potent inhibitor of $^{125}$I-TSH binding than 5C9 IgG, TSMAb 1-7 IgGs or 9D33 IgG (Table 1a). K1-70 IgG or Fab inhibiting effects on $^{125}$I-TSH binding are shown in Table 1b. K1-70 IgG diluted in HBD serum showed dose dependent inhibition ranging from 13.5±2.3% at 0.03 µg/mL to 95.9±0.8% at 100 µg/mL. The inhibiting effects of K1-70 Fab was comparable to the effects of K1-70 IgG at the same concentrations (Table 1b). Tables 1a and 1b also show the effects on $^{125}$I-TSH binding to TSHR coated tubes by K1-18 and K1-70 and different MAbs IgGs diluted in the coated tube assay buffer; in the case of all MAbs except 5C9 these effects were comparable to the results observed when MAbs were diluted in HBD serum. Table 2a shows inhibition of $^{125}$I-TSH binding to TSHR coated tubes by different preparations of K1-18, K1 donor serum and K1-donor serum IgG. In this experiment, approximately 12% inhibition was observed with as little as 0.01 µg/mL of K1-18 IgG diluted in HBD sera and the inhibition increased in a dose dependent manner up to 95% inhibition at 10 µg/mL of K1-18 IgG. K1-18 Fab at 0.01 µg/mL in HBD sera showed 5.6±7.3% inhibition and the inhibition increased in a dose dependent manner to a maximum inhibition of 82.2±0.9% at 10 µg/mL. This can be compared to $^{125}$I-TSH binding inhibition by donor serum IgG diluted in HBD sera; 13.7±1.3% inhibition at 0.125 mg/mL increasing in a dose dependent manner to 76.5±1.5% inhibition at 1 mg/mL. Donor serum at different dilutions also showed dose dependent inhibition of $^{125}$I-TSH binding; 9.1±0.8% inhibition and 1/160 dilution to 81.1±0.4% inhibition at 1/10 dilution. The data in Table 2a showed that purified K1-18 IgG was 6600 times more active in terms of inhibition of TSH binding compared to K1 donor serum IgG. When K1-18 IgG and donor serum IgG were diluted in assay buffer the ability of K1-18 IgG to inhibit TSH binding was 4700 times greater than that of the donor serum IgG (Table 2a). Table 2b shows inhibition of $^{125}$I-TSH binding to the TSHR in coated tube assay by different preparations of K1-18 compared to the effect of Thyroid Stimulating Autoantibody reference preparation 90/672 from National Institute for Biological Standards and Control (NIBSC; Potters Bar, UK). K1-18 IgG diluted in HBD serum showed $^{125}$I-TSH binding inhibiting activity of 69 NIBSC 90/672 units/mg (mean of activity calculated at three concentrations of K1-18 IgG; 30 ng/mL, 100 ng/mL and 300 ng/mL) (Table 2b). $^{125}$I-TSH binding inhibiting activity of K1-18 Fab (diluted in serum) calculated in the same experiment was 46 NIBSC 90/672 units/mg (activity at 30 ng/mL, 100 ng/mL and 300 ng/mL of K1-18 Fab was used for the calculations) (Table 2b). This can be compared with M22 IgG $^{125}$I-TSH binding inhibiting activity of 131 NIBSC units/mg (Table 2b). $^{125}$I-TSH binding inhibiting activities of dilutions of donor serum and donor serum IgG compared to the activity of NIBSC 90/672 are shown in Table 2c. $^{125}$I-TSH binding inhibiting activity of the donor serum was 0.075 NIBSC 90/672 units/mL (mean of values at 40× and 20× dilutions) and of donor serum IgG diluted in HBD serum was 0.011 units/mg (mean of values at 0.1; 0.3 and 1.0 mg/mL) (Table 2c). This can be compared to the activity of K1-18 IgG (diluted in HBD serum) measured in the same experiment of 63.3 NIBSC 90/672 units/mg (mean of values at 30, 100 and 300 ng/mL) and the activity of K1-70 IgG (diluted in HBD serum) of 114 units/mg (mean of values at 10, 30 and 100 ng/mL) (Table 2c). Consequently in this assay system the specific activity of K1-18 IgG was 5755× that of the donor serum IgG. Similarly, the specific activity of K1-70 IgG was 10,364× that of the donor serum IgG.

Scatchard Analysis of K1-18 and K1-70 Binding to TSHR Coated Tubes

The binding affinity of K1-18 IgG for the TSHR (full length) was 6.7±1.0×10$^9$ L/mol (mean±SD; n=3) while binding affinity of K1-18 Fab was 1.8±1.0×10$^9$ L/mol (mean±SD; n=3). Binding affinity of K1-18 IgG for the TSHR260 was 5.9±1.0×10$^9$ L/mol (mean±SD; n=3). K1-70 IgG binding affinity for the TSHR (full length) was 3.9±0.8×10$^{10}$ L/mol (mean±SD; n=3) while binding affinity of K1-70 Fab was 2.3±0.3×10$^{10}$ L/mol (mean±SD; n=3). Binding affinity of K1-70 IgG for the TSHR260 was 3.1±0.4×10$^{10}$ L/mol (mean±SD; n=3) and of K1-70 Fab it was 9.3±0.4×10$^9$ L/mol (mean±SD; n=3). This can be compared to binding affinity of porcine TSH to the TSHR (full length) of 6.0±0.9×10$^9$ L/mol (mean±SD, n=5) (Nakatake et al 2006 supra).

Inhibition of TSH-Biotin Binding to the TSHR Measured by ELISA

The effects of K1-18 IgG on TSH-biotin binding to TSHR coated ELISA plate wells was studied and compared to the effects of various other MAbs. As shown in Table 3a K1-18 IgG diluted in HBD serum had a dose dependent inhibiting effect on TSH-biotin binding with 10.0±0.8% inhibition at 0.01 µg/mL, essentially maximum inhibition of 96.2±0.2% at 1 µg/mL and a maximum inhibition plateau at concentrations of 3 µg/mL and above. This can be compared to M22 IgG (diluted in HBD serum) inhibiting effect of 17.5±2.0% at 0.01 µg/mL and 98.3±0.0% at 1 µg/mL (Table 3a). TSH-biotin binding inhibiting activity of K1-18 IgG at 1 µg/mL (diluted in HBD serum) was greater than 5C9 IgG, TSMAb 1-7 IgGs and 9D33 IgG as illustrated by the examples shown in Table 3a. When K1-18 IgG was tested diluted in ELISA assay buffer (50 mmol/L NaCl, 10 mmol/L Tris pH 7.8, 0.1% v/v Triton X-100, 1 mg/mL BSA) the inhibiting effects were essentially the same as when the dilutions were made in HBD serum (Table 3a). As shown by the examples in Table 3b K1-18 Fab diluted in HBD serum or in ELISA assay buffer was also an effective inhibitor of TSH-biotin binding in the ELISA. The inhibiting effects of K1-18 IgG diluted in ELISA assay buffer with addition of control MAb IgG (5B3 which is a human MAb to glutamic acid decarboxylase) at 100 µg/mL is shown in Table 3c. When diluted in the buffer containing control MAb K1-18 IgG showed similar TSH-biotin binding inhibition activity as when diluted in buffer containing BSA or in HBD serum (Table 3c). Consequently, the presence of an unrelated human MAb IgG at high concentration (100 µg/mL) had no effect on the inhibiting activity of K1-18 IgG nor M22 IgG nor 5C9 IgG. Table 3d shows the effects of K1-70 on TSH-biotin binding to the TSHR and these are comparable to the effects of K1-18 or M22 (Tables 3a & 3b). K1-70 IgG diluted in HBD serum had a dose dependent inhibiting effect on TSH-biotin binding with 13.6±1.4%; 74.1±0.4% and 97.4±0.2% inhibition at 0.01 µg/mL; 0.1 µg/mL and 1 µg/mL, respectively. K1-70 Fab was similarly active with inhibitions of 18.2±0.6%; 88.3±0.3% and 96.9±0.1% at 0.01 µg/mL; 0.1 µg/mL and 1 µg/mL, respectively. When K1-70 IgG or Fab preparations were diluted in ELISA assay buffer the inhibiting activities were essentially the same compared to dilutions made in HBD serum (Table 3d). The ability of K1-18 IgG to inhibit binding of M22 Fab-POD to TSHR coated ELISA plate wells is shown in Table 4a. K1-18 IgG diluted in HBD serum inhibited M22 Fab-POD binding in a dose dependent manner; in particular 21.0±1.3%, 81.6±0.5% and 97.2±0.1% inhibitions were observed at 0.03 µg/mL, 0.3 µg/mL and 3 µg/mL, respectively. This effect was comparable to the inhibiting effect of M22 IgG (diluted in HBD serum) of 51.0±2.4%, 93.2±0.3% and 98.0±0.2% at 0.03 µg/mL, 0.3 µg/mL and 3 µg/mL, respectively. K1-18 Fab showed similar ability to inhibit M22 Fab-POD binding as K1-18 IgG (Table 4b). As shown in Table 4a, K1-18 and M22 ability to inhibit labelled M22 binding to the TSHR were greater than the inhibiting activities of 5C9, TSMAbs 1-7 and 9D33. Inhibiting effects of all MAbs studied when diluted in ELISA assay buffer were similar to those observed when diluted in HBD serum (Table 4a and b). The inhibiting effects of K1-18 on M22 Fab-POD binding to the TSHR can be compared to the effects of K1-70 (Table 4c). K1-70 IgG diluted in HBD serum showed 34.5±3.8%, 91.1±0.3% and 97.6±0.1% inhibition at 0.03 µg/mL, 0.3 µg/mL and 3 µg/mL, respectively. Similar percentage inhibitions were observed when K1-70 IgG was diluted in ELISA assay buffer (Table 4c). As illustrated in Table 4c K1-70 Fab diluted in HBD serum or in ELISA assay buffer showed similar M22-POD binding inhibiting activity as K1-70 IgG.

Inhibition of $^{125}$I-Labelled K1-18 IgG or Fab Binding to TSHR Coated Tubes

In the presence of a control human MAb 4B4 IgG at concentrations from 0.01-100 µg/mL (diluted in HBD serum) binding of $^{125}$I-K1-18 IgG was essentially not affected (Table 5a). This can be compared with the effects of different concentrations of unlabelled K1-18 IgG (diluted in HBD serum); increasing doses of 0.001; 0.01; 0.1 and 1.0 µg/mL caused inhibition of binding of $^{125}$I-labelled K1-18 of 11.1±4.4%, 22.9±2.4%, 69.0±0.5% and 91.7±0.8%, respectively. Unlabelled K1-18 Fab tested at concentrations from 0.001-100 µg/mL showed inhibitions ranged from 10.3±2.2% (at 0.03 µg/mL) to 84.8±0.9% (at 100 µg/mL) (Table 5b). K1-70 IgG and Fab (both tested in the range of concentrations from 0.001-100 µg/mL) also inhibited $^{125}$I-K1-18 IgG binding in a dose dependent manner to an essentially complete inhibition of 95.1±0.3% at 10 µg/mL of K1-70 IgG and 92.8±1.1% at 3 µg/mL of K1-70 Fab (Table 5b). In addition, binding of $^{125}$I-K1-18 IgG was inhibited in a dose dependent manner by M22 IgG, M22 Fab, 5C9 IgG, TSMAb 1-7 IgGs and 9D33 IgG (Table 5a and 5b). When the same experiments were carried out using various MAb preparations diluted in coated tube assay buffer the inhibiting effects of the respective preparations were comparable to the effect observed when diluted in HBD serum except in the case of 5C9 IgG (Table 5a). In the case of 5C9 diluted in assay buffer the maximum inhibition at 100 µg/mL was 91.3±0.4% compared to 57.7±2.4% when diluted in HBD serum and the inhibitions at 0.01 µg/mL were 11.7±1.8% and −1.8±2.7%, respectively (Table 5a). Binding of $^{125}$I-K1-18 IgG to TSHR coated tubes was inhibited by the lymphocyte donor serum resulting in 35.2% and 59.3% inhibition at serum dilutions of 1:20 and 1:10, respectively (Table 5c). Sera from 20 Graves' patients inhibited binding of $^{125}$I-K1-18 IgG and the inhibiting effect was comparable to the inhibiting effect on $^{125}$I-TSH binding (Table 5c). Table 5c also shows the effect of dilutions of sera from two patients with blocking TRAbs (B1 and B2) and sera from two patients with stimulating TRAbs (S1 and S2) on both $^{125}$I-K1-18 IgG and $^{125}$I-TSH binding. Effect of various MAbs on $^{125}$I-K1-18 Fab binding to the TSHR coated tubes is shown in Table 5d. Both, unlabelled K1-18 IgG and K1-18 Fab had dose dependent inhibiting effect on $^{125}$I-K1-18 Fab binding and these effects were comparable to the effects of M22 IgG, M22 Fab and K1-70 IgG (Table 5d). 5C9 IgG, TSMAbs 1-7 IgGs and 9D33 IgG also inhibited on $^{125}$I-K1-18 Fab binding, however, their effects were smaller compared to M22, K1-18 and K1-70 preparations (Table 5d).

Stimulation of Cyclic AMP Production in CHO Cells Expressing the TSHR

K1-18 IgG stimulated cyclic AMP production in CHO cells expressing the TSHR in a dose dependent manner as shown in Table 6a. In hypotonic buffer, the levels of cyclic AMP in the presence of 0.1 ng/mL K1-18 IgG were 1.56±0.32 pmol/L, at 1.0 ng/mL were 4.08±0.28 pmol/L, at 10 ng/mL were 31.66±5.06 pmol/L, at 100 ng/mL were 64.95±9.61 pmol/L and at 1000 ng/mL they were 67.90±10.44 pmol/L. The cyclic AMP levels at different concentrations of K1-18 Fab in hypotonic buffer were 1.72±0.82 pmol/L, 9.99±3.52 pmol/L, 53.22 pmol/L and 66.94±6.93 pmol/L at 1 ng/mL, 10 ng/mL, 100 ng/mL and 1000 ng/mL of K1-18 Fab, respectively. M22 Fab at 1 ng/mL in hypotonic buffer stimulated cyclic AMP production of 29.80±0.97 pmol/L and at 10 ng/mL of 57.41±5.05 pmol/L (Table 6a). Table 6a also shows the effect of K1-18 IgG or Fab on cyclic AMP stimulation in CHO cells expressing the TSHR tested under the isotonic conditions. As illustrated by examples in Table 6a both K1-18 IgG and Fab caused increase of cyclic AMP production under isotonic conditions although the levels of cyclic AMP produced were lower compared to experiments using hypotonic conditions. Comparison of stimulating activity of M22 IgG and K1-18 IgG tested in hypotonic buffer is shown in Table 6b. At 3 ng/mL concentration M22 IgG stimulated 24.3±2.3 pmol/mL of cyclic AMP while K1-18 IgG 8.3±0.5 pmol/mL. At 10 ng/mL M22 IgG and K1-18 IgG caused stimulation of 50.3±1.6 and 25.0±1.0 pmol/mL of cyclic AMP respectively and at 100 ng/mL 64.6±1.9 and 62.6±2.7 pmol/mL respectively. The stimulating activity of K1-18 IgG and Fab was also assessed relative to the activity of NIBSC reference preparation 90/672 (Table 6c). Calculated cyclic AMP stimulating activity of K1-18 IgG was 155 NIBSC 90/672 units/mg (mean of activity calculated at three concentrations of K1-18 IgG; 1 ng/mL, 3 ng/mL and 10 ng/mL) (Table 6c). Cyclic AMP stimulating activity of K1-18 Fab calculated in the same experiment was 22 NIBSC 90/672 units/mg (activity at 10 ng/mL, 30 ng/mL and 100 ng/mL of K1-18 Fab were used for the calculations) (Table 6c). This can be compared with M22 IgG cyclic AMP stimulating activity of 286 NIBSC units/mg (Table 6c). For comparative purposes the stimulating activities of porcine TSH, native human TSH and recombinant human TSH in isotonic and in hypotonic buffers are shown in Table 6d.

Further examples shown in Table 6e concern the stimulating effects of K1-18 IgG, M22 IgG or pTSH when mixed together in different combinations. The stimulating effect of pTSH, M22 or K1-18 appeared to be enhanced when two stimulators were mixed together compared to the effect of the stimulator alone at the same concentrations. In particular, cyclic AMP production of 11.01±0.99 pmol/mL (mean±SD) at 0.1 ng/mL pTSH alone and 35.17±6.38 pmol/mL (mean±SD) at 1 ng/mL of M22 IgG increased to 47.22±3.89 pmol/mL (mean±SD) when 0.1 ng/mL pTSH and 1 ng/mL of M22 IgG were mixed together. Also a mixture of 0.1 ng/mL of pTSH and 10 ng/mL of K1-18 IgG had a greater stimulating effect than these stimulators alone (Table 6e). Furthermore, two stimulating antibodies mixed together were more potent than a single antibody at the same concentrations. For example, 29.95±1.18 pmol/mL (mean±SD) of cyclic AMP was produced in response to 5 ng/mL of K1-18 IgG, 20.20±2.48 pmol/mL (mean±SD) was produced in response to 0.5 ng/mL of M22 IgG while 44.01±7.19 pmol/mL (mean±SD) cyclic AMP was produced in response to 5 ng/mL of K1-18 and 0.5 ng/mL of M22 mixed together (Table 6e).

The results of two experiments in which the ability of the K1-18 and K1-70 donor serum and donor serum IgG to stimulate cyclic AMP were compared to the stimulating activity of NIBSC 90/672 are shown in Tables 6f and 6g. In experiment 1, the stimulating activity of donor serum was 4.7±0.1 pmol/mL of cyclic AMP at 30 times dilution compared to the effect of HBD serum at the same dilution of 1.7±0.4 pmol/mL while the stimulating activity of donor serum IgG was 7.7±1.0 pmol/mL at 30 µg/mL which represented activity relative to NIBSC 90/672 of 0.013 units/mg (Table 6f). In experiment 2, donor serum diluted 30 times caused stimulation of cyclic AMP to 9.5±0.7 pmol/mL while donor serum IgG at 30 µg/mL caused stimulation to 15.6±0.7 pmol/mL which represented activity relative to NIBSC 90/672 of 0.014 units/mg (Table 6g). K1-18 IgG TSHR stimulating activity was inhibited by human MAbs with TSH antagonist activity (K1-70 and 5C9) as illustrated by the examples shown in Table 6h. In particular, K1-18 IgG at 10 ng/mL caused stimulation of cyclic AMP to 50.0±3.3 pmol/mL and this was reduced to 3.8±1.0 pmol/mL in the presence of 0.1 µg/mL of K1-70 IgG (92% inhibition). In the presence of 10 ng/mL of K1-18 IgG and 0.1 µg/mL of 5C9 IgG cyclic AMP levels were 4.4±1.5 pmol/mL (91% inhibition). At higher concentrations of K1-70 IgG or 5C9 IgG the inhibiting effect was complete (100% inhibition) (Table 6h). In further experiments the effect of K1-70 IgG mixed together with 5C9 IgG on K1-18 IgG stimulating activity was studied (Table 6i). As shown in the Table 6I K1-18 IgG stimulation at 10 ng/mL was effectively inhibited by 0.1 µg/mL of 5C9 IgG or 0.1 µg/mL of K1-70 IgG. When K1-70 IgG and 5C9 IgG were mixed to give a final total concentration of 0.1 µg/mL the stimulating activity of K1-18 IgG was also effectively inhibited (97.3% inhibition). However at lower concentrations K1-70 IgG and 5C9 IgG when mixed together were more effective inhibitors of K1-18 IgG stimulating activity than one antibody alone. For example, at 0.001 µg/mL K1-70 IgG and 5C9 IgG individually caused no inhibition (0% and 1% respectively) while when mixed together to the same final concentration of total IgG (ie 0.001 µg/mL) the inhibition was 25.5%. Table 6I also shows that cyclic AMP concentration in the presence of K1-70 IgG (100 µg/mL) was similar to that observed in the presence of assay buffer while in the presence of 5C9 IgG (100 µg/mL) the concentration of cyclic AMP was lower (0.89±0.13; 0.89±0.15 and 0.55±0.14, respectively) (mean±SD of triplicate determinations). When K1-70 IgG and 5C9 IgG were mixed together (final concentration of 100 µg/mL of total IgG) cyclic AMP concentrations were not reduced below the levels observed in the presence of buffer (ie not lower than basal or constitutive activity levels). For comparison essentially complete inhibition of M22 IgG (3 ng/mL) stimulating activity was observed at 1 µg/mL of 5C9 IgG or 1 µg/mL of K1-70 IgG (97.1% and 96.6% inhibition respectively) and inhibitions at 0.1 µg/mL of 5C9 IgG or 0.1 µg/mL of K1-70 IgG were 92.8% and 75.5%, respectively (Table 6j). However, when 5C9 and K1-70 were mixed together to a final total IgG concentration of 0.1 µg/mL 91.9% inhibition was observed (Table 6j). The effects of mixtures of K1-70 IgG and 9D33 IgG on K1-18 IgG stimulating activity are shown in Table 6k. In the case of 9D33 IgG 95% inhibition was observed at 1 µg/mL while K1-70 IgG at 0.1 µg/mL showed the same inhibition (95% inhibition). When the two blocking MAbs (9D33 and K1-70) were mixed together to a final total IgG concentration of 0.1 µg/mL 95% inhibition was also observed (Table 6k). 9D33 IgG at 10 µg/mL was able to essentially completely inhibit M22 IgG cyclic AMP stimulation (94% inhibition) while lower concentrations of K1-70 IgG (1 µg/mL) had similar effect (96% inhibition) (Table 6l).

Essentially complete inhibition of M22 activity (96% inhibition) was evident at 1 μg/mL of the 9D33 and K1-70 mixture (Table 6l). This is comparable to the inhibiting effect of a mixture of 9D33 and K1-70 (1 μg/mL) on TSH stimulating activity (97% inhibition) (Table 6m). However, it should be noted that TSH stimulating activity was inhibited more effectively by K1-70 IgG alone (98% inhibition at 1 μg/mL) than by 9D33 IgG alone (95% inhibition at 100 μg/mL) (Table 6m). Table 6n shows the effect of the lymphocyte donor serum and three patient sera containing TRAbs with blocking activity (B1-B3) on TSHR stimulating activity of TSH, M22 IgG and K1-18 IgG. The donor serum inhibited TSH, M22 IgG and K1-18 IgG stimulating activities (63.8%, 80.1% and 79.5% inhibitions, respectively). Three different sera with blocking TRAbs that had a strong inhibiting effect on TSH and M22 IgG stimulation also inhibited the stimulating activity of K1-18 IgG (Table 6n). The inhibiting effects of the different patient sera on TSH, M22 IgG or K1-18 IgG stimulating activities were comparable.

Measurement of Antagonist (Blocking) Activity

Incubation of CHO cells expressing the TSHR with porcine TSH at 3 ng/mL caused stimulation of cyclic AMP production to 62.6±3.9 pmol/mL (Table 7a). In the presence of increasing amounts of K1-70 IgG stimulating activity of porcine TSH was inhibited in a dose dependent manner. In particular in the presence of 0.01, 0.05, 0.1 and 1 μg/mL of K1-70 IgG the levels of cyclic AMP were 60.1±1.6, 31.4±1.9, 5.8±2.8 and 2.0±0.2 pmol/mL respectively which represent 4.0%, 49.8%, 90.7% and 96.8% inhibition respectively relative to the effect of control MAb IgG (5B3) (Table 7a). Table 7a also show the inhibiting effects of 5C9 IgG for comparison. The effects of K1-70 Fab on stimulating activity of porcine TSH under 2 different experimental conditions are shown in Table 7b. In the presence of K1-70 Fab at 1 μg/mL porcine TSH stimulating activity was essentially completely inhibited in both conditions (ie in isotonic and in hypotonic medium). The effect of K1-70 Fab was dose dependent in the range of concentrations studied (0.003 μg/mL to 3 μg/mL) with as little as 0.05 μg/mL of Fab showing an ability to reduce porcine TSH stimulation down to 28.9±1.1 pmol/mL cyclic AMP from 39.5±1.9 pmol/mL in the presence of 1 μg/mL of control MAb (under isotonic conditions) (Table 7b). The potency of K1-70 Fab under hypotonic conditions was similar to that observed under isotonic conditions (Table 7b).

Increasing concentrations of K1-70 IgG (range 0.001-100 μg/mL) did not show any ability to inhibit TSHR constitutive (basal) activity as illustrated by the examples shown in Table 7c. This contrasts with the effects of 5C9 IgG as shown in Table 7c for comparison. The blocking mouse antibody 9D33 tested in the same experiment had no ability to affect TSHR constitutive activity (Table 7c) and some weak stimulating activity (about 2× basal) was observed with high concentrations of 9D33. Blocking activity of K1-70 IgG was compared to the blocking activity of the lymphocyte donor serum as shown in Table 7d. Cyclic AMP levels after incubation with porcine TSH at 1 ng/mL were 61.7±4.3 pmol/mL and the levels dropped in the presence of donor serum (10× dilution) to 14.9±1.2 pmol/mL (75.9% inhibition) and to 51.6±2.6 pmol/mL with serum diluted 20 times (16.4% inhibition). Donor serum at higher dilutions did not have a detectable effect on TSH stimulating activity. The effect of donor serum can be compared to the effect of K1-70 IgG that at 0.1 μg/mL had a similar effect as serum diluted 10 times (67.6% and 75.9% inhibition respectively) (Table 7d). K1-70 IgG had the ability to block cyclic AMP stimulating activity of porcine TSH, human TSH and human recombinant TSH as illustrated by the examples in Table 7e. K1-70 IgG at 0.1 μg/mL was an effective blocker of stimulating activity of all three TSH preparations tested under hypotonic medium conditions. Blocking activity of K1-70 IgG was less effective under isotonic medium conditions (Table 7e). Effects of K1-70 IgG on M22 IgG mediated stimulation of cyclic AMP production in CHO cells expressing the TSHR are shown in Table 7f. Cyclic AMP levels observed at 3 ng/mL of M22 IgG were 33.1±1.8 pmol/mL and these decreased in the presence of K1-70 IgG for example, 4.3±2.4 pmol/mL at 0.1 μg/mL (87% inhibition) (Table 7f). The effects of K1-70 IgG were comparable to the effects of 5C9 IgG tested in the same experiment (Table 7f). Furthermore, K1-70 IgG showed the ability to block cyclic AMP stimulating activity of TRAbs in sera from patients with Graves' disease and the examples in Tables 7g-7k illustrate that 100 μg/mL concentrations of K1-70 IgG caused complete inhibition of stimulating activity in all 15 sera studied (inhibition of T1-T15 ranged from 90.8% to 98.7%). The effects of K1-70 IgG on the stimulating activities of sera T1-T15 were comparable to the effects of 5C9 IgG and 9D33 IgG tested in the same experiment except for one serum ie T11 (Table 7j). Stimulating activity of serum T11 was only weakly inhibited by 100 μg/mL of 5C9 IgG (8.5% inhibition) while in the presence of 100 μg/mL of K1-70 the inhibition was essentially complete (95.1% inhibition) (Table 7j). Effective inhibition (87.1%) of T11 was also observed with 100 μg/mL 9D33 (Table 7j). The effect of different blocking MAbs at different concentrations (0.01-100 μg/mL) on the stimulating activities of three Graves' sera (including serum T11) is shown in more detail in Tables 7l-7n. These experiments showed that K1-70 IgG, 5C9 IgG and 9D33 IgG are effective inhibitors at concentrations as low as 0.1 μg/mL except in the case of serum T11 on which 5C9 IgG had little or no effect (Table 7n). Table 7o shows inhibition of porcine TSH stimulation by K1-70 IgG and 5C9 IgG when the two blocking MAbs were mixed together in one experiment. These experiments showed that the two blocking MAbs were effective in combination in their ability to inhibit TSH stimulation of cyclic AMP production. In addition the effect of K1-70 IgG and 5C9 IgG mixed together on the constitutive activity of the TSHR was tested. As shown in Tables 7c and 7p K1-70 IgG had no effect on TSHR basal activity in contrast to 5C9 IgG. When K1-70 and 5C9 IgGs were mixed together to give a final IgG concentration of 2 μg/mL cyclic AMP levels dropped slightly from 58.04±8.52 pmol/mL (mean±SD, n=3) in the presence of buffer only to 55.28±6.17 pmol/mL (mean±SD, n=3) ie 4.8% inhibition (Table 7p). However, when 5C9 IgG was mixed with 5B3 IgG (control antibody to glutamic acid decarboxylase) to give a final IgG concentration of 2 μg/mL constitutive activity of the TSHR was inhibited to 52.1% of basal values (cyclic AMP level 27.78±2.96 pmol/mL; mean±SD, n=3) (Table 7p). These experiments show that in the presence of K1-70 IgG, 5C9 IgG is unable to act as an effective inhibitor of TSHR constitutive activity.

Effect of the TSHR Mutations on K1-18 Stimulating Activity

The effect of K1-18 IgG on stimulation of cyclic AMP production was tested using CHO cells expressing TSHRs with the following amino acid mutations: Lys58Ala, Arg80Ala, Tyr82Ala, Glu107Ala, Arg109Ala, Lys129Ala, Phe130Ala, Phe134Ala, Lys183Ala, Asp203Ala, Arg255Asp (Table 8a-k and summarised in Table 10). Mutation of TSHR amino acids Lys58, Arg80, Tyr82, Glu107, Arg109, Lys129, Phe130, Phe 134 and Asp203 to alanine had no effect on K1-18 IgG's ability to stimulate cyclic AMP production. The ability of K-18 IgG to stimulate cyclic AMP production was lost completely with CHO cells expressing TSHR containing mutations Lys183Ala and Arg255Asp and cyclic AMP concentrations in response to K1-18 IgG were similar to the concentrations observed in the presence of cyclic AMP buffer only (Table 8i and 8k). However, responsiveness to TSH was retained with the Lys183Ala and Arg255Asp mutations. In an additional series of experiments the effects of mutations of various amino acids of the TSHR on K1-18 IgG cyclic AMP stimulating activity was tested further (Tables 14a-14v and summarised in Table 16). Mutations (to alanine) of TSHR residues Asp43, Ile60, Glu61, Thr104, His105, Lys250, Arg255, Thr257, Asp276 and Ser281 had no effect on K1-18 IgG's ability to stimulate cyclic AMP production. Mutations of TSHR Asp151, Glu178, Lys209, Gln235, Glu251 to alanine caused a small reduction of K1-18 IgG stimulating activity, however, these mutations also affected TSH stimulating activity therefore the interactions with these TSHR residues were not considered specific for K1-18. In contrast, mutations of TSHR Glu157Ala, Lys183Asp, Tyr185Ala and Asp232Ala resulted in loss of the ability of K1-18 IgG to stimulate cyclic AMP (less than 20% of the wild type activity; Tables 14g, 14i, 14j, 14m). Furthermore, the ability of K1-18 IgG to stimulate the TSHR mutated at Tyr206, Trp258 and Arg274 to alanine was reduced to approximately 40-60% of the wild type activity (Tables 14k, 14s, 14t).

Effect of the TSHR Mutations on K1-70 Blocking Activity

The effect of K1-70 IgG on TSH stimulation of cyclic AMP production was tested in CHO cells expressing TSHRs containing mutations of the following amino acids to alanine: Lys58, Arg80, Tyr82, Glu107, Arg109, Lys129, Phe130, Phe134, Lys183 and Asp203. In addition the effect of TSHR mutation Arg255Asp was tested. (Table 9 a-k and summarised in Table 10). Mutation of TSHR amino acids Arg80, Glu107, Lys129, Phe130, Phe134 and Asp203 to alanine had no effect on K1-70 IgG's ability to inhibit TSH stimulated cyclic AMP production. The ability of K1-70 to inhibit TSH stimulated cyclic AMP production was reduced by mutation of TSHR Lys58, Tyr82, Arg109 and Lys183 to alanine. The mutation Lys58Ala had the greatest effect (Table 9a) followed by Arg109Ala, Lys183Ala and Tyr82Ala that had the smallest effect (Tables 9e, 9i, 9c respectively and Table 10). However, none of the mutations studied caused a complete loss of K1-70 IgG ability to block TSH stimulated cyclic AMP production. In an additional series of experiments the effects of mutations of various amino acids of the TSHR on K1-70 IgG blocking activity was tested further (Tables 15a-15v and summarised in Table 16). The ability of K1-70 to inhibit TSH stimulated cyclic AMP production in TSHR transfected CHO cells was not affected by the TSHR mutations Asp43, Thr104, His105, Asp151, Tyr185, Tyr206, Lys209, Asp232, Gln235, Glu251, Arg255, Thr257, Trp258, and Arg274 to alanine nor mutations Asp160Lys and Lys183Asp. Mutations (to alanine) at TSHR Glu178 and Ser281 had a small effect on the ability of K1-70 IgG to block the stimulating activity of TSH (80-100% of the wild type activity; Tables 15h and 15v). TSHR mutations Glu61, Lys250 and Asp276 to alanine caused some effect (60-80% of the wild type) on K1-70 IgG blocking activity (Tables 15c, 15o, 15u) while TSHR mutation Ile60Ala caused reduction of K1-70 IgG blocking activity to 40-60% of the wild type activity (Table 15b).

Inhibition of $^{125}$I-Labelled K1-70 IgG or Fab Binding to the TSHR

Binding of $^{125}$I-K1-70 IgG to TSHR coated tubes was inhibited in a dose dependent manner by unlabelled K1-70 IgG and at concentrations of 0.003 μg/mL, 0.03 μg/mL, 0.3 μg/mL and 3 μg/mL (diluted in HBD serum) the inhibitions were 10.2±2.4%; 36.5±1.9%; 84.4±0.8% and 92.0±0.5%, respectively (Table 11a). As shown in Table 11a binding of $^{125}$I-K1-70 IgG was inhibited in a very similar way by M22 IgG (diluted in HBD serum); 6.2% (mean of duplicate determinations); 33.8±0.9%; 84.6±1.1% and 91.6±0.5% inhibitions at 0.003 μg/mL, 0.03 μg/mL, 0.3 μg/mL and 3 μg/mL concentrations. M22 Fab showed a greater potency to inhibit $^{125}$I-K1-70 IgG binding at lower concentrations with the inhibitions of 16.7±6.0%; 60.2±1.8%; 89.9±01% and 92.0±0.3% at 0.003 μg/mL, 0.03 μg/mL, 0.3 μg/mL and 3 μg/mL concentrations (in HBD serum) (Table 11a). Also, K1-18 IgG and Fab inhibited $^{125}$I-K1-70 IgG binding to the TSHR in a dose dependent manner (Table 11b). Dilutions of K1-18 IgG at 0.03 μg/mL, 0.3 μg/mL and 3 μg/mL (in HBD serum) showed 20.0±1.9%, 73.9±0.6% and 91.0±0.3% inhibition respectively and K1-18 Fab at 0.03 μg/mL, 0.3 μg/mL and 3 μg/mL (in HBD serum) showed 10.2±2.1%, 60.9±1.1% and 80.5±0.6% inhibition respectively (Table 11b). In contrast higher concentrations of 5C9 IgG were required to inhibit $^{125}$I-K1-70 IgG binding; 1 μg/mL was needed for 15.4±3.4% inhibition and 100 μg/mL showed 68.5±0.7% inhibition (Table 11a). Tables 11a and 11b also show the effects of various human MAbs on $^{125}$I-K1-70 binding in assay buffer. The effects are stronger when dilutions were made in assay buffer compared with HBD sera. The effects of different mouse monoclonal antibodies to the TSHR with TSHR stimulating activity (TSMAbs 1-7) and with TSHR blocking activity (9D33) on $^{125}$I-K1-70 IgG binding to the TSHR are shown in Table 11c. All TSMAbs tested had the ability to inhibit $^{125}$I-K1-70 IgG binding and 100 μg/mL concentrations (in HBD serum) caused inhibition ranging from 33.5±3.7% (TSMAb 3) to 59.6±0.6% (TSMAb 5) (Table 11c). 9D33 IgG at 100 μg/mL (in HBD serum) showed 51.1±1.7% inhibition (Table 11c). When these MAbs were diluted in assay buffer the % inhibitions were slightly higher compared with HBD sera in some cases and slightly lower in others (Table 11c). Further experiments showed that $^{125}$I-K1-70 Fab binding to the TSHR was also effectively inhibited by K1-18 IgG, K1-18 Fab, M22 IgG, M22 Fab, K1-70 IgG, K1-70 Fab, and mouse TSMAbs in a dose dependent manner (Table 11d). Graves' patient sera n=20) containing TSHR autoantibodies with $^{125}$I-TSH binding inhibition activity in the range from 15.9% to 80.0% (in the TSHR coated tube assay) also showed the ability to inhibit $^{125}$I-K1-70 IgG or Fab binding to the TSHR (range 19.2% to 77.6% and 15.9% to 72.8%, respectively) (Table 11e). The % inhibitions for the three labelled ligands tested were comparable in the case of each serum (Table 11e). None of the HBD sera (n=10) had an effect on $^{125}$I-labelled TSH, K1-70 IgG or Fab binding (Table 11e). Table 11e shows examples of experiments using two sera with TSHR stimulating activity (S1 and S2) and two sera with TSHR blocking activity (B1 and B2). Sera with either type of activity inhibited $^{125}$I-labelled TSH, K1-70 IgG or Fab binding in a dose dependent manner and the degree of inhibition of binding of the different ligands was comparable for each serum (Table 11e).

Kinetics of K1-18 and K1-70 Binding to the TSHR $^{125}$I-labelled K1-70 IgG and Fab binding to TSHR (full length) coated tubes at room temperature reached a maximum after 180 min (45.5% and 37.1% binding respectively). 50% maximal binding occurred after about 35 min (FIG. 1*a*). $^{125}$I-labelled K1-70 IgG binding to TSHR260 coated tubes reached 36.2% at 180 min and 50% maximal binding was observed after 60 min incubation (FIG. 1*b*). Time course of $^{125}$I-labelled K1-70 Fab binding to the TSHR260 was similar to that observed for K1-70 IgG with the maximum binding after 60 min incubation of 37.3% and 50% maximal binding after approximately 60 min (FIG. 1*c*). Addition of unlabelled K1-70 IgG or Fab, K1-18 IgG or Fab, M22 IgG (all at 1 mg/mL), porcine TSH (100 mU/mL) or assay buffer to either $^{125}$I-K1-70 IgG or $^{125}$I-K1-70 Fab bound to TSHR (full length) coated tubes did not result in detectable dissociation even after 180 min of incubation (FIGS. 1d, 1e and 1f). However, after addition of unlabelled M22 Fab (1 mg/mL) to $^{125}$I-K1-70 IgG or $^{125}$I-K1-70 Fab bound to TSHR coated tubes 41.2% and 27.9% respectively of the counts bound dissociated after 180 min incubation (FIGS. 1d and 1f). The dissociating effect of various unlabelled ligands on $^{125}$I-labelled K1-70 IgG bound to TSHR260 is shown in FIG. 1g. Porcine TSH, M22 IgG and K1-18 IgG had no effect while M22 Fab and K1-70 Fab caused approximately 30% of bound $^{125}$I-labelled K1-70 IgG to dissociate from TSHR260 after 30 min incubation and thereafter dissociation did not increase further up to 180 min (FIG. 1g). K1-18 Fab had similar effect as shown in FIG. 1h. $^{125}$I-K1-70 Fab binding to TSHR260 coated tubes was not dissociated by incubation with unlabelled K1-70 IgG, K1-18 IgG, M22 IgG (all at 1 mg/mL), porcine TSH (100 mU/mL) or assay buffer. Incubation with unlabelled M22 Fab or K1-70 Fab (1 mg/mL) caused dissociation of $^{125}$I-K1-70 Fab binding to TSHR260 (58.9% and 62% respectively) (FIG. 1i). $^{125}$I-labelled K1-18 IgG binding to TSHR coated tubes at room temperature reached a maximum after 180 min of 32.7% in the case of tubes coated with the full length TSHR and 23.3% in the case of tubes coated with TSHR260 (FIG. 1j). 50% maximal binding was observed after approx. 45 min in the case of full length TSHR and after approx. 50 min in the case of TSHR260 (FIG. 1j). $^{125}$I-labelled K1-18 IgG bound to full length TSHR coated tubes was not dissociated to a small extent by incubation with unlabelled porcine TSH while incubation with unlabelled K1-18 IgG, M22 IgG, K1-70 IgG, K1-18 Fab and K1-70 Fab had a slightly greater effect (approx. 25% dissociation after 180 min) (FIG. 1k). In contrast, M22 Fab caused 29% dissociation of $^{125}$I-K1-18 IgG bound to full length TSHR after 60 min incubation increasing to 43% dissociation after 180 min incubation (34.5% of $^{125}$I-K1-18 IgG bound in the absence of M22 Fab compared to 24.5% and 19.8% after 60 and 180 min incubation with M22 Fab respectively) (FIG. 1k). In the case of $^{125}$I-labelled K1-18 IgG bound to TSHR260 coated tubes incubation with porcine TSH had no dissociating effect (FIG. 1l). In contrast incubation with unlabelled M22 Fab, K1-70 Fab and K1-18 Fab caused bound $^{125}$I-K1-18 IgG to dissociate from TSHR260. In the presence of M22 Fab and K1-70 Fab dissociation was rapid (approximately 50% after 30 min incubation) while incubation with K1-18 Fab caused 50% dissociation after 90 min (FIG. 1l). Intact M22 IgG, K1-70 IgG and K1-18 IgG had lesser ability to dissociate $^{125}$I-K1-18 IgG from TSHR260 with approximately 30% dissociation observed after 180 min incubation (FIG. 1l). A separate series of experiments showed that $^{125}$I-labelled porcine TSH was not able to bind to TSHR260 coated tubes. Binding of $^{125}$I-TSH to tubes coated with the full length TSHR was described before (Nakatake et al 2006 supra).

Effects of K1-18 or K1-70 IgG in an ELISA Based on TSHR260-AP

The ability of K1-18 IgG to form a "bridge" between the full length TSHR immobilised on ELISA plate wells and TSHR260-AP in the liquid phase is illustrated by the examples shown in Table 12a. OD405 nm values increased in a dose dependent manner with increasing concentrations of K1-18 IgG (diluted in HBD sera). In particular, OD405 nm values were 0.013, 0.191, 0.511, 0.660 and 0.706 at 0.005, 0.05, 0.5, 10 and 100 µg/mL K1-18 IgG respectively compared to OD405 nm of −0.002 in the presence of HBD serum alone. K1-70 IgG (diluted in HBD sera) also bound well in the bridging ELISA and showed OD 405 nm values of 0.045, 0.290, 0.661, 0.738 and 0.794 at 0.005, 0.05, 0.5, 10 and 100 µg/mL K1-70 IgG concentrations respectively (Table 12a). The effects of K1-18 and K1-70 IgGs can be compared to the ability of M22 IgG to bind to TSHR260-AP preparations as shown in Table 12a. In the assay, increasing doses of M22 IgG (ranging from 0.005 µg/mL to 10 µg/mL diluted in HBD sera) bound increasing amounts of the TSHRs with the OD405 nm values ranging between 0.045 and 0.796. When dilutions of MAbs were made in ELISA assay buffer rather than HBD sera, absorbances at 450 nm were higher particularly in the case of 5C9 (Table 12a). The principle of the "bridge type" ELISA on which divalent IgG binds to two molecules of the TSHR has been validated further by the results of the experiments shown in Table 12b. Intact IgGs of human MAbs to the TSHR (M22, 5C9, K1-18 and K1-70) showed dose dependent binding in the ELISA while the monovalent Fab fragments of the same MAbs showed little or no response (Table 12b). Mouse TSMAbs 1-7 also bound well in the TSHR260-AP ELISA as illustrated by the examples in Table 12c. OD 405 nm signal ranged from 0.103 to 0.561 at 10 µg/mL concentrations of TSMAbs 1-7 (Table 12c). Mouse TSHR blocking MAb 9D33 also bound in this assay system with an OD 405 nm signal of 0.481 at 10 µg/mL (Table 12d). Patient sera containing TRAbs with stimulating activity i.e. sera that showed an ability to stimulate cyclic AMP activity in CHO cells expressing the TSHR reacted well in the TSHR260-AP ELISA. Table 12e shows examples of 6 different sera tested at different dilutions and the OD405 nm signal ranged from 0.407 to 0.924 at 1/5 dilutions in HBD sera. Furthermore sera from patients with blocking type TSHR autoantibodies bound well in the TSHR260-AP ELISA as illustrated by the examples in Table 12f with the OD 405 nm signal ranging from 0.323 to 0.896 at 1/10 dilutions in HBD sera. Table 12g shows more examples of binding of patient sera in the TSHR260-AP ELISA. TRAb concentrations in the TSHR260-AP ELISA were calculated from a calibration curve prepared from the NIBSC reference preparation 90/672 and compared to TRAb concentrations (expressed as NIBSC U/L) measured in the same sera using a TSHR coated tubes assay. There was good overall agreement in TRAb measurements made using the TSHR260-AP ELISA and by inhibition of TSH binding to full length TSHR (coated tube assay) (r=0.913, n=57) (FIG. 2a). Table 12h shows that patient serum TRAbs have the ability to inhibit binding of M22 Fab labelled with peroxidase to TSHR260 coated onto ELISA plate wells. Comparison of TRAb measurement in an assay based on inhibition of M22 Fab binding to full length TSHR correlated well with results in the assay based on inhibition of M22 Fab binding to TSHR260 (r=0.761; n=56) (FIG. 2b). Other comparison data are shown in FIGS. 2c and 2d. The effect of TSHR R255 mutation on binding of antibodies in the TSHR260-AP ELISA was tested. In these experiments full length preparations of TSHR containing the mutation R255D were coated on the plate wells and the ELISA carried out using the standard protocol described above. As shown in Table 12i binding of K1-70 IgG or 9D33 IgG were only affected slightly by the TSHR R255D mutation. In contrast, M22 IgG binding was markedly affected by TSHR R255D mutation with the OD signal reduced at all concentrations studied (Table 12i). The TSHR R255D mutation had little effect on higher concentrations of K1-18 IgG but lower concentrations (0.1 µg/mL and below) were much less effective in the assay using the mutated receptor (Table 12i). Table 12j also shows that OD 405 nm signal with 10 Graves' sera (not selected for TSHR stimulating or blocking activity) was reduced when TSHR R255D coated plates were used compared to wild type TSHR. The degree of the signal reduction varied with different sera (Table 12j). Patient TSHR blocking sera bound well in the TSHR260-AP ELISA (Table 12f) and the binding of the same sera to TSHR R255D is shown in Table 12k. The OD 405 nm signal values in experiments with wild type TSHR and TSHR mutated at R255D are similar and consequently the effect of TSHR R255D mutation on binding of the blocking sera does not appear evident in this assay system. The effect of R255D mutation on binding of patient blocking sera in the TSHR260-AP ELISA can be compared to the effect of the same mutation on binding of patient sera with thyroid stimulating activity. Table 12 l shows binding of six stimulating sera (S1-S6 sera are the same as in Table 12e) to TSHR R255D. In the case of all six sera the OD 405 nm values were lower in the assays with TSHR R255D compared to wild type TSHR. The degree of the signal reduction varied; in the case of sera S4, S5 and S6 (diluted 1:5 in HBD pool serum) the signal dropped from 0.646, 0.407 and 0.531 in the experiments with the wild type TSHR to 0.193, 0.133 and 0.342 in the experiments with TSHR R255D, respectively (Table 12l). The reduction in OD 405 nm values in the case of sera with high levels of TRAb (sera S1-S3 in Table 12e and 12l) was clearly evident at higher serum dilutions. For example, OD 405 nm signal in the case of sera S1, S2 and S3 (diluted 1:20 in HBD pool) of 0.583, 0.407 and 0.453 in the experiments with the wild type TSHR were clearly reduced to 0.193, 0.117 and 0.210 in the experiments with TSHR R255D, respectively. The examples shown in Tables 12k and 12l suggest that sera with TSHR stimulating activities can be differentiated from sera with TSHR blocking activities in some cases at least on the basis of differences in binding to the TSHR containing R255D mutation. Binding of patient sera with stimulating activities tends to be affected by the mutation while binding of patient sera with blocking activities tends not to be.

Temperature Stability of Different TSHR Preparations

In the temperature stability experiments $OD_{450}$ nm values of binding of M22 Fab-peroxidase to the full length TSHR in the ELISA were 1.748, 0.268 and 0.126 respectively for (a) preparations stored at −80° C. (untreated), (b) incubated for 24 hours at room temperature followed by return to −80° C. and (c) incubated for 48 hours at room temperature followed by return to −80° C., respectively. Consequently full length TSHR preparations stored at room temperature for 48 and 24 hours showed respectively only 7% and 15% activity relative to untreated preparations. M22 Fab-peroxidase binding $OD_{450}$ nm values were 2.293 for untreated TSHR260 and 1.836 and 1.676 for TSHR260 stored at room temperature for 24 and 48 hours respectively. The activity of TSHR260 stored at room temperature for 24 and 48 hours relative to untreated preparations was 80% and 73% respectively. Similar results were observed in the case of TSHR260-AP with $OD_{450}$ nm of 2.106 and 1.983 for samples stored at room temperature for 24 and 48 hours respectively compared to 2.395 for untreated samples. This represented 88% and 83% binding activity after 24 and 48 hours room temperature storage relative to untreated TSHR260-AP. In the experiments with untreated TSHR LRD C-CAP the $OD_{450}$ nm was 1.826 and after 24 and 48 hour room temp storage 1.158 and 1.155, respectively. TSHR LRD C-CAP showed 63% activity relative to untreated preparations after 24 and 48 hour storage at room temperature. The above described experiments showed that the ability to bind M22 of TSHR260, TSHR260-AP and TSHR LRD C-CAP after room temp treatment was greater than the full length TSHR preparations. This indicates that TSHR260, TSHR260-AP and TSHR LRD C-CAP are more stable at room temperature compared to full length TSHR.

Variable Region Sequences

Sequence analysis of the genes coding for K1-18 indicated that the HC V region genes were from the VH5-51*01 family, the D genes from the D3-16*02 (or D3-16*01) family and the JH genes from the J3*02 family. In the case of the LC, V region genes were from the V3-20*01 family and J region genes from the JK-1*01 germline. The HC nucleotide and amino acid sequences are shown in FIG. 3 (SEQ ID No 1-18) and the LC nucleotide and amino acid sequences are shown in FIG. 4 (SEQ ID No 19-36). There are somatic mutations in the HC gene sequence compared to the germline sequences; in particular 1 silent mutation and, 1 replacement mutation in CDR 1, 1 silent and 3 replacement mutations in CDR 2, 3 replacement mutations in FRW3 and 1 silent and 1 replacement mutation in CDR 3. The replacement/silent mutation (R/S) ratio for the CDRs is 2.7, however, in addition to the mutations there is an 8 base pair long insertion in the CDR 3. The HC CDR1 (SEQ ID No 6 and 16) is 5 amino acids long, CDR 2 (SEQ ID No 7 and 17) is 17 amino acids long and the CDR 3 (SEQ ID No 8 and 18) is 13 amino acids long (FIGS. 3b and 3d, respectively). In the LC sequence there are: 2 replacement mutations in CDR1, 1 silent mutation in FWR2 and 3 replacement mutations in CDR 3 with the overall R/S mutation ratio of 5.0 (FWRs and CDRs). The LC CDR 1 (SEQ ID No 24 and 34) is made up of 12 amino acids, CDR 2 (SEQ ID No 25 and 35) of 7 amino acids and CDR 3 (SEQ ID No 26 and 36) of 9 amino acids (FIGS. 4b and 4d, respectively). K1-70 HC V region is from the VH5-51*01 germline, D genes from the D1-7*01 family and JH genes from the J4*02 family. LC genes are from the LV1-51*01 germline combined with JL genes from the LJ7*01. The HC nucleotide and amino acid sequences are shown in FIG. 5 (SEQ ID No 37-54) the preferred LC nucleotide and amino acid sequences are shown in FIGS. 6c and 6d (SEQ ID No 63-72). In the K1-70 HC sequence there are three replacement mutations in FWR1, 3 replacement mutations in CDR1, 1 replacement mutation in FWR2, 2 silent mutation in CDR 2, 4 replacement mutations in FWR3 and 1 replacement mutation in FWR4. Overall (FWRs and CDRs) R/S mutation ratio is 6.0. In addition there are 2 insertions in the CDR 3; a 5 base pair insertion in the junction between V and D genes and a 12 base pair insertion at the junction between D and J genes (FIGS. 5b and 5d; SEQ ID No 41 and 51)). The HC CDR 1 (SEQ ID No 42 and 52) is 5 amino acids long, CDR 2 (SEQ ID No 43 and 53) is 17 amino acids long and CDR 3 (SEQ ID No 44 and 54) is 10 amino acids long (FIGS. 5b and 5d, respectively). K1-70 LC genes show 1 silent mutation in FWR1, 1 silent and 1 replacement mutations in FWR2 and 1 replacement mutation in FWR3. There are 1 silent and 2 replacement mutations in the CDR1 and 2 replacement mutations in the CDR3. Overall (FWRs and CDRs) R/S mutation ratio is 2.0. In addition there is a 2 base pair insertion between the LC V and J genes. The LC CDR 1 (SEQ ID No 70) is made up of 13 amino acids, CDR 2 (SEQ ID No 71) of 7 amino acids and CDR 3 (SEQ ID No 72) 11 amino acids (FIG. 6d).

K1-70 Fab Structure

The structure of Fab K1-70 has been determined at 2.22 Å resolution (FIG. 8). The Ramachandran plot parameters and the refinement statistics were within the range acceptable for correct structure refinement. The asymmetric unit contains two complete Fab K1-70 molecules, Fab A and Fab B. Fab A contains heavy chain A and light chain B, while Fab B contains heavy chain C and light chain D. The two Fab molecules are not related by non-crystallographic symmetry due to differences in the elbow angles (Fab A=145.5°, Fab B=163.1°). There are no breaks in main chain electron density in the structure, but some residues are missing at the termini. In Fab A heavy chain A and light chain B consist of residues 1 to 227 and 4 to 211, respectively, and in Fab B heavy chain C and light chain D consist of residues 1 to 227 and 2 to 212, respectively. The residues in Fab A and Fab B are numbered according to Kabat's system (Kabat E et al 1991 supra). See FIGS. 8 and 9a for details. Electron density could not be observed for the side chains of residues 1, 58, 129 and 213 of heavy chain A; side chains of residues 18, 94, 110, 126, 156, 163 and 166 of light chain B; side chains of residues 1, 58 and 218 of heavy chain C; and side chains of residues 17, 18, 94, 108, 156, 172, 184, 187 and 190 of light chain D. The absence of these side chains in the electron density map indicates that they are highly mobile, mainly due to their being positioned in solvent accessible regions of the crystal structure. The root mean square deviation (r.m.s.d) for the two molecules of Fab, calculated using LSQKAB (CCP4), are 0.20 Å for VH domains (117 Cα atoms), 0.23 Å for VL domains (106 Cα atoms), 0.22 Å for CH domains (96 Cα atoms) and 0.29 Å for CL domains (97 Cα atoms). This demonstrates that even though the elbow angles between the two Fab molecules differ, the domains themselves show minimal differences. The structure of K1-70 Fab is standard (FIG. 9a); the canonical structures adopted by the six CDRs are 1, 1 and 2 for LC CDR1, LC CDR2 and LC CDR3 respectively and 1 and 2 Å for HC CDR1 and HC CDR2 respectively. The HC CDR3 has not been assigned any canonical class due to greater variations in sequence and conformation. Disulphide bonds are present between cysteine residues LC23-LC88, LC134-LC194, HC22-HC92, HC142-HC208. In the crystal structure of K1-70 Fab LC CDR1 is 13 residues long, LC CDR2 is 7 residues long and LC CDR3 is 11 residues long. HC CDR1 is made up of 5 residues, HC CDR2 of 17 residues and HC CDR3 of 12 residues. For further analysis of the structure the side chains of LC CDR3 Arg94 and HC CDR2 Arg58 (for which the electron density was missing in the diffraction data set) were added. In the description of the structure below the values in brackets refer to the values obtained including these side chains. There are 158 hydrogen bonds within the LC and 177 within the HC. 52 (52) residues from the LC are involved in interface contact with 44 (45) residues from the HC. There are 7 hydrogen bonds and 2 salt bridges that keep the two chains in their relative position. The solvent accessible surface area (ASA) for the LC CDR1 is 525 (485) Å$^2$, LC CDR2 is 508 (508) Å$^2$, LC CDR3 is 257 (442) Å$^2$, HC CDR1 is 120 Å$^2$, HC CDR2 is 759 (842) Å$^2$ and HC CDR3 is 557 (528) Å$^2$. The distribution of charged amino acids on the surface of the antigen binding site of K1-70 Fab has been analysed and is shown in FIG. 9b. The surface of the combining site is dominated by negatively charged residues on one side and by positively charged residues on the other side. The acidic patches on the antigen binding surface are contributed from LC residues: Asp27B (CDR1), Asp50 (CDR2), Asp92 (CDR3) and from HC residues: Asp31 (CDR1), Asp54 and Asp56 (CDR2) and Asp96 (CDR3). The basic patches are contributed from the LC residues: Lys53 and Arg54 (CDR1) and Arg94 (CDR3) and from the HC residues: Arg58 (CDR2) and Arg 101 (CDR3). In addition, LC Lys 66 which is outside the CDR regions also contributes to a basic patch on the surface. Overall, the positively charged area on the antigen binding surface of K1-70 is made up predominantly by the LC residues while the negatively charged area by the HC residues. The antigen binding surface of K1-70 is also rich in aromatic residues with 5 tyrosines, one phenylalanine and three tryptophans from the HC and the LC CDRs (FIG. 9c). In addition, four tyrosines and one phenylalanine from the FRW regions contribute to the surface area. The overall surface of the K1-70 antigen binding area is highly irregular with a cavity near to the centre. The cavity is surrounded mostly by aromatic residues and by LC Asp50 (FIGS. 9b and 9c). Furthermore, the interior of the cavity is also populated by aromatic residues. This suggests that aromatic contacts may be important for the interaction between K1-70 and the TSHR with the prominent aromatic residue on the surface of the TSHR "fitting" into the cavity on the K1-70 surface.

Recombinant K1-70 Fab

Table 17a shows that recombinant K1-70 Fab in *E. coli* culture supernatant had the ability to inhibit $^{125}$I-TSH binding to the TSHR. The inhibiting effect was complete at lower dilutions of the culture supernatants (91.9% at 1:2 dilution) while increasing dilutions of the supernatant cause dose dependent inhibiting effect (27.9% inhibition at 1:256 dilution) (Table 17a). The effect of recombinant K1-70 Fab on TSH mediated stimulation of cyclic AMP production in CHO cells expressing the TSHR is shown in Table 17b. Different dilutions of culture supernatants showed dose dependent inhibition of cyclic AMP stimulation; from 89.3% inhibition at 1:5 dilution to 39.7% inhibition at 1:40 dilution (Table 17b). Control culture supernatants from non-induced *E. coli* cultures did not produced detectable inhibition of TSH binding or inhibition of TSH mediated cyclic AMP stimulation (Tables 17a &b).

SUMMARY AND CONCLUSIONS

The experiments described above show that two monoclonal autoantibodies to the TSHR with very different biological activities (K1-18 stimulating and K1-70 blocking) can be isolated from a single preparation of a patient's lymphocytes. Consequently, the patient's immune system was producing both types of TSHR autoantibody ie stimulating type and blocking type at the same time. Once isolated (as described above) in the form of monoclonal autoantibodies, the properties of the two types of TSHR autoantibody can be investigated without interference from each other. The characteristics of the new human MAb with TSHR stimulating activity (K1-18) have been described and compared to the characteristics of some other known TSHR MAbs. Specifically of a stimulating human MAb (M22), a blocking human MAb (5C9), a blocking human Mab (K1-70), a blocking mouse MAb (9D33) and mouse stimulating MAbs (TSMAbs 1-7). Also the characteristics of the new human MAb with TSH antagonist activity (K1-70) have been described and compared to the characteristics of known MAbs. Specifically of a blocking human MAb (5C9), a blocking mouse MAb (9D33), a stimulating human MAb (M22), a stimulating human MAb (K1-18) and mouse stimulating MAbs (TSMAbs 1-7). It has been shown that the new human stimulating TSHR MAb K1-18 has properties similar to M22 in terms of:—inhibition of binding of labelled TSH to the TSHR, inhibition of binding of each other to the TSHR, inhibition of binding of blocking human MAbs (5C9 and K1-70) to the TSHR, inhibition of binding of mouse blocking and stimulating MAbs (9D33 and TSMAbs 1-7). Also the patient serum TRAbs inhibited binding of K1-18 to the TSHR. Furthermore, both M22 and K1-18 bind to the TSHR with a high affinity and are able to bind to a TSHR fragment consisting of amino acids 22-260 linked to alkaline phosphatase. Antibodies such as M22 and K1-18 have the ability to stimulate TSHR cyclic AMP activity although the potency of the two antibodies differs by about 1.5 fold. The studies show that the properties of TSHR stimulating autoantibodies are similar in different patients and they are representative of the properties of TSHR stimulating autoantibodies in all patients with Graves' disease studied so far. A summary of K1-18 characteristics is shown in Table 13a. Our experiments also showed that the new blocking type human MAb K1-70 (obtained from the same sample of lymphocytes as the stimulating MAb K1-18) has the ability to:—inhibit binding of labelled TSH to the TSHR, inhibit binding of human MAbs (M22, K1-18 and 5C9) to the TSHR, inhibit binding of mouse blocking and stimulating MAbs (9D33 and TSMAbs 1-7) to the TSHR.

Furthermore binding of K1-70 to the TSHR was inhibited by patient serum TRAbs. K1-70 showed potent TSH antagonist activity and the ability to block stimulation of the TSHR by all patient serum TRAbs tested. K1-70 was shown to be a more effective inhibitor of TSH binding to the TSHR than 5C9. K1-70 binds to the TSHR with a high affinity and is able to bind to the TSHR fragment of amino acids 22-260 linked to the alkaline phosphatase. Consequently, K1-70 has the characteristics of patient sera with blocking TRAbs including the high binding affinity for the TSHR, the ability to inhibit TSH and M22 binding to the TSHR and the ability to block ligand induced TSHR stimulation at low concentrations of antibody. However, K1-70 has no effect on TSHR constitutive activity while 5C9 does. A summary of K1-70 characteristics is shown in Table 13b. K1-18 ability to stimulate cyclic AMP activity in CHO cells expressing TSHRs was lost when TSHR was mutated at Glu157Ala, Lys183Ala, Tyr185Ala, Asp232Ala or Arg255Asp. K1-70 ability to block TSH mediated cyclic AMP activity in CHO cells expressing TSHRs was reduced in the case of TSHR mutations Lys58Ala, Ile60Ala, Arg109Ala, Lys183Ala, Lys250Ala and slightly reduced by the TSHR mutation Tyr82Ala. Both K1-18 and K1-70 as well as M22 reacted well with the TSHR fragment of 22-260 in an ELISA based on TSHR 260-AP. Furthermore a panel of patient serum TSHR autoantibodies reacted well with TSHR amino acids 22-260 in the same assay. Patient sera with either type of TRAb activities (stimulating and blocking) bound to TSHR260 in the ELISA. In addition, ELISA plate wells coated with the TSHR fragment of amino acids 22-260 bound M22-peroxidase (from RSR Ltd) well and this M22-peroxidase binding was inhibited by a panel of patient serum TSHR autoantibodies. This inhibition of M22-peroxidase binding by the patient serum TSHR autoantibodies was similar to inhibition of M22-peroxidase binding to full length TSHR. Surprisingly therefore the TSHR fragment of amino acids 22-260 (or perhaps a smaller fragment) appears to be sufficient for routine assays of TSHR autoantibodies. Furthermore, M22 also bound well to a longer fragment of the TSHR (TSHR LRD C-CAP). In stability studies, the ability of M22 to bind TSHR260, TSHR260-AP and TSHR LRD C-CAP after they had been pre-incubated at room temperature was greater than the full length TSHR preparations which had been pre-incubated under the same conditions. This indicates that TSHR260, TSHR260-AP and TSHR LRD C-CAP are more stable at room temperature compared to full length TSHR. The TSHR mutation Arg255Asp had no effect on binding of K1-70 IgG while K1-18 IgG (at lower concentrations ie 0.1 µg/mL and below) bound less effectively to the mutated receptor. The experiments with different patient serum TRAbs indicate that sera with TSHR stimulating activities can be differentiated from sera with TSHR blocking activities on the basis of differences in binding to the TSHR containing R255D mutation. Binding of patient sera with stimulating activities is affected by the mutation while binding of patient sera with blocking activities is affected less or not at all. The experiments provide nucleotide and amino acid sequences of K1-18 and K1-70. Although heavy chain V genes of K1-18, K1-70 are derived from the same germline which belongs to the same family as the other stimulating human MAb M22 heavy chain V genes they are all combined with D and J genes from different families; furthermore K1-18 uses the kappa light chain, whereas M22 and K1-70 use lambda light chains. 5C9 (the other blocking type human MAb) germline genes are different from M22, K1-18 and K1-70 except that 5C9 and K1-70 use J4 heavy chain genes. Amino acid sequences of the CDRs of stimulating MAbs (M22 and K1-18) and blocking MAbs (5C9 and K1-70) are essentially different in particular within the heavy and the light chains CDR3s. These observations indicate that each of the 4 human autoantibodies is derived from distinct germlines. Also different CDR sequences may show similar biological activities towards the TSHR. The X-ray diffraction data provide molecular details of K1-70 Fab structure including the topography of the antigen binding site. A recombinant K1-70 Fab produced by cloning and expression of the K1-70 HC (SEQ ID No 46) and K1-70 LC (SEQ ID No 63 with SEQ ID No 64) in *E. coli* showed the ability to inhibit $^{125}$I-labelled TSH binding to the TSHR and the ability to inhibit TSH mediated stimulation of TSHR cyclic AMP activity. Overall the results indicate that antibodies in accordance with the invention such as K1-18 and K1-70 show similar TSHR binding activity and similar biological effects on TSHR function as TSHR MAbs described previously (M22 and 5C9) and as TSHR autoantibodies found in different sera from patients with autoimmune thyroid disease.

TABLE 1a

Inhibition of $^{125}$I-TSH binding to TSHR coated tubes by K1-18 IgG and different TSHR monoclonal antibodies

| Test sample | Inhibition of binding (%) Dilutions in assay buffer (mean ± SD) | Inhibition of binding (%) Dilutions in HBD (mean ± SD) |
|---|---|---|
| K1-18 IgG | | |
| 100 µg/mL | 91.4 ± 0.7 | 95.9 ± 0.2 |
| 30 µg/mL | 89.5 ± 1.0 | 96.0 ± 0.3 |
| 10 µg/mL | 91.1 ± 1.1 | 96.0 ± 0.5 |
| 3 µg/mL | 89.1 ± 0.4 | 95.3 ± 0.5 |
| 1 µg/mL | 89.3 ± 1.3 | 94.0 ± 0.7 |
| 0.3 µg/mL | 89.7 ± 0.7 | 82.6 ± 1.0 |
| 0.1 µg/mL | 78.5 ± 0.6 | 62.0 ± 1.6 |
| 0.03 µg/mL | 45.2 ± 2.3 | 26.6 ± 1.2 |
| 0.01 µg/mL | 21.1 ± 2.3 | 9.3 ± 2.1 |
| 0.003 µg/mL | 0.5* | 11.4 ± 3.0 |
| 0.001 µg/mL | −4.6* | 1.6 ± 3.2 |
| M22 IgG | | |
| 100 µg/mL | 91.4 ± 1.8 | 96.5 ± 0.1 |
| 30 µg/mL | 89.2 ± 0.5 | 96.1 ± 0.5 |
| 10 µg/mL | 89.3 ± 0.6 | 96.1 ± 0.5 |
| 3 µg/mL | 89.6 ± 0.4 | 96.0 ± 0.6 |
| 1 µg/mL | 89.9 ± 1.7 | 95.5 ± 0.3 |
| 0.3 µg/mL | 88.6 ± 1.2 | 89.9 ± 0.2 |
| 0.1 µg/mL | 87.2 ± 1.2 | 76.1 ± 2.2 |
| 0.03 µg/mL | 58.3 ± 1.5 | 41.6 ± 3.5 |
| 0.01 µg/mL | 23.4 ± 3.4 | 18.0 ± 0.8 |
| 0.003 µg/mL | 7.1* | 11.1 ± 2.9 |
| 0.001 µg/mL | 1.5* | 10.6 ± 8.7 |
| 5C9 IgG | | |
| 100 µg/mL | 82.9 ± 1.0 | 35.3 ± 2.8 |
| 10 µg/mL | 40.5 ± 0.3 | 40.9 ± 1.1 |
| 1 µg/mL | 23.5 ± 2.9 | 19.7 ± 1.2 |
| 0.1 µg/mL | 21.3* | 16.2 ± 4.3 |
| 0.01 µg/mL | 15.9* | 4.1 ± 2.2 |
| TSMAb 1 IgG | | |
| 100 µg/mL | 61.1 ± 4.1 | 54.1 ± 4.1 |
| 10 µg/mL | 48.1 ± 1.7 | 43.4 ± 1.1 |
| 1 µg/mL | 29.3 ± 1.5 | 26.5 ± 0.5 |
| 0.1 µg/mL | 11.0 ± 1.7 | 6.8 ± 1.7 |
| 0.01 µg/mL | 2.6 ± 2.1 | 2.4* |

TABLE 1a-continued

Inhibition of $^{125}$I-TSH binding to TSHR coated tubes by K1-18 IgG and different TSHR monoclonal antibodies

| Test sample | Inhibition of binding (%) Dilutions in assay buffer (mean ± SD) | Inhibition of binding (%) Dilutions in HBD (mean ± SD) |
|---|---|---|
| TSMAb 2 IgG | | |
| 100 μg/mL | 77.6 ± 7.7 | 48.0 ± 4.4 |
| 10 μg/mL | 37.7 ± 2.6 | 39.0 ± 0.5 |
| 1 μg/mL | 29.1 ± 2.5 | 33.6* |
| 0.1 μg/mL | 23.4 ± 2.7 | 15.9 ± 0.8 |
| 0.01 μg/mL | 1.6 ± 1.5 | 0.7 ± 1.7 |
| TSMAb 3 IgG | | |
| 100 μg/mL | 81.1 ± 2.9 | 54.3 ± 3.3 |
| 10 μg/mL | 58.1 ± 1.1 | 44.7 ± 2.8 |
| 1 μg/mL | 35.2 ± 1.5 | 37.7 ± 0.7 |
| 0.1 μg/mL | 30.7 ± 0.8 | 15.7 ± 4.9 |
| 0.01 μg/mL | 9.0 ± 0.5 | −2.5 ± 4.1 |
| TSMAb 4 IgG | | |
| 100 μg/mL | 57.2 ± 4.7 | 63.5 ± 5.6 |
| 10 μg/mL | 40.8 ± 1.3 | 56.5 ± 1.2 |
| 1 μg/mL | 39.8 ± 0.8 | 53.9 ± 2.3 |
| 0.1 μg/mL | 42.8 ± 1.4 | 32.1 ± 3.3 |
| 0.01 μg/mL | 33.3* | 8.6 ± 7.2 |
| TSMAb 5 IgG | | |
| 100 μg/mL | 87.8 ± 1.0 | 61.9 ± 2.8 |
| 10 μg/mL | 64.6 ± 1.1 | 56.9 ± 1.9 |
| 1 μg/mL | 43.9 ± 1.1 | 53.8 ± 2.6 |
| 0.1 μg/mL | 39.7 ± 0.9 | 38.6 ± 2.4 |
| 0.01 μg/mL | 15.9 ± 9.4 | 7.5 ± 0.6 |
| TSMAb 6 IgG | | |
| 100 μg/mL | 68.6 ± 2.5 | 46.9 ± 2.6 |
| 10 μg/mL | 32.8 ± 0.9 | 40.8 ± 2.3 |
| 1 μg/mL | 28.9 ± 3.0 | 40.2 ± 0.9 |
| 0.1 μg/mL | 24.6 ± 0.6 | 30.2 ± 1.3 |
| 0.01 μg/mL | 9.5 ± 5.8 | 19.6 ± 0.6 |
| TSMAb 7 IgG | | |
| 100 μg/mL | 69.4 ± 3.4 | 45.9 ± 1.1 |
| 10 μg/mL | 43.9 ± 0.6 | 42.0 ± 0.7 |
| 1 μg/mL | 28.5 ± 4.8 | 37.7 ± 1.6 |
| 0.1 μg/mL | 19.8 ± 1.5 | 19.9 ± 1.5 |
| 0.01 μg/mL | −3.1 ± 5.2 | 8.0 ± 2.1 |
| 9D33 IgG | | |
| 100 μg/mL | 75.6 ± 1.2 | 67.4 ± 4.6 |
| 10 μg/mL | 58.7 ± 4.1 | 60.5 ± 2.6 |
| 1 μg/mL | 50.9 ± 2.9 | 50.8 ± 2.2 |
| 0.1 μg/mL | 48.3 ± 2.6 | 30.5 ± 2.7 |
| 0.01 μg/mL | 15.8 ± 3.0 | 3.6 ± 3.3 |
| 5B3 IgG | | |
| 100 μg/mL | 22.4 ± 1.5 | −3.9 ± 5.7 |
| 10 μg/mL | −5.7 ± 2.1 | −1.9 ± 1.5 |
| 1 μg/mL | −1.7 ± 5.3 | −4.9 ± 3.4 |
| 0.1 μg/mL | −5.0 ± 3.7 | 4.4 ± 2.5 |
| 0.01 μg/mL | −5.8* | 2.6* |

Results shown are mean ± SD of triplicate determinations.
*mean of duplicate determinations.
HBD = pool of healthy blood donor sera. 5B3 is a human MAb to glutamic acid decarboxylase (negative control).
$^{125}$I-TSH binding in the presence of assay buffer was 11%.
$^{125}$I-TSH binding in the presence of HBD pool was 11.5%.
Assay buffer is 50 mmol/L NaCl, 10 mmol/L Tris pH 7.8, 0.1% Triton X-100.

TABLE 1b

Inhibition of $^{125}$I-TSH binding to TSHR coated tubes by K1-70 IgG and K1-70 Fab and by various TSHR monoclonal antibodies

| Test sample | Inhibition of binding (%) Dilutions in assay buffer (mean ± SD) | Inhibition of binding (%) Dilutions in HBD (mean ± SD) |
|---|---|---|
| K1-70 IgG | | |
| 100 μg/mL | 94.6 ± 0.2 | 95.9 ± 0.8 |
| 30 μg/mL | 93.3 ± 0.4 | 94.9 ± 0.4 |
| 10 μg/mL | 92.7 ± 0.8 | 93.9 ± 1.4 |
| 3 μg/mL | 91.8 ± 0.5 | 94.1 ± 0.4 |
| 1 μg/mL | 92.3 ± 0.4 | 91.9 ± 0.9 |
| 0.3 μg/mL | 91.3 ± 1.1 | 83.5 ± 1.3 |
| 0.1 μg/mL | 86.9 ± 1.1 | 50.0 ± 1.6 |
| 0.03 μg/mL | 50.5 ± 2.0 | 13.5 ± 2.3 |
| 0.01 μg/mL | 8.3 ± 2.8 | −7.0 ± 1.9 |
| 0.003 μg/mL | −3.7 ± 1.6 | 0.8 ± 4.7 |
| 0.001 μg/mL | −6.1 ± 5.5 | −3.0 ± 2.2 |
| K1-70 Fab | | |
| 100 μg/mL | 87.3 ± 0.9 | 93.1 ± 1.2 |
| 30 μg/mL | 89.0 ± 0.1 | 92.5 ± 0.8 |
| 10 μg/mL | 87.2 ± 0.9 | 91.2 ± 0.2 |
| 3 μg/mL | 88.2 ± 0.4 | 91.6 ± 0.5 |
| 1 μg/mL | 88.1 ± 0.7 | 91.8 ± 1.3 |
| 0.3 μg/mL | 87.5 ± 0.3 | 88.1 ± 2.3 |
| 0.1 μg/mL | 85.0 ± 0.4 | 71.6 ± .3.1 |
| 0.03 μg/mL | 70.3 ± 0.6 | 40.7 ± 0.6 |
| 0.01 μg/mL | 24.8 ± 1.3 | 18.9 ± 0.5 |
| 0.003 μg/mL | 2.7 ± 2.8 | *−1.7 |
| 0.001 μg/mL | −2.6 ± 3.5 | 7.2 ± 2.8 |
| M22 IgG | | |
| 100 μg/mL | 88.5 ± 0.9 | 96.2 ± 0.5 |
| 30 μg/mL | 90.0 ± 2.4 | 94.3 ± 0.3 |
| 10 μg/mL | 87.5 ± 1.4 | 93.4 ± 1.6 |
| 3 μg/mL | 89.5 ± 2.5 | 94.6 ± 0.7 |
| 1 μg/mL | 91.6 ± 0.8 | 92.6 ± 1.6 |
| 0.3 μg/mL | 89.9 ± 0.6 | 82.2 ± 2.0 |
| 0.1 μg/mL | 84.3 ± 0.9 | 62.1 ± 1.7 |
| 0.03 μg/mL | 48.3 ± 0.9 | 31.4 ± 3.8 |
| 0.01 μg/mL | 7.5 ± 1.1 | −0.3 ± 5.5 |
| 0.003 μg/mL | −1.5 ± 5.5 | −1.8 ± 4.0 |
| 0.001 μg/mL | −11.0 ± 0.7 | 1.2 ± 6.9 |
| M22 Fab | | |
| 100 μg/mL | 91.3 ± 0.1 | 94.4 ± 0.8 |
| 30 μg/mL | 89.9 ± 3.1 | 93.5 ± 0.7 |
| 10 μg/mL | 90.1 ± 1.6 | 93.9 ± 0.7 |
| 3 μg/mL | 87.5 ± 1.2 | 93.4 ± 0.5 |
| 1 μg/mL | 89.2 ± 0.4 | 92.5 ± 0.5 |
| 0.3 μg/mL | 87.3 ± 0.7 | 90.0 ± 0.2 |
| 0.1 μg/mL | 86.7 ± 0.5 | 77.1 ± 2.9 |
| 0.03 μg/mL | 71.4 ± 1.4 | 35.3 ± 3.3 |
| 0.01 μg/mL | 27.1 ± 2.7 | 8.7 ± 4.9 |
| 0.003 μg/mL | 1.1 ± 6.8 | −7.9 ± 0.3 |
| 0.001 μg/mL | −9.3 ± 2.1 | −11.2 ± 1.9 |
| 5C9 IgG | | |
| 100 μg/mL | 92.5 ± 0.4 | 59.2 ± 5.3 |
| 10 μg/mL | 76.7 ± 1.3 | 39.9 ± 5.6 |
| 1 μg/mL | 38.7 ± 0.7 | 24.8 ± 0.8 |
| 0.1 μg/mL | 24.4 ± 4.5 | 7.0 ± 2.4 |
| 0.01 μg/mL | 8.3 ± 3.3 | −5.5 ± 4.8 |
| 0.001 μg/mL | −11.2 ± 2.9 | −8.0 ± 1.1 |

See legend to Table 1a for details.
$^{125}$I-TSH binding in the presence of assay buffer was 13.4%.
$^{125}$I-TSH binding in the presence of HBD pool was 11.5%.

TABLE 2a

Inhibition of $^{125}$I-TSH binding to TSHR coated tubes by K1 donor serum and IgG and by K1-18 IgG and Fab

| Test sample | Inhibition of binding (%) Dilutions in assay buffer (mean ± SD) | Inhibition of binding (%) Dilutions in HBD (mean ± SD) |
|---|---|---|
| K1 donor serum dilution | | |
| 1/10 | 94.7 ± 0.9 | 81.1 ± 0.4 |
| 1/20 | 89.3 ± 0.7 | 62.4 ± 3.5 |
| 1/40 | 67.0 ± 1.0 | 39.0 ± 0.9 |
| 1/80 | 34.0 ± 3.8 | 19.8 ± 1.9 |
| 1/160 | 13.1 ± 3.1 | 9.1 ± 0.8 |
| 1/320 | 6.6 ± 0.9 | 2.17 ± 1.5 |
| K1 donor serum IgG | | |
| 1 mg/mL | 89.6 ± 0.8 | 76.5 ± 1.5 |
| 0.5 mg/mL | 79.4 ± 0.7 | 52.3 ± 0.7 |
| 0.25 mg/mL | 52.1 ± 2.0 | 27.8 ± 0.4 |
| 0.125 mg/mL | 29.5 ± 2.6 | 13.7 ± 1.3 |
| K1-18 IgG | | |
| 100 µg/mL | 93.7 ± 0.6 | 95.7 ± 0.6 |
| 30 µg/mL | 93.3 ± 0.5 | 95.3 ± 0.0 |
| 10 µg/mL | 93.3 ± 1.1 | 95.3 ± 0.4 |
| 3 µg/mL | 94.2 ± 1.4 | 94.3 ± 0.6 |
| 1 µg/mL | 93.3 ± 1.0 | 92.0 ± 0.4 |
| 0.3 µg/mL | 90.9 ± 1.3 | 80.4 ± 2.2 |
| 0.1 µg/mL | 78.0 ± 0.4 | 54.0 ± 2.4 |
| 0.03 µg/mL | 38.8 ± 2.2 | 25.5 ± 3.2 |
| 0.01 µg/mL | 14.6 ± 5.2 | 11.8 ± 6.1 |
| 0.003 µg/mL | 0.2 ± 0.2 | 2.4 ± 4.2 |
| 0.001 µg/mL | 0.5 ± 0.9 | 0.9 ± 1.5 |
| K1-18 Fab | | |
| 100 µg/mL | 88.9 ± 0.8 | 81.7 ± 1.6 |
| 30 µg/mL | 85.6 ± 0.3 | 81.3 ± 1.4 |
| 10 µg/mL | 82.9 ± 1.1 | 82.2 ± 0.9 |
| 3 µg/mL | 79.3 ± 0.9 | 80.9 ± 2.1 |
| 1 µg/mL | 77.0 ± 1.8 | 76.8 ± 1.6 |
| 0.3 µg/mL | 72.4 ± 1.1 | 60.6 ± 1.3 |
| 0.1 µg/mL | 56.2 ± 4.2 | 35.7 ± 3.3 |
| 0.03 µg/mL | 25.6 ± 4.9 | 15.9 ± 4.6 |
| 0.01 µg/mL | 7.4 ± 4.8 | 5.6 ± 7.3 |
| 0.003 µg/mL | 2.4 ± 3.9 | 0.5 ± 0.86 |
| 0.001 µg/mL | 0.0 ± 0.0 | 2.1 ± 2.2 |

See legend to Table 1a for details.
$^{125}$I-TSH binding in the presence of assay buffer was 10.8%.
$^{125}$I-TSH binding in the presence of HBD pool was 12.4%.

TABLE 2b

Inhibition of $^{125}$I-TSH binding to TSHR coated tubes by WHO reference preparation NIBSC 90/672 and by K1-18 IgG and Fab preparations

| Test sample | Samples diluted in serum Inhibition of binding (%) (mean ± SD) | units/L | units/mg | mean units/mg | Samples diluted in assay buffer Inhibition of binding (%) (mean ± SD) | units/L | units/mg | mean units/mg |
|---|---|---|---|---|---|---|---|---|
| NIBSC 90/672 | | | | | | | | |
| 0.125 units/L | 0 | | | | 0 | | | |
| 0.25 units/L | 0 | | | | 0 | | | |
| 0.5 units/L | 5.6 ± 2.5 | | | | 3.1 ± 1.6 | | | |
| 1.0 units/L | 8.1 ± 5.8 | | | | 14.0 ± 2.6 | | | |
| 2.0 units/L | 18.2 ± 1.2 | | | | 26.2 ± 4.2 | | | |
| 4.0 units/L | 34.8 ± 0.6 | | | | 49.0 ± 4.3 | | | |
| 8.0 units/L | 65.3 ± 0.3 | | | | 62.7 ± 0.2 | | | |
| 40.0 units/L | 90.9 ± 0.5 | | | | 91.0 ± 0.6 | | | |
| M22 IgG | | | | | | | | |
| 0.3 ng/mL | 0 | | | | 0 | | | |
| 1 ng/mL | 0 | | | | 4.5 ± 1.6 | | | |
| 3 ng/mL | 0 | | | | 10.9 ± 3.5 | | | |
| 10 ng/mL | 13.0 ± 1.51 | 1.5 | 150 | | 26.4 ± 0.1 | 2.5 | 250 | |
| 30 ng/mL | 37.6 ± 1.7 | 4.3 | 143 | 131 | 64.1 ± 3.2 | 8.6 | 287 | 266 |
| 100 ng/mL | 70.4 ± 1.1 | 9.9 | 99 | | 87.6 ± 0.6 | 26 | 260 | |
| 300 ng/mL | 87.9 ± 0.1 | | | | 87.6 ± 0.5 | | | |
| 1000 ng/mL | 92.5 ± 0.5 | | | | 91.2 ± 0.3 | | | |
| K1-18 IgG | | | | | | | | |
| 0.3 ng/mL | 0 | | | | 0.6 ± 1.9 | | | |
| 1 ng/mL | 0 | | | | 4.5 ± 2.9 | | | |
| 3 ng/mL | 0 | | | | 7.8 ± 2.1 | | | |
| 10 ng/mL | 6.4 ± 0.8 | | | | 21.4 ± 1.8 | 1.52 | 152 | |
| 30 ng/mL | 24.7 ± 4.7 | 2.7 | 90 | | 49.9 ± 4.2 | 5.3 | 177 | 181 |
| 100 ng/mL | 60.2 ± 1.7 | 7 | 70 | 69 | 84.3 ± 0.9 | 21.5 | 215 | |
| 300 ng/mL | 79.9 ± 1.7 | 14.5 | 48 | | 87.8 ± 1.1 | | | |
| 1000 ng/mL | 90.7 ± 0.8 | | | | 90.1 ± 0.3 | | | |
| K1-18 Fab | | | | | | | | |
| 0.3 ng/mL | 0 | | | | 2.0 ± 0.9 | | | |
| 1 ng/mL | 0 | | | | 5.7 ± 3.0 | | | |
| 3 ng/mL | 0 | | | | 7.8 ± 5.4 | | | |

TABLE 2b-continued

Inhibition of $^{125}$I-TSH binding to TSHR coated tubes by WHO reference preparation NIBSC 90/672 and by K1-18 IgG and Fab preparations

| | Samples diluted in serum | | | | Samples diluted in assay buffer | | | |
|---|---|---|---|---|---|---|---|---|
| Test sample | Inhibition of binding (%) (mean ± SD) | units/L | units/mg | mean units/mg | Inhibition of binding (%) (mean ± SD) | units/L | units/mg | mean units/mg |
| 10 ng/mL | 2.6 ± 3.2 | | | | 16.6 ± 1.9 | 1.2 | 120 | |
| 30 ng/mL | 17.1 ± 1.0 | 1.9 | 63 | | 34.5 ± 1.1 | 3.12 | 104 | 86 |
| 100 ng/mL | 41.0 ± 2.4 | 4.6 | 46 | 46 | 58.7 ± 0.7 | 7.1 | 71 | |
| 300 ng/mL | 66.6 ± 0.9 | 8.4 | 28 | | 70.8 ± 2.5 | 15 | 50 | |
| 1000 ng/mL | 74.4 ± 4.3 | | | | 75.7 ± 0.8 | | | |
| 4B4 IgG | | | | | | | | |
| 0.3 ng/mL | 0 | | | | 5.0 ± 3.5 | | | |
| 3 ng/mL | 0 | | | | 0.8 ± 1.9 | | | |
| 30 ng/mL | 0 | | | | 1.9 ± 0.8 | | | |
| 300 ng/mL | 0 | | | | 0.7 ± 2.0 | | | |
| 4B4 Fab | | | | | | | | |
| 0.3 ng/mL | 0 | | | | 10.7 ± 3.9 | | | |
| 3 ng/mL | 0 | | | | 8.9 ± 2.5 | | | |
| 30 ng/mL | 0 | | | | 0 | | | |
| 300 ng/mL | 0 | | | | 0.5 ± 0.5 | | | |

See legend for Table 1a for details. $^{125}$I-TSH binding in the presence of assay buffer was 17.7%. $^{125}$I-TSH binding in the presence of HBD pool was 16.0%.

TABLE 2c

Inhibition of $^{125}$I-TSH binding to TSHR coated tubes by lymphocyte donor serum IgG

| | Samples diluted in serum | | | | Samples diluted in assay buffer | | | |
|---|---|---|---|---|---|---|---|---|
| Test sample | Inhibition of binding (%) (mean ± SD) | units/L | units/mg (or U/mL in undil serum) | mean units/mg (or mean units/mL) | Inhibition of binding (%) (mean ± SD) | units/L | units/mg (or U/mL in undil serum) | mean units/mg (or mean units/mL) |
| NIBSC 90/672 | | | | | | | | |
| 0.125 units/L | 2.4 ± 0.7 | | | | 5.1 ± 4.2 | | | |
| 0.25 units/L | 3.5 ± 2.0 | | | | 0.9 ± 1.4 | | | |
| 0.5 units/L | 9.3 ± 2.7 | | | | 2.8 ± 2.2 | | | |
| 1 unit/L | 15.5 ± 1.7 | | | | 14.1 ± 2.7 | | | |
| 2 units/L | 22.9 ± 6.4 | | | | 27.2 ± 5.4 | | | |
| 4 units/L | 49.2 ± 1.2 | | | | 53.3 ± 2.1 | | | |
| 8 units/L | 63.2 ± 1.1 | | | | 62.2 ± 1.8 | | | |
| 40 units/L | 90.0 ± 0.1 | | | | 90.9 ± 1.0 | | | |
| Donor serum | | | | | | | | |
| diluted 160x | 3.5 ± 1.9 | | | | 5.3 ± 0.7 | | | |
| diluted 80x | 10.4 ± 1.0 | | | | 17.9 ± 2.9 | 1.25 | (0.1) | |
| diluted 40x | 23.3 ± 2.6 | 2 | (0.08) | (0.075) | 39.5 ± 1.3 | 2.8 | (0.112) | (0.144) |
| diluted 20x | 39.7 ± 4.4 | 3.3 | (0.07) | | 67.8 ± 1.6 | 11 | (0.22) | |
| Donor serum IgG | | | | | | | | |
| 0.01 mg/mL | 0 | | | | 5.1 ± 8.5 | | | |
| 0.03 mg/mL | 0.4 ± 2.7 | | | | 4.4 ± 2.7 | | | |
| 0.1 mg/mL | 13.5 ± 1.6 | 0.8 | 0.008 | | 19.8 ± 1.5 | 1.4 | 0.014 | |
| 0.3 mg/mL | 36.1 ± 3.0 | 3.0 | 0.010 | 0.011 | 60.6 ± 2.8 | 7 | 0.023 | 0.024 |
| 1 mg/mL | 72.3 ± 1.2 | 13.5 | 0.014 | | 87.2 ± 2.0 | 34 | 0.034 | |
| HBD | | | | | | | | |
| diluted 160x | 0 | | | | 0 | | | |
| diluted 80x | 0 | | | | 0 | | | |
| diluted 40x | 0 | | | | 0 | | | |
| diluted 20x | 0 | | | | 0 | | | |
| HBD IgG | | | | | | | | |
| 0.01 mg/mL | 0 | | | | 0 | | | |
| 0.1 mg/mL | 0 | | | | 0 | | | |
| 1 mg/mL | 0 | | | | 0 | | | |

TABLE 2c-continued

Inhibition of $^{125}$I-TSH binding to TSHR coated tubes by lymphocyte donor serum IgG

| Test sample | Samples diluted in serum | | | | Samples diluted in assay buffer | | | |
|---|---|---|---|---|---|---|---|---|
| | Inhibition of binding (%) (mean ± SD) | units/ L | units/ mg (or U/mL in undil serum) | mean units/ mg (or mean units/mL) | Inhibition of binding (%) (mean ± SD) | units/L | units/ mg (or U/mL in undil serum) | mean units/ mg (or mean units/mL) |
| K1-18 IgG | | | | | | | | |
| 0.3 ng/mL | 0 | | | | 0 | | | |
| 1 ng/mL | 0 | | | | 1.7 ± 4.4 | | | |
| 3 ng/mL | 0 | | | | 12.9 ± 7.0 | | | |
| 10 ng/mL | 6.0 ± 1.3 | | | | 20.5 ± 6.4 | 1.4 | 140 | |
| 30 ng/mL | 24.4 ± 1.8 | 2.1 | 70.0 | | 48.1 ± 5.5 | 3.5 | 116.7 | 150.4 |
| 100 ng/mL | 53.6 ± 0.6 | 5.0 | 50.0 | 63.3 | 79.7 ± 2.8 | 22.5 | 225 | |
| 300 ng/mL | 79.7 ± 0.6 | 21 | 70.0 | | 88.5 ± 2.6 | 36 | 120 | |
| 1000 ng/mL | 91.3 ± 0.7 | | | | 86.6 ± 5.3 | | | |
| K1-70 IgG | | | | | | | | |
| 0.3 ng/mL | 0 | | | | 0 | | | |
| 1 ng/mL | 0 | | | | 0 | | | |
| 3 ng/mL | 1.0 ± 5.9 | | | | 5.2 ± 4.0 | 0.56 | 186.7 | |
| 10 ng/mL | 14.9 ± 2.1 | 1.0 | 100 | | 21.1 ± 2.1 | 1.45 | 145 | 166.1 |
| 30 ng/mL | 36.4 ± 1.6 | 3.5 | 117 | 114 | 55.8 ± 0.6 | 5 | 166.7 | |
| 100 ng/mL | 71.9 ± 1.4 | 12.5 | 125 | | 89.8 ± 0.7 | | | |
| 300 ng/mL | 89.4 ± 0.6 | | | | 89.2 ± 0.6 | | | |
| 1000 ng/mL | 93.2 ± 0.7 | | | | 90.7 ± 1.4 | | | |

See legend to Table 1a for details. $^{125}$I-TSH binding in the presence of assay buffer was 12.6%. $^{125}$I-TSH binding in the presence of HBD pool was 12.9%.

TABLE 3a

Inhibition of TSH-biotin binding to TSHR coated ELISA plate wells by K1-18 IgG and different TSHR monoclonal antibodies

| Test sample | Inhibition of binding (%) Dilutions in assay buffer (mean ± SD) | Inhibition of binding (%) Dilutions in HBD (mean ± SD) |
|---|---|---|
| K1-18 IgG | | |
| 100 µg/mL | 96.9 ± 0.2 | 98.6 ± 0.1 |
| 30 µg/mL | 96.7 ± 0.2 | 98.4 ± 0.1 |
| 10 µg/mL | 96.2 ± 0.2 | 98.3 ± 0.1 |
| 3 µg/mL | 96.6 ± 0.2 | 98.2 ± 0.1 |
| 1 µg/mL | 96.6 ± 0.3 | 96.2 ± 0.2 |
| 0.3 µg/mL | 93.8 ± 0.4 | 90.7 ± 0.3 |
| 0.1 µg/mL | 76.3 ± 1.8 | 55.0 ± 0.2 |
| 0.03 µg/mL | 33.8 ± 1.2 | 31.9 ± 0.2 |
| 0.01 µg/mL | 12.9 ± 2.8 | 10.0 ± 0.8 |
| 0.003 µg/mL | 1.6 ± 0.5 | 1.4 ± 2.1 |
| 0.001 µg/mL | −4.2 ± 0.9 | −3.7 ± 1.1 |
| M22 IgG | | |
| 100 µg/mL | 96.8 ± 0.2 | 98.8 ± 0.1 |
| 30 µg/mL | 97.0 ± 0.1 | 98.8 ± 0.1 |
| 10 µg/mL | 97.0 ± 0.1 | 98.7 ± 0.1 |
| 3 µg/mL | 97.1 ± 0.1 | 98.6 ± 0.1 |
| 1 µg/mL | 97.0 ± 0.1 | 98.3 ± 0.0 |
| 0.3 µg/mL | 96.0 ± 0.2 | 95.5 ± 0.1 |
| 0.1 µg/mL | 88.3 ± 1.1 | 78.2 ± 0.7 |
| 0.03 µg/mL | 35.2 ± 2.4 | 33.3 ± 2.0 |
| 0.01 µg/mL | 14.9 ± 2.0 | 17.5 ± 2.0 |
| 0.003 µg/mL | 9.2 ± 3.4 | 12.1 ± 4.7 |
| 0.001 µg/mL | 0.4* | 7.8 ± 5.1 |
| 5C9 IgG | | |
| 100 µg/mL | 54.3 ± 1.3 | 37.1 ± 2.2 |
| 10 µg/mL | 37.8 ± 2.1 | 37.4 ± 0.9 |
| 1 µg/mL | 31.4 ± 1.9 | 28.5 ± 1.6 |
| 0.1 µg/mL | 26.1 ± 3.2 | 10.4 ± 1.6 |
| 0.01 µg/mL | 7.5 ± 0.9 | −2.6 ± 2.3 |
| TSMAb 1 IgG | | |
| 100 µg/mL | 84.3 ± 0.8 | 82.6 ± 2.2 |
| 10 µg/mL | 73.4 ± 2.8 | 74.6 ± 1.3 |
| 1 µg/mL | 44.3 ± 1.2 | 47.9* |
| 0.1 µg/mL | 3.8 ± 5.9 | 21.2 ± 1.5 |
| 0.01 µg/mL | −6.3 ± 3.3 | 12.8 ± 2.9 |
| TSMAb 2 IgG | | |
| 100 µg/mL | 85.2 ± 0.3 | 78.6 ± 1.4 |
| 10 µg/mL | 77.0 ± 0.7 | 75.1 ± 0.6 |
| 1 µg/mL | 67.3 ± 1.5 | 65.0 ± 1.0 |
| 0.1 µg/mL | 39.6 ± 0.8 | 29.1 ± 0.7 |
| 0.01 µg/mL | 8.8 ± 0.4 | 7.5 ± 0.1 |
| TSMAb 3 IgG | | |
| 100 µg/mL | 82.6 ± 0.1 | 78.6 ± 1.4 |
| 10 µg/mL | 77.0 ± 0.7 | 75.1 ± 0.6 |
| 1 µg/mL | 67.3 ± 1.5 | 65.0 ± 1.0 |
| 0.1 µg/mL | 39.6 ± 0.8 | 29.1 ± 0.7 |
| 0.01 µg/mL | 8.8 ± 0.4 | 7.5 ± 0.1 |
| TSMAb 4 IgG | | |
| 100 µg/mL | 73.1 ± 1.8 | 81.0 ± 1.5 |
| 10 µg/mL | 72.0 ± 0.5 | 79.6 ± 0.3 |
| 1 µg/mL | 73.1 ± 1.3 | 73.3 ± 1.3 |
| 0.1 µg/mL | 59.0 ± 1.7 | 50.1 ± 1.6 |
| 0.01 µg/mL | 18.9 ± 0.7 | 14.8 ± 3.8 |
| TSMAb 5 IgG | | |
| 100 µg/mL | 89.9 ± 0.3 | 85.2 ± 0.1 |
| 10 µg/mL | 85.8 ± 0.7 | 82.8 ± 0.4 |
| 1 µg/mL | 79.0 ± 2.2 | 79.2 ± 0.7 |
| 0.1 µg/mL | 60.9 ± 4.0 | 55.2 ± 0.9 |
| 0.01 µg/mL | 19.1 ± 3.1 | 19.3 ± 0.4 |

TABLE 3a-continued

Inhibition of TSH-biotin binding to TSHR coated ELISA plate wells by K1-18 IgG and different TSHR monoclonal antibodies

| Test sample | Inhibition of binding (%) Dilutions in assay buffer (mean ± SD) | Inhibition of binding (%) Dilutions in HBD (mean ± SD) |
|---|---|---|
| TSMAb 6 IgG | | |
| 100 μg/mL | 80.3 ± 1.0 | 77.8 ± 0.6 |
| 10 μg/mL | 73.0 ± 0.6 | 75.6 ± 0.4 |
| 1 μg/mL | 69.5 ± 2.5 | 73.6 ± 0.9 |
| 0.1 μg/mL | 58.5 ± 3.1 | 54.7 ± 2.3 |
| 0.01 μg/mL | 16.9 ± 3.1 | 19.2 ± 1.8 |
| TSMAb 7 IgG | | |
| 100 μg/mL | 83.1 ± 0.7 | 77.6 ± 0.5 |
| 10 μg/mL | 75.3 ± 0.2 | 73.4 ± 0.8 |
| 1 μg/mL | 62.8 ± 2.3 | 67.4 ± 1.9 |
| 0.1 μg/mL | 38.2 ± 7.1 | 36.8 ± 3.4 |
| 0.01 μg/mL | 14.1 ± 3.8 | 20.5 ± 1.7 |
| 9D33 IgG | | |
| 100 μg/mL | 86.8 ± 0.3 | 84.0 ± 0.3 |
| 10 μg/mL | 84.8 ± 0.2 | 83.2 ± 0.2 |
| 1 μg/mL | 81.8 ± 0.1 | 76.0 ± 0.4 |
| 0.1 μg/mL | 59.7 ± 0.5 | 39.0 ± 1.5 |
| 0.01 μg/mL | 15.3 ± 0.9 | 10.1 ± 4.2 |
| 5B3 IgG | | |
| 100 μg/mL | 1.3 ± 1.9 | −2.3 ± 2.2 |
| 10 μg/mL | −8.4 ± 2.3 | −1.6 ± 3.3 |
| 1 μg/mL | −8.3 ± 3.8 | −3.5 ± 0.5 |
| 0.1 μg/mL | −7.8 ± 10.0 | −1.2 ± 4.3 |
| 0.01 μg/mL | −5.9 ± 4.4 | −5.1 ± 3.3 |

Results shown are mean ± SD of triplicate determinations.
*mean of duplicate determinations HBD = pool of healthy blood donor sera. 5B3 is a human MAb to glutamic acid decarboxylase (negative control). Assay buffer is 50 mmol/L NaCl, 10 mmol/L Tris pH 7.8, 0.1% Triton X-100, 1 mg/mL BSA.

TABLE 3b

Inhibition of TSH-biotin binding to TSHR coated ELISA plate wells by K1-18 IgG and K1-18 Fab

| Test sample | Inhibition of binding (%) Dilutions in assay buffer (mean ± SD) | Inhibition of binding (%) Dilutions in HBD (mean ± SD) |
|---|---|---|
| K1-18 IgG | | |
| 100 μg/mL | 97.0 ± 0.2 | 98.1 ± 0.0 |
| 30 μg/mL | 97.0 ± 0.1 | 97.9 ± 0.2 |
| 10 μg/mL | 96.9 ± 0.1 | 97.9 ± 0.1 |
| 3 μg/mL | 96.8 ± 0.2 | 97.9 ± 0.0 |
| 1 μg/mL | 96.3 ± 0.1 | 96.8 ± 0.0 |
| 0.3 μg/mL | 94.2 ± 0.1 | 87.8 ± 0.1 |
| 0.1 μg/mL | 78.1 ± 0.3 | 61.8 ± 1.2 |
| 0.03 μg/mL | 34.9 ± 0.3 | 26.3 ± 1.1 |
| 0.01 μg/mL | 13.7 ± 0.4 | 8.2 ± 1.2 |
| 0.003 μg/mL | 8.5 ± 1.1 | 3.0 ± 2.9 |
| 0.001 μg/mL | 0.8 ± 2.6 | −1.9 ± 0.1 |
| K1-18 Fab | | |
| 100 μg/mL | 93.8 ± 0.2 | 95.6 ± 0.1 |
| 30 μg/mL | 93.6 ± 0.2 | 95.6 ± 0.1 |
| 10 μg/mL | 93.3 ± 0.1 | 95.6 ± 0.3 |
| 3 μg/mL | 92.9 ± 0.6 | 95.3 ± 0.2 |
| 1 μg/mL | 91.2 ± 0.2 | 92.9 ± 0.4 |
| 0.3 μg/mL | 85.1 ± 0.4 | 80.3 ± 0.2 |
| 0.1 μg/mL | 61.7 ± 1.6 | 47.7 ± 0.7 |
| 0.03 μg/mL | 28.9 ± 2.6 | 18.2 ± 1.6 |
| 0.01 μg/mL | 10.5 ± 3.0 | 5.7* |
| 0.003 μg/mL | 5.1 ± 0.9 | 3.1 ± 4.7 |
| 0.001 μg/mL | −0.1 ± 2.3 | 0.3 ± 2.2 |

TABLE 3b-continued

Inhibition of TSH-biotin binding to TSHR coated ELISA plate wells by K1-18 IgG and K1-18 Fab

| Test sample | Inhibition of binding (%) Dilutions in assay buffer (mean ± SD) | Inhibition of binding (%) Dilutions in HBD (mean ± SD) |
|---|---|---|
| M22 Fab | | |
| 0.1 μg/mL | 92.9 ± 0.3 | 89.7 ± 0.5 |
| 0.03 μg/mL | 57.0 ± 1.5 | 49.9 ± 2.2 |
| 0.01 μg/mL | 18.6 ± 3.0 | 16.3 ± 3.2 |
| 0.003 μg/mL | 5.3 ± 1.8 | 5.4 ± 5.6 |
| 0.001 μg/mL | −0.1 ± 0.5 | −1.4 ± 7.0 |

See legend to Table 3a for details. Results of negative control MAb (5B3 IgG) are shown in Table 3a.

TABLE 3c

Inhibition of TSH-biotin binding to TSHR coated plate wells by K1-18 IgG (effect of different assay conditions)

| Test sample | % Inhibition (mean ± SD) Dilutions in assay buffer | % Inhibition (mean ± SD) Dilutions in HBD | % Inhibition (mean ± SD) Dilutions in assay buffer + 100 μg/mL 5B3 IgG |
|---|---|---|---|
| K1-18 IgG | | | |
| 100 μg/mL | 96.9 ± 0.2 | 98.6 ± 0.1 | 96.7 ± 0.1 |
| 30 μg/mL | 96.7 ± 0.2 | 98.4 ± 0.1 | 96.7 ± 0.2 |
| 10 μg/mL | 96.2 ± 0.2 | 98.3 ± 0.1 | 96.6 ± 0.1 |
| 3 μg/mL | 96.6 ± 0.2 | 98.2 ± 0.1 | 96.6 ± 0.1 |
| 1 μg/mL | 96.6 ± 0.3 | 96.2 ± 0.2 | 96.4 ± 0.0 |
| 0.3 μg/mL | 93.8 ± 0.4 | 90.7 ± 0.3 | 94.8 ± 0.1 |
| 0.1 μg/mL | 76.3 ± 1.8 | 55.0 ± 0.2 | 82.8 ± 0.4 |
| 0.03 μg/mL | 33.8 ± 1.2 | 31.9 ± 0.2 | 45.6 ± 1.1 |
| 0.01 μg/mL | 12.9 ± 2.8 | 10.0 ± 0.8 | 17.6 ± 4.9 |
| 0.003 μg/mL | 1.6 ± 0.5 | 1.4 ± 2.1 | 4.6 ± 1.3 |
| 0.001 μg/mL | −4.2 ± 0.9 | −3.7 ± 1.1 | −4.0 ± 5.2 |
| M22 IgG | | | |
| 100 μg/mL | 96.8 ± 0.2 | 98.8 ± 0.1 | 97.2 ± 0.9 |
| 30 μg/mL | 97.0 ± 0.1 | 98.8 ± 0.1 | 97.0 ± 0.1 |
| 10 μg/mL | 97.0 ± 0.1 | 98.7 ± 0.1 | 97.0 ± 0.0 |
| 3 μg/mL | 97.1 ± 0.1 | 98.6 ± 0.1 | 96.9 ± 0.0 |
| 1 μg/mL | 97.0 ± 0.1 | 98.3 ± 0.0 | 96.8 ± 0.0 |
| 0.3 μg/mL | 96.0 ± 0.2 | 95.5 ± 0.1 | 96.4 ± 0.0 |
| 0.1 μg/mL | 88.3 ± 1.1 | 78.2 ± 0.7 | 91.2 ± 0.1 |
| 0.03 μg/mL | 35.2 ± 2.4 | 33.3 ± 2.0 | 43.6 ± 3.4 |
| 0.01 μg/mL | 14.9 ± 2.0 | 17.5 ± 2.0 | 12.9 ± 2.0 |
| 0.003 μg/mL | 9.2 ± 3.4 | 12.1 ± 4.7 | −0.5 ± 5.1 |
| 0.001 μg/mL | 0.4* | 7.8 ± 5.1 | −7.7 ± 5.8 |
| 5C9 IgG | | | |
| 100 μg/mL | 91.2 ± 0.8 | 48.6 ± 1.8 | 92.3 ± 0.3 |
| 10 μg/mL | 58.2 ± 0.5 | 42.6 ± 4.6 | 63.9 ± 0.8 |
| 1 μg/mL | 42.9 ± 1.6 | 35.7 ± 4.0 | 46.7 ± 1.7 |
| 0.1 μg/mL | 34.9 ± 4.0 | 21.6 ± 4.7 | 36.3 ± 2.0 |
| 0.01 μg/mL | 16.1 ± 2.9 | 7.5 ± 5.4 | 20.7 ± 2.9 |
| 5B3 IgG | | | |
| 100 μg/mL | 8.3 ± 2.4 | 10.9 ± 2.9 | 1.1 ± 3.6 |
| 10 μg/mL | 0.9 ± 0.6 | 11.6 ± 3.3 | −4.8 ± 1.8 |
| 1 μg/mL | −1.0 ± 0.2 | 8.0 ± 1.7 | −4.8 ± 3.2 |
| 0.1 μg/mL | −2.0 ± 0.7 | 8.6 ± 1.9 | −6.4 ± 2.6 |

See legend to Table 3a for details.

TABLE 3d

Inhibition of TSH-biotin binding to TSHR coated plate wells by K1-70 IgG and K1-70 Fab

| Test sample | Inhibition of binding (%) Dilutions in assay buffer (mean ± SD) | Inhibition of binding (%) Dilutions in HBD (mean ± SD) |
|---|---|---|
| K1-70 IgG | | |
| 100 μg/mL | 97.2 ± 0.2 | 98.2 ± 0.1 |
| 30 μg/mL | 97.2 ± 0.1 | 98.2 ± 0.1 |
| 10 μg/mL | 97.3 ± 0.1 | 97.9 ± 0 |
| 3 μg/mL | 97.2 ± 0.2 | 97.8 ± 0.1 |
| 1 μg/mL | 97.3 ± 0.1 | 97.4 ± 0.2 |
| 0.3 μg/mL | 97.0 ± 0.1 | 93.8 ± 0.1 |
| 0.1 μg/mL | 91.3 ± 0.8 | 74.1 ± 0.4 |
| 0.03 μg/mL | 45.0 ± 3.1 | 35.0 ± 1.0 |
| 0.01 μg/mL | 10.7 ± 0.7 | 13.6 ± 1.4 |
| 0.003 μg/mL | −1.7 ± 2.6 | 12.1 ± 2.8 |
| 0.001 μg/mL | −0.1 ± 3.9 | 3.5 ± 1.8 |
| K1-70 Fab | | |
| 100 μg/mL | 96.5 ± 0.2 | 97.3 ± 0.1 |
| 30 μg/mL | 96.4 ± 0 | 97.4 ± 0.2 |
| 10 μg/mL | 96.3 ± 0.1 | 97.3 ± 0 |
| 3 μg/mL | 97.3 ± 0.2 | 97.3 ± 0.1 |
| 1 μg/mL | 96.2 ± 0.1 | 96.9 ± 0.1 |
| 0.3 μg/mL | 95.8 ± 0.1 | 95.8 ± 0.7 |
| 0.1 μg/mL | 94.2 ± 0.6 | 88.3 ± 0.3 |
| 0.03 μg/mL | 57.6 ± 1.2 | 55.5 ± 1.5 |
| 0.01 μg/mL | 23.4 ± 3.1 | 18.2 ± 0.6 |
| 0.003 μg/mL | 18.3 ± 0.6 | 9.2 ± 5.6 |
| 0.001 μg/mL | −3.2 ± 3.3 | 4.8 ± 4.7 |

See legend to Table 3a for details. Results of negative control MAb (5B3 IgG) are shown in Table 3a.

TABLE 4a

Inhibition of M22-peroxidase binding to TSHR coated ELISA plate wells by K1-18 IgG and different TSHR monoclonal antibodies

| Test sample | Inhibition of binding (%) Dilutions in assay buffer (mean ± SD) | Inhibition of binding (%) Dilutions in HBD (mean ± SD) |
|---|---|---|
| K1-18 IgG | | |
| 100 μg/mL | 98.4 ± 0.1 | 98.0 ± 0.1 |
| 30 μg/mL | 98.2 ± 0.1 | 97.8 ± 0.1 |
| 10 μg/mL | 98.2 ± 0.1 | 97.6 ± 0.2 |
| 3 μg/mL | 98.1 ± 0.1 | 97.2 ± 0.1 |
| 1 μg/mL | 97.2 ± 0.3 | 94.5 ± 0.0 |
| 0.3 μg/mL | 92.1 ± 0.7 | 81.6 ± 0.5 |
| 0.1 μg/mL | 73.9 ± 7.1 | 49.8 ± 0.6 |
| 0.03 μg/mL | 29.9 ± 5.3 | 21.0 ± 1.3 |
| 0.01 μg/mL | 9.1 ± 3.7 | 1.2 ± 4.6 |
| 0.003 μg/mL | −1.7 ± 4.0 | 0.4 ± 4.3 |
| 0.001 μg/mL | −5.2 ± 4.7 | −0.0 ± 2.0 |
| M22 IgG | | |
| 100 μg/mL | 98.9 ± 0.1 | 98.6 ± 0.1 |
| 30 μg/mL | 98.6 ± 0.1 | 98.4 ± 0.0 |
| 10 μg/mL | 98.6 ± 0.1 | 98.4 ± 0.1 |
| 3 μg/mL | 98.4 ± 0.1 | 98.0 ± 0.2 |
| 1 μg/mL | 98.3 ± 0.0 | 97.4 ± 0.1 |
| 0.3 μg/mL | 96.7 ± 0.3 | 93.2 ± 0.3 |
| 0.1 μg/mL | 90.6 ± 0.9 | 79.4 ± 0.5 |
| 0.03 μg/mL | 66.0 ± 2.1 | 51.0 ± 2.4 |
| 0.01 μg/mL | 29.5 ± 0.9 | 22.7 ± 3.7 |
| 0.003 μg/mL | 5.7 ± 1.4 | 8.8 ± 4.4 |
| 0.001 μg/mL | 2.0 ± 4.1 | 2.6 ± 3.4 |
| 5C9 IgG | | |
| 100 μg/mL | 24.6 ± 1.3 | 19.6 ± 5.3 |
| 10 μg/mL | 13.2 ± 2.6 | 13.0 ± 2.6 |
| 1 μg/mL | 12.1 ± 2.1 | 7.8 ± 2.4 |
| 0.1 μg/mL | 7.1 ± 0.9 | 6.3 ± 2.7 |
| 0.01 μg/mL | 0.6 ± 3.6 | 0.9 ± 1.0 |
| TSMAb 1 IgG | | |
| 100 μg/mL | 74.0 ± 0.6 | 71.0 ± 1.2 |
| 10 μg/mL | 68.6 ± 0.4 | 63.5 ± 1.9 |
| 1 μg/mL | 39.0 ± 1.8 | 30.6 ± 3.8 |
| 0.1 μg/mL | 8.8 ± 1.8 | 2.4 ± 3.4 |
| 0.01 μg/mL | 4.3 ± 1.7 | −6.3 ± 1.1 |
| TSMAb 2 IgG | | |
| 100 μg/mL | 63.1 ± 0.2 | 65.2 ± 3.9 |
| 10 μg/mL | 58.3 ± 1.2 | 62.4 ± 1.2 |
| 1 μg/mL | 52.8 ± 0.7 | 56.4 ± 3.9 |
| 0.1 μg/mL | 29.5 ± 1.6 | 25.8 ± 2.8 |
| 0.01 μg/mL | 5.6 ± 2.8 | 8.4 ± 3.8 |
| TSMAb 3 IgG | | |
| 100 μg/mL | 34.5 ± 0.5 | 42.7 ± 2.9 |
| 10 μg/mL | 38.4 ± 1.5 | 40.7 ± 3.1 |
| 1 μg/mL | 34.3 ± 1.5 | 29.8 ± 2.5 |
| 0.1 μg/mL | 19.4 ± 1.6 | 16.7 ± 7.1 |
| 0.01 μg/mL | 8.2 ± 1.3 | 3.8 ± 3.1 |
| TSMAb 4 IgG | | |
| 100 μg/mL | 56.6 ± 2.8 | 55.2 ± 3.1 |
| 10 μg/mL | 56.0 ± 1.7 | 55.4 ± 1.8 |
| 1 μg/mL | 55.6 ± 1.3 | 52.4 ± 1.3 |
| 0.1 μg/mL | 40.2 ± 1.6 | 25.2 ± 0.7 |
| 0.01 μg/mL | 13.7 ± 3.5 | 11.6 ± 5.0 |
| TSMAb 5 IgG | | |
| 100 μg/mL | 67.2 ± 1.2 | 63.7 ± 1.7 |
| 10 μg/mL | 65.4 ± 1.0 | 63.6 ± 2.3 |
| 1 μg/mL | 63.4 ± 1.0 | 59.2 ± 1.1 |
| 0.1 μg/mL | 54.3 ± 2.8 | 37.1 ± 1.9 |
| 0.01 μg/mL | 22.6 ± 1.3 | 9.1 ± 2.9 |
| TSMAb 6 IgG | | |
| 100 μg/mL | 62.9 ± 4.4 | 56.3 ± 2.0 |
| 10 μg/mL | 55.8 ± 1.1 | 52.2 ± 1.5 |
| 1 μg/mL | 54.7 ± 0.7 | 51.3 ± 1.1 |
| 0.1 μg/mL | 40.7 ± 2.5 | 37.3 ± 5.7 |
| 0.01 μg/mL | 11.6 ± 2.5 | 2.9 ± 1.6 |
| TSMAb 7 IgG | | |
| 100 μg/mL | 51.2 ± 1.0 | 46.8 ± 0.2 |
| 10 μg/mL | 54.1 ± 4.4 | 46.1 ± 1.2 |
| 1 μg/mL | 46.9 ± 1.1 | 44.9 ± 2.2 |
| 0.1 μg/mL | 28.9 ± 2.9 | 28.3 ± 8.5 |
| 0.01 μg/mL | 3.9 ± 1.5 | 1.4 ± 1.4 |
| 9D33 IgG | | |
| 100 μg/mL | 64.1 ± 1.7 | 65.9 ± 0.3 |
| 10 μg/mL | 64.2 ± 1.7 | 66.7 ± 1.4 |
| 1 μg/mL | 60.1 ± 0.9 | 57.8 ± 1.2 |
| 0.1 μg/mL | 35.1 ± 2.0 | 24.1 ± 1.9 |
| 0.01 μg/mL | 14.8 ± 3.5 | 6.2 ± 4.9 |
| 5B3 IgG | | |
| 100 μg/mL | 8.1 ± 0.9 | 3.8 ± 2.5 |
| 10 μg/mL | 2.4 ± 1.2 | 4.9 ± 7.1 |
| 1 μg/mL | 3.4 ± 1.7 | 9.7 ± 3.9 |
| 0.1 μg/mL | 1.4 ± 1.9 | 3.0 ± 3.1 |
| 0.01 μg/mL | 2.2 ± 6.1 | 4.3 ± 3.0 |

Results shown are mean ± SD of triplicate determinations.
*mean of duplicate determinations
HBD = pool of healthy blood donor sera. 5B3 is a human MAb to glutamic acid decarboxylase (negative control). Assay buffer is 50 mmol/L NaCl, 10 mmol/L Tris pH 7.8, 0.1% Triton X-100, 1 mg/mL BSA.

TABLE 4b

Inhibition of M22-peroxidase binding to TSHR coated ELISA plate wells by K1-18 IgG, K1-18 Fab and M22 Fab preparations

| Test sample | Inhibition of binding (%) Dilutions in assay buffer (mean ± SD) | Inhibition of binding (%) Dilutions in HBD (mean ± SD) |
|---|---|---|
| K1-18 IgG | | |
| 3 μg/mL | 97.7 ± 0.1 | 96.7 ± 0.3 |
| 1 μg/mL | 96.5 ± 0.4 | 93.2 ± 0.3 |
| 0.3 μg/mL | 91.9 ± 0.8 | 82.2 ± 1.2 |
| 0.1 μg/mL | 71.9 ± 0.6 | 45.3 ± 1.5 |
| 0.03 μg/mL | 37.2 ± 2.6 | 24.4 ± 1.7 |
| 0.01 μg/mL | 16.7 ± 0.9 | 4.7 ± 0.6 |
| 0.003 μg/mL | 6.5* | 2.6* |
| K1-18 Fab | | |
| 100 μg/mL | 95.1 ± 0.8 | 93.4 ± 0.4 |
| 30 μg/mL | 94.8 ± 0.1 | 92.6 ± 0.2 |
| 10 μg/mL | 93.6 ± 0.4 | 92.0 ± 0.3 |
| 3 μg/mL | 92.5 ± 0.1 | 91.7 ± 0.5 |
| 1 μg/mL | 90.4 ± 0.1 | 87.5 ± 0.9 |
| 0.3 μg/mL | 79.5 ± 0.1 | 70.4 ± 1.7 |
| 0.1 μg/mL | 53.5 ± 0.3 | 47.3 ± 6.3 |
| 0.03 μg/mL | 24.6 ± 3.4 | 14.5 ± 4.7 |
| 0.01 μg/mL | 11.2 ± 1.9 | 11.7 ± 7 |
| 0.003 μg/mL | 6.3 ± 1.1 | 4.9 ± 7.9 |
| 0.001 μg/mL | 3.6* | 2.4 ± 5.0 |
| M22 Fab | | |
| 3 μg/mL | 97.5 ± 0.3 | 96.8 ± 0.3 |
| 1 μg/mL | 97.2 ± 0.3 | 96.4 ± 0.2 |
| 0.3 μg/mL | 96.9 ± 0.1 | 94.7 ± 0.3 |
| 0.1 μg/mL | 93.9 ± 0.5 | 85.2 ± 0.3 |
| 0.03 μg/mL | 80.0 ± 1.1 | 60.0 ± 4.9 |
| 0.01 μg/mL | 44.7 ± 2.0 | 28.8 ± 1.1 |
| 0.003 μg/mL | 17.4 ± 3.8 | 13.1 ± 3.1 |
| 0.001 μg/mL | 5.0* | 8.5* |

See legend to Table 4a for details. Results of negative control MAb (5B3 IgG) are shown in Table 4a.

TABLE 4c

Inhibition of M22-peroxidase binding to TSHR coated ELISA plate wells by K1-70 IgG and K1-70 Fab preparations

| Test sample | Inhibition of binding (%) Dilutions in assay buffer (mean ± SD) | Inhibition of binding (%) Dilutions in HBD (mean ± SD) |
|---|---|---|
| K1-70 IgG | | |
| 100 μg/mL | 98.5 ± 0.3 | 98.3 ± 0.2 |
| 30 μg/mL | 98.2 ± 0.1 | 97.9 ± 0.1 |
| 10 μg/mL | 97.9 ± 0.2 | 97.8 ± 0.1 |
| 3 μg/mL | 98.1 ± 0.2 | 97.6 ± 0.1 |
| 1 μg/mL | 98.1 ± 0.1 | 96.4 ± 0.2 |
| 0.3 μg/mL | 97.3 ± 0.3 | 91.1 ± 0.3 |
| 0.1 μg/mL | 93.0 ± 0.3 | 69.7 ± 0.7 |
| 0.03 μg/mL | 71.8 ± 4.2 | 34.5 ± 3.8 |
| 0.01 μg/mL | 28.0 ± 2.8 | 9.2 ± 2.6 |
| 0.003 μg/mL | 6.4 ± 3.1 | 9.6* |
| 0.001 μg/mL | −5.0 ± 2.7 | 0.8* |
| K1-70 Fab | | |
| 100 μg/mL | 97.4 ± 0.1 | 97.4 ± 0.1 |
| 30 μg/mL | 97.6 ± 0.05 | 97.5 ± 0.2 |
| 10 μg/mL | 97.5 ± 0.1 | 97.1 ± 0.1 |
| 3 μg/mL | 97.2 ± 0.2 | 96.5 ± 0.5 |
| 1 μg/mL | 97.2 ± 0.1 | 96.1 ± 0.3 |
| 0.3 μg/mL | 96.8 ± 0.2 | 94.4 ± 0.1 |
| 0.1 μg/mL | 94.6 ± 0.2 | 86.0 ± 0.4 |
| 0.03 μg/mL | 82.0 ± 0.7 | 58.8 ± 1.2 |
| 0.01 μg/mL | 57.5 ± 3.7 | 27.9 ± 3.2 |
| 0.003 μg/mL | 21.8 ± 3.9 | 8.2 ± 2.1 |
| 0.001 μg/mL | 4.9 ± 0.4 | −6.6 ± 1.9 |

TABLE 4c-continued

Inhibition of M22-peroxidase binding to TSHR coated ELISA plate wells by K1-70 IgG and K1-70 Fab preparations

| Test sample | Inhibition of binding (%) Dilutions in assay buffer (mean ± SD) | Inhibition of binding (%) Dilutions in HBD (mean ± SD) |
|---|---|---|
| K1-18 IgG | | |
| 1 μg/mL | 96.3 ± 0.2 | 94.6 ± 0.2 |
| 0.1 μg/mL | 71.9 ± 0.9 | 56.3 ± 1.1 |
| 0.03 μg/mL | 35.7 ± 4.2 | 13.6 ± 0.8 |
| 0.01 μg/mL | 8.9 ± 3.2 | −4.0 ± 4.9 |
| 0.003 μg/mL | −1.9* | −1.3 ± 2.9 |

See legend to Table 4a for details. Results of negative control MAb (5B3 IgG) are shown in Table 4a.

TABLE 5A

Inhibition of $^{125}$I-K1-18 IgG binding to TSHR coated tubes by K1-18 IgG, K1-18 Fab, K1-70 IgG and other MAbs

| Test sample | Inhibition of binding (%) Dilutions in assay buffer (mean ± SD) | Inhibition of binding (%) Dilutions in HBD (mean ± SD) |
|---|---|---|
| K1-18 IgG | | |
| 100 μg/mL | 94.0 ± 0.9 | 94.9 ± 0.2 |
| 30 μg/mL | 93.2 ± 0.3 | 94.7 ± 0.2 |
| 10 μg/mL | 92.4 ± 1.5 | 93.6 ± 0.9 |
| 3 μg/mL | 93.0 ± 0.3 | 93.5 ± 0.8 |
| 1 μg/mL | 92.6 ± 0.4 | 91.7 ± 0.8 |
| 0.3 μg/mL | 91.0 ± 0.5 | 84.6 ± 0.5 |
| 0.1 μg/mL | 82.9 ± 1.8 | 69.0 ± 0.5 |
| 0.03 μg/mL | 52.7 ± 0.9 | 36.0 ± 1.8 |
| 0.01 μg/mL | 19.4 ± 4.1 | 22.9 ± 2.4 |
| 0.003 μg/mL | 9.2 ± 2.6 | 7.2 ± 3.5 |
| 0.001 μg/mL | 1.9 ± 7.2 | 11.1 ± 4.4 |
| M22 IgG | | |
| 100 μg/ml | 94.5 ± 1.2 | 95.5 ± 0.9 |
| 30 μg/mL | 93.3 ± 0.9 | 94.3 ± 1.2 |
| 10 μg/mL | 93.3 ± 0.8 | 94.9 ± 0.2 |
| 3 μg/mL | 93.4 ± 0.6 | 94.6 ± 0.1 |
| 1 μg/mL | 92.3 ± 0.4 | 94.1 ± 0.4 |
| 0.3 μg/mL | 92.2 ± 0.3 | 92.4 ± 0.6 |
| 0.1 μg/mL | 87.1 ± 0.5 | 80.9 ± 0.3 |
| 0.03 μg/mL | 53.3 ± 3.4 | 56.5 ± 1.7 |
| 0.01 μg/mL | 18.3 ± 5.3 | 36.9 ± 5.4 |
| 0.003 μg/mL | 5.1 ± 3.1 | 14.3 ± 3.4 |
| 0.001 μg/mL | −1.6 ± 3.8 | 11.0 ± 0.4 |
| M22 Fab | | |
| 100 μg/ml | 95.0 ± 0.6 | 94.1 ± 0.9 |
| 10 μg/mL | 91.8 ± 0.8 | 92.6 ± 1.2 |
| 1 μg/mL | 91.6 ± 0.8 | 92.8 ± 0.2 |
| 0.1 μg/mL | 90.2 ± 0.1 | 87.4 ± 0.5 |
| 0.01 μg/mL | 39.1 ± 2.8 | 48.0 ± 1.0 |
| 0.001 μg/mL | 2.9 ± 2.8 | 9.3* |
| K1-70 IgG | | |
| 100 μg/ml | 94.6 ± 1.2 | 95.2 ± 2.0 |
| 30 μg/mL | 94.6 ± 0.6 | 95.2 ± 0.1 |
| 10 μg/mL | 94.5 ± 0.2 | 94.5 ± 0.3 |
| 3 μg/mL | 93.1 ± 1.0 | 94.6 ± 0.5 |
| 1 μg/mL | 93.6 ± 1.4 | 93.1 ± 0.1 |
| 0.3 μg/mL | 92.7 ± 0.5 | 88.6 ± 0.3 |
| 0.1 μg/mL | 89.0 ± 1.9 | 87.1 ± 1.3 |
| 0.03 μg/mL | 55.7 ± 1.4 | 58.6 ± 2.0 |
| 0.01 μg/mL | 18.5 ± 4.1 | 48.7 ± 1.3 |
| 0.003 μg/mL | 1.5 ± 2.9 | 17.5 ± 3.9 |
| 0.001 μg/mL | 1.3 ± 4.1 | 10.7 ± 0.9 |
| 4B4 IgG | | |
| 100 μg/mL | 20.7 ± 2.7 | −1.6 ± 2.3 |
| 10 μg/mL | 5.1 ± 3.9 | 0.6 ± 3.0 |
| 1 μg/mL | 4.5 ± 2.9 | 7.4 ± 5.4 |

TABLE 5A-continued

Inhibition of $^{125}$I-K1-18 IgG binding to TSHR coated tubes by K1-18 IgG, K1-18 Fab, K1-70 IgG and other MAbs

| Test sample | Inhibition of binding (%) Dilutions in assay buffer (mean ± SD) | Inhibition of binding (%) Dilutions in HBD (mean ± SD) |
|---|---|---|
| 0.1 µg/mL | −2.3 ± 2.0 | 1.8 ± 4.3 |
| 0.01 µg/mL | −3.5 ± 4.24 | −0.8 ± 1.3 |
| 4B4 Fab | | |
| 100 µg/mL | −6.3 ± 0.8 | −0.2 ± 1.0 |
| 10 µg/mL | −4.9 ± 3.9 | 3.0 ± 1.5 |
| 5C9 IgG | | |
| 100 µg/mL | 91.3 ± 0.4 | 57.7 ± 2.4 |
| 10 µg/mL | 65.9 ± 1.4 | 46.7 ± 0.6 |
| 1 µg/mL | 48.0 ± 7.5 | 26.8* |
| 0.1 µg/mL | 33.4 ± 0.2 | 21.3 ± 6.4 |
| 0.01 µg/mL | 11.7 ± 1.8 | −1.8 ± 2.7 |
| TSMAb 1 IgG | | |
| 100 µg/mL | 56.1 ± 2.0 | 62.5 ± 4.0 |
| 10 µg/mL | 46.0 ± 2.2 | 57.8 ± 1.5 |
| 1 µg/mL | 41.0 ± 0.4 | 36.3 ± 1.0 |
| 0.1 µg/mL | 17.6 ± 4.5 | 3.8 ± 3.8 |
| 0.01 µg/mL | 3.6 ± 9.5 | −6.9 ± 3.4 |
| TSMAb 2 IgG | | |
| 100 µg/mL | 72.8 ± 5.9 | 64.5 ± 7.3 |
| 10 µg/mL | 48.2 ± 1.5 | 62.0 ± 2.6 |
| 1 µg/mL | 43.2 ± 2.0 | 48.8 ± 2.8 |
| 0.1 µg/mL | 37.1 ± 0.6 | 30.2 ± 3.2 |
| 0.01 µg/mL | 7.6 ± 1.2 | 4.9 ± 2.0 |
| TSMAb 3 IgG | | |
| 100 µg/mL | 62.7 ± 1.2 | 64.8 ± 7.4 |
| 10 µg/mL | 54.2 ± 0.4 | 55.6 ± 0.4 |
| 1 µg/mL | 54.3 ± 1.3 | 46.1 ± 1.3 |
| 0.1 µg/mL | 45.7 ± 5.1 | 24.0 ± 8.5 |
| 0.01 µg/mL | 23.4 ± 3.8 | −1.5 ± 2.0 |
| TSMAb 4 IgG | | |
| 100 µg/mL | 64.4 ± 2.0 | 81.6 ± 3.8 |
| 10 µg/mL | 59.7 ± 0.4 | 75.7 ± 2.1 |
| 1 µg/mL | 57.5 ± 1.5 | 70.5 ± 4.6 |
| 0.1 µg/mL | 48.5 ± 0.7 | 39.2 ± 0.3 |
| 0.01 µg/mL | 12.3 ± 2.9 | 5.1 ± 0.9 |
| TSMAb 5 IgG | | |
| 100 µg/mL | 71.9 ± 1.0 | 85.3 ± 3.4 |
| 10 µg/mL | 67.7 ± 1.5 | 78.9 ± 1.6 |
| 1 µg/mL | 60.5 ± 1.0 | 70.8 ± 1.1 |
| 0.1 µg/mL | 52.7 ± 0.7 | 47.7 ± 1.8 |
| 0.01 µg/mL | 14.4 ± 1.5 | 17.5 ± 9.9 |
| TSMAb 6 IgG | | |
| 100 µg/mL | 72.0 ± 1.6 | 71.3 ± 1.6 |
| 10 µg/mL | 49.3 ± 0.6 | 60.5 ± 1.1 |
| 1 µg/mL | 46.9 ± 1.1 | 57.0 ± 0.6 |
| 0.1 µg/mL | 40.4 ± 2.4 | 38.6 ± 3.8 |
| 0.01 µg/mL | 19.1 ± 2.4 | 9.6 ± 2.4 |
| TSMAb 7 IgG | | |
| 100 µg/mL | 68.7 ± 1.0 | 65.3 ± 4.1 |
| 10 µg/mL | 53.4 ± 0.5 | 59.9 ± 1.3 |
| 1 µg/mL | 41.0 ± 0.2 | 54.8 ± 2.3 |
| 0.1 µg/mL | 29.4 ± 1.4 | 28.6 ± 1.0 |
| 0.01 µg/mL | 4.3 ± 2.0 | −1.0 ± 3.0 |
| 9D33 IgG | | |
| 100 µg/mL | 72.5 ± 0.8 | 68.7 ± 2.2 |
| 10 µg/mL | 63.2 ± 0.8 | 68.1 ± 1.5 |
| 1 µg/mL | 63.0 ± 0.9 | 62.1 ± 2.1 |
| 0.1 µg/mL | 54.8 ± 1.4 | 33.8 ± 3.0 |
| 0.01 µg/mL | 20.9 ± 0.7 | 5.3 ± 1.5 |
| 5B3 IgG | | |
| 100 µg/mL | 6.7 ± 2.1 | 29.4 ± 3.4 |
| 10 µg/mL | −2.7 ± 1.1 | −0.1* |
| 1 µg/mL | −3.8 ± 1.0 | −6.2 ± 0.7 |
| 0.1 µg/mL | −4.8 ± 1.8 | −7.8 ± 0.6 |
| 0.01 µg/mL | −4.2 ± 3.2 | −8.1 ± 1.4 |

Results shown are mean ± SD of triplicate determinations.
*mean of duplicate determinations
HBD = pool of healthy blood donor sera. 4B4 is a human MAb to glutamic acid decarboxylase (negative control). 5B3 is a human MAb to glutamic acid decarboxylase (negative control).
$^{125}$I-K1-18 IgG binding in the presence of assay buffer was 13.6%.
$^{125}$I-K1-18 IgG binding in the presence of HBD pool was 13.8%.
Assay buffer is 50 mmol/L NaCl, 10 mmol/L Tris pH 7.8, 0.1% Triton X-100.

TABLE 5B

Inhibition of $^{125}$I-K1-18 IgG binding to TSHR coated tubes by K1-18 IgG, K1-18 Fab, K1-70 IgG and K1-70 Fab preparations

| Test sample | Inhibition of binding (%) Dilutions in assay buffer (mean ± SD) | Inhibition of binding (%) Dilutions in HBD (mean ± SD) |
|---|---|---|
| K1-18 IgG | | |
| 100 µg/ml | 94.5 ± 0.8 | 96.1 ± 0.0 |
| 30 µg/mL | 93.8 ± 1.2 | 95.6 ± 0.9 |
| 10 µg/mL | 92.5 ± 1.4 | 94.0 ± 1.2 |
| 3 µg/mL | 93.0 ± 0.5 | 94.0 ± 0.3 |
| 1 µg/mL | 92.8 ± 1.0 | 91.1 ± 0.5 |
| 0.3 µg/mL | 90.9 ± 0.5 | 78.3 ± 3.4 |
| 0.1 µg/mL | 78.9 ± 2.9 | 49.4 ± 2.3 |
| 0.03 µg/mL | 39.3 ± 1.6 | 15.1 ± 2.9 |
| 0.01 µg/mL | 14.9 ± 2.1 | 5.8 ± 5.5 |
| 0.003 µg/mL | 2.9 ± 5.4 | −0.3 ± 2.5 |
| 0.001 µg/mL | 6.9 ± 5.1 | 2.7 ± 1.8 |
| K1-18 Fab | | |
| 100 µg/ml | 86.2 ± 2.2 | 84.8 ± 0.9 |
| 30 µg/mL | 83.0 ± 0.8 | 85.0 ± 0.8 |
| 10 µg/mL | 81.8 ± 0.7 | 83.0 ± 1.7 |
| 3 µg/mL | 81.9 ± 1.3 | 83.4 ± 1.1 |
| 1 µg/mL | 77.5 ± 1.6 | 80.2 ± 1.7 |
| 0.3 µg/mL | 71.1 ± 0.8 | 65.5 ± 1.5 |
| 0.1 µg/mL | 56.7 ± 0.8 | 39.0 ± 2.3 |
| 0.03 µg/mL | 24.8 ± 0.2 | 10.3 ± 2.2 |
| 0.01 µg/mL | 8.8 ± 2.6 | 1.8 ± 2.0 |
| 0.003 µg/mL | 0.8 ± 4.5 | 1.0 ± 1.6 |
| 0.001 µg/mL | −2.6 ± 5.2 | −1.0 ± 3.4 |
| K1-70 IgG | | |
| 100 µg/ml | 94.5 ± 0.6 | 95.3 ± 0.1 |
| 30 µg/mL | 93.1 ± 1.0 | 93.9 ± 1.9 |
| 10 µg/mL | 91.9 ± 0.4 | 95.1 ± 0.3 |
| 3 µg/mL | 92.9 ± 0.9 | 94.1 ± 0.6 |
| 1 µg/mL | 92.0 ± 0.7 | 92.9 ± 0.4 |
| 0.3 µg/mL | 91.5 ± 0.2 | 82.2 ± 0.6 |
| 0.1 µg/mL | 89.2 ± 1.5 | 55.6 ± 1.2 |
| 0.03 µg/mL | 45.6 ± 2.8 | 17.8 ± 2.1 |
| 0.01 µg/mL | 6.8 ± 1.0 | 6.1 ± 4.2 |
| 0.003 µg/mL | 0.1 ± 2.2 | 2.1 ± 3.4 |
| 0.001 µg/mL | −1.7 ± 2.2 | −0.0 ± 2.3 |
| K1-70 Fab | | |
| 100 µg/ml | 93.3 ± 0.6 | 92.5 ± 0.3 |
| 30 µg/mL | 92.2 ± 1.5 | 91.8 ± 2.1 |
| 10 µg/mL | 92.4 ± 1.2 | 92.6 ± 0.4 |
| 3 µg/mL | 91.1 ± 0.8 | 92.8 ± 1.1 |
| 1 µg/mL | 91.0 ± 0.5 | 92.1 ± 0.2 |
| 0.3 µg/mL | 89.6 ± 0.1 | 88.1 ± 1.1 |
| 0.1 µg/mL | 87.6 ± 1.5 | 75.2 ± 1.1 |
| 0.03 µg/mL | 68.8 ± 2.3 | 35.0 ± 3.5 |
| 0.01 µg/mL | 25.6 ± 4.3 | 16.2 ± 1.2 |

TABLE 5B-continued

Inhibition of $^{125}$I-K1-18 IgG binding to TSHR coated tubes by K1-18 IgG, K1-18 Fab, K1-70 IgG and K1-70 Fab preparations

| Test sample | Inhibition of binding (%) Dilutions in assay buffer (mean ± SD) | Inhibition of binding (%) Dilutions in HBD (mean ± SD) |
|---|---|---|
| 0.003 µg/mL | 4.1 ± 4.8 | 3.7 ± 2.6 |
| 0.001 µg/mL | −3.9 ± 0.8 | −3.2 ± 4.0 |
| M22 Fab | | |
| 1 µg/mL | 90.5 ± 0.7 | 91.8 ± 0.4 |
| 0.3 µg/mL | 87.7 ± 4.0 | 87.8 ± 1.8 |
| 0.01 µg/mL | 90.2 ± 0.6 | 77.4 ± 1.7 |
| 0.03 µg/mL | 77.0 ± 1.1 | 39.5 ± 0.7 |
| 0.01 µg/mL | 29.1 ± 6.0 | 10.5 ± 2.9 |
| 0.003 µg/mL | 1.9 ± 3.1 | 1.0 ± 0.5 |
| 0.001 µg/mL | −7.3 ± 3.5 | 3.8 ± 2.6 |
| 4B4 IgG | | |
| 100 µg/mL | 17.7 ± 1.8 | −3.5 ± 2.2 |
| 10 µg/mL | −0.5 ± 2.1 | 0.6 ± 5.3 |
| 1 µg/mL | 2.1 ± 1.5 | −1.2 ± 1.5 |

See legend to Table 5a for details.
$^{125}$I-K1-18 IgG binding in the presence of assay buffer was 19.1%.
$^{125}$I-K1-18 IgG binding in the presence of HBD pool was 15.3%.

TABLE 5c

Inhibition of $^{125}$I-K1-18 IgG binding to TSHR coated tubes by patient sera positive for TRAb (stimulating and blocking) and by donor serum K1

| Test sample | % Inhibition of $^{125}$I-K1-18 IgG binding | % Inhibition of $^{125}$I-TSH binding |
|---|---|---|
| G1 | 37.8 | 38.6 |
| G2 | 43.1 | 31.5 |
| G3 | 36.5 | 35.6 |
| G4 | 44.1 | 47.1 |
| G5 | 42.6 | 44.7 |
| G6 | 54.5 | 52.1 |
| G7 | 25.5 | 15.9 |
| G8 | 48.2 | 41.8 |
| G9 | 79.5 | 80.0 |
| G10 | 63.1 | 68.7 |
| G11 | 37.2 | 31.0 |
| G12 | 37.2 | 29.7 |
| G13 | 63.1 | 57.9 |
| G14 | 56.4 | 49.3 |
| G15 | 43.8 | 38.6 |
| G16 | 44.0 | 42.9 |
| G17 | 27.7 | 24.5 |
| G18 | 44.5 | 39.1 |
| G19 | 23.2 | 20.6 |
| G20 | 54.4 | 38.4 |
| HBD 1 | 1.9 | −12.6 |
| HBD 2 | −1.2 | −4.2 |
| HBD 3 | 7.7 | −5.4 |
| HBD 4 | 5.7 | −11.8 |
| HBD 5 | 14.7 | −4.7 |
| HBD 6 | 11.8 | 1.8 |
| HBD 7 | 0.0 | −13.7 |
| HBD 8 | 1.5 | −12.8 |
| HBD 9 | 0.2 | −11.0 |
| HBD 10 | 1.1 | −10.6 |
| K1 donor serum | | |
| diluted 10x | 59.3 | 67.2 |
| diluted 20x | 35.2 | 44.0 |
| diluted 40x | 14.2 | 24.8 |
| diluted 80x | 6.9 | 11.9 |
| diluted 160x | 5.1 | 2.7 |
| diluted 320x | 5.7 | 2.1 |
| B1 | | |
| diluted 5x | 88.1 | 91.5 |
| diluted 10x | 77.6 | 83.9 |
| diluted 20x | 57.1 | 65.8 |
| diluted 40x | 35.5 | 39.6 |
| diluted 80x | 18.7 | 20.7 |
| diluted 160x | 11.6 | 7.5 |
| diluted 320x | 5.4 | −2.5 |
| B2 | | |
| diluted 20x | 90.3 | 93.5 |
| diluted 40x | 79.1 | 86.5 |
| diluted 80x | 58.7 | 68.7 |
| diluted 160x | 32.9 | 42.8 |
| diluted 320x | 32.6 | 20.4 |
| diluted 640x | 10.7 | 10.5 |
| diluted 1280x | 9.6 | 14.1 |
| S1 | | |
| diluted 5x | 80.6 | 82.0 |
| diluted 10x | 66.9 | 66.5 |
| diluted 20x | 52.0 | 47.1 |
| diluted 40x | 32.4 | 32.5 |
| diluted 80x | 13.6 | 17.4 |
| diluted 160x | 15.8 | 5.2 |
| diluted 320x | 10.2 | 2.3 |
| S2 | | |
| diluted 5x | 58.0 | 55.1 |
| diluted 10x | 41.5 | 33.7 |
| diluted 20x | 27.9 | 18.4 |
| diluted 40x | 19.5 | 9.5 |
| diluted 80x | 10.6 | 7.7 |
| diluted 160x | 6.7 | −0.7 |

G1-G20 are sera from patients with Graves' disease positive for TRAbs. HBD 1-10 are individual sera from healthy blood donors. B1 and B2 are sera from patients with blocking type TRAb. S1 and S2 are sera from patients with stimulating type TRAb.

TABLE 5d

Inhibition of $^{125}$I-K1-18 Fab binding to TSHR coated tubes by K1-18 IgG, K1-18 Fab and K1-70 IgG preparations

| Test sample | Inhibition of binding (%) Dilutions in assay buffer (mean ± SD) | Inhibition of binding (%) Dilutions in HBD (mean ± SD) |
|---|---|---|
| K1-18 IgG | | |
| 100 µg/mL | 94.8 ± 0.8 | 96.0 ± 0.8 |
| 30 µg/mL | 94.5 ± 0.8 | 95.7 ± 1.2 |
| 10 µg/mL | 94.8 ± 2.6 | 94.5 ± 1.6 |
| 3 µg/mL | 93.7 ± 0.5 | 94.0 ± 0.2 |
| 1 µg/mL | 93.3 ± 0.7 | 91.9 ± 0.7 |
| 0.3 µg/mL | 91.1 ± 0.9 | 83.5 ± 1.9 |
| 0.1 µg/mL | 78.5 ± 2.5 | 57.0 ± 2.8 |
| 0.3 µg/mL | 22.0 ± 1.4 | 23.5 ± 2.1 |
| 0.01 µg/mL | 8.6 ± 1.4 | 11.0 ± 2.7 |
| 0.003 µg/mL | 1.4 ± 1.7 | 9.0 ± 2.5 |
| 0.001 µg/mL | −3.0 ± 6.1 | 9.4 ± 5.3 |
| K1-18 Fab | | |
| 100 µg/mL | 86.2 ± 3.3 | 84.8 ± 1.0 |
| 30 µg/mL | 84.2 ± 2.6 | 82.6 ± 0.9 |
| 10 µg/mL | 83.5 ± 3.0 | 81.6 ± 1.8 |
| 3 µg/mL | 81.1 ± 0.1 | 82.8 ± 1.0 |
| 1 µg/mL | 81.5 ± 3.8 | 79.2 ± 1.4 |
| 0.1 µg/mL | 62.5 ± 0.9 | 43.9 ± 1.3 |

TABLE 5d-continued

Inhibition of $^{125}$I-K1-18 Fab binding to TSHR coated tubes by K1-18 IgG, K1-18 Fab and K1-70 IgG preparations

| Test sample | Inhibition of binding (%) Dilutions in assay buffer (mean ± SD) | Inhibition of binding (%) Dilutions in HBD (mean ± SD) |
|---|---|---|
| M22 IgG | | |
| 100 µg/mL | 94.9 ± 0.3 | 95.9 ± 0.2 |
| 30 µg/mL | 93.9 ± 2.0 | 95.2 ± 2.4 |
| 10 µg/mL | 95.3 ± 1.1 | 95.5 ± 0.2 |
| 3 µg/mL | 94.4 ± 0.7 | 95.1 ± 0.4 |
| 1 µg/mL | 93.4 ± 0.5 | 93.6 ± 1.0 |
| 0.3 µg/mL | 92.5 ± 0.5 | 87.1 ± 0.6 |
| 0.1 µg/mL | 69.8 ± 2.0 | 61.5 ± 1.4 |
| 0.03 µg/mL | 14.7 ± 3.2 | 23.8 ± 1.9 |
| 0.01 µg/mL | 8.0 ± 10.2 | 10.9 ± 2.5 |
| 0.003 µg/mL | 9.0 ± 10.3 | 10.8 ± 5.8 |
| 0.001 µg/mL | 2.9 ± 2.4 | 2.9 ± 3.7 |
| M22 Fab | | |
| 100 µg/mL | 94.5 ± 0.4 | 94.5 ± 1.1 |
| 10 µg/mL | 92.0 ± 2.1 | 92.8 ± 1.5 |
| 1 µg/mL | 91.4 ± 0.5 | 92.8 ± 0.4 |
| 0.1 µg/mL | 79.5 ± 1.2 | 84.5 ± 0.2 |
| 0.01 µg/mL | 3.1 ± 3.3 | 20.4 ± 5.6 |
| 0.001 µg/mL | −0.7 ± 6.4 | 4.7 ± 3.9 |
| K1-70 IgG | | |
| 100 µg/mL | 94.8 ± 2.2 | 95.6 ± 1.8 |
| 30 µg/mL | 95.1 ± 0.4 | 95.5 ± 0.6 |
| 10 µg/mL | 94.6 ± 1.0 | 95.8 ± 0.4 |
| 3 µg/mL | 94.5 ± 0.5 | 95.3 ± 0.3 |
| 1 µg/mL | 94.0 ± 0.5 | 94.0 ± 0.2 |
| 0.3 µg/mL | 93.4 ± 0.6 | 87.7 ± 0.9 |
| 0.1 µg/mL | 73.8 ± 0.6 | 60.1 ± 2.8 |
| 0.03 µg/mL | 24.1 ± 5.8 | 28.7 ± 1.5 |
| 0.01 µg/mL | 4.8 ± 3.5 | 11.7 ± 4.6 |
| 0.003 µg/mL | 2.2 ± 2.2 | 6.4 ± 2.2 |
| 0.001 µg/mL | −3.9 ± 4.3 | 4.7 ± 3.5 |
| 4B4 IgG | | |
| 100 µg/mL | 17.9 ± 3.9 | 2.7 ± 5.2 |
| 10 µg/mL | −1.35 ± 3.2 | 1.3 ± 0.7 |
| 1 µg/mL | −2.16 ± 3.6 | 5.5 ± 3.6 |
| 0.1 µg/mL | −4.5 ± 2.4 | 1.6 ± 1.7 |
| 0.01 µg/mL | −8.9 ± 1.3 | 1.9 ± 1.1 |
| 4B4 Fab | | |
| 100 µg/mL | −7.8 ± 3.5 | −0.8 ± 2.2 |
| 10 µg/mL | −8.5 ± 1.4 | 1.6 ± 2.8 |
| 5C9 IgG | | |
| 100 µg/mL | 85.2 ± 1.0 | 61.3 ± 1.6 |
| 10 µg/mL | 63.8 ± 2.1 | 49.8 ± 1.6 |
| 1 µg/mL | 52.5 ± 1.3 | 23.2 ± 1.9 |
| 0.1 µg/mL | 27.7 ± 1.5 | 6.3 ± 0.4 |
| 0.01 µg/mL | 3.0 ± 2.7 | 5.7 ± 8.8 |
| TSMAb 1 IgG | | |
| 100 µg/mL | 67.0 ± 2.0 | 76.8 ± 1.5 |
| 10 µg/mL | 61.1 ± 3.1 | 67.7 ± 5.0 |
| 1 µg/mL | 48.5 ± 0.8 | 43.4 ± 1.6 |
| 0.1 µg/mL | 13.1 ± 2.0 | 12.8 ± 2.7 |
| 0.01 µg/mL | −0.1 ± 2.6 | 6.3 ± 2.7 |
| TSMAb 2 IgG | | |
| 100 µg/mL | 82.8 ± 1.8 | 83.9 ± 3.1 |
| 10 µg/mL | 60.5 ± 2.5 | 77.1 ± 1.4 |
| 1 µg/mL | 57.5 ± 0.9 | 63.1 ± 2.9 |
| 0.1 µg/mL | 39.5 ± 1.4 | 32.1 ± 2.8 |
| 0.01 µg/mL | 4.7 ± 4.2 | 6.5 ± 3.8 |
| TSMAb 3 IgG | | |
| 100 µg/mL | 76.5 ± 2.4 | 78.5 ± 4.1 |
| 10 µg/mL | 68.6 ± 1.3 | 72.4 ± 1.1 |
| 1 µg/mL | 66.0 ± 1.9 | 59.4 ± 1.8 |
| 0.1 µg/mL | 41.3 ± 1.2 | 19.7 ± 3.9 |
| 0.01 µg/mL | 5.5 ± 0.4 | 1.4 ± 3.9 |
| TSMAb 4 IgG | | |
| 100 µg/mL | 71.4 ± 1.5 | 82.7 ± 2.4 |
| 10 µg/mL | 67.6 ± 0.6 | 80.5 ± 1.1 |
| 1 µg/mL | 66.2 ± 0.2 | 70.3 ± 1.5 |
| 0.1 µg/mL | 46.1 ± 0.6 | 31.1 ± 4.0 |
| 0.01 µg/mL | 8.1 ± 2.1 | 2.5 ± 1.9 |
| TSMAb 5 IgG | | |
| 100 µg/mL | 87.3 ± 0.9 | 86.4 ± 2.7 |
| 10 µg/mL | 79.8 ± 1.3 | 81.1 ± 2.1 |
| 1 µg/mL | 69.9 ± 0.9 | 75.9 ± 1.4 |
| 0.1 µg/mL | 50.0 ± 3.0 | 44.1 ± 0.6 |
| 0.01 µg/mL | 4.2 ± 2.5 | 3.3 ± 4.5 |
| TSMAb 6 IgG | | |
| 100 µg/mL | 75.8 ± 2.5 | 77.5 ± 1.9 |
| 10 µg/mL | 59.0 ± 0.7 | 75.4 ± 0.5 |
| 1 µg/mL | 56.3 ± 4.0 | 70.0 ± 1.8 |
| 0.1 µg/mL | 43.9 ± 0.8 | 40.2 ± 2.5 |
| 0.01 µg/mL | *5.6 | 7.1 ± 3.4 |
| TSMAb 7 IgG | | |
| 100 µg/mL | 78.0 ± 0.4 | 77.4 ± 1.3 |
| 10 µg/mL | 61.8 ± 2.2 | 72.5 ± 2.9 |
| 1 µg/mL | 51.1 ± 1.5 | 62.8 ± 1.0 |
| 0.1 µg/mL | 30.2 ± 1.2 | 31.3 ± 1.5 |
| 0.01 µg/mL | 2.0 ± 7.0 | 5.6 ± 0.8 |
| 9D33 IgG | | |
| 100 µg/mL | 81.5 ± 2.0 | 77.3 ± 2.2 |
| 10 µg/mL | 69.5 ± 3.9 | 73.9 ± 0.9 |
| 1 µg/mL | 66.5 ± 0.9 | 64.8 ± 0.7 |
| 0.1 µg/mL | 48.6 ± 2.7 | 32.1 ± 1.1 |
| 0.01 µg/mL | 7.9 ± 1.8 | 2.3 ± 3.0 |
| 5B3 IgG | | |
| 100 µg/mL | 6.3 ± 4.5 | −1.1 ± 4.8 |
| 10 µg/mL | 0.6 ± 3.9 | −0.1 ± 0.8 |
| 1 µg/mL | −0.9 ± 1.7 | −3.1 ± 3.5 |
| 0.1 µg/mL | −3.6 ± 2.5 | −8.3 ± 2.0 |
| 0.01 µg/mL | −0.0 ± 2.3 | −8.6 ± 1.3 |

See legend to Table 5a for details. $^{125}$I-K1-18 Fab binding in the presence of assay buffer was 10%. $^{125}$I-K1-18 Fab binding in the presence of HBD pool was 9.4%.

TABLE 6a

Comparison of stimulation of cyclic AMP production by K1-18 IgG, K1-18 Fab and M22 Fab in CHO cells expressing the TSHR

| Test sample | Stimulation of cyclic AMP production in isotonic buffer (pmol/mL cyclic AMP mean ± SD) | Stimulation of cyclic AMP production in hypotonic buffer (pmol/mL cyclic AMP mean ± SD) |
|---|---|---|
| Cyclic AMP buffer | 0.88 ± 0.12 | 1.48 ± 0.13 |
| K1-18 IgG | | |
| 1000 ng/mL | 51.16 ± 5.29 | 67.90 ± 10.44 |
| 100 ng/mL | 22.95 ± 2.90 | 64.95 ± 9.61 |
| 30 ng/mL | 9.63 ± 0.76 | 50.72 ± 3.69 |
| 10 ng/mL | 4.81 ± 0.22 | 31.66 ± 5.06 |
| 3 ng/mL | 1.61 ± 0.77 | 12.55 ± 1.75 |
| 1 ng/mL | 1.56 ± 0.40 | 4.08 ± 0.28 |
| 0.3 ng/mL | 1.14 ± 0.10 | 2.32 ± 0.47 |
| 0.1 ng/mL | 1.29 ± 0.31 | 1.56 ± 0.32 |
| 0.03 ng/mL | 0.95 ± 0.04 | 1.26 ± 0.30 |

TABLE 6a-continued

Comparison of stimulation of cyclic AMP production by K1-18 IgG, K1-18 Fab and M22 Fab in CHO cells expressing the TSHR

| Test sample | Stimulation of cyclic AMP production in isotonic buffer (pmol/mL cyclic AMP mean ± SD) | Stimulation of cyclic AMP production in hypotonic buffer (pmol/mL cyclic AMP mean ± SD) |
|---|---|---|
| K1-18 Fab | | |
| 1000 ng/mL | 35.73 ± 2.25 | 66.94 ± 6.93 |
| 100 ng/mL | 8.93 ± 0.18 | * 53.22 |
| 30 ng/mL | 2.97 ± 0.82 | 27.99 ± 6.25 |
| 10 ng/mL | 1.65 ± 0.20 | 9.99 ± 3.52 |
| 3 ng/mL | 1.14 ± 0.19 | 2.93 ± 0.17 |
| 1 ng/mL | 0.79 ± 0.10 | 1.72 ± 0.82 |
| 0.3 ng/mL | 0.71 ± 0.10 | 1.13 ± 0.24 |
| 0.1 ng/mL | 0.84 ± 0.41 | 1.33 ± 0.53 |
| 0.03 ng/mL | 0.50 ± 0.44 | 0.68 ± 0.18 |
| M22 Fab | | |
| 10 ng/mL | 34.71 ± 1.43 | 57.41 ± 5.05 |
| 3 ng/mL | 16.30 ± 1.49 | 55.34 ± 7.49 |
| 1 ng/mL | 9.14 ± 0.82 | 29.80 ± 0.97 |
| 0.3 ng/mL | 2.19 ± 0.19 | 10.08 ± 0.95 |
| 0.1 ng/mL | 1.38 ± 0.07 | 3.83 ± 0.30 |

Results shown are mean ± SD of triplicate determinations.
*mean of duplicate determinations. Test samples were diluted in cyclic AMP buffer.

TABLE 6b

Stimulation of cyclic AMP production by K1-18 IgG, M22 IgG and pTSH in CHO cells expressing the TSHR

| Test sample | Cyclic AMP production concentration (pmol/mL mean ± SD) |
|---|---|
| Cyclic AMP buffer | 1.3 ± 0.2 |
| K1-18 IgG | |
| 300 ng/mL | 63.3 ± 3.7 |
| 100 ng/mL | 62.6 ± 2.7 |
| 30 ng/mL | 38.4 ± 3.1 |
| 10 ng/mL | 25.0 ± 1.0 |
| 3 ng/mL | 8.3 ± 0.5 |
| 1 ng/mL | 3.0 ± 1.0 |
| 0.3 ng/mL | 1.7 ± 0.3 |
| 0.1 ng/mL | 0.9 ± 0.2 |
| 0.03 ng/mL | 1.0 ± 0.2 |
| 0.01 ng/mL | 1.0 ± 0.2 |
| M22 IgG | |
| 100 ng/mL | 64.6 ± 1.9 |
| 30 ng/mL | 60.9 ± 3.5 |
| 10 ng/mL | 50.3 ± 1.6 |
| 3 ng/mL | 24.3 ± 2.3 |
| 1 ng/mL | 8.1 ± 1.2 |
| 0.3 ng/mL | 2.9 ± 0.9 |
| pTSH | |
| 3 ng/mL | 55.4 ± 7.3 |
| 1 ng/mL | 51.7 ± 3.6 |
| 0.3 ng/mL | 18.5 ± 1.5 |
| 0.1 ng/mL | 7.2 ± 0.6 |
| 0.03 ng/mL | 2.4 ± 0.7 |
| 0.01 ng/mL | 1.4 ± 0.3 |

See legend to Table 6a for details.

TABLE 6c

Stimulation of cyclic AMP production by NIBSC reference preparation 90/672 and by K1-18 IgG and Fab preparations compared to M22 IgG

| Test sample | Cyclic AMP concentration (pmol/mL mean ± SD) | units/L | units/mg | mean units/mg |
|---|---|---|---|---|
| Cyclic AMP buffer NIBSC 90/672 | 1.36 ± 0.39 | | | |
| 3 units/L | 60.37 ± 3.73 | | | |
| 1 unit/L | 27.43 ± 3.52 | | | |
| 0.3 units/L | 12.47 ± 0.23 | | | |
| 0.1 units/L | 5.00 ± 0.69 | | | |
| K1-18 IgG | | | | |
| 100 ng/mL | 73.05 ± 3.43 | | | |
| 30 ng/mL | 63.68 ± 1.54 | | | |
| 10 ng/mL | 41.91 ± 3.97 | 1.85 | 185 | |
| 3 ng/mL | 16.87 ± 0.96 | 0.48 | 160 | 155 |
| 1 ng/mL | 5.36 ± 0.68 | 0.12 | 120 | |
| 0.3 ng/mL | 1.91 ± 0.45 | | | |
| K1-18 Fab | | | | |
| 100 ng/mL | 51.38 ± 1.87 | 2.40 | 24 | |
| 30 ng/mL | 22.25 ± 0.81 | 0.70 | 23 | 22 |
| 10 ng/mL | 8.34 ± 1.91 | 0.18 | 18 | |
| 3 ng/mL | 3.40 ± 0.52 | | | |
| 1 ng/mL | 1.91 ± 0.30 | | | |
| 0.3 ng/mL | 1.30 ± 0.32 | | | |
| M22 IgG | | | | |
| 10 ng/mL | 58.88 ± 8.96 | 2.9 | 290 | |
| 3 ng/mL | 24.57 ± 6.55 | 0.8 | 267 | 286 |
| 1 ng/mL | 12.01 ± 2.52 | 0.3 | 300 | |
| 0.3 ng/mL | 2.36 ± 0.29 | | | |
| 4B4 IgG | | | | |
| 10 ng/mL | 1.00 ± 0.33 | | | |
| 1 ng/mL | 1.09 ± 0.22 | | | |
| 4B4 Fab | | | | |
| 10 ng/mL | 0.89 ± 0.11 | | | |
| 1 ng/mL | 0.68* | | | |

See legend to Table 6a for details. 4B4 is a human MAb to glutamic acid decarboxylase (negative control). Test samples were diluted in hypotonic cyclic AMP buffer.

TABLE 6d

Comparison of stimulation of cyclic AMP production by porcine (p), native human (h) and recombinant human (rh) TSH in CHO cells expressing the TSHR

| Test sample | Cyclic AMP concentration in isotonic buffer (pmol/mL mean ± SD) | Cyclic AMP concentration in hypotonic buffer (pmol/mL mean ± SD) |
|---|---|---|
| Cyclic AMP buffer | 1.3 ± 0.5 | 2.0 ± 0.1 |
| pTSH | | |
| 20 ng/mL | 73.9 ± 12.7 | 89.9 ± 10.1 |
| 3 ng/mL | 46.6 ± 3.3 | 76.6 ± 0.0 |
| 2 ng/mL | 49.5 ± 3.9 | 77.6 ± 9.2 |
| 1 ng/mL | 37.8 ± 3.8 | 69.0 ± 1.4 |
| 0.3 ng/mL | 14.3 ± 1.1 | 34.1 ± 2.8 |
| 0.1 ng/mL | 4.0 ± 0.4 | 11.0 ± 0.6 |
| 0.03 ng/mL | 2.0 ± 0.3 | 4.1 ± 0.3 |
| 0.01 ng/mL | 1.4 ± 0.2 | 2.4 ± 0.2 |
| Native hTSH | | |
| 250 ng/mL | 57.9 ± 7.2 | 79.3 ± 1.0 |
| 100 ng/mL | 41.6 ± 3.0 | 74.4 ± 0.9 |
| 50 ng/mL | 29.0 ± 0.8 | 69.4 ± 11.7 |
| 25 ng/mL | 19.9 ± 1.2 | 55.2 ± 2.7 |
| 10 ng/mL | 9.6 ± 1.7 | 37.8 ± 2.0 |

TABLE 6d-continued

Comparison of stimulation of cyclic AMP production by porcine (p), native human (h) and recombinant human (rh) TSH in CHO cells expressing the TSHR

| Test sample | Cyclic AMP concentration in isotonic buffer (pmol/mL mean ± SD) | Cyclic AMP concentration in hypotonic buffer (pmol/mL mean ± SD) |
|---|---|---|
| 2.5 ng/mL | 3.7 ± 0.4 | 11.6 ± 0.2 |
| 1 ng/mL | 2.0 ± 1.2 | 6.1 ± 0.6 |
| rhTSH | | |
| 250 ng/mL | 46.2 ± 10.2 | 67.4 ± 4.6 |
| 100 ng/mL | 35.4 ± 2.5 | 63.0 ± 7.9 |
| 50 ng/mL | 24.5 ± 1.3 | 44.7 ± 4.3 |
| 25 ng/mL | 14.4 ± 0.6 | 30.6 ± 1.4 |
| 10 ng/mL | 6.2 ± 1.1 | 14.3 ± 1.2 |
| 2.5 ng/mL | 2.1 ± 0.4 | 6.0 ± 1.9 |
| 1 ng/mL | 1.4 ± 0.3 | 3.0 ± 0.3 |

See legend to Table 6a for details. pTSH was from RSR Ltd, Cardiff, CF23 8HE, UK. Native hTSH was an NIBSC reference preparation 81/565. rhTSH was an NIBSC reference preparation 94/674.

TABLE 6e

Stimulation of cyclic AMP production in TSHR transfected CHO cells by pTSH, M22 IgG and K1-18 IgG mixed together in different combinations

| Test sample | Cyclic AMP (pmol/mL; mean ± SD) |
|---|---|
| cyclic AMP buffer | 1.00 ± 0.72 |
| 10 ng/mL 5B3 IgG | 1.58* |
| 1 ng/mL 5B3 IgG | 1.19* |
| 0.1 ng/mL 5B3 IgG | 1.53* |
| 0.1 ng/mL pTSH | 11.01 ± 0.99 |
| 1 ng/mL M22 IgG | 35.17 ± 6.38 |
| 0.1 ng/mL pTSH + 1 ng/mL M22 IgG | 47.22 ± 3.89 |
| 0.05 ng/mL pTSH | 5.83* |
| 0.5 ng/mL M22 IgG | 20.20* |
| 0.05 ng/mL pTSH + 0.5 ng/mL M22 IgG | 25.99 ± 2.19 |
| 0.1 ng/mL pTSH | 11.01 ± 0.99 |
| 10 ng/mL K1-18 IgG | 45.09 ± 6.15 |
| 0.1 ng/mL pTSH + 10 ng/mL K1-18 IgG | 52.84 ± 6.76 |
| 0.05 ng/mL pTSH | 5.83* |
| 5 ng/mL K1-18 IgG | 29.95* |
| 0.05 ng/mL pTSH + 5 ng/mL K1-18 IgG | 29.87 ± 4.34 |
| 10 ng/mL K1-18 IgG | 45.09 ± 6.15 |
| 1 ng/mL M22 IgG | 35.17 ± 6.38 |
| 10 ng/mL K1-18 IgG + 1 ng/mL M22 IgG | 52.84 ± 6.76 |
| 5 ng/mL K1-18 IgG | 29.95* |
| 0.5 ng/mL M22 IgG | 20.20* |
| 5 ng/mL K1-18 IgG + 0.5 ng/mL M22 IgG | 44.01 ± 7.19 |

See legend to Table 6a for details. 5B3 is a human MAb to glutamic acid decarboxylase (negative control). Test samples were diluted in hypotonic cyclic AMP buffer.

TABLE 6f

Stimulation of cyclic AMP production in TSHR transfected CHO cells by NIBSC reference preparation 90/672 and by K1-18 IgG, donor serum and donor serum IgG (experiment 1)

| Test sample | Cyclic AMP concentration (pmol/mL mean ± SD) | units/L | units/mg | mean units/mg |
|---|---|---|---|---|
| Cyclic AMP buffer | 1.5 ± 0.3 | | | |
| NIBSC 90/672 | | | | |
| 3 units/L | 37.6 ± 3.9 | | | |
| 1 unit/L | 19.0 ± 1.4 | | | |
| 0.3 units/L | 6.8 ± 0.5 | | | |
| 0.1 units/L | 2.7 ± 0.3 | | | |

TABLE 6f-continued

Stimulation of cyclic AMP production in TSHR transfected CHO cells by NIBSC reference preparation 90/672 and by K1-18 IgG, donor serum and donor serum IgG (experiment 1)

| Test sample | Cyclic AMP concentration (pmol/mL mean ± SD) | units/L | units/mg | mean units/mg |
|---|---|---|---|---|
| K1 donor IgG | | | | |
| 30 µg/mL | 7.7 ± 1.0 | 0.45 | 0.013 | 0.013 |
| 10 µg/mL | 3.3 ± 0.2 | | | |
| 3 µg/mL | 1.8 ± 0.3 | | | |
| K1 donor serum | | | | |
| diluted 10x | 3.2 ± 0.4 | | | |
| diluted 30x | 4.7 ± 0.1 | 0.29 | | |
| diluted 100x | 2.8 ± 0.0 | | | |
| diluted 300x | 2.4 ± 0.3 | | | |
| HBD serum | | | | |
| diluted 10x | 1.8 ± 0.1 | | | |
| diluted 30x | 1.7 ± 0.4 | | | |
| diluted 100x | 1.4 ± 0.4 | | | |
| HBD serum IgG | | | | |
| 30 µg/mL | 1.2 ± 0.2 | | | |
| 10 µg/mL | 1.2 ± 0.2 | | | |
| 3 µg/mL | 2.1 ± 0.2 | | | |

See legend to Table 6a for details. HBD = serum from a healthy blood donor (HBD IgG was isolated from the same serum). Test samples were diluted in hypotonic cyclic AMP buffer.

TABLE 6g

Stimulation of cyclic AMP production in TSHR transfected CHO cells by NIBSC reference preparation 90/672 and by K1-18 IgG, donor serum and donor serum IgG (experiment 2)

| Test sample | Cyclic AMP concentration (pmol/mL mean ± SD) | units/L | units/mg | mean units/mg |
|---|---|---|---|---|
| Cyclic AMP buffer | 2.5* | | | |
| NIBSC 90/672 | | | | |
| 3 units/L | 64.6 ± 6.9 | | | |
| 1 unit/L | 36.4 ± 4.6 | | | |
| 0.3 units/L | 10.2 ± 1.0 | | | |
| 0.1 units/L | 4.3 ± 0.5 | | | |
| K1 donor serum IgG | | | | |
| 30 µg/mL | 15.6 ± 0.7 | 0.42 | 0.014 | 0.014 |
| 10 µg/mL | *5.7 | | | |
| 3 µg/mL | 2.2 ± 0.3 | | | |
| K1 donor serum | | | | |
| Diluted 10x | 6.9 ± 0.6 | | | |
| Diluted 30x | 9.5 ± 0.7 | 0.28 | | |
| Diluted 100x | 6.6 ± 0.9 | | | |
| Diluted 300x | 3.9 ± 2.4 | | | |
| HBD serum | | | | |
| Diluted 10x | 3.0 ± 0.7 | | | |
| Diluted 30x | 1.5 ± 1.5 | | | |
| Diluted 100x | 2.1 ± 0.3 | | | |
| HBD serum IgG | | | | |
| 30 µg/mL | 2.0 ± 0.2 | | | |
| 10 µg/mL | 2.1 ± 0.2 | | | |
| 3 µg/mL | 2.3 ± 0.9 | | | |

See legend to Table 6a for details. HBD = serum from a healthy blood donor (HBD IgG was isolated from the same serum). Test samples were diluted in hypotonic cyclic AMP buffer.

TABLE 6h

Inhibition of K1-18 IgG TSHR stimulating activity by human MAbs K1-70 and 5C9 IgGs with TSH antagonist activity

| Test sample | Cyclic AMP concentration (pmol/mL mean ± SD) | % Inhibition |
|---|---|---|
| Cyclic AMP buffer | 1.6 ± 0.2 | |
| K1-70 IgG 100 µg/mL | 1.1 ± 0.2 | |
| 5B3 IgG 100 µg/mL | 1.6 ± 0.5 | |
| 5C9 IgG 100 µg/mL | 1.0 ± 0.1 | |
| 10 ng/mL K1-18 IgG | 50.0 ± 3.3 | |
| 10 ng/mL K1-18 IgG + 100 µg/mL 5B3 IgG | 61.1 ± 5.9 | 0 |
| 10 ng/mL K1-18 IgG + 100 µg/mL K1-70 IgG | 1.3 ± 1.7 | 97 |
| 10 ng/mL K1-18 IgG + 50 µg/mL K1-70 IgG | 0.9 ± 1.5 | 98 |
| 10 ng/mL K1-18 IgG + 10 µg/mL K1-70 IgG | 0.1 ± 0.0 | 100 |
| 10 ng/mL K1-18 IgG + 5 µg/mL K1-70 IgG | 0.0 ± 0.0 | 100 |
| 10 ng/mL K1-18 IgG + 1 µg/mL K1-70 IgG | 0.1 ± 0.0 | 100 |
| 10 ng/mL K1-18 IgG + 0.5 µg/mL K1-70 IgG | 0.0 ± 0.0 | 100 |
| 10 ng/mL K1-18 IgG + 0.1 µg/mL K1-70 IgG | 3.8 ± 1.0 | 92 |
| 10 ng/mL K1-18 IgG + 0.01 µg/mL K1-70 IgG | 48.6 ± 1.7 | 3 |
| 10 ng/mL K1-18 IgG + 0.001 µg/mL K1-70 IgG | 52.1 ± 11.4 | 0 |
| 10 ng/mL K1-18 IgG + 100 µg/mL 5C9 IgG | 0.1 ± 0.0 | 100 |
| 10 ng/mL K1-18 IgG + 50 µg/mL 5C9 IgG | 0.1* | 100 |
| 10 ng/mL K1-18 IgG + 10 µg/mL 5C9 IgG | 1.4 ± 1.5 | 97 |
| 10 ng/mL K1-18 IgG + 5 µg/mL 5C9 IgG | 1.5 ± 2.4 | 97 |
| 10 ng/mL K1-18 IgG + 1 µg/mL 5C9 IgG | 0.9 ± 1.4 | 98 |
| 10 ng/mL K1-18 IgG + 0.5 µg/mL 5C9 IgG | 0.3* | 99 |
| 10 ng/mL K1-18 IgG + 0.1 µg/mL 5C9 IgG | 4.4 ± 1.5 | 91 |
| 10 ng/mL K1-18 IgG + 0.01 µg/mL 5C9 IgG | 51.8 ± 4.9 | 0 |
| 10 ng/mL K1-18 IgG + 0.001 µg/mL 5C9 IgG | 40.4 ± 7.0 | 19 |

See legend to Table 6a for details. 5B3 is a human MAb to glutamic acid decarboxylase (negative control). Test samples were diluted in hypotonic cyclic AMP buffer.

TABLE 6i

Inhibition of K1-18 IgG stimulation of cyclic AMP production in TSHR transfected CHO cells by K1-70 and 5C9 IgGs mixed together

| Test sample | Cyclic AMP concentration (pmol/mL; mean ± SD) | % Inhibition |
|---|---|---|
| Cyclic AMP buffer | 0.89 ± 0.15 | |
| 10 ng/mL K1-18 IgG | 50.3 ± 4.97 | |
| 100 µg/mL 5B3 IgG | 1.20 ± 0.24 | |
| 100 µg/mL 5C9 IgG | 0.55 ± 0.14 | |
| 100 µg/mL K1-70 IgG | 0.89 ± 0.13 | |
| 100 µg/mL (K1-70 IgG + 5C9 IgG)[a] | 0.86 ± 0.17 | |
| 10 ng/mL K1-18 + 100 µg/mL 5B3 IgG | 52.8 ± 0.21 | 0 |
| 10 ng/mL KM 8 + 10 µg/mL 5B3 IgG | 48.5 ± 2.16 | 3.5 |
| 10 ng/mL K1-18 + 100 µg/mL 5C9 IgG | 0.66 ± 0.25 | 98.7 |
| 10 ng/mL K1-18 + 10 µg/mL 5C9 IgG | 0.21 ± 0.18 | 99.6 |
| 10 ng/mL K1-18 + 1 µg/mL 5C9 IgG | 0.29 ± 0.25 | 99.4 |
| 10 ng/mL K1-18 + 0.1 µg/mL 5C9 IgG | 0.50 ± 0.62 | 99.0 |
| 10 ng/mL K1-18 + 0.01 µg/mL 5C9 IgG | 37.7 ± 1.75 | 25.0 |
| 10 ng/mL K1-18 + 0.001 µg/mL 5C9 IgG | 51.2 ± 2.6 | 0 |
| 10 ng/mL K1-18 + 100 µg/mL K1-70 IgG | 0.74 ± 0.12 | 98.5 |
| 10 ng/mL K1-18 + 10 µg/mL K1-70 IgG | 0.38 ± 0.20 | 99.2 |
| 10 ng/mL K1-18 + 1 µg/mL K1-70 IgG | 0.37 ± 0.15 | 99.3 |
| 10 ng/mL K1-18 + 0.1 µg/mL K1-70 IgG | 1.88 ± 0.06 | 96.3 |
| 10 ng/mL K1-18 + 0.01 µg/mL K1-70 IgG | 40.4 ± 3.19 | 19.6 |
| 10 ng/mL K1-18 + 0.001 µg/mL K1-70 | 49.74 ± 1.73 | 1.0 |
| 10 ng/mL K1-18 + 100 µg/mL (K1-70 IgG + 5C9 IgG)[a] | 0.57 ± 0.18 | 98.9 |
| 10 ng/mL K1-18 +10 µg/mL (K1-70 IgG + 5C9 IgG)[a] | 0.59 ± 0.11 | 98.8 |
| 10 ng/mL K1-18 + 1 µg/mL (K1-70 IgG + 5C9 IgG)[a] | 0.39 ± 0.09 | 99.2 |
| 10 ng/mL K1-18 + 0.1 µg/mL (K1-70 IgG + 5C9 IgG)[a] | 1.37 ± 0.92 | 97.3 |
| 10 ng/mL K1-18 + 0.01 µg/mL (K1-70 IgG + 5C9 IgG)[a] | 34.15 ± 0.62 | 32.0 |
| 18 10 ng/mL + 0.001 µg/mL (K1-70 IgG + 5C9 IgG)[a] | 37.4 ± 1.84 | 25.5 |

See legend to Table 6a for details. 5B3 is a human MAb to glutamic acid decarboxylase (negative control).
[a] The total final concentration of IgG mixture is shown; ie in the case of 100 µg/mL (K1-70 IgG + 5C9 IgG) the mixture contains 50 µg/mL K1-70 IgG and 50 µg/mL 5C9 IgG. Consequently, the combined effect of two IgGs at 100 µg/mL can be compared to the effect of the single IgG at the same concentration (100 µg/mL). Test samples were diluted in hypotonic cyclic AMP buffer.
µg/mL

TABLE 6j

Inhibition of M22 IgG stimulation of cyclic AMP production in TSHR transfected CHO cells by K1-70 and 5C9 IgGs mixed together

| Test sample | Cyclic AMP concentration (pmol/mL; mean ± SD) | % Inhibition |
|---|---|---|
| Cyclic AMP buffer | 1.8 ± 0.2 | |
| 3 ng/mL M22 IgG | 44.4 ± 7.1 | |
| 100 µg/mL 5B3 IgG | 2.3 ± 0.2 | |
| 100 µg/mL 5C9 IgG | 1.7 ± 0.2 | |
| 100 µg/mL K1-70 IgG | 1.8 ± 0.2 | |
| 100 µg/mL (K1-70 IgG + 5C9 IgG)[a] | 1.9 ± 0.2 | |
| 3 ng/mL M22 IgG + 100 µg/mL 5B3 IgG | 51.3 ± 1.2 | 0 |
| 3 ng/mL M22 IgG + 10 µg/mL 5B3 IgG | 44.7 ± 4.3 | 0 |
| 3 ng/mL M22 IgG + 100 µg/mL 5C9 IgG | 1.3 ± 0.2 | 97.1 |
| 3 ng/mL M22 IgG + 10 µg/mL 5C9 IgG | 2.5 ± 1.6 | 94.4 |
| 3 ng/mL M22 IgG + 1 µg/mL 5C9 IgG | 1.3 ± 0.1 | 97.1 |
| 3 ng/mL M22 IgG + 0.1 µg/mL 5C9 IgG | 3.2 ± 0.5 | 92.8 |

TABLE 6j-continued

Inhibition of M22 IgG stimulation of cyclic AMP production in TSHR transfected CHO cells by K1-70 and 5C9 IgGs mixed together

| Test sample | Cyclic AMP concentration (pmol/mL; mean ± SD) | % Inhibition |
|---|---|---|
| 3 ng/mL M22 IgG + 0.01 μg/mL 5C9 IgG | 33.2 ± 1.5 | 25.2 |
| 3 ng/mL M22 IgG + 0.001 μg/mL 5C9 IgG | 41.0 ± 1.9 | 7.7 |
| 3 ng/mL M22 IgG + 100 μg/mL K1-70 IgG | 1.4 ± 0.1 | 96.8 |
| 3 ng/mL M22 IgG + 10 μg/mL K1-70 IgG | 1.2 ± 0.1 | 97.3 |
| 3 ng/mL M22 IgG + 1 μg/mL K1-70 IgG | 1.5 ± 0.2 | 96.6 |
| 3 ng/mL M22 IgG + 0.1 ng/mL K1-70 IgG | 10.9 ± 3.7 | 75.5 |
| 3 ng/mL M22 IgG + 0.01 μg/mL K1-70 IgG | 38.4 ± 3.2 | 13.5 |
| 3 ng/mL M22 IgG + 0.001 μg/mL K1-70 IgG | 40.5 ± 1.3 | 8.8 |
| 3 ng/mL M22 IgG + 100 μg/mL (K1-70 IgG + 5C9 IgG)[a] | 1.7 ± 0.1 | 96.2 |
| 3 ng/mL M22 IgG + 10 μg/mL (K1-70 IgG + 5C9 IgG)[a] | 1.8 ± 0.2 | 95.9 |
| 3 ng/mL M22 IgG + 1 μg/mL (K1-70 IgG + 5C9 IgG)[a] | 1.4 ± 0.1 | 96.8 |
| 3 ng/mL M22 IgG + 0.1 μg/mL (K1-70 IgG + 5C9 IgG)[a] | 3.6 ± 0.4 | 91.9 |
| 3 ng/mL M22 IgG + 0.01 μg/mL (K1-70 IgG + 5C9 IgG)[a] | 39.1 ± 7.9 | 11.9 |
| 3 ng/mL M22 IgG + 0.001 μg/mL (K1-70 IgG + 5C9 IgG)[a] | 36.5 ± 2.8 | 17.8 |

See legend to Table 6i for details.

TABLE 6k

Inhibition of K1-18 IgG stimulation of cyclic AMP production in TSHR transfected CHO cells by K1-70 and 9D33 IgGs mixed together

| Test sample | Cyclic AMP concentration (pmol/mL; mean ± SD) | % Inhibition |
|---|---|---|
| Cyclic AMP buffer | 1.5 ± 0.05 | |
| 10 ng/mL K1-18 IgG | 37.0 ± 0.9 | |
| 100 μg/mL 5B3 IgG | 1.3 ± 0.1 | |
| 100 μg/mL 9D33 IgG | 2.0 ± 0.6 | |
| 100 μg/mL K1-70 IgG | 1.3 ± 0.1 | |
| 100 μg/mL (K1-70 IgG + 9D33 IgG)[a] | 1.3 ± 0.2 | |
| 10 ng/mL K1-18 IgG + 100 μg/mL 5B3 IgG | 41.9 ± 4.3 | −13 |
| 10 ng/mL K1-18 IgG + 10 μg/mL 5B3 IgG | 35.4 ± 1.6 | 4 |
| 10 ng/mL K1-18 IgG + 100 μg/mL 9D33 IgG | 2.2 ± 0.7 | 94 |
| 10 ng/mL K1-18 IgG + 10 μg/mL 9D33 IgG | 1.9 ± 0.6 | 95 |
| 10 ng/mL K1-18 IgG + 1 μg/mL 9D33 IgG | 1.9 ± 0.2 | 95 |
| 10 ng/mL K1-18 IgG + 0.1 μg/mL 9D33 IgG | 5.3 ± 1.1 | 86 |
| 10 ng/mL K1-18 IgG + 0.01 μg/mL 9D33 IgG | 31.32 ± 3.3 | 15 |
| 10 ng/mL K1-18 IgG + 0.001 μg/mL 9D33 IgG | 35.8 ± 2.3 | 3 |
| 10 ng/mL K1-18 IgG + 100 μg/mL K1-70 IgG | 1.4 ± 0.4 | 96 |
| 10 ng/mL K1-18 IgG + 10 μg/mL K1-70 IgG | 0.9 ± 0.1 | 98 |
| 10 ng/mL KM-18 IgG + 1 μg/mL K1-70 IgG | 1.1 ± 0.5 | 97 |
| 10 ng/mL K1-18 IgG + 0.1 μg/mL K1-70 IgG | 1.7 ± 0.8 | 95 |
| 10 ng/mL K1-18 IgG + 0.01 μg/mL K1-70 IgG | 27.7 ± 0.8 | 25 |
| 10 ng/mL K1-18 IgG + 0.001 μg/mL K1-70 IgG | 37.4 ± 1.3 | −1 |
| 10 ng/mL K1-18 IgG + 100 μg/mL (K1-70 IgG + 9D33 IgG)[a] | 1.2 ± 0.1 | 97 |
| 10 ng/mL K1-18 IgG + 10 μg/mL (K1-70 IgG + 9D33 IgG)[a] | 0.9 ± 0.2 | 98 |
| 10 ng/mL K1-18 IgG + 1 μg/mL (K1-70 IgG + 9D33 IgG)[a] | 1.1 ± 0.1 | 97 |
| 10 ng/mL K1-18 IgG + 0.1 μg/mL (K1-70 IgG + 9D33 IgG)[a] | 1.7 ± 0.05 | 95 |
| 10 ng/mL K1-18 IgG + 0.01 μg/mL (K1-70 IgG + 9D33 IgG)[a] | 29.4 ± 0.6 | 20 |
| 10 ng/mL K1-18 IgG + 0.001 μg/mL (K1-70 IgG + 9D33 IgG)[a] | 35.2 ± 1.7 | 5 |

See legend to Table 6i for details.

[a]The total final concentration of IgG mixture is shown; ie in the case of 100 μg/mL (K1-70 IgG + 9D33 IgG) the mixture contains 50 μg/mL K1-70 IgG and 50 μg/mL 9D33 IgG. Consequently, the combined effect of two IgGs at 100 μg/mL can be compared to the effect of the single IgG at the same concentration (100 μg/mL).

TABLE 6l

Inhibition of M22 IgG stimulation of cyclic AMP production in TSHR transfected CHO cells by K1-70 and 9D33 IgGs mixed together

| Test sample | Cyclic AMP concentration (pmol/mL; mean ± SD) | % Inhibition |
|---|---|---|
| Cyclic AMP buffer | 0.52 ± 0.3 | |
| 3 ng/mL M22 IgG | 21.33 ± 1.3 | |
| 100 μg/mL 5B3 IgG | 1.10 ± 0.3 | |
| 100 μg/mL 9D33 IgG | 1.31 ± 0.4 | |
| 100 μg/mL K1-70 IgG | 0.47 ± 0.1 | |
| 100 μg/mL (K1-70 IgG + 9D33 IgG)[a] | 0.45 ± 0.02 | |
| 3 ng/mL M22 IgG + 100 μg/mL 5B3 IgG | 28.13 ± 3.9 | 0 |
| 3 ng/mL M22 IgG + 10 μg/mL 5B3 IgG | 21.55 ± 1.2 | 0 |
| 3 ng/mL M22 IgG + 100 μg/mL 9D33 IgG | 1.01 ± 0.18 | 95 |
| 3 ng/mL M22 IgG + 10 μg/mL 9D33 IgG | 1.20 ± 0.1 | 94 |
| 3 ng/mL M22 IgG + 1 μg/mL 9D33 IgG | 1.48 ± 0.1 | 93 |
| 3 ng/mL M22 IgG + 0.1 μg/mL 9D33 IgG | 7.19 ± 1.6 | 66 |
| 3 ng/mL M22 IgG + 0.01 μg/mL 9D33 IgG | 21.00 ± 1.25 | 2 |
| 3 ng/mL M22 IgG + 0.001 μg/mL 9D33 IgG | 19.36 ± 7.3 | 9 |
| 3 ng/mL M22 IgG + 100 μg/mL K1-70 IgG | 0.77 ± 0.3 | 96 |
| 3 ng/mL M22 IgG + 10 μg/mL K1-70 IgG | 0.72 ± 0.3 | 97 |
| 3 ng/mL M22 IgG + 1 μg/mL K1-70 IgG | 0.82 ± 0.1 | 96 |
| 3 ng/mL M22 IgG + 0.1 μg/mL K1-70 IgG | 4.82 ± 0.7 | 77 |
| 3 ng/mL M22 IgG + 0.01 μg/mL K1-70 IgG | 18.67 ± 1.9 | 12 |
| 3 ng/mL M22 IgG + 0.001 μg/mL K1-70 IgG | 19.82 ± 0.3 | 7 |
| 3 ng/mL M22 IgG + 100 μg/mL (K1-70 IgG + 9D33 IgG)[a] | 0.77 ± 0.1 | 96 |
| 3 ng/mL M22 IgG + 10 μg/mL (K1-70 IgG + 9D33 IgG)[a] | 0.56 ± 0.4 | 97 |
| 3 ng/mL M22 IgG + 1 μg/mL (K1-70 IgG + 9D33 IgG)[a] | 0.90 ± 0.4 | 96 |
| 3 ng/mL M22 IgG + 0.1 μg/mL (K1-70 IgG + 9D33 IgG)[a] | 3.34 ± 2.4 | 84 |
| 3 ng/mL M22 IgG + 0.01 μg/mL (K1-70 IgG + 9D33 IgG)[a] | 18.20 ± 2.0 | 15 |
| 3 ng/mL M22 IgG + 0.001 μg/mL (K1-70 IgG + 9D33 IgG)[a] | 21.09 ± 0.6 | 1 |

See legend to Table 6i for details.

[a]The total final concentration of IgG mixture is shown; ie in the case of 100 μg/mL (K1-70 IgG + 9D33 IgG) the mixture contains 50 μg/mL K1-70 IgG and 50 μg/mL 9D33 IgG. Consequently, the combined effect of two IgGs at 100 μg/mL can be compared to the effect of the single IgG at the same concentration (100 μg/mL).

TABLE 6m

Inhibition of pTSH stimulation of cyclic AMP production in TSHR transfected CHO cells by K1-70 and 9D33 IgGs mixed together

| Test sample | Cyclic AMP concentration (pmol/mL; mean ± SD) | % Inhibition |
|---|---|---|
| Cyclic AMP buffer | 6.04 ± 1.78 | |
| 3 ng/mL pTSH | 70.82 ± 1.75 | |
| 100 µg/mL 5B3 IgG | 3.29 ± 0.18 | |
| 100 µg/mL 9D33 IgG | 1.58 + 0.25 | |
| 100 µg/mL K1-70 IgG | 1.27 ± 0.17 | |
| 100 µg/mL (K1-70 IgG + 9D33 IgG)$^a$ | 0.41 ± 0.68 | |
| 3 ng/mL pTSH + 100 µg/mL 5B3 IgG | 65.74* | 7 |
| 3 ng/mL pTSH + 10 µg/mL 5B3 IgG | 65.97 ± 7.7 | 7 |
| 3 ng/mL pTSH + 100 µg/mL 9D33 IgG | 3.26 ± 0.17 | 95 |
| 3 ng/mL pTSH + 10 µg/mL 9D33 IgG | 9.17 ± 1.46 | 87 |
| 3 ng/mL pTSH + 1 µg/mL 9D33 IgG | 23.60 ± 1.33 | 67 |
| 3 ng/mL pTSH + 0.1 µg/mL 9D33 IgG | 50.73 ± 5.03 | 28 |
| 3 ng/mL pTSH + 0.01 µg/mL 9D33 IgG | 67.60 ± 7.15 | 5 |
| 3 ng/mL pTSH + 0.001 µg/mL 9D33 IgG | 61.65 ± 6.60 | 13 |
| 3 ng/mL pTSH + 100 µg/mL K1-70 IgG | 1.46 ± 0.11 | 98 |
| 3 ng/mL pTSH + 10 µg/mL K1-70 IgG | 1.52 ± 0.25 | 98 |
| 3 ng/mL pTSH + 1 µg/mL K1-70 IgG | 1.70 ± 0.19 | 98 |
| 3 ng/mL pTSH + 0.1 µg/mL K1-70 IgG | 27.50 ± 3.26 | 61 |
| 3 ng/mL pTSH + 0.01 µg/mL K1-70 IgG | 74.70 ± 9.2 | 0 |
| 3 ng/mL pTSH + 0.001 µg/mL K1-70 IgG | 86.95 ± 4.38 | 0 |
| 3 ng/mL pTSH + 100 µg/mL (K1-70 IgG + 9D33 IgG)$^a$ | 1.69 ± 0.12 | 98 |
| 3 ng/mL pTSH + 10 µg/mL (K1-70 IgG + 9D33 IgG)$^a$ | 1.39 ± 0.08 | 98 |
| 3 ng/mL pTSH + 1 µg/mL (K1-70 IgG + 9D33 IgG)$^a$ | 1.90 ± 0.13 | 97 |
| 3 ng/mL pTSH + 0.1 µg/mL (K1-70 IgG + 9D33 IgG)$^a$ | 16.30 ± 1.16 | 77 |
| 3 ng/mL pTSH + 0.01 µg/mL (K1-70 IgG + 9D33 IgG)$^a$ | 61.50 ± 5.06 | 13 |
| 3 ng/mL pTSH + 0.001 µg/mL (K1-70 IgG + 9D33 IgG)$^a$ | 72.11 ± 5.5 | 0 |

See legend to Table 6i for details.
$^a$The total final concentration of IgG mixture is shown; ie in the case of 100 µg/mL (K1-70 IgG + 9D33 IgG) the mixture contains 50 µg/mL K1-70 IgG and 50 µg/mL 9D33 IgG. Consequently, the combined effect of two IgGs at 100 µg/mL can be compared to the effect of the single IgG at the same concentration (100 µg/mL).

TABLE 6n

Effect of K1 donor serum and serum TRAbs with blocking activity on stimulating activity of TSH, M22 IgG and K1-18 IgG

| Test sample | Cyclic AMP concentration (pmol/mL mean ± SD) | % Inhibition |
|---|---|---|
| Cyclic AMP buffer | 0.9 ± 0.2 | |
| 3 ng/mL pTSH | 73.7 ± 6.0 | |
| 3 ng/mL M22 IgG | 42.0 ± 9.5 | |
| 10 ng/mL K1-18 IgG | 44.1 ± 3.3 | |
| HBD control | 0.5 ± 0.4 | |
| HBD + 3 ng/mL pTSH | 99.4 ± 4.3 | 0 |
| HBD + 3 ng/mL M22 IgG | 34.7 ± 3.9 | 0 |
| HBD + 10 ng/mL K1-18 IgG | 22.0 ± 3.1 | 0 |
| B1 | 2.0 ± 0.1 | |
| B1 + 3 ng/mL pTSH | 32.0 ± 5.2 | 67.8 |
| B1 + 3 ng/mL M22 IgG | 4.5 ± 1.3 | 87.0 |
| B1 + 10 ng/mL K1-18 IgG | 3.8 ± 1.2 | 82.7 |
| B2 | 1.0 ± 0.7 | |
| B2 + 3 ng/mL pTSH | 1.7 ± 0.2 | 98.3 |
| B2 + 3 ng/mL M22 IgG | 0.9 ± 0.1 | 97.4 |
| B2 + 10 ng/mL K1-18 IgG | 0.6 ± 0.3 | 97.3 |
| B3 | 0.4 ± 0.1 | |
| B3 + 3 ng/mL pTSH | 9.3 ± 2.2 | 90.6 |
| B3 + 3 ng/mL M22 IgG | 4.9 ± 0.7 | 85.9 |
| B3 + 10 ng/mL K1-18 IgG | 6.1 ± 0.6 | 72.3 |
| Donor K1 | 3.8 ± 1.5 | |
| K1 + 3 ng/mL pTSH | 36.0 ± 3.7 | 63.8 |
| K1 + 3 ng/mL M22 IgG | 6.9 ± 0.8 | 80.1 |
| K1 + 10 ng/mL K1-18 IgG | 4.5 ± 0.2 | 79.5 |

See legend to Table 6a for details. pTSH = porcine TSH. B1-B3 are sera from patients with blocking type TRAb. HBD = healthy blood donor serum. Test samples were diluted in hypotonic cyclic AMP buffer.

TABLE 7a

Inhibition of porcine (p) TSH stimulation of cyclic AMP production in TSHR transfected CHO cells by K1-70 and 5C9 IgGs

| Test sample | Cyclic AMP concentration (pmol/mL mean ± SD) | % Inhibition |
|---|---|---|
| Cyclic AMP buffer only | 1.6 ± 0.3 | |
| 3 ng/mL pTSH | 62.6 ± 3.9 | 0 |
| 5B3 IgG | | |
| 100 µg/mL + 3 ng/mL pTSH | 66.7 ± 3.7 | 0 |
| 10 µg/mL + 3 ng/mL pTSH | 67.8 ± 3.7 | 0 |
| K1-70 IgG | | |
| 3 µg/mL + 3 ng/mL pTSH | 1.7 ± 0.6 | 97.3 |
| 1 µg/mL + 3 ng/mL pTSH | 2.0 ± 0.2 | 96.8 |
| 0.3 µg/mL + 3 ng/mL pTSH | 2.5 ± 0.9 | 96.0 |
| 0.1 µg/mL + 3 ng/mL pTSH | 5.8 ± 2.8 | 90.7 |
| 0.075 µg/mL + 3 ng/mL pTSH | 11.6 ± 2.0 | 81.5 |
| 0.05 µg/mL + 3 ng/mL pTSH | 31.4 ± 1.9 | 49.8 |
| 0.025 µg/mL + 3 ng/mL pTSH | 50.5 ± 7.3 | 19.3 |
| 0.01 µg/mL + 3 ng/mL pTSH | 60.1 ± 1.6 | 4.0 |
| 0.003 µg/mL + 3 ng/mL pTSH | 59.5 ± 5.1 | 5.0 |
| 3 µg/mL + no pTSH | 0.8 ± 0.1 | |
| 5C9 IgG | | |
| 3 µg/mL + 3 ng/mL pTSH | 4.5 ± 1.5 | 92.8 |
| 1 µg/mL + 3 ng/mL pTSH | 4.8 ± 0.7 | 92.3 |
| 0.3 µg/mL + 3 ng/mL pTSH | 7.8 ± 2.1 | 87.5 |
| 0.1 µg/mL + 3 ng/mL pTSH | 11.4 ± 1.1 | 81.8 |
| 0.0075 µg/mL + 3 ng/mL pTSH | 14.7 ± 0.6 | 76.5 |
| 0.05 µg/mL + 3 ng/mL pTSH | 23.3 ± 2.9 | 62.8 |
| 0.025 µg/mL + 3 ng/mL pTSH | 46.3 ± 4.6 | 26.0 |
| 0.01 µg/mL + 3 ng/mL pTSH | 61.8 ± 4.8 | 1.0 |
| 0.003 µg/mL + 3 ng/mL pTSH | 56.1 ± 7.5 | 10.4 |
| 3 µg/mL + no pTSH | 0.9 ± 0.1 | |

Results shown are mean ± SD of triplicate determinations. 5B3 is a human MAb to glutamic acid decarboxylase (negative control). Test samples were diluted in hypotonic cyclic AMP buffer.

TABLE 7b

Inhibition of porcine (p) TSH stimulation of cyclic AMP production in TSHR transfected CHO cells by K1-70 IgG and Fab preparations

| Test sample | Cyclic AMP concentration in hypotonic medium (pmol/mL mean ± SD) | Cyclic AMP concentration in isotonic medium (pmol/mL mean ± SD) |
|---|---|---|
| Cyclic AMP buffer only | 2.4 ± 0.4 | 0.7 ± 0.1 |
| 3 µg/mL 5B3 IgG | 1.9 ± 0.3 | 0.5 ± 0.1 |
| 3 µg/mL K1-70 IgG | 2.3 ± 0.9 | 0.5 ± 0.1 |
| 3 µg/mL K1-70 Fab | 2.3 ± 0.8 | 0.8 ± 0.2 |
| 3 ng/mL pTSH | 65.2 ± 11.2 | 42.4 ± 1.1 |

TABLE 7b-continued

Inhibition of porcine (p) TSH stimulation of cyclic AMP production in TSHR transfected CHO cells by K1-70 IgG and Fab preparations

| Test sample | Cyclic AMP concentration in hypotonic medium (pmol/mL mean ± SD) | Cyclic AMP concentration in isotonic medium (pmol/mL mean ± SD) |
|---|---|---|
| 5B3 IgG | | |
| 3 µg/mL + 3 ng/mL pTSH | 75.7 ± 11.4 | 42.5 ± 2.8 |
| 1 µg/mL + 3 ng/mL pTSH | 71.9 ± 14.3 | 39.5 ± 1.9 |
| K1-70 IgG | | |
| 3 µg/mL + 3 ng/mL pTSH | 3.0 ± 1.2 | 1.1 ± 0.2 |
| 1 µg/mL + 3 ng/mL pTSH | 4.0 ± 0.7 | 2.2 ± 0.2 |
| 0.3 µg/mL + 3 ng/mL pTSH | 4.5 ± 0.6 | 8.2 ± 0.4 |
| 0.1 µg/mL + 3 ng/mL pTSH | 8.4 ± 0.9 | 27.0 ± 3.5 |
| 0.075 µg/mL + 3 ng/mL pTSH | 16.3 ± 1.3 | 33.3 ± 0.7 |
| 0.05 µg/mL + 3 ng/mL pTSH | 24.5 ± 5.2 | 36.5 ± 2.2 |
| 0.025 µg/mL + 3 ng/mL pTSH | 71.0 ± 4.5 | 38.1 ± 3.8 |
| 0.01 µg/mL + 3 ng/mL pTSH | 64.0 ± 9.9 | 45.0 ± 3.0 |
| 0.003 µg/mL + 3 ng/mL pTSH | 72.5 ± 16.2 | 40.8 ± 3.5 |
| K1-70 Fab | | |
| 3 µg/mL + 3 ng/mL pTSH | 3.7 ± 0.3 | 1.8 ± 0.5 |
| 1 µg/mL + 3 ng/mL pTSH | 3.8 ± 0.2 | 2.1 ± 0.8 |
| 0.3 µg/mL + 3 ng/mL pTSH | 5.2 ± 1.0 | 5.6 ± 1.3 |
| 0.1 µg/mL + 3 ng/mL pTSH | 12.9 ± 1.4 | 18.5 ± 2.1 |
| 0.075 µg/mL + 3 ng/mL pTSH | 14.1 ± 1.0 | 22.4 ± 0.4 |
| 0.05 µg/mL + 3 ng/mL pTSH | 28.9 ± 1.5 | 28.9 ± 1.1 |
| 0.025 µg/mL + 3 ng/mL pTSH | 59.9 ± 5.8 | 42.4 ± 1.1 |
| 0.01 µg/mL + 3 ng/mL pTSH | 58.8 ± 1.5 | 43.2 ± 4.0 |
| 0.003 µg/mL + 3 ng/mL pTSH | 56.3 ± 6.0 | 41.2 ± 1.0 |

See legend to Table 7a for details. Test samples were diluted in cyclic AMP buffer.

TABLE 7c

The effect of human and mouse TSHR blocking MAbs (K1-70, 5C9 and 9D33) on the constitutive activity (ie basal activity) of the TSHR

| Test sample | Cyclic AMP concentration (pmol/mL mean ± SD) | % Inhibition |
|---|---|---|
| Cyclic AMP buffer only | 18.7 ± 2.3 | 0 |
| K1-70 IgG | | |
| 100 µg/mL | 17.6 ± 1.6 | 6 |
| 10 µg/mL | 17.3 ± 0.3 | 7 |
| 3 µg/mL | 18.1 ± 0.7 | 3 |
| 1 µg/mL | 16.8 ± 0.5 | 10 |
| 0.3 µg/mL | 18.9 ± 1.2 | 0 |
| 0.1 µg/mL | 19.6 ± 0.8 | 0 |
| 0.01 µg/mL | 19.1 ± 2.6 | 0 |
| 0.001 µg/mL | 20.3 ± 3.1 | 0 |
| 5C9 IgG | | |
| 100 µg/mL | 9.0 ± 1.0 | 52 |
| 10 µg/mL | 8.3 ± 0.9 | 56 |
| 3 µg/mL | 6.9 ± 0.8 | 63 |
| 1 µg/mL | 7.4 ± 1.3 | 61 |
| 0.3 µg/mL | 9.3 ± 1.2 | 50 |
| 0.1 µg/mL | 16.3 ± 0.9 | 13 |
| 0.01 µg/mL | 18.6 ± 1.7 | 1 |
| 0.001 µg/mL | 19.1 ± 0.8 | 0 |
| 9D33 IgG | | |
| 100 µg/mL | 38.0 ± 1.9 | 0 |
| 10 µg/mL | 34.3 ± 1.4 | 0 |
| 3 µg/mL | 32.3 ± 2.3 | 0 |
| 1 µg/mL | 35.5 ± 4.3 | 0 |
| 0.3 µg/mL | 26.4 ± 1.2 | 0 |
| 0.1 µg/mL | 23.9 ± 2.7 | 0 |
| 0.01 µg/mL | 20.3 ± 1.2 | 0 |
| 0.001 µg/mL | 18.8 ± 2.1 | 0 |

See legend to Table 7a for details. The experiments were carried out using CHO cell line expressing wild type TSHR at approximately $5 \times 10^5$ receptors per cell.

TABLE 7d

Effect of K1 donor serum on TSH mediated stimulation of cyclic AMP in CHO cells expressing TSHR

| Test sample | Cyclic AMP concentration (pmol/mL mean ± SD) | % Inhibition |
|---|---|---|
| Cyclic AMP buffer | 1.7 ± 1.0 | |
| 1 ng/mL pTSH | 61.7 ± 4.3 | |
| 3 µg/mL K1-70 IgG | 1.7 ± 0.1 | |
| 1 ng/mL pTSH + 3 µg/mL K1-70 IgG | 3.6 ± 0.6 | 94.2 |
| 1 ng/mL pTSH + 1 µg/mL K1-70 IgG | 3.9 ± 0.1 | 93.7 |
| 1 ng/mL pTSH + 0.3 µg/mL K1-70 IgG | 3.3 ± 0.4 | 94.7 |
| 1 ng/mL pTSH + 0.1 µg/mL K1-70 IgG | 20.0 ± 1.2 | 67.6 |
| 1 ng/mL pTSH + 0.03 µg/mL K1-70 IgG | 52.2 ± 11.2 | 18.2 |
| 1 ng/mL pTSH + 0.01 µg/mL K1-70 IgG | 67.7 ± 3.7 | 0 |
| 1 ng/mL pTSH + 0.003 µg/mL K1-70 IgG | 72.4 ± 5.5 | 0 |
| 1 ng/mL pTSH + 0.001 µg/mL K1-70 IgG | 58.7 ± 2.2 | 4.9 |
| 1 ng/mL pTSH + 0.0003 µg/mL K1-70 IgG | 66.2 ± 1.7 | 0 |
| 100 µg/mL 5B3 IgG | 2.6 ± 0.2 | |
| 1 ng/mL pTSH + 100 µg/mL 5B3 IgG | 79.3 ± 8.9 | 0 |
| 1 ng/mL pTSH + 10 µg/mL 5B3 IgG | 80.7 ± 1.1 | 0 |
| 1 ng/mL pTSH + K1 donor serum 10x diluted | 14.9 ± 1.2 | 75.9 |
| 1 ng/mL pTSH + K1 donor serum 20x diluted | 51.6 ± 2.6 | 16.4 |
| 1 ng/mL pTSH + K1 donor serum 40x diluted | 63.0 ± 3.4 | 0 |
| 1 ng/mL pTSH + K1 donor serum 80x diluted | 64.4 ± 3.5 | 0 |
| 1 ng/mL pTSH + K1 donor serum 160x diluted | 63.9 ± 3.6 | 0 |
| K1 donor serum 10x diluted | 4.7 ± 0.3 | |
| 1 ng/mL pTSH + HBD 10x diluted | 101.3 ± 5.1 | 0 |
| 1 ng/mL pTSH + HBD 20x diluted | 88.6 ± 6.4 | 0 |
| HBD 10x diluted | 2.2 ± 1.0 | |

See legend to Table 7a for details. HBD = pool of healthy blood donor sera. pTSH = porcine TSH.

TABLE 7e

Effect of K1-70 IgG on stimulation of cyclic AMP production by porcine (p), human (h) and recombinant human (rh) TSH in CHO cells expressing the TSHR

| Test sample | Cyclic AMP concentration in hypotonic medium (pmol/mL mean ± SD) | Cyclic AMP concentration in isotonic medium (pmol/mL mean ± SD) |
|---|---|---|
| Cyclic AMP buffer | 2.5 ± 0.5 | 1.1 ± 0.4 |
| 100 µg/mL 5B3 IgG | 2.2 ± 0.6 | 1.4 ± 0.5 |
| 100 µg/mL K1-70 IgG | 2.5 ± 0.5 | 1.1 ± 0.2 |
| pTSH 3 ng/mL | 48.1 ± 0.9 | 41.1 ± 2.2 |
| pTSH 3 ng/mL + 100 µg/mL K1-70 IgG | 0.1 ± 0.0 | 1.3 ± 0.3 |
| pTSH 3 ng/mL + 10 µg/mL K1-70 IgG | 0.2 ± 0.1 | 1.2 ± 0.3 |
| pTSH 3 ng/mL + 1 µg/mL K1-70 IgG | 0.1* | 2.0 ± 0.4 |
| pTSH 3 ng/mL + 0.1 µg/mL K1-70 IgG | 3.3 ± 2.8 | 24.4 ± 1.2 |
| pTSH 3 ng/mL + 0.01 µg/mL K1-70 IgG | 53.8 ± 3.4 | 39.7 ± 3.0 |
| pTSH 3 ng/mL + 0.001 µg/mL K1-70 IgG | 44.9 ± 1.8 | 36.6 ± 5.8 |
| 100 ng/mL hTSH | 56.8 ± 0.1 | 42.3 ± 4.5 |
| 100 ng/mL hTSH + 100 µg/mL K1-70 IgG | 0.1* | 1.3 ± 0.3 |
| 100 ng/mL hTSH + 10 µg/mL K1-70 IgG | 0.1 ± 0.0 | 1.0 ± 0.3 |
| 100 ng/mL hTSH + 1 µg/mL K1-70 IgG | 0.2 ± 0.1 | 1.9 ± 0.2 |
| 100 ng/mL hTSH + 0.1 µg/mL K1-70 IgG | 0.1 ± 0.0 | 29.8 ± 1.5 |
| 100 ng/mL hTSH + 0.01 µg/mL K1-70 IgG | 55.2* | 37.9 ± 2.7 |
| 100 ng/mL hTSH + 0.001 µg/mL K1-70 IgG | 55.0 ± 3.0 | 38.8 ± 2.8 |
| 100 ng/mL rhTSH | 37.8 ± 4.9 | 29.9 ± 2.3 |
| 100 ng/mL rhTSH + 100 µg/mL K1-70 IgG | 0.3 ± 0.1 | 0.9 ± 0.1 |
| 100 ng/mL rhTSH + 10 µg/mL K1-70 IgG | 0.2 ± 0.1 | 0.7 ± 0.2 |
| 100 ng/mL rhTSH + 1 µg/mL K1-70 IgG | 0.3* | 1.3 ± 0.6 |
| 100 ng/mL rhTSH + 0.1 µg/mL K1-70 IgG | 0.3 ± 0.1 | 10.2 ± 0.9 |
| 100 ng/mL rhTSH + 0.01 µg/mL K1-70 IgG | 27.3 ± 5.5 | 21.4 ± 1.0 |
| 100 ng/mL rhTSH + 0.001 µg/mL K1-70 IgG | 30.8 ± 1.4 | 23.0 ± 3.8 |
| 100 ng/mL rhTSH + 100 µg/mL K1-70 IgG | 36.7 ± 3.4 | 28.1 ± 1.5 |

See legend to Table 7a for details.
*mean of duplicate determinations. Test samples were diluted in cyclic AMP buffer.

TABLE 7f

Effect of K1-70 IgG on M22 IgG mediated stimulation of cyclic AMP production in CHO cells expressing the TSHR

| Test sample | Cyclic AMP concentration (pmol/mL mean ± SD) | % Inhibition |
|---|---|---|
| Cyclic AMP buffer | 1.4 ± 0.4 | |
| K1-70 IgG 100 µg/mL | 1.1 ± 0.5 | |
| 5B3 IgG 100 µg/mL | 1.2 ± 0.5 | |
| 5C9 IgG 100 µg/mL | 0.5 ± 0.2 | |
| 3 ng/mL M22 IgG | 33.1 ± 1.8 | 0 |
| 3 ng/mL M22 IgG + 100 µg/ml 5B3 IgG | 41.8 ± 5.3 | 0 |
| 3 ng/mL M22 IgG + 100 µg/ml K1-70 IgG | 0.6 ± 0.3 | 98.2 |
| 3 ng/mL M22 IgG + 50 µg/ml K1-70 IgG | 0.8 ± 0.4 | 97.6 |
| 3 ng/mL M22 IgG + 10 µg/ml K1-70 IgG | 0.6 ± 0.4 | 98.2 |
| 3 ng/mL M22 IgG + 5 µg/ml K1-70 IgG | 0.1 ± 0.2 | 99.7 |
| 3 ng/mL M22 IgG + 1 µg/ml K1-70 IgG | 0.6 ± 0.2 | 98.2 |
| 3 ng/mL M22 IgG + 0.5 g/ml K1-70 IgG | 0.5 ± 0.3 | 98.5 |
| 3 ng/mL M22 IgG + 0.1 µg/ml K1-70 IgG | 4.3 ± 2.4 | 87.0 |
| 3 ng/mL M22 IgG + 0.01 µg/ml K1-70 IgG | 33.0 ± 3.2 | 0 |
| 3 ng/mL M22 IgG + 0.001 µg/ml K1-70 IgG | 35.9 ± 3.2 | 0 |
| 3 ng/mL M22 IgG + 100 µg/ml 5C9 IgG | 0.4 ± 0.4 | 98.8 |
| 3 ng/mL M22 IgG + 50 µg/ml 5C9 IgG | 0.3 ± 0.1 | 99.1 |
| 3 ng/mL M22 IgG + 10 µg/ml 5C9 IgG | 0.3 ± 0.1 | 99.1 |
| 3 ng/mL M22 IgG + 5 µg/ml 5C9 IgG | 0.2 ± 0.2 | 99.4 |
| 3 ng/mL M22 IgG + 1 µg/ml 5C9 IgG | 0.8 ± 0.4 | 97.6 |
| 3 ng/mL M22 IgG + 0.5 µg/ml 5C9 IgG | 1.0 ± 0.1 | 97.0 |
| 3 ng/mL M22 IgG + 0.1 µg/ml 5C9 IgG | 2.9 ± 0.6 | 91.2 |
| 3 ng/mL M22 IgG + 0.01 µg/ml 5C9 IgG | 42.3 ± 7.1 | 0 |
| 3 ng/mL M22 IgG + 0.001 µg/ml 5C9 IgG | 39.3 ± 3.6 | 0 |

See legend to Table 7a for details. HBD = pool of healthy blood donor sera.

TABLE 7g

Effect of K1-70 IgG on TSHR stimulating activity of TRAb positive patient sera (T1-T3)

| Test sample | Cyclic AMP concentration (pmol/mL mean ± SD) | % Inhibition |
|---|---|---|
| Cyclic AMP buffer | 2.0 ± 0.6 | |
| HBD | 1.7 ± 0.2 | |
| HBD + 100 μg/mL 5B3 IgG | 2.0 ± 0.1 | |
| HBD + 100 μg/mL K1-70 IgG | 1.2 ± 0.1 | |
| HBD + 100 μg/mL 5C9 IgG | 0.9 ± 0.3 | |
| HBD + 100 μg/mL 9D33 IgG | 1.9 ± 0.1 | |
| T1 serum | 99.8 ± 6.1 | 0 |
| T1 serum + 100 μg/mL 5B3 IgG | 94.9 ± 14.2 | 4.9 |
| T1 serum + 100 μg/mL K1-70 IgG | 1.4 ± 0.3 | 98.6 |
| T1 serum + 100 μg/mL 5C9 IgG | 1.3 ± 0.2 | 98.7 |
| T1 serum + 100 μg/mL 9D33 IgG | 4.6 ± 0.7 | 95.4 |
| T2 serum | 61.8 ± 6.3 | 0 |
| T2 serum + 100 μg/mL 5B3 IgG | 62.0 ± 14.6 | 0 |
| T2 serum + 100 μg/mL K1-70 IgG | 1.5 ± 0.1 | 97.6 |
| T2 serum + 100 μg/mL 5C9 IgG | 1.1 ± 0.3 | 98.2 |
| T2 serum + 100 μg/mL 9D33 IgG | 2.0 ± 0.2 | 96.8 |
| T3 serum | 63.3 ± 9.7 | 0 |
| T3 serum + 100 μg/mL 5B3 IgG | 54.2 ± 3.8 | 14.4 |
| T3 serum + 100 μg/mL K1-70 IgG | 1.2 ± 0.3 | 98.1 |
| T3 serum + 100 μg/mL 5C9 IgG | 1.4 ± 0.2 | 97.8 |
| T3 serum + 100 μg/mL 9D33 IgG | 3.7 ± 1.0 | 94.2 |
| 100 μg/mL 5B3 IgG | 1.0 ± 0.4 | |
| 100 μg/mL K1-70 IgG | 0.8 ± 0.1 | |
| 100 μg/mL 5C9 IgG | 1.0 ± 0.5 | |
| 100 μg/mL 9D33 IgG | 2.1 ± 0.5 | |

See legend to Table 7a for details. HBD = pool of healthy blood donor sera. Sera were diluted to a final concentration of 1:10 in hypotonic cyclic AMP assay buffer.

TABLE 7h

Effect of K1-70 IgG on TSHR stimulating activity of TRAb positive patient sera (T4-T6)

| Test sample | Cyclic AMP concentration (pmol/mL mean ± SD) | % Inhibition |
|---|---|---|
| Cyclic AMP buffer | 1.9 ± 0.4 | |
| HBD | 2.4 ± 0.1 | |
| HBD + 100 μg/mL 5B3 IgG | 3.0 ± 0.1 | |
| HBD + 100 μg/mL K1-70 IgG | 2.1 ± 0.2 | |
| HBD + 100 μg/mL 5C9 IgG | 1.8 ± 0.9 | |
| HBD + 100 μg/mL 9D33 | 3.9 ± 0.5 | |
| T4 serum | 78.9 ± 8.2 | 0 |
| T4 serum + 100 μg/mL 5B3 IgG | 55.0 ± 14.0 | 30.3 |
| T4 serum + 100 μg/mL K1-70 IgG | 3.0 ± 0.4 | 96.2 |
| T4 serum + 100 μg/mL 5C9 IgG | 1.9 ± 0.3 | 97.6 |
| T4 serum + 100 μg/mL 9D33 | 4.1 ± 1.1 | 94.8 |
| T5 serum | 66.6* | 0 |
| T5 serum + 100 μg/mL 5B3 IgG | 66.7 ± 5.3 | 0 |
| T5 serum + μg/mL K1-70 IgG 100 | 1.6 ± 0.4 | 97.6 |
| T5 serum + 100 μg/mL 5C9 IgG | 1.1 ± 0.2 | 98.3 |
| T5 serum + 100 μg/mL 9D33 | 2.9 ± 0.2 | 95.6 |
| T6 serum | 83.0 ± 6.9 | 0 |
| T6 serum + 100 μg/mL 5B3 IgG | 81.5 ± 20.5 | 1.8 |
| T6 serum + μg/mL K1-70 IgG 100 | 2.5 ± 0.1 | 97.0 |
| T6 serum + 100 μg/mL 5C9 IgG | 1.8 ± 0.4 | 97.8 |
| T6 serum + 100 μg/mL 9D33 | 5.0 ± 1.0 | 94.0 |
| 100 μg/mL 5B3 IgG | 2.6 ± 0.7 | |
| 100 μg/mL K1-70 IgG | 1.4 ± 0.5 | |
| 100 μg/mL 5C9 IgG | 1.2 ± 0.3 | |
| 100 μg/mL 9D33 | 2.0 ± 0.6 | |

See legend to Table 7g for details.
*mean of duplicate determinations.
HBD = pool of healthy blood donor sera.

TABLE 7i

Effect of K1-70 IgG on TSHR stimulating activity of TRAb positive patient sera (T7-T9)

| Test sample | Cyclic AMP concentration (pmol/mL mean ± SD) | % Inhibition |
|---|---|---|
| Cyclic AMP buffer | 2.9 ± 1.1 | |
| HBD | 3.1 ± 0.4 | |
| HBD + 100 μg/mL 5B3 IgG | 4.0 ± 0.4 | |
| HBD + 100 μg/mL K1-70 IgG | 2.7 ± 0.1 | |
| HBD + 100 μg/mL 5C9 IgG | 2.7 ± 1.4 | |
| HBD + 100 μg/mL 9D33 IgG | 5.4 ± 0.3 | |
| T7 serum | 90.6* | 0 |
| T7 serum + 100 μg/mL 5B3 IgG | 91.9 ± 29.6 | 0 |
| T7 serum + 100 μg/mL K1-70 IgG | 3.2 ± 0.4 | 96.5 |
| T7 serum + 100 μg/mL 5C9 IgG | 2.1 ± 0.5 | 97.7 |
| T7 serum + 100 μg/mL 9D33 IgG | 6.3 ± 1.2 | 93.0 |
| T8 serum | 85.6* | 0 |
| T8 serum + 100 μg/mL 5B3 IgG | 76.3 ± 10.7 | 10.9 |
| T8 serum + 100 μg/mL K1-70 IgG | 3.2 ± 0.5 | 96.3 |
| T8 serum + 100 μg/mL 5C9 IgG | 1.8 ± 0.3 | 97.9 |
| T8 serum + 100 μg/mL 9D33 IgG | 4.3 ± 0.6 | 95.0 |
| T9 serum | 56.4 ± 0.0 | 0 |
| T9 serum + 100 μg/mL 5B3 IgG | 53.2* | 0 |
| T9 serum + 100 μg/mL K1-70 IgG | 5.2 ± 0.5 | 90.8 |
| T9 serum + 100 μg/mL 5C9 IgG | 3.0 ± 0.4 | 94.7 |
| T9 serum + 100 μg/mL 9D33 IgG | 7.2 ± 1.1 | 87.2 |
| 100 μg/mL 5B3 IgG | 2.7 ± 0.3 | |
| 100 μg/mL K1-70 IgG | 1.6 ± 0.4 | |
| 100 μg/mL 5C9 IgG | 1.0 ± 0.5 | |
| 100 μg/mL 9D33 IgG | 2.4 ± 0.4 | |

See legend to Table 7g for details.
*mean of duplicate determinations.
HBD = pool of healthy blood donor sera.

TABLE 7j

Effect of K1-70 IgG on TSHR stimulating activity of TRAb positive patient sera (T10-T12)

| Test sample | Cyclic AMP concentration (pmol/mL mean ± SD) | % Inhibition |
|---|---|---|
| Cyclic AMP buffer | 1.8 ± 0.2 | |
| HBD | 2.2 ± 0.2 | |
| HBD + 100 μg/mL 5B3 IgG | 2.4 ± 0.4 | |
| HBD + 100 μg/mL K1-70 IgG | 1.7 ± 0.0 | |
| HBD + 100 μg/mL 5C9 IgG | 1.1 ± 0.3 | |
| HBD + 100 μg/mL 9D33 IgG | 3.2 ± 0.6 | |
| T10 serum | 56.3 ± 5.2 | 0 |
| T10 serum + 100 μg/mL 5B3 IgG | 59.3 ± 7.1 | 0 |
| T10 serum + 100 μg/mL K1-70 IgG | 1.8 ± 0.2 | 96.8 |
| T10 serum + 100 μg/mL 5C9 IgG | 0.9 ± 0.1 | 98.4 |
| T10 serum + 100 μg/mL 9D33 IgG | 2.6 ± 0.3 | 95.4 |
| T11 serum | 41.0 ± 4.5 | 0 |
| T11 serum + 100 μg/mL 5B3 IgG | 39.7 ± 1.8 | 3.2 |
| T11 serum + 100 μg/mL K1-70 IgG | 2.0 ± 0.2 | 95.1 |
| T11 serum + 100 μg/mL 5C9 IgG | 37.5 ± 3.9 | 8.5 |
| T11 serum + 100 μg/mL 9D33 IgG | 5.3 ± 1.6 | 87.1 |
| T12 serum | 43.2 ± 3.1 | 0 |
| T12 serum + 100 μg/mL 5B3 IgG | 43.3 ± 4.0 | 0 |
| T12 serum + 100 μg/mL K1-70 IgG | 1.8 ± 0.0 | 95.8 |
| T12 serum + 100 μg/mL 5C9 IgG | 1.6 ± 0.7 | 96.3 |
| T12 serum + 100 μg/mL 9D33 IgG | 3.6 ± 0.1 | 91.7 |
| 100 μg/mL 5B3 IgG | 2.0 ± 0.4 | |
| 100 μg/mL K1-70 IgG | 1.1 ± 0.1 | |
| 100 μg/mL 5C9 IgG | 0.9 ± 0.1 | |
| 100 μg/mL 9D33 IgG | 1.9 ± 0.4 | |

See legend to Table 7g for details. HBD = pool of healthy blood donor sera.

TABLE 7k

Effect of K1-70 IgG on TSHR stimulating activity of TRAb positive patient sera (T13-T15)

| Test sample | Cyclic AMP concentration (pmol/mL mean ± SD) | % Inhibition |
|---|---|---|
| Cyclic AMP buffer | 1.6 ± 0.2 | |
| HBD | 2.2 ± 0.4 | |
| HBD + 100 µg/mL 5B3 IgG | 5.1 ± 1.2 | |
| HBD + 100 µg/mL K1-70 IgG | 2.1 ± 0.8 | |
| HBD + 100 µg/mL 5C9 IgG | 1.0 ± 0.2 | |
| HBD + 100 µg/mL 9D33 IgG | 3.3 ± 0.3 | |
| T13 serum | 48.5 ± 3.8 | 0 |
| T13 serum + 100 µg/mL 5B3 IgG | 37.6 ± 3.4 | 22.5 |
| T13 serum + 100 µg/mL K1-70 IgG | 2.1 ± 0.3 | 95.7 |
| T13 serum + 100 µg/mL 5C9 IgG | 1.2 ± 0.3 | 97.5 |
| T13 serum + 100 µg/mL 9D33 IgG | 3.8 ± 0.3 | 92.2 |
| T14 serum | 27.2 ± 3.6 | 0 |
| T14 serum + 100 µg/mL 5B3 IgG | 20.5 ± 2.3 | 24.6 |
| T14 serum + 100 µg/mL K1-70 IgG | 1.9 ± 0.4 | 93.0 |
| T14 serum + 100 µg/mL 5C9 IgG | 1.4 ± 0.5 | 94.9 |
| T14 serum + 100 µg/mL 9D33 IgG | 2.8 ± 0.3 | 89.7 |
| T15 serum | 51.3* | 0 |
| T15 serum + 100 µg/mL 5B3 IgG | 41.9 ± 4.0 | 18.3 |
| T15 serum + 100 µg/mL K1-70 IgG | 2.7 ± 0.1 | 94.7 |
| T15 serum + 100 µg/mL 5C9 IgG | 1.6 ± 0.3 | 96.9 |
| T15 serum + 100 µg/mL 9D33 IgG | 3.9 ± 0.2 | 92.4 |
| 100 µg/mL 5B3 IgG | 4.1 ± 0.9 | |
| 100 µg/mL K1-70 IgG | 2.6 ± 1.5 | |
| 100 µg/mL 5C9 IgG | 0.9 ± 0.2 | |
| 100 µg/mL 9D33 IgG | 2.3 ± 0.2 | |

See legend to Table 7g for details.
*mean of duplicate determinations.
HBD = pool of healthy blood donor sera.

TABLE 7l

Effect on T5 serum stimulating activity of different concentrations of TSHR blocking monoclonal antibodies (K1-70, 5C9, 9D33)

| Test sample | Cyclic AMP concentration (pmol/mL mean ± SD) | % Inhibition |
|---|---|---|
| Cyclic AMP buffer | 1.4 ± 0.5 | |
| HBD diluted 10x | 2.8 ± 0.7 | |
| Serum T5 diluted 10x | 63.9 ± 5.9 | |
| 5B3 IgG (negative control) | | |
| 100 µg/mL | 1.1 ± 0.5 | |
| 100 µg/mL + T5 | 55.9 ± 5.5 | 12.5 |
| 10 µg/mL + T5 | 61.9 ± 2.6 | 3.1 |
| 1 µg/mL + T5 | 61.3 ± 5.5 | 4.1 |
| 0.1 µg/mL + T5 | 59.4* | 7.0 |
| K1-70 IgG | | |
| 100 µg/mL | 1.0 ± 0.3 | |
| 100 µg/mL + T5 | 1.4 ± 0.6 | 97.8 |
| 10 µg/mL + T5 | 0.9 ± 0.1 | 98.6 |
| 1 µg/mL + T5 | 1.4 ± 0.1 | 97.8 |
| 0.1 µg/mL + T5 | 8.3 ± 1.1 | 87.0 |
| 0.01 µg/mL + T5 | 52.4 ± 4.8 | 18.0 |
| 5C9 IgG | | |
| 100 µg/mL | 1.1 ± 0.3 | |
| 100 µg/mL + T5 | 0.7 ± 0.1 | 98.9 |
| 10 µg/mL + T5 | 0.7 ± 0.0 | 98.9 |
| 1 µg/mL + T5 | 1.4 ± 0.5 | 97.8 |
| 0.1 µg/mL + T5 | 5.6 ± 0.3 | 91.2 |
| 0.01 µg/mL + T5 | 52.9 ± 2.0 | 17.2 |
| 9D33 IgG | | |
| 100 µg/mL | 2.4 ± 0.2 | |
| 100 µg/mL + T5 | 3.0 ± 0.2 | 95.3 |
| 10 µg/mL + T5 | 2.3 ± 0.2 | 96.4 |
| 1 µg/mL + T5 | 4.1 ± 0.3 | 93.6 |
| 0.1 µg/mL + T5 | 28.3 ± 0.8 | 55.7 |
| 0.01 µg/mL + T5 | 49.2 ± 3.5 | 23.0 |

See legend to Table 7a for details. T5 = TRAb positive serum with thyroid stimulating activity; T5 serum was diluted to a final concentration of 1:10 in hypotonic cyclic AMP buffer. HBD = pool of healthy blood donor sera.

TABLE 7m

Effect on T8 serum stimulating activity of different concentrations of TSHR blocking monoclonal antibodies (K1-70, 5C9, 9D33)

| Test sample | Cyclic AMP concentration (pmol/mL mean ± SD) | % Inhibition |
|---|---|---|
| Cyclic AMP buffer | 1.7 ± 0.2 | |
| HBD diluted 10x | 2.5 ± 1.0 | |
| Serum T8 diluted 10x | 52.3 ± 10.5 | |
| 5B3 IgG | | |
| 100 µg/mL | 2.1 ± 0.5 | |
| 100 µg/mL + T8 | 50.5 ± 3.1 | 3 |
| 10 µg/mL + T8 | 56.0 ± 14.7 | 0 |
| 1 µg/mL + T8 | 51.4 ± 2.7 | 2 |
| 0.1 µg/mL + T8 | 50.7 ± 10.2 | 3 |
| K1-70 IgG | | |
| 100 µg/mL | 1.8 ± 0.2 | |
| 100 µg/mL + T8 | 2.4 ± 0.3 | 95 |
| 10 µg/mL + T8 | 2.1 ± 0.7 | 96 |
| 1 µg/mL + T8 | 2.5 ± 0.2 | 95 |
| 0.1 µg/mL + T8 | 5.8 ± 0.3 | 89 |
| 0.01 µg/mL + T8 | 63.4 ± 8.0 | 0 |
| 5C9 IgG | | |
| 100 µg/mL | 1.2 ± 0.2 | |
| 100 µg/mL + T8 | 1.7 ± 0.8 | 97 |
| 10 µg/mL + T8 | 1.7 ± 0.2 | 97 |
| 1 µg/mL + T8 | 2.2 ± 0.3 | 96 |
| 0.1 µg/mL + T8 | 4.6 ± 0.5 | 91 |
| 0.01 µg/mL + T8 | 53.7 ± 7.1 | 0 |
| 9D33 IgG | | |
| 100 µg/mL | 2.4 ± 0.5 | |
| 100 µg/mL + T8 | 3.6 ± 0.8 | 93 |
| 10 µg/mL + T8 | 3.7 ± 0.5 | 93 |
| 1 µg/mL + T8 | 4.7 ± 0.2 | 91 |
| 0.1 µg/mL + T8 | 22.9 ± 0.4 | 56 |
| 0.01 µg/mL + T8 | 45.8 ± 4.9 | 12 |

See legend to Table 7a for details. T8 = TRAb positive serum with TSH receptor stimulating activity; T8 serum was diluted to a final concentration of 1:10 in hypotonic cyclic AMP bufferHBD = pool of healthy blood donor sera.

TABLE 7n

Effect on T11 serum stimulating activity of different concentrations of TSHR blocking monoclonal antibodies (K1-70, 5C9, 9D33)

| Test sample | Cyclic AMP concentration (pmol/mL mean ± SD) | % Inhibition |
|---|---|---|
| Cyclic AMP buffer | 1.2 ± 0.4 | |
| HBD diluted 10x | 1.8 ± 0.4 | |
| Serum T11 diluted 10x | 25.2 ± 4.4 | |
| 5B3 IgG | | |
| 100 µg/mL | 1.0 ± 0.2 | |
| 100 µg/mL + T11 | 18.4 ± 1.3 | 27.0 |
| 10 µg/mL + T11 | 18.8 ± 1.3 | 25.4 |

TABLE 7n-continued

Effect on T11 serumstimulating activity of different concentrations of TSHR blocking monoclonal antibodies (K1-70, 5C9, 9D33)

| Test sample | Cyclic AMP concentration (pmol/mL mean ± SD) | % Inhibition |
|---|---|---|
| 1 µg/mL + T11 | 19.8 ± 1.2 | 21.4 |
| 0.1 µg/mL + T11 | 17.7 ± 2.1 | 29.8 |
| K1-70 IgG | | |
| 100 µg/mL | 0.9 ± 0.2 | |
| 100 µg/mL + T11 | 1.0 ± 0.3 | 96.0 |
| 10 µg/mL + T11 | 1.1 ± 0.1 | 95.6 |
| 1 µg/mL + T11 | 1.1 ± 0.1 | 95.6 |
| 0.1 µg/mL + T11 | 2.4 ± 0.3 | 90.5 |
| 0.01 µg/mL + T11 | 22.1 ± 0.8 | 12.3 |
| 5C9 IgG | | |
| 100 µg/mL | 0.9 ± 0.1 | |
| 100 µg/mL + T11 | 22.4 ± 1.9 | 11.1 |
| 10 µg/mL + T11 | 21.7 ± 0.5 | 13.9 |
| 1 µg/mL + T11 | 19.4 ± 2.2 | 23.0 |
| 0.1 µg/mL + T11 | 20.2 ± 0.4 | 19.8 |
| 0.01 µg/mL + T11 | 24.1 ± 0.5 | 4.3 |
| 9D33 IgG | | |
| 100 µg/mL | 1.3 ± 0.2 | |
| 100 µg/mL + T11 | 2.1 ± 0.1 | 94.8 |
| 10 µg/mL + T11 | 2.5 ± 0.1 | 90.1 |
| 1 µg/mL + T11 | 3.1 ± 0.3 | 87.7 |
| 0.1 µg/mL + T11 | 12.5 ± 0.3 | 50.4 |
| 0.01 µg/mL + T11 | 20.9 ± 0.3 | 17.1 |

See legend to Table 7a for details. T11 = TRAb positive serum with TSH receptor stimulating activity; T11 serum was diluted to a final concentration of 1:10 in hypotonic cyclic AMP buffer. HBD = pool of healthy blood donor sera.

TABLE 7o

Inhibition of porcine (p) TSH stimulation of cyclic AMP production in TSHR transfected CHO cells by K1-70 and 5C9 mixed together

| Test Sample | Cyclic AMP concentration (pmol/mL mean ± SD) | % Inhibition |
|---|---|---|
| Cyclic AMP buffer | 0.6 ± 0.1 | |
| pTSH 3 ng/mL | 64.2 ± 3.5 | |
| 100 µg/mL 5B3 | 0.9 ± 0.2 | |
| 100 µg/mL 5C9 | 0.2 ± 0.0 | |
| 100 µg/mL K1-70 | 0.6 ± 0.2 | |
| 100 µg/mL (K1-70 + 5C9)[a] | 0.7 ± 0.5 | |
| pTSH 3 ng/mL + 100 µg/mL 5B3 | 63.9 ± 5.1 | 0.5 |
| pTSH 3 ng/mL + 10 µg/mL 5B3 | 66.9 ± 6.5 | 0 |
| pTSH 3 ng/mL + 100 µg/mL 5C9 | 0.5 ± 0.0 | 99.2 |
| pTSH 3 ng/mL + 10 µg/mL 5C9 | 1.3 ± 0.4 | 98.0 |
| pTSH 3 ng/mL + 1 µg/mL 5C9 | 4.2 ± 0.6 | 93.5 |
| pTSH 3 ng/mL + 0.1 µg/mL 5C9 | 13.7 ± 4.9 | 78.7 |
| pTSH 3 ng/mL + 0.01 µg/mL 5C9 | 64.6 ± 1.4 | 0 |
| pTSH 3 ng/mL + 0.001 µg/mL 5C9 | 64.1 ± 7.3 | 0.2 |
| pTSH 3 ng/mL + 100 µg/mL K1-70 | 0.7 ± 0.1 | 98.9 |
| pTSH 3 ng/mL + 10 µg/mL K1-70 | 1.0 ± 0.6 | 98.4 |
| pTSH 3 ng/mL + 1 µg/mL K1-70 | 0.7 ± 0.4 | 98.9 |
| pTSH 3 ng/mL + 0.1 µg/mL K1-70 | 5.9 ± 2.8 | 90.8 |
| pTSH 3 ng/mL + 0.01 µg/mL K1-70 | 52.0 ± 3.0 | 19.0 |
| pTSH 3 ng/mL + 0.001 µg/mL K1-70 | 59.4 ± 3.7 | 7.5 |
| pTSH 3 ng/mL + 100 µg/mL (K1-70 + 5C9)[a] | 1.1 ± 0.4 | 98.3 |
| pTSH 3 ng/mL + 10 µg/mL (K1-70 + 5C9)[a] | 0.5 ± 0.1 | 99.2 |
| pTSH 3 ng/mL + 1 µg/mL (K1-70 + 5C9)[a] | 2.5 ± 0.3 | 96.1 |
| pTSH 3 ng/mL + 0.1 µg/mL (K1-70 + 5C9)[a] | 9.4 ± 4.0 | 85.4 |
| pTSH 3 ng/mL + 0.01 µg/mL (K1-70 + 5C9)[a] | 49.4 ± 2.9 | 23.0 |
| pTSH 3 ng/mL + 0.001 µg/mL (K1-70 + 5C9)[a] | 48.3 ± 4.8 | 24.8 |

See legend to Table 7a for details. K1-70, 5C9 and 5B3: purified IgG of the MAbs were used in all experiments.
[a]In some experiments the MAbs were mixed in equal proportions and the concentration shown for a mixture represents the total amount of IgG added i.e.: 100 µg/mL (K1-70 + 5C9) = 50 µg/mL of K1-70 + 50 µg/mL of 5C9 used in the experiment.

TABLE 7p

The effect of K1-70 and 5C9 IgGs mixed together on the constitutive activity (ie basal activity) of the TSHR

| Test Sample | Cyclic AMP production (pmol/mL mean ± SD) | % Inhibition |
|---|---|---|
| cyclic AMP buffer only | 58.04 ± 8.52 | |
| 0.1 µg/mL 5C9 IgG | 68.21 ± 2.81 | 0 |
| 0.2 µg/mL 5C9 IgG | 58.75 ± 3.92 | 0 |
| 1 µg/mL 5C9 IgG | 31.40 ± 0.89 | 45.9 |
| 2 µg/mL 5C9 IgG | 31.75 ± 2.73 | 45.3 |
| 0.01 µg/mL K1-70 IgG | 92.24 ± 3.92 | 0 |
| 0.1 µg/mL K1-70 IgG | 62.77 ± 2.18 | 0 |
| 0.2 µg/mL K1-70 IgG | 58.75 ± 3.92 | 0 |
| 1 µg/mL K1-70 IgG | 61.52 ± 5.04 | 0 |
| 2 µg/mL K1-70 IgG | 52.12 ± 1.84 | 10.2 |
| 0.01 µg/mL 5B3 IgG | 58.16 ± 9.42 | 0 |
| 0.1 µg/mL 5B3 IgG | 58.75 ± 3.92 | 0 |
| 0.2 µg/mL 5B3 IgG | 53.30 ± 3.36 | 8.2 |
| 1 µg/mL 5B3 IgG | 54.39 ± 2.62 | 6.3 |
| 2 µg/mL 5B3 IgG | 50.57 ± 2.39 | 12.9 |
| 0.01 µg/mL 5C9 IgG + K1-70 IgG[a] | 83.80 ± 5.12 | 0 |
| 0.1 µg/mL 5C9 IgG + K1-70 IgG[a] | 76.28 ± 1.72 | 0 |
| 0.2 µg/mL 5C9 IgG + K1-70 IgG[a] | 71.85 ± 5.96 | 0 |
| 1 µg/mL 5C9 IgG + K1-70 IgG[a] | 67.70 ± 12.58 | 0 |
| 2 µg/mL 5C9 IgG + K1-70 IgG[a] | 55.28 ± 6.17 | 4.8 |
| 0.01 µg/mL 5C9 IgG + 5B3 IgG[a] | 73.53 ± 4.31 | 0 |
| 0.1 µg/mL 5C9 IgG + 5B3 IgG[a] | 82.26 ± 12.07 | 0 |
| 0.2 µg/mL 5C9 IgG + 5B3 IgG[a] | 62.03 ± 1.22 | 0 |
| 1 µg/mL 5C9 IgG + 5B3 IgG[a] | 36.49 ± 1.10 | 37.1 |
| 2 µg/mL 5C9 IgG + 5B3 IgG[a] | 27.78 ± 2.96 | 52.1 |

See legend to Table 7a for details. The experiments were carried out using CHO cells expressing wild type TSHR at approximately 5 × 10[5] receptors per cells.
[a]The total final concentration of IgG mixture is shown; ie in the case of 2 µg/mL K1-70 IgG + 5C9 IgG, the mixture contains 1 µg/mL K1-70 IgG and 1 µg/mL 5C9 IgG. Consequently, the combined effect of two IgGs at 2 µg/mL can be compared to the effect of the single IgG at the same concentration (2 µg/mL).

TABLE 8a

Cyclic AMP levels in CHO cells expressing wild type TSHR and TSHR with Lys58 mutated to Ala. Effect of different dilutions of human monoclonal antibody to the TSHR (K1-18) with TSH agonist activity

| | Cyclic AMP produced (pmol/mLpmol/mL) mean ± SD (n = 3) | | Mutated/ |
|---|---|---|---|
| | Wild type TSHR | Mutated TSHR | Wild type (%) |
| Cyclic AMP assay buffer | 2.32 ± 0.37 | 8.23 ± 0.00 | 355 |
| K1-18 | | | |
| 0.3 ng/mL | 4.69 ± 0.95 | 12.02 ± 1.52 | 256 |
| 1 ng/mL | 8.95 ± 0.18 | 19.35 ± 3.45 | 216 |
| 3 ng/mL | 25.47 ± 4.30 | 43.07 ± 13.04 | 169 |
| 10 ng/mL | 66.57 ± 3.17 | 69.61 ± 1.25 | 105 |

TABLE 8a-continued

Cyclic AMP levels in CHO cells expressing wild type TSHR and TSHR with Lys58 mutated to Ala. Effect of different dilutions of human monoclonal antibody to the TSHR (K1-18) with TSH agonist activity

| | Cyclic AMP produced (pmol/mLpmol/mL) mean ± SD (n = 3) | | Mutated/ Wild type (%) |
|---|---|---|---|
| | Wild type TSHR | Mutated TSHR | |
| 30 ng/mL | 84.18 ± 11.86 | 79.39 ± 9.40 | 94 |
| 100 ng/mL TSH | 98.12 ± 5.31 | 102.88 ± 3.31 | 105 |
| 0.01 ng/mL | 3.11 ± 1.09 | 7.16 ± 0.97 | 230 |
| 0.03 ng/mL | 4.43 ± 0.67 | 10.00 ± 0.29 | 226 |
| 0.1 ng/mL | 10.11 ± 1.27 | 17.24 ± 1.77 | 171 |
| 0.3 ng/mL | 41.25 ± 5.41 | 45.94 ± 1.43 | 111 |
| 1 ng/mL | 74.52 ± 3.07 | 75.22* | 101 |
| 3 ng/mL | 95.34 ± 6.60 | 83.71 ± 7.10 | 88 |

Results shown are mean ± SD of triplicate determinations.
*duplicate determination. Samples diluted in hypotonic cyclic AMP buffer.

TABLE 8b

Cyclic AMP levels in CHO cells expressing wild type TSHR and TSHR with Arg80 mutated to Ala. Effect of different dilutions of human monoclonal antibody to the TSHR (K1-18) with TSH agonist activity

| | Cyclic AMP produced (pmol/mLpmol/mL) mean ± SD (n = 3) | | Mutated/ Wild type (%) |
|---|---|---|---|
| | Wild type TSHR | Mutated TSHR | |
| Cyclic AMP assay buffer K1-18 | 1.65 ± 0.40 | 4.76 ± 1.30 | 288 |
| 0.3 ng/mL | 2.46 ± 0.49 | 4.59 ± 0.41 | 187 |
| 1 ng/mL | 5.11 ± 0.77 | 7.22 ± 0.69 | 141 |
| 3 ng/mL | 10.65 ± 1.17 | 13.81 ± 2.53 | 130 |
| 10 ng/mL | 31.34 ± 5.31 | 31.72 ± 1.53 | 101 |
| 30 ng/mL | 50.15 ± 6.02 | 45.47 ± 3.59 | 91 |
| 100 ng/mL TSH | 66.30 ± 6.93 | 64.50 ± 0.51 | 97 |
| 0.01 ng/mL | 2.00 ± 0.81 | 4.06 ± 0.36 | 203 |
| 0.03 ng/mL | 3.68 ± 0.28 | 6.19 ± 0.95 | 168 |
| 0.1 ng/mL | 9.10 ± 1.19 | 13.31 ± 1.94 | 146 |
| 0.3 ng/mL | 22.19 ± 1.46 | 27.66 ± 2.20 | 125 |
| 1 ng/mL | 57.48 ± 4.57 | 54.55 ± 10.40 | 95 |
| 3 ng/mL | 58.48 ± 8.87 | 56.95 ± 3.97 | 97 |

See legend to Table 8a for details.

TABLE 8c

Cyclic AMP levels in CHO cells expressing wild type TSHR and TSHR with Tyr82 mutated to Ala. Effect of different dilutions of human monoclonal antibody to the TSHR (K1-18) with TSH agonist activity

| | Cyclic AMP produced (pmol/mLpmol/mL) mean ± SD (n = 3) | | Mutated/ Wild type (%) |
|---|---|---|---|
| | Wild type TSHR | Mutated TSHR | |
| Cyclic AMP assay buffer K1-18 | 0.52 ± 0.09 | 1.88 ± 0.25 | 362 |
| 0.3 ng/mL | 1.39 ± 0.10 | 4.72 ± 0.95 | 340 |
| 1 ng/mL | 2.95 ± 0.51 | 5.48 ± 0.91 | 186 |
| 3 ng/mL | 7.22 ± 1.08 | 13.26 ± 1.61 | 184 |
| 10 ng/mL | 26.07 ± 1.15 | 28.73 ± 2.65 | 110 |
| 30 ng/mL | 36.96 ± 2.55 | 41.91 ± 5.06 | 113 |
| 100 ng/mL TSH | 50.72 ± 6.93 | 57.64 ± 1.84 | 114 |
| 0.01 ng/mL | 1.01 ± 0.42 | 2.60 ± 0.44 | 257 |
| 0.03 ng/mL | 4.39 ± 1.65 | 4.10 ± 0.63 | 93 |
| 0.1 ng/mL | 9.67 ± 1.07 | 9.64 ± 1.49 | 100 |
| 0.3 ng/mL | 29.80 ± 2.51 | 33.66 ± 4.57 | 113 |
| 1 ng/mL | 53.34 ± 4.68 | 49.96 ± 0.72 | 94 |
| 3 ng/mL | 56.56 ± 4.76 | 61.34 ± 4.96 | 108 |

See legend to Table 8a for details.

TABLE 8d

Cyclic AMP levels in CHO cells expressing wild type TSHR and TSHR with Glu107 mutated to Ala. Effect of different dilutions of human monoclonal antibody to the TSHR (K1-18) with TSH agonist activity

| | Cyclic AMP produced (pmol/mLpmol/mL) mean ± SD (n = 3) | | Mutated/ Wild type (%) |
|---|---|---|---|
| | Wild type TSHR | Mutated TSHR | |
| Cyclic AMP assay buffer K1-18 (ng/mL) | 0.91 ± 0.15 | 7.16 ± 0.17 | 787 |
| 0.3 ng/mL | 1.78 ± 0.20 | 9.30 ± 1.48 | 522 |
| 1 ng/mL | 3.73 ± 0.09 | 10.96 ± 0.69 | 294 |
| 3 ng/mL | 11.06 ± 1.45 | 20.55 ± 3.83 | 186 |
| 10 ng/mL | 30.04 ± 2.34 | 31.49 ± 2.70 | 105 |
| 30 ng/mL | 49.28 ± 3.28 | 40.92 ± 2.03 | 83 |
| 100 ng/mL TSH (ng/mL) | 57.80 ± 5.23 | 53.62 ± 3.86 | 93 |
| 0.01 ng/mL | 1.41 ± 0.10 | 8.20 ± 1.87 | 582 |
| 0.03 ng/mL | 1.99 ± 0.09 | 8.92 ± 2.93 | 448 |
| 0.1 ng/mL | 5.54 ± 0.60 | 8.24 ± 0.60 | 149 |
| 0.3 ng/mL | 16.27 ± 4.48 | 15.72 ± 0.81 | 97 |
| 1 ng/mL | 44.20 ± 3.64 | 30.22 ± 2.62 | 68 |
| 3 ng/mL | 53.86 ± 7.00 | 43.91 ± 2.61 | 82 |

See legend to Table 8a for details.

TABLE 8e

Cyclic AMP levels in CHO cells expressing wild type TSHR and TSHR with Arg109 mutated to Ala. Effect of different dilutions of human monoclonal antibody to the TSHR (K1-18) with TSH agonist activity

| | Cyclic AMP produced (pmol/mLpmol/mL) mean ± SD (n = 3) | | Mutated/ Wild type (%) |
|---|---|---|---|
| | Wild type TSHR | Mutated TSHR | |
| Cyclic AMP assay buffer | 1.75 ± 0.35 | 3.42 ± 0.41 | 195 |

TABLE 8e-continued

Cyclic AMP levels in CHO cells expressing wild type TSHR and TSHR with Arg109 mutated to Ala. Effect of different dilutions of human monoclonal antibody to the TSHR (K1-18) with TSH agonist activity

| | Cyclic AMP produced (pmol/mLpmol/mL) mean ± SD (n = 3) | | Mutated/ Wild type (%) |
|---|---|---|---|
| | Wild type TSHR | Mutated TSHR | |
| K1-18 (ng/mL) | | | |
| 0.3 ng/mL | 2.66 ± 0.13 | 5.31 ± 0.11 | 200 |
| 1 ng/mL | 5.81 ± 0.13 | 9.39 ± 0.88 | 162 |
| 3 ng/mL | 12.86 ± 0.77 | 17.99 ± 3.94 | 140 |
| 10 ng/mL | 40.46 ± 1.76 | 40.55 ± 3.48 | 100 |
| 30 ng/mL | 58.91 ± 9.28 | 50.84 ± 1.01 | 86 |
| 100 ng/mL | 66.01 ± 4.85 | 59.9 ± 1.25 | 91 |
| TSH (ng/mL) | | | |
| 0.01 ng/mL | 2.74 ± 0.37 | 3.15 ± 0.22 | 115 |
| 0.03 ng/mL | 4.24 ± 0.24 | 4.92 ± 0.54 | 116 |
| 0.1 ng/mL | 9.39 ± 1.16 | 8.39 ± 0.46 | 89 |
| 0.3 ng/mL | 39.63 ± 2.57 | 39.17 ± 1.70 | 99 |
| 1 ng/mL | 61.19 ± 8.50 | 43.82 ± 1.69 | 72 |
| 3 ng/mL | 70.6 ± 10.03 | 55.16 ± 2.59 | 78 |

See legend to Table 8a for details.

TABLE 8f

Cyclic AMP levels in CHO cells expressing wild type TSHR and TSHR with Lys129 mutated to Ala. Effect of different dilutions of human monoclonal antibody to the TSHR (K1-18) with TSH agonist activity

| | Cyclic AMP produced (pmol/mLpmol/mL) mean ± SD (n = 3) | | Mutated/ Wild type (%) |
|---|---|---|---|
| | Wild type TSHR | Mutated TSHR | |
| Cyclic AMP assay buffer | 1.72 ± 0.44 | 2.69 ± 0.25 | 156 |
| K1-18 | | | |
| 0.3 ng/mL | 2.49 ± 0.34 | 3.24 ± 0.03 | 130 |
| 1 ng/mL | 4.78 ± 0.88 | 5.53 ± 1.04 | 116 |
| 3 ng/mL | 12.22 ± 0.32 | 10.58 ± 0.61 | 87 |
| 10 ng/mL | 30.88 ± 3.70 | 23.53 ± 1.04 | 76 |
| 30 ng/mL | 44.61 ± 4.59 | 33.46 ± 2.66 | 75 |
| 100 ng/mL | 52.57 ± 1.30 | 52.88 ± 2.31 | 101 |
| TSH | | | |
| 0.01 ng/mL | 2.01 ± 0.40 | 2.69 ± 0.44 | 134 |
| 0.03 ng/mL | 3.32 ± 0.26 | 5.34 ± 0.05 | 161 |
| 0.1 ng/mL | 9.69 ± 0.91 | 12.69 ± 1.06 | 131 |
| 0.3 ng/mL | 26.14 ± 2.72 | 29.0 ± 1.07 | 111 |
| 1 ng/mL | 46.33 ± 2.29 | 40.78 ± 5.20 | 88 |
| 3 ng/mL | 48.07 ± 2.77 | 48.50 ± 5.38 | 101 |

See legend to Table 8a for details.

TABLE 8g

Cyclic AMP levels in CHO cells expressing wild type TSHR and TSHR with Phe130 mutated to Ala. Effect of different dilutions of human monoclonal antibody to the TSHR (K1-18) with TSH agonist activity

| | Cyclic AMP produced (pmol/mLpmol/mL) mean ± SD (n = 3) | | Mutated/ Wild type (%) |
|---|---|---|---|
| | Wild type TSHR | Mutated TSHR | |
| Cyclic AMP assay buffer | 1.96 ± 0.22 | 3.38 ± 0.47 | 172 |
| K1-18 | | | |
| 0.3 ng/mL | 3.23 ± 0.26 | 4.01 ± 0.03 | 124 |
| 1 ng/mL | 6.24 ± 0.70 | 6.71 ± 0.35 | 108 |
| 3 ng/mL | 15.42 ± 1.00 | 14.89 ± 12.46 | 97 |
| 10 ng/mL | 49.72 ± 5.36 | 36.36 ± 2.23 | 73 |
| 30 ng/mL | 51.57 ± 8.02 | 54.0 ± 2.20 | 66 |
| 100 ng/mL | 98.73 ± 8.67 | 78.11 ± 7.43 | 79 |
| TSH | | | |
| 0.01 ng/mL | 2.28 ± 0.15 | 3.05 ± 0.29 | 134 |
| 0.03 ng/mL | 3.77 ± 0.83 | 4.12 ± 0.55 | 109 |
| 0.1 ng/mL | 9.55 ± 0.15 | 9.61 ± 1.14 | 101 |
| 0.3 ng/mL | 28.77 ± 1.08 | 35.64 ± 3.00 | 124 |
| 1 ng/mL | 76.83 ± 10.33 | 66.16 ± 4.97 | 86 |
| 3 ng/mL | 93.08 ± 7.22 | 80.37 ± 3.05 | 86 |

See legend to Table 8a for details.

TABLE 8h

Cyclic AMP levels in CHO cells expressing wild type TSHR and TSHR with Phe134 mutated to Ala. Effect of different dilutions of human monoclonal antibody to the TSHR (K1-18) with TSH agonist activity

| | Cyclic AMP produced (pmol/mL) mean ± SD (n = 3) | | Mutated/Wild type (%) |
|---|---|---|---|
| | Wild type TSHR | Mutated TSHR | |
| Cyclic AMP assay buffer | 1.85 ± 0.37 | 4.62 ± 0.89 | 250 |
| K1-18 | | | |
| 0.3 ng/mL | 2.44 ± 0.12 | 2.71 ± 0.65 | 234 |
| 1 ng/mL | 5.97 ± 0.63 | 9.56 ± 0.52 | 160 |
| 3 ng/mL | 13.43 ± 0.46 | 24.24 ± 1.93 | 180 |
| 10 ng/mL | 35.49 ± 1.71 | 43.41 ± 1.29 | 122 |
| 30 ng/mL | 46.48 ± 3.34 | 66.25 ± 11.73 | 143 |
| 100 ng/mL | 58.93 ± 10.42 | 78.69 ± 6.43 | 134 |
| TSH | | | |
| 0.01 ng/mL | 2.50 ± 0.43 | 4.73 ± 0.24 | 189 |
| 0.03 ng/mL | 4.29 ± 0.33 | 6.05 ± 0.21 | 141 |
| 0.1 ng/mL | 10.60 ± 0.56 | 12.70 ± 2.22 | 120 |
| 0.3 ng/mL | 28.93 ± 3.07 | 27.28 ± 1.96 | 94 |
| 1 ng/mL | 52.55 ± 3.97 | 53.68 ± 4.76 | 102 |
| 3 ng/mL | 61.09 ± 8.26 | 61.51 ± 0.99 | 101 |

See legend to Table 8a for details.

TABLE 8i

Cyclic AMP levels in CHO cells expressing wild type TSHR and TSHR with Lys183 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Experiment 1 | | | |
| Cyclic AMP assay buffer | 1.49 ± 0.31 | 4.54 ± 0.23 | 305 |
| K1-18 | | | |
| 0.3 ng/mL | 2.67 ± 0.30 | 4.41 ± 0.07 | 165 |
| 1 ng/mL | 5.69 ± 0.26 | 4.72 ± 0.53 | 83 |
| 3 ng/mL | 14.43 ± 2.30 | 4.55 ± 0.32 | 32 |
| 10 ng/mL | 43.94 ± 2.59 | 4.73 ± 0.57 | 11 |
| 30 ng/mL | 73.60 ± 9.07 | 4.58 ± 0.29 | 6 |
| 100 ng/mL TSH | 84.59 ± 5.65 | 5.31 ± 1.38 | 6 |
| 0.01 ng/mL | 1.80 ± 0.13 | 4.95 ± 0.23 | 275 |
| 0.03 ng/mL | 3.91 ± 0.06 | 6.94 ± 1.04 | 177 |
| 0.1 ng/mL | 8.92 ± 1.47 | 13.04 ± 1.12 | 146 |
| 0.3 ng/mL | 33.01 ± 3.49 | 34.95 ± 1.12 | 106 |
| 1 ng/mL | 76.07 ± 4.42 | 57.18 ± 2.97 | 75 |
| 3 ng/mL | 86.17 ± 2.02 | 69.15 ± 3.34 | 80 |
| Experiment 2 | | | |
| Cyclic AMP assay buffer | 0.53 ± 0.27 | 3.72 ± 0.19 | 702 |
| K1-18 | | | |
| 0.3 ng/mL | 1.93 ± 0.92 | 3.25 ± 0.23 | 168 |
| 1 ng/mL | 3.59 ± 0.47 | 2.77 ± 1.32 | 77 |
| 3 ng/mL | 6.56 ± 2.29 | 3.24 ± 0.63 | 49 |
| 10 ng/mL | 27.79 ± 1.77 | 0.58 ± 0.89 | 2 |
| 30 ng/mL | 46.16 ± 5.72 | 1.97 ± 0.11 | 4 |
| 100 ng/mL TSH | 61.78 ± 3.78 | 0.92 ± 1.17 | 1 |
| 0.01 ng/mL | 1.30 ± 0.20 | 3.73 ± 0.10 | 287 |
| 0.03 ng/mL | 3.00 ± 0.12 | 5.37 ± 0.31 | 179 |
| 0.1 ng/mL | 6.69 ± 0.41 | 10.08 ± 0.82 | 151 |
| 0.3 ng/mL | 26.22 ± 6.92 | 27.84 ± 2.8 | 106 |
| 1 ng/mL | 68.12 ± 15.71 | 55.78 ± 2.52 | 82 |
| 3 ng/mL | 69.75 ± 13.30 | 72.17 ± 8.74 | 103 |

See legend to Table 8a for details.

TABLE 8j

Cyclic AMP levels in CHO cells expressing wild type TSHR and TSHR with Asp203 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Cyclic AMP assay buffer | 1.64 ± 0.17 | 6.06 ± 0.16 | 370 |
| K1-18 | | | |
| 0.3 ng/mL | 2.68 ± 0.21 | 8.14 ± 0.24 | 304 |
| 1 ng/mL | 5.60 ± 0.27 | 12.54 ± 0.46 | 224 |
| 3 ng/mL | 11.54 ± 2.20 | 26.08 ± 2.19 | 226 |
| 10 ng/mL | 38.16 ± 0.90 | 49.54 ± 2.38 | 130 |
| 30 ng/mL | 60.04 ± 6.18 | 67.45 ± 4.04 | 112 |
| 100 ng/mL TSH | 76.63 ± 4.54 | 78.94 ± 3.75 | 103 |
| 0.01 ng/mL | 2.29 ± 0.18 | 5.30 ± 0.53 | 231 |
| 0.03 ng/mL | 3.56 ± 0.21 | 7.13 ± 0.29 | 200 |
| 0.1 ng/mL | 8.45 ± 0.07 | 13.02 ± 2.00 | 154 |
| 0.3 ng/mL | 26.33 ± 1.63 | 33.77 ± 1.37 | 128 |
| 1 ng/mL | 65.72 ± 5.74 | 58.56 ± 3.02 | 89 |
| 3 ng/mL | 77.11 ± 4.86 | 69.26 ± 0.68 | 90 |

See legend to Table 8a for details.

TABLE 8k

Cyclic AMP levels in CHO cells expressing wild type TSHR and TSHR with Arg255 mutated to Asp. Effect of different dilutions of human monoclonal antibody to the TSHR (K1-18) with TSH agonist activity

| | Cyclic AMP produced (pmol/mL) mean ± SD (n = 31) | | |
|---|---|---|---|
| | Wild type TSHR | Mutated TSHR | Mutated/Wild type (%) |
| Experiment 1 | | | |
| Cyclic AMP assay buffer | 2.65 ± 0.20 | 1.89 ± 0.28 | 71 |
| K1-18 | | | |
| 0.3 ng/mL | 4.40 ± 0.67 | 1.93 ± 0.23 | 44 |
| 1 ng/mL | 8.93 ± 2.17 | 2.19 ± 0.25 | 25 |
| 3 ng/mL | 16.31 ± 1.29 | 4.14 ± 0.95 | 25 |
| 10 ng/mL | 42.50 ± 3.42 | 7.87 ± 0.53 | 19 |
| 30 ng/mL | 49.10 ± 9.27 | 15.59 ± 1.15 | 32 |
| 100 ng/mL TSH | 55.17 ± 10.84 | 31.58 ± 6.83 | 57 |
| 0.01 ng/mL | 4.36 ± 1.05 | 2.59 ± 0.31 | 59 |
| 0.03 ng/mL | v9.19 ± 1.74 | 6.47 ± 0.10 | 70 |
| 0.1 ng/mL | 26.86 ± 2.67 | 19.18 ± 2.69 | 71 |
| 0.3 ng/mL | 42.03 ± 6.15 | 51.67 ± 3.38 | 123 |
| 1 ng/mL | 60.08 ± 4.20 | 68.59 ± 7.07 | 114 |
| 3 ng/mL | 61.27 ± 2.99 | 57.72 ± 9.50 | 94 |
| Experiment 2 | | | |
| Cyclic AMP assay buffer | 1.80 ± 0.14 | 2.35 ± 0.45 | 131 |
| K1-18 | | | |
| 0.3 ng/mL | 2.26 ± 0.22 | 2.13 ± 0.19 | 94 |
| 1 ng/mL | 5.21 ± 0.60 | 1.93 ± 0.67 | 37 |
| 3 ng/mL | 11.23 ± 1.35 | 3.49 ± 0.08 | 31 |
| 10 ng/mL | 30.58 ± 1.89 | 6.08 ± 0.93 | 20 |
| 30 ng/mL | 51.91 ± 5.11 | 7.96 ± 0.29 | 15 |
| 100 ng/mL TSH | 67.17 ± 5.84 | 20.23 ± 0.48 | 30 |
| 0.01 ng/mL | 2.21 ± 0.25 | 1.49 ± 0.25 | 67 |
| 0.03 ng/mL | 3.61 ± 0.28 | 2.81 ± 0.38 | 78 |
| 0.1 ng/mL | 7.86 ± 3.02 | 6.92 ± 0.35 | 88 |
| 0.3 ng/mL | 27.07 ± 2.08 | 21.24* | 78 |
| 1 ng/mL | 54.24 ± 5.41 | 41.06 ± 1.0 | 76 |
| 3 ng/mL | 58.14 ± 3.02 | 52.35 ± 3.20 | 90 |

TABLE 8k-continued

Cyclic AMP levels in CHO cells expressing wild type TSHR and TSHR with Arg255 mutated to Asp. Effect of different dilutions of human monoclonal antibody to the TSHR (K1-18) with TSH agonist activity

| | Cyclic AMP produced (pmol/mL) mean ± SD (n = 31) | | |
|---|---|---|---|
| | Wild type TSHR | Mutated TSHR | Mutated/Wild type (%) |
| Experiment 3 | | | |
| Cyclic AMP assay buffer | 4.02 ± 0.14 | 5.88 ± 0.27 | 146 |
| K1-18 | | | |
| 0.3 ng/mL | 5.65 ± 0.61 | 5.76 ± 0.33 | 102 |
| 1 ng/mL | 9.40 ± 0.97 | 5.93 ± 0 | 63 |
| 3 ng/mL | 21.39 ± 0.55 | 6.06 ± 0.40 | 28 |
| 10 ng/mL | 67.31 ± 4.56 | 9.44 ± 0.82 | 14 |
| 30 ng/mL | 131.53 ± 5.0 | 13.46 ± 1.25 | 10 |
| 100 ng/mL | 226.28 ± 15.17 | 30.07 ± 5.98 | 13 |
| TSH | | | |
| 0.01 ng/mL | 5.19 ± 0.15 | 6.46 ± 0.13 | 124 |
| 0.03 ng/mL | 9.82 ± 0.96 | 9.44 ± 0.27 | 96 |
| 0.1 ng/mL | 24.96* | 22.74 ± 2.24 | 91 |
| 0.3 ng/mL | 91.70 ± 3.45 | 68.89 ± 3.12 | 75 |
| 1 ng/mL | 191.94 ± 11.08 | 154.26 ± 4.66 | 80 |
| 3 ng/mL | 226.42 ± 16.78 | 201.17 ± 16.22 | 89 |

See legend to Table 8a for details.

TABLE 9a

TSH induced cyclic AMP production in CHO cells expressing wild type TSHR and TSHR with Lys58 mutated to Ala. Effect of different dilutions of human monoclonal antibody to the TSHR (K1-70) with TSH antagonist activity Experiment 1

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 1.86 ± 0.41 | 5.03 ± 0.29 | 270 |
| TSH[b] | 68.83 ± 0.70 | 78.46 ± 4.71 | 114 |
| 5B3 10 µg/mL + TSH[b] | 82.85 ± 10.89 | 81.62 ± 5.07 | 99 |
| 5B3 100 µg/mL + TSH[b] | 80.67 ± 13.25 | 81.61 ± 5.04 | 101 |
| K1-70 0.001 µg + TSH[b] | 92.76 ± 13.12 | 104.76 ± 7.65 | 113 |
| K1-70 0.01 µg + TSH[b] | 82.54 ± 2.17 | 108.22 ± 8.17 | 131 |
| K1-70 0.1 µg + TSH[b] | 4.26 ± 0.83 | 85.28 ± 6.13 | 2002 |
| K1-70 1.0 µg + TSH[b] | 1.56 ± 0.20 | 61.47 ± 2.61 | 3940 |
| K1-70 10 µg + TSH[b] | 1.72 ± 0.34 | 33.11 ± 4.67 | 1925 |
| K1-70 100 µg + TSH[b] | 1.58 ± 0.05 | 18.75 ± 4.91 | 1187 |
| K1-70 100 µg | 1.04 ± 0.61 | 4.06 ± 0.66 | 390 |
| TSH (2) | 74.30 ± 18.86 | 85.20 ± 4.48 | 115 |

| Antibody concentration | % inhibition of TSH stimulation[c] | |
|---|---|---|
| | Wild type TSHR | Mutated TSHR |
| 5B3 10 µg/mL | 0 | 0 |
| 5B3 100 µg/mL | 0 | 0 |
| K1-70 0.001 µg | 0 | 0 |
| K1-70 0.01 µg/mL | 0 | 0 |
| K1-70 0.1 µg/mL | 94 | 0 |
| K1-70 1 µg/mL | 98 | 22 |
| K1-70 10 µg/mL | 98 | 58 |
| K1-70 100 µg/mL | 98 | 76 |
| TSH (2) | 0 | 0 |

TABLE 9a-continued

TSH induced cyclic AMP production in CHO cells expressing wild type TSHR and TSHR with Lys58 mutated to Ala. Effect of different dilutions of human monoclonal antibody to the TSHR (K1-70) with TSH antagonist activity Experiment 2

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 1.49 ± 0.21 | 3.68 ± 0.45 | 247 |
| TSH[b] | 97.87 ± 4.55 | 96.77 ± 9.54 | 99 |
| 5B3 10 µg/mL + TSH[b] | 105.71 ± 16.43 | 92.91 ± 1.17 | 88 |
| 5B3 100 µg/mL + TSH[b] | 90.43 ± 5.84 | 95.85 ± 6.56 | 106 |
| K1-70 0.001 µg + TSH[b] | 101.80 ± 13.32 | 105.33 ± 11.55 | 103 |
| K1-70 0.01 µg + TSH[b] | 115.21 ± 7.84 | 107.32 ± 11.90 | 93 |
| K1-70 0.1 µg + TSH[b] | 8.94 ± 2.47 | 83.06 ± 10.21 | 929 |
| K1-70 1.0 µg + TSH[b] | 1.71 ± 0.40 | 60.95 ± 3.72 | 3564 |
| K1-70 10 µg + TSH[b] | 1.27 ± 0.47 | 25.12 ± 4.15 | 1978 |
| K1-70 100 µg + TSH[b] | 1.31 ± 0.33 | 17.34 ± 1.35 | 1324 |
| K1-70 100 µg | 1.38 ± 1.81 | 2.56 ± 0.20 | 186 |
| TSH (2) | 102.41 ± 6.78 | 95.84 ± 1.30 | 94 |

| Antibody concentration | % inhibition of TSH stimulation[c] | |
|---|---|---|
| | Wild type TSHR | Mutated TSHR |
| 5B3 10 µg/mL | 0 | 4 |
| 5B3 100 µg/mL | 8 | 1 |
| K1-70 0.001 µg | 0 | 0 |
| K1-70 0.01 µg/mL | 0 | 0 |
| K1-70 0.1 µg/mL | 91 | 14 |
| K1-70 1 µg/mL | 98 | 37 |
| K1-70 10 µg/mL | 99 | 74 |
| K1-70 100 µg/mL | 99 | 82 |
| TSH (2) | 0 | 1 |

[a]Test samples in hypotonic cyclic AMP assay buffer.
[b]TSH final concentration = 3 ng/mL
[c]% inhibition = 100 × [1 − (cyclic AMP in the presence of test samples and TSH/cyclic AMP in the presence of cyclic AMP buffer and TSH)]. 5B3 is a human monoclonal antibody to GAD (negative control for K1-70)

TABLE 9b

TSH induced cyclic AMP production in CHO cells expressing wild type TSHR and TSHR with Arg80 mutated to Ala. Effect of different dilutions of human monoclonal antibody to the TSHR (K1-70) with TSH antagonist activity

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 3.44 ± 0.35 | 4.01 ± 0.07 | 117 |
| TSH[b] | 85.04 ± 5.88 | 105.33 ± 10.10 | 124 |
| 5B3 10 µg/mL + TSH[b] | 103.34 ± 14.25 | 104.97 ± 12.48 | 102 |
| 5B3 100 µg/mL + TSH[b] | 94.76 ± 19.53 | 101.43 ± 4.34 | 107 |
| K1-70 0.001 µg + TSH[b] | 79.24 ± 9.29 | 90.78 ± 8.65 | 115 |
| K1-70 0.01 µg + TSH[b] | 83.30 ± 7.42 | 99.26 ± 7.04 | 119 |
| K1-70 0.1 µg + TSH[b] | 40.75 ± 8.82 | 38.83 ± 8.04 | 95 |
| K1-70 1.0 µg + TSH[b] | 5.0 ± 0.72 | 6.71 ± 1.42 | 134 |
| K1-70 10 µg + TSH[b] | 3.17 ± 0.18 | 5.14 ± 1.43 | 162 |
| K1-70 100 µg + TSH[b] | 4.67 ± 0.32 | 4.83 ± 0.25 | 103 |
| K1-70 100 µg | 2.98 ± 0.13 | 3.19 ± 0.51 | 107 |
| TSH (2) | 93.53 ± 17.83 | 88.18 ± 2.24 | 94 |

TABLE 9b-continued

TSH induced cyclic AMP production in CHO cells expressing wild type TSHR and TSHR with Arg80 mutated to Ala. Effect of different dilutions of human monoclonal antibody to the TSHR (K1-70) with TSH antagonist activity

| | % inhibition of TSH stimulation[c] | |
|---|---|---|
| Antibody concentration | Wild type TSHR | Mutated TSHR |
| 5B3 10 μg/mL | 0 | 0.3 |
| 5B3 100 μg/mL | 0 | 4 |
| K1-70 0.001 μg | 7 | 14 |
| K1-70 0.01 μg/mL | 2 | 6 |
| K1-70 0.1 μg/mL | 52 | 63 |
| K1-70 1 μg/mL | 94 | 94 |
| K1-70 10 μg/mL | 96 | 95 |
| K1-70 100 μg/mL | 95 | 95 |
| TSH (2) | 0 | 16 |

See legend to Table 9a for details.

TABLE 9c

TSH induced cyclic AMP production in CHO cells expressing wild type TSHR and TSHR with Tyr82 mutated to Ala. Effect of different dilutions of human monoclonal antibody to the TSHR (K1-70) with TSH antagonist activity Experiment 1

| | Cyclic AMP produced (pmol/mL; mean ± SD, n = 3) | | Mutated/wild type (%) |
|---|---|---|---|
| Test sample[a] | Wild type TSHR | Mutated TSHR | |
| Cyclic AMP assay buffer only | 1.38 ± 0.19 | 2.00 ± 0.22 | 145 |
| TSH[b] | 153.65 ± 17.41 | 165.92 ± 11.45 | 108 |
| 5B3 10 μg/mL + TSH[b] | 163.14 ± 13.71 | 139.01 ± 5.40 | 85 |
| 5B3 100 μg/mL + TSH[b] | 146.23 ± 19.81 | 139.28 ± 11.07 | 95 |
| K1-70 0.001 μg + TSH[b] | 172.63 ± 16.69 | 103.81 ± 9.73 | 60 |
| K1-70 0.01 μg + TSH[b] | 146.19 ± 29.10 | 99.95 ± 12.23 | 68 |
| K1-70 0.1 μg + TSH[b] | 21.73 ± 3.85 | 69.85 ± 16.62 | 321 |
| K1-70 1.0 μg + TSH[b] | 1.88 ± 0.24 | 31.82 ± 3.29 | 1696 |
| K1-70 10 μg + TSH[b] | 1.35 ± 0.26 | 11.74 ± 1.33 | 870 |
| K1-70 100 μg + TSH[b] | 1.05 ± 0.07 | 7.88 ± 2.09 | 750 |
| K1-70 100 μg | 0.84 ± 0.12 | 1.81 ± 0.13 | 215 |
| TSH (2) | 159.76 ± 4.28 | 92.29 ± 5.79 | 58 |

| | % inhibition of TSH stimulation[c] | |
|---|---|---|
| Antibody concentration | Wild type TSHR | Mutated TSHR |
| 5B3 10 μg/mL | 0 | 16 |
| 5B3 100 μg/mL | 5 | 16 |
| K1-70 0.001 μg | 0 | 62 |
| K1-70 0.01 μg/mL | 5 | 40 |
| K1-70 0.1 μg/mL | 86 | 60 |
| K1-70 1 μg/mL | 99 | 81 |
| K1-70 10 μg/mL | 99 | 93 |
| K1-70 100 μg/mL | 99 | 95 |
| TSH (2) | 0 | 44 |

Experiment 2

| | Cyclic AMP produced (pmol/mL; mean ± SD, n = 3) | | Mutated/wild type (%) |
|---|---|---|---|
| Test sample[a] | Wild type TSHR | Mutated TSHR | |
| Cyclic AMP assay buffer only | 0.62 ± 0.16 | 5.67 ± 0.29 | 915 |
| TSH[b] | 59.91 ± 5.85 | 74.61 ± 6.62 | 125 |
| 5B3 10 μg/mL + TSH[b] | 73.66 ± 23.18 | 71.92 ± 5.39 | 96 |
| 5B3 100 μg/mL + TSH[b] | 68.87 ± 10.44 | 68.46 ± 3.41 | 99 |
| K1-70 0.001 μg + TSH[b] | 97.15 ± 2.87 | 89.47 ± 9.17 | 92 |
| K1-70 0.01 μg + TSH[b] | 81.95 ± 4.74 | 95.68 ± 7.62 | 117 |
| K1-70 0.1 μg + TSH[b] | 5.79 ± 0.68 | 50.57 ± 19.35 | 873 |
| K1-70 1.0 μg + TSH[b] | 1.01 ± 0.36 | 14.55 ± 0.65 | 1440 |
| K1-70 10 μg + TSH[b] | 1.02 ± 0.19 | 9.07 ± 0.70 | 889 |
| K1-70 100 μg + TSH[b] | 1.00 ± 0.19 | 7.28 ± 0.44 | 728 |
| K1-70 100 μg | 0.84 ± 0.14 | 5.32 ± 0.74 | 633 |
| TSH (2) | 61.54 ± 7.58 | 57.87 ± 1.52 | 94 |

| | % inhibition of TSH stimulation[c] | |
|---|---|---|
| Antibody concentration | Wild type TSHR | Mutated TSHR |
| 5B3 10 μg/mL | 0 | 4 |
| 5B3 100 μg/mL | 0 | 8 |
| K1-70 0.001 μg | 0 | 0 |
| K1-70 0.01 μg/mL | 0 | 0 |
| K1-70 0.1 μg/mL | 90 | 32 |
| K1-70 1 μg/mL | 98 | 80 |
| K1-70 10 μg/mL | 98 | 88 |
| K1-70 100 μg/mL | 98 | 90 |
| TSH (2) | 0 | 22 |

See legend to Table 9a for details.

TABLE 9d

TSH induced cyclic AMP production in CHO cells expressing wild type TSHR and TSHR with Glu107 mutated to Ala. Effect of different dilutions of human monoclonal antibody to the TSHR (K1-70) with TSH antagonist activity

| | Cyclic AMP produced (pmol/mL; mean ± SD, n = 3) | | Mutated/wild type (%) |
|---|---|---|---|
| Test sample[a] | Wild type TSHR | Mutated TSHR | |
| Cyclic AMP assay buffer only | 1.60 ± 0.19 | 5.29 ± 0.36 | 331 |
| TSH[b] | 76.22 ± 4.52 | 83.70 ± 3.92 | 110 |
| 5B3 10 μg/mL + TSH[b] | 85.30 ± 5.68 | 70.93 ± 5.64 | 83 |
| 5B3 100 μg/mL + TSH[b] | 81.64 ± 5.48 | 66.84 ± 7.24 | 82 |
| K1-70 0.001 μg + TSH[b] | 103.6 ± 5.93 | 94.45 ± 8.21 | 91 |
| K1-70 0.01 μg + TSH[b] | 89.43 ± 19.6 | 82.88 ± 4.50 | 93 |
| K1-70 0.1 μg + TSH[b] | 12.10 ± 2.22 | 4.97 ± 0.59 | 41 |
| K1-70 1.0 μg + TSH[b] | 1.71 ± 0.32 | 2.71 ± 0.05 | 158 |
| K1-70 10 μg + TSH[b] | 1.49 ± 0.16 | 2.45 ± 0.13 | 164 |
| K1-70 100 μg + TSH[b] | 1.86 ± 0.23 | 2.75 ± 0.17 | 148 |
| K1-70 100 μg | 1.60 ± 0.07 | 1.80 ± 0.30 | 113 |
| TSH (2) | 93.75 ± 9.25 | 73.24 ± 5.57 | 78 |

| | % inhibition of TSH stimulation[c] | |
|---|---|---|
| Antibody concentration | Wild type TSHR | Mutated TSHR |
| 5B3 10 μg/mL | 0 | 15 |
| 5B3 100 μg/mL | 0 | 17 |
| K1-70 0.001 μg | 0 | 0 |
| K1-70 0.01 μg/mL | 0 | 1 |
| K1-70 0.1 μg/mL | 84 | 94 |
| K1-70 1 μg/mL | 98 | 97 |
| K1-70 10 μg/mL | 98 | 97 |
| K1-70 100 μg/mL | 98 | 97 |
| TSH (2) | 0 | 12 |

See legend to Table 9a for details.

TABLE 9e

TSH induced cyclic AMP production in CHO cells expressing wild type TSHR and TSHR with Arg109 mutated to Ala. Effect of different dilutions of human monoclonal antibody to the TSHR (K1-70) with TSH antagonist activity Experiment 1

| Test sample[a] | Cyclic AMP produced (pmol/mL; mean ± SD, n = 3) | | Mutated/ wild type (%) |
|---|---|---|---|
| | Wild type TSHR | Mutated TSHR | |
| Cyclic AMP assay buffer only | 1.94 ± 0.35 | 4.42 ± 0.55 | 228 |
| TSH[b] | 67.67 ± 4.90 | 32.90 ± 2.55 | 49 |
| 5B3 10 µg/mL + TSH[b] | 65.84 ± 1.73 | 34.41 ± 1.67 | 52 |
| 5B3 100 µg/mL + TSH[b] | 68.54 ± 1.22 | 34.51 ± 5.03 | 50 |
| K1-70 0.001 µg + TSH[b] | 66.99 ± 8.59 | 34.24 ± 0.25 | 51 |
| K1-70 0.01 µg + TSH[b] | 66.85 ± 2.02 | 32.56 ± 1.04 | 49 |
| K1-70 0.1 µg + TSH[b] | 6.41 ± 0.32 | 24.84 ± 1.94 | 388 |
| K1-70 1.0 µg + TSH[b] | 1.60 ± 0.28 | 24.45 ± 0.49 | 1528 |
| K1-70 10 µg + TSH[b] | 1.51 ± 0.08 | 18.92 ± 2.16 | 1253 |
| K1-70 100 µg + TSH[b] | 1.36 ± 0.17 | 14.05 ± 3.4 | 1033 |
| K1-70 100 µg | 1.48 ± 0.1 | 3.39 ± 0.29 | 229 |
| TSH (2) | 67.54 ± 2.56 | 33.30 ± 2.27 | 49 |

| Antibody concentration | % inhibition of TSH stimulation[c] | |
|---|---|---|
| | Wild type TSHR | Mutated TSHR |
| 5B3 10 µg/mL | 3 | 0 |
| 5B3 100 µg/mL | 0 | 0 |
| K1-70 0.001 µg | 1 | 0 |
| K1-70 0.01 µg/mL | 1 | 0 |
| K1-70 0.1 µg/mL | 91 | 24 |
| K1-70 1 µg/mL | 98 | 26 |
| K1-70 10 µg/mL | 98 | 42 |
| K1-70 100 µg/mL | 98 | 57 |
| TSH (2) | 0.1 | 0 |

Experiment 2

| Test sample[a] | Cyclic AMP produced (pmol/mL; mean ± SD, n = 3) | | Mutated/ wild type (%) |
|---|---|---|---|
| | Wild type TSHR | Mutated TSHR | |
| Cyclic AMP assay buffer only | 0.89 ± 0.19 | 1.61 ± 0.14 | 181 |
| TSH[b] | 60.73 ± 7.97 | 53.41 ± 3.69 | 88 |
| 5B3 10 µg/mL + TSH[b] | 68.59 ± 2.26 | 60.65 ± 0.63 | 88 |
| 5B3 100 µg/mL + TSH[b] | 66.50 ± 2.55 | 56.57 ± 3.26 | 85 |
| K1-70 0.001 µg + TSH[b] | 55.89 ± 6.77 | 61.82 ± 17.17 | 111 |
| K1-70 0.01 µg + TSH[b] | 61.90 ± 1.57 | 46.01 ± 0.91 | 74 |
| K1-70 0.1 µg + TSH[b] | 5.54 ± 1.21 | 30.32 ± 3.35 | 547 |
| K1-70 1.0 µg + TSH[b] | 1.32 ± 0.21 | 25.25 ± 1.54 | 1913 |
| K1-70 10 µg + TSH[b] | 0.97* | 14.80 ± 0 | 1526 |
| K1-70 100 µg + TSH[b] | 0.88 ± 0.11 | 9.14 ± 0.91 | 1039 |
| K1-70 100 µg | 1.02 ± 0.06 | 1.26 ± 0.41 | 124 |
| TSH (2) | 67.80 ± 3.83 | 50.39 ± 2.52 | 74 |

| Antibody concentration | % inhibition of TSH stimulation[c] | |
|---|---|---|
| | Wild type TSHR | Mutated TSHR |
| 5B3 10 µg/mL | 0 | 0 |
| 5B3 100 µg/mL | 0 | 0 |
| K1-70 0.001 µg | 8 | 0 |
| K1-70 0.01 µg/mL | 0 | 14 |
| K1-70 0.1 µg/mL | 91 | 43 |
| K1-70 1 µg/mL | 98 | 53 |
| K1-70 10 µg/mL | 98 | 72 |
| K1-70 100 µg/mL | 99 | 83 |
| TSH (2) | 0 | 6 |

*duplicate determination
See legend to Table 9a for details.

TABLE 9f

TSH induced cyclic AMP production in CHO cells expressing wild type TSHR and TSHR with Lys129 mutated to Ala. Effect of different dilutions of human monoclonal antibody to the TSHR (K1-70) with TSH antagonist activity

| Test sample[a] | Cyclic AMP produced (pmol/mL; mean ± SD, n = 3) | | Mutated/ wild type (%) |
|---|---|---|---|
| | Wild type TSHR | Mutated TSHR | |
| Cyclic AMP assay buffer only | 3.10 ± 2.74 | 3.37 ± 0.85 | 109 |
| TSH[b] | 50.03 ± 3.0 | 49.2 ± 6.7 | 98 |
| 5B3 10 µg/mL + TSH[b] | 53.88 ± 3.67 | 50.5 ± 3.43 | 94 |
| 5B3 100 µg/mL + TSH[b] | 52.60 ± 6.43 | 42.63 ± 2.35 | 81 |
| K1-70 0.001 µg + TSH[b] | 49.48 ± 6.51 | 44.76 ± 2.58 | 90 |
| K1-70 0.01 µg + TSH[b] | 51.04 ± 0.00 | 38.66 ± 2.03 | 76 |
| K1-70 0.1 µg + TSH[b] | 4.70 ± 1.25 | 9.86 ± 1.14 | 210 |
| K1-70 1.0 µg + TSH[b] | 0.74 ± 0.06 | 3.23 ± 0.15 | 436 |
| K1-70 10 µg + TSH[b] | 0.80 ± 0.33 | 2.83 ± 0.71 | 354 |
| K1-70 100 µg + TSH[b] | 1.12 ± 0.46 | 2.82 ± 0.21 | 251 |
| K1-70 100 µg | 0.88 ± 0.21 | 3.06 ± 1.11 | 348 |
| TSH (2) | 53.1 ± 8.0 | 47.9 ± 0.41 | 90 |

| Antibody concentration | % inhibition of TSH stimulation[c] | |
|---|---|---|
| | Wild type TSHR | Mutated TSHR |
| 5B3 10 µg/mL | 0 | 0 |
| 5B3 100 µg/mL | 0 | 13 |
| K1-70 0.001 µg | 1 | 9 |
| K1-70 0.01 µg/mL | 0 | 21 |
| K1-70 0.1 µg/mL | 91 | 80 |
| K1-70 1 µg/mL | 99 | 93 |
| K1-70 10 µg/mL | 98 | 94 |
| K1-70 100 µg/mL | 98 | 94 |
| TSH (2) | 0 | 3 |

See legend for Table 9a for details.

TABLE 9g

TSH induced cyclic AMP production in CHO cells expressing wild type TSHR and TSHR with Phe130 mutated to Ala. Effect of different dilutions of human monoclonal antibody to the TSHR (K1-70) with TSH antagonist activity

| Test sample[a] | Cyclic AMP produced (pmol/mL; mean ± SD, n = 3) | | Mutated/ wild type (%) |
|---|---|---|---|
| | Wild type TSHR | Mutated TSHR | |
| Cyclic AMP assay buffer only | 1.39 ± 0.29 | 3.53 ± 0.49 | 254 |
| TSH[b] | 79.42 ± 5.15 | 120.74 ± 2.87 | 152 |
| 5B3 10 µg/mL + TSH[b] | 78.18 ± 1.95 | 110.76 ± 1.49 | 142 |
| 5B3 100 µg/mL + TSH[b] | 86.94 ± 15.80 | 113.8 ± 11.11 | 131 |
| K1-70 0.001 µg + TSH[b] | 82.73 ± 3.36 | 102.43 ± 7.59 | 124 |
| K1-70 0.01 µg + TSH[b] | 83.95 ± 5.31 | 103.90 ± 7.14 | 124 |
| K1-70 0.1 µg + TSH[b] | 4.86 ± 1.52 | 12.71 ± 3.24 | 262 |
| K1-70 1.0 µg + TSH[b] | 1.56 ± 0.61 | 2.87 ± 0.28 | 184 |
| K1-70 10 µg + TSH[b] | 1.27 ± 0.15 | 2.22 ± 0.40 | 175 |
| K1-70 100 µg + TSH[b] | 1.18 ± 0.09 | 2.68 ± 0.41 | 242 |
| K1-70 100 µg | 1.23 ± 0.08 | 2.37 ± 0.26 | 193 |
| TSH (2) | 89.12 ± 4.45 | 95.39 ± 7.44 | 107 |

| Antibody concentration | % inhibition of TSH stimulation[c] | |
|---|---|---|
| | Wild type TSHR | Mutated TSHR |
| 5B3 10 µg/mL | 2 | 8 |
| 5B3 100 µg/mL | 0 | 6 |
| K1-70 0.001 µg | 0 | 15 |
| K1-70 0.01 µg/mL | 0 | 14 |
| K1-70 0.1 µg/mL | 94 | 89 |
| K1-70 1 µg/mL | 98 | 98 |
| K1-70 10 µg/mL | 98 | 98 |

TABLE 9g-continued

TSH induced cyclic AMP production in CHO cells expressing wild type TSHR and TSHR with Phe130 mutated to Ala. Effect of different dilutions of human monoclonal antibody to the TSHR (K1-70) with TSH antagonist activity

| | | |
|---|---|---|
| K1-70 100 µg/mL | 99 | 98 |
| TSH (2) | 0 | 0 |

See legend to Table 9a for details

TABLE 9h

TSH induced cyclic AMP production in CHO cells expressing wild type TSHR and TSHR with Phe134 mutated to Ala. Effect of different dilutions of human monoclonal antibody to the TSHR (K1-70) with TSH antagonist activity

| | Cyclic AMP produced (pmol/mL; mean ± SD, n = 3) | | Mutated/wild type |
|---|---|---|---|
| Test sample[a] | Wild type TSHR | Mutated TSHR | (%) |
| Cyclic AMP assay buffer only | 6.83 ± 1.44 | 14.86 ± 2.75 | 218 |
| TSH[b] | 108.08 ± 13.83 | 111.16 ± 2.0 | 103 |
| 5B3 10 µg/mL + TSH[b] | 131.38 ± 6.77 | 101.30 ± 8.44 | 77 |
| 5B3 100 µg/mL + TSH[b] | 112.49 ± 2.66 | 115.54 ± 9.72 | 103 |
| K1-70 0.001 µg + TSH[b] | 137.02 ± 27.32 | 106.92 ± 15.54 | 78 |
| K1-70 0.01 µg + TSH[b] | 120.16 ± 3.88 | 111.84 ± 6.01 | 93 |
| K1-70 0.1 µg + TSH[b] | 8.09 ± 1.00 | 27.86 ± 3.72 | 344 |
| K1-70 1.0 µg + TSH[b] | 2.02 ± 0.39 | 5.59 ± 1.40 | 277 |
| K1-70 10 µg + TSH[b] | 1.88 ± 0.35 | 4.00 ± 1.77 | 213 |
| K1-70 100 µg + TSH[b] | 1.48 ± 0.33 | 3.50 ± 0.09 | 236 |
| K1-70 100 µg | 1.34 ± 0.40 | 2.86 ± 0.41 | 213 |
| TSH (2) | 142.29 ± 13.46 | 101.70 ± 1.33 | 71 |

| | % inhibition of TSH stimulation[c] | |
|---|---|---|
| Antibody concentration | Wild type TSHR | Mutated TSHR |
| 5B3 10 µg/mL | 0 | 9 |
| 5B3 100 µg/mL | 0 | 0 |
| K1-70 0.001 µg | 0 | 4 |
| K1-70 0.01 µg/mL | 0 | 0 |
| K1-70 0.1 µg/mL | 93 | 75 |
| K1-70 1 µg/mL | 98 | 95 |
| K1-70 10 µg/mL | 98 | 96 |
| K1-70 100 µg/mL | 99 | 97 |
| TSH (2) | 0 | 9 |

See legend to Table 9a for details.

TABLE 9i

TSH induced cyclic AMP production in CHO cells expressing wild type TSHR and TSHR with Lys183 mutated to Ala. Effect of different dilutions of human monoclonal antibody to the TSHR (K1-70) with TSH antagonist activity Experiment 1

| | Cyclic AMP produced (pmol/mL; mean ± SD, n = 3) | | Mutated/wild type |
|---|---|---|---|
| Test sample[a] | Wild type TSHR | Mutated TSHR | (%) |
| Cyclic AMP assay buffer only | 0.43 ± 0.69 | 3.20 ± 0.15 | 744 |
| TSH[b] | 61.1 ± 2.48 | 75.8 ± 8.25 | 124 |
| 5B3 10 µg/mL + TSH[b] | 62.03 ± 12.77 | 57.82 ± 7.43 | 93 |
| 5B3 100 µg/mL + TSH[b] | 69.24 ± 6.19 | 63.12 ± 10.69 | 91 |
| K1-70 0.001 µg + TSH[b] | 83.86 ± 6.22 | 64.26 ± 2.45 | 77 |
| K1-70 0.01 µg + TSH[b] | 91.30 ± 15.24 | 61.76 ± 5.46 | 68 |
| K1-70 0.1 µg + TSH[b] | 9.35 ± 4.52 | 35.73 ± 5.57 | 382 |
| K1-70 1.0 µg + TSH[b] | 0.94 ± 0.34 | 4.02 ± 0.35 | 428 |
| K1-70 10 µg + TSH[b] | 0.52 ± 0.44 | 2.13 ± 0.89 | 410 |
| K1-70 100 µg + TSH[b] | 1.22 ± 0.32 | 1.88 ± 0.17 | 154 |
| K1-70 100 µg | 0.02 ± 0.01 | 1.42 ± 0.18 | 7100 |
| TSH (2) | 83.6 ± 2.95 | 62.16 ± 4.39 | 74 |

| | % inhibition of TSH stimulation[c] | |
|---|---|---|
| Antibody concentration | Wild type TSHR | Mutated TSHR |
| 5B3 10 µg/mL | 0 | 24 |
| 5B3 100 µg/mL | 0 | 17 |
| K1-70 0.001 µg | 0 | 15 |
| K1-70 0.01 µg/mL | 0 | 19 |
| K1-70 0.1 µg/mL | 85 | 53 |
| K1-70 1 µg/mL | 98 | 95 |
| K1-70 10 µg/mL | 99 | 97 |
| K1-70 100 µg/mL | 98 | 98 |
| TSH (2) | 0 | 18 |

Experiment 2

| | Cyclic AMP produced (pmol/mL; mean ± SD, n = 3) | | Mutated/wild type |
|---|---|---|---|
| Test sample[a] | Wild type TSHR | Mutated TSHR | (%) |
| Cyclic AMP assay buffer only | 2.28 ± 0.08 | 4.86 ± 0.69 | 213 |
| TSH[b] | 78.45 ± 5.2 | 100.68 ± 6.89 | 128 |
| 5B3 10 µg/mL + TSH[b] | 87.4 ± 1.07 | 91.25 ± 1.14 | 104 |
| 5B3 100 µg/mL + TSH[b] | 82.72 ± 3.42 | 91.89 ± 0.00 | 111 |
| K1-70 0.001 µg + TSH[b] | 94.13 ± 3.00 | 98.03 ± 9.02 | 104 |
| K1-70 0.01 µg + TSH[b] | 101.52 ± 6.79 | 103.40 ± 5.88 | 102 |
| K1-70 0.1 µg + TSH[b] | 19.94 ± 4.38 | 69.63 ± 3.65 | 349 |
| K1-70 1.0 µg + TSH[b] | 2.26 ± 0.17 | 13.36 ± 3.85 | 591 |
| K1-70 10 µg + TSH[b] | 2.24 ± 0.33 | 4.32 ± 0.30 | 193 |
| K1-70 100 µg + TSH[b] | 2.29 ± 0.42 | 4.01 ± 0.56 | 175 |
| K1-70 100 µg | 2.32 ± 0.21 | 3.26 ± 0.08 | 141 |
| TSH (2) | 79.45 ± 4.3 | 77.34 ± 3.86 | 97 |

| | % inhibition of TSH stimulation[c] | |
|---|---|---|
| Antibody concentration | Wild type TSHR | Mutated TSHR |
| 5B3 10 µg/mL | 0 | 9 |
| 5B3 100 µg/mL | 0 | 9 |
| K1-70 0.001 µg | 0 | 3 |
| K1-70 0.01 µg/mL | 0 | 0 |
| K1-70 0.1 µg/mL | 75 | 31 |
| K1-70 1 µg/mL | 97 | 87 |
| K1-70 10 µg/mL | 97 | 96 |
| K1-70 100 µg/mL | 97 | 96 |
| TSH (2) | 0 | 23 |

See legend to Table 9a for details.

TABLE 9j

TSH induced cyclic AMP production in CHO cells expressing wild type TSHR and TSHR with Asp203 mutated to Ala. Effect of different dilutions of human monoclonal antibody to the TSHR (K1-70) with TSH antagonist activity

| | Cyclic AMP produced (pmol/mL; mean ± SD, n = 3) | | Mutated/wild type (%) |
|---|---|---|---|
| Test sample[a] | Wild type TSHR | Mutated TSHR | |
| Cyclic AMP assay buffer only | 1.55 ± 0.40 | 5.22 ± 0.77 | 337 |
| TSH[b] | 71.0 ± 6.52 | 53.85 ± 2.96 | 76 |

TABLE 9j-continued

TSH induced cyclic AMP production in CHO cells expressing wild type TSHR and TSHR with Asp203 mutated to Ala. Effect of different dilutions of human monoclonal antibody to the TSHR (K1-70) with TSH antagonist activity

| | | | |
|---|---|---|---|
| 5B3 10 μg/mL + TSH[b] | 72.22 ± 3.73 | 64.34 ± 5.43 | 89 |
| 5B3 100 μg/mL + TSH[b] | 72.78 ± 4.65 | 61.38 ± 1.95 | 84 |
| K1-70 0.001 μg + TSH[b] | 79.43 ± 2.28 | 65.83 ± 4.66 | 83 |
| K1-70 0.01 μg + TSH[b] | 80.84 ± 4.72 | 63.32 ± 8.41 | 78 |
| K1-70 0.1 μg + TSH[b] | 7.51 ± 0.12 | 15.13 ± 3.92 | 201 |
| K1-70 1.0 μg + TSH[b] | 1.33 ± 0.03 | 4.43 ± 0.96 | 333 |
| K1-70 10 μg + TSH[b] | 0.39 ± 0.31 | 4.37 ± 0.56 | 1121 |
| K1-70 100 μg + TSH[b] | 0.62 ± 0.45 | 4.55 ± 1.57 | 734 |
| K1-70 100 μg | 0.53 ± 0.27 | 3.79 ± 0.59 | 715 |
| TSH (2) | 68.0 ± 3.15 | 59.29 ± 9.87 | 87 |

| | % inhibition of TSH stimulation[c] | |
|---|---|---|
| Antibody concentration | Wild type TSHR | Mutated TSHR |
| 5B3 10 μg/mL | 0 | 0 |
| 5B3 100 μg/mL | 0 | 0 |
| K1-70 0.001 μg | 0 | 0 |
| K1-70 0.01 μg/mL | 0 | 0 |
| K1-70 0.1 μg/mL | 89 | 72 |
| K1-70 1 μg/mL | 98 | 92 |
| K1-70 10 μg/mL | 99 | 92 |
| K1-70 100 μg/mL | 99 | 92 |
| TSH (2) | 0 | 0 |

See legend to Table 9a for details.

TABLE 9k

TSH induced cyclic AMP production in CHO cells expressing wild type TSHR and TSHR with Arg255 mutated to Asp. Effect of different dilutions of human monoclonal antibody to the TSHR (K1-70) with TSH antagonist activity

| | Cyclic AMP produced (pmol/mL; mean ± SD, n = 3) | | Mutated/ wild type (%) |
|---|---|---|---|
| Test sample[a] | Wild type TSHR | Mutated TSHR R255D | |
| Cyclic AMP assay buffer only | 1.95 ± 0.25 | 2.17 ± 0.78 | 111 |
| TSH[b] | 66.48 ± 5.07 | 57.84 ± 4.45 | 87 |
| 5B3 10 μg/mL + TSH[b] | 69.15 ± 0.73 | 59.42 ± 3.05 | 86 |
| 5B3 100 μg/mL + TSH[b] | 83.38 ± 7.53 | 62.20 ± 10.14 | 75 |
| K1-70 0.001 μg + TSH[b] | 74.70 ± 1.78 | 55.65 ± 3.99 | 74 |
| K1-70 0.01 μg + TSH[b] | 77.09 ± 6.60 | 56.26 ± 3.14 | 73 |
| K1-70 0.1 μg + TSH[b] | 24.06 ± 0.32 | 5.67 ± 1.26 | 24 |
| K1-70 1.0 μg + TSH[b] | 3.22 ± 0.64 | 1.56 ± 0.34 | 48 |
| K1-70 10 μg + TSH[b] | 2.38 ± 0.28 | 0.10 ± 0.08 | 4 |
| K1-70 100 μg + TSH[b] | 1.99 ± 0.14 | 1.05 ± 0.56 | 53 |
| K1-70 100 μg | 1.85 ± 0.44 | 0.60 ± 0.47 | 32 |
| TSH (2) | 64.84 ± 8.16 | 50.21 ± 5.27 | 77 |

| | % inhibition of TSH stimulation[c] | |
|---|---|---|
| Antibody concentration | Wild type TSHR | Mutated TSHR |
| 5B3 10 μg/mL | 0 | 0 |
| 5B3 100 μg/mL | 0 | 0 |
| K1-70 0.001 μg | 0 | 4 |
| K1-70 0.01 μg/mL | 0 | 3 |
| K1-70 0.1 μg/mL | 64 | 90 |
| K1-70 1 μg/mL | 95 | 97 |
| K1-70 10 μg/mL | 96 | 100 |
| K1-70 100 μg/mL | 97 | 98 |
| TSH (2) | 2 | 13 |

See legend to Table 9a for details.

TABLE 10

Summary of effects of TSHR mutations (relative to wild type) on the ability of K1-18 IgG to stimulate the TSHR and K1-70 IgG to block TSH stimulation of the TSHR

| TSHR mutation | Stimulation of cyclic AMP production by K1-18 IgG | Blocking by K1-70 of TSH stimulation of cyclic AMP production |
|---|---|---|
| Wild type | +++++ | +++++ |
| Lys58 Ala | +++++ | ++ |
| Arg80 Ala | +++++ | +++++ |
| Tyr82 Ala | +++++ | ++++ |
| Glu107 Ala | +++++ | +++++ |
| Arg109 Ala | +++++ | +++ |
| Lys129 Ala | +++++ | +++++ |
| Phe130 Ala | +++++ | +++++ |
| Phe134 Ala | +++++ | +++++ |
| Lys183 Ala | 0 | +++ |
| Asp203 Ala | +++++ | +++++ |
| Arg255 Asp | 0 | +++++ |

Effects of TSHR mutations were expressed as a percentage of activity observed with wild type as follows:-
+++++ = 100% wild type activity;
++++ = <100-80% of wild type activity;
+++ = <80-60% of wild type activity;
++ = <60-40% of wild type activity;
+ = <40-20% of wild type activity;
0 = <20% of wild type activity.

TABLE 11a

Inhibition of $^{125}$I-K1-70 IgG binding to TSHR coated tubes by human monoclonal TSHR autoantibodies

| Test sample | Inhibition of binding (%) Dilutions in assay buffer (mean ± SD) | Inhibition of binding (%) Dilutions in HBD (mean ± SD) |
|---|---|---|
| M22 IgG | | |
| 100 μg/mL | 92.2 ± 0.2 | 94.0 ± 0.6 |
| 30 μg/mL | 90.5 ± 0.4 | 94.4 ± 1.1 |
| 10 μg/mL | 90.2 ± 0.7 | 92.5 ± 0.1 |
| 3 μg/mL | 89.5 ± 1.0 | 91.6 ± 0.5 |
| 1 μg/mL | 89.0 ± 0.1 | 90.4 ± 0.7 |
| 0.3 μg/mL | 87.7 ± 0.4 | 84.6 ± 1.1 |
| 0.1 μg/mL | 84.5 ± 0.4 | 65.5 ± 0.2 |
| 0.03 μg/mL | 70.4 ± 1.1 | 33.8 ± 0.9 |
| 0.01 μg/mL | 43.4 ± 1.9 | 17.1 ± 2.4 |
| 0.003 μg/mL | 16.7 ± 3.7 | 6.2* |
| 0.001 μg/mL | 5.5 ± 0.7 | 3.0 ± 3.6 |
| M22 Fab | | |
| 100 μg/mL | 93.2 ± 0.5 | 93.1 ± 0.2 |
| 30 μg/mL | 92.2 ± 0.7 | 93.2 ± 0.3 |
| 10 μg/mL | 89.4 ± 1.3 | 92.6 ± 0.4 |
| 3 μg/mL | 89.1 ± 1.0 | 92.0 ± 0.3 |
| 1 μg/mL | 88.8 ± 0.8 | 91.7 ± 0.7 |
| 0.3 μg/mL | 88.0 ± 0.4 | 89.9 ± 0.1 |
| 0.1 μg/mL | 86.5 ± 0.1 | 82.5 ± 0.4 |
| 0.03 μg/mL | 79.7 ± 0.4 | 60.2 ± 1.8 |
| 0.01 μg/mL | 63.5 ± 0.8 | 34.0 ± 2.1 |
| 0.003 μg/mL | 31.0 ± 3.3 | 16.7 ± 6.0 |
| 0.001 μg/mL | 15.9 ± 3.1 | 9.3 ± 1.3 |
| K1-70 IgG | | |
| 100 μg/mL | 93.0 ± 0.3 | 94.6 ± 0.7 |
| 30 μg/mL | 92.3 ± 0.2 | 93.7 ± 0.5 |
| 10 μg/mL | 90.8 ± 1.0 | 92.6 ± 0.4 |
| 3 μg/mL | 89.7 ± 0.4 | 92.0 ± 0.5 |
| 1 μg/mL | 89.9 ± 0.7 | 91.8 ± 0.9 |
| 0.3 μg/mL | 89.0 ± 0.5 | 84.4 ± 0.8 |
| 0.1 μg/mL | 86.7 ± 0.5 | 67.4 ± 0.7 |
| 0.03 μg/mL | 77.0 ± 0.6 | 36.5 ± 1.9 |
| 0.01 μg/mL | 50.7 ± 1.5 | 19.9 ± 5.8 |
| 0.003 μg/mL | 17.0 ± 0.8 | 10.2 ± 2.4 |
| 0.001 μg/mL | 3.4 ± 0.7 | 4.8 ± 4.8 |

TABLE 11a-continued

Inhibition of $^{125}$I-K1-70 IgG binding to TSHR coated tubes by human monoclonal TSHR autoantibodies

| Test sample | Inhibition of binding (%) Dilutions in assay buffer (mean ± SD) | Inhibition of binding (%) Dilutions in HBD (mean ± SD) |
|---|---|---|
| 5C9 IgG | | |
| 100 µg/mL | 93.3 ± 0.2 | 68.5 ± 0.7 |
| 10 µg/mL | 84.8 ± 0.8 | 22.7 ± 1.0 |
| 1 µg/mL | 56.4 ± 0.9 | 15.4 ± 3.4 |
| 0.1 µg/mL | 24.6 ± 0.4 | 4.4 ± 2.7 |
| 0.01 µg/mL | 4.5 ± 2.4 | 2.8 ± 4.5 |
| 5B3 IgG | | |
| 100 µg/mL | 15.2 ± 2.5 | 1.1* |
| 10 µg/mL | −2.1 ± 1.3 | −0.7 ± 2.2 |
| 1 µg/mL | −2.6 ± 1.1 | 0.0* |
| 0.1 µg/mL | 1.0 ± 2.7 | 9.4 ± 4.2 |
| 0.01 µg/mL | 3.2 ± 3.4 | 3.2 ± 3.4 |
| 0.001 µg/mL | −1.5 ± 4.3 | 3.7 ± 2.1 |

Results shown are mean ± SD of triplicate determinations.
*duplicate determination.
HBD = pool of healthy blood donor sera.
5B3 is a human MAb to glutamic acid decarboxylase (negative control).
$^{125}$I-K1-70 IgG in the presence of assay buffer gave 20.4% binding.
$^{125}$I-K1-70 IgG in the presence of HBD pool gave 20.5% binding.
Assay buffer is 50 mmol/L NaCl, 10 mmol/L Tris pH 7.8, 0.1% Triton X-100.

TABLE 11b

Inhibition of $^{125}$I-K1-70 IgG binding to TSHR coated tubes by human monoclonal TSHR autoantibodies

| Test sample | Inhibition of binding (%) Dilutions in assay buffer (mean ± SD) | Inhibition of binding (%) Dilutions in HBD (mean ± SD) |
|---|---|---|
| K1-18 IgG | | |
| 100 µg/mL | 92.9 ± 0.2 | 93.5 ± 0.2 |
| 30 µg/mL | 91.2 ± 0.7 | 92.2 ± 0.6 |
| 10 µg/mL | 91.8 ± 0.3 | 92.5 ± 0.7 |
| 3 µg/mL | 90.5 ± 1.0 | 91.0 ± 0.3 |
| 1 µg/mL | 89.6 ± 1.2 | 85.8 ± 0.3 |
| 0.3 µg/mL | 86.4 ± 0.8 | 73.9 ± 0.8 |
| 0.1 µg/mL | 77.9 ± 0.2 | 48.6 ± 0.9 |
| 0.03 µg/mL | 53.9 ± 1.9 | 20.0 ± 1.9 |
| 0.01 µg/mL | 30.2 ± 2.1 | 3.1 ± 2.0 |
| 0.003 µg/mL | 17.0 ± 3.1 | −2.7 ± 7.9 |
| 0.001 µg/mL | 7.2 ± 2.5 | −3.0 ± 3.9 |
| K1-18 Fab | | |
| 100 µg/mL | 86.0 ± 1.4 | 83.6 ± 0.3 |
| 30 µg/mL | 83.3 ± 1.5 | 83.2 ± 1.4 |
| 10 µg/mL | 81.9 ± 0.9 | 82.0 ± 0.2 |
| 3 µg/mL | 79.4 ± 1.1 | 80.5 ± 0.6 |
| 1 µg/mL | 78.5 ± 1.8 | 75.6 ± 1.0 |
| 0.3 µg/mL | 71.4 ± 1.7 | 60.9 ± 1.1 |
| 0.1 µg/mL | 62.8 ± 5.1 | 38.4 ± 1.2 |
| 0.03 µg/mL | 31.3 ± 1.0 | 10.2 ± 2.1 |
| 0.01 µg/mL | 23.7 ± 5.4 | 1.1 ± 2.6 |
| 0.003 µg/mL | 15.2 ± 3.4 | −3.5 ± 3.1 |
| 0.001 µg/mL | 13.8 ± 5.9 | 0.5 ± 4.4 |
| K1-70 IgG | | |
| 100 µg/mL | 93.8 ± 0.2 | 93.6 ± 0.4 |
| 30 µg/mL | 93.1 ± 0.5 | 94.3 ± 0.2 |
| 10 µg/mL | 92.3 ± 0.3 | 93.1 ± 0.6 |
| 3 µg/mL | 90.7 ± 0.4 | 91.7 ± 0.4 |
| 1 µg/mL | 90.8 ± 0.4 | 90.4 ± 0.3 |
| 0.3 µg/mL | 89.2 ± 0.6 | 82.7 ± 0.6 |
| 0.1 µg/mL | 87.1 ± 0.6 | 62.8 ± 1.1 |
| 0.03 µg/mL | 74.2 ± 1.5 | 33.6 ± 1.8 |
| 0.01 µg/mL | 50.9 ± 0.8 | 11.4 ± 3.6 |

TABLE 11b-continued

Inhibition of $^{125}$I-K1-70 IgG binding to TSHR coated tubes by human monoclonal TSHR autoantibodies

| Test sample | Inhibition of binding (%) Dilutions in assay buffer (mean ± SD) | Inhibition of binding (%) Dilutions in HBD (mean ± SD) |
|---|---|---|
| 0.003 µg/mL | 24.0 ± 4.5 | 2.2 ± 6.2 |
| 0.001 µg/mL | 15.3 ± 1.1 | −7.6 ± 2.8 |
| K1-70 Fab | | |
| 100 µg/mL | 91.5 ± 0.2 | 90.8 ± 0.6 |
| 30 µg/mL | 90.7 ± 0.1 | 91.0 ± 0.7 |
| 10 µg/mL | 89.8 ± 1.2 | 90.6 ± 0.1 |
| 3 µg/mL | 89.4 ± 0.3 | 90.9 ± 0.4 |
| 1 µg/mL | 88.3 ± 0.4 | 89.5 ± 0.3 |
| 0.3 µg/mL | 88.0 ± 0.1 | 87.3 ± 0.6 |
| 0.1 µg/mL | 87.5 ± 0.8 | 76.5 ± 0.4 |
| 0.03 µg/mL | 81.7 ± 0.6 | 49.6 ± 0.4 |
| 0.01 µg/mL | 64.8 ± 2.7 | 21.6 ± 3.8 |
| 0.003 µg/mL | 32.7 ± 2.7 | 5.6 ± 6.0 |
| 0.001 µg/mL | 12.2 ± 2.3 | −3.6 ± 1.0 |

See legend to Table 11a for details.
$^{125}$I-K1-70 IgG in the presence of assay buffer gave 20.4% binding.
$^{125}$I-K1-70 IgG in the presence of HBD pool gave 20.5% binding.
Effect of 5B3 IgG (human MAb to glutamic acid decarboxylase; negative control) is shown in Table 11a.

TABLE 11c

Inhibition of $^{125}$I-K1-70 IgG binding to TSHR coated tubes by mouse monoclonal TSHR antibodies

| Test sample | Inhibition of binding (%) Dilutions in assay buffer (mean ± SD) | Inhibition of binding (%) Dilutions in HBD (mean ± SD) |
|---|---|---|
| TSMAb 1 IgG | | |
| 100 µg/mL | 47.4 ± 1.2 | 44.7 ± 0.5 |
| 10 µg/mL | 23.0 ± 0.5 | 37.7 ± 1.2 |
| 1 µg/mL | 14.8 ± 0.5 | 16.8 ± 2.3 |
| 0.1 µg/mL | 2.3 ± 2.3 | −2.2 ± 1.9 |
| 0.01 µg/mL | −1.0 ± 4.4 | −3.3 ± 2.9 |
| TSMAb 2 IgG | | |
| 100 µg/mL | 53.7 ± 1.4 | 43.8 ± 0.9 |
| 10 µg/mL | 14.5 ± 1.4 | 35.5 ± 1.3 |
| 1 µg/mL | 9.3 ± 1.6 | 28.6 ± 0.6 |
| 0.1 µg/mL | 6.5 ± 2.3 | 10.2 ± 0.8 |
| 0.01 µg/mL | 0.3 ± 3.4 | 1.2 ± 3.6 |
| TSMAb 3 IgG | | |
| 100 µg/mL | 54.8 ± 2.8 | 33.5 ± 3.7 |
| 10 µg/mL | 25.4 ± 2.9 | 24.9 ± 2.8 |
| 1 µg/mL | 14.6 ± 0.9 | 18.5 ± 0.8 |
| 0.1 µg/mL | 13.1 ± 0.7 | 4.8 ± 1.7 |
| 0.01 µg/mL | 5.3 ± 0.7 | −1.3 ± 0.3 |
| TSMAb 4 IgG | | |
| 100 µg/mL | 47.7 ± 2.6 | 54.2 ± 1.7 |
| 10 µg/mL | 31.9 ± 0.7 | 52.8 ± 2.5 |
| 1 µg/mL | 29.9 ± 1.0 | 42.8 ± 1.2 |
| 0.1 µg/mL | 22.6 ± 1.6 | 18.6 ± 0.2 |
| 0.01 µg/mL | 6.7 ± 0.6 | 2.3 ± 3.1 |
| TSMAb 5 IgG | | |
| 100 µg/mL | 72.5 ± 1.3 | 59.6 ± 0.6 |
| 10 µg/mL | 53.1 ± 1.6 | 53.8 ± 0.7 |
| 1 µg/mL | 33.8 ± 3.9 | 46.3 ± 1.3 |
| 0.1 µg/mL | 25.7 ± 0.7 | 30.6 ± 1.5 |
| 0.01 µg/mL | 10.9 ± 3.1 | 7.2 ± 1.4 |
| TSMAb 6 IgG | | |
| 100 µg/mL | 59.5 ± 3.2 | 48.1 ± 2.1 |
| 10 µg/mL | 23.9 ± 3.0 | 47.4 ± 4.1 |
| 1 µg/mL | 19.2 ± 2.3 | 37.0 ± 1.4 |

TABLE 11c-continued

Inhibition of $^{125}$I-K1-70 IgG binding to TSHR coated tubes by mouse monoclonal TSHR antibodies

| Test sample | Inhibition of binding (%) Dilutions in assay buffer (mean ± SD) | Inhibition of binding (%) Dilutions in HBD (mean ± SD) |
|---|---|---|
| 0.1 µg/mL | 16.6 ± 1.1 | 22.0 ± 1.2 |
| 0.01 µg/mL | 7.8 ± 0.5 | 3.6 ± 1.6 |
| TSMAb 7 IgG | | |
| 100 µg/mL | 61.2 ± 0.8 | 44.7 ± 1.6 |
| 10 µg/mL | 41.2 ± 2.3 | 41.8 ± 2.7 |
| 1 µg/mL | 19.4 ± 3.7 | 33.1 ± 1.4 |
| 0.1 µg/mL | 13.4 ± 1.5 | 13.0 ± 1.2 |
| 0.01 µg/mL | 2.9 ± 1.2 | −2.1 ± 0.4 |
| 9D33 IgG | | |
| 100 µg/mL | 61.4 ± 0.4 | 51.1 ± 1.7 |
| 10 µg/mL | 41.7 ± 1.6 | 48.0 ± 2.2 |
| 1 µg/mL | 37.2 ± 4.0 | 40.5 ± 3.6 |
| 0.1 µg/mL | 24.8 ± 1.1 | 14.8 ± 0.2 |
| 0.01 µg/mL | 9.4 ± 1.1 | 0.6 ± 0.4 |
| 5B3 IgG | | |
| 100 µg/mL | 1.3 ± 0.6 | −0.9 ± 2.6 |
| 10 µg/mL | 2.3 ± 2.3 | −1.5 ± 1.5 |
| 1 µg/mL | 4.2 ± 5.3 | −1.5 ± 5.4 |
| 0.1 µg/mL | −1.2 ± 1.3 | −3.6 ± 3.3 |
| 0.01 µg/mL | −3.6 ± 1.8 | −5.8 ± 1.9 |

See legend to Table 11a for details.
$^{125}$I-K1-70 IgG in the presence of assay buffer gave 20.3% binding.
$^{125}$I-K1-70 IgG in the presence of HBD pool gave 19.5% binding.

TABLE 11d

Inhibition of $^{125}$I-K1-70 Fab binding to TSHR coated tubes by human and mouse monoclonal TSHR antibodies

| Test sample | Inhibition of binding (%) Dilutions in assay buffer (mean ± SD) | Inhibition of binding (%) Dilutions in HBD (mean ± SD) |
|---|---|---|
| K1-18 IgG | | |
| 100 µg/mL | 95.3 ± 0.2 | 96.0 ± 0.0 |
| 30 µg/mL | 94.5 ± 0.1 | 95.6 ± 0.4 |
| 10 µg/mL | 94.0 ± 0.4 | 94.8 ± 0.3 |
| 3 µg/mL | 93.3 ± 0.5 | 93.0 ± 0.5 |
| 1 µg/mL | 93.1 ± 0.3 | 89.4 ± 0.7 |
| 0.3 µg/mL | 92.6 ± 0.8 | 77.7 ± 1.5 |
| 0.1 µg/mL | 83.6 ± 0.3 | 51.0 ± 3.2 |
| 0.03 µg/mL | 63.1 ± 0.6 | 17.2 ± 2.6 |
| 0.01 µg/mL | 30.3 ± 2.1 | 2.2 ± 7.8 |
| 0.003 µg/mL | 11.4 ± 4.1 | −9.4 ± 3.1 |
| 0.001 µg/mL | 5.9 ± 5.6 | −6.8 ± 5.4 |
| K1-18 Fab | | |
| 100 µg/mL | 86.4 ± 0.5 | 85.7 ± 1.6 |
| 30 µg/mL | 83.2 ± 0.1 | 85.4 ± 0.8 |
| 10 µg/mL | 80.8 ± 0.9 | 83.2 ± 0.7 |
| 3 µg/mL | 80.6 ± 1.9 | 82.6 ± 0.5 |
| 1 µg/mL | 79.0 ± 1.5 | 78.7 ± 1.6 |
| 0.3 µg/mL | 75.9 ± 0.2 | 63.9 ± 1.3 |
| 0.1 µg/mL | 62.9 ± 0.7 | 36.9 ± 2.2 |
| 0.03 µg/mL | 38.8 ± 0.4 | 7.9 ± 1.5 |
| 0.01 µg/mL | 16.7 ± 0.4 | −0.8 ± 4.7 |
| 0.003 µg/mL | 5.0 ± 4.6 | −9.6 ± 4.8 |
| 0.001 µg/mL | 3.8 ± 5.8 | −8.2 ± 5.6 |
| M22 IgG | | |
| 100 µg/mL | 97.2 ± 0.3 | 96.5 ± 0.5 |
| 30 µg/mL | 96.3 ± 0.5 | 95.8 ± 0.3 |
| 10 µg/mL | 95.8 ± 0.5 | 95.4 ± 0.7 |
| 3 µg/mL | 95.4 ± 0.4 | 95.1 ± 0.4 |
| 1 µg/mL | 94.5 ± 0.9 | 93.1 ± 0.2 |
| 0.3 µg/mL | 93.1 ± 0.3 | 86.6 ± 3.3 |
| 0.1 µg/mL | 89.4 ± 0.4 | 68.2 ± 0.4 |
| 0.03 µg/mL | 72.7 ± 1.3 | 32.7 ± 1.3 |
| 0.01 µg/mL | 41.0 ± 2.4 | 5.7 ± 2.0 |
| 0.003 µg/mL | 19.3 ± 3.1 | −5.8 ± 2.8 |
| 0.001 µg/mL | 12.1 ± 4.8 | −3.1 ± 5.5 |
| M22 Fab | | |
| 100 µg/mL | 97.7 ± 0.1 | 94.9 ± 0.5 |
| 30 µg/mL | 96.2 ± 0.3 | 95.3 ± 0.2 |
| 10 µg/mL | 95.5 ± 0.1 | 94.8 ± 0.5 |
| 3 µg/mL | 94.2 ± 0.2 | 94.1 ± 0.4 |
| 1 µg/mL | 93.6 ± 0.5 | 93.7 ± 0.7 |
| 0.3 µg/mL | 92.7 ± 0.4 | 92.2 ± 0.7 |
| 0.1 µg/mL | 91.8 ± 0.2 | 86.4 ± 1.8 |
| 0.03 µg/mL | 83.9 ± 0.8 | 66.8 ± 0.8 |
| 0.01 µg/mL | 61.6 ± 1.2 | 36.6 ± 1.0 |
| 0.003 µg/mL | 29.7 ± 1.4 | 11.5 ± 1.9 |
| 0.001 µg/mL | 10.9 ± 0.5 | 7.7 ± 7.3 |
| K1-70 IgG | | |
| 100 µg/mL | 97.7 ± 0.2 | 97.7 ± 0.2 |
| 30 µg/mL | 97.7 ± 0.2 | 97.4 ± 0.2 |
| 10 µg/mL | 96.9 ± 0.3 | 96.6 ± 0.2 |
| 3 µg/mL | 95.5 ± 0.5 | 96.2 ± 0.5 |
| 1 µg/mL | 95.2 ± 0.3 | 94.1 ± 0.4 |
| 0.3 µg/mL | 94.2 ± 0.2 | 97.0 ± 0.1 |
| 0.1 µg/mL | 93.5 ± 0.7 | 66.5 ± 1.4 |
| 0.03 µg/mL | 89.0 ± 0.5 | 37.8 ± 3.3 |
| 0.01 µg/mL | 66.2 ± 2.1 | 10.6 ± 1.6 |
| 0.003 µg/mL | 27.7 ± 3.8 | −0.8 ± 2.6 |
| 0.001 µg/mL | 5.5 ± 1.0 | −8.8 ± 2.4 |
| K1-70 Fab | | |
| 100 µg/mL | 96.7 ± 0.4 | 96.3 ± 0.1 |
| 30 µg/mL | 95.1 ± 0.9 | 95.7 ± 0.4 |
| 10 µg/mL | 93.6 ± 0.0 | 94.8 ± 0.5 |
| 3 µg/mL | 93.5 ± 0.2 | 94.9 ± 0.3 |
| 1 µg/mL | 93.5 ± 0.1 | 94.2 ± 0.3 |
| 0.3 µg/mL | 92.7 ± 0.4 | 91.4 ± 0.5 |
| 0.1 µg/mL | 92.2 ± 0.3 | 81.9 ± 0.5 |
| 0.03 µg/mL | 89.0 ± 0.3 | 57.2 ± 2.6 |
| 0.01 µg/mL | 75.6 ± 1.3 | 25.3 ± 3.9 |
| 0.003 µg/mL | 40.0 ± 3.9 | 2.5 ± 5.8 |
| 0.001 µg/mL | 11.9 ± 2.6 | −2.5 ± 3.2 |
| 5C9 IgG | | |
| 100 µg/mL | 93.3 ± 0.9 | 40.6 ± 3.8 |
| 10 µg/mL | 80.4 ± 2.4 | 20.7 ± 1.1 |
| 1 µg/mL | 41.5 ± 3.2 | 8.1 ± 5.5 |
| 0.1 µg/mL | 21.9 ± 0.6 | 6.0 ± 8.6 |
| 0.01 µg/mL | 10.9 ± 1.6 | −4.4 ± 5.9 |
| TSMAb 1 IgG | | |
| 100 µg/mL | 48.8 ± 1.9 | 46.3 ± 1.6 |
| 10 µg/mL | 29.9 ± 0.4 | 41.4 ± 1.3 |
| 1 µg/mL | 21.9 ± 1.5 | 25.0 ± 2.0 |
| 0.1 µg/mL | 4.1 ± 3.0 | 8.4 ± 4.3 |
| 0.01 µg/mL | −2.5 ± 2.5 | 3.5 ± 3.5 |
| TSMAb 2 IgG | | |
| 100 µg/mL | 56.3 ± 2.1 | 38.3 ± 3.0 |
| 10 µg/mL | 24.0 ± 3.8 | 34.7 ± 1.2 |
| 1 µg/mL | 16.8 ± 1.4 | 26.9 ± 2.9 |
| 0.1 µg/mL | 13.0 ± 2.2 | 12.5 ± 1.7 |
| 0.01 µg/mL | 4.0 ± 2.1 | 8.6 ± 8.6 |
| TSMAb 3 IgG | | |
| 100 µg/mL | 58.9 ± 3.2 | 32.6 ± 2.6 |
| 10 µg/mL | 30.3 ± 1.8 | 29.0 ± 3.4 |
| 1 µg/mL | 29.3 ± 3.2 | 18.2 ± 2.1 |
| 0.1 µg/mL | 21.1 ± 1.9 | 3.6 ± 1.3 |
| 0.01 µg/mL | 7.2 ± 1.7 | 2.4 ± 3.7 |

TABLE 11d-continued

Inhibition of $^{125}$I-K1-70 Fab binding to TSHR coated tubes by human and mouse monoclonal TSHR antibodies

| Test sample | Inhibition of binding (%) Dilutions in assay buffer (mean ± SD) | Inhibition of binding (%) Dilutions in HBD (mean ± SD) |
|---|---|---|
| TSMAb 4 IgG | | |
| 100 µg/mL | 53.8 ± 3.4 | 57.8 ± 3.3 |
| 10 µg/mL | 41.8 ± 2.1 | 53.5 ± 1.4 |
| 1 µg/mL | 38.8 ± 2.2 | 41.2 ± 0.1 |
| 0.1 µg/mL | 29.9 ± 1.3 | 12.8 ± 1.6 |
| 0.01 µg/mL | 8.6 ± 1.2 | −1.4 ± 1.7 |
| TSMAb 5 IgG | | |
| 100 µg/mL | 81.8 ± 1.5 | 57.5 ± 1.6 |
| 10 µg/mL | 62.0 ± 5.7 | 57.0 ± 2.6 |
| 1 µg/mL | 41.2 ± 0.9 | 52.3 ± 1.2 |
| 0.1 µg/mL | 34.4 ± 1.4 | 28.8 ± 1.2 |
| 0.01 µg/mL | 14.4 ± 1.9 | 6.8 ± 0.4 |
| TSMAb 6 IgG | | |
| 100 µg/mL | 68.3 ± 2.9 | 43.9 ± 1.0 |
| 10 µg/mL | 28.9 ± 3.7 | 39.2 ± 3.8 |
| 1 µg/mL | 25.4 ± 2.4 | 36.9 ± 4.7 |
| 0.1 µg/mL | 19.5 ± 2.0 | 19.2 ± 1.6 |
| 0.01 µg/mL | 4.9 ± 0.7 | 0.2 ± 0.9 |
| TSMAb 7 IgG | | |
| 100 µg/mL | 59.8 ± 2.8 | 38.2 ± 2.1 |
| 10 µg/mL | 40.6 ± 1.2 | 39.5 ± 5.5 |
| 1 µg/mL | 21.7 ± 2.1 | 30.7 ± 2.8 |
| 0.1 µg/mL | 13.5 ± 1.7 | 9.3 ± 2.7 |
| 0.01 µg/mL | −1.7 ± 1.6 | −2.9 ± 2.3 |
| 9D33 IgG | | |
| 100 µg/mL | 62.7 ± 2.5 | 55.7 ± 7.1 |
| 10 µg/mL | 48.0 ± 2.6 | 47.7 ± 1.7 |
| 1 µg/mL | 43.8 ± 1.8 | 38.8 ± 3.3 |
| 0.1 µg/mL | 29.7 ± 3.4 | 12.7 ± 1.8 |
| 0.01 µg/mL | 5.0 ± 0.4 | −1.2 ± 2.7 |
| 5B3 IgG | | |
| 100 µg/mL | 1.4 ± 0.6 | −8.6 ± 1.2 |
| 10 µg/mL | −2.1 ± 2.6 | −5.7 ± 4.4 |
| 1 µg/mL | −1.7 ± 0.2 | −7.8 ± 2.2 |
| 0.1 µg/mL | 2.2 ± 0.8 | −8.7 ± 0.8 |
| 0.01 µg/mL | −1.7 ± 1.7 | −5.3 ± 7.0 |
| 0.001 µg/mL | −1.8 ± 3.1 | −12.1 ± 2.8 |

See legend to Table 11a for details.
$^{125}$I-K1-70 Fab in the presence of assay buffer gave 20.3% binding.
$^{125}$I-K1-70 Fab in the presence of HBD pool gave 19.5% binding.

TABLE 11e

Inhibition of $^{125}$I-K1-70 Fab, $^{125}$I-K1-70 IgG and $^{125}$I-TSH binding to TSHR coated tubes by patient sera

| Test Sample | % Inhibition of $^{125}$I-K1-70 Fab binding | % Inhibition of $^{125}$I-K1-70 IgG binding | % Inhibition of $^{125}$I-TSH binding |
|---|---|---|---|
| G1 | 43.7 | 47.6 | 38.6 |
| G2 | 29.0 | 33.8 | 31.5 |
| G3 | 33.3 | 44.7 | 35.6 |
| G4 | 39.2 | 47.5 | 47.1 |
| G5 | 40.9 | 41.1 | 44.7 |
| G6 | 50.2 | 55.1 | 52.1 |
| G7 | 15.9 | 19.2 | 15.9 |
| G8 | 34.6 | 41.5 | 41.8 |
| G9 | 72.8 | 77.6 | 80.0 |
| G10 | 55.2 | 62.4 | 68.7 |
| G11 | 32.7 | 38.3 | 31.0 |
| G12 | 30.8 | 42.1 | 29.7 |
| G13 | 47.3 | 51.8 | 57.9 |
| G14 | 49.7 | 53.3 | 49.3 |
| G15 | 41.1 | 48.4 | 38.6 |
| G16 | 36.9 | 43.3 | 42.9 |
| G17 | 17.5 | 23.3 | 24.5 |
| G18 | 33.9 | 40.6 | 39.1 |
| G19 | 22.2 | 33.4 | 20.6 |
| G20 | 33.5 | 38.1 | 38.4 |
| HBD 1 | −4.7 | −6.5 | −12.6 |
| HBD 2 | −1.7 | −3.5 | −4.2 |
| HBD 3 | 1.2 | −2.8 | −5.4 |
| HBD 4 | −3.4 | 0.8 | −11.8 |
| HBD 5 | −0.5 | 5.6 | −4.7 |
| HBD 6 | 1.6 | 4.1 | 1.8 |
| HBD 7 | −9.0 | −2.4 | −13.7 |
| HBD 8 | −4.6 | 0.8 | −12.8 |
| HBD 9 | −0.6 | 1.2 | −11.0 |
| HBD 10 | −4.3 | 2.1 | −10.6 |
| K1 donor serum | | | |
| diluted 10x | 72.9 | 73.7 | 67.2 |
| diluted 20x | 52.2 | 56.6 | 44.0 |
| diluted 40x | 29.5 | 39.5 | 24.8 |
| diluted 80x | 15.5 | 26.2 | 11.9 |
| diluted 160x | 7.8 | 15.3 | 2.7 |
| diluted 320x | 3.2 | 8.0 | 2.1 |
| B1 | | | |
| diluted 5x | 85.7 | 89.0 | 91.5 |
| diluted 10x | 76.5 | 81.7 | 83.9 |
| diluted 20x | 60.6 | 68.1 | 65.8 |
| diluted 40x | 38.4 | 51.3 | 39.6 |
| diluted 80x | 21.0 | 36.9 | 20.7 |
| diluted 160x | 8.6 | 20.4 | 7.5 |
| diluted 320x | 3.6 | 10.7 | −2.5 |
| B2 | | | |
| diluted 5x | 90.4 | 89.9 | 93.5 |
| diluted 10x | 84.6 | 86.6 | 86.5 |
| diluted 20x | 71.9 | 78.1 | 68.7 |
| diluted 40x | 52.4 | 63.1 | 42.8 |
| diluted 80x | 34.9 | 45.1 | 20.4 |
| diluted 160x | 18.6 | 29.5 | 10.5 |
| diluted 320x | 10.7 | 16.6 | 14.1 |
| S1 | | | |
| diluted 5x | 73.6 | 72.1 | 82.0 |
| diluted 10x | 58.6 | 60.2 | 66.5 |
| diluted 20x | 45.1 | 45.7 | 47.1 |
| diluted 40x | 32.9 | 34.5 | 32.5 |
| diluted 80x | 19.7 | 21.6 | 17.4 |
| diluted 160x | 9.7 | 13.7 | 5.2 |
| diluted 320x | 2.2 | 4.7 | 2.3 |
| S2 | | | |
| diluted 5x | 50.0 | 54.7 | 55.1 |
| diluted 10x | 34.8 | 38.9 | 33.7 |
| diluted 20x | 24.2 | 22.9 | 18.4 |
| diluted 40x | 11.8 | 16.0 | 9.5 |
| diluted 80x | 5.6 | 9.4 | 7.7 |
| diluted 160x | 0.3 | 4.9 | −0.7 |

See legend to Table 11a for details.
Dilutions were made in HBD pool serum
HBD 1-10 = healthy blood donor sera 1-10.
B1, B2 = sera from two different patients with TSHR blocking autoantibodies.
S1, S2 = sera from two different patients with TSHR stimulating autoantibodies.

TABLE 12a

Binding of human MAbs to TSHR260-AP in an ELISA

| | Mean absorbance at 405 nm | |
|---|---|---|
| Test sample | Test sample diluted in HBD | Test sample diluted in assay buffer |
| Assay buffer | | −0.005 |
| HBD serum | −0.002 | |
| K1-18 IgG | | |
| 250 μg/mL | 0.722 | 1.197 |
| 100 μg/mL | 0.706 | 0.993 |
| 10 μg/mL | 0.660 | 0.800 |
| 1 μg/mL | 0.578 | 0.715 |
| 0.5 μg/mL | 0.511 | 0.673 |
| 0.1 μg/mL | 0.292 | 0.545 |
| 0.05 μg/mL | 0.191 | 0.396 |
| 0.01 μg/mL | 0.053 | 0.255 |
| 0.005 μg/mL | 0.013 | 0.136 |
| K1-70 IgG | | |
| 250 μg/mL | 0.817 | 1.134 |
| 100 μg/mL | 0.794 | 1.030 |
| 10 μg/mL | 0.738 | 0.885 |
| 1 μg/mL | 0.677 | 0.806 |
| 0.5 μg/mL | 0.661 | 0.802 |
| 0.1 μg/mL | 0.440 | 0.713 |
| 0.05 μg/mL | 0.290 | 0.593 |
| 0.01 μg/mL | 0.086 | 0.183 |
| 0.005 μg/mL | 0.045 | 0.085 |
| M22 IgG | | |
| 250 μg/mL | 0.833 | 1.007 |
| 100 μg/mL | 0.851 | 0.967 |
| 10 μg/mL | 0.796 | 0.872 |
| 1 μg/mL | 0.726 | 0.821 |
| 0.5 μg/mL | 0.657 | 0.776 |
| 0.1 μg/mL | 0.365 | 0.653 |
| 0.05 μg/mL | 0.204 | 0.484 |
| 0.01 μg/mL | 0.030 | 0.101 |
| 0.005 μg/mL | 0.045 | 0.075 |
| 5C9 IgG | | |
| 250 μg/mL | 0.058 | 1.124 |
| 100 μg/mL | 0.027 | 0.669 |
| 10 μg/mL | 0.004 | 0.099 |
| 1 μg/mL | 0.045 | 0.011 |
| 0.5 μg/mL | 0.016 | −0.005 |
| 0.1 μg/mL | −0.005 | −0.013 |
| 0.05 μg/mL | −0.003 | −0.008 |
| 0.01 μg/mL | 0.017 | −0.001 |
| 0.005 μg/mL | 0.020 | −0.009 |
| 5B3 IgG | | |
| 250 μg/mL | 0.012 | 0.018 |
| 100 μg/mL | 0.003 | −0.011 |
| 10 μg/mL | −0.006 | −0.014 |
| 1 μg/mL | 0.049 | −0.004 |
| 0.5 μg/mL | −0.001 | −0.006 |
| 0.1 μg/mL | −0.002 | −0.013 |
| 0.05 μg/mL | −0.006 | −0.009 |
| 0.01 μg/mL | 0.027 | 0.012 |
| 0.005 μg/mL | −0.002 | −0.012 |

TSHR260-AP is a fusion protein consisting of a fragment of human TSHR (amino acids 22-260) e with alkaline phosphatase. HBD = pool of healthy blood donor sera. Test samples were diluted in HBD serum or assay buffer. Assay buffer is 50 mmol/L NaCl, 10 mmol/L Tris pH 7.8, 0.1% Triton X-100, 1 mg/mL BSA. 5B3 is a human MAb to glutamic acid decarboxylase (negative control). Mean absorbance = mean of duplicate determinations.

TABLE 12b

Binding of human TSHR MAbs (IgG and Fab preparations) in the TSHR260-AP based ELISA

| | Mean absorbance at 405 nm Dilutions in HBD | | Mean absorbance at 405 nm Dilutions in assay buffer | |
|---|---|---|---|---|
| Test sample | IgG | Fab | IgG | Fab |
| M22 IgG | | | | |
| 250 μg/mL | 0.833 | 0.031 | 1.007 | 0.077 |
| 100 μg/mL | 0.851 | — | 0.967 | — |
| 10 μg/mL | 0.796 | 0.010 | 0.872 | 0.034 |
| 1 μg/mL | 0.726 | — | 0.821 | — |
| 0.5 μg/mL | 0.657 | — | 0.776 | — |
| 0.1 μg/mL | 0.365 | −0.007 | 0.653 | 0.015 |
| 0.05 μg/mL | 0.204 | — | 0.484 | — |
| 0.01 μg/mL | 0.030 | — | 0.101 | — |
| 0.005 μg/mL | 0.045 | −0.013 | 0.075 | −0.004 |
| 5C9 IgG | | | | |
| 250 μg/mL | 0.058 | −0.008 | 1.124 | 0.204 |
| 100 μg/mL | 0.027 | — | 0.669 | — |
| 10 μg/mL | 0.004 | −0.008 | 0.099 | 0.016 |
| 1 μg/mL | 0.045 | — | 0.011 | — |
| 0.5 μg/mL | 0.016 | — | −0.005 | — |
| 0.1 μg/mL | −0.005 | −0.009 | −0.013 | −0.009 |
| 0.05 μg/mL | −0.003 | — | −0.008 | — |
| 0.01 μg/mL | 0.017 | — | −0.001 | — |
| 0.005 μg/mL | 0.020 | −0.012 | −0.009 | 0.000 |
| K1-18 IgG | | | | |
| 250 μg/mL | 0.722 | −0.007 | 1.197 | 0.049 |
| 100 μg/mL | 0.706 | — | 0.993 | — |
| 10 μg/mL | 0.660 | −0.002 | 0.800 | 0.008 |
| 1 μg/mL | 0.578 | — | 0.715 | — |
| 0.5 μg/mL | 0.511 | — | 0.673 | — |
| 0.1 μg/mL | 0.292 | −0.011 | 0.545 | 0.002 |
| 0.05 μg/mL | 0.191 | — | 0.396 | — |
| 0.01 μg/mL | 0.053 | — | 0.255 | — |
| 0.005 μg/mL | 0.013 | −0.011 | 0.136 | −0.004 |
| K1-70 IgG | | | | |
| 250 μg/mL | 0.817 | 0.020 | 1.134 | 0.056 |
| 100 μg/mL | 0.794 | — | 1.030 | — |
| 10 μg/mL | 0.738 | 0.018 | 0.885 | 0.033 |
| 1 μg/mL | 0.677 | — | 0.806 | — |
| 0.5 μg/mL | 0.661 | — | 0.802 | — |
| 0.1 μg/mL | 0.440 | −0.010 | 0.713 | 0.007 |
| 0.05 μg/mL | 0.290 | — | 0.593 | — |
| 0.01 μg/mL | 0.086 | — | 0.183 | — |
| 0.005 μg/mL | 0.045 | −0.010 | 0.085 | −0.004 |
| 5B3 IgG | | | | |
| 250 μg/mL | 0.012 | — | 0.018 | — |
| 100 μg/mL | 0.003 | — | −0.011 | — |
| 10 μg/mL | −0.006 | — | −0.014 | — |
| 1 μg/mL | 0.049 | — | −0.004 | — |
| 0.5 μg/mL | −0.001 | — | −0.006 | — |
| 0.1 μg/mL | −0.002 | — | −0.013 | — |
| 0.05 μg/mL | −0.006 | — | −0.009 | — |
| 0.01 μg/mL | 0.027 | — | 0.012 | — |
| 0.005 μg/mL | −0.002 | — | −0.012 | — |
| 4B4 IgG | | | | |
| 250 μg/mL | — | −0.009 | — | −0.004 |
| 100 μg/mL | — | — | — | — |
| 10 μg/mL | — | −0.009 | — | 0.012 |
| 1 μg/mL | — | — | — | — |
| 0.5 μg/mL | — | — | — | — |
| 0.1 μg/mL | — | −0.001 | — | −0.006 |
| 0.05 μg/mL | — | — | — | — |
| 0.01 μg/mL | — | — | — | — |
| 0.005 μg/mL | — | −0.014 | — | 0.000 |

See legend to Table 12a for details. 4B4 is a human MAb to glutamic acid decarboxylase (negative control).

TABLE 12c

Binding of mouse TSMAbs in the TSHR260-AP ELISA

| Test sample | Mean absorbance at 405 nm Dilutions in HBD |
|---|---|
| HBD | −0.010 |
| TSMAb 1 | |
| 10 μg/mL | 0.166 |
| 0.5 μg/mL | 0.036 |
| 0.05 μg/mL | −0.002 |
| 0.005 μg/mL | 0.006 |
| TSMAb 2 | |
| 10 μg/mL | 0.410 |
| 0.5 μg/mL | 0.191 |
| 0.05 μg/mL | 0.033 |
| 0.005 μg/mL | 0.003 |
| TSMAb 3 | |
| 10 μg/mL | 0.103 |
| 0.5 μg/mL | 0.029 |
| 0.05 μg/mL | −0.001 |
| 0.005 μg/mL | 0.003 |
| TSMAb 4 | |
| 10 μg/mL | 0.428 |
| 0.5 μg/mL | 0.253 |
| 0.05 μg/mL | 0.048 |
| 0.005 μg/mL | 0.013 |
| TSMAb 5 | |
| 10 μg/mL | 0.561 |
| 0.5 μg/mL | 0.319 |
| 0.05 μg/mL | 0.054 |
| 0.005 μg/mL | 0.011 |
| TSMAb 6 | |
| 10 μg/mL | 0.486 |
| 0.5 μg/mL | 0.310 |
| 0.05 μg/mL | 0.090 |
| 0.005 μg/mL | 0.002 |
| TSMAb 7 | |
| 10 μg/mL | 0.357 |
| 0.5 μg/mL | 0.184 |
| 0.05 μg/mL | 0.027 |
| 0.005 μg/mL | 0.004 |
| K1-70 IgG | |
| 10 μg/mL | 1.252 |
| 1 μg/mL | 1.122 |
| 0.5 μg/mL | 1.038 |
| 0.1 μg/mL | 0.606 |
| 0.05 μg/mL | 0.348 |
| 0.01 μg/mL | 0.069 |
| 0.005 μg/mL | 0.076 |
| M22 IgG | |
| 10 μg/mL | 1.272 |
| 1 μg/mL | 1.094 |
| 0.5 μg/mL | 1.018 |
| 0.1 μg/mL | 0.548 |
| 0.05 μg/mL | 0.292 |
| 0.01 μg/mL | 0.043 |
| 0.005 μg/mL | 0.011 |

See legend to Table 12a for details. Binding of 5B3 and 4B4 (human MAbs to glutamic acid decarboxylase; negative controls) is shown in Table 12b.

TABLE 12d

Binding of mouse TSHR blocking MAb (9D33) in the TSHR260-AP ELISA

| Test sample | Mean absorbance at 405 nm Dilutions in HBD |
|---|---|
| HBD | 0.003 |
| 9D33 IgG | |
| 10 μg/mL | 0.481 |
| 1 μg/mL | 0.329 |
| 0.5 μg/mL | 0.273 |
| 0.1 μg/mL | 0.102 |
| 0.05 μg/mL | 0.056 |
| 0.01 μg/mL | 0.011 |
| 0.005 μg/mL | 0.006 |
| K1-70 IgG | |
| 10 μg/mL | 1.324 |
| 1 μg/mL | 1.164 |
| 0.5 μg/mL | 1.083 |
| 0.1 μg/mL | 0.639 |
| 0.05 μg/mL | 0.388 |
| 0.01 μg/mL | 0.094 |
| 0.005 μg/mL | 0.059 |
| M22 IgG | |
| 10 μg/mL | 1.360 |
| 1 μg/mL | 1.172 |
| 0.5 μg/mL | 1.093 |
| 0.1 μg/mL | 0.599 |
| 0.05 μg/mL | 0.332 |
| 0.01 μg/mL | 0.064 |
| 0.005 μg/mL | 0.032 |

See legend to Table 12a for details. Binding of 5B3 and 4B4 (human MAbs to glutamic acid decarboxylase; negative controls) is shown in Table 12b.

TABLE 12e

Binding of patient sera with TSHR stimulating activity in the TSHR260-AP ELISA

| Test sample | TSHR260-AP ELISA Mean absorbance at 405 nm | TRAb conc[1] (μg/mL) | TRAb conc[2] (U/L) | Inhibition of TSH binding ELISA TRAb conc[2] (U/L) | Stimulation of cyclic AMP production[3] (pmol/mL) |
|---|---|---|---|---|---|
| HBD | 0.003 | 0 | 0 | 0 | |
| S1 | | | | | |
| diluted 1:5 | 0.924 | 0.31 | 38.0 | >40 | 37.2 |
| diluted 1:10 | 0.788 | 0.18 | 19.7 | 31.1 | |
| diluted 1:20 | 0.583 | 0.10 | 9.5 | 16.2 | |
| diluted 1:40 | 0.378 | 0.05 | 5.2 | 7.1 | |
| S2 | | | | | |
| diluted 1:5 | 0.740 | 0.17 | 17.9 | 36.0 | 47.6 |
| diluted 1:10 | 0.595 | 0.10 | 9.8 | 23.6 | |
| diluted 1:20 | 0.407 | 0.06 | 5.7 | 13.6 | |
| diluted 1:40 | 0.235 | 0.03 | 2.9 | 6.6 | |
| S3 | | | | | |
| diluted 1:5 | 0.868 | 0.25 | 28.5 | >40 | 35.9 |
| diluted 1:10 | 0.651 | 0.12 | 11.8 | 34.0 | |
| diluted 1:20 | 0.453 | 0.06 | 6.5 | 23.5 | |
| diluted 1:40 | 0.290 | 0.04 | 3.8 | 12.2 | |
| S4 | | | | | |
| diluted 1:5 | 0.646 | 0.11 | 11.6 | 19.8 | 107.5 |
| diluted 1:10 | 0.362 | 0.05 | 4.9 | 7.6 | |
| diluted 1:20 | 0.171 | 0.02 | 2.0 | 3.1 | |
| diluted 1:40 | 0.080 | 0.01 | 1.0 | 1.4 | |
| S5 | | | | | |
| diluted 1:5 | 0.407 | 0.06 | 5.7 | 9.4 | 40.6 |
| diluted 1:10 | 0.221 | 0.03 | 2.7 | 4.4 | |

TABLE 12e-continued

Binding of patient sera with TSHR stimulating activity in the TSHR260-AP ELISA

| | TSHR260-AP ELISA | | | Inhibition of TSH binding ELISA TRAb conc² (U/L) | Stimulation of cyclic AMP production³ (pmol/mL) |
|---|---|---|---|---|---|
| Test sample | Mean absorbance at 405 nm | TRAb conc¹ (μg/mL) | TRAb conc² (U/L) | | |
| diluted 1:20 | 0.109 | 0.01 | 1.3 | 2.1 | |
| diluted 1:40 | 0.059 | 0.01 | 0.9 | 1.1 | |
| S6 | | | | | |
| diluted 1:5 | 0.531 | 0.08 | 8.2 | 19.9 | 43.5 |
| diluted 1:10 | 0.363 | 0.05 | 5.0 | 9.2 | |
| diluted 1:20 | 0.213 | 0.03 | 2.6 | 4.7 | |
| diluted 1:40 | 0.124 | 0.02 | 1.5 | 2.0 | |

See legend to Table 12a for details
[1]Read off M22 IgG calibration curve (0.005, 0.001, 0.05, 0.1, 0.5, 1.0 and 10 μg/mL was run in each assay).
[2]Units are NIBSC 90/672.
[3]Stimulation of cyclic AMP production was tested (serum diluted 1:10 in hypotonic cyclic AMP buffer) using CHO cells expressing the full length TSHR.
S1 = TSHR stimulating patient serum 1. S2 = TSHR stimulating patient serum 2. S3 = TSHR stimulating patient serum 3. S4 = TSHR stimulating patient serum 4. S5 = TSHR stimulating patient serum 5. S6 = TSHR stimulating patient serum 6. Serum dilutions for both ELISAs were made in HBD.

TABLE 12f

Binding of patient sera with TSHR blocking activity in the TSHR260-AP ELISA

| | TSHR260-AP ELISA | | TRAb level measured in TSHR coated tube assay | |
|---|---|---|---|---|
| | Diluted in HBD | Diluted in assay buffer | % inhibition of ¹²⁵I-TSH binding | U/L |
| Test sample | Mean absorbance at 405 nm | Mean absorbance at 405 nm | | |
| B1 | | | | |
| undiluted | 0.859 | 0.859 | NT | NT |
| diluted 1:10 | 0.484 | 0.667 | 73 | 16.8 |
| diluted 1:20 | 0.284 | 0.457 | 45 | 4.3 |
| diluted 1:40 | 0.154 | 0.243 | 22 | 1.4 |
| diluted 1:80 | 0.078 | 0.119 | 4 | 0.1 |
| diluted 1:160 | 0.037 | 0.062 | 0 | 0 |
| diluted 1:320 | 0.021 | 0.032 | NT | NT |
| B2 | | | | |
| undiluted | 0.323 | 0.323 | NT | NT |
| diluted 1:10 | 0.097 | 0.165 | 82 | 25.6 |
| diluted 1:20 | 0.052 | 0.114 | 70 | 14.6 |
| diluted 1:40 | 0.029 | 0.063 | 47 | 4.5 |
| diluted 1:80 | 0.015 | 0.036 | 23 | 2 |
| diluted 1:160 | 0.008 | 0.018 | 9 | 0.7 |
| diluted 1:320 | 0.007 | 0.014 | NT | NT |
| B3 | | | | |
| diluted 1:10 | 0.896 | 1.061 | 85[a] | NT |
| diluted 1:20 | 0.588 | 0.768 | 73[a] | NT |
| diluted 1:40 | 0.320 | 0.443 | 51[a] | NT |
| diluted 1:80 | 0.168 | 0.218 | 34[a] | NT |
| diluted 1:160 | 0.091 | 0.104 | 22[a] | NT |
| diluted 1:320 | 0.041 | 0.054 | 13[a] | NT |
| B4 | | | | |
| diluted 1:10 | 0.729 | 0.826 | 94[a] | NT |
| diluted 1:20 | 0.612 | 0.734 | 91[a] | NT |
| diluted 1:40 | 0.453 | 0.592 | 80[a] | NT |
| diluted 1:80 | 0.270 | 0.353 | 55[a] | NT |
| diluted 1:160 | 0.141 | 0.153 | 33[a] | NT |
| diluted 1:320 | 0.068 | 0.066 | 17[a] | NT |

TABLE 12f-continued

Binding of patient sera with TSHR blocking activity in the TSHR260-AP ELISA

| | TSHR260-AP ELISA | | TRAb level measured in TSHR coated tube assay | |
|---|---|---|---|---|
| | Diluted in HBD | Diluted in assay buffer | % inhibition of ¹²⁵I-TSH binding | U/L |
| Test sample | Mean absorbance at 405 nm | Mean absorbance at 405 nm | | |
| B5 | | | | |
| diluted 1:10 | 0.772 | 0.910 | 98 | >40 |
| diluted 1:20 | 0.652 | 0.835 | 97 | >40 |
| diluted 1:40 | 0.470 | 0.735 | 95 | >40 |
| diluted 1:80 | 0.291 | 0.522 | 90 | 36.2 |
| diluted 1:160 | 0.155 | 0.276 | 76 | 12.0 |
| diluted 1:320 | 0.077 | 0.130 | 45 | 3.0 |

See legend to Table 12a for details.
NT = not tested.
B1 = TSHR blocking patient serum 1 (K1 lymphocyte donor serum). B2 = TSHR blocking patient serum 2. B3 = TSHR blocking patient serum 3. B4 = TSHR blocking patient serum 4. B5 = TSHR blocking patient serum 5. Serum dilutions were made in HBD or assay buffer.
[a]the inhibition of ¹²⁵I-TSH binding was carried out using the PEG precipitation assay (Southgate K, Creagh F, Teece M, Kingwood C, Rees Smith B. A receptor assay for the measurement of TSH receptor antibodies in unextracted serum. Clin Endocrinol 1984; 20: 539-548).

TABLE 12g

Binding of patient sera in the TSHR260-AP ELISA

| Test sample | Mean absorbance @ 405 nm | TRAb concentration read off M22 IgG calibration curve (μg/mL) | TRAb concentration in TSHR260-AP ELISA (U/L) | TRAb concentration in TSHR coated tube assay (U/L) |
|---|---|---|---|---|
| Serum 1 | 0.06 | 0.007 | 0.7 | 1.0 |
| Serum 2 | 0.072 | 0.008 | 0.9 | 1.0 |
| Serum 3 | 0.067 | 0.008 | 0.8 | 1.1 |
| Serum 4 | −0.004 | 0.000 | 0 | 1.1 |
| Serum 5 | 0.38 | 0.052 | 5.2 | 1.2 |
| Serum 6 | 0.099 | 0.012 | 1.2 | 1.2 |
| Serum 7 | 0.051 | 0.006 | 0.6 | 1.2 |
| Serum 8 | 0.113 | 0.014 | 1.3 | 1.4 |
| Serum 9 | 0.07 | 0.008 | 0.8 | 1.4 |
| Serum 10 | 0.157 | 0.019 | 1.9 | 1.5 |
| Serum 11 | 0.191 | 0.025 | 2.5 | 2.0 |
| Serum 12 | 0.157 | 0.019 | 1.9 | 2.1 |
| Serum 13 | 0.23 | 0.029 | 2.9 | 2.2 |
| Serum 14 | 0.047 | 0.006 | 0.7 | 2.7 |
| Serum 15 | 0.198 | 0.026 | 2.6 | 2.7 |
| Serum 16 | 0.238 | 0.032 | 3.2 | 3.0 |
| Serum 17 | 0.296 | 0.041 | 4.1 | 3.0 |
| Serum 18 | 0.322 | 0.042 | 4.3 | 3.6 |
| Serum 19 | 0.326 | 0.043 | 4.3 | 3.7 |
| Serum 20 | 0.088 | 0.011 | 1.1 | 4.7 |
| Serum 21 | 0.005 | <0.005 | <0.6 | 5.1 |
| Serum 22 | 0.383 | 0.056 | 5.5 | 5.1 |
| Serum 23 | 0.211 | 0.026 | 2.6 | 5.7 |
| Serum 24 | 0.461 | 0.071 | 7 | 6.4 |
| Serum 25 | 0.453 | 0.067 | 6.6 | 6.6 |
| Serum 26 | 0.295 | 0.038 | 3.8 | 6.7 |
| Serum 27 | 0.419 | 0.062 | 6.2 | 7.1 |
| Serum 28 | 0.363 | 0.050 | 5 | 8.1 |
| Serum 29 | 0.526 | 0.086 | 8.6 | 8.5 |
| Serum 30 | 0.611 | 0.112 | 11.3 | 11.8 |
| Serum 31 | 0.49 | 0.077 | 7.7 | 14.3 |
| Serum 32 | 0.621 | 0.116 | 11.7 | 16.9 |
| Serum 33 | 0.696 | 0.150 | 15.6 | 17.8 |

TABLE 12g-continued

Binding of patient sera in the TSHR260-AP ELISA

| Test sample | Mean absorbance @ 405 nm | TRAb concentration read off M22 IgG calibration curve (μg/mL) | TRAb concentration in TSHR260-AP ELISA (U/L) | TRAb concentration in TSHR coated tube assay (U/L) |
|---|---|---|---|---|
| Serum 34 | 0.592 | 0.104 | 10.4 | 19.0 |
| Serum 35 | 0.832 | 0.259 | 30.4 | 21.1 |
| Serum 36 | 0.78 | 0.222 | 24.5 | 21.2 |
| Serum 37 | 0.782 | 0.224 | 24.6 | 21.5 |
| Serum 38 | 0.754 | 0.196 | 21.1 | 21.7 |
| Serum 39 | 1.008 | 1.375 | >61 | 26.2 |
| Serum 40 | −0.008 | 0 | 0 | 0 |
| Serum 41 | −0.005 | 0 | 0 | 0 |
| Serum 42 | −0.006 | 0 | 0 | 0 |
| Serum 43 | −0.004 | 0 | 0 | 0 |
| Serum 44 | −0.007 | 0 | 0 | 0 |
| Serum 45 | −0.007 | 0 | 0 | 0 |
| Serum 46 | −0.002 | <0.005 | <0.6 | 0 |
| Serum 47 | −0.001 | 0 | 0 | 0 |
| Serum 48 | 0.0095 | <0.005 | <0.6 | 0 |
| Serum 49 | −0.002 | 0 | 0 | 0 |
| Serum 50 | 0.003 | 0 | 0 | 0 |
| Serum 51 | 0.005 | <0.005 | <0.6 | 0 |
| Serum 52 | 0.008 | <0.005 | <0.6 | 0 |
| Serum 53 | −0.003 | 0 | 0 | 0 |
| Serum 54 | −0.005 | 0 | 0 | 0 |
| Serum 55 | −0.006 | 0 | 0 | <1 |
| Serum 56 | 0.0065 | <0.005 | <0.6 | 0 |
| Serum 57 | −0.004 | 0 | 0 | 0 |
| Serum 58 | 0.001 | 0 | 0.0 | <1 |
| Serum 59 | 0.041 | 0.005 | 0.6 | 0 |

See legend to Table 12a for details. Sera 1-39 are from patients diagnosed with or suspected of having Graves' disease. Sera 1-39 were positive for TRAb in the coated tube assay (based on inhibition of $^{125}$I-binding to full length TSHR coated on the tubes). Sera 40-59 were from healthy blood donors and were negative for TRAb in the coated tube assay.

TABLE 12h

Measurement of serum TRAb by inhibition of M22-peroxidase binding to the TSHR260 in an ELISA

| Test sample | TRAb ELISA (full length TSHR coated on plates) | | | TRAb ELISA (TSHR260 coated on plates) | | |
|---|---|---|---|---|---|---|
| | Mean absorbance at 450 nm | % inhibition of TSH-biotin binding | TRAb concentr. (U/L) | Mean absorbance at 450 nm | % inhibition of M22 Fab-peroxidase binding | TRAb concentr. (U/L) |
| Serum 60 | 0.224 | 90 | 30.7 | 0.196 | 92 | >40 |
| Serum 61 | 0.514 | 77 | 15.2 | 0.569 | 77 | 14.7 |
| Serum 62 | 0.605 | 73 | 12.4 | 0.470 | 81 | 24.7 |
| Serum 63 | 1.555 | 30 | 2.1 | 1.109 | 55 | 3.7 |
| Serum 64 | 1.639 | 26 | 1.7 | 1.208 | 51 | 3.1 |
| Serum 65 | 1.488 | 33 | 2.4 | 1.341 | 45 | 2.4 |
| Serum 66 | 1.267 | 43 | 3.6 | 0.706 | 71 | 8.5 |
| Serum 67 | 1.066 | 52 | 5.1 | 0.908 | 63 | 5.3 |
| Serum 68 | 1.341 | 40 | 3.1 | 0.704 | 71 | 8.6 |
| Serum 69 | 1.414 | 37 | 2.7 | 0.764 | 69 | 7.3 |
| Serum 70 | 0.704 | 68 | 10.0 | 0.797 | 67 | 6.7 |
| Serum 71 | 1.691 | 24 | 1.5 | 0.797 | 67 | 6.7 |
| Serum 72 | 2.404 | −8 | 0 | 2.791 | −14 | 0 |
| Serum 73 | 2.203 | 1 | 0.1 | 2.509 | −3 | 0 |
| Serum 74 | 2.228 | 0 | 0.1 | 2.737 | −12 | 0 |
| Serum 75 | 2.274 | −2 | 0 | 2.758 | −13 | 0 |
| Serum 76 | 2.178 | 2 | 0.2 | 2.215 | 10 | 0.3 |
| Serum 77 | 2.292 | −3 | 0 | 2.152 | 12 | 0.3 |
| Serum 78 | 2.425 | −9 | 0 | 2.676 | −9 | 0 |
| Serum 79 | 2.397 | −8 | 0 | 3.363 | −37 | 0 |
| Serum 80 | 2.410 | −8 | 0 | 2.905 | −19 | 0 |
| Serum 81 | 2.148 | 4 | 0.2 | 2.523 | −3 | 0 |

Sera 60-71 are from patients diagnosed with or suspected of Graves" disease. Sera 60-71 were positive for TRAb in the coated tube assay (based on inhibition of $^{125}$I-TSH binding to full length TSHR coated on the tubes). Sera 72-81 were from healthy blood donors that were negative for TRAb in the coated tube assay.

TABLE 12i

Ability of TSHR MAbs to bind to full length wild type TSHR and TSHR Arg255 Asp coated on ELISA plate wells. TSHR260-AP used to detect MAb binding

| Test sample | Wild type TSHR Mean absorbance at 405 nm | Arg255 Asp TSHR Mean absorbance at 405 nm |
|---|---|---|
| HBD | 0.003 | 0.005 |
| K1-70 IgG | | |
| 10 μg/mL | 1.324 | 1.357 |
| 1 μg/mL | 1.164 | 1.141 |
| 0.5 μg/mL | 1.083 | 0.998 |
| 0.1 μg/mL | 0.639 | 0.322 |
| 0.05 μg/mL | 0.388 | 0.146 |
| 0.01 μg/mL | 0.094 | 0.021 |
| 0.005 μg/mL | 0.059 | 0.008 |
| M22 IgG | | |
| 10 μg/mL | 1.360 | 0.551 |
| 1 μg/mL | 1.172 | 0.340 |
| 0.5 μg/mL | 1.093 | 0.262 |
| 0.1 μg/mL | 0.599 | 0.050 |
| 0.05 μg/mL | 0.332 | 0.017 |
| 0.01 μg/mL | 0.064 | −0.002 |
| 0.005 μg/mL | 0.032 | −0.007 |
| K1-18 IgG | | |
| 10 μg/mL | 1.187 | 1.111 |
| 1 μg/mL | 0.986 | 0.888 |
| 0.5 μg/mL | 0.876 | 0.710 |
| 0.1 μg/mL | 0.452 | 0.176 |
| 0.05 μg/mL | 0.301 | 0.099 |
| 0.01 μg/mL | 0.072 | 0.014 |
| 0.005 μg/mL | 0.038 | 0.002 |

TABLE 12i-continued

Ability of TSHR MAbs to bind to full length wild type TSHR and TSHR Arg255 Asp coated on ELISA plate wells. TSHR260-AP used to detect MAb binding

| Test sample | Wild type TSHR Mean absorbance at 405 nm | Arg255 Asp TSHR Mean absorbance at 405 nm |
|---|---|---|
| 9D33 IgG | | |
| 10 µg/mL | 0.481 | 0.534 |
| 1 µg/mL | 0.329 | 0.322 |
| 0.5 µg/mL | 0.273 | 0.242 |
| 0.1 µg/mL | 0.102 | 0.053 |
| 0.05 µg/mL | 0.056 | 0.020 |
| 0.01 µg/mL | 0.011 | −0.004 |
| 0.005 µg/mL | 0.006 | 0.001 |

See legend to Table 12a for details. Serum dilutions were made in HBD.

TABLE 12j

Ability of patient sera to bind to full length wild type TSHR and TSHR Arg255 Asp coated on ELISA plate wells. TSHR260-AP used to detect binding

| Test sample Patient sera | Wild type TSHR Mean absorbance at 405 nm | µg/mL (read off K1-70 IgG calibration) | Arg255 Asp TSHR Mean absorbance at 405 nm | µg/mL (read off K1-70 IgG calibration) | TRAb level in TSHR coated tube assay U/L |
|---|---|---|---|---|---|
| Serum 1 | 0.707 | 0.121 | 0.558 | 0.176 | 14.7 |
| Serum 2 | 0.798 | 0.159 | 0.677 | 0.227 | 17.1 |
| Serum 3 | 0.647 | 0.102 | 0.237 | 0.076 | 8.1 |
| Serum 4 | 0.692 | 0.116 | 0.585 | 0.187 | 12.3 |
| Serum 5 | 0.560 | 0.081 | 0.169 | 0.057 | 9.9 |
| Serum 6 | 0.278 | 0.034 | 0.096 | 0.036 | 5.9 |
| Serum 7 | 0.388 | 0.050 | 0.167 | 0.056 | 5.6 |
| Serum 8 | 0.367 | 0.047 | 0.112 | 0.040 | 8.3 |
| Serum 9 | 0.198 | 0.023 | 0.074 | 0.029 | 11.3 |
| Serum 10 | 0.788 | 0.154 | 0.447 | 0.137 | 17 |
| HBD | 0.003 | 0 | 0.005 | 0 | 0 |

See legend to Table 12a for details. Serum 1-10 are from patients with detectable TRAb levels in the coated tube assay. A calibration curve using K1-70 IgG (0.005, 0.01, 0.05, 0.1, 0.5, 1.0 and 10 µg/mL) was run in each assay.

TABLE 12k

Ability of patient sera with TSHR blocking activity to bind to full length wild type TSHR and TSHR Arg255 Asp coated on ELISA plate wells. TSHR260-AP used to detect binding

| Test sample | TSHR260-AP ELISA | | | |
|---|---|---|---|---|
| | Wild type TSHR | | Arg255 Asp TSHR | |
| | Mean absorbance at 405 nm | µg/mL IgG[a] read off M22 IgG calibration | Mean absorbance at 405 nm | µg/mL IgG[b] read off K1-70 IgG calibration |
| Serum 1 | | | | |
| undiluted | 0.859 | 0.30 | 0.879 | 0.47 |
| 1:10 | 0.484 | 0.09 | 0.202 | 0.08 |
| 1:20 | 0.284 | 0.05 | NT | NT |
| 1:40 | 0.154 | 0.02 | NT | NT |
| 1:50 | NT | NT | 0.027 | 0.02 |
| 1:80 | 0.078 | 0.01 | NT | NT |
| 1:100 | NT | NT | 0.015 | 0.02 |
| 1:160 | 0.037 | 0.01 | NT | NT |
| 1:320 | 0.021 | 0.00 | NT | NT |
| Serum 2 | | | | |
| undiluted | 0.323 | 0.05 | 0.274 | 0.11 |
| 1:10 | 0.097 | 0.02 | 0.021 | 0.02 |
| 1:20 | 0.052 | 0.01 | NT | NT |
| 1:40 | 0.029 | 0.00 | NT | NT |
| 1:50 | NT | NT | 0.005 | 0.00 |
| 1:80 | 0.015 | 0.00 | NT | NT |
| 1:100 | NT | NT | 0.009 | 0.00 |
| 1:160 | 0.008 | 0.00 | NT | NT |
| 1:320 | 0.007 | 0.00 | NT | NT |
| Serum 3 | | | | |
| 1:10 | 0.896 | 0.46 | 0.510 | 0.19 |
| 1:20 | 0.588 | 0.13 | NT | NT |
| 1:40 | 0.320 | 0.06 | NT | NT |
| 1:50 | NT | NT | 0.056 | 0.04 |
| 1:80 | 0.168 | 0.03 | NT | NT |
| 1:100 | NT | NT | 0.020 | 0.02 |
| 1:160 | 0.091 | 0.02 | NT | NT |
| 1:320 | 0.041 | 0.01 | NT | NT |
| Serum 4 | | | | |
| 1:10 | 0.729 | 0.21 | 0.639 | 0.25 |
| 1:20 | 0.612 | 0.14 | NT | NT |
| 1:40 | 0.453 | 0.08 | NT | NT |
| 1:50 | NT | NT | 0.107 | 0.05 |
| 1:80 | 0.270 | 0.05 | NT | NT |
| 1:100 | NT | NT | 0.040 | 0.03 |
| 1:160 | 0.141 | 0.02 | NT | NT |
| 1:320 | 0.068 | 0.01 | NT | NT |
| Serum 5 | | | | |
| 1:10 | 0.772 | 0.21 | 0.536 | 0.2 |
| 1:20 | 0.652 | 0.14 | NT | NT |
| 1:40 | 0.470 | 0.08 | NT | NT |
| 1:50 | NT | NT | 0.114 | 0.06 |
| 1:80 | 0.291 | 0.05 | NT | NT |
| 1:100 | NT | NT | 0.035 | 0.03 |
| 1:160 | 0.155 | 0.03 | NT | NT |
| 1:320 | 0.077 | 0.01 | NT | NT |

See legend to Table 12a for details.

NT = not tested.

Serum 1 = K1 lymphocyte donor serum. Serum 2 = patient serum with TSHR blocking autoantibodies. Serum 3 = patient serum with TSHR blocking autoantibodies. Serum 4 = patient serum with TSHR blocking autoantibodies. Serum 5 = patient serum with TSHR blocking autoantibodies. Serum dilutions were made in HBD.

[a] A calibration curve using M22 IgG (0.005, 0.01, 0.05, 0.1, 0.5, 1.0 and 10 µg/mL) was run in each assay.

[b] A calibration curve using K1-70 IgG (0.005, 0.01, 0.05, 0.1, 0.5, 1.0 and 10 µg/mL) was run in each assay.

TABLE 12l

Ability of patient sera with TSHR stimulating activity to bind to full length wild type TSHR and TSHR Arg255 Asp coated on ELISA plate wells. TSHR260-AP used to detect binding.

| | TSHR260-AP ELISA | | | |
|---|---|---|---|---|
| | Wild type TSHR | | Arg255 Asp TSHR | |
| Test sample | Mean absorbance at 405 nm | µg/mL IgG[a] read off M22 IgG calibration | Mean absorbance at 405 nm | µg/mL IgG[b] read off K1-70 IgG calibration |
| HBD | 0.003 | 0 | −0.01 | 0 |
| S1 | | | | |
| diluted 1:5 | 0.924 | 0.31 | 0.66 | 0.26 |
| diluted 1:10 | 0.788 | 0.18 | 0.40 | 0.15 |
| diluted 1:20 | 0.583 | 0.10 | 0.19 | 0.08 |
| diluted 1:40 | 0.378 | 0.05 | 0.09 | 0.04 |
| S2 | | | | |
| diluted 1:5 | 0.740 | 0.17 | 0.50 | 0.19 |
| diluted 1:10 | 0.595 | 0.10 | 0.26 | 0.10 |
| diluted 1:20 | 0.407 | 0.06 | 0.12 | 0.05 |
| diluted 1:40 | 0.235 | 0.03 | 0.05 | 0.03 |
| S3 | | | | |
| diluted 1:5 | 0.868 | 0.25 | 0.75 | 0.32 |
| diluted 1:10 | 0.651 | 0.12 | 0.74 | 0.16 |
| diluted 1:20 | 0.453 | 0.06 | 0.21 | 0.09 |
| diluted 1:40 | 0.290 | 0.04 | 0.10 | 0.04 |
| S4 | | | | |
| diluted 1:5 | 0.646 | 0.11 | 0.19 | 0.08 |
| diluted 1:10 | 0.362 | 0.05 | 0.07 | 0.04 |
| diluted 1:20 | 0.171 | 0.02 | 0.02 | 0.02 |
| diluted 1:40 | 0.080 | 0.01 | 0.00 | 0.01 |
| S5 | | | | |
| diluted 1:5 | 0.407 | 0.06 | 0.13 | 0.06 |
| diluted 1:10 | 0.221 | 0.03 | 0.04 | 0.02 |
| diluted 1:20 | 0.109 | 0.01 | 0.01 | 0.01 |
| diluted 1:40 | 0.059 | 0.01 | 0.01 | 0.01 |
| S6 | | | | |
| diluted 1:5 | 0.531 | 0.08 | 0.34 | 0.13 |
| diluted 1:10 | 0.363 | 0.05 | 0.16 | 0.07 |
| diluted 1:20 | 0.213 | 0.03 | 0.06 | 0.03 |
| diluted 1:40 | 0.124 | 0.02 | 0.03 | 0.02 |

See legend to Table 12a for details. Serum dilutions were made in HBD. Sera S1-S6 are the same sera shown in Table 12e.
[a] A calibration curve using M22 IgG (0.005, 0.01, 0.05, 0.1, 0.5, 1.0 and 10 µg/mL) was run in each assay.
[b] A calibration curve using K1-70 IgG (0.005, 0.01, 0.05, 0.1, 0.5, 1.0 and 10 µg/mL) was run in each assay.

TABLE 13a

Summary of stimulating MAb K1-18 (IgG1 kappa) properties

| | | | |
|---|---|---|---|
| TSHR binding affinity | IgG | $0.7 \times 10^{10}$ L/mol | |
| | Fab | $0.13 \times 10^{10}$ L/mol | |
| Inhibition of $^{125}$I-TSH binding to the TSHR | IgG (1 µg/mL) | 94% | Table 1a |
| | | 181 units/mg (NIBSC 90/672) | Table 2b |
| | Fab (1 µg/mL) | 77% | Table 1a |
| | | 86 units/mg (NIBSC 90/672) | Table 2b |
| Inhibition of TSH-biotin binding to the TSHR | IgG (1 µg/mL) | 96% | Table 3a |
| | Fab (1 µg/mL) | 93% | Table 3b |
| Inhibition of M22 Fab peroxidase binding to the TSHR | IgG (1 µg/mL) | 95% | Table 4a |
| | Fab (1 µg/mL) | 88% | Table 4b |
| Stimulation of cyclic AMP in CHO cells expressing TSHR | IgG (100 µg/mL) | 40× basal | Table 6a |
| | | 155 units/mg (NIBSC 90/672) | Table 6c |
| | Fab (100 µg/mL) | 35× basal | Table 6a |
| | | 22 units/mg (NIBSC 90/672) | Table 6c |
| Binding to TSHR 260-AP | IgG (1 µg/mL) | OD405 = 0.828 | Table 12a |
| V regions | Heavy chain (IgG1) | VH5-51*01 D3-16*02 (D3-16*01) J3*02 | FIG. 3a and FIG. 3c |
| | Light chain (kappa) | V3-20*01 JK-1*01 | FIG. 4a and FIG. 4c |

TABLE 13b

Summary of blocking MAb K1-70 (IgG1 kappa) properties

| | | | |
|---|---|---|---|
| TSHR binding affinity | IgG | $3.9 \pm 0.8 \times 10^{10}$ L/mol | |
| Inhibition of $^{125}$I-TSH binding to the TSHR | IgG (1 µg/mL) | 92 % | Table 1b |
| | | 166 units/mg (NIBSC 90/672) | |
| | Fab (1 µg/mL) | 92% | Table 1b |

TABLE 13b-continued

Summary of blocking MAb K1-70 (IgG1 kappa) properties

| | | | |
|---|---|---|---|
| Inhibition of TSH-biotin binding to the TSHR | IgG (1 µg/mL) | 97% | Table 3d |
| | Fab (1 µg/mL) | 97% | Table 3d |
| Inhibition of M22 Fab peroxidase binding to the TSHR | IgG (1 µg/mL) | 96% | Table 4c |
| | Fab (1 µg/mL) | 96% | Table 4c |
| Blocking TSH mediated cyclic AMP stimulation in CHO cells expressing TSHR | IgG (1 µg/mL) | 94% | Table 7b |
| | Fab (1 µg/mL) | 94% | Table 7b |
| Binding to TSHR 260-AP | IgG (1 µg/mL) | OD405 = 1.016 | Table 12a |
| V regions | Heavy chain (IgG1) | VH5-51*01<br>D1-7*01<br>J4*02 | FIG. 5a and FIG. 5c |
| | Light chain (kappa) | LV1-51*01<br>LJ7*01 | FIG. 6c |

TABLE 14a

Cyclic AMP production in CHO cells expressing wild type TSHR and TSHR with Asp43 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Cyclic AMP assay buffer | 2.52 ± 0.23 | 2.60 ± 0.33 | 103 |
| K1-18 | | | |
| 0.3 ng/mL | 3.84 ± 0.42 | 3.35 ± 0.20 | 87 |
| 1 ng/mL | 7.35 ± 0.07 | 5.53 ± 0.15 | 75 |
| 3 ng/mL | 17.04 ± 0.62 | 11.59 ± 0.42 | 68 |
| 10 ng/mL | 37.74 ± 0.67 | 26.69 ± 1.57 | 71 |
| 30 ng/mL | 51.46 ± 2.52 | 40.80 ± 0.74 | 79 |
| 100 ng/mL | 57.08 ± 4.79 | 48.50 ± 4.25 | 85 |
| TSH | | | |
| 0.01 ng/mL | 2.85 ± 0.08 | 2.84 ± 0.14 | 100 |
| 0.03 ng/mL | 3.81 ± 0.06 | 4.30 ± 0.10 | 113 |
| 0.1 ng/mL | 8.70 ± 0.49 | 10.35 ± 2.47 | 119 |
| 0.3 ng/mL | 22.78 ± 1.49 | 19.69 ± 1.60 | 86 |
| 1 ng/mL | 46.09 ± 0.00 | 39.56 ± 0.31 | 86 |
| 3 ng/mL | 54.16 ± 3.56 | 47.87 ± 0.09 | 88 |

Results shown are mean ± SD of triplicate determinations. Test samples diluted in hypotonic cyclic AMP assay buffer.

TABLE 14b

Cyclic AMP production in CHO cells expressing wild type TSHR and TSHR with Ile60 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Cyclic AMP assay buffer | 1.00 ± 0.09 | 5.02 ± 1.03 | 502 |
| K1-18 | | | |
| 0.3 ng/mL | 2.58 ± 0.33 | 7.76 ± 0.36 | 301 |
| 1 ng/mL | 5.33 ± 0.59 | 10.94 ± 0.61 | 205 |
| 3 ng/mL | 12.64 ± 2.43 | 23.29 ± 1.42 | 184 |
| 10 ng/mL | 51.08 ± 11.46 | 44.53 ± 4.03 | 87 |
| 30 ng/mL | 69.95 ± 3.59 | 57.58 ± 2.07 | 82 |
| 100 ng/mL | 87.39 ± 6.54 | 67.02 ± 4.87 | 77 |
| TSH | | | |
| 0.01 ng/mL | 1.51 ± 0.49 | 5.40 ± 0.84 | 358 |
| 0.03 ng/mL | 3.34 ± 1.14 | 5.93 ± 0.56 | 178 |
| 0.1 ng/mL | 5.58 ± 2.31 | 11.24 ± 1.18 | 201 |
| 0.3 ng/mL | 29.97 ± 6.61 | 28.85 ± 1.39 | 96 |
| 1 ng/mL | 64.61 ± 4.81 | 49.65 ± 5.10 | 77 |
| 3 ng/mL | 73.22 ± 4.70 | 60.45 ± 7.70 | 83 |

See legend to Table 14a for details.

TABLE 14c

Cyclic AMP production in CHO cells expressing wild type TSHR and TSHR with Glu61 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Cyclic AMP assay buffer | 1.47 ± 0.15 | 5.22 ± 0.71 | 355 |
| K1-18 | | | |
| 0.3 ng/mL | 1.79 ± 0.19 | 6.02 ± 0.33 | 336 |
| 1 ng/mL | 3.68 ± 0.26 | 8.45 ± 0.76 | 230 |
| 3 ng/mL | 9.15 ± 0.43 | 15.04 ± 1.69 | 164 |
| 10 ng/mL | 32.03 ± 0.84 | 34.30 ± 1.21 | 107 |
| 30 ng/mL | 63.25 ± 0.99 | 55.51 ± 6.57 | 88 |
| 100 ng/mL | 73.14 ± 1.81 | 81.13 ± 7.20 | 111 |
| TSH | | | |
| 0.01 ng/mL | 1.09 ± 0.28 | 5.12 ± 0.48 | 470 |
| 0.03 ng/mL | 1.75 ± 0.06 | 6.46 ± 0.67 | 369 |
| 0.1 ng/mL | 2.91 ± 0.16 | 7.88 ± 0.56 | 271 |
| 0.3 ng/mL | 7.29 ± 0.10 | 13.74 ± 0.45 | 188 |
| 1 ng/mL | 26.58 ± 1.60 | 34.30 ± 1.21 | 129 |
| 3 ng/mL | 57.99 ± 3.45 | 63.63 ± 5.01 | 110 |

See legend to Table 14a for details

TABLE 14d

Cyclic AMP production in CHO cells expressing wild type TSHR and TSHR with Thr104 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Experiment 1 | | | |
| Cyclic AMP assay buffer | 1.34 ± 0.29 | 3.56 ± 0.24 | 266 |
| K1-18 | | | |
| 0.3 ng/mL | 2.95 ± 0.47 | 4.64 ± 0.14 | 157 |
| 1 ng/mL | 6.14 ± 0.36 | 7.38 ± 0.38 | 120 |
| 3 ng/mL | 14.80 ± 1.02 | 14.53 ± 1.12 | 98 |
| 10 ng/mL | 39.45 ± 12.99 | 21.62 ± 16.74 | 55 |
| 30 ng/mL | 68.16 ± 7.99 | 35.85 ± 26.65 | 53 |
| 100 ng/mL | 83.92 ± 10.03 | 62.56 ± 6.94 | 75 |
| TSH | | | |
| 0.01 ng/mL | 1.37 ± 0.21 | 2.58 ± 0.21 | 188 |
| 0.03 ng/mL | 1.58 ± 0.10 | 3.20 ± 0.60 | 203 |
| 0.1 ng/mL | 1.83 ± 0.88 | 3.64 ± 0.19 | 199 |
| 0.3 ng/mL | 3.20** | 5.38 ± 0.07 | 168 |
| 1 ng/mL | 15.90 ± 0.95 | 15.80 ± 0.41 | 99 |
| 3 ng/mL | 47.64 ± 6.10 | 34.47 ± 1.54 | 72 |
| Experiment 2 | | | |
| Cyclic AMP assay buffer | 1.04 ± 0.26 | 3.70 ± 0.49 | 356 |
| K1-18 | | | |
| 0.3 ng/mL | 4.94 ± 0.29 | 6.65 ± 0.23 | 135 |
| 1 ng/mL | 9.47 ± 0.98 | 10.37 ± 1.18 | 110 |
| 3 ng/mL | 26.53 ± 2.22 | 21.47 ± 3.41 | 81 |
| 10 ng/mL | 54.89 ± 1.67 | 38.87 ± 3.69 | 71 |
| 30 ng/mL | 79.51 ± 5.35 | 50.95 ± 3.65 | 64 |
| 100 ng/mL | 78.3 ± 6.52 | 64.82 ± 5.61 | 83 |
| TSH | | | |
| 0.01 ng/mL | 2.10 ± 0.39 | 4.28 ± 0.18 | 204 |
| 0.03 ng/mL | 4.48 ± 0.53 | 5.71 ± 0.77 | 127 |
| 0.1 ng/mL | 10.27 ± 1.87 | 9.80 ± 0.53 | 95 |
| 0.3 ng/mL | 35.72 ± 5.54 | 35.74 ± 1.21 | 100 |
| 1 ng/mL | 71.99 ± 7.40 | 57.09 ± 2.53 | 79 |
| 3 ng/mL | 79.18 ± 6.82 | 58.46 ± 0.86 | 74 |

See legend to Table 14a for details.
**single determination.

TABLE 14e

Cyclic AMP production in CHO cells expressing wild type TSHR and TSHR with His105 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Cyclic AMP assay buffer | 2.02 ± 0.26 | 3.51 ± 0.31 | 173 |
| K1-18 | | | |
| 0.3 ng/mL | 2.51 ± 0.14 | 3.91 ± 0.29 | 156 |
| 1 ng/mL | 4.59 ± 0.48 | 4.99 ± 0.14 | 109 |
| 3 ng/mL | 9.26 ± 0.49 | 10.42 ± 0.32 | 113 |
| 10 ng/mL | 39.21 ± 2.49 | 27.25 ± 0.37 | 69 |
| 30 ng/mL | 69.70 ± 5.97 | 51.22 ± 4.24 | 73 |
| 100 ng/mL | 99.18 ± 3.63 | 78.03 ± 4.40 | 79 |
| TSH | | | |
| 0.01 ng/mL | 1.56 ± 0.28 | 4.80 ± 2.60 | 308 |
| 0.03 ng/mL | 2.42 ± 0.39 | 3.55 ± 0.20 | 147 |
| 0.1 ng/mL | 4.09 ± 0.79 | 4.82 ± 0.29 | 118 |
| 0.3 ng/mL | 11.44 ± 2.32 | 11.88 ± 2.77 | 104 |
| 1 ng/mL | 45.62 ± 1.99 | 34.56 ± 1.21 | 76 |
| 3 ng/mL | 77.89 ± 8.17 | 58.28 ± 4.66 | 75 |

See legend to Table 14a for details.

TABLE 14f

Cyclic AMP production in CHO cells expressing wild type TSHR and TSHR with Asp151 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Cyclic AMP assay buffer | 1.90 ± 0.61 | 5.93 ± 0.60 | 312 |
| K1-18 | | | |
| 0.3 ng/mL | 4.01 ± 0.43 | 7.36 ± 0.35 | 184 |
| 1 ng/mL | 9.64 ± 0.27 | 11.42 ± 2.31 | 118 |
| 3 ng/mL | 20.53 ± 1.64 | 18.27 ± 0.51 | 89 |
| 10 ng/mL | 54.20 ± 1.61 | 40.81 ± 7.12 | 75 |
| 30 ng/mL | 81.74 ± 5.92 | 51.20 ± 5.41 | 63 |
| 100 ng/mL | 79.82 ± 4.86 | 66.01 ± 5.14 | 83 |
| TSH | | | |
| 0.01 ng/mL | 2.96 ± 0.26 | 6.19 ± 0.36 | 209 |
| 0.03 ng/mL | 5.36 ± 0.60 | 7.99 ± 1.12 | 149 |
| 0.1 ng/mL | 14.33 ± 1.46 | 14.12 ± 0.67 | 99 |
| 0.3 ng/mL | 43.55 ± 6.31 | 35.02 ± 4.18 | 80 |
| 1 ng/mL | 73.50 ± 9.55 | 48.53 ± 6.40 | 66 |
| 3 ng/mL | 80.67 ± 3.49 | 54.55 ± 3.53 | 68 |

See legend to Table 14a for details.

TABLE 14g

Cyclic AMP production in CHO cells expressing wild type TSHR and TSHR with Glu157 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Cyclic AMP assay buffer | 1.89 ± 0.08 | 9.18 ± 0.08 | 485 |
| K1-18 | | | |
| 0.3 ng/mL | 3.77 ± 0.18 | 11.44 ± 3.63 | 303 |
| 1 ng/mL | 7.52 ± 0.26 | 9.76 ± 0.93 | 130 |
| 3 ng/mL | 19.14 ± 0.40 | 9.31 ± 0.91 | 49 |
| 10 ng/mL | 45.88 ± 1.10 | 14.37 ± 6.84 | 31 |

TABLE 14g-continued

Cyclic AMP production in CHO cells expressing wild type TSHR and TSHR with Glu157 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| 30 ng/mL | 56.81 ± 5.21 | 11.01 ± 3.30 | 19 |
| 100 ng/mL TSH | 64.73 ± 5.17 | 9.39 ± 2.46 | 15 |
| 0.01 ng/mL | 2.55 ± 0.32 | 11.48 ± 1.63 | 450 |
| 0.03 ng/mL | 3.56 ± 0.17 | 11.67 ± 1.56 | 328 |
| 0.1 ng/mL | 8.19 ± 0.96 | 13.43 ± 1.26 | 164 |
| 0.3 ng/mL | 21.83 ± 0.73 | 25.78 ± 4.64 | 118 |
| 1 ng/mL | 46.44 ± 3.10 | 40.14 ± 1.60 | 86 |
| 3 ng/mL | 52.73 ± 2.18 | 60.81 ± 5.71 | 115 |

See legend to Table 14a for details.

TABLE 14h

Cyclic AMP production in CHO cells expressing wild type TSHR and TSHR with Glu178 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Cyclic AMP assay buffer K1-18 | 1.39 ± 0.21 | 9.71 ± 0.36 | 699 |
| 0.3 ng/mL | 3.10 ± 0.45 | 10.89 ± 0.67 | 351 |
| 1 ng/mL | 7.67 ± 0.57 | 13.37 ± 0.56 | 174 |
| 3 ng/mL | 19.48 ± 2.03 | 20.66* | 106 |
| 10 ng/mL | 56.35 ± 2.84 | 40.02* | 71 |
| 30 ng/mL | 72.19 ± 2.66 | 46.23 ± 1.87 | 64 |
| 100 ng/mL TSH | 77.30 ± 4.83 | 61.85 ± 3.91 | 80 |
| 0.01 ng/mL | 1.99 ± 0.11 | 9.29 ± 1.00 | 467 |
| 0.03 ng/mL | 4.84 ± 0.30 | 11.60 ± 0.21 | 240 |
| 0.1 ng/mL | 12.93 ± 0.64 | 14.83 ± 2.25 | 115 |
| 0.3 ng/mL | 47.70 ± 4.82 | 33.72 ± 3.43 | 71 |
| 1 ng/mL | 79.36 ± 7.46 | 43.12 ± 1.05 | 54 |
| 3 ng/mL | 74.89 ± 8.91 | 54.84 ± 4.58 | 73 |

See legend to Table 14a for details.
*mean of duplicate.

TABLE 14i

Cyclic AMP production in CHO cells expressing wild type TSHR and TSHR with Lys183 mutated to Asp. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Cyclic AMP assay buffer K1-18 | 2.23 ± 0.06 | 2.51 ± 0.63 | 113 |
| 0.3 ng/mL | 4.15 ± 0.47 | 2.40 ± 0.34 | 58 |
| 1 ng/mL | 8.37 ± 2.15 | 2.20 ± 0.54 | 26 |
| 3 ng/mL | 18.71 ± 2.79 | 3.05 ± 0.46 | 16 |
| 10 ng/mL | 54.30 ± 2.14 | 2.35 ± 0.77 | 4 |
| 30 ng/mL | 89.01 ± 13.58 | 2.24 ± 0.79 | 3 |
| 100 ng/mL TSH | 109.78 ± 16.33 | 2.30 ± 0.72 | 2 |
| 0.01 ng/mL | 2.48 ± 0.32 | 4.08 ± 1.06 | 165 |
| 0.03 ng/mL | 4.62 ± 0.25 | 7.18 ± 0.78 | 155 |
| 0.1 ng/mL | 17.59 ± 8.60 | 19.10 ± 3.55 | 109 |
| 0.3 ng/mL | 40.35 ± 5.38 | 51.68 ± 4.48 | 128 |
| 1 ng/mL | 92.49 ± 2.61 | 93.34 ± 4.90 | 101 |
| 3 ng/mL | 103.97 ± 13.32 | 106.27 ± 8.71 | 102 |

See legend to Table 14a for details.

TABLE 14j

Cyclic AMP production in CHO cells expressing wild type TSHR and TSHR with Tyr185 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Experiment 1 | | | |
| Cyclic AMP assay buffer K1-18 (ng/mL) | 2.04 ± 0.15 | 3.02 ± 0.58 | 148 |
| 0.3 ng/mL | 3.69 ± 0.22 | 2.68 ± 0.19 | 73 |
| 1 ng/mL | 7.76 ± 1.36 | 2.95 ± 0.51 | 38 |
| 3 ng/mL | 22.97 ± 1.30 | 2.31 ± 0.50 | 10 |
| 10 ng/mL | 55.05 ± 5.19 | 3.21 ± 0.80 | 6 |
| 30 ng/mL | 97.56 ± 6.65 | 4.58 ± 0.63 | 5 |
| 100 ng/mL TSH (ng/mL) | 120.10 ± 15.75 | 5.57 ± 1.20 | 5 |
| 0.01 ng/mL | 2.60 ± 0.30 | 3.33 ± 0.81 | 128 |
| 0.03 ng/mL | 4.27 ± 0.38 | 3.85 ± 0.37 | 90 |
| 0.1 ng/mL | 10.94 ± 1.68 | 8.36 ± 0.98 | 76 |
| 0.3 ng/mL | 32.33 ± 2.26 | 21.15 ± 3.60 | 65 |
| 1 ng/mL | 84.95 ± 2.47 | 37.84 ± 1.45 | 45 |
| 3 ng/mL | 124.05 ± 7.70 | 42.9 ± 5.23 | 35 |
| Experiment 2 | | | |
| Cyclic AMP assay buffer K1-18 (ng/mL) | 2.15 ± 0.04 | 4.23 ± 0.89 | 197 |
| 0.3 ng/mL | 7.38 ± 0.53 | 4.33 ± 0.20 | 59 |
| 1 ng/mL | 7.51 ± 1.67 | 4.39 ± 0.45 | 58 |
| 3 ng/mL | 28.12 ± 0.86 | 4.10 ± 0.68 | 15 |
| 10 ng/mL | 50.76 ± 7.00 | 4.38 ± 1.82 | 9 |
| 30 ng/mL | 89.92 ± 4.11 | 3.90 ± 1.06 | 4 |
| 100 ng/mL TSH (ng/mL) | 105.22 ± 5.18 | 7.08 ± 0.31 | 7 |
| 0.01 ng/mL | 3.89 ± 0.51 | 3.82 ± 0.64 | 98 |
| 0.03 ng/mL | 5.52 ± 0.31 | 5.60 ± 1.20 | 101 |
| 0.1 ng/mL | 13.28 ± 0.63 | 12.32 ± 0.57 | 93 |
| 0.3 ng/mL | 35.35 ± 2.72 | 30.54 ± 3.00 | 86 |

TABLE 14j-continued

Cyclic AMP production in CHO cells expressing wild type TSHR and TSHR with Tyr185 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| 1 ng/mL | 82.08 ± 4.80 | 50.65 ± 1.32 | 62 |
| 3 ng/mL | 91.67 ± 10.28 | 56.30 ± 6.87 | 61 |

See legend to Table 14a for details.

TABLE 14k

Cyclic AMP production in CHO cells expressing wild type TSHR and TSHR with Tyr206 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Experiment 1 | | | |
| Cyclic AMP assay buffer K1-18 | 1.50 ± 0.27 | 2.47 ± 0.13 | 165 |
| 0.3 ng/mL | 1.19 ± 1.22 | 2.68 ± 0.23 | 225 |
| 1 ng/mL | 6.57 ± 0.16 | 3.11 ± 0.24 | 47 |
| 3 ng/mL | 16.50 ± 1.42 | 1.75 ± 0.81 | 11 |
| 10 ng/mL | 31.40 ± 14.65 | 8.14 ± 2.38 | 26 |
| 30 ng/mL | 62.92 ± 1.83 | 15.07 ± 1.02 | 24 |
| 100 ng/mL | 61.48 ± 14.14 | 20.32 ± 12.27 | 33 |
| TSH | | | |
| 0.01 ng/mL | 2.09 ± 0.51 | 1.74 ± 1.50 | 83 |
| 0.03 ng/mL | 2.93 ± 0.48 | 3.64 ± 0.84 | 124 |
| 0.1 ng/mL | 9.04 ± 0.73 | 8.40 ± 0.72 | 93 |
| 0.3 ng/mL | 19.08 ± 12.79 | 19.83 ± 6.50 | 104 |
| 1 ng/mL | 59.48 ± 1.26 | 38.98 ± 1.84 | 66 |
| 3 ng/mL | 75.64 ± 2.36 | 46.68 ± 2.01 | 62 |
| Experiment 2 | | | |
| Cyclic AMP assay buffer K1-18 | 1.96 ± 0.19 | 4.35 ± 0.24 | 222 |
| 0.3 ng/mL | 5.09 ± 1.70 | 4.50 ± 0.37 | 88 |
| 1 ng/mL | 7.69 ± 1.28 | 6.23 ± 0.55 | 81 |
| 3 ng/mL | 18.47 ± 1.00 | 8.07 ± 0.28 | 44 |
| 10 ng/mL | 55.94 ± 8.77 | 22.41 ± 2.17 | 40 |
| 30 ng/mL | 69.92 ± 4.84 | 33.57 ± 1.65 | 48 |
| 100 ng/mL | 85.46 ± 15.91 | 45.40 ± 3.53 | 53 |
| TSH | | | |
| 0.01 ng/mL | 3.63 ± 1.30 | 4.90 ± 1.14 | 135 |
| 0.03 ng/mL | 4.60 ± 0.31 | 6.64 ± 0.51 | 144 |
| 0.1 ng/mL | 10.82 ± 0.50 | 19.25 ± 5.14 | 178 |
| 0.3 ng/mL | 34.70 ± 5.34 | 38.33 ± 1.28 | 110 |
| 1 ng/mL | 65.17 ± 6.68 | 60.87 ± 6.66 | 93 |
| 3 ng/mL | 75.13 ± 8.64 | 73.06 ± 3.01 | 97 |

See legend to Table 14a for details.

TABLE 14l

Cyclic AMP production in CHO cells expressing wild type TSHR and TSHR with Lys209 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Cyclic AMP assay buffer K1-18 | 1.97 ± 0.24 | 4.79 ± 0.77 | 243 |
| 0.3 ng/mL | 4.08 ± 0.19 | 5.52 ± 0.33 | 135 |
| 1 ng/mL | 9.47 ± 0.42 | 8.07 ± 0.57 | 85 |
| 3 ng/mL | 21.43 ± 1.03 | 12.65 ± 1.18 | 59 |
| 10 ng/mL | 62.15 ± 8.08 | 32.55 ± 4.45 | 52 |
| 30 ng/mL | 91.57 ± 5.64 | 43.71 ± 9.76 | 48 |
| 100 ng/mL | 99.88 ± 10.13 | 69.49 ± 7.10 | 70 |
| TSH | | | |
| 0.01 ng/mL | 3.02 ± 0.62 | 5.16 ± 0.11 | 171 |
| 0.03 ng/mL | 4.59 ± 0.54 | 5.87 ± 0.17 | 128 |
| 0.1 ng/mL | 14.25 ± 1.09 | 9.27 ± 0.81 | 65 |
| 0.3 ng/mL | 38.20 ± 6.84 | 24.27 ± 1.60 | 64 |
| 1 ng/mL | 87.25 ± 1.51 | 39.31 ± 5.78 | 45 |
| 3 ng/mL | 101.72 ± 11.82 | 63.25 ± 6.11 | 62 |

See legend to Table 14a for details.

TABLE 14m

Cyclic AMP production in CHO cells expressing wild type TSHR and TSHR with Asp232 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Experiment 1 | | | |
| Cyclic AMP assay buffer K1-18 | 2.02 ± 0.09 | 1.33 ± 0.21 | 66 |
| 0.3 ng/mL | 2.54 ± 0.06 | 0.99 ± 0.10 | 39 |
| 1 ng/mL | 6.16 ± 0.44 | 1.31 ± 0.05 | 21 |
| 3 ng/mL | 14.61 ± 0.83 | 1.80 ± 0.36 | 12 |
| 10 ng/mL | 38.90 ± 1.79 | 3.61 ± 0.02 | 9 |
| 30 ng/mL | 60.13 ± 3.16 | 8.21 ± 0.04 | 14 |
| 100 ng/mL | 65.85 ± 1.99 | 16.17 ± 0.08 | 25 |
| TSH | | | |
| 0.01 ng/mL | 1.69 ± 0.21 | 1.40 ± 0.08 | 83 |
| 0.03 ng/mL | 2.46 ± 0.20 | 2.16 ± 0.13 | 88 |
| 0.1 ng/mL | 6.18 ± 0.69 | 5.39 ± 0.28 | 87 |
| 0.3 ng/mL | 18.94 ± 0.29 | 15.11 ± 0.50 | 80 |
| 1 ng/mL | 45.19 ± 3.14 | 31.85 ± 1.24 | 70 |
| 3 ng/mL | 61.65 ± 5.29 | 40.95 ± 2.42 | 66 |
| Experiment 2 | | | |
| Cyclic AMP assay buffer K1-18 | 1.74 ± 1.29 | 2.80 ± 0.16 | 161 |
| 0.3 ng/mL | 4.93 ± 0.61 | 2.86 ± 0.15 | 58 |
| 1 ng/mL | 8.65 ± 0.84 | 3.53 ± 0.52 | 41 |
| 3 ng/mL | 21.61 ± 0.47 | 4.78 ± 0.27 | 22 |
| 10 ng/mL | 54.40 ± 0.93 | 1.76 ± 0.18 | 3 |
| 30 ng/mL | 86.44 ± 6.25 | 3.79 ± 0.17 | 4 |
| 100 ng/mL | 99.65 ± 10.16 | 6.49 ± 0.05 | 7 |

TABLE 14m-continued

Cyclic AMP production in CHO cells expressing wild type TSHR and TSHR with Asp232 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| TSH | | | |
| 0.01 ng/mL | 4.16 ± 1.96 | 2.58 ± 0.09 | 62 |
| 0.03 ng/mL | 4.92 ± 0.92 | 4.10 ± 0.23 | 83 |
| 0.1 ng/mL | 11.24 ± 1.01 | 9.44 ± 0.60 | 84 |
| 0.3 ng/mL | 31.44 ± 1.09 | 23.47 ± 1.51 | 75 |
| 1 ng/mL | 74.30 ± 2.40 | 44.35 ± 1.57 | 60 |
| 3 ng/mL | 96.39 ± 4.85 | 62.02 ± 8.15 | 64 |

See legend to Table 14a for details.

TABLE 14n

Cyclic AMP production in CHO cells expressing wild type TSHR and TSHR with Gln235 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Experiment 1 | | | |
| Cyclic AMP assay buffer | 0.70 ± 0.09 | 1.98 ± 0.62 | 283 |
| K1-18 | | | |
| 0.3 ng/mL | 1.80 ± 0.35 | 2.51 ± 0.43 | 139 |
| 1 ng/mL | 4.34 ± 0.52 | 4.48 ± 0.64 | 103 |
| 3 ng/mL | 9.25 ± 2.14 | 6.01 ± 1.95 | 65 |
| 10 ng/mL | 33.66 ± 5.21 | 18.80 ± 1.99 | 56 |
| 30 ng/mL | 79.70 ± 7.46 | 30.92 ± 2.83 | 39 |
| 100 ng/mL | 74.66 ± 3.56 | 47.71 ± 1.54 | 64 |
| TSH | | | |
| 0.01 ng/mL | 1.09 ± 0.35 | 1.75 ± 0.00 | 161 |
| 0.03 ng/mL | 2.31 ± 0.17 | 2.89 ± 0.03 | 125 |
| 0.1 ng/mL | 6.54 ± 0.20 | 5.97 ± 1.62 | 91 |
| 0.3 ng/mL | 26.48 ± 0.68 | 17.61 ± 0.48 | 67 |
| 1 ng/mL | 67.72 ± 7.23 | 44.19 ± 18.05 | 65 |
| 3 ng/mL | 83.50* | 46.59 ± 8.21 | 56 |
| Experiment 2 | | | |
| Cyclic AMP assay buffer | 1.85 ± 0.32 | 4.10 ± 0.42 | 222 |
| K1-18 | | | |
| 0.3 ng/mL | 2.58 ± 0.21 | 4.27 ± 1.53 | 166 |
| 1 ng/mL | 5.15 ± 0.85 | 7.30 ± 0.74 | 142 |
| 3 ng/mL | 14.11 ± 0.27 | 12.33 ± 3.43 | 87 |
| 10 ng/mL | 32.68 ± 5.49 | 24.02 ± 3.07 | 74 |
| 30 ng/mL | 58.74 ± 1.82 | 32.71 ± 2.05 | 56 |
| 100 ng/mL | 66.70 ± 2.49 | 43.93 ± 0.41 | 66 |
| TSH | | | |
| 0.01 ng/mL | 1.93 ± 0.13 | 3.42 ± 0.30 | 177 |
| 0.03 ng/mL | 2.75 ± 0.41 | 4.55 ± 0.24 | 165 |
| 0.1 ng/mL | 7.25 ± 1.02 | 7.77 ± 1.16 | 107 |
| 0.3 ng/mL | 25.26 ± 0.96 | 17.14 ± 0.56 | 68 |
| 1 ng/mL | 50.96 ± 2.69 | 31.70 ± 1.10 | 62 |
| 3 ng/mL | 69.68 ± 2.04 | 37.14 ± 1.16 | 53 |

See legend to Table 14a for details.
*mean of duplicate.

TABLE 14o

Cyclic AMP production in CHO cells expressing wild type TSHR and TSHR with Lys250 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Cyclic AMP assay buffer | 1.41 ± 0.87 | 6.48 ± 0.22 | 460 |
| K1-18 | | | |
| 0.3 ng/mL | 3.20 ± 0.31 | 10.50 ± 0.55 | 328 |
| 1 ng/mL | 8.57 ± 0.31 | 23.44 ± 6.81 | 274 |
| 3 ng/mL | 27.68 ± 3.34 | 35.88 ± 0.55 | 130 |
| 10 ng/mL | 54.04 ± 4.74 | 68.33 ± 5.39 | 126 |
| 30 ng/mL | 85.58 ± 3.88 | 91.29 ± 2.75 | 107 |
| 100 ng/mL | 81.79 ± 1.55 | 100.62 ± 8.66 | 123 |
| TSH | | | |
| 0.01 ng/mL | 4.00 ± 0.10 | 8.29 ± 0.69 | 207 |
| 0.03 ng/mL | 6.66 ± 0.59 | 12.58 ± 0.44 | 189 |
| 0.1 ng/mL | 19.66 ± 2.56 | 28.81 ± 3.56 | 147 |
| 0.3 ng/mL | 44.98 ± 3.85 | 66.19 ± 0.67 | 147 |
| 1 ng/mL | 75.67 ± 6.21 | 87.90 ± 5.38 | 116 |
| 3 ng/mL | 87.19 ± 1.94 | 110.23 ± 9.68 | 126 |

See legend to Table 14a for details.

TABLE 14p

Cyclic AMP production in CHO cells expressing wild type TSHR and TSHR with Glu251 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Cyclic AMP assay buffer | 1.22 ± 0.42 | 6.69 ± 2.73 | 548 |
| K1-18 | | | |
| 0.3 ng/mL | 2.36 ± 0.37 | 6.85 ± 0.56 | 290 |
| 1 ng/mL | 6.40 ± 0.43 | 9.70 ± 1.01 | 152 |
| 3 ng/mL | 19.16 ± 1.47 | 19.57 ± 1.63 | 102 |
| 10 ng/mL | 55.42 ± 4.77 | 39.70 ± 4.02 | 72 |
| 30 ng/mL | 84.02* | 66.74 ± 3.34 | 79 |
| 100 ng/mL | 111.09 ± 6.17 | 78.15 ± 0.89 | 70 |
| TSH | | | |
| 0.01 ng/mL | 1.64 ± 0.28 | 3.99 ± 0.94 | 243 |
| 0.03 ng/mL | 2.67 ± 0.32 | 5.99 ± 2.43 | 224 |
| 0.1 ng/mL | 9.75 ± 1.97 | 11.18 ± 1.33 | 115 |
| 0.3 ng/mL | 33.26 ± 9.03 | 22.15 ± 3.42 | 67 |
| 1 ng/mL | 77.73 ± 4.07 | 53.68 ± 1.90 | 69 |
| 3 ng/mL | 109.36 ± 2.78 | 71.71* | 66 |

See legend to Table 14a for details.
*mean of duplicate.

TABLE 14q

Cyclic AMP production in CHO cells expressing wild type TSHR and TSHR with Arg255 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Cyclic AMP assay buffer | 2.29 ± 1.04 | 4.37 ± 0.75 | 191 |
| K1-18 | | | |
| 0.3 ng/mL | 4.64 ± 0.55 | 5.46 ± 0.19 | 118 |
| 1 ng/mL | 8.87 ± 0.31 | 8.37 ± 0.20 | 94 |
| 3 ng/mL | 18.48 ± 0.81 | 13.80 ± 1.77 | 75 |
| 10 ng/mL | 55.33 ± 0.69 | 42.85 ± 1.72 | 77 |
| 30 ng/mL | 73.94 ± 4.06 | 59.25 ± 2.70 | 80 |
| 100 ng/mL | 79.57 ± 6.78 | 77.80 ± 4.90 | 98 |
| TSH | | | |
| 0.01 ng/mL | 2.94 ± 0.54 | 4.72 ± 0.33 | 161 |
| 0.03 ng/mL | 4.82 ± 0.70 | 6.78 ± 0.49 | 141 |
| 0.1 ng/mL | 9.25 ± 0.11 | 11.66 ± 0.75 | 126 |
| 0.3 ng/mL | 36.20 ± 3.81 | 36.72 ± 3.56 | 101 |
| 1 ng/mL | 69.17 ± 5.01 | 61.95 ± 3.97 | 90 |
| 3 ng/mL | 88.05* | 80.08 ± 0.72 | 91 |

See legend to Table 14a for details.
*mean of duplicate.

TABLE 14r

Cyclic AMP production in CHO cells expressing wild type TSHR and TSHR with Thr257 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Cyclic AMP assay buffer | 1.01 ± 0.34 | 1.13 ± 0.45 | 112 |
| K1-18 | | | |
| 0.3 ng/mL | 1.50 ± 0.68 | 1.54 ± 0.29 | 103 |
| 1 ng/mL | 3.60 ± 0.36 | 2.69 ± 1.11 | 75 |
| 3 ng/mL | 8.09 ± 0.45 | 7.13 ± 0.88 | 88 |
| 10 ng/mL | 27.52 ± 3.28 | 20.22 ± 1.90 | 73 |
| 30 ng/mL | 64.52 ± 1.71 | 39.26 ± 3.48 | 61 |
| 100 ng/mL | 100.30 ± 2.04 | 81.11 ± 5.12 | 81 |
| TSH | | | |
| 0.01 ng/mL | 1.67 ± 0.27 | 1.50 ± 0.29 | 90 |
| 0.03 ng/mL | 3.13 ± 0.68 | 2.92 ± 0.45 | 93 |
| 0.1 ng/mL | 8.30 ± 0.37 | 7.65 ± 1.51 | 92 |
| 0.3 ng/mL | 24.05 ± 2.75 | 25.30 ± 0.41 | 105 |
| 1 ng/mL | 64.57 ± 3.16 | 60.69 ± 3.98 | 94 |
| 3 ng/mL | 102.12 ± 9.89 | 88.24 ± 12.78 | 86 |

See legend to Table 14a for details.

TABLE 14s

Cyclic AMP production in CHO cells expressing wild type TSHR and TSHR with Trp258 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Experiment 1 | | | |
| Cyclic AMP assay buffer | 0.90 ± 0.08 | 2.05 ± 0.38 | 228 |
| K1-18 | | | |
| 0.3 ng/mL | 2.29 ± 0.25 | 2.93 ± 0.39 | 128 |
| 1 ng/mL | 5.47 ± 0.90 | 4.39 ± 0.24 | 80 |
| 3 ng/mL | 15.27 ± 1.02 | 11.47 ± 0.72 | 75 |
| 10 ng/mL | 45.65 ± 2.67 | 25.35 ± 2.59 | 56 |
| 30 ng/mL | 70.22 ± 8.09 | 40.36 ± 0.00 | 57 |
| 100 ng/mL | 77.74 ± 5.05 | 52.44 ± 4.72 | 67 |
| TSH | | | |
| 0.01 ng/mL | 1.22 ± 0.34 | 1.93 ± 0.24 | 158 |
| 0.03 ng/mL | 1.85 ± 0.62 | 2.88 ± 0.09 | 156 |
| 0.1 ng/mL | 4.89 ± 0.35 | 7.51 ± 1.57 | 154 |
| 0.3 ng/mL | 17.37 ± 0.87 | 22.29 ± 3.45 | 128 |
| 1 ng/mL | 52.88 ± 6.38 | 45.69 ± 7.63 | 86 |
| 3 ng/mL | 70.63 ± 3.87 | 53.97 ± 3.81 | 76 |
| Experiment 2 | | | |
| Cyclic AMP assay buffer | 1.45 ± 0.28 | 0.92 ± 0.21 | 63 |
| K1-18 | | | |
| 0.3 ng/mL | 1.68 ± 0.21 | 1.53 ± 0.31 | 91 |
| 1 ng/mL | 5.21 ± 0.29 | 3.29 ± 0.75 | 63 |
| 3 ng/mL | 15.99 ± 1.07 | 6.25 ± 0.22 | 39 |
| 10 ng/mL | 41.40 ± 4.90 | 15.64 ± 0.90 | 38 |
| 30 ng/mL | 77.09 ± 1.32 | 38.59 ± 1.52 | 50 |
| 100 ng/mL | 106.57 ± 3.64 | 57.31 ± 2.41 | 54 |
| TSH | | | |
| 0.01 ng/mL | 2.02 ± 0.51 | 1.56 ± 0.18 | 77 |
| 0.03 ng/mL | 1.96 ± 0.06 | 2.76 ± 0.71 | 141 |
| 0.1 ng/mL | 4.49 ± 0.81 | 7.04 ± 0.83 | 156 |
| 0.3 ng/mL | 13.47 ± 1.96 | 17.26 ± 4.12 | 128 |
| 1 ng/mL | 43.24 ± 1.20 | 49.17 ± 5.52 | 114 |
| 3 ng/mL | 84.76 ± 9.98 | 84.70* | 100 |

See legend to Table 14a for details.
*mean of duplicate.

TABLE 14t

Cyclic AMP production in CHO cells expressing wild type TSHR and TSHR with Arg274 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Experiment 1 | | | |
| Cyclic AMP assay buffer | 1.58 ± 0.21 | 1.71 ± 0.07 | 108 |
| K1-18 | | | |
| 0.3 ng/mL | 1.75 ± 0.14 | 1.74 ± 0.17 | 99 |
| 1 ng/mL | 3.17 ± 0.20 | 1.97 ± 0.82 | 62 |
| 3 ng/mL | 10.91 ± 1.52 | 3.46 ± 0.07 | 32 |
| 10 ng/mL | 28.17 ± 2.38 | 9.44 ± 0.80 | 34 |

TABLE 14t-continued

Cyclic AMP production in CHO cells expressing wild type TSHR and TSHR with Arg274 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| 30 ng/mL | 71.50 ± 3.54 | 27.91 ± 1.72 | 39 |
| 100 ng/mL TSH | 96.37 ± 4.71 | 70.48 ± 5.61 | 73 |
| 0.01 ng/mL | 1.86 ± 0.23 | 1.97 ± 0.06 | 106 |
| 0.03 ng/mL | 3.32 ± 0.07 | 4.14 ± 1.36 | 125 |
| 0.1 ng/mL | 14.60 ± 1.90 | 9.38 ± 0.23 | 64 |
| 0.3 ng/mL | 48.54 ± 4.12 | 27.28 ± 1.62 | 56 |
| 1 ng/mL | 91.18 ± 4.31 | 67.63 ± 0.93 | 74 |
| 3 ng/mL | 118.63 ± 16.76 | 98.80 ± 7.10 | 83 |
| Experiment 2 | | | |
| Cyclic AMP assay buffer K1-18 | 2.08 ± 0.14 | 1.65 ± 0.12 | 79 |
| 0.3 ng/mL | 2.70 ± 0.08 | 1.71 ± 0.13 | 63 |
| 1 ng/mL | 5.96 ± 0.25 | 2.65 ± 0.20 | 44 |
| 3 ng/mL | 14.95 ± 0 | 5.45 ± 0.28 | 36 |
| 10 ng/mL | 51.80 ± 4.35 | 14.83 ± 1.86 | 29 |
| 30 ng/mL | 81.16 ± 2.80 | 35.53 ± 0.93 | 44 |
| 100 ng/mL TSH | 97.09 ± 10.91 | 60.73 ± 3.26 | 63 |
| 0.01 ng/mL | 2.49 ± 0.39 | 1.37 ± 0.18 | 55 |
| 0.03 ng/mL | 5.12 ± 0.22 | 2.94 ± 0.11 | 57 |
| 0.1 ng/mL | 13.66 ± 1.00 | 8.29 ± 0.74 | 61 |
| 0.3 ng/mL | 39.93 ± 2.47 | 25.47 ± 0.43 | 64 |
| 1 ng/mL | 74.35 ± 5.04 | 58.49 ± 4.84 | 79 |
| 3 ng/mL | 88.28 ± 15.49 | 73.19 ± 3.18 | 82 |

See legend to Table 14a for details.

TABLE 14u

Cyclic AMP production in CHO cells expressing wild type TSHR and TSHR with Asp276 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Cyclic AMP assay buffer K1-18 | 1.05 ± 0.23 | 13.94 ± 2.05 | 1328 |
| 0.3 ng/mL | 2.27 ± 0.23 | 17.17 ± 0.64 | 756 |
| 1 ng/mL | 6.16 ± 0.90 | 23.79 ± 1.67 | 386 |
| 3 ng/mL | 17.36 ± 0.80 | 32.67 ± 3.05 | 188 |
| 10 ng/mL | 52.57 ± 0 | 56.94 ± 0.50 | 108 |
| 30 ng/mL | 81.08 ± 11.47 | 65.05 ± 4.25 | 80 |
| 100 ng/mL TSH | 87.81 ± 14.82 | 86.02 ± 6.77 | 98 |
| 0.01 ng/mL | 2.45 ± 0.68 | 14.29 ± 1.97 | 583 |
| 0.03 ng/mL | 4.78 ± 0.57 | 17.64 ± 0.44 | 369 |
| 0.1 ng/mL | 16.19 ± 0.95 | 21.70 ± 4.65 | 134 |
| 0.3 ng/mL | 44.34 ± 6.02 | 45.58 ± 1.03 | 103 |
| 1 ng/mL | 77.19 ± 4.48 | 68.31 ± 7.05 | 88 |
| 3 ng/mL | 95.50 ± 7.45 | 76.02 ± 5.12 | 80 |

See legend to Table 14a for details.

TABLE 14v

Cyclic AMP production in CHO cells expressing wild type TSHR and TSHR with Ser281 mutated to Ala. Effect of different dilutions of human monoclonal antibody to the TSHR (K1-18) with TSH agonist activity

| | Cyclic AMP produced (pmol/mL) mean ± SD (n = 3) | | |
|---|---|---|---|
| | Wild type TSHR | Mutated TSHR | Mutated/Wild type (%) |
| Cyclic AMP assay buffer K1-18 (ng/mL) | 1.72 ± 0.28 | 2.04 ± 0.29 | 119 |
| 0.3 ng/mL | 3.09 ± 0.17 | 3.62 ± 0.35 | 117 |
| 1 ng/mL | 6.04 ± 0.42 | 7.01 ± 0.55 | 116 |
| 3 ng/mL | 18.37 ± 1.19 | 15.23 ± 0.92 | 83 |
| 10 ng/mL | 43.48 ± 0.76 | 31.25 ± 1.85 | 72 |
| 30 ng/mL | 72.75 ± 5.88 | 55.19 ± 0.59 | 76 |
| 100 ng/mL TSH (ng/mL) | 81.95 ± 2.57 | 65.22 ± 6.42 | 80 |
| 0.01 ng/mL | 2.03 ± 0.30 | 2.84 ± 0.06 | 140 |
| 0.03 ng/mL | 3.65 ± 0.64 | 4.69 ± 0.05 | 128 |
| 0.1 ng/mL | 9.65 ± 1.53 | 11.33 ± 0.62 | 117 |
| 0.3 ng/mL | 31.40 ± 0.93 | 27.48 ± 2.15 | 88 |
| 1 ng/mL | 61.04 ± 3.63 | 51.63 ± 0.54 | 85 |
| 3 ng/mL | 82.58 ± 2.92 | 67.98 ± 2.73 | 82 |

See legend to Table 14a for details.

TABLE 15a

TSH induced cyclic AMP production in CHO cells expressing wild type TSHR and TSHR with Asp43 mutated to Ala. Effect of different dilutions of human monoclonal antibody to the TSHR (K1-70) with TSH antagonist activity

| Test sample[a] | Cyclic AMP produced (pmol/mL; mean ± SD (n = 3)) | | Mutated/wild type (%) |
|---|---|---|---|
| | Wild type TSHR | Mutated TSHR | |
| Cyclic AMP assay buffer only | 3.57 ± 1.18 | 1.40 ± 0.04 | 39 |
| TSH[b] | 93.92 ± 3.88 | ND | ND |
| 5B3 10 µg/mL + TSH[b] | 106.48 ± 12.76 | 73.73 ± 6.47 | 69 |
| 5B3 100 µg/mL + TSH[b] | 104.40 ± 2.12 | 57.99 ± 7.76 | 56 |
| K1-70 0.001 µg + TSH[b] | 109.98 ± 20.13 | 65.19 ± 11.37 | 59 |
| K1-70 0.01 µg + TSH[b] | 118.99 ± 3.21 | 61.42 ± 3.26 | 52 |
| K1-70 0.1 µg + TSH[b] | 82.87 ± 6.76 | 23.56 ± 12.03 | 28 |
| K1-70 1.0 µg + TSH[b] | 3.37 ± 0.81 | 1.82 ± 0.25 | 54 |
| K1-70 10 µg + TSH[b] | 2.05 ± 0.10 | 0.97 ± 0.16 | 47 |
| K1-70 100 µg + TSH[b] | 2.34 ± 0.18 | 1.16 ± 0.25 | 50 |
| K1-70 100 µg | 1.89 ± 0.12 | 1.64 ± 0.98 | 87 |
| [b]TSH (2) | 92.19 ± 5.64 | 60.27 ± 7.64 | 65 |

| Antibody concentration | % inhibition of TSH stimulation[c] | |
|---|---|---|
| | Wild type TSHR | Mutated TSHR |
| 5B3 10 µg/mL | 0 | 0 |
| 5B3 100 µg/mL | 0 | 4 |
| K1-70 0.001 µg | 0 | 0 |
| K1-70 0.01 µg/mL | 0 | 0 |
| K1-70 0.1 µg/mL | 12 | 61 |
| K1-70 1 µg/mL | 96 | 97 |
| K1-70 10 µg/mL | 98 | 98 |
| K1-70 100 µg/mL | 98 | 98 |
| [b]TSH (2) | 2 | 0 |

[a]Test samples in hypotonic cyclic AMP assay buffer.
[b]TSH final concentration = 3 ng/mL.
[c]% inhibition = 100 × [1 − (cyclic AMP in the presence of test samples and TSH/cyclic AMP in the presence of cyclic AMP buffer and TSH)]. 5B3 is a human monoclonal antibody to GAD (negative control for K1-70).
ND = not determined.
TSH(2) = run at the end of assay.

TABLE 15b

TSH induced cyclic AMP production in CHO cells expressing wild type TSHR and TSHR with Ile60 mutated to Ala. Effect of different dilutions of human monoclonal antibody to the TSHR (K1-70) with TSH antagonist activity

Experiment 1

| Test sample[a] | Cyclic AMP produced (pmol/mL; mean ± SD (n = 3)) | | Mutated/wild type (%) |
|---|---|---|---|
| | Wild type TSHR | Mutated TSHR | |
| Cyclic AMP assay buffer only | 1.78 ± 0.12 | 4.07 ± 0.08 | 229 |
| TSH[b] | 90.09 ± 1.19 | 51.32 ± 3.85 | 57 |
| 5B3 10 µg/mL + TSH[b] | 95.17 ± 4.45 | 54.77 ± 12.78 | 58 |
| 5B3 100 µg/mL + TSH[b] | 88.16 ± 5.03 | 43.98 ± 3.05 | 50 |
| K1-70 0.001 µg + TSH[b] | 91.53 ± 28.48 | 42.91 ± 2.83 | 47 |
| K1-70 0.01 µg + TSH[b] | 92.89 ± 10.08 | 47.49 ± 2.80 | 51 |
| K1-70 0.1 µg + TSH[b] | 8.45 ± 0.58 | 44.85 ± 7.20 | 531 |
| K1-70 1.0 µg + TSH[b] | 2.39 ± 0.42 | 21.99 ± 1.61 | 920 |
| K1-70 10 µg + TSH[b] | 1.78 ± 0.21 | 10.90 ± 0.67 | 612 |
| K1-70 100 µg + TSH[b] | 1.54 ± 021 | 7.61 ± 0.53 | 494 |
| K1-70 100 µg | 1.12 ± 0.51 | 3.84 ± 0.56 | 343 |
| [b]TSH (2) | 82.90 ± 1.87 | 45.09 ± 0.90 | 54 |

| Antibody concentration | % inhibition of TSH stimulation[c] | |
|---|---|---|
| | Wild type TSHR | Mutated TSHR |
| 5B3 10 µg/mL | 0 | 0 |
| 5B3 100 µg/mL | 2 | 14 |
| K1-70 0.001 µg | 0 | 16 |
| K1-70 0.01 µg/mL | 0 | 7 |
| K1-70 0.1 µg/mL | 91 | 13 |
| K1-70 1 µg/mL | 97 | 57 |
| K1-70 10 µg/mL | 98 | 79 |
| K1-70 100 µg/mL | 98 | 85 |
| [b]TSH (2) | 8 | 12 |

Experiment 2

| Test sample[a] | Cyclic AMP produced (pmol/mL; mean ± SD (n = 3)) | | Mutated/wild type (%) |
|---|---|---|---|
| | Wild type TSHR | Mutated TSHR | |
| Cyclic AMP assay buffer only | 1.16 ± 0.21 | 5.06 ± 0.31 | 436 |
| TSH[b] | 81.69 ± 3.88 | 65.78 ± 5.98 | 81 |
| 5B3 10 µg/mL + TSH[b] | 102.63 ± 13.71 | 54.69 ± 7.88 | 53 |
| 5B3 100 µg/mL + TSH[b] | 107.64 ± 13.05 | 66.83 ± 6.83 | 62 |
| K1-70 0.001 µg + TSH[b] | 93.21 ± 9.01 | 57.98 ± 6.22 | 62 |
| K1-70 0.01 µg + TSH[b] | 92.99 ± 6.39 | 58.40 ± 1.47 | 63 |
| K1-70 0.1 µg + TSH[b] | 4.12 ± 0.54 | 54.06 ± 5.59 | 1312 |
| K1-70 1.0 µg + TSH[b] | 1.16 ± 0.09 | 14.82 ± 1.13 | 1278 |
| K1-70 10 µg + TSH[b] | 1.85 ± 0.28 | 11.15 ± 2.09 | 603 |
| K1-70 100 µg + TSH[b] | 1.71 ± 0.56 | 7.87 ± 0.63 | 460 |
| K1-70 100 µg | 1.50 ± 0.25 | 4.13 ± 0.28 | 275 |
| [b]TSH (2) | 82.55 ± 7.76 | 56.96 ± 7.01 | 69 |

| Antibody concentration | % inhibition of TSH stimulation[c] | |
|---|---|---|
| | Wild type TSHR | Mutated TSHR |
| 5B3 10 µg/mL | 0 | 17 |
| 5B3 100 µg/mL | 0 | 0 |
| K1-70 0.001 µg | 0 | 12 |
| K1-70 0.01 µg/mL | 0 | 11 |
| K1-70 0.1 µg/mL | 95 | 18 |
| K1-70 1 µg/mL | 99 | 77 |
| K1-70 10 µg/mL | 98 | 83 |
| K1-70 100 µg/mL | 98 | 88 |
| [b]TSH (2) | 0 | 13 |

See legend to Table 15a for details.

TABLE 15c

TSH induced cyclic AMP production in CHO cells expressing wild type TSHR and TSHR with Glu61 mutated to Ala. Effect of different dilutions of human monoclonal antibody to the TSHR (K1-70) with TSH antagonist activity

| Test sample[a] | Cyclic AMP produced (pmol/mL; mean ± SD (n = 3)) | | Mutated/wild type (%) |
|---|---|---|---|
| | Wild type TSHR | Mutated TSHR | |
| Cyclic AMP assay buffer only | 0.63 ± 0.27 | 1.49 ± 0.48 | 237 |
| TSH[b] | 115.33 ± 1.56 | 77.74 ± 6.57 | 67 |
| 5B3 10 µg/mL + TSH[b] | 114.68 ± 8.12 | 77.87 ± 8.10 | 68 |
| 5B3 100 µg/mL + TSH[b] | 127.08 ± 6.55 | 70.47 ± 2.85 | 55 |
| K1-70 0.001 µg + TSH[b] | 102.62 ± 6.91 | 72.39 ± 4.36 | 71 |
| K1-70 0.01 µg + TSH[b] | 109.66 ± 14.99 | 71.93 ± 9.10 | 66 |
| K1-70 0.1 µg + TSH[b] | 43.68 ± 13.73 | 54.35 ± 9.85 | 124 |
| K1-70 1.0 µg + TSH[b] | 1.35 ± 0.08 | 1.18 ± 0.23 | 87 |
| K1-70 10 µg + TSH[b] | 1.25 ± 0.35 | 0.76 ± 0.23 | 60.8 |
| K1-70 100 µg + TSH[b] | 0.61 ± 0.46 | 0.91 ± 0.36 | 149 |
| K1-70 100 µg | 0.49 ± 0.47 | 1.69 ± 0.34 | 345 |
| [b]TSH (2) | 126.05 ± 6.29 | 64.74 ± 4.96 | 51 |

| Antibody concentration | % inhibition of TSH stimulation[c] | |
|---|---|---|
| | Wild type TSHR | Mutated TSHR |
| 5B3 10 µg/mL | 1 | 0 |
| 5B3 100 µg/mL | 0 | 9 |
| K1-70 0.001 µg | 11 | 7 |
| K1-70 0.01 µg/mL | 5 | 7 |
| K1-70 0.1 µg/mL | 62 | 30 |
| K1-70 1 µg/mL | 99 | 98 |
| K1-70 10 µg/mL | 99 | 99 |
| K1-70 100 µg/mL | 99 | 99 |
| [b]TSH (2) | 0 | 17 |

See legend to Table 15a for details.

TABLE 15d

TSH induced cyclic AMP production in CHO cells expressing wild type TSHR and TSHR with Thr104 mutated to Ala. Effect of different dilutions of human monoclonal antibody to the TSHR (K1-70) with TSH antagonist activity

| Test sample[a] | Cyclic AMP produced (pmol/mL; mean ± SD (n = 3)) | | Mutated/wild type (%) |
|---|---|---|---|
| | Wild type TSHR | Mutated TSHR | |
| Cyclic AMP assay buffer only | 0.89 ± 0.29 | 1.36 ± 0.89 | 153 |
| TSH[b] | 83.78 ± 6.86 | 63.69 ± 1.38 | 76 |
| 5B3 10 µg/mL + TSH[b] | 83.61 ± 3.29 | 59.13 ± 0.82 | 71 |
| 5B3 100 µg/mL + TSH[b] | 88.04 ± 5.58 | 60.01 ± 3.04 | 68 |
| K1-70 0.001 µg + TSH[b] | 90.15 ± 15.94 | 64.74 ± 6.20 | 72 |
| K1-70 0.01 µg + TSH[b] | 92.33 ± 8.48 | 54.64 ± 1.42 | 59 |
| K1-70 0.1 µg + TSH[b] | 34.13 ± 3.95 | 24.89 ± 3.39 | 73 |
| K1-70 1.0 µg + TSH[b] | 1.58 ± 0.16 | 2.55 ± 0.11 | 161 |
| K1-70 10 µg + TSH[b] | 1.07 ± 0.33 | 2.15 ± 1.06 | 201 |
| K1-70 100 µg + TSH[b] | 1.19 ± 0.35 | 1.86 ± 0.06 | 156 |
| K1-70 100 µg | 0.74 ± 0.30 | 1.48 ± 0.13 | 200 |
| [b]TSH (2) | 83.61 ± 3.30 | 57.01 ± 1.62 | 68 |

| Antibody concentration | % inhibition of TSH stimulation[c] | |
|---|---|---|
| | Wild type TSHR | Mutated TSHR |
| 5B3 10 µg/mL | 0 | 7 |
| 5B3 100 µg/mL | 0 | 6 |
| K1-70 0.001 µg | 0 | 0 |
| K1-70 0.01 µg/mL | 0 | 14 |
| K1-70 0.1 µg/mL | 59 | 61 |
| K1-70 1 µg/mL | 98 | 96 |

TABLE 15d-continued

TSH induced cyclic AMP production in CHO cells expressing wild type TSHR and TSHR with Thr104 mutated to Ala. Effect of different dilutions of human monoclonal antibody to the TSHR (K1-70) with TSH antagonist activity

| K1-70 10 µg/mL | 99 | 97 |
| K1-70 100 µg/mL | 99 | 97 |
| [b]TSH (2) | 0.2 | 10 |

See legend to Table 15a for details.

TABLE 15e

TSH induced cyclic AMP production in CHO cells expressing wild type TSHR and TSHR with His105 mutated to Ala. Effect of different dilutions of human monoclonal antibody to the TSHR (K1-70) with TSH antagonist activity

| Test sample[a] | Cyclic AMP produced (pmol/mL; mean ± SD (n = 3)) | | Mutated/wild type (%) |
| --- | --- | --- | --- |
| | Wild type TSHR | Mutated TSHR | |
| Cyclic AMP assay buffer only | 0.64 ± 0.08 | 0.99 ± 0.06 | 155 |
| TSH[b] | 93.59 ± 6.12 | 65.93 ± 4.03 | 70 |
| 5B3 10 µg/mL + TSH[b] | 91.63 ± 10.00 | 75.20 ± 5.73 | 82 |
| 5B3 100 µg/mL + TSH[b] | 133.84 ± 27.40 | 66.67 ± 1.51 | 50 |
| K1-70 0.001 µg + TSH[b] | 135.86 ± 3.01 | 89.32 ± 7.04 | 66 |
| K1-70 0.01 µg + TSH[b] | 119.40 ± 22.33 | 82.69 ± 6.53 | 69 |
| K1-70 0.1 µg + TSH[b] | 24.43 ± 4.03 | 10.46 ± 2.84 | 43 |
| K1-70 1.0 µg + TSH[b] | 1.34 ± 0.26 | 1.47 ± 0.40 | 110 |
| K1-70 10 µg + TSH[b] | 1.96 ± 2.03 | 0.70 ± 0.16 | 36 |
| K1-70 100 µg + TSH[b] | 0.70 ± 0.24 | 0.80 ± 0.24 | 114 |
| K1-70 100 µg | 0.89 ± 0.19 | 0.66 ± 0.13 | 74 |
| [b]TSH (2) | 116.74 ± 5.43 | 58.53 ± 2.95 | 50 |

| Antibody concentration | % inhibition of TSH stimulation[c] | |
| --- | --- | --- |
| | Wild type TSHR | Mutated TSHR |
| 5B3 10 µg/mL | 2 | 0 |
| 5B3 100 µg/mL | 0 | 0 |
| K1-70 0.001 µg | 0 | 0 |
| K1-70 0.01 µg/mL | 0 | 0 |
| K1-70 0.1 µg/mL | 74 | 84 |
| K1-70 1 µg/mL | 99 | 98 |
| K1-70 10 µg/mL | 98 | 99 |
| K1-70 100 µg/mL | 99 | 99 |
| [b]TSH (2) | 0 | 11 |

See legend to Table 15a for details.

TABLE 15f

TSH induced cyclic AMP production in CHO cells expressing wild type TSHR and TSHR with Asp151 mutated to Ala. Effect of different dilutions of human monoclonal antibody to the TSHR (K1-70) with TSH antagonist activity

| Test sample[a] | Cyclic AMP produced (pmol/mL; mean ± SD (n = 3)) | | Mutated/wild type (%) |
| --- | --- | --- | --- |
| | Wild type TSHR | Mutated TSHR | |
| Cyclic AMP assay buffer only | 1.06 ± 0.22 | 2.03 ± 0.48 | 192 |
| TSH[b] | 74.09 ± 8.63 | 45.72 ± 0.43 | 62 |
| 5B3 10 µg/mL + TSH[b] | 76.94 ± 7.67 | 40.70 ± 2.59 | 53 |
| 5B3 100 µg/mL + TSH[b] | 81.59 ± 6.54 | 46.24 ± 1.77 | 57 |
| K1-70 0.001 µg + TSH[b] | 80.09 ± 1.95 | 45.85 ± 4.25 | 57 |
| K1-70 0.01 µg + TSH[b] | 80.41 ± 8.03 | 44.71 ± 2.24 | 56 |
| K1-70 0.1 µg + TSH[b] | 13.74 ± 6.49 | 10.24 ± 0.91 | 75 |
| K1-70 1.0 µg + TSH[b] | 1.10 ± 0.24 | 2.04 ± 0.41 | 185 |
| K1-70 10 µg + TSH[b] | 1.21 ± 0.33 | 1.60 ± 0.35 | 132 |
| K1-70 100 µg + TSH[b] | 1.06 ± 0.54 | 1.68 ± 0.19 | 158 |
| K1-70 100 µg | 1.20 ± 0.13 | 1.72 ± 0.68 | 143 |
| [b]TSH (2) | 95.46 ± 17.64 | 41.53 ± 1.51 | 44 |

| Antibody concentration | % inhibition of TSH stimulation[c] | |
| --- | --- | --- |
| | Wild type TSHR | Mutated TSHR |
| 5B3 10 µg/mL | 0 | 11 |
| 5B3 100 µg/mL | 0 | 0 |
| K1-70 0.001 µg | 0 | 0 |
| K1-70 0.01 µg/mL | 0 | 2 |
| K1-70 0.1 µg/mL | 81 | 78 |
| K1-70 1 µg/mL | 99 | 96 |
| K1-70 10 µg/mL | 98 | 97 |
| K1-70 100 µg/mL | 99 | 96 |
| [b]TSH (2) | 0 | 9 |

See legend to Table 15a for details.

TABLE 15g

TSH induced cyclic AMP production in CHO cells expressing wild type TSHR and TSHR with Asp160 mutated to Lys. Effect of different dilutions of human monoclonal antibody to the TSHR (K1-70) with TSH antagonist activity

| Test sample[a] | Cyclic AMP produced (pmol/mL; mean ± SD (n = 3)) | | Mutated/wild type (%) |
| --- | --- | --- | --- |
| | Wild type TSHR | Mutated TSHR | |
| Cyclic AMP assay buffer only | 0.71 ± 0.10 | 5.83 ± 0.11 | 821 |
| M22[b] | 65.25 ± 4.95 | 51.70 ± 2.57 | 79 |
| 5B3 10 µg/mL + M22[b] | 75.97 ± 4.49 | 52.50 ± 4.25 | 69 |
| 5B3 100 µg/mL + M22[b] | 76.92 ± 9.97 | 45.83 ± 3.53 | 60 |
| K1-70 0.001 µg + M22[b] | 88.89 ± 11.87 | 51.99 ± 6.36 | 58 |
| K1-70 0.01 µg + M22[b] | 81.52 ± 12.62 | 41.02 ± 6.06 | 50 |
| K1-70 0.1 µg + M22[b] | 10.95 ± 1.07 | 9.26 ± 2.35 | 85 |
| K1-70 1.0 µg + M22[b] | 0.46 ± 0.06 | 0.25 ± 0.06 | 54 |
| K1-70 10 µg + M22[b] | 0.63 ± 0.33 | 0.07 ± 0.08 | 11 |
| K1-70 100 µg + M22[b] | 0.52 ± 0.46 | 0.27 ± 0.12 | 52 |
| K1-70 100 µg | 1.00 ± 0.68 | 0.09 ± 0.06 | 9 |
| [b]M22 (2) | 71.04 ± 1.30 | 45.81 ± 5.56 | 64 |

| Antibody concentration | % inhibition of TSH stimulation[c] | |
| --- | --- | --- |
| | Wild type TSHR | Mutated TSHR |
| 5B3 10 µg/mL | 0 | 0 |
| 5B3 100 µg/mL | 0 | 11 |
| K1-70 0.001 µg | 0 | 0 |
| K1-70 0.01 µg/mL | 0 | 21 |
| K1-70 0.1 µg/mL | 83 | 82 |
| K1-70 1 µg/mL | 99 | 99 |
| K1-70 10 µg/mL | 99 | 100 |
| K1-70 100 µg/mL | 99 | 99 |
| [b]M22 (2) | 0 | 11 |

See legend to Table 15a for details.

TABLE 15h

TSH induced cyclic AMP production in CHO cells expressing wild type TSHR and TSHR with Glu178 mutated to Ala. Effect of different dilutions of human monoclonal antibody to the TSHR (K1-70) with TSH antagonist activity

Experiment 1

| Test sample[a] | Cyclic AMP produced (pmol/mL; mean ± SD (n = 3)) | | Mutated/wild type (%) |
|---|---|---|---|
| | Wild type TSHR | Mutated TSHR | |
| Cyclic AMP assay buffer only | 0.35 ± 0.47 | 9.18 ± 0.59 | 2623 |
| TSH[b] | 52.9 ± 3.27 | 56.61 ± 6.05 | 107 |
| 5B3 10 µg/mL + TSH[b] | 65.73 ± 1.11 | 57.61 ± 2.52 | 88 |
| 5B3 100 µg/mL + TSH[b] | 65.49 ± 4.50 | 57.04 ± 7.63 | 87 |
| K1-70 0.001 µg + TSH[b] | 63.14 ± 5.08 | 45.91 ± 1.28 | 73 |
| K1-70 0.01 µg + TSH[b] | 60.67 ± 7.43 | 47.28 ± 2.68 | 78 |
| K1-70 0.1 µg + TSH[b] | 6.32 ± 2.70 | 37.53 ± 7.25 | 594 |
| K1-70 1.0 µg + TSH[b] | 0.78 ± 0.64 | 6.96 ± 0.61 | 892 |
| K1-70 10 µg + TSH[b] | 0.66 ± 0.34 | 5.65 ± 0.22 | 856 |
| K1-70 100 µg + TSH[b] | 0.42 ± 0.22 | 6.80 ± 0.16 | 1619 |
| K1-70 100 µg | 0.01* | 6.11 ± 0.14 | 61100 |
| [b]TSH (2) | 77.16 ± 8.61 | 50.08 ± 5.73 | 65 |

| Antibody concentration | % inhibition of TSH stimulation[c] | |
|---|---|---|
| | Wild type TSHR | Mutated TSHR |
| 5B3 10 µg/mL | 0 | 0 |
| 5B3 100 µg/mL | 0 | 0 |
| K1-70 0.001 µg | 0 | 19 |
| K1-70 0.01 µg/mL | 0 | 16 |
| K1-70 0.1 µg/mL | 88 | 34 |
| K1-70 1 µg/mL | 99 | 88 |
| K1-70 10 µg/mL | 99 | 90 |
| K1-70 100 µg/mL | 99 | 88 |
| [b]TSH (2) | 0 | 12 |

Experiment 2

| Test sample[a] | Cyclic AMP produced (pmol/mL; mean ± SD (n = 3)) | | Mutated/wild type (%) |
|---|---|---|---|
| | Wild type TSHR | Mutated TSHR | |
| Cyclic AMP assay buffer only | 1.83 ± 0.13 | 6.13 ± 0.45 | 335 |
| TSH[b] | 87.25 ± 10.43 | 46.20 ± 2.13 | 53 |
| 5B3 10 µg/mL + TSH[b] | 100.35 ± 7.09 | 54.97 ± 4.10 | 55 |
| 5B3 100 µg/mL + TSH[b] | 98.11 ± 11.88 | 44.98 ± 4.80 | 46 |
| K1-70 0.001 µg + TSH[b] | 103.37 ± 16.45 | 49.40 ± 4.23 | 48 |
| K1-70 0.01 µg + TSH[b] | 96.22 ± 16.49 | 48.01 ± 5.37 | 50 |
| K1-70 0.1 µg + TSH[b] | 20.35 ± 9.35 | 30.71 ± 3.37 | 151 |
| K1-70 1.0 µg + TSH[b] | 1.13 ± 0.62 | 5.78 ± 0.42 | 512 |
| K1-70 10 µg + TSH[b] | 1.43 ± 0.34 | 4.88 ± 0.15 | 341 |
| K1-70 100 µg + TSH[b] | 1.54 ± 0.24 | 4.84 ± 0.32 | 314 |
| K1-70 100 µg | 1.08 ± 0.32 | 3.73 ± 0.64 | 345 |
| [b]TSH (2) | 88.09 ± 7.60 | 44.11 ± 1.34 | 50 |

| Antibody concentration | % inhibition of TSH stimulation[c] | |
|---|---|---|
| | Wild type TSHR | Mutated TSHR |
| 5B3 10 µg/mL | 0 | 0 |
| 5B3 100 µg/mL | 0 | 3 |
| K1-70 0.001 µg | 0 | 0 |
| K1-70 0.01 µg/mL | 0 | 0 |
| K1-70 0.1 µg/mL | 77 | 34 |
| K1-70 1 µg/mL | 99 | 87 |
| K1-70 10 µg/mL | 98 | 89 |
| K1-70 100 µg/mL | 98 | 90 |
| [b]TSH (2) | 0 | 5 |

See legend to Table 15a for details.

TABLE 15i

TSH induced cyclic AMP production in CHO cells expressing wild type TSHR and TSHR with Lys183 mutated to Asp. Effect of different dilutions of human monoclonal antibody to the TSHR (K1-70) with TSH antagonist activity

| Test sample[a] | Cyclic AMP produced (pmol/mL; mean ± SD (n = 3)) | | Mutated/wild type (%) |
|---|---|---|---|
| | Wild type TSHR | Mutated TSHR | |
| Cyclic AMP assay buffer only | 0.83 ± 0.70 | 1.26 ± 0.02 | 152 |
| TSH[b] | 85.81 ± 4.18 | 117.28 ± 3.46 | 137 |
| 5B3 10 µg/mL + TSH[b] | 93.70 ± 8.12 | 104.75 ± 8.56 | 112 |
| 5B3 100 µg/mL + TSH[b] | 108.83 ± 3.13 | 127.83 ± 6.64 | 117 |
| K1-70 0.001 µg + TSH[b] | 90.69 ± 2.74 | 101.41 ± 11.08 | 112 |
| K1-70 0.01 µg + TSH[b] | 97.27 ± 2.97 | 101.74 ± 14.23 | 105 |
| K1-70 0.1 µg + TSH[b] | 69.05 ± 10.81 | 33.97 ± 2.51 | 49 |
| K1-70 1.0 µg + TSH[b] | 2.33 ± 0.54 | 3.04 ± 1.07 | 130 |
| K1-70 10 µg + TSH[b] | 1.74 ± 0.11 | 0.85 ± 0.38 | 49 |
| K1-70 100 µg + TSH[b] | 1.61 ± 0.27 | 0.98 ± 0.23 | 61 |
| K1-70 100 µg | 1.46 ± 0.16 | 0.84 ± 0.26 | 58 |
| [b]TSH (2) | 97.81 ± 21.58 | 93.44 ± 3.40 | 96 |

| Antibody concentration | % inhibition of TSH stimulation[c] | |
|---|---|---|
| | Wild type TSHR | Mutated TSHR |
| 5B3 10 µg/mL | 0 | 11 |
| 5B3 100 µg/mL | 0 | 0 |
| K1-70 0.001 µg | 0 | 14 |
| K1-70 0.01 µg/mL | 0 | 13 |
| K1-70 0.1 µg/mL | 20 | 71 |
| K1-70 1 µg/mL | 97 | 97 |
| K1-70 10 µg/mL | 98 | 99 |
| K1-70 100 µg/mL | 98 | 99 |
| [b]TSH (2) | 0 | 20 |

See legend for Table 15a for details.

TABLE 15j

TSH induced cyclic AMP production in CHO cells expressing wild type TSHR and TSHR with Tyr185 mutated to Ala. Effect of different dilutions of human monoclonal antibody to the TSHR (K1-70) with TSH antagonist activity

| Test sample[a] | Cyclic AMP produced (pmol/mL; mean ± SD (n = 3)) | | Mutated/wild type (%) |
|---|---|---|---|
| | Wild type TSHR | Mutated TSHR | |
| Cyclic AMP assay buffer only | 1.20 ± 0.46 | 2.17 ± 0.33 | 181 |
| TSH[b] | 100.81 ± 7.98 | 52.49 ± 3.51 | 52 |
| 5B3 10 µg/mL + TSH[b] | 125.53 ± 9.18 | 47.02 ± 2.22 | 37 |
| 5B3 100 µg/mL + TSH[b] | 97.32 ± 11.29 | 56.13 ± 6.76 | 58 |
| K1-70 0.001 µg + TSH[b] | 118.92 ± 0 | 51.39 ± 4.61 | 43 |
| K1-70 0.01 µg + TSH[b] | 120.80 ± 7.93 | 46.06 ± 1.89 | 38 |
| K1-70 0.1 µg + TSH[b] | 15.05 ± 4.72 | 10.84 ± 2.53 | 72 |
| K1-70 1.0 µg + TSH[b] | 1.30 ± 0.32 | 2.10 ± 0.52 | 162 |
| K1-70 10 µg + TSH[b] | 1.61 ± 0.80 | 1.64 ± 0.49 | 102 |
| K1-70 100 µg + TSH[b] | 1.38 ± 0.09 | 2.07 ± 0.62 | 150 |
| K1-70 100 µg | 1.30 ± 0.17 | 1.54 ± 0.39 | 118 |
| [b]TSH (2) | 131.33 ± 9.02 | 41.01 ± 1.66 | 31.2 |

| Antibody concentration | % inhibition of TSH stimulation[c] | |
|---|---|---|
| | Wild type TSHR | Mutated TSHR |
| 5B3 10 µg/mL | 0 | 10 |
| 5B3 100 µg/mL | 3 | 0 |
| K1-70 0.001 µg | 0 | 2 |
| K1-70 0.01 µg/mL | 0 | 12 |

See legend to Table 15a for details.

TABLE 15j-continued

TSH induced cyclic AMP production in CHO cells expressing wild type TSHR and TSHR with Tyr185 mutated to Ala. Effect of different dilutions of human monoclonal antibody to the TSHR (K1-70) with TSH antagonist activity

| | | |
|---|---|---|
| K1-70 0.1 µg/mL | 85 | 79 |
| K1-70 1 µg/mL | 99 | 96 |
| K1-70 10 µg/mL | 98 | 97 |
| K1-70 100 µg/mL | 99 | 96 |
| [b]TSH (2) | 0 | 22 |

See legend to Table 15a for details.

TABLE 15k

TSH induced cyclic AMP production in CHO cells expressing wild type TSHR and TSHR with Tyr206 mutated to Ala. Effect of different dilutions of human monoclonal antibody to the TSHR (K1-70) with TSH antagonist activity

| Test sample[a] | Cyclic AMP produced (pmol/mL; mean ± SD, n = 3) | | Mutated/ wild type (%) |
|---|---|---|---|
| | Wild type TSHR | Mutated TSHR | |
| Cyclic AMP assay buffer only | 1.45 ± 0.33 | 2.33 ± 0.17 | 161 |
| TSH[b] | 92.20 ± 5.95 | 82.89 ± 7.13 | 90 |
| 5B3 10 µg/mL + TSH[b] | 94.47 ± 3.74 | 74.63 ± 5.45 | 79 |
| 5B3 100 µg/mL + TSH[b] | 101.41 ± 6.91 | 75.18 ± 4.79 | 74 |
| K1-70 0.001 µg + TSH[b] | 102.14 ± 23.36 | 68.25 ± 5.23 | 67 |
| K1-70 0.01 µg + TSH[b] | 92.18 ± 10.18 | 73.26 ± 6.48 | 79 |
| K1-70 0.1 µg + TSH[b] | 9.63 ± 0.78 | 7.55 ± 0.73 | 78 |
| K1-70 1.0 µg + TSH[b] | 2.01 ± 1.50 | 2.46 ± 0.55 | 122 |
| K1-70 10 µg + TSH[b] | 1.45 ± 0.19 | 2.18 ± 0.16 | 150 |
| K1-70 100 µg + TSH[b] | 1.62 ± 0.44 | 2.31 ± 0.08 | 143 |
| K1-70 100 µg | 1.44 ± 0.23 | 2.13 ± 0.38 | 148 |
| [b]TSH (2) | 107.85 ± 5.97 | 69.48 ± 2.42 | 64 |

| Antibody concentration | % inhibition of TSH stimulation[c] | |
|---|---|---|
| | Wild type TSHR | Mutated TSHR |
| 5B3 10 µg/mL | 0 | 10 |
| 5B3 100 µg/mL | 0 | 9 |
| K1-70 0.001 µg | 0 | 18 |
| K1-70 0.01 µg/mL | 0 | 12 |
| K1-70 0.1 µg/mL | 90 | 91 |
| K1-70 1 µg/mL | 98 | 97 |
| K1-70 10 µg/mL | 98 | 97 |
| K1-70 100 µg/mL | 98 | 97 |
| [b]TSH (2) | 0 | 16 |

See legend to Table 15a for details.

TABLE 15l

TSH induced cyclic AMP production in CHO cells expressing wild type TSHR and TSHR with Lys209 mutated to Ala. Effect of different dilutions of human monoclonal antibody to the TSHR (K1-70) with TSH antagonist activity

| Test sample[a] | Cyclic AMP produced (pmol/mL; mean ± SD, n = 3) | | Mutated/ wild type (%) |
|---|---|---|---|
| | Wild type TSHR | Mutated TSHR | |
| Cyclic AMP assay buffer only | 0.88 ± 0.03 | 2.14 ± 0.56 | 243 |
| TSH[b] | 78.97 ± 8.73 | 57.94 ± 4.39 | 73 |
| 5B3 10 µg/mL + TSH[b] | 76.61 ± 6.55 | 56.52 ± 4.26 | 74 |
| 5B3 100 µg/mL + TSH[b] | 87.72 ± 5.48 | 55.93 ± 3.69 | 64 |
| K1-70 0.001 µg + TSH[b] | 97.83 ± 2.41 | 52.17 ± 7.95 | 53 |
| K1-70 0.01 µg + TSH[b] | 99.22* | 42.31 ± 6.68 | 43 |
| K1-70 0.1 µg + TSH[b] | 9.58 ± 1.13 | 5.45 ± 2.69 | 57 |
| K1-70 1.0 µg + TSH[b] | 1.36 ± 0.10 | 1.43 ± 0.13 | 105 |
| K1-70 10 µg + TSH[b] | 0.88 ± 0 | 1.37 ± 0.29 | 156 |
| K1-70 100 µg + TSH[b] | 0.98 ± 0.24 | 1.58 ± 0.10 | 161 |
| K1-70 100 µg | 0.81 ± 0.09 | 1.84 ± 0.32 | 227 |
| [b]TSH (2) | 91.50 ± 6.84 | 47.73 ± 3.41 | 52 |

| Antibody concentration | % inhibition of TSH stimulation[c] | |
|---|---|---|
| | Wild type TSHR | Mutated TSHR |
| 5B3 10 µg/mL | 3 | 2 |
| 5B3 100 µg/mL | 0 | 3 |
| K1-70 0.001 µg | 0 | 10 |
| K1-70 0.01 µg/mL | 0 | 27 |
| K1-70 0.1 µg/mL | 88 | 91 |
| K1-70 1 µg/mL | 98 | 98 |
| K1-70 10 µg/mL | 99 | 98 |
| K1-70 100 µg/mL | 99 | 97 |
| [b]TSH (2) | 0 | 18 |

See legend to Table 15a for details.

TABLE 15m

TSH induced cyclic AMP production in CHO cells expressing wild type TSHR and TSHR with Asp232 mutated to Ala. Effect of different dilutions of human monoclonal antibody to the TSHR (K1-70) with TSH antagonist activity

| Test sample[a] | Cyclic AMP produced (pmol/mL; mean ± SD, n = 3) | | Mutated/ wild type (%) |
|---|---|---|---|
| | Wild type TSHR | Mutated TSHR | |
| Cyclic AMP assay buffer only | 1.93 ± 0.10 | 2.61 ± 0.62 | 135 |
| TSH[b] | 82.02 ± 7.26 | 57.02 ± 6.10 | 70 |
| 5B3 10 µg/mL + TSH[b] | 86.80 ± 8.83 | 51.42 ± 3.83 | 59 |
| 5B3 100 µg/mL + TSH[b] | 92.84 ± 3.94 | 53.61 ± 5.00 | 58 |
| K1-70 0.001 µg + TSH[b] | 96.66 ± 2.53 | 56.21 ± 2.78 | 58 |
| K1-70 0.01 µg + TSH[b] | 93.85 ± 4.23 | 32.28 ± 7.68 | 34 |
| K1-70 0.1 µg + TSH[b] | 4.46 ± 1.38 | 2.98 ± 0.19 | 67 |
| K1-70 1.0 µg + TSH[b] | 1.66 ± 0.13 | 2.03 ± 0.10 | 122 |
| K1-70 10 µg TSH[b] | 1.71 ± 0.25 | 2.35 ± 0.21 | 137 |
| K1-70 100 µg + TSH[b] | 1.81 ± 0.34 | 2.62 ± 0.17 | 145 |
| K1-70 100 µg | 1.13 ± 0.97 | 2.18 ± 0.32 | 193 |
| [b]TSH (2) | 82.64 ± 7.95 | 62.58 ± 3.86 | 76 |

| Antibody concentration | % inhibition of TSH stimulation[c] | |
|---|---|---|
| | Wild type TSHR | Mutated TSHR |
| 5B3 10 µg/mL | 0 | 10 |
| 5B3 100 µg/mL | 0 | 6 |
| K1-70 0.001 µg | 0 | 1 |
| K1-70 0.01 µg/mL | 0 | 43 |
| K1-70 0.1 µg/mL | 95 | 95 |
| K1-70 1 µg/mL | 98 | 96 |
| K1-70 10 µg/mL | 98 | 96 |
| K1-70 100 µg/mL | 98 | 95 |
| [b]TSH (2) | 0 | 0 |

See legend to Table 15a for details.

TABLE 15n

TSH induced cyclic AMP production in CHO cells expressing wild type TSHR and TSHR with Gln235 mutated to Ala. Effect of different dilutions of human monoclonal antibody to the TSHR (K1-70) with TSH antagonist activity

Experiment 1

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 1.55 ± 0.63 | 3.85 ± 0.62 | 248 |
| TSH[b] | 79.85 ± 5.00 | 55.54 ± 2.28 | 70 |
| 5B3 10 µg/mL + TSH[b] | 80.10 ± 8.09 | 63.73 ± 3.15 | 80 |
| 5B3 100 µg/mL + TSH[b] | 93.18 ± 7.43 | 58.27 ± 3.67 | 63 |
| K1-70 0.001 µg + TSH[b] | 75.94 ± 9.09 | 50.44 ± 3.80 | 66 |
| K1-70 0.01 µg + TSH[b] | 83.71 ± 2.23 | 51.03 ± 3.63 | 61 |
| K1-70 0.1 µg + TSH[b] | 7.69 ± 0.71 | 23.70 ± 3.03 | 308 |
| K1-70 1.0 µg + TSH[b] | 1.05 ± 0.12 | 5.05 ± 0.37 | 481 |
| K1-70 10 µg + TSH[b] | 1.81 ± 0.58 | 3.76 ± 0.11 | 208 |
| K1-70 100 µg + TSH[b] | 1.43 ± 0.56 | 4.93 ± 0.84 | 345 |
| K1-70 100 µg | 0.76 ± 0.42 | 3.59 ± 0.48 | 472 |
| [b]TSH (2) | 80.04 ± 7.76 | 48.55 ± 4.54 | 61 |

| Antibody concentration | % inhibition of TSH stimulation[c] | |
|---|---|---|
| | Wild type TSHR | Mutated TSHR |
| 5B3 10 µg/mL | 0 | 0 |
| 5B3 100 µg/mL | 0 | 0 |
| K1-70 0.001 µg | 5 | 9 |
| K1-70 0.01 µg/mL | 0 | 8 |
| K1-70 0.1 µg/mL | 90 | 57 |
| K1-70 1 µg/mL | 99 | 91 |
| K1-70 10 µg/mL | 98 | 93 |
| K1-70 100 µg/mL | 98 | 91 |
| [b]TSH (2) | 0 | 13 |

Experiment 2

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 0.88 ± 0.09 | 2.06 ± 0.39 | 234 |
| TSH[b] | 56.39 ± 3.44 | 56.59 ± 2.20 | 100 |
| 5B3 10 µg/mL + TSH[b] | 62.97 ± 1.58 | 48.72 ± 6.02 | 77 |
| 5B3 100 µg/mL + TSH[b] | 60.63 ± 1.31 | 57.90 ± 6.25 | 95 |
| K1-70 0.001 µg + TSH[b] | 61.57 ± 5.25 | 54.73 ± 13.72 | 89 |
| K1-70 0.01 µg + TSH[b] | 55.31 ± 5.21 | 61.63 ± 17.52 | 111 |
| K1-70 0.1 µg + TSH[b] | 30.91 ± 2.16 | 27.18 ± 5.31 | 88 |
| K1-70 1.0 µg + TSH[b] | 1.95 ± 1.37 | 2.82 ± 0.34 | 145 |
| K1-70 10 µg + TSH[b] | 1.15 ± 0.35 | 1.40 ± 0.15 | 122 |
| K1-70 100 µg + TSH[b] | 1.12 ± 0.41 | 1.65 ± 0.29 | 147 |
| K1-70 100 µg | 0.63 ± 0.11 | 1.20 ± 0.07 | 190 |
| [b]TSH (2) | 77.33 ± 18.51 | 55.10 ± 2.99 | 71 |

| Antibody concentration | % inhibition of TSH stimulation[c] | |
|---|---|---|
| | Wild type TSHR | Mutated TSHR |
| 5B3 10 µg/mL | 0 | 14 |
| 5B3 100 µg/mL | 0 | 0 |
| K1-70 0.001 µg | 0 | 3 |
| K1-70 0.01 µg/mL | 2 | 0 |
| K1-70 0.1 µg/mL | 45 | 52 |
| K1-70 1 µg/mL | 97 | 95 |
| K1-70 10 µg/mL | 98 | 98 |
| K1-70 100 µg/mL | 98 | 97 |
| [b]TSH (2) | 0 | 3 |

See legend to Table 15a for details.

TABLE 15o

TSH induced cyclic AMP production in CHO cells expressing wild type TSHR and TSHR with Lys250 mutated to Ala. Effect of different dilutions of human monoclonal antibody to the TSHR (K1-70) with TSH antagonist activity

Experiment 1

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 1.37 ± 0.11 | 5.15 ± 0.63 | 376 |
| TSH[b] | 77.89 ± 4.29 | 64.69 ± 4.82 | 83 |
| 5B3 10 µg/mL + TSH[b] | 77.80 ± 3.64 | 67.66 ± 1.21 | 87 |
| 5B3 100 µg/mL + TSH[b] | 79.92 ± 5.52 | 66.12 ± 2.92 | 83 |
| K1-70 0.001 µg + TSH[b] | 80.20 ± 4.04 | 64.15 ± 0 | 80 |
| K1-70 0.01 µg + TSH[b] | 68.64 ± 9.75 | 57.52 ± 4.14 | 84 |
| K1-70 0.1 µg + TSH[b] | 5.75 ± 0.88 | 42.40 ± 1.47 | 737 |
| K1-70 1.0 µg + TSH[b] | 1.67 ± 0.29 | 6.09 ± 0.05 | 365 |
| K1-70 10 µg + TSH[b] | 1.37 ± 0.06 | 4.29 ± 0.62 | 313 |
| K1-70 100 µg + TSH[b] | 1.48 ± 0.08 | 4.75 ± 0.08 | 319 |
| K1-70 100 µg | 1.66 ± 0.33 | 3.17 ± 0.19 | 191 |
| [b]TSH (2) | 84.45 ± 1.63 | 58.26 ± 3.24 | 69 |

| Antibody concentration | % inhibition of TSH stimulation[c] | |
|---|---|---|
| | Wild type TSHR | Mutated TSHR |
| 5B3 10 µg/mL | 0.1 | 0 |
| 5B3 100 µg/mL | 0 | 0 |
| K1-70 0.001 µg | 0 | 1 |
| K1-70 0.01 µg/mL | 12 | 11 |
| K1-70 0.1 µg/mL | 93 | 34 |
| K1-70 1 µg/mL | 98 | 91 |
| K1-70 10 µg/mL | 98 | 93 |
| K1-70 100 µg/mL | 98 | 93 |
| [b]TSH (2) | 0 | 10 |

Experiment 2

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 0.36 ± 0.14 | 0.90 ± 0.36 | 250 |
| TSH[b] | 86.55 ± 2.19 | 54.99 ± 5.70 | 64 |
| 5B3 10 µg/mL + TSH[b] | 90.58 ± 4.34 | 47.09 ± 1.88 | 52 |
| 5B3 100 µg/mL + TSH[b] | 87.52 ± 2.25 | 54.67 ± 4.74 | 62 |
| K1-70 0.001 µg + TSH[b] | 88.48 ± 4.56 | 44.31 ± 3.00 | 50 |
| K1-70 0.01 µg + TSH[b] | 86.20 ± 7.37 | 45.44 ± 2.16 | 53 |
| K1-70 0.1 µg + TSH[b] | 8.81 ± 0.84 | 27.64 ± 1.41 | 314 |
| K1-70 1.0 µg + TSH[b] | 1.05 ± 0.35 | 1.98 ± 0.29 | 189 |
| K1-70 10 µg + TSH[b] | 0.76 ± 0.58 | 0.72 ± 0.11 | 95 |
| K1-70 100 µg + TSH[b] | 0.40 ± 0.09 | 0.64 ± 0.16 | 160 |
| K1-70 100 µg | 0.61 ± 0.20 | 0.90 ± 0.15 | 148 |
| [b]TSH (2) | 75.91 ± 7.48 | 51.08 ± 3.64 | 67 |

| Antibody concentration | % inhibition of TSH stimulation[c] | |
|---|---|---|
| | Wild type TSHR | Mutated TSHR |
| 5B3 10 µg/mL | 0 | 14 |
| 5B3 100 µg/mL | 0 | 1 |
| K1-70 0.001 µg | 0 | 19 |
| K1-70 0.01 µg/mL | 0 | 17 |
| K1-70 0.1 µg/mL | 90 | 50 |
| K1-70 1 µg/mL | 99 | 96 |
| K1-70 10 µg/mL | 99 | 99 |
| K1-70 100 µg/mL | 99 | 99 |
| [b]TSH (2) | 12 | 7 |

See legend to Table 15a for details.

TABLE 15p

TSH induced cyclic AMP production in CHO cells expressing wild type TSHR and TSHR with Glu251 mutated to Ala. Effect of different dilutions of human monoclonal antibody to the TSHR (K1-70) with TSH antagonist activity

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 1.78 ± 0.15 | 4.76 ± 0.73 | 267 |
| TSH[b] | 97.46 ± 6.92 | 76.06 ± 10.78 | 78 |
| 5B3 10 µg/mL + TSH[b] | 92.91 ± 4.18 | 68.71 ± 3.38 | 74 |
| 5B3 100 µg/mL + TSH[b] | 86.30 ± 10.26 | 76.69 ± 7.01 | 89 |
| K1-70 0.001 µg + TSH[b] | 90.50 ± 10.61 | 76.43 ± 13.91 | 84 |
| K1-70 0.01 µg + TSH[b] | 88.13 ± 2.76 | 60.62 ± 2.31 | 69 |
| K1-70 0.1 µg + TSH[b] | 4.06 ± 0.74 | 6.28 ± 2.22 | 155 |
| K1-70 1.0 µg + TSH[b] | 1.73 ± 0.11 | 2.17 ± 0.04 | 125 |
| K1-70 10 µg + TSH[b] | 1.58 ± 0.15 | 3.18 ± 1.36 | 201 |
| K1-70 100 µg + TSH[b] | 1.66 ± 0.03 | 2.72 ± 0.52 | 164 |
| K1-70 100 µg | 1.54 ± 0.15 | 4.41 ± 1.24 | 286 |
| [b]TSH (2) | 104.06 ± 3.26 | 87.36 ± 14.82 | 84 |

| Antibody concentration | % inhibition of TSH stimulation[c] | |
|---|---|---|
| | Wild type TSHR | Mutated TSHR |
| 5B3 10 µg/mL | 5 | 10 |
| 5B3 100 µg/mL | 11 | 0 |
| K1-70 0.001 µg | 7 | 0 |
| K1-70 0.01 µg/mL | 10 | 20 |
| K1-70 0.1 µg/mL | 96 | 92 |
| K1-70 1 µg/mL | 98 | 97 |
| K1-70 10 µg/mL | 98 | 96 |
| K1-70 100 µg/mL | 98 | 96 |
| [b]TSH (2) | 0 | 0 |

See legend to Table 15a for details.

TABLE 15q

TSH induced cyclic AMP production in CHO cells expressing wild type TSHR and TSHR with Arg255 mutated to Ala. Effect of different dilutions of human monoclonal antibody to the TSHR (K1-70) with TSH antagonist activity

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 1.65 ± 0.42 | 2.04 ± 0.48 | 124 |
| TSH[b] | 62.43 ± 4.24 | 63.86 ± 4.18 | 102 |
| 5B3 10 µg/mL + TSH[b] | 75.59* | 56.36 ± 3.72 | 75 |
| 5B3 100 µg/mL + TSH[b] | 68.28 ± 4.90 | 62.53 ± 5.33 | 92 |
| K1-70 0.001 µg + TSH[b] | 89.67 ± 5.46 | 65.87 ± 8.49 | 73 |
| K1-70 0.01 µg + TSH[b] | 87.27 ± 9.27 | 55.02 ± 4.02 | 63 |
| K1-70 0.1 µg + TSH[b] | 33.63 ± 2.97 | 19.38 ± 3.27 | 58 |
| K1-70 1.0 µg + TSH[b] | 2.30 ± 0.34 | 3.96 ± 1.02 | 172 |
| K1-70 10 µg + TSH[b] | 1.28 ± 1.09 | 2.38 ± 0.52 | 186 |
| K1-70 100 µg + TSH[b] | 2.88 ± 1.98 | 1.94 ± 0.45 | 67 |
| K1-70 100 µg | 1.16 ± 0.45 | 1.34 ± 0.50 | 116 |
| [b]TSH (2) | 68.39 ± 1.88 | 59.58 ± 1.64 | 87 |

| Antibody concentration | % inhibition of TSH stimulation[c] | |
|---|---|---|
| | Wild type TSHR | Mutated TSHR |
| 5B3 10 µg/mL | 0 | 12 |
| 5B3 100 µg/mL | 0 | 2 |
| K1-70 0.001 µg | 0 | 0 |
| K1-70 0.01 µg/mL | 0 | 14 |
| K1-70 0.1 µg/mL | 46 | 70 |
| K1-70 1 µg/mL | 96 | 94 |
| K1-70 10 µg/mL | 98 | 96 |
| K1-70 100 µg/mL | 95 | 97 |
| [b]TSH (2) | 0 | 7 |

See legend to Table 15a for details.

TABLE 15r

TSH induced cyclic AMP production in CHO cells expressing wild type TSHR and TSHR with Thr257 mutated to Ala. Effect of different dilutions of human monoclonal antibody to the TSHR (K1-70) with TSH antagonist activity

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 0.67 ± 0.13 | 2.08 ± 0.22 | 310 |
| TSH[b] | 66.07 ± 7.95 | 93.16 ± 6.69 | 141 |
| 5B3 10 µg/mL + TSH[b] | 85.93 ± 3.35 | 94.23 ± 2.23 | 110 |
| 5B3 100 µg/mL + TSH[b] | 83.73 ± 9.86 | 86.78 ± 13.03 | 104 |
| K1-70 0.001 µg + TSH[b] | 88.71 ± 17.01 | 87.21 ± 14.51 | 98 |
| K1-70 0.01 µg + TSH[b] | 84.72 ± 18.03 | 97.91 ± 10.18 | 116 |
| K1-70 0.1 µg + TSH[b] | 55.12 ± 14.21 | 80.13 ± 9.78 | 145 |
| K1-70 1.0 µg + TSH[b] | 1.66 ± 0.44 | 3.97 ± 0.06 | 239 |
| K1-70 10 µg + TSH[b] | 0.91 ± 0.37 | 2.00 ± 0.28 | 220 |
| K1-70 100 µg + TSH[b] | 0.87 ± 0.31 | 2.25 ± 0.24 | 259 |
| K1-70 100 µg | 1.14 ± 0.11 | 1.44 ± 0.15 | 126 |
| [b]TSH (2) | 92.96 ± 1.88 | 85.41 ± 4.14 | 92 |

| Antibody concentration | % inhibition of TSH stimulation[c] | |
|---|---|---|
| | Wild type TSHR | Mutated TSHR |
| 5B3 10 µg/mL | 0 | 0 |
| 5B3 100 µg/mL | 0 | 7 |
| K1-70 0.001 µg | 0 | 6 |
| K1-70 0.01 µg/mL | 0 | 0 |
| K1-70 0.1 µg/mL | 17 | 14 |
| K1-70 1 µg/mL | 97 | 96 |
| K1-70 10 µg/mL | 99 | 98 |
| K1-70 100 µg/mL | 99 | 98 |
| [b]TSH (2) | 0 | 8 |

See legend to Table 15a for details.

TABLE 15s

TSH induced cyclic AMP production in CHO cells expressing wild type TSHR and TSHR with Trp258 mutated to Ala. Effect of different dilutions of human monoclonal antibody to the TSHR (K1-70) with TSH antagonist activity

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 1.09 ± 0.13 | 1.93 ± 0.27 | 177 |
| TSH[b] | 58.81 ± 3.32 | 59.87 ± 5.65 | 102 |
| 5B3 10 µg/mL + TSH[b] | 67.66 ± 2.16 | 50.71 ± 1.58 | 75 |
| 5B3 100 µg/mL + TSH[b] | 72.85 ± 11.12 | 57.62 ± 12.06 | 79 |
| K1-70 0.001 µg + TSH[b] | 64.08 ± 4.50 | 51.10 ± 5.86 | 80 |
| K1-70 0.01 µg + TSH[b] | 68.76 ± 7.18 | 51.22 ± 2.22 | 74 |
| K1-70 0.1 µg + TSH[b] | 12.46 ± 3.44 | 11.56 ± 5.39 | 93 |
| K1-70 1.0 µg + TSH[b] | 0.99 ± 0.52 | 1.38 ± 0.12 | 139 |

TABLE 15s-continued

TSH induced cyclic AMP production in CHO cells expressing wild type TSHR and TSHR with Trp258 mutated to Ala. Effect of different dilutions of human monoclonal antibody to the TSHR (K1-70) with TSH antagonist activity

| | | | |
|---|---|---|---|
| K1-70 10 µg + TSH[b] | 0.64 ± 0.08 | 1.06 ± 0.21 | 166 |
| K1-70 100 µg + TSH[b] | 0.77 ± 0.27 | 1.38 ± 0.65 | 179 |
| K1-70 100 µg | 0.52 ± 0.23 | 1.34 ± 0.29 | 258 |
| [b]TSH (2) | 69.57 ± 4.31 | 47.82 ± 3.23 | 69 |

| | % inhibition of TSH stimulation[c] | |
|---|---|---|
| Antibody concentration | Wild type TSHR | Mutated TSHR |
| 5B3 10 µg/mL | 0 | 15 |
| 5B3 100 µg/mL | 0 | 4 |
| K1-70 0.001 µg | 0 | 15 |
| K1-70 0.01 µg/mL | 0 | 14 |
| K1-70 0.1 µg/mL | 79 | 81 |
| K1-70 1 µg/mL | 98 | 98 |
| K1-70 10 µg/mL | 99 | 98 |
| K1-70 100 µg/mL | 99 | 98 |
| [b]TSH (2) | 0 | 20 |

See legend to Table 15a for details.

TABLE 15t

TSH induced cyclic AMP production in CHO cells expressing wild type TSHR and TSHR with Arg274 mutated to Ala. Effect of different dilutions of human monoclonal antibody to the TSHR (K1- 70) with TSH antagonist activity

| | Cyclic AMP produced (pmol/mL; mean ± SD, n = 3) | | Mutated/ wild type |
|---|---|---|---|
| Test sample[a] | Wild type TSHR | Mutated TSHR | (%) |
| Cyclic AMP assay buffer only | 1.91 ± 0.23 | 2.61 ± 0.37 | 137 |
| TSH[b] | 97.06 ± 3.16 | 99.22 ± 9.24 | 102 |
| 5B3 10 µg/mL + TSH[b] | 115.56 ± 7.73 | 106.00 ± 9.5 | 92 |
| 5B3 10 µg/mL + TSH[b] | 120.83 ± 30.02 | 95.33 ± 4.48 | 79 |
| K1-70 0.001 µg + TSH[b] | 146.34 ± 0 | 117.54 ± 6.34 | 80 |
| K1-70 0.01 µg + TSH[b] | 133.74 ± 11.45 | 105.88 ± 9.33 | 79 |
| K1-70 0.1 µg + TSH[b] | 9.83 ± 1.02 | 4.09 ± 0.09 | 42 |
| K1-70 1.0 µg + TSH[b] | 1.99 ± 0.45 | 1.70 ± 0.34 | 85 |
| K1-70 10 µg + TSH[b] | 1.49 ± 0.15 | 1.90 ± 0.14 | 128 |
| K1-70 100 µg + TSH[b] | 1.54 ± 0.16 | 1.62 ± 0.21 | 105 |
| K1-70 100 µg | 1.30 ± 0.25 | 1.75 ± 0.34 | 135 |
| [b]TSH (2) | 109.43 ± 12.79 | 100.21 ± 9.82 | 92 |

| | % inhibition of TSH stimulation[c] | |
|---|---|---|
| Antibody concentration | Wild type TSHR | Mutated TSHR |
| 5B3 10 µg/mL | 0 | 0 |
| 5B3 100 µg/mL | 0 | 4 |
| K1-70 0.001 µg | 0 | 0 |
| K1-70 0.01 µg/mL | 0 | 0 |
| K1-70 0.1 µg/mL | 90 | 96 |
| K1-70 1 µg/mL | 98 | 98 |
| K1-70 10 µg/mL | 98 | 98 |
| K1-70 100 µg/mL | 98 | 98 |
| [b]TSH (2) | 0 | 0 |

See legend to Table 15a for details.

TABLE 15u

TSH induced cyclic AMP production in CHO cells expressing wild type TSHR and TSHR with Asp276 mutated to Ala. Effect of different dilutions of human monoclonal antibody to the TSHR (K1-70) with TSH antagonist activity

Experiment 1

| | Cyclic AMP produced (pmol/mL; mean ± SD, n = 3) | | Mutated/ wild type |
|---|---|---|---|
| Test sample[a] | Wild type TSHR | Mutated TSHR | (%) |
| Cyclic AMP assay buffer only | 1.19 ± 0.45 | 7.20 ± 0.74 | 605 |
| TSH[b] | 78.01 ± 7.81 | 71.24 ± 4.72 | 91 |
| 5B3 10 µg/mL + TSH[b] | 79.58 ± 5.41 | 66.78 ± 3.68 | 84 |
| 5B3 100 µg/mL + TSH[b] | 72.68 ± 2.09 | 68.46 ± 7.03 | 94 |
| K1-70 0.001 µg + TSH[b] | 76.64 ± 4.38 | 68.87 ± 4.91 | 90 |
| K1-70 0.01 µg + TSH[b] | 71.64 ± 8.57 | 63.50 ± 3.61 | 89 |
| K1-70 0.1 µg + TSH[b] | 9.89 ± 3.19 | 67.79 ± 9.74 | 685 |
| K1-70 1.0 µg + TSH[b] | 1.02 ± 0.24 | 10.21 ± 0.58 | 1001 |
| K1-70 10 µg + TSH[b] | 0.36 ± 0.31 | 5.07 ± 1.35 | 1408 |
| K1-70 100 µg + TSH[b] | 0.70 ± 0.26 | 5.14 ± 3.18 | 734 |
| K1-70 100 µg | 0.21 ± 0.30 | 3.56 ± 0.74 | 1695 |
| [b]TSH (2) | 74.30 ± 8.20 | 67.04 ± 6.95 | 90 |

| | % inhibition of TSH stimulation[c] | |
|---|---|---|
| Antibody concentration | Wild type TSHR | Mutated TSHR |
| 5B3 10 µg/mL | 0 | 6 |
| 5B3 100 µg/mL | 7 | 4 |
| K1-70 0.001 µg | 2 | 3 |
| K1-70 0.01 µg/mL | 8 | 11 |
| K1-70 0.1 µg/mL | 87 | 5 |
| K1-70 1 µg/mL | 99 | 86 |
| K1-70 10 µg/mL | 99 | 93 |
| K1-70 100 µg/mL | 99 | 93 |
| [b]TSH (2) | 5 | 6 |

Experiment 2

| | Cyclic AMP produced (pmol/mL; mean ± SD, n = 3) | | Mutated/ wild type |
|---|---|---|---|
| Test sample[a] | Wild type TSHR | Mutated TSHR | (%) |
| Cyclic AMP assay buffer only | 0.65 ± 0.27 | 12.17 ± 1.47 | 1872 |
| TSH[b] | 95.81 ± 9.24 | 74.82 ± 9.47 | 78 |
| 5B3 10 µg/mL + TSH[b] | 106.73 ± 8.52 | 71.56 ± 4.30 | 67 |
| 5B3 100 µg/mL + TSH[b] | 101.10 ± 2.58 | 75.93 ± 6.03 | 75 |
| K1-70 0.001 µg + TSH[b] | 104.99 ± 10.76 | 72.63 ± 9.99 | 69 |
| K1-70 0.01 µg + TSH[b] | 108.84 ± 12.41 | 78.47 ± 3.50 | 72 |
| K1-70 0.1 µg + TSH[b] | 18.40 ± 12.30 | 66.36 ± 5.38 | 361 |
| K1-70 1.0 µg + TSH[b] | 1.49 ± 0.67 | 9.63 ± 1.53 | 646 |
| K1-70 10 µg + TSH[b] | 0.85 ± 0.28 | 6.66 ± 0.81 | 784 |
| K1-70 100 µg + TSH[b] | 1.58 ± 0.41 | 6.53 ± 1.33 | 413 |
| K1-70 100 µg | 0.64 ± 0.04 | 5.88 ± 1.36 | 919 |
| [b]TSH (2) | 92.86 ± 4.90 | 61.21 ± 1.70 | 66 |

| | % inhibition of TSH stimulation[c] | |
|---|---|---|
| Antibody concentration | Wild type TSHR | Mutated TSHR |
| 5B3 10 µg/mL | 0 | 4 |
| 5B3 100 µg/mL | 0 | 0 |
| K1-70 0.001 µg | 0 | 3 |
| K1-70 0.01 µg/mL | 0 | 0 |
| K1-70 0.1 µg/mL | 81 | 11 |
| K1-70 1 µg/mL | 98 | 87 |
| K1-70 10 µg/mL | 99 | 91 |
| K1-70 100 µg/mL | 98 | 91 |
| [b]TSH (2) | 3 | 18 |

See legend to Table 15a for details.

TABLE 15v

TSH induced cyclic AMP production in CHO cells expressing wild type TSHR and TSHR with Ser281 mutated to Ala. Effect of different dilutions of human monoclonal antibody to the TSHR (K1-70) with TSH antagonist activity

Experiment 1

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 1.27 ± 0.10 | 1.47 ± 0.26 | 116 |
| TSH[b] | 87.93 ± 17.36 | 69.80 ± 10.34 | 79 |
| 5B3 10 µg/mL + TSH[b] | 84.72 ± 5.57 | 56.72 ± 2.69 | 67 |
| 5B3 100 µg/mL + TSH[b] | 87.99 ± 4.63 | 62.11 ± 5.75 | 71 |
| K1-70 0.001 µg + TSH[b] | 86.36* | 56.42 ± 8.88 | 65 |
| K1-70 0.01 µg + TSH[b] | 79.79 ± 8.53 | 50.66 ± 7.96 | 63 |
| K1-70 0.1 µg + TSH[b] | 25.52 ± 8.47 | 40.25 ± 1.49 | 158 |
| K1-70 1.0 µg + TSH[b] | 1.47 ± 0.12 | 2.19 ± 0.52 | 150 |
| K1-70 10 µg + TSH[b] | 1.51 ± 0.11 | 2.08 ± 0.95 | 138 |
| K1-70 100 µg + TSH[b] | 1.18 ± 0.32 | 1.52 ± 0.19 | 129 |
| K1-70 100 µg | 0.99 ± 0.29 | 1.22 ± 0.07 | 123 |
| [b]TSH (2) | 99.13 ± 16.11 | 56.62 ± 5.48 | 57 |

| Antibody concentration | % inhibition of TSH stimulation[c] | |
|---|---|---|
| | Wild type TSHR | Mutated TSHR |
| 5B3 10 µg/mL | 4 | 19 |
| 5B3 100 µg/mL | 0 | 11 |
| K1-70 0.001 µg | 2 | 19 |
| K1-70 0.01 µg/mL | 9 | 27 |
| K1-70 0.1 µg/mL | 71 | 42 |
| K1-70 1 µg/mL | 98 | 97 |
| K1-70 10 µg/mL | 98 | 97 |
| K1-70 100 µg/mL | 99 | 98 |
| [b]TSH (2) | 0 | 19 |

Experiment 2

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 0.51 ± 0.27 | 2.70 ± 0.22 | 529 |
| TSH[b] | 75.33 ± 3.18 | 68.98 ± 3.03 | 92 |
| 5B3 10 µg/mL + TSH[b] | 82.84 ± 2.66 | 66.07 ± 3.09 | 80 |
| 5B3 100 µg/mL + TSH[b] | 82.89 ± 4.01 | 72.42 ± 3.12 | 87 |
| K1-70 0.001 µg + TSH[b] | 77.43 ± 3.86 | 53.94 ± 3.95 | 70 |
| K1-70 0.01 µg + TSH[b] | 87.16 ± 9.24 | 51.53 ± 6.84 | 59 |
| K1-70 0.1 µg + TSH[b] | 18.38 ± 2.79 | 40.45 ± 9.45 | 220 |
| K1-70 1.0 µg + TSH[b] | 0.60 ± 0.27 | 2.56 ± 0.63 | 427 |
| K1-70 10 µg + TSH[b] | 0.38 ± 0.07 | 2.17 ± 0.83 | 571 |
| K1-70 100 µg + TSH[b] | 0.42 ± 0.20 | 1.85 ± 0.40 | 440 |
| K1-70 100 µg | 0.22 ± 0.07 | 2.08 ± 1.29 | 945 |
| [b]TSH (2) | 83.91 ± 6.87 | 65.94 ± 6.27 | 79 |

| Antibody concentration | % inhibition of TSH stimulation[c] | |
|---|---|---|
| | Wild type TSHR | Mutated TSHR |
| 5B3 10 µg/mL | 0 | 4 |
| 5B3 100 µg/mL | 0 | 0 |
| K1-70 0.001 µg | 0 | 22 |
| K1-70 0.01 µg/mL | 0 | 25 |
| K1-70 0.1 µg/mL | 76 | 41 |
| K1-70 1 µg/mL | 99 | 96 |
| K1-70 10 µg/mL | 99 | 97 |
| K1-70 100 µg/mL | 99 | 97 |
| [b]TSH (2) | 0 | 4 |

See legend to Table 15a for details.

TABLE 16

Summary of effects of TSHR mutations (relative to wild type) on the ability of K1-18 IgG to stimulate cyclic AMP and K1-70 IgG to block TSH stimulation of cyclic AMP production in TSHR transfected CHO cells

| TSHR mutation | Stimulation (relative to wild type) of cyclic AMP production by TSH | Stimulation (relative to wild type) of cyclic AMP production by K1-18 IgG | Blocking (relative to wild type) of TSH stimulation of cyclic AMP production by K1-70 IgG |
|---|---|---|---|
| Wild type | +++++ | +++++ | +++++ |
| Asp43 Ala | +++++ | +++++ | +++++ |
| Ile60 Ala | +++++ | +++++ | ++ |
| Glu61 Ala | +++++ | +++++ | +++ |
| Thr104 Ala | +++++ | +++++ | +++++ |
| His105 Ala | +++++ | +++++ | +++++ |
| Asp151 Ala | ++++ | ++++ | +++++ |
| Glu157 Ala | +++++ | 0 | NT |
| Glu178 Ala | +++ | ++++ | ++++ |
| Tyr185 Ala | ++++ | 0 | +++++ |
| Tyr206 Ala | +++++ | ++ | +++++ |
| Lys209 Ala | ++++ | ++++ | +++++ |
| Asp232 Ala | ++++ | 0 | +++++ |
| Gln235 Ala | ++++ | ++++ | +++++ |
| Lys250 Ala | +++++ | +++++ | +++ |
| Glu251 Ala | ++++ | ++++ | +++++ |
| Arg255 Ala | +++++ | +++++ | +++++ |
| Thr257 Ala | +++++ | +++++ | +++++ |
| Trp258 Ala | +++++ | ++ | +++++ |
| Arg274 Ala | +++++ | ++ | +++++ |
| Asp276 Ala | +++++ | +++++ | +++ |
| Ser281 Ala | +++++ | +++++ | ++++ |
| Asp160 Lys | 0 | NT | +++++ |
| Lys183 Asp* | +++++ | 0 | +++++ |

Relative effects of TSHR mutations were expressed as a percentage of activity observed with wild type as follows: +++++ = 100% wild type activity; ++++ = <100-80% of wild type activity; +++ = <80-60% of wild type activity; ++ = <60-40% of wild type activity; + = <40-20% of wild type activity; 0 = <20% of wild type activity.
*Blocking of stimulation for this mutation was carried out using stimulation by M22 as the mutant did not respond to TSH stimulation. M22 Fab final concentration = 3 ng/mL.

TABLE 17a

Inhibition of $^{125}$I-TSH binding to TSHR coated tubes by recombinant K1-70 Fab expressed in *E coli* HB2151 cells

| Test sample | Dilution of culture supernatant (or concentration[1] of K1-70 Fab ng/mL) | % of $^{125}$I-TSH binding | % inhibition[2] |
|---|---|---|---|
| Assay buffer only | | 12.4 | 0 |
| K1-70 Fab transformed cells but non-induced | 1:2 | 11.4 | 8.0 |
| | 1:4 | 12.3 | 0.7 |
| | 1:8 | 10.9 | 12.4 |
| | 1:16 | 11.8 | 5.0 |
| | 1:32 | 12.6 | −1.4 |
| | 1:64 | 11.9 | 3.9 |
| | 1:128 | 11.5 | 7.6 |
| | 1:256 | 10.8 | 13.5 |
| | 1:512 | 10.4 | 16.3 |
| | 1:1024 | 10.7 | 14.2 |
| K1-70 Fab transformed cells and induced | 1:2 (700) | 1.0 | 91.9 |
| | 1:4 (350) | 1.3 | 89.4 |
| | 1:8 (175) | 1.5 | 87.8 |
| | 1:16 (87.5) | 1.3 | 89.6 |
| | 1:32 (44.8) | 1.5 | 88.0 |
| | 1:64 (22.4) | 3.4 | 72.9 |
| | 1:128 (11.2) | 6.1 | 51.3 |
| | 1:256 (5.6) | 9.0 | 27.9 |
| | 1:512 (2.8) | 10.8 | 13.1 |
| | 1:1024 (1.4) | 11.6 | 6.6 |
| K1-70 Fab (from hybridoma produced IgG) | (100) | 1.6 | 87.5 |
| | (50) | 1.7 | 86.1 |
| | (25) | 2.2 | 81.9 |
| | (10) | 6.6 | 47.0 |
| | (5) | 9.9 | 20.0 |

TABLE 17a-continued

Inhibition of $^{125}$I-TSH binding to TSHR coated tubes by recombinant K1-70 Fab expressed in *E coli* HB2151 cells

| Test sample | Dilution of culture supernatant (or concentration[1] of K1-70 Fab ng/mL) | % of $^{125}$I-TSH binding | % inhibition[2] |
|---|---|---|---|
| | (2.5) | 11.0 | 11.5 |
| | (1) | 12.4 | 0.4 |

[1]Concentration of recombinant K1-70 Fab in culture supernatant measured using the Easy-Titer Human IgG (H = L) assay kit (Pierce Biotechnology) using different concentrations of hybridoma produced K1-70 Fab as a calibration curve
[2]inhibition of binding was calculated using the formula: % inhibition = 100 − [A/B × 100] where A = % of $^{125}$I-TSH binding in the presence of test sample; and B = % of $^{125}$I-TSH binding in the presence of assay buffer (50 mM NaCl, 10 mM Tris, pH 7.8, 1% Triton X-100 and 1 mg/mL BSA).

TABLE 17b

Inhibition of TSH mediated stimulation of cyclic AMP production in CHO cells expressing the TSHR by recombinant K1-70 Fab expressed in *E coli* HB2151 cells

| Test sample | Dilution[2] of culture supernatant (or concentration[3] of K1-70 Fab ng/mL) | Cyclic AMP (pmol/mL) mean ± SD (n = 3) | % inhibition of TSH stimulation of cyclic AMP[4] |
|---|---|---|---|
| Assay buffer[1] only | | 2.39 ± 0.20 | |
| TSH 3 ng/mL | | 61.87 ± 2.74 | 0 |
| K1-70 Fab transformed cells but non-induced | 1:10 | 5.67 ± 0.31 | |
| K1-70 Fab transformed cells but non-induced + | 1:5 | 7 0.95 ± 6.32 | −14.7 |
| | 1:10 | 76.24 ± 6.55 | −23.2 |
| 3 ng/mL TSH | 1:20 | 67.11 ± 3.51 | −8.5 |
| | 1:40 | 61.05 ± 8.44 | 1.3 |
| | 1:80 | 64.94 ± 5.20 | −5.0 |
| K1-70 Fab transformed and induced cells | 1:10 (140) | 2.74 ± 0.59 | |
| K1-70 Fab transformed and induced cells + 3 ng/mL TSH | 1:5 (280) | 6.64 ± 0.07 | 89.3 |
| | 1:10 (140) | 9.71 ± 1.50 | 84.3 |
| | 1:20 (70) | 18.55 ± 3.30 | 70.0 |
| | 1:40 (35) | 37.29 ± 6.47 | 39.7 |
| | 1:80 (17.5) | 51.68 ± 3.59 | 16.5 |
| K1-70 Fab (from hybridoma produced IgG) | (100,000) | 1.71 ± 0.36 | |
| K1-70 Fab (from hybridoma produced IgG) + 3 ng/mL TSH | (100,000) | 1.66 ± 0.08 | 97.3 |
| | (10,000) | 2.20 ± 0.17 | 96.4 |
| | (1,000) | 3.11 ± 0.09 | 95.0 |
| | (100) | 6.52 ± 0.07 | 89.5 |
| | (10) | 55.13 ± 5.26 | 10.9 |

[1]Assay buffer: Hanks' buffered salt solution (NaCl free) containing 1 g/L glucose, 20 mmol/L HEPES, 222 mmol/L sucrose, 15 g/L BSA and 0.5 mmol/L 2-isobutyl-1-methylxanthine pH7.4
[2]Dilutions in assay buffer
[3]Concentration of recombinant K1-70 Fab in culture supernatant measured using the Easy-Titer Human IgG (H = L) assay kit (Pierce Biotechnology) using different concentrations of hybridoma produced K1-70 Fab as a calibration curve
[4]% inhibition of TSH stimulation of cyclic AMP: % inhibition = 100 − [A/B × 100] where A = stimulation of cyclic AMP by 3 ng/mL TSH in the presence of test sample; and B = stimulation of cyclic AMP by 3 ng/mL TSH.

The invention claimed is:

1. An isolated human monoclonal or recombinant antibody or fragment thereof that binds to the TSH receptor, wherein the antibody or fragment thereof reduces TSH ligand-induced stimulation of production of cAMP by the TSH receptor relative to TSH ligand-induced stimulation of production of cAMP by the TSH receptor in the absence of the antibody or fragment thereof but wherein the antibody or fragment thereof has no effect on constitutive activity of the TSH receptor, wherein the antibody or fragment thereof, at 1 µg/ml, inhibits greater than 90% of $^{125}$I-TSH binding to TSHR, TSH-biotin binding to TSHR, and TSH-mediated stimulation of cAMP production in CHO cells expressing TSHR, wherein the antibody or fragment thereof comprises an antibody variable region heavy chain (VH) domain comprising the amino acid sequence shown in residues 1-138 in SEQ ID NO:51 and an antibody variable region light chain (VL) domain comprising the amino acid sequence shown in residues 1-130 of SEQ ID NO:69.

2. The antibody or fragment thereof of claim 1, wherein the antibody or fragment thereof exhibits a binding affinity for the TSH receptor of at least $10^8$ L/mol.

3. An isolated nucleic acid encoding: a VH domain comprising an amino acid sequence having the sequence shown in residues 1-138 of SEQ ID NO:51; and/or a VL domain comprising an amino acid sequence having the sequence shown in residues 1-130 of SEQ ID NO:69.

4. The isolated nucleic acid of claim 3, wherein: the nucleic acid encoding the VH domain comprises the sequence shown in nt 1-414 of SEQ ID NO:46; and the nucleic acid encoding the VL domain comprises the sequence shown in nt 1-390 of SEQ ID NO:64.

5. A vector comprising the isolated nucleic acid of claim 4.

6. A host cell comprising the vector of claim 5.

7. A pharmaceutical composition comprising the antibody or fragment thereof of claim 1 and a pharmaceutically acceptable carrier.

8. The antibody or fragment thereof of claim 1, wherein the antibody VH domain comprises the amino acid sequence shown in SEQ ID NO:51 and wherein the antibody VL domain comprises the amino acid sequence shown in SEQ ID NO:69.

9. An isolated human monoclonal or recombinant antibody or fragment thereof that binds to a TSH receptor having the amino acid sequence shown in SEQ ID NO:74, wherein the antibody or fragment thereof comprises a heavy chain variable domain comprising complementarity determining regions (CDRs) comprising the amino acid sequences shown in SEQ ID NOs:52, 53 and 54 and a light chain variable domain comprising CDRs comprising the amino acid sequences shown in SEQ ID NO:70, 71 and 72.

10. The antibody or fragment thereof of claim 9, wherein the antibody VH domain comprises the amino acid sequence shown in SEQ ID NO:51 and wherein the antibody VL domain comprises the amino acid sequence shown in SEQ ID NO:69.

11. The antibody or fragment thereof of claim 9, wherein the antibody or fragment thereof exhibits a binding affinity for the TSH receptor of at least $10^8$ L/mol.

12. A pharmaceutical composition comprising the antibody or fragment thereof of claim 9 and a pharmaceutically acceptable carrier.

* * * * *

SEQUENCE LISTING

<160> NUMBER OF SEQ ID NOS: 85

<210> SEQ ID NO 1
<211> LENGTH: 687
<212> TYPE: DNA
<213> ORGANISM: Homo sapiens

<400> SEQUENCE: 1

```
gaagtgcagc tggtggagtc tggagcagag gtgaaaaagc ccggggagtc tctgaagatc      60
tcctgcaagg gttctggata cagctttacc aactactgga tcggctgggt gcgccagatg     120 cccggaaag gcctggagtg gatggggatc atctatcctt atgactctga taccagatat     180 agccgtcct tcgaaggcca ggtcaccatc tcagccgaca gtccatcag gaccgcctac      240 ctgcactgga gcagcctgaa ggcctcggac accgccatgt attactgtgt gagacccgc      300 gatgggagct atccttatga tgcttttgat atctggggcc aagggacaat ggtcaccgtc     360
tcttcagcct ccaccaaggg cccatcggtc ttccccctgg caccctcctc caagagcacc     420
tctgggggca gcggccct gggctgcctg gtcaaggact acttccccga accggtgacg      480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca caaggtgga caagagagtt     660 gagcccaaat cttgtgacaa aactagt                                        687
```

<210> SEQ ID NO 2
<211> LENGTH: 15

<212> TYPE: DNA
<213> ORGANISM: Homo sapiens

<400> SEQUENCE: 2
aactactgga tcggc                                                            15

<210> SEQ ID NO 3
<211> LENGTH: 51
<212> TYPE: DNA
<213> ORGANISM: Homo sapiens

<400> SEQUENCE: 3
atcatctatc cttatgactc tgataccaga tatagcccgt ccttcgaagg c                    51

<210> SEQ ID NO 4
<211> LENGTH: 39
<212> TYPE: DNA
<213> ORGANISM: Homo sapiens

<400> SEQUENCE: 4
ccccgcgatg ggagctatcc ttatgatgct tttgatatc                                  39

<210> SEQ ID NO 5
<211> LENGTH: 229
<212> TYPE: PRT
<213> ORGANISM: Homo sapiens

<400> SEQUENCE: 5

Glu Val Gln Leu Val Glu Ser Gly Ala Glu Val Lys Lys Pro Gly Glu
 1               5                  10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Tyr Asp Ser Asp Thr Arg Tyr Ser Pro Ser Phe
    50                  55                  60

Glu Gly Gln Val Thr Ile Ser Ala Asp Lys Ser Ile Arg Thr Ala Tyr
65                  70                  75                  80

Leu His Trp Ser Ser Leu Lys Ala Ser Asp Thr Ala Met Tyr Tyr Cys
                85                  90                  95

Val Arg Pro Arg Asp Gly Ser Tyr Pro Tyr Asp Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr Ser
225

<210> SEQ ID NO 6
<211> LENGTH: 5
<212> TYPE: PRT
<213> ORGANISM: Homo sapiens

<400> SEQUENCE: 6

Asn Tyr Trp Ile Gly
1               5

<210> SEQ ID NO 7
<211> LENGTH: 17
<212> TYPE: PRT
<213> ORGANISM: Homo sapiens

<400> SEQUENCE: 7

Ile Ile Tyr Pro Tyr Asp Ser Asp Thr Arg Tyr Ser Pro Ser Phe Glu
1               5                   10                  15

Gly

<210> SEQ ID NO 8
<211> LENGTH: 13
<212> TYPE: PRT
<213> ORGANISM: Homo sapiens

<400> SEQUENCE: 8

Pro Arg Asp Gly Ser Tyr Pro Tyr Asp Ala Phe Asp Ile
1               5                   10

<210> SEQ ID NO 9
<211> LENGTH: 57
<212> TYPE: DNA
<213> ORGANISM: Homo sapiens

<400> SEQUENCE: 9
atggggtcaa ccgccatcct cgccctcctc ctgggtgttc tccaaggagt ctgtggc      57

<210> SEQ ID NO 10
<211> LENGTH: 672
<212> TYPE: DNA
<213> ORGANISM: Homo sapiens

<400> SEQUENCE: 10
gaggtgcagc tggtgcagtc tggagcagag gtgaaaaagc ccggggagtc tctgaagatc      60
tcctgcaagg gttctggata cagctttacc aactactgga tcggctgggt gcgccagatg     120
cccgggaaag gcctggagtg gatggggatc atctatcctt atgactctga taccagatat     180
agcccgtcct tcgaaggcca ggtcaccatc tcagccgaca gtccatcag gaccgcctac      240
ctgcactgga gcagcctgaa ggcctcggac accgccatgt attactgtgt gagaccccgc     300
gatgggagct atccttatga tgcttttgat atctggggcc aagggacaat ggtcaccgtc     360
tcttcagcct ccaccaaggg cccatcggtc ttccccctgg cacctcctc caagagcacc      420
tctgggggca gcgcggccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagacagtt     660
gagcgcaaat ct                                                          672

<210> SEQ ID NO 11
<211> LENGTH: 15
<212> TYPE: DNA
<213> ORGANISM: Homo sapiens

<400> SEQUENCE: 11
aactactgga tcggc                                                         15

<210> SEQ ID NO 12
<211> LENGTH: 51
<212> TYPE: DNA
<213> ORGANISM: Homo sapiens

<400> SEQUENCE: 12
atcatctatc cttatgactc tgataccaga tatagcccgt ccttcgaagg c                 51

<210> SEQ ID NO 13
<211> LENGTH: 39
<212> TYPE: DNA
<213> ORGANISM: Homo sapiens

<400> SEQUENCE: 13
ccccgcgatg ggagctatcc ttatgatgct tttgatatc                               39

<210> SEQ ID NO 14
<211> LENGTH: 19
<212> TYPE: PRT
<213> ORGANISM: Homo sapiens

<400> SEQUENCE: 14

Met Gly Ser Thr Ala Ile Leu Ala Leu Leu Leu Gly Val Leu Gln Gly
1               5                   10                  15

Val Cys Gly

<210> SEQ ID NO 15
<211> LENGTH: 224
<212> TYPE: PRT
<213> ORGANISM: Homo sapiens

<400> SEQUENCE: 15

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Trp Ile Gly Trp Val Arg Gln Met Pro Gly Lys Gly Leu Glu Trp Met
            35                  40                  45

Gly Ile Ile Tyr Pro Tyr Asp Ser Asp Thr Arg Tyr Ser Pro Ser Phe
        50                  55                  60

Glu Gly Gln Val Thr Ile Ser Ala Asp Lys Ser Ile Arg Thr Ala Tyr
65                  70                  75                  80

Leu His Trp Ser Ser Leu Lys Ala Ser Asp Thr Ala Met Tyr Tyr Cys
                85                  90                  95

Val Arg Pro Arg Asp Gly Ser Tyr Pro Tyr Asp Ala Phe Asp Ile Trp
                100                 105                 110

Gly Gln Gly Thr Met Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

```
Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Gln Thr Tyr Ile Cys Asn Val Asn
    195                 200                 205

His Lys Pro Ser Asn Thr Lys Val Asp Lys Thr Val Glu Arg Lys Ser
    210                 215                 220
```

<210> SEQ ID NO 16
<211> LENGTH: 5
<212> TYPE: PRT
<213> ORGANISM: Homo sapiens

<400> SEQUENCE: 16

```
Asn Tyr Trp Ile Gly
1               5
```

<210> SEQ ID NO 17
<211> LENGTH: 17
<212> TYPE: PRT
<213> ORGANISM: Homo sapiens

<400> SEQUENCE: 17

```
Ile Ile Tyr Pro Tyr Asp Ser Asp Thr Arg Tyr Ser Pro Ser Phe Glu
1               5                   10                  15

Gly
```

<210> SEQ ID NO 18
<211> LENGTH: 13
<212> TYPE: PRT
<213> ORGANISM: Homo sapiens

<400> SEQUENCE: 18

```
Pro Arg Asp Gly Ser Tyr Pro Tyr Asp Ala Phe Asp Ile
1               5                   10
```

<210> SEQ ID NO 19
<211> LENGTH: 618
<212> TYPE: DNA
<213> ORGANISM: Homo sapiens

<400> SEQUENCE: 19

```
gaaattgtgt tgacgcagtc tccaggcacc ctgtctttgt ctccagggga aagagccacc      60
ctctcctgca gggccagtca gagtgttagc aacaactact tagcctggta ccagcagaag     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cattgtggta gctcactgag gcgttcggc      300
caagggacca aggtggaaat caaacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaactctacg cctgcgaagt cacccatcag     600
ggcctgagct cgcccgtc                                                   618
```

```
<210> SEQ ID NO 20
<211> LENGTH: 36
<212> TYPE: DNA
<213> ORGANISM: Homo sapiens

<400> SEQUENCE: 20
agggccagtc agagtgttag caacaactac ttagcc                              36

<210> SEQ ID NO 21
<211> LENGTH: 21
<212> TYPE: DNA
<213> ORGANISM: Homo sapiens

<400> SEQUENCE: 21
ggtgcatcca gcagggccac t                                              21

<210> SEQ ID NO 22
<211> LENGTH: 27
<212> TYPE: DNA
<213> ORGANISM: Homo sapiens

<400> SEQUENCE: 22
cagcattgtg gtagctcact gagggcg                                        27

<210> SEQ ID NO 23
<211> LENGTH: 206
<212> TYPE: PRT
<213> ORGANISM: Homo sapiens

<400> SEQUENCE: 23
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Cys Gly Ser Ser Leu
                85                  90                  95

Arg Ala Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val
        195                 200                 205

```
<210> SEQ ID NO 24
<211> LENGTH: 12
```

```
<212> TYPE: PRT
<213> ORGANISM: Homo sapiens

<400> SEQUENCE: 24

Arg Ala Ser Gln Ser Val Ser Asn Asn Tyr Leu Ala
1               5                   10

<210> SEQ ID NO 25
<211> LENGTH: 7
<212> TYPE: PRT
<213> ORGANISM: Homo sapiens

<400> SEQUENCE: 25

Gly Ala Ser Ser Arg Ala Thr
1               5

<210> SEQ ID NO 26
<211> LENGTH: 9
<212> TYPE: PRT
<213> ORGANISM: Homo sapiens

<400> SEQUENCE: 26

Gln His Cys Gly Ser Ser Leu Arg Ala
1               5

<210> SEQ ID NO 27
<211> LENGTH: 60
<212> TYPE: DNA
<213> ORGANISM: Homo sapiens

<400> SEQUENCE: 27
atggaaaccc cagcgcagct tctcttcctc ctgctactct ggctcccaga taccaccgga      60

<210> SEQ ID NO 28
<211> LENGTH: 621
<212> TYPE: DNA
<213> ORGANISM: Homo sapiens

<400> SEQUENCE: 28
gaaattgtgt tgacgcagtc tccaggcacc ctgtctttgt ctccagggga aagagccacc      60
ctctcctgca gggccagtca gagtgttagc aacaactact tagcctggta ccagcagaag     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cattgtggta gctcactgag gcgttcggc      300 caagggacca aggtggaaat caaacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaactctacg cctgcgaagt cacccatcag     600
ggcctgagct cgcccgtcac a                                               621

<210> SEQ ID NO 29
<211> LENGTH: 36
<212> TYPE: DNA
<213> ORGANISM: Homo sapiens

<400> SEQUENCE: 29
agggccagtc agagtgttag caacaactac ttagcc                               36
```

-continued

<210> SEQ ID NO 30
<211> LENGTH: 21
<212> TYPE: DNA
<213> ORGANISM: Homo sapiens

<400> SEQUENCE: 30
ggtgcatcca gcagggccac t                                             21

<210> SEQ ID NO 31
<211> LENGTH: 27
<212> TYPE: DNA
<213> ORGANISM: Homo sapiens

<400> SEQUENCE: 31
cagcattgtg gtagctcact gagggcg                                       27

<210> SEQ ID NO 32
<211> LENGTH: 20
<212> TYPE: PRT
<213> ORGANISM: Homo sapiens

<400> SEQUENCE: 32

Met Glu Thr Pro Ala Gln Leu Leu Phe Leu Leu Leu Leu Trp Leu Pro
1               5                   10                  15

Asp Thr Thr Gly
            20

<210> SEQ ID NO 33
<211> LENGTH: 207
<212> TYPE: PRT
<213> ORGANISM: Homo sapiens

<400> SEQUENCE: 33

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Asn
            20                  25                  30

Tyr Leu Ala Trp Tyr Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Cys Gly Ser Ser Leu
                85                  90                  95

Arg Ala Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr
              195                 200                 205

<210> SEQ ID NO 34
<211> LENGTH: 12
<212> TYPE: PRT
<213> ORGANISM: Homo sapiens

<400> SEQUENCE: 34

Arg Ala Ser Gln Ser Val Ser Asn Asn Tyr Leu Ala
1               5                   10

<210> SEQ ID NO 35
<211> LENGTH: 7
<212> TYPE: PRT
<213> ORGANISM: Homo sapiens

<400> SEQUENCE: 35

Gly Ala Ser Ser Arg Ala Thr
1               5

<210> SEQ ID NO 36
<211> LENGTH: 9
<212> TYPE: PRT
<213> ORGANISM: Homo sapiens

<400> SEQUENCE: 36

Gln His Cys Gly Ser Ser Leu Arg Ala
1               5

<210> SEQ ID NO 37
<211> LENGTH: 679
<212> TYPE: DNA
<213> ORGANISM: Homo sapiens

<400> SEQUENCE: 37
caggttcagc tggtgcagtc tggagcagag gtgaaaaagc ccgggcagtc tctgaagatc      60
tcctgtaagg cttctggata cagcttaacc gacaactgga tcggctgggt gcgccagaag     120
cccgggaaag gcctggagtg gatggggatc atctatcctg gtgactctga caccagatac     180
agtccgtcct tccaaggcca ggtcaccatc tcagccgaca gtccatcaa caccgcctac      240
ctgcagtgga gcagcctgaa ggcctcggac accgccatat attactgtgt gggactcgat     300
tggaactaca accccctgcg atactggggc ccgggaaccc tggtcaccgt ctcctcagcc     360
tccaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactagtg                                                  679

<210> SEQ ID NO 38
<211> LENGTH: 15
<212> TYPE: DNA
<213> ORGANISM: Homo sapiens

<400> SEQUENCE: 38
gacaactgga tcggc                                                       15

```
<210> SEQ ID NO 39
<211> LENGTH: 51
<212> TYPE: DNA
<213> ORGANISM: Homo sapiens

<400> SEQUENCE: 39
atcatctatc ctggtgactc tgacaccaga tacagtccgt ccttccaagg c        51

<210> SEQ ID NO 40
<211> LENGTH: 30
<212> TYPE: DNA
<213> ORGANISM: Homo sapiens

<400> SEQUENCE: 40
ctcgattgga actacaaccc cctgcgatac                                 30

<210> SEQ ID NO 41
<211> LENGTH: 226
<212> TYPE: PRT
<213> ORGANISM: Homo sapiens

<400> SEQUENCE: 41
```

Gln Val Gln Leu Val Gln Ser Gly Ala Glu Val Lys Lys Pro Gly Gln
1               5                   10                  15

Ser Leu Lys Ile Ser Cys Lys Ala Ser Gly Tyr Ser Leu Thr Asp Asn
            20                  25                  30

Trp Ile Gly Trp Val Arg Gln Lys Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Ile Tyr Tyr Cys
                85                  90                  95

Val Gly Leu Asp Trp Asn Tyr Asn Pro Leu Arg Tyr Trp Gly Pro Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr Ser
225

```
<210> SEQ ID NO 42
<211> LENGTH: 5
<212> TYPE: PRT
<213> ORGANISM: Homo sapiens

<400> SEQUENCE: 42
```

```
Asp Asn Trp Ile Gly
1               5

<210> SEQ ID NO 43
<211> LENGTH: 17
<212> TYPE: PRT
<213> ORGANISM: Homo sapiens

<400> SEQUENCE: 43

Ile Ile Tyr Pro Gly Asp Ser Asp Thr Arg Tyr Ser Pro Ser Phe Gln
1               5                   10                  15
Gly

<210> SEQ ID NO 44
<211> LENGTH: 10
<212> TYPE: PRT
<213> ORGANISM: Homo sapiens

<400> SEQUENCE: 44

Leu Asp Trp Asn Tyr Asn Pro Leu Arg Tyr
1               5                   10

<210> SEQ ID NO 45
<211> LENGTH: 57
<212> TYPE: DNA
<213> ORGANISM: Homo sapiens

<400> SEQUENCE: 45
atggggtcaa ccgccatcct cgccctcctc ctggctgttc tccagggagt ctgtgcc        57

<210> SEQ ID NO 46
<211> LENGTH: 663
<212> TYPE: DNA
<213> ORGANISM: Homo sapiens

<400> SEQUENCE: 46
gaggtgcagc tggtgcagtc tggagcagag gtgaaaaagc ccggcagtc tctgaagatc      60 tcctgtaagg cttctggata cagcttaacc gacaactgga tcggctgggt gcgccagaag    120
cccgggaaag gcctggagtg gatggggatc atctatcctg gtgactctga caccagatac    180
agtccgtcct tccaaggcca ggtcaccatc tcagccgaca gtccatcaa caccgcctac     240 ctgcagtgga gcagcctgaa ggcctcggac accgccatat attactgtgt gggactcgat    300
tggaactaca ccccctgcg atactgggc cgggaaccc tggtcaccgt ctcctcagcc       360
tccaccaagg gcccatcggt cttccccctg gcaccctcct ccaagagcac ctctggggc     420 acagcggccc tgggctgcct ggtcaaggac tacttcccg aaccggtgac ggtgtcgtgg     480
aactcaggcg ccctgaccag cggcgtgcac accttcccgg ctgtcctaca gtcctcagga   540
ctctactccc tcagcagcgt ggtgaccgtg ccctccagca gcttgggcac ccagacctac   600
atctgcaacg tgaatcacaa gcccagcaac accaaggtgg acaagacagt tgagcgcaaa   660
tct                                                                 663

<210> SEQ ID NO 47
<211> LENGTH: 15
<212> TYPE: DNA
<213> ORGANISM: Homo sapiens

<400> SEQUENCE: 47
gacaactgga tcggc                                                    15
```

<210> SEQ ID NO 48
<211> LENGTH: 51
<212> TYPE: DNA
<213> ORGANISM: Homo sapiens

<400> SEQUENCE: 48
atcatctatc ctggtgactc tgacaccaga tacagtccgt ccttccaagg c          51

<210> SEQ ID NO 49
<211> LENGTH: 30
<212> TYPE: DNA
<213> ORGANISM: Homo sapiens

<400> SEQUENCE: 49
ctcgattgga actacaaccc cctgcgatac                                   30

<210> SEQ ID NO 50
<211> LENGTH: 19
<212> TYPE: PRT
<213> ORGANISM: Homo sapiens

<400> SEQUENCE: 50

Met Gly Ser Thr Ala Ile Leu Ala Leu Leu Leu Ala Val Leu Gln Gly
 1               5                  10                  15

Val Cys Ala

<210> SEQ ID NO 51
<211> LENGTH: 221
<212> TYPE: PRT
<213> ORGANISM: Homo sapiens

<400> SEQUENCE: 51

Glu Val Gln Leu Val Gln Ser Gly Ala Glu Val Lys Lys Pro Gly Gln
 1               5                  10                  15

Ser Leu Lys Ile Ser Cys Lys Ala Ser Gly Tyr Ser Leu Thr Asp Asn
            20                  25                  30

Trp Ile Gly Trp Val Arg Gln Lys Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Ile Tyr Tyr Cys
                85                  90                  95

Val Gly Leu Asp Trp Asn Tyr Asn Pro Leu Arg Tyr Trp Gly Pro Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro

```
                195                 200                 205
Ser Asn Thr Lys Val Asp Lys Thr Val Glu Arg Lys Ser
    210                 215                 220

<210> SEQ ID NO 52
<211> LENGTH: 5
<212> TYPE: PRT
<213> ORGANISM: Homo sapiens

<400> SEQUENCE: 52

Asp Asn Trp Ile Gly
1               5

<210> SEQ ID NO 53
<211> LENGTH: 17
<212> TYPE: PRT
<213> ORGANISM: Homo sapiens

<400> SEQUENCE: 53

Ile Ile Tyr Pro Gly Asp Ser Asp Thr Arg Tyr Ser Pro Ser Phe Gln
1               5                  10                  15
Gly

<210> SEQ ID NO 54
<211> LENGTH: 10
<212> TYPE: PRT
<213> ORGANISM: Homo sapiens

<400> SEQUENCE: 54

Leu Asp Trp Asn Tyr Asn Pro Leu Arg Tyr
1               5                  10

<210> SEQ ID NO 55
<211> LENGTH: 639
<212> TYPE: DNA
<213> ORGANISM: Homo sapiens

<400> SEQUENCE: 55
ctgcctgtgc tgactcagcc accctcagtg tccgtgtccc caggacagac agccagcatc     60
acctgctctg gagataaaatt ggggataaa tatgcttgct ggtatcagca gaagccaggc    120
cagtcccctg tgctggtcat ctatcaagat agcaagcggc cctcaggat ccctgagcga    180 ttctctggct ccaactctgg gaacacagcc actctgacca tcagcgggac ccaggctatg    240
gatgaggctg actattactg tcaggcgtgg gacagcagca ctgccgtggt attcggcgga    300
gggaccaagc tgaccgtcct aggtcagccc aaggctgccc cctcggtcac tctgttcccg    360
ccctcctctg aggagcttca agccaacaag gccacactgg tgtgtctcat aagtgacttc    420
tacccgggag ccgtgacagt ggcctggaag gcagatagca gccccgtcaa ggcgggagtg    480
gagaccacca cacctccaa acaaagcaac aacaagtacg cggccagcag ctatctgagc    540
ctgacgcctg agcagtggaa gtcccacaga agctacagct gccaggtcac gcatgaaggg    600
agcaccgtgg agaagacagt ggcccctaca gaatgttca                          639

<210> SEQ ID NO 56
<211> LENGTH: 33
<212> TYPE: DNA
<213> ORGANISM: Homo sapiens

<400> SEQUENCE: 56
tctggagata aattggggga taaatatgct tgc                                 33
```

<210> SEQ ID NO 57
<211> LENGTH: 21
<212> TYPE: DNA
<213> ORGANISM: Homo sapiens

<400> SEQUENCE: 57
caagatagca agcggccctc a                                              21

<210> SEQ ID NO 58
<211> LENGTH: 30
<212> TYPE: DNA
<213> ORGANISM: Homo sapiens

<400> SEQUENCE: 58
caggcgtggg acagcagcac tgccgtggta                                     30

<210> SEQ ID NO 59
<211> LENGTH: 213
<212> TYPE: PRT
<213> ORGANISM: Homo sapiens

<400> SEQUENCE: 59

Leu Pro Val Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 60
<211> LENGTH: 11
<212> TYPE: PRT
<213> ORGANISM: Homo sapiens

<400> SEQUENCE: 60

```
Ser Gly Asp Lys Leu Gly Asp Lys Tyr Ala Cys
1               5                   10
```

<210> SEQ ID NO 61
<211> LENGTH: 7
<212> TYPE: PRT
<213> ORGANISM: Homo sapiens

<400> SEQUENCE: 61

```
Gln Asp Ser Lys Arg Pro Ser
1               5
```

<210> SEQ ID NO 62
<211> LENGTH: 10
<212> TYPE: PRT
<213> ORGANISM: Homo sapiens

<400> SEQUENCE: 62

```
Gln Ala Trp Asp Ser Ser Thr Ala Val Val
1               5                   10
```

<210> SEQ ID NO 63
<211> LENGTH: 57
<212> TYPE: DNA
<213> ORGANISM: Homo sapiens

<400> SEQUENCE: 63

```
atggcctggt ctcctctcct cctcaccctt ctcattcact gcacagggtc ctgggcc      57
```

<210> SEQ ID NO 64
<211> LENGTH: 648
<212> TYPE: DNA
<213> ORGANISM: Homo sapiens

<400> SEQUENCE: 64

```
cagtctgtgt tgacgcagcc gccctcagtg tctgcggccc caggacagaa ggtcaccatt      60
tcctgctccg gaagcagctc cgacattggg agtaattatg tatcctggta ccagcagttc     120
ccgggaacag cccccaaact cctcatttat gacaataata agcgaccctc agcgattcct     180
gaccgattct ctggctccaa gtctggcacg tcagccaccc tgggcatcac cggactccag     240
actggggacg aggccgatta ttactgcgga acatgggata gcagactggg tattgctgtg     300
ttcggaggag gcacccagct gaccgtcctc ggtcagccca aggctgcccc atcggtcact     360
ctgttcccac cctcctctga ggagcttcaa gccaacaagg ccacactggt gtgtctcgta     420
agtgacttct acccgggagc cgtgacagtg gcctggaagg cagatggcag ccccgtcaag     480
gtgggagtgg agaccaccaa accctccaaa caaagcaaca acaagtatgc ggccagcagc     540
tacctgagcc tgacgcccga gcagtggaag tcccacagaa gctacagctg ccgggtcacg     600
catgaaggga gcaccgtgga agacagtgt gccccctacag aatgttca                  648
```

<210> SEQ ID NO 65
<211> LENGTH: 39
<212> TYPE: DNA
<213> ORGANISM: Homo sapiens

<400> SEQUENCE: 65

```
tccggaagca gctccgacat tgggagtaat tatgtatcc                            39
```

<210> SEQ ID NO 66
<211> LENGTH: 21
<212> TYPE: DNA

```
<213> ORGANISM: Homo sapiens

<400> SEQUENCE: 66
gacaataata agcgaccctc a                                          21

<210> SEQ ID NO 67
<211> LENGTH: 33
<212> TYPE: DNA
<213> ORGANISM: Homo sapiens

<400> SEQUENCE: 67
ggaacatggg atagcagact gggtattgct gtg                             33

<210> SEQ ID NO 68
<211> LENGTH: 19
<212> TYPE: PRT
<213> ORGANISM: Homo sapiens

<400> SEQUENCE: 68

Met Ala Trp Ser Pro Leu Leu Leu Thr Leu Leu Ile His Cys Thr Gly
1               5                   10                  15

Ser Trp Ala

<210> SEQ ID NO 69
<211> LENGTH: 216
<212> TYPE: PRT
<213> ORGANISM: Homo sapiens

<400> SEQUENCE: 69

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asp Ile Gly Ser Asn
            20                  25                  30

Tyr Val Ser Trp Tyr Gln Gln Phe Pro Gly Thr Ala Pro Lys Leu Leu
        35                  40                  45

Ile Tyr Asp Asn Asn Lys Arg Pro Ser Ala Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Arg Leu
                85                  90                  95

Gly Ile Ala Val Phe Gly Gly Gly Thr Gln Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Val Ser Asp Phe Tyr
    130                 135                 140

Pro Gly Ala Val Thr Val Ala Trp Lys Ala Asp Gly Ser Pro Val Lys
145                 150                 155                 160

Val Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Arg Val Thr His Glu Gly Ser Thr Val Glu Lys
        195                 200                 205

Thr Val Ala Pro Thr Glu Cys Ser
    210                 215
```

```
<210> SEQ ID NO 70
<211> LENGTH: 13
<212> TYPE: PRT
<213> ORGANISM: Homo sapiens

<400> SEQUENCE: 70

Ser Gly Ser Ser Ser Asp Ile Gly Ser Asn Tyr Val Ser
1               5                   10

<210> SEQ ID NO 71
<211> LENGTH: 7
<212> TYPE: PRT
<213> ORGANISM: Homo sapiens

<400> SEQUENCE: 71

Asp Asn Asn Lys Arg Pro Ser
1               5

<210> SEQ ID NO 72
<211> LENGTH: 11
<212> TYPE: PRT
<213> ORGANISM: Homo sapiens

<400> SEQUENCE: 72

Gly Thr Trp Asp Ser Arg Leu Gly Ile Ala Val
1               5                   10

<210> SEQ ID NO 73
<211> LENGTH: 20
<212> TYPE: PRT
<213> ORGANISM: Homo sapiens
<220> FEATURE:
<221> NAME/KEY: MISC_FEATURE
<223> OTHER INFORMATION: K1-70 LC protein sequence of the 2-21
      consecutive N-terminal amino acids obtained by Edman reaction

<400> SEQUENCE: 73

Ser Val Leu Thr Gln Pro Pro Ser Val Ser Ala Ala Pro Gly Gln Lys
1               5                   10                  15

Val Thr Ile Ser
            20

<210> SEQ ID NO 74
<211> LENGTH: 764
<212> TYPE: PRT
<213> ORGANISM: Homo sapiens

<400> SEQUENCE: 74

Met Arg Pro Ala Asp Leu Leu Gln Leu Val Leu Leu Leu Asp Leu Pro
1               5                   10                  15

Arg Asp Leu Gly Gly Met Gly Cys Ser Ser Pro Pro Cys Glu Cys His
            20                  25                  30

Gln Glu Glu Asp Phe Arg Val Thr Cys Lys Asp Ile Gln Arg Ile Pro
        35                  40                  45

Ser Leu Pro Pro Ser Thr Gln Thr Leu Lys Leu Ile Glu Thr His Leu
    50                  55                  60

Arg Thr Ile Pro Ser His Ala Phe Ser Asn Leu Pro Asn Ile Ser Arg
65                  70                  75                  80

Ile Tyr Val Ser Ile Asp Val Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110
```

```
Asn Leu Thr Tyr Ile Asp Pro Asp Ala Leu Lys Glu Leu Pro Leu Leu
            115                 120                 125

Lys Phe Leu Gly Ile Phe Asn Thr Gly Leu Lys Met Phe Pro Asp Leu
        130                 135                 140

Thr Lys Val Tyr Ser Thr Asp Ile Phe Phe Ile Leu Glu Ile Thr Asp
145                 150                 155                 160

Asn Pro Tyr Met Thr Ser Ile Pro Val Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly Tyr Ala Phe Asn Gly Thr Lys Leu Asp Ala Val Tyr Leu Asn
        195                 200                 205

Lys Asn Lys Tyr Leu Thr Val Ile Asp Lys Asp Ala Phe Gly Gly Val
210                 215                 220

Tyr Ser Gly Pro Ser Leu Leu Asp Val Ser Gln Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Lys Lys Leu Pro Leu Ser Leu Ser Phe Leu His Leu
            260                 265                 270

Thr Arg Ala Asp Leu Ser Tyr Pro Ser His Cys Cys Ala Phe Lys Asn
        275                 280                 285

Gln Lys Lys Ile Arg Gly Ile Leu Glu Ser Leu Met Cys Asn Glu Ser
290                 295                 300

Ser Met Gln Ser Leu Arg Gln Arg Lys Ser Val Asn Ala Leu Asn Ser
305                 310                 315                 320

Pro Leu His Gln Glu Tyr Glu Glu Asn Leu Gly Asp Ser Ile Val Gly
                325                 330                 335

Tyr Lys Glu Lys Ser Lys Phe Gln Asp Thr His Asn Asn Ala His Tyr
            340                 345                 350

Tyr Val Phe Phe Glu Glu Gln Glu Asp Glu Ile Ile Gly Phe Gly Gln
        355                 360                 365

Glu Leu Lys Asn Pro Gln Glu Glu Thr Leu Gln Ala Phe Asp Ser His
370                 375                 380

Tyr Asp Tyr Thr Ile Cys Gly Asp Ser Glu Asp Met Val Cys Thr Pro
385                 390                 395                 400

Lys Ser Asp Glu Phe Asn Pro Cys Glu Asp Ile Met Gly Tyr Lys Phe
                405                 410                 415

Leu Arg Ile Val Val Trp Phe Val Ser Leu Leu Ala Leu Leu Gly Asn
            420                 425                 430

Val Phe Val Leu Leu Ile Leu Leu Thr Ser His Tyr Lys Leu Asn Val
        435                 440                 445

Pro Arg Phe Leu Met Cys Asn Leu Ala Phe Ala Asp Phe Cys Met Gly
450                 455                 460

Met Tyr Leu Leu Leu Ile Ala Ser Val Asp Leu Tyr Thr His Ser Glu
465                 470                 475                 480

Tyr Tyr Asn His Ala Ile Asp Trp Gln Thr Gly Pro Gly Cys Asn Thr
                485                 490                 495

Ala Gly Phe Phe Thr Val Phe Ala Ser Glu Leu Ser Val Tyr Thr Leu
            500                 505                 510

Thr Val Ile Thr Leu Glu Arg Trp Tyr Ala Ile Thr Phe Ala Met Arg
        515                 520                 525
```

```
Leu Asp Arg Lys Ile Arg Leu Arg His Ala Cys Ala Ile Met Val Gly
        530                 535                 540

Gly Trp Val Cys Cys Phe Leu Leu Ala Leu Leu Pro Leu Val Gly Ile
545                 550                 555                 560

Ser Ser Tyr Ala Lys Val Ser Ile Cys Leu Pro Met Asp Thr Glu Thr
                565                 570                 575

Pro Leu Ala Leu Ala Tyr Ile Val Phe Val Leu Thr Leu Asn Ile Val
            580                 585                 590

Ala Phe Val Ile Val Cys Cys Cys Tyr Val Lys Ile Tyr Ile Thr Val
        595                 600                 605

Arg Asn Pro Gln Tyr Asn Pro Gly Asp Lys Asp Thr Lys Ile Ala Lys
625                 615                 620

Arg Met Ala Val Leu Ile Phe Thr Asp Phe Ile Cys Met Ala Pro Ile
625                 630                 635                 640

Ser Phe Tyr Ala Leu Ser Ala Ile Leu Asn Lys Pro Leu Ile Thr Val
                645                 650                 655

Ser Asn Ser Lys Ile Leu Leu Val Leu Phe Tyr Pro Leu Asn Ser Cys
                660                 665                 670

Ala Asn Pro Phe Leu Tyr Ala Ile Phe Thr Lys Ala Phe Gln Arg Asp
            675                 680                 685

Val Phe Ile Leu Leu Ser Lys Phe Gly Ile Cys Lys Arg Gln Ala Gln
690                 695                 700

Ala Tyr Arg Gly Gln Arg Val Pro Pro Lys Asn Ser Thr Asp Ile Gln
705                 710                 715                 720

Val Gln Lys Val Thr His Asp Met Arg Gln Gly Leu His Asn Met Glu
                725                 730                 735

Asp Val Tyr Glu Leu Ile Glu Asn Ser His Leu Thr Pro Lys Lys Gln
            740                 745                 750

Gly Gln Ile Ser Glu Glu Tyr Met Gln Thr Val Leu
            755                 760

<210> SEQ ID NO 75
<211> LENGTH: 267
<212> TYPE: PRT
<213> ORGANISM: Homo sapiens

<400> SEQUENCE: 75

Met Arg Pro Ala Asp Leu Leu Gln Leu Val Leu Leu Leu Asp Leu Pro
1               5                   10                  15

Arg Asp Leu Gly Gly Met Gly Cys Ser Ser Pro Pro Cys Glu Cys His
            20                  25                  30

Gln Glu Glu Asp Phe Arg Val Thr Cys Lys Asp Ile Gln Arg Ile Pro
        35                  40                  45

Ser Leu Pro Pro Ser Thr Gln Thr Leu Lys Leu Ile Glu Thr His Leu
    50                  55                  60

Arg Thr Ile Pro Ser His Ala Phe Ser Asn Leu Pro Asn Ile Ser Arg
65                  70                  75                  80

Ile Tyr Val Ser Ile Asp Val Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110

Asn Leu Thr Tyr Ile Asp Pro Asp Ala Leu Lys Glu Leu Pro Leu Leu
        115                 120                 125

Lys Phe Leu Gly Ile Phe Asn Thr Gly Leu Lys Met Phe Pro Asp Leu
    130                 135                 140
```

Thr Lys Val Tyr Ser Thr Asp Ile Phe Phe Ile Leu Glu Ile Thr Asp
145                 150                 155                 160

Asn Pro Tyr Met Thr Ser Ile Pro Val Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly Tyr Ala Phe Asn Gly Thr Lys Leu Asp Ala Val Tyr Leu Asn
            195                 200                 205

Lys Asn Lys Tyr Leu Thr Val Ile Asp Lys Asp Ala Phe Gly Gly Val
            210                 215                 220

Tyr Ser Gly Pro Ser Leu Leu Asp Val Ser Gln Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Asn His His His His His His
            260                 265

<210> SEQ ID NO 76
<211> LENGTH: 336
<212> TYPE: PRT
<213> ORGANISM: Homo sapiens

<400> SEQUENCE: 76

Met Arg Pro Ala Asp Leu Leu Gln Leu Val Leu Leu Leu Asp Leu Pro
1               5                   10                  15

Arg Asp Leu Gly Gly Met Gly Cys Ser Ser Pro Pro Cys Glu Cys His
            20                  25                  30

Gln Glu Glu Asp Phe Arg Val Thr Cys Lys Asp Ile Gln Arg Ile Pro
            35                  40                  45

Ser Leu Pro Pro Ser Thr Gln Thr Leu Lys Leu Ile Glu Thr His Leu
    50                  55                  60

Arg Thr Ile Pro Ser His Ala Phe Ser Asn Leu Pro Asn Ile Ser Arg
65                  70                  75                  80

Ile Tyr Val Ser Ile Asp Val Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110

Asn Leu Thr Tyr Ile Asp Pro Asp Ala Leu Lys Glu Leu Pro Leu Leu
            115                 120                 125

Lys Phe Leu Gly Ile Phe Asn Thr Gly Leu Lys Met Phe Pro Asp Leu
130                 135                 140

Thr Lys Val Tyr Ser Thr Asp Ile Phe Phe Ile Leu Glu Ile Thr Asp
145                 150                 155                 160

Asn Pro Tyr Met Thr Ser Ile Pro Val Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly Tyr Ala Phe Asn Gly Thr Lys Leu Asp Ala Val Tyr Leu Asn
            195                 200                 205

Lys Asn Lys Tyr Leu Thr Val Ile Asp Lys Asp Ala Phe Gly Gly Val
            210                 215                 220

Tyr Ser Gly Pro Ser Leu Leu Asp Val Ser Gln Thr Ser Val Thr Ala
225                 230                 235                 240

Leu Pro Ser Lys Gly Leu Glu His Leu Lys Glu Leu Ile Ala Arg Asn

```
                    245                 250                 255
Thr Trp Thr Leu Lys Lys Leu Pro Leu Ser Leu Ser Phe Leu His Leu
            260                 265                 270

Thr Arg Ala Asp Leu Ser Tyr Pro Ser His Cys Cys Ala Phe Lys Asn
        275                 280                 285

Gln Lys Lys Ile Arg Gly Ile Leu Glu Ser Leu Met Cys Asn Glu Ser
    290                 295                 300

Ser Tyr Asp Tyr Thr Ile Cys Gly Asp Ser Glu Asp Met Val Cys Thr
305                 310                 315                 320

Pro Lys Ser Asp Glu Phe Asn Pro Cys Glu His His His His His His
                325                 330                 335

<210> SEQ ID NO 77
<211> LENGTH: 36
<212> TYPE: DNA
<213> ORGANISM: Homo sapiens

<400> SEQUENCE: 77
cactgcgaat tcaaaatgag gccggcggac ttgctg                          36

<210> SEQ ID NO 78
<211> LENGTH: 48
<212> TYPE: DNA
<213> ORGANISM: Homo sapiens

<400> SEQUENCE: 78
gttctcctcc tcaactggga tgatgttaag agtccaggtg tttcttgc             48

<210> SEQ ID NO 79
<211> LENGTH: 48
<212> TYPE: DNA
<213> ORGANISM: Homo sapiens

<400> SEQUENCE: 79
gcaagaaaca cctggactct aacatcatc ccagttgagg aggagaac              48

<210> SEQ ID NO 80
<211> LENGTH: 54
<212> TYPE: DNA
<213> ORGANISM: Homo sapiens

<400> SEQUENCE: 80
gcagctctcg agtcagtggt ggtggtggtg gtgtgtctgc tcgaagcggc cggc      54

<210> SEQ ID NO 81
<211> LENGTH: 20
<212> TYPE: DNA
<213> ORGANISM: Homo sapiens

<400> SEQUENCE: 81
taatacgact cactataggg                                            20

<210> SEQ ID NO 82
<211> LENGTH: 50
<212> TYPE: DNA
<213> ORGANISM: Homo sapiens

<400> SEQUENCE: 82
tgtccccaca tatggtgtag tcataactgc tctcattaca catcaaggac           50

<210> SEQ ID NO 83
```

```
<211> LENGTH: 18
<212> TYPE: DNA
<213> ORGANISM: Homo sapiens

<400> SEQUENCE: 83
tagaaggcac agtcgagg                                                 18

<210> SEQ ID NO 84
<211> LENGTH: 50
<212> TYPE: DNA
<213> ORGANISM: Homo sapiens

<400> SEQUENCE: 84
gtccttgatg tgtaatgaga gcagttatga ctacaccata tgtggggaca              50

<210> SEQ ID NO 85
<211> LENGTH: 59
<212> TYPE: DNA
<213> ORGANISM: Homo sapiens

<400> SEQUENCE: 85
gctactcgag ctagtggtgg tggtggtggt gttcacacgg gttgaactca tcggacttg    59
```